(12) United States Patent
Martin et al.

(10) Patent No.: US 8,143,243 B2
(45) Date of Patent: *Mar. 27, 2012

(54) COMPOUNDS FOR THE TREATMENT OF HEPATITIS C

(75) Inventors: Scott W. Martin, Middletown, CT (US); Carl P. Bergstrom, Madison, CT (US); Robert G. Gentles, Wallingford, CT (US); Kap-Sun Yeung, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 455 days.

This patent is subject to a terminal disclaimer.

(21) Appl. No.: 12/369,222

(22) Filed: Feb. 11, 2009

(65) Prior Publication Data

US 2009/0275561 A1 Nov. 5, 2009

Related U.S. Application Data

(63) Continuation-in-part of application No. 12/180,994, filed on Jul. 28, 2008, now Pat. No. 7,652,004.

(60) Provisional application No. 61/049,944, filed on May 2, 2008, provisional application No. 60/954,814, filed on Aug. 9, 2007.

(51) Int. Cl.
*A61P 31/00* (2006.01)
*A61K 31/55* (2006.01)
*C07D 223/14* (2006.01)

(52) U.S. Cl. .................................. 514/214.01; 540/576

(58) Field of Classification Search ............. 514/214.01; 540/576
See application file for complete search history.

(56) References Cited

U.S. PATENT DOCUMENTS

| | | | |
|---|---|---|---|
| 7,153,848 B2 | 12/2006 | Hudyma et al. | |
| 7,399,758 B2 | 7/2008 | Meanwell et al. | |
| 7,452,876 B2 | 11/2008 | Yeung et al. | |
| 7,456,165 B2 | 11/2008 | Bergstrom et al. | |
| 7,456,166 B2 | 11/2008 | Bender et al. | |
| 7,456,167 B2 | 11/2008 | Bergstrom | |
| 7,473,688 B2 | 1/2009 | Bergstrom et al. | |
| 7,517,872 B2 | 4/2009 | Nickel et al. | |
| 7,521,441 B2 | 4/2009 | Gentles et al. | |
| 7,521,442 B2 | 4/2009 | Gentles et al. | |
| 7,521,444 B2 | 4/2009 | Bender et al. | |
| 7,538,102 B2 | 5/2009 | Yeung et al. | |
| 7,538,103 B2 | 5/2009 | Hewawasam et al. | |
| 7,541,351 B2 | 6/2009 | Bender et al. | |
| 7,541,353 B2 | 6/2009 | Gentles et al. | |
| 7,652,004 B2 * | 1/2010 | Martin et al. | 514/214.01 |
| 2008/0227769 A1 | 9/2008 | Gentles et al. | |
| 2009/0018163 A1 | 1/2009 | Schmitz et al. | |
| 2009/0042860 A1 | 2/2009 | Bergstrom et al. | |
| 2009/0130056 A1 | 5/2009 | Bender et al. | |
| 2009/0130057 A1 | 5/2009 | Hewawasam et al. | |

FOREIGN PATENT DOCUMENTS

| | | |
|---|---|---|
| WO | WO 2005/080399 | 9/2005 |
| WO | WO 2006/046030 | 5/2006 |
| WO | WO 2006/046039 | 5/2006 |
| WO | WO 2007/029029 | 3/2007 |
| WO | WO 2007/129119 | 11/2007 |

OTHER PUBLICATIONS

U.S. Appl. No. 60/894,881, filed Mar. 14, 2007, Yeung et al.
U.S. Appl. No. 61/039,961, filed Mar. 27, 2008, Bender et al.
U.S. Appl. No. 61/039,973, filed Mar. 27, 2008, Yang et al.
U.S. Appl. No. 61/039,976, filed Mar. 27, 2008, Yeung et al.
U.S. Appl. No. 12/434,748, filed Mar. 4, 2009, Martin et al.
Ikegashira, K. et al., "Discovery of Conformationally Constrained Tetracyclic Compounds as Potent Hepatitis C Virus NS5B RNA Polymerase Inhibitors", Journal of Medicinal Chemistry, vol. 49, No. 24, pp. 6950-6953 (2006).

* cited by examiner

*Primary Examiner* — Brenda Coleman
(74) *Attorney, Agent, or Firm* — James Epperson

(57) ABSTRACT

The invention encompasses compounds of formula I as well as compositions and methods of using the compounds. The compounds have activity against hepatitis C virus (HCV) and are useful in treating those infected with HCV.

3 Claims, No Drawings

COMPOUNDS FOR THE TREATMENT OF HEPATITIS C

CROSS-REFERENCE TO RELATED APPLICATIONS

This application is a Continuation-in-part of U.S. nonprovisional application Ser. No. 12/180,994 filed Jul. 28, 2008 and claims the benefit of U.S. Provisional Application Ser. Nos. 61/049,944 filed May 2, 2008 and 60/954,814 filed Aug. 9, 2007.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

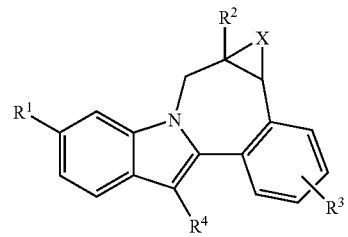

where:

$R^1$ is $CO_2R^5$ or $CONR^6R^7$;

$R^2$ is furanyl, pyrrolyl, thienyl, pyrazolyl, isoxazolyl, isothiazolyl, imidazolyl, oxazolyl, thiazolyl, oxadiazolyl, triazolyl, or tetrazolyl, and is substituted with 0-2 substituents selected from oxo, amino, alkylthio, alkyl, and haloalkyl, and 1 substituent selected from $CO_2R^5$, $CON(R^{12})_2$, and $COR^{13}$;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, $alkylSO_2$, $cycloalkylSO_2$, $haloalkylSO_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, $alkylSO_2$, $cycloalkylSO_2$, $haloalkylSO_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;

$R^{12}$ is hydrogen, alkyl, alkoxyalkyl, aminoalkyl, (alkylamino)alkyl, (dialkylamino)alkyl, or $(R^{11})$alkyl;

$R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from alkyl, alkoxyalkyl, amino, alkylamino, dialkylamino, $R^{11}$, aminoalkyl, (alkylamino)alkyl, (dialkylamino)alkyl, $(R^{11})$alkyl, or $CO_2R^5$;

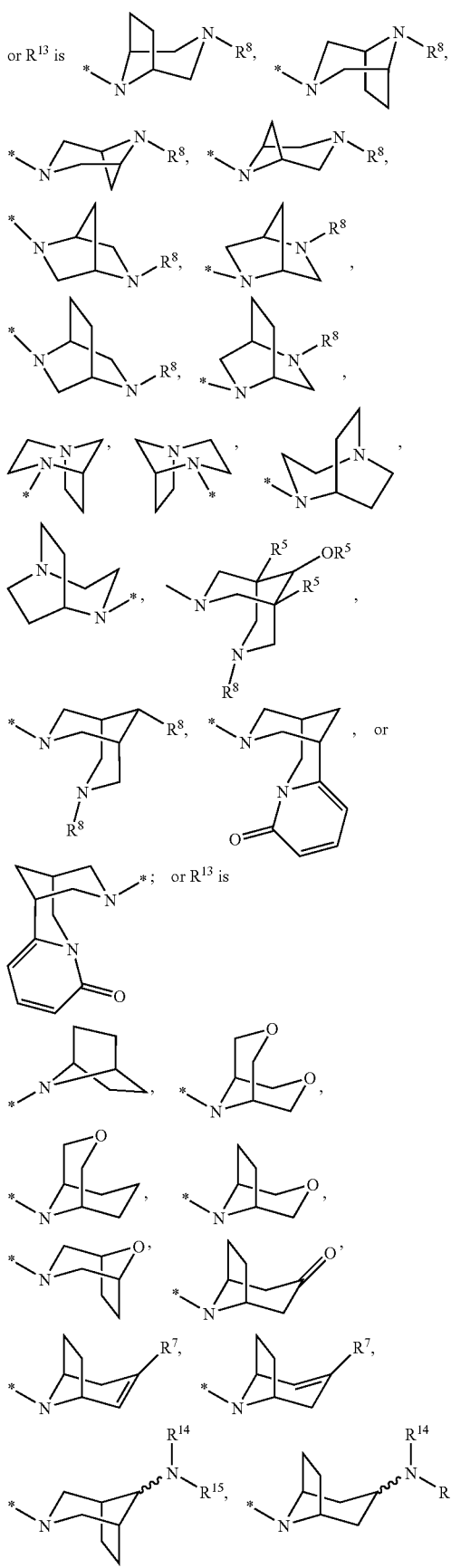

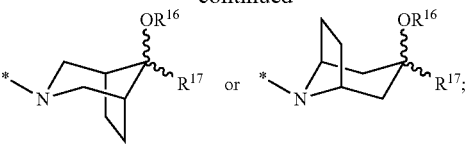

or $R^{13}$ is a [4.3.0] or [3.3.0]bicyclic diamine attached to the carbonyl through one nitrogen, and is substituted with 0-2 $R^8$ substituents;

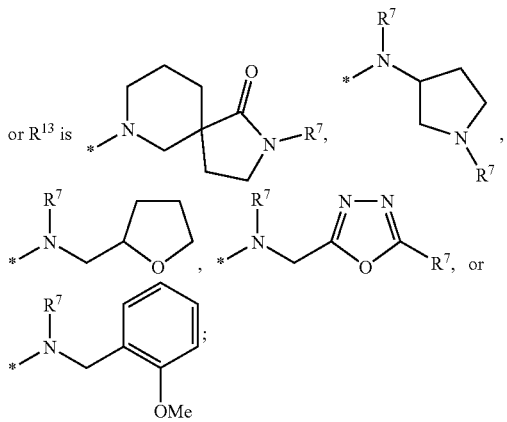

$R^{14}$ is hydrogen, alkyl, cycloalkyl, (cycloalkyl)alkyl, aminoalkyl, (alkylamino)alkyl, (dialkylamino)alkyl, or benzyl;

$R^{15}$ is hydrogen, alkyl, cycloalkyl, (cycloalkyl)alkyl, aminoalkyl, (alkylamino)alkyl, (dialkylamino)alkyl, or benzyl;

or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

$R^{16}$ is hydrogen or alkyl;

$R^{17}$ is hydrogen, alkyl, or cycloalkyl; and

X is methylene, a bond, or absent;

or a pharmaceutically acceptable salt thereof.

Another aspect of the invention is a compound of formula I where:

$R^1$ is $CO_2R^5$ or $CONR^6R^7$;

$R^2$ is furanyl, pyrrolyl, thienyl, pyrazolyl, isoxazolyl, isothiazolyl, imidazolyl, oxazolyl, thiazolyl, oxadiazolyl, triazolyl, or tetrazolyl, and is substituted with 0-2 substituents selected from oxo, amino, alkyl, and haloalkyl, and 1 substituent selected from $CO_2R^5$, $CON(R^{12})_2$, and $COR^{13}$;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkylSO$_2$, cycloalkylSO$_2$, haloalkylSO$_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, morpholinyl, thiomorpholinyl, homopiperidinyl, homopiperazinyl, or homomorpholinyl, and is substituted with 0-1 alkyl substituents;

$R^{12}$ is hydrogen, alkyl, alkoxyalkyl, aminoalkyl, (alkylamino)alkyl, (dialkylamino)alkyl, or $(R^{11})$alkyl;

$R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from alkyl, alkoxyalkyl, amino, alkylamino, dialkylamino, $R^{11}$, aminoalkyl, (alkylamino)alkyl, (dialkylamino)alkyl, $(R^{11})$alkyl, or $CO_2R^5$;

or $R^{13}$ is

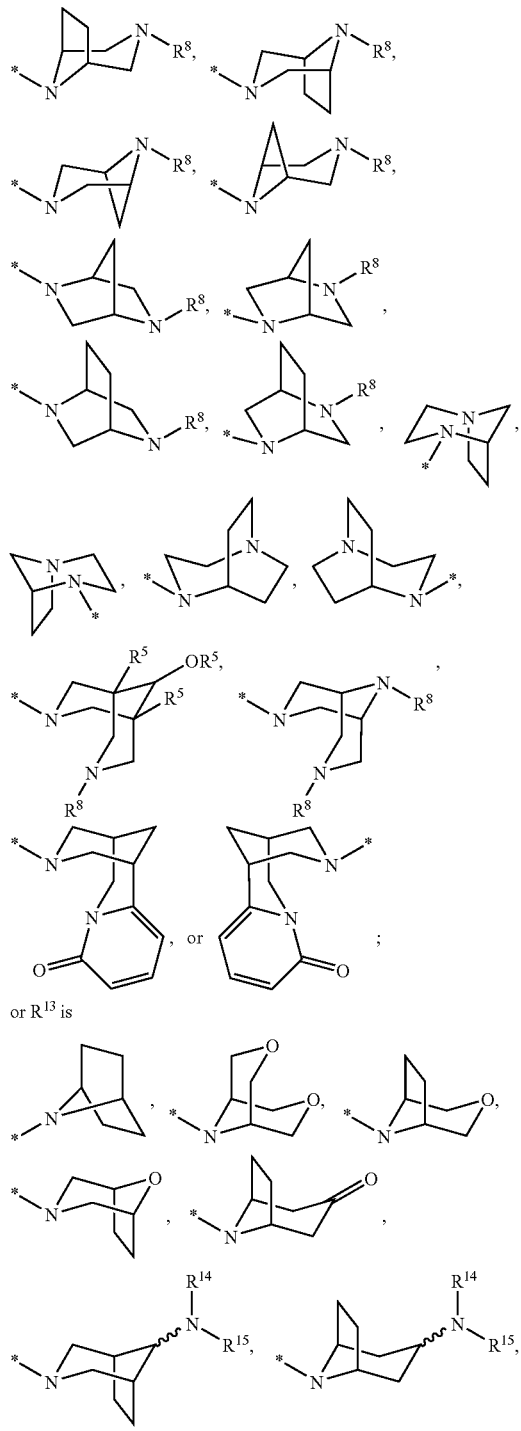

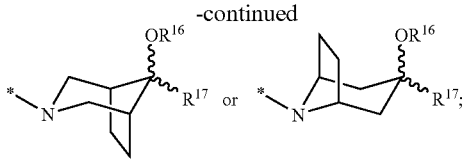

or $R^{13}$ is a [4.3.0] or [3.3.0]bicyclic diamine attached to the carbonyl through one nitrogen, and is substituted with 0-2 $R^8$ substituents;

or $R^{13}$ is

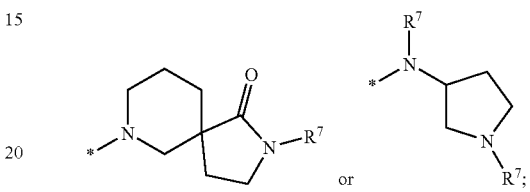

$R^{14}$ is hydrogen, alkyl, cycloalkyl, (cycloalkyl)alkyl, aminoalkyl, (alkylamino)alkyl, (dialkylamino)alkyl, or benzyl;

$R^{15}$ is hydrogen, alkyl, cycloalkyl, (cycloalkyl)alkyl, aminoalkyl, (alkylamino)alkyl, (dialkylamino)alkyl, or benzyl;

or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

$R^{16}$ is hydrogen or alkyl;

$R^{17}$ is hydrogen, alkyl, or cycloalkyl; and

X is methylene, a bond, or absent;

or a pharmaceutically acceptable salt thereof.

Another aspect of the invention is a compound of formula I where:

$R^1$ is $CO_2R^5$ or $CONR^6R^7$;

$R^2$ is furanyl, pyrrolyl, thienyl, pyrazolyl, oxazolyl, thiazolyl, isoxazolyl, isothiazolyl, oxadiazolyl, triazolyl, or tetrazolyl, and is substituted with 0-2 substituents selected from oxo, amino, and alkyl, and 1 substituent selected from $CO_2R^5$, $CON(R^{12})_2$, and $COR^{13}$;

$R^3$ is hydrogen, halo, alkyl, alkenyl, hydroxy, benzyloxy, or alkoxy;

$R^4$ is cycloalkyl;

$R^5$ is hydrogen or alkyl;

$R^6$ is hydrogen, alkyl, alkyl$SO_2$, cycloalkyl$SO_2$, haloalkyl$SO_2$, $(R^9)(R^{10})NSO_2$, or $(R^{11})SO_2$;

$R^7$ is hydrogen or alkyl;

$R^8$ is hydrogen, alkyl, cycloalkyl, (cycloalkyl)alkyl, alkylcarbonyl, cycloalkylcarbonyl, haloalkylcarbonyl, alkoxycarbonyl, alkyl$SO_2$, cycloalkyl$SO_2$, haloalkyl$SO_2$, aminocarbonyl, (alkylamino)carbonyl, (dialkylamino)carbonyl, benzyl, benzyloxycarbonyl, or pyridinyl;

$R^9$ is hydrogen or alkyl;

$R^{10}$ is hydrogen or alkyl;

$R^{11}$ is azetidinyl, pyrrolidinyl, piperidinyl, piperazinyl, N-alkylpiperazinyl, morpholinyl, thiomorpholinyl, homopiperidinyl, homopiperazinyl, or homomorpholinyl;

$R^{12}$ is hydrogen, alkyl, alkoxyalkyl, aminoalkyl, (alkylamino)alkyl, (dialkylamino)alkyl, or $(R^{11})$alkyl;

$R^{13}$ is azetidinyl, pyrrolidinyl, piperidinyl, piperazinyl, morpholinyl, thiomorpholinyl, homopiperidinyl, homopiperazinyl, or homomorpholinyl, and is substituted with 0-3 substituents selected from alkyl, amino, alkylamino, dialkylamino, $R^{11}$, aminoalkyl, (alkylamino)alkyl, (dialkylamino)alkyl, or $(R^{11})$alkyl;

or R¹³ is

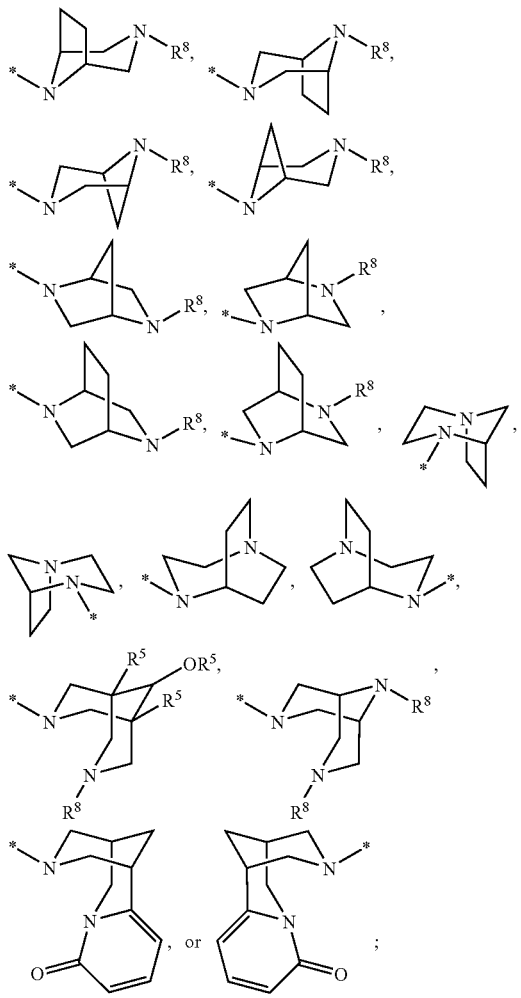

or R¹³ is

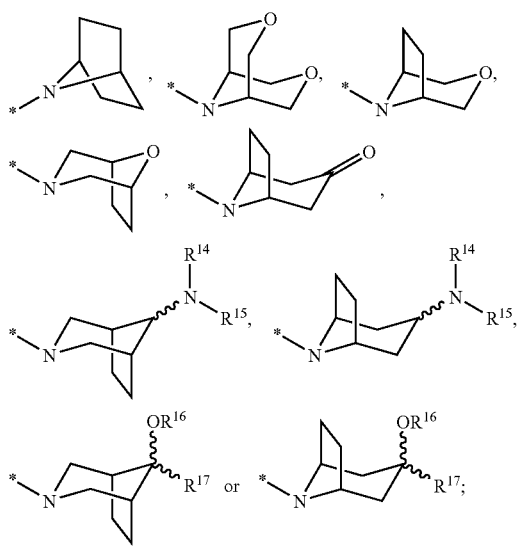

or R¹³ is a [4.3.0] or [3.3.0]bicyclic diamine attached to the carbonyl through one nitrogen, and is substituted with 0-2 R⁸ substituents;

or R¹³ is

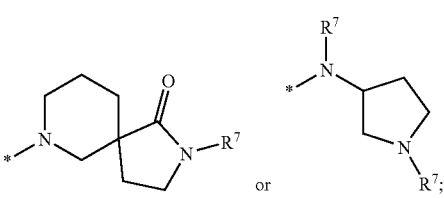

$R^{14}$ is hydrogen, alkyl, cycloalkyl, (cycloalkyl)alkyl, aminoalkyl, (alkylamino)alkyl, (dialkylamino)alkyl, or benzyl;

$R^{15}$ is hydrogen, alkyl, cycloalkyl, (cycloalkyl)alkyl, aminoalkyl, (alkylamino)alkyl, (dialkylamino)alkyl, or benzyl;

or $NR^{14}R^{15}$ taken together is azetidinyl, pyrrolidinyl, piperidinyl, piperazinyl, N-(alkyl)piperazinyl, morpholinyl, thiomorpholinyl, homopiperidinyl, or homomorpholinyl;

$R^{16}$ is hydrogen or alkyl;

$R^{17}$ is hydrogen, alkyl, or cycloalkyl; and

X is methylene, a bond, or absent;

or a pharmaceutically acceptable salt thereof.

Another aspect of the invention is a compound of formula I where $R^1$ is $CONR^6R^7$; $R^6$ is $alkylSO_2$, $cycloalkylSO_2$, $haloalkylSO_2$, $(R^9)_2NSO_2$, or $(R^{10})SO_2$; and $R^7$ is hydrogen.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $alkylSO_2$, $cycloalkylSO_2$, $(R^9)(R^{10})NSO_2$ or $(R^{11})SO_2$.

Another aspect of the invention is a compound of formula I where $R^2$ is pyrazolyl substituted with 2 substituents selected from alkyl and haloalkyl and 1 $COR^{13}$ substituent $R^{13}$ is

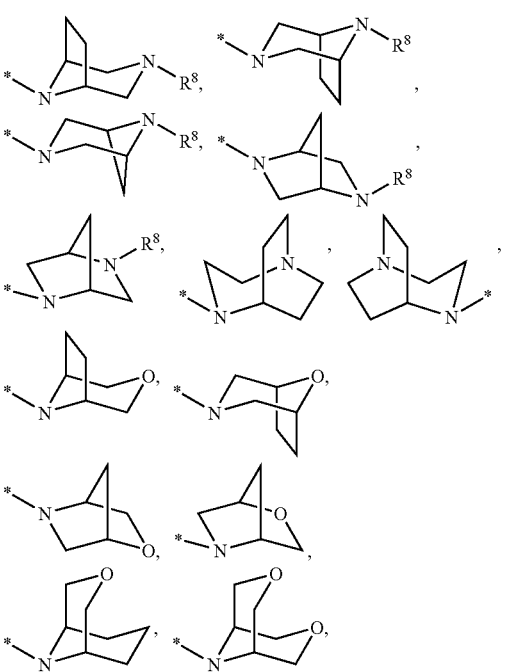

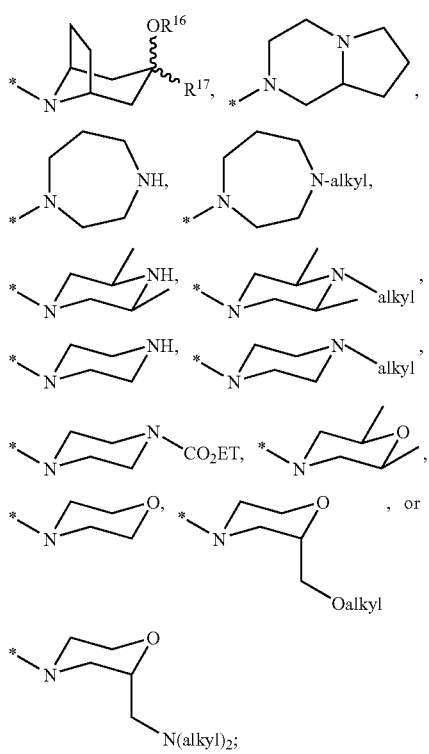

$R^8$ is hydrogen or alkyl; $R^{16}$ is hydrogen or alkyl; and $R^{17}$ is alkyl.

Another aspect of the invention is a compound of formula I where X is methylene.

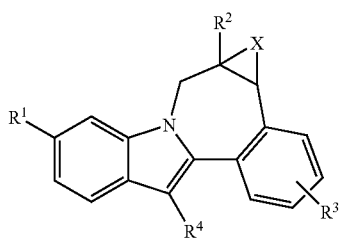

Another aspect of the invention is a compound of formula I where X is a bond.

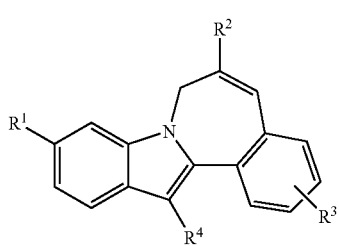

Another aspect of the invention is a compound of formula I where X is absent.

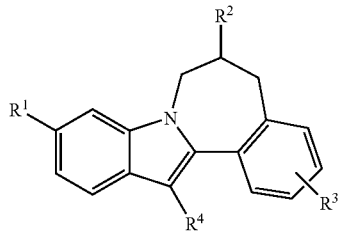

Another aspect of the invention is a compound of formula I according to the following stereochemistry.

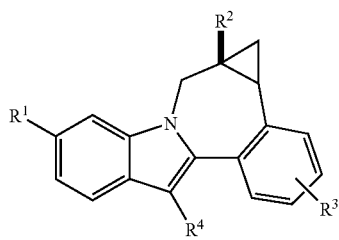

Another aspect of the invention is a compound of formula I according to the following stereochemistry.

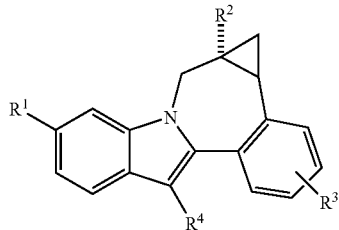

Another aspect of the invention is a compound of formula I according to the following stereochemistry.

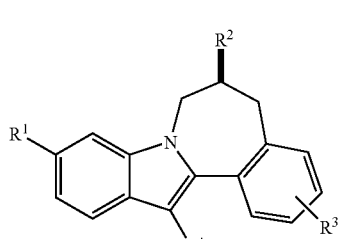

Another aspect of the invention is a compound of formula I according to the following stereochemistry.

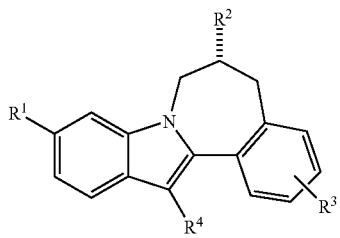

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and X can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the compound below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art.

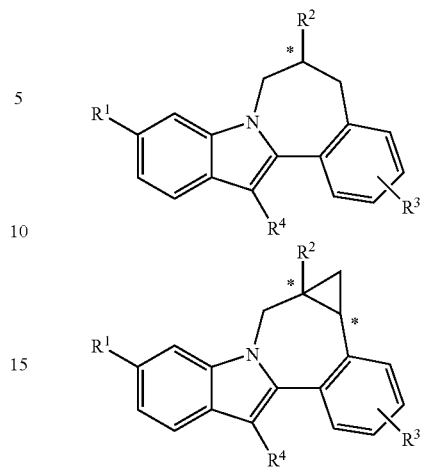

Synthetic Methods

The compounds may be made by methods known in the art including those described below. Some reagents and intermediates are known in the art. Other reagents and intermediates can be made by methods known in the art using available materials. The variables (e.g. numbered "R" substituents) used to describe the synthesis of the compounds are intended only to illustrate how to make the compounds and are not to be confused with variables used in the claims or in other sections of the specification. Abbreviations used within the schemes generally follow conventions used in the art.

The scheme shown below illustrates methods that can be used for making intermediates and compounds.

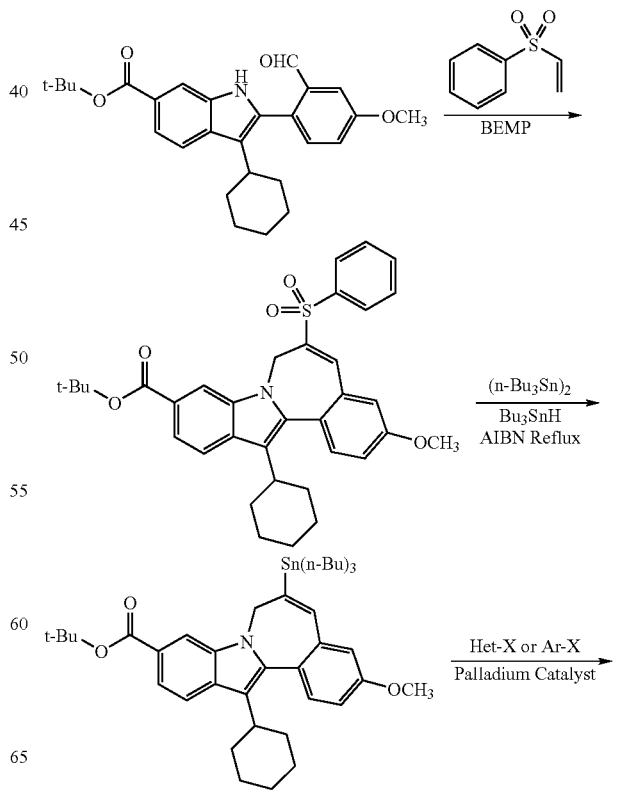

13
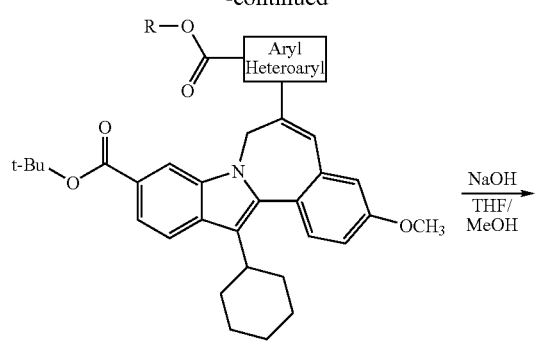
14
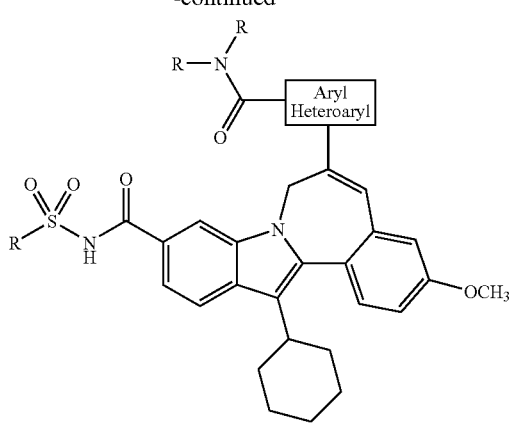
Alternatively, the reaction sequence can be modified as shown below.
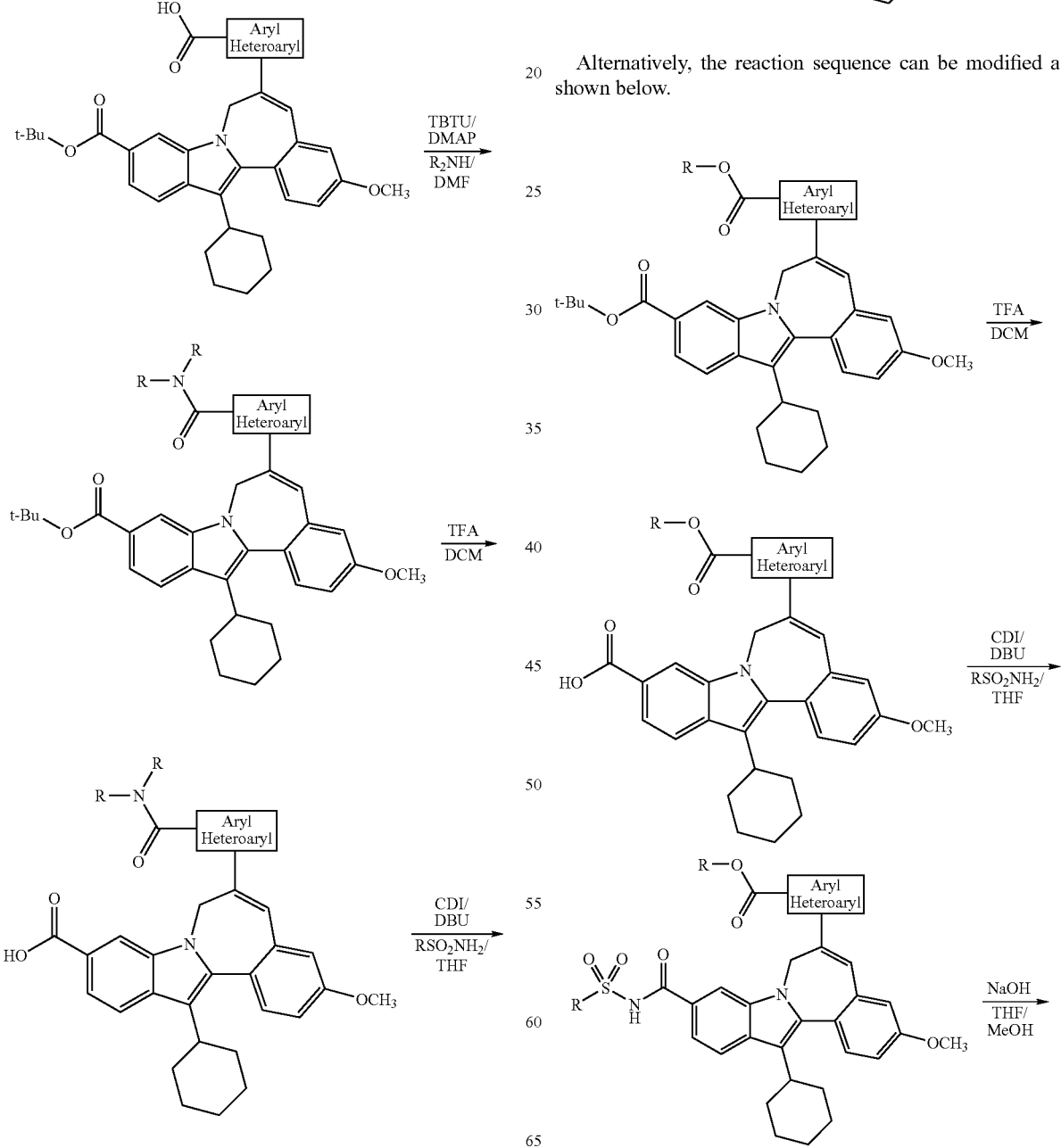

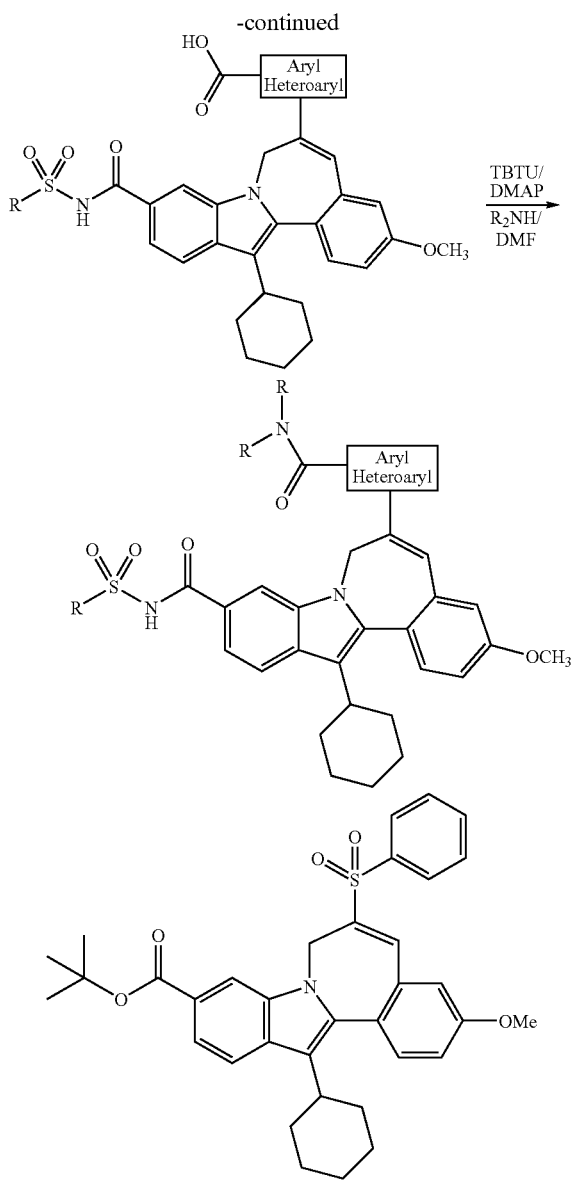

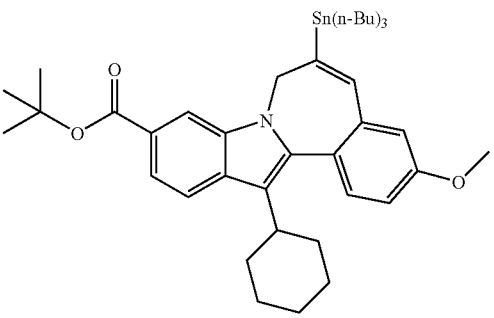

7H-Indolo[2,1-a][2]benzazepine-10-carboxylic acid, 13-cyclohexyl-3-methoxy-6-(phenylsulfonyl)-, tert-butyl ester To a solution of 3-cyclohexyl-2-(2-formyl-4-methoxyphenyl)-1H-indole-6-carboxylate (6.00 g, 13.8 mmol) in dioxane (28.0 mL) and BEMP (7.97 mL, 27.6 mmol) was added phenyl vinyl sulfone (27.6 g, 2.21 mmol). The resulting mixture was stirred in a sealed tube in a microwave at 120° C. for 15 min. The resulting solution was concentrated under reduced pressure. Silica gel chromatography ($CH_2Cl_2$) of the concentrate afforded the title compound 6.36 g (79%) as a yellow oil. MS m/z 584 ($MH^+$). 1H NMR (500 MHz, CHLOROFORM-d) δ ppm 1.18-1.33 (1H, m), 1.34-1.45 (2H, m), 1.49-57 (1H, m), 1.64 (9H, s.), 1.74-1.82 (2H, m), 1.90-2.09 (4H, m), 2.73 (1H, m,), 3.93 (3H, s), 4.38 (1H, broad d), 5.08 (1H, br. d), 7.09 (1H, d, J=2.75 Hz), 7.12-7.18 (3H, m), 7.22 (1H, d, J=7.45 Hz), 7.30 (1H, s), 7.48 (1H, d, J=8.85 Hz), 7.54 (1H, dd, J=8.55, 1.22 Hz), 7.61 (2H, m), 7.67 (1H, d, J=8.55), 8.01 (1H, s).

7H-indolo[2,1-a][2]benzazepine-10-carboxylic acid, 13-cyclohexyl-3-methoxy-6-(tributylstannyl)-, 1,1-dimethylethyl ester. 1,1-dimethylethyl 13-cyclohexyl-3-(methyloxy)-6-(tributylstannanyl)-7H-indolo[2,1-a][2]benzazepine-10-carboxylate. 7H-indolo[2,1-a][2]benzazepine-10-carboxylic acid, 13-cyclohexyl-3-methoxy-6-(phenylsulfonyl)-, 1,1-dimethylethyl ester (1.00 g, 1.71 mMol) was dissolved in 26 mL of benzene along with bis (tributyltin) (2.8 mL, 5.54 mMol), tributyltin hydride (136 uL, 0.513 mMol) and triethylamine (1.05 mL, 7.5 mMol). The solution was sparged for approximately for 10 minutes with nitrogen then 2,2'-bisazoisobutyronitrile (AIBN) (96 mg, 0.58 mMol) added to the reaction. The reaction was heated to reflux under nitrogen for 2 hr. The reaction was followed by LC-MS using the following HPLC conditions: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7. To the reaction was added tributyltin hydride (0.45 mL, 1.7 mMol) and AIBN (95 mg, 0.58 mMol), the reaction heated to reflux for 2 hrs, and analyzed for progress. AIBN (99 mg, 0.60 mMol) added to the reaction and the reaction heated to reflux under for an additional 6 hrs using a timer. The reaction was analyzed by LC-MS for progress then tributyltin hydride (1.0 ml, 3.8 mMol) and AIBN (97 mg, 0.59 mMol) was added and the reaction heated to reflux for 2 hrs 20 min. The reaction was analyzed by LC-MS and AIBN (97 mg, 0.59 mMol) added to the reaction. The reaction was heated for 1 hr under nitrogen at reflux and the cooled and analyzed by LC-MS. Volatiles were removed in vacuo from the reaction and the reaction was purified by column chromatography using a $C_{18}$ packing of 190 g of YMC GEL ODS-A, 120 A spherical 75 uM. The reaction residue (6.67 g of yellow oil) was dissolved in a minimum of dichloromethane and the solution applied onto the reverse phase column packed in 10% dichloromethane in acetonitrile. Initial elution was done using 10% dichloromethane in acetonitrile followed by elution with 15% dichloromethane in acetonitrile. The chromatography was monitored by TLC using Whatman MKC18F reverse phase 1"×3" 200 uM thickness TLC plates eluting using 15% dichloromethane in acetonitrile. Compound observation was accomplished by UV lamp at 254 nm and iodine staining of TLC plates. Product fractions were collected and volatiles removed in vacuo to yield 647 mg (52%) as a pale yellow foam. 1H NMR (500 MHz, CHLOROFORM-D) δ ppm 0.71-0.83 (m, 9H) 0.85-0.96 (m, 3H) 0.95-1.08 (m, 6H) 1.15-1.27 (m, 7H) 1.27-1.49 (m, 11H) 1.53 (s, 5H) 1.60-1.67 (m, 9H) 1.68-1.82 (m, 2H) 1.84-1.96 (m, 1H) 1.96-2.16 (m, 3H) 2.74-2.91 (m, 1H) 3.90 (s, 3H) 4.16-4.40 (m, 1H) 4.82-5.03 (m, 1H) 6.72-6.90 (m, 2H) 6.96 (dd, J=8.55, 2.44 Hz, 1H) 7.43 (d, J=8.55 Hz, 1H) 7.66 (dd, J=8.39, 1.37 Hz, 1H) 7.81 (d, J=8.55 Hz, 1H) 8.04 (s, 1H) LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=10 min; Flow rate=5 ml/min; Wavelength=220 nm; Column=Waters Xterra, 3 mm×50 mm, S7. Retention Time=4.2 min, MS m/z 734 (MH+).

7H-indolo[2,1-a][2]benzazepine-10-carboxylic acid, 13-cyclohexyl-3-methoxy-6-(tributylstannyl)-, 1,1-dimethylethyl ester 1,1-dimethylethyl 13-cyclohexyl-3-(methyloxy)-6-(tributylstannanyl)-7H-indolo[2,1-a][2]benzazepine-10-carboxylate An assembly of a three necked flask fitted with an argon bubbler, reflux condenser and dropping funnel was flame dried and then cooled under a stream of argon. The flask was then charged with benzene (5 mL) and 7H-indolo[2,1-a][2]benzazepine-10-carboxylic acid, 13-cyclohexyl-3-methoxy-6-(phenylsulfonyl)-, 1,1-dimethylethyl ester 1 (500 mg, 0.857 mmol). The resultant mixture was sonicated under argon for 5 min (to remove oxygen) and then heated under reflux. A solution of tri-N-butyltin hydride (0.459 ml, 1.713 mmol) and 2,2'-azobis(2-methylpropionitrile (52.0 mg, 0.317 mmol) in degassed benzene (5 mL) was then added to the dropping funnel. Approximately 2.5 mL of this solution was added dropwise over a period of approximately 30 min, and the resultant solution was left to stir under reflux for 1.5 h. The remaining solution was added dropwise, slowly over a period of approximately 30 min, and heating was continued for a further 1.5 h. The mixture was then evaporated under reduced pressure to remove volatiles. The residue was slurried in hexane and applied to a silica gel biotage cartridge and then loaded onto a silica gel column equilibrated in 100% hexanes. The product was then eluted using a step gradient of ethyl acetate-hexane: 0-100%, then 2-98%, then 5-95%. Homogeneous fractions were combined and evaporated to give yellow oil. This was placed under high vacuum overnight to give the title compound as a viscous yellow colored oil. [373 mg, 57%]. The product was stored under nitrogen in a refrigerator.

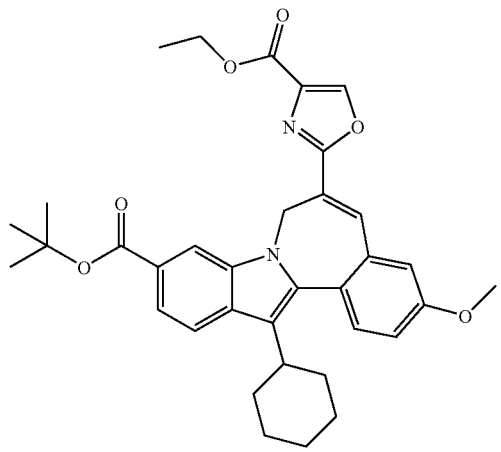

tert-butyl 13-cyclohexyl-6-(4-(ethoxycarbonyl)-1,3-oxazol-2-yl)-3-methoxy-7H-indolo[2,1-a][2]benzazepine-10-carboxylate 1,1-dimethylethyl 13-cyclohexyl-3-(methyloxy)-6-(tributylstannanyl)-7H-indolo[2,1-a][2]benzazepine-10-carboxylate (266 mg, 0.36 mMol) was dissolved in 3.4 mL of 1,4-dioxane in a 2 dram vial. Ethyl 2-chlorooxazole-4-carboxylate (83.4 mg, 0.47 mMol) was dissolved in the reaction followed by the addition of bis(triphenylphosphine)palladium(II) chloride (17.7 mg, 0.025 mMol). The reaction was capped under nitrogen and heated in an oil bath at 100 C for 17 hrs, after which the reaction was cooled and the reaction progress was measured by LC-MS. To the reaction mixture was added bis(triphenylphosphine)palladium(II) chloride (10 mg, 0.014 mMol). The reaction was capped under nitrogen and heated for an additional 5 hrs at 100 C. The reaction was concentrated in vacuo and the residue adsorbed onto silica gel purified by silica gel chromatography eluting with a gradient of dichloromethane to 2% ethyl acetate in dichloromethane to yield 233 mg of a yellow solid product. 1H NMR (500 MHz, CHLOROFORM-D) δ ppm 1.13-1.37 (m, 4H) 1.37-1.44 (m, 4H) 1.46-1.55 (m, 1H) 1.64 (s, 9H) 1.68-1.81 (m, 2H) 1.83-1.98 (m, 3H) 1.98-2.13 (m, 3H) 2.74-2.88 (m, 1H) 3.91 (s, 3H) 4.34-4.48 (m, 3H) 5.84-6.00 (m, 1H) 7.00 (d, J=2.44 Hz, 1H) 7.08 (dd, J=8.55, 2.75 Hz, 1H) 7.53 (d, J=8.85 Hz, 1H) 7.69 (dd, J=8.55, 1.22 Hz, 1H) 7.74 (s, 1H) 7.82 (d, J=8.24 Hz, 1H) 8.21 (s, 1H) 8.30 (s, 1H); LC-MS: Shimadzu Analytical HPLC using Discovery VP software: % A=10% methanol, 90% water, 0.1% trifluoroacetic acid % B=90% methanol, 10% water, 0.1% trifluoroacetic acid; Initial % B=0; Final % B=100; Gradient=3 min; Runtime=5 min; Flow rate=5 ml/min; Wavelength=220 nm; Column=Phenomenex Luna 3.0 mm×50 mm S10; Retention Time=3.4 min, MS m/z 583 (MH+).

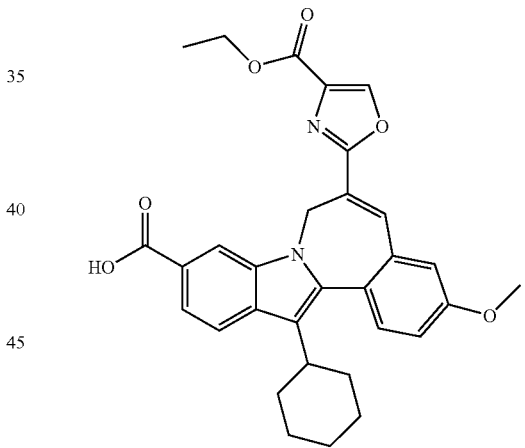

7H-indolo[2,1-a][2]benzazepine-10-carboxylic acid, 13-cyclohexyl-6-[4-(ethoxycarbonyl)-2-oxazolyl]-3-methoxytert-butyl 13-cyclohexyl-6-(4-(ethoxycarbonyl)-1,3-oxazol-2-yl)-3-methoxy-7H-indolo[2,1-a][2]benzazepine-10-carboxylate (109 mg, 0.19 mMol) was dissolved in 2 mL of 1,2-dichloroethane and 2 mL of trifluoroacetic acid added to the reaction. The reaction was stirred at room temperature for 1.5 hrs. Volatiles were removed and the product dried in vacuo to yield 102 mg of a yellow solid. 1H NMR (500 MHz, CHLOROFORM-D) δ ppm 1.11-1.37 (m, 4H) 1.42 (t, J=7.02 Hz, 4H) 1.48-1.62 (m, 1H) 1.77 (d, J=10.07 Hz, 2H) 1.86-2.13 (m, 4H) 2.73-2.90 (m, 1H) 2.98-3.39 (m, 6H) 3.92 (s, 3H) 4.30-4.53 (m, 3H) 5.87-6.03 (m, 1H) 7.02 (d, J=2.44 Hz, 1H) 7.09 (dd, J=8.70, 2.59 Hz, 1H) 7.75 (s, 1H) 7.79 (dd, J=8.39, 1.37 Hz, 1H) 7.88 (d, J=8.55 Hz, 1H) 8.24 (s, 1H) 8.50 (s, 1H); LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=2 min; Runtime=3 min; Flow rate=5 ml/min; Wavelength=220 nm; Column=Phenomenex Luna 3.0 mm×50 mm S10; Retention Time=1.7 min, MS m/z 525 (MH$^-$).

1H) 7.10 (dd, J=8.70, 2.59 Hz, 1H) 7.45-7.65 (m, 2H) 7.71 (s, 1H) 7.89 (d, J=8.55 Hz, 1H) 8.20 (s, 1H) 8.29 (s, 1H) 9.36 (s, 1H); LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=2 min; Runtime=4 min; Flow rate=5 ml/min; Wavelength=220 nm; Column=Phenomenex Luna 3.0 mm×50 mm S10; Retention Time=1.9 min, MS m/z 631 (MH$^-$), m/z 633 (MH$^+$).

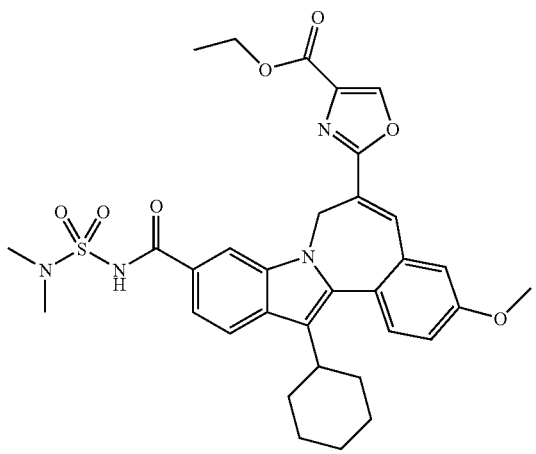

Ethyl 2-(13-cyclohexyl-10-(((dimethylamino)sulfonyl)carbamoyl)-3-methoxy-7H-indolo[2,1-a][2]benzazepin-6-yl)-1,3-oxazole-4-carboxylate

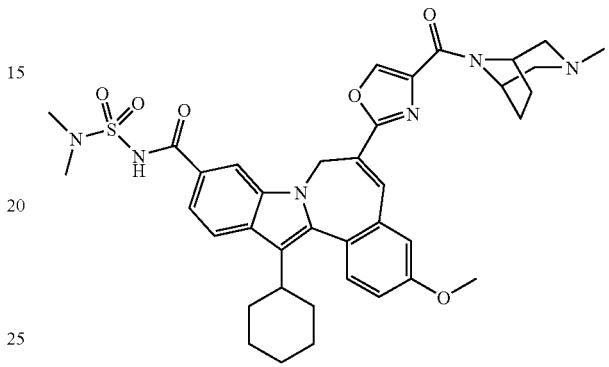

13-cyclohexyl-N-((dimethylamino)sulfonyl)-3-methoxy-6-(4-((3-methyl-3,8-diazabicyclo[3.2.1]oct-8-yl)carbonyl)-1,3-oxazol-2-yl)-7H-indolo[2,1-a][2]benzazepine-10-carboxamide Ethyl 2-(13-cyclohexyl-10-(((dimethylamino)sulfonyl)carbamoyl)-3-methoxy-7H-indolo[2,1-a][2]benzazepin-6-yl)-1,3-oxazole-4-carboxylate. 7H-indolo[2,1-a][2]benzazepine-10-carboxylic acid, 13-cyclohexyl-6-[4-(ethoxycarbonyl)-2-oxazolyl]-3-methoxy- (115 mg, 0.22 mMol) was dissolved in 3 ml of anhydrous THF and 1,1'-carbonyldiimidazole (61 mg, 0.38 mMol) added to the reaction. The reaction was stirred under nitrogen for 1 hr 20 min at room temperature then heated to reflux under nitrogen for 45 minutes. The reaction was cooled and dimethylsulfamide (186 mg, 1.49 mMol) was added to the reaction followed by 1,8-diazabicyclo[5.4.0]undec-7-ene (39 uL, 0.26 mMol) (DBU). The reaction was heated at 55 C for 16 hrs under nitrogen. The reaction was partitioned between dichloromethane and 0.1M monosodium phosphate. The dichloromethane extract was washed with 0.1M monosodium phosphate then dried over sodium sulfate. Volatiles were removed in vacuo to yield 167 mg of crude yellow product. One-half of the crude sample was dissolved in a mixture of acetonitrile and methanol and purified by reverse phase prep HPLC under the following conditions: Shimadzu preparative HPLC using Discovery VP software: % A=10% acetonitrile, 90% water, 0.1% TFA % B=90% acetonitrile, 10% water, 0.1% TFA; Initial % B=50; Final % B=100; Gradient=12 min; Runtime=17 min; Flow rate=25 ml/min; Wavelength=220 nm; Column=Waters Sunfire 19 mm×100 mm. Product retention time=12.25 min to 17 min (tailing due to solubility). Obtained 25.2 mg of amorphous yellow solid. 1H NMR (500 MHz, CHLOROFORM-D) δ ppm 1.18-1.30 (m, 2H) 1.34-1.46 (m, 5H) 1.47-1.62 (m, 1H) 1.70-1.85 (m, 2H) 1.86-2.21 (m, 4H) 2.72-2.92 (m, 1H) 3.07 (s, 6H) 3.92 (s, 3H) 4.08-4.34 (m, 2H) 4.41 (q, J=7.22 Hz, 3H) 5.75-5.99 (m, 1H) 7.02 (d, J=2.75 Hz, Ethyl 2-(13-cyclohexyl-10-(((dimethylamino)sulfonyl) carbamoyl)-3-methoxy-7H-indolo[2,1-a][2]benzazepin-6-yl)-1,3-oxazole-4-carboxylate (35.7 mg, 0.056 mMol) was dissolved in 0.6 ml of THF in a 2 dram vial. Tetrabutylammonium hydroxide (170 uL, 0.17 mMol) as a 1M solution in methanol was added to the reaction. The reaction was capped and stirred for 3 hrs at room temperature. The reaction was partitioned between 1N hydrochloric acid and dichloromethane. The organic phase was washed with 1N hydrochloric acid and dried over sodium sulfate. The material was concentrated to dryness, dried in vacuo and used without further purification. The hydrolysis product (0.056 mMol) was dissolved in 1 mL of DMF and TBTU (39 mg, 0.12 mMol) added. The reaction was stirred at room temperature under nitrogen for approximately 50 minutes then add DMAP (37.9 mg, 0.31 mMol) was added followed by 3-methyl-3,8-diaza-bicyclo[3.2.1]octane dihydrochloride (23 mg, 0.11 mMol). The reaction was stirred for 4 hrs at room temperature under nitrogen atmosphere until complete, then added to 20 mL of water and extracted with dichloromethane, washed organic layer with water and dry over sodium sulfate to yield 50 mg of crude product. The product was purified by Prep HPLC under the following conditions: Shimadzu preparative HPLC using Discovery VP software: % A=10% acetonitrile, 90% water, 0.1% TFA % B=90% acetonitrile, 10% water, 0.1% TFA; Initial % B=30; Final % B=100; Gradient=12 min; Runtime=20 min; Flow rate=25 ml/min; Wavelength=220 nm; Column=Waters Sunfire 19 mm×100 mm. Product retention time=6.1 min. Product fractions were concentrated in vacuo to yield 30.5 mg of the title compound as a trifluoroacetic acid salt. 1H NMR (500 MHz, CHLOROFORM-D) δ ppm 1.09-1.30 (m, 1H) 1.31-1.61 (m, 3H) 1.68-1.85 (m, 2H) 1.87-2.20 (m, 5H) 2.26-2.44 (m, 2H) 2.51-2.66 (m, 1H) 2.77-2.90 (m, 1H) 2.91-3.01 (m, 3H) 3.04 (s, 6H)

3.12 (d, J=11.90 Hz, 1H) 3.23 (d, J=11.60 Hz, 1H) 3.78 (d, J=12.21 Hz, 1H) 3.94 (s, 3H) 4.24 (d, J=13.12 Hz, 1H) 4.43 (d, J=14.34 Hz, 1H) 5.01 (d, J=5.80 Hz, 1H) 5.13-5.47 (m, 1H) 5.85 (d, J=14.04 Hz, 1H) 6.02 (s, 1H) 7.03 (d, J=2.75 Hz, 1H) 7.12 (dd, J=8.70, 2.59 Hz, 1H) 7.25-7.32 (m, 1H) 7.56 (d, J=8.55 Hz, 1H) 7.69 (s, 1H) 7.88 (d, J=8.24 Hz, 1H) 8.18 (s, 1H) 8.28 (s, 1H) 8.52 (s, 1H) 11.72 (s, 1H); LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=2 min; Runtime=3 min; Flow rate=5 ml/min; Wavelength=220 nm; Column=Phenomenex Luna 3.0 mm×50 mm S10 Retention Time=1.7 min, MS m/z 711 (MH⁻), m/z 713 (MH⁺).

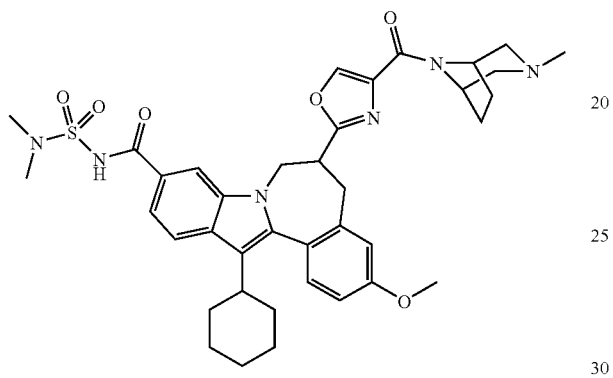

13-Cyclohexyl-N-((dimethylamino)sulfonyl)-3-methoxy-6-(4-((3-methyl-3,8-diazabicyclo[3.2.1]oct-8-yl)carbonyl)-1,3-oxazol-2-yl)-6,7-dihydro-5H-indolo[2,1-a][2]benzazepine-10-carboxamide 13-Cyclohexyl-N-((dimethylamino)sulfonyl)-3-methoxy-6-(4-((3-methyl-3,8-diazabicyclo[3.2.1]oct-8-yl)carbonyl)-1,3-oxazol-2-yl)-7H-indolo[2,1-a][2]benzazepine-10-carboxamide (26.5 mg, 0.037 mMol) was dissolved in 1 mL of THF and 0.3 mL of methanol added followed by 10 mg of 10% palladium on carbon. The reaction was placed under hydrogen at 1 atmosphere (balloon) and stirred for 18 hrs at room temperature. The reaction was filtered through a celite plug and rinsed with acetonitrile. Volatiles were removed from the filtrate in vacuo and the residue was dissolved in acetonitrile and purified by Prep HPLC under the following conditions: Shimadzu preparative HPLC using Discovery VP software: % A=10% acetonitrile, 90% water, 0.1% TFA % B=90% acetonitrile, 10% water, 0.1% TFA; Initial % B=30; Final % B=100; Gradient=12 min; Runtime=17 min; Flow rate=25 ml/min; Wavelength=220 nm; Column=Waters Sunfire 19 mm×100 mm. Product retention time=5.3 minutes. The title compound was isolated as a TFA salt, 17.6 mg obtained. 1H NMR (500 MHz, CHLOROFORM-D) δ ppm 1.20-1.33 (m, 1.1H) 1.33-1.54 (m, 2.1H) 1.65 (t, J=10.99 Hz, 1.1H) 1.74-1.86 (m, 1.9H) 1.89-2.11 (m, 5.6H) 2.11-2.44 (m, 3.0H) 2.71-2.86 (m, 3.2H) 2.87-2.98 (m, 2.9H) 2.98-3.10 (m, 7.7H) 3.08-3.45 (m, 6.1H) 3.72-3.83 (m, 0.9H) 3.82-3.93 (m, 3.1H) 3.92-4.00 (m, 0.8H) 4.05 (dd, J=14.80, 5.65 Hz, 0.8H) 4.55-5.12 (m, 2.6H) 5.60 (d, J=12.82 Hz, 0.3H) 6.64-7.12 (m, 2.0H) 7.29-7.62 (m, 1.8H) 7.77-7.97 (m, 1.2H) 7.97-8.43 (m, 1.2H) 8.55-9.33 (m, 0.7H) 11.70 (s, 0.5H). LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=5 min; Flow rate=5 ml/min; Wavelength=220 nm; Column=Gemini 4.6 mm×50 mm S5; Retention Time=2.2 min, MS m/z 715 (MH⁺), m/z 713 (MH⁻).

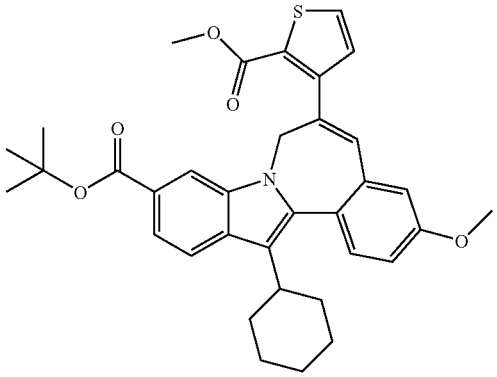

7H-indolo[2,1-a][2]benzazepine-10-carboxylic acid, 13-cyclohexyl-3-methoxy-6-[2-(methoxycarbonyl)-3-thienyl]-, 1,1-dimethylethyl ester. 7H-indolo[2,1-a][2]benzazepine-10-carboxylic acid, 13-cyclohexyl-3-methoxy-6-(tributylstannyl)-, 1,1-dimethylethyl ester (140 mg, 0.19 mMol) was dissolved in 2 mL of 1,4-dioxane along with methyl 3-bromothiophene-2-carboxylate (79 mg, 0.36 mMol) in a 2 dram vial. To the reaction was added bis(triphenylphosphine)palladium dichloride (9.2 mg, 0.013 mMol). The reaction was capped under a nitrogen atmosphere and heated to 100 C for 4.5 hrs. The reaction was cooled and filtered through a 0.45 uM nylon syringe filter and the volatiles removed in vacuo to yield 226 mg of a yellow oil. The title compound was purified by silica gel chromatography eluting with 30% hexanes in dichloromethane to yield 73 mg (66%) of product. 1H NMR (500 MHz, CHLOROFORM-D) δ ppm 0.92 (t, J=7.32 Hz, 2H) 1.24-1.44 (m, 6H) 1.57 (s, 9H) 1.58-1.71 (m, 2H) 1.77 (d, J=8.85 Hz, 2H) 1.85-1.99 (m, 1H) 2.00-2.17 (m, 3H) 2.83-2.93 (m, 1H) 3.82 (s, 3H) 3.88 (s, 3H) 4.71 (s, 1H) 5.10 (s, 1H) 6.80 (s, 1H) 6.83 (d, J=4.88 Hz, 1H) 6.90 (d, J=2.75 Hz, 1H) 7.01 (dd, J=8.55, 2.75 Hz, 1H) 7.40 (d, J=5.19 Hz, 1H) 7.51 (d, J=8.85 Hz, 1H) 7.63 (dd, J=8.55, 1.22 Hz, 1H) 7.82 (d, J=8.55 Hz, 1H) 7.88 (s, 1H); LC-MS: Shimadzu Analytical HPLC using Discovery VP software: % A=10% methanol, 90% water, 0.1% trifluoroacetic acid % B=90% methanol, 10% water, 0.1% trifluoroacetic acid; Initial % B=0; Final % B=100; Gradient=2 min; Runtime=5 min; Flow rate=5 ml/min; Wavelength=220 nm; Column=Phenomenex Luna 3.0 mm×50 mm S10; Retention Time=2.95 min, MS m/z 584 (MH⁺).

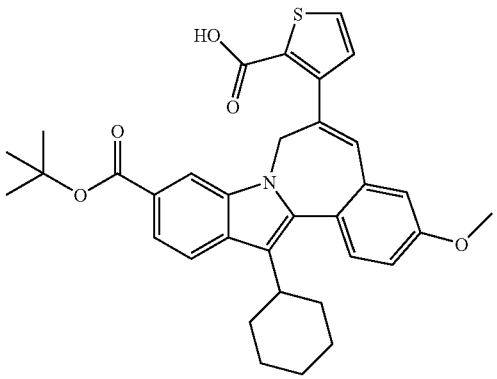

7H-indolo[2,1-a][2]benzazepine-10-carboxylic acid, 6-(2-carboxy-3-thienyl)-13-cyclohexyl-3-methoxy-, 10-(1,1-dimethylethyl) ester 7H-indolo[2,1-a][2]benzazepine-10-carboxylic acid, 13-cyclohexyl-3-methoxy-6-[2-(methoxycarbonyl)-3-thienyl]-, 1,1-dimethylethyl ester (65 mg, 0.11 mMol) was dissolved in 1 mL of THF in a 2 dram vial. To this solution was added 1.0M tetrabutylammonium hydroxide (0.33 mL, 0.33 mMol) in methanol. The reaction was capped and stirred at room temperature for 3 hrs then monitored by HPLC. Additional 1.0M tetrabutylammonium hydroxide (0.10 mL, 0.1 mMol) in methanol was added to the reaction and the reaction stirred capped at room temperature for an additional 21 hrs. The reaction was partitioned between dichloromethane and 0.1M citric acid. The aqueous phase was extracted with dichloromethane and the organic extracts were combined and dried over sodium sulfate. Volatiles were removed in vacuo to yield 72 mg of crude product. LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=5 min; Flow rate=5 ml/min; Wavelength=220 nm; Column=Phenomenex Luna 3.0 mm×50 mm S10; Retention Time=2.50 min, MS m/z 570 (MH$^+$).

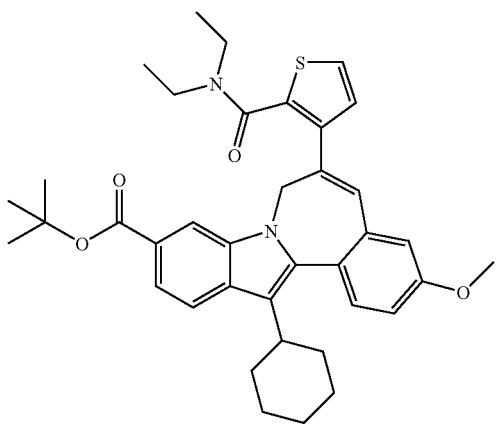

7H-indolo[2,1-a][2]benzazepine-10-carboxylic acid, 13-cyclohexyl-6-[2-[(diethylamino)carbonyl]-3-thienyl]-3-methoxy-, 1,1-dimethylethyl ester 7H-indolo[2,1-a][2]benzazepine-10-carboxylic acid, 6-(2-carboxy-3-thienyl)-13-cyclohexyl-3-methoxy-, 10-(1,1-dimethylethyl) ester (36 mg, 0.063 mMol) was dissolved in 0.7 mL of anhydrous DMF and TBTU (36.5 mg, 0.114 mMol) added to the reaction. The reaction was capped under nitrogen and stirred at room temperature for 1.5 hrs. DMAP (29 mg, 0.24 mMol) was then dissolved in the reaction then diethyl amine (26 uL, 0.25 mMol) added. The reaction was capped under a nitrogen atmosphere and stirred for 21 hrs at room temperature. The reaction was added to 15 mL of water and the aqueous suspension extracted with dichloromethane. The organic phase was washed sequentially with 0.1M citric acid, water and dried over sodium sulfate, filtered and volatiles removed in vacuo to yield a amber oil. LC-MS: Shimadzu Analytical HPLC using Discovery VP software: % A=10% methanol, 90% water, 0.1% trifluoroacetic acid % B=90% methanol, 10% water, 0.1% trifluoroacetic acid; Initial % B=50; Final % B=100; Gradient=5 min; Runtime=6 min; Flow rate=5 ml/min; Wavelength=220 nm; Column=Phenomenex Luna 3.0 mm×50 mm S10; Retention Time=4.64 min, MS m/z 625 (MH$^+$), 647 (M+Na)$^+$.

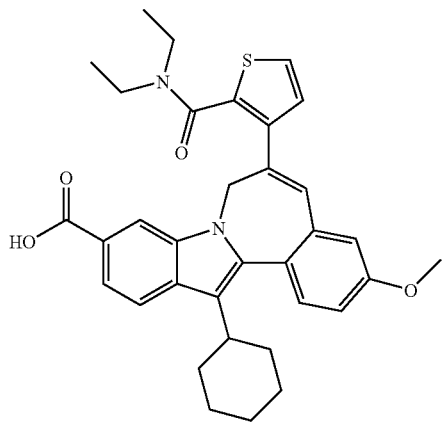

7H-indolo[2,1-a][2]benzazepine-10-carboxylic acid, 13-cyclohexyl-6-[2-[(diethylamino)carbonyl]-3-thienyl]-3-methoxy-. 7H-indolo[2,1-a][2]benzazepine-10-carboxylic acid, 13-cyclohexyl-6-[2-[(diethylamino)carbonyl]-3-thienyl]-3-methoxy-, 1,1-dimethylethyl ester (39 mg, 0.06 mMol) was dissolved in 1 mL of 1,2-dichloroethane and 1 mL of trifluoroacetic acid was added. The reaction was stirred at room temperature for 2 hrs then volatiles were removed in vacuo. The reaction product was repeatedly dissolved in benzene and volatiles removed in vacuo to aid in the removal of residual TFA. Weight of product was 39 mg as an amorphous solid. LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=5 min; Flow rate=5 ml/min; Wavelength=220 nm; Column=Phenomenex Luna 3.0 mm×50 mm S10; Retention Time=2.31, MS m/z 569 (MH$^+$).

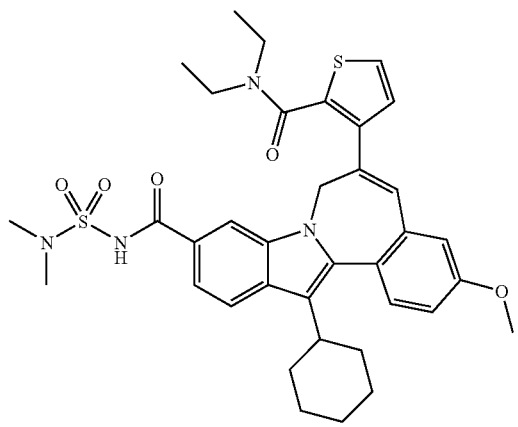

7H-indolo[2,1-a][2]benzazepine-10-carboxamide, 13-cyclohexyl-6-[2-[(diethylamino)carbonyl]-3-thienyl]-N-[(dimethylamino)sulfonyl]-3-methoxy-. 7H-indolo[2,1-a][2]benzazepine-10-carboxylic acid, 13-cyclohexyl-6-[2-[(diethylamino)carbonyl]-3-thienyl]-3-methoxy- (36.7 mg, 0.064 mmol) was dissolved in THF (1 ml) and carbonyldiimidazole (19 mg, 0.117 mmol) added to the reaction. The reaction was stirred under a nitrogen atmosphere at room temperature for 1.5 hours. The reaction was then heated to 60 C for 1.5 hours, then cooled and dimethylsulfamide (55 mg, 0.444 mmol) was added to the reaction followed by DBU (13.3 uL, 0.089 mmol). The reaction was capped under a nitrogen atmosphere and heated at 65 C to 70 C overnight. The reaction was cooled then partitioned between dichloromethane and 1N aqueous hydrochloric acid. The aqueous phase was back extracted with dichloromethane and the organic layers combined and washed sequentially with 1N aqueous hydrochloric acid, aqueous 0.1M NaH2PO4. The dichloromethane phase was dried over sodium sulfate, filtered and volatiles removed in vacuo to yield 47 mg of brown film. The sample was dissolved in acetonitrile/DMF (1:1) and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 50 solvent A/50% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. Solvent was removed from the product fraction in vacuo to yield 18.1 mg of an amorphous yellow solid. 1H NMR (500 MHz, CHLOROFORM-D) δ ppm 0.53 (br.s, 3H) 0.96 (br.s, 3H) 1.04-1.44 (m, 4H) 1.51 (d, J=10.07 Hz, 1H) 1.78 (d, J=9.46 Hz, 2H) 1.88-2.13 (m, 4H) 2.40-2.52 (m, 1H) 2.80-2.97 (m, 3H) 3.05 (s, 6H) 3.57 (br.s, 1H) 3.89 (s, 3H) 4.49 (d, J=14.65 Hz, 1H) 5.20 (d, J=14.04 Hz, 1H) 6.93 (d, J=2.75 Hz, 1H) 6.98 (s, 1H) 7.02 (dd, J=8.70, 2.59 Hz, 1H) 7.11 (d, J=5.19 Hz, 1H) 7.38 (d, J=4.88 Hz, 1H) 7.41-7.52 (m, 2H) 7.86 (d, J=8.55 Hz, 1H) 8.01 (s, 1H) 9.18 (s, 1H); LC-MS retention time 2.19 min; 673 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

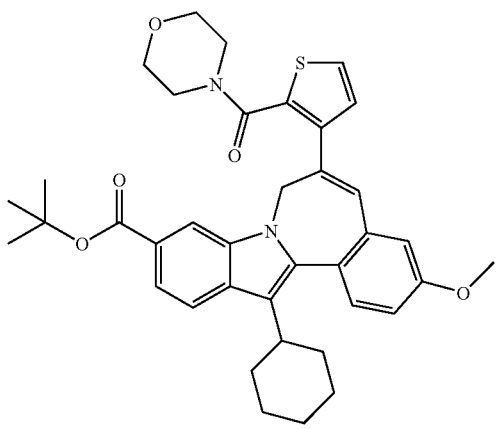

tert-Butyl 13-cyclohexyl-3-methoxy-6-(2-(4-morpholinylcarbonyl)-3-thienyl)-7H-indolo[2,1-a][2]benzazepine-10-carboxylate. In a 2 dram vial, 7H-indolo[2,1-a][2]benzazepine-10-carboxylic acid, 6-(2-carboxy-3-thienyl)-13-cyclohexyl-3-methoxy-, 10-(1,1-dimethylethyl) ester (33.7 mg, 0.059 mmol) and O-(1H-Benzotriazol-1-yl)-N,N,N',N'-tetramethyluronium tetrafluoroborate (34.2 mg, 0.106 mmol) was dissolved in DMF (0.7 ml) to give a clear yellow solution. The reaction was capped under a nitrogen atmosphere and stirred at room temperature for 1 hr 20 min. DMAP (28.9 mg, 0.237 mmol) was dissolved in the reaction then morpholine (10.5 µl, 0.121 mmol) was added. The reaction was capped under a nitrogen atmosphere and stirred at room temperature for 2 days. Pour reaction into 15 mL of water. A pale yellow precipitate forms. Extract into dichloromethane. Wash dichloromethane solution with 0.1M aqueous citric acid, back extract aqueous using dichloromethane. Combine dichloromethane phases wash 1× with water and dry over sodium sulfate. Remove volatiles in vacuo to yield 45 mg of the title product as a yellow oil. LC-MS: Shimadzu Analytical HPLC using Discovery VP software: % A=10% methanol, 90% water, 0.1% trifluoroacetic acid % B=90% methanol, 10% water, 0.1% trifluoroacetic acid; Initial % B=50; Final % B=100; Gradient=6 min; Runtime=6 min; Flow rate=5 ml/min; Wavelength=220 nm; Column=Phenomenex Luna 3.0 mm×50 mm S10; Retention Time=4.38 min, MS m/z 639 (MH+).

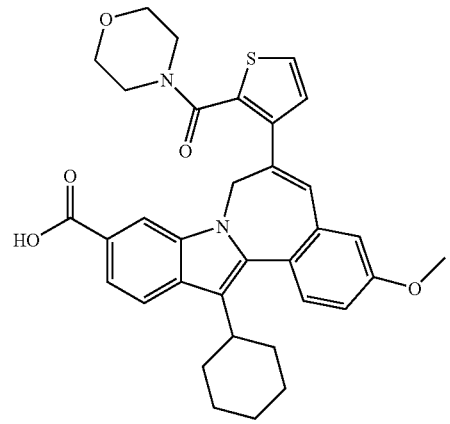

13-Cyclohexyl-3-methoxy-6-(2-(4-morpholinylcarbonyl)-3-thienyl)-7H-indolo[2,1-a][2]benzazepine-10-carboxylic acid. In a 2 dram vial, dissolve tert-Butyl 13-cyclohexyl-3-methoxy-6-(2-(4-morpholinylcarbonyl)-3-thienyl)-7H-indolo[2,1-a][2]benzazepine-10-carboxylate (37.7 mg, 0.059 mmol) in 1,2-Dichloroethane (1 mL) add TFA (1 mL, 12.98 mmol). The reaction was capped under a nitrogen atmosphere and stirred at room temperature for 1.5 hrs. Transfer reaction contents to a 25 mL pear flask using benzene to rinse. Remove volatiles in vacuo. Dissolve product in benzene and rotovap to aid in trace TFA removal. Obtained 41 mg of title compound as a yellow brown film. A LC-MS was obtained to confirm product and the product used in the next step without further purification. LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=5 min; Flow rate=5 ml/min; Wavelength=220 nm; Column=Waters Xterra, 3 mm×50 mm, S7. Retention Time=1.73 min, MS m/z 583 (MH+), m/z 581 (M−H)−.

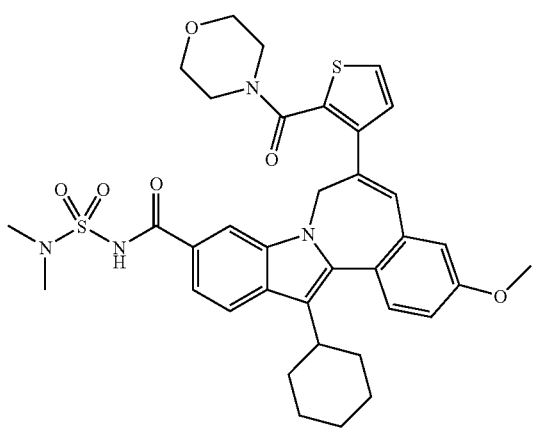

13-Cyclohexyl-N-(dimethylsulfamoyl)-3-methoxy-6-(2-(4-morpholinylcarbonyl)-3-thienyl)-7H-indolo[2,1-a][2]benzazepine-10-carboxamide In a 2 dram vial, dissolve 13-Cyclohexyl-3-methoxy-6-(2-(4-morpholinylcarbonyl)-3-thienyl)-7H-indolo[2,1-a][2]benzazepine-10-carboxylic acid (38 mg, 0.065 mmol) in 1 mL of anhydrous THF, add CDI (19.03 mg, 0.117 mmol) to the reaction. The reaction was capped under a nitrogen atmosphere and stirred at room temperature for approximately 1 hour. The reaction was heated capped under nitrogen at 65 C for 1 hour, then cooled to room temperature and N,N-Dimethylsulfamide (44.3 mg, 0.357 mmol) then DBU (13.8 µL, 0.092 mmol) added to the reaction. The reaction was capped and heated under nitrogen over night at 65° C. Analysis of an aliquot by LC-MS indicated that the reaction was incomplete. To the reaction was added more dimethylsulfamide (19 mg, 0.153 mmol) and DBU (13.8 uL, 0.092 mmol). The reaction was capped under a nitrogen atmosphere and heated at 69 C for 3.25 hrs. Analysis of the reaction by LC-MS indicated that the reaction was complete. The reaction was partitioned between dichloromethane and 1N aqueous hydrochloric acid. The aqueous layer was extracted with dichloromethane. The organic layers were combined and washed sequentially with 1N aqueous hydrochloric acid then 0.1M sodium dihydrogen phosphate ($NaH_2PO_4$) and dried over sodium sulfate. Volatiles were removed in vacuo to give a yellow oil/film. The crude title compound was dried in vacuo overnight at room temperature. Weight of crude product is 43 mg as a yellow/brown solid. Dissolve in a mixture of acetonitrile and DMF and purify by reverse phase HPLC under the following conditions: Shimadzu Preparative HPLC running Discovery VP software, % A=10% acetonitrile, 90% water, 0.1% TFA % B=90% acetonitrile, 10% water, 0.1% TFA; Initial % B=50; Final % B=100; Gradient=15 min; Runtime=25 min; Flow rate=25 ml/min; Wavelength=220 nm; Column=Waters Sunfire 19 mm×100 mm. Product collection time=9.72 min. to 10.49 min. Volatiles were removed in vacuo from the product fraction to yield 14.2 mg of the title compound as a yellow solid. 1H NMR (500 MHz, CHLOROFORM-D) δ ppm 1.17-1.30 (m, 1H) 1.32-1.50 (m, 2H) 1.55 (d, J=11.29 Hz, 1H) 1.78 (d, J=10.99 Hz, 2H) 1.90-2.16 (m, 4H) 2.42-2.58 (m, 1H) 2.60-2.86 (m, 4H) 2.85-2.94 (m, 2H) 2.95-3.04 (m, 2H) 3.06 (s, 6H) 3.10-3.30 (m, 1H) 3.91 (s, 3H) 4.56 (d, J=14.65 Hz, 1H) 5.09 (d, J=14.65 Hz, 1H) 6.87 (s, 1H) 6.93 (d, J=2.75 Hz, 1H) 7.05 (dd, J=8.70, 2.59 Hz, 1H) 7.08 (d, J=4.88 Hz, 1H) 7.45 (d, J=4.88 Hz, 1H) 7.47-7.54 (m, 2H) 7.83 (s, 1H) 7.91 (d, J=8.55 Hz, 1H) 9.59 (s, 1H). LC-MS: Shimadzu Analytical HPLC using Discovery VP software: % A=5% acetonitrile, 95% water, 10 mmol Ammonium Acetate % B=95% acetonitrile, 5% water, 10 mmol Ammonium Acetate; Initial % B=0; Final % B=100; Gradient=3 min; Runtime=4 min; Flow rate=5 ml/min; Wavelength=220 nm; Column=Waters Xterra, 3 mm×50 mm, S7. Retention Time=2.05 min, MS m/z 689 (MH+), m/z 687 (M−H)−.

7H-indolo[2,1-a][2]benzazepine-10-carboxylic acid, 13-cyclohexyl-6-[4-(ethoxycarbonyl)-2-(methylthio)-5-thiazolyl]-3-methoxy-, 1,1-dimethylethyl ester

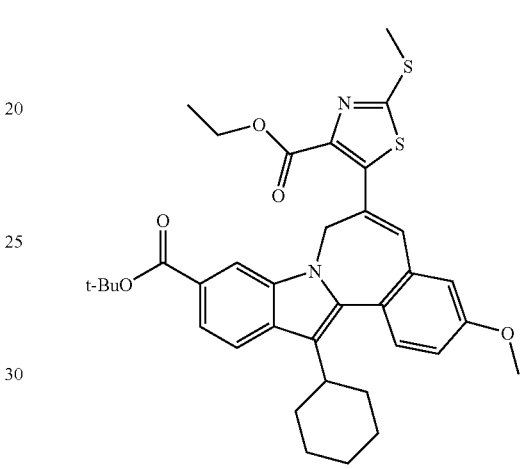

7H-indolo[2,1-a][2]benzazepine-10-carboxylic acid, 13-cyclohexyl-3-methoxy-6-(tributylstannyl)-, 1,1-dimethylethyl ester (203 mg, 0.277 mmol) was dissolved in 1,4-dioxane (2.7 ml)) in a 2-5 mL tapered microwave vessel with magnetic stir bar. To the reaction was added ethyl 5-bromo-2-(methylthio)thiazole-4-carboxylate (171 mg, 0.606 mmol), and bis(triphenylphosphine)palladium(II) chloride (14.9 mg, 0.021 mmol). The reaction was capped under a nitrogen atmosphere and heated to 100 C for 17.5 hrs. HPLC analysis of the reaction indicated only approximately 45% conversion of starting material. Additional catalyst bis(triphenylphosphine)palladium(II) chloride (5.7 mg) was added to the reaction and the reaction was heated under a nitrogen atmosphere at 110 C for 23 hrs. Volatiles were removed from the reaction mixture in vacuo and the crude reaction mixture was dissolved in a 8 ml of a DMF/acetonitrile mixture and purified as four 2 mL injections using reverse phase HPLC. The sample was purified on a Shimadzu high pressure liquid chromatography system employing Discovery VP software interfaced with a SCL-10A controller, SIL-10A autosampler and FRC-10A fraction collector. The sample was dissolved in acetonitrile and DMF purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 40% solvent A/60% solvent B to 0% solvent A/100% solvent B, a gradient time of 15 minutes with a run time of 30 minutes using % A=10% acetonitrile, 90% water, 0.1% TFA % B=90% acetonitrile, 10% water, 0.1% TFA solvent system. Retention time of product=26.6 min. Volatiles from the product fractions were removed in vacuo using a speed vac at a medium heating setting.

1H NMR (500 MHz, CHLOROFORM-D) δ ppm 1.16-1.26 (m, 1H) 1.30 (t, J=7.02 Hz, 3H) 1.33-1.56 (m, 3H) 1.60 (s, 10H) 1.63-1.83 (m, 5H) 1.94 (br.s, 1H) 1.98-2.16 (m, 3H) 2.71 (s, 3H) 2.82-2.92 (m, 1H) 3.90 (s, 3H) 4.28 (q, J=7.02 Hz, 2H) 4.53 (d, J=14.95 Hz, 1H) 5.52 (d, J=14.65 Hz, 1H) 6.98 (d, J=2.75 Hz, 1H) 7.03 (dd, J=8.85, 2.75 Hz, 1H) 7.49-7.54 (m, 2H) 7.65 (dd, J=8.55, 1.53 Hz, 1H) 7.81 (d, J=8.55 Hz, 1H) 8.13 (d, J=1.22 Hz, 1H).

LC-MS retention time 3.08 min; 645 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The scheme shown below is illustrative of methods that can be used to make intermediates and compounds.

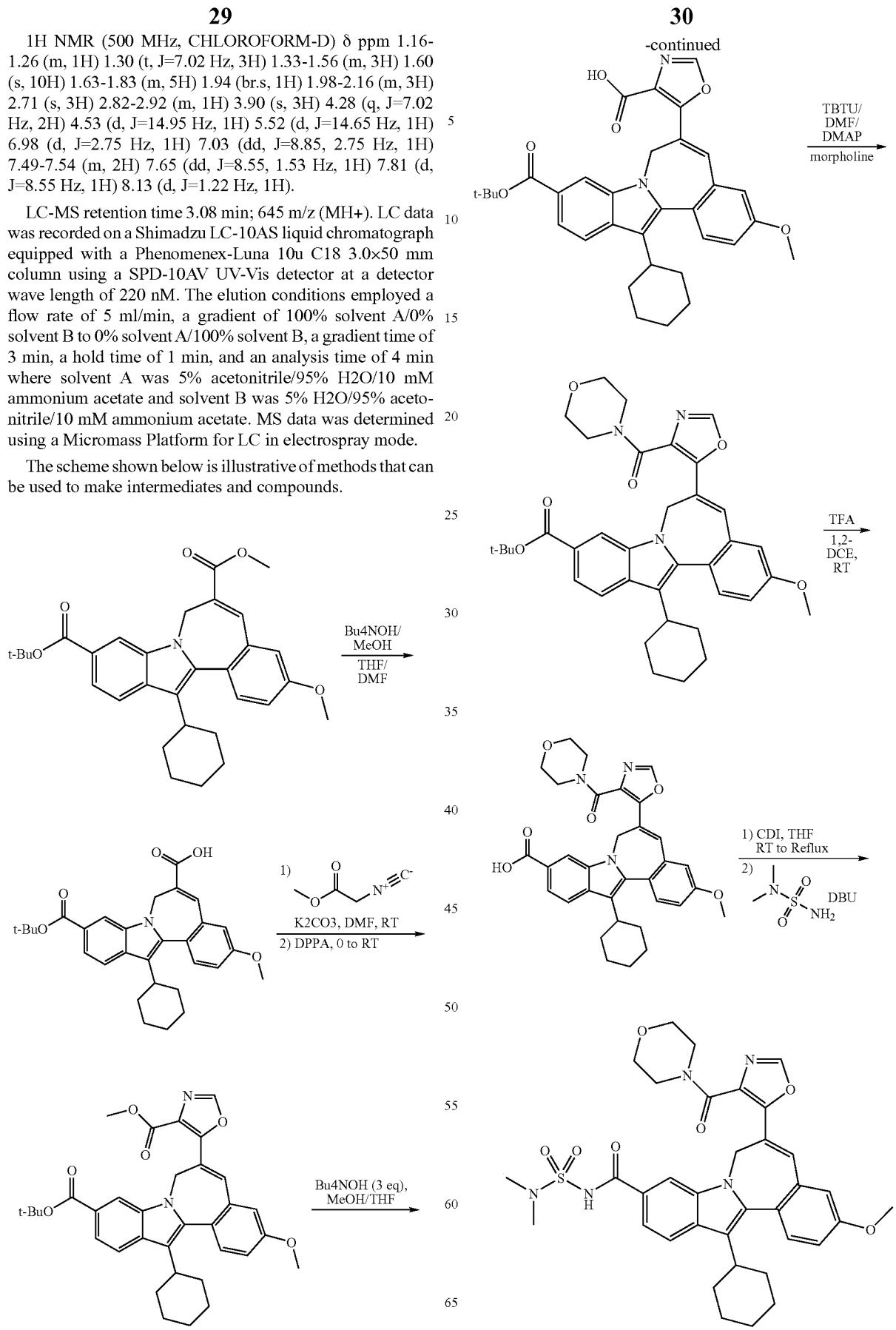

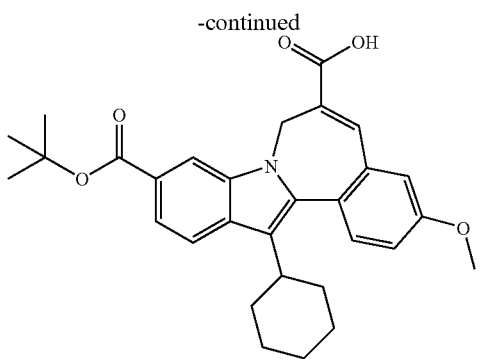

10-(tert-butoxycarbonyl)-13-cyclohexyl-3-methoxy-7H-indolo[2,1-a][2]benzazepine-6-carboxylic acid. Dissolve 10-(1,1-dimethylethyl) 6-methyl 13-cyclohexyl-3-(methyloxy)-7H-indolo[2,1-a][2]benzazepine-6,10-dicarboxylate (5.53 g, 11.02 mmol) in THF (70 ml) with heating, add DMF (20 ml) to maintain solubility, allow to cool to room temperature then add tetrabutylammonium hydroxide (33.1 ml, 33.1 mmol) 10M in methanol. Stir reaction at room temperature for 2 hrs then add 0.1N aqueous 0.1N hydrochloric acid to the reaction followed by 01M aqueous NaH2PO4. Separate phases, wash organic layer sequentially with 1.0N aqueous hydrochloric acid, 0.1M aqueous NaH2PO4. Back extract aqueous 1× using ethyl acetate. Combine ethyl acetate fractions and wash sequentially with 0.1M aqueous NaH2PO4 and brine. Dry over magnesium sulfate, filter and remove solvents in vacuo to yield a bright yellow solid. Dry product in vacuo at room temperature to give 5.2 μg (97%). 1H NMR (500 MHz, CHLOROFORM-D) δ ppm 1.12-1.28 (m, 2H) 1.28-1.45 (m, 2H) 1.46-1.60 (m, 2H) 1.63 (s, 9H) 1.66-1.96 (m, 4H) 1.96-2.16 (m, 3H) 2.76-2.84 (m, 1H) 3.91 (s, 3H) 4.18 (br.s., 1H) 5.66 (br.s, 1H) 7.00 (d, J=2.44 Hz, 1H) 7.10 (dd, J=8.55, 2.75 Hz, 1H) 7.53 (d, J=8.54 Hz, 1H) 7.65-7.71 (m, 1H) 7.82 (d, J=8.24 Hz, 1H) 7.93 (s, 1H) 8.22 (s, 1H). LC-MS retention time 1.47 min; 486 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

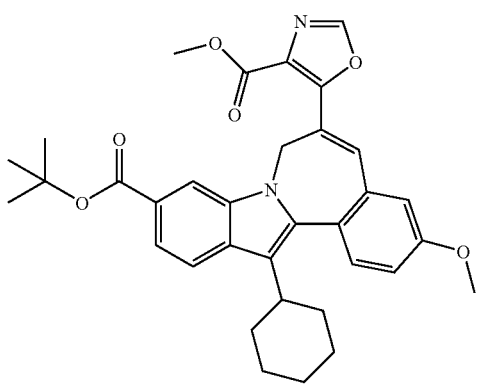

tert-Butyl 13-cyclohexyl-3-methoxy-6-(4-(methoxycarbonyl)-1,3-oxazol-5-yl)-7H-indolo[2,1-a][2]benzazepine-10-carboxylate. 10-(tert-butoxycarbonyl)-13-cyclohexyl-3-methoxy-7H-indolo[2,1-a][2]benzazepine-6-carboxylic acid (1.00 g, 2.051 mmol) was dissolve in DMF (10 ml) and potassium carbonate (0.624 g, 4.51 mmol) was added to the reaction followed by methyl isocyanoacetate (0.24 ml, 2.64 mmol). The reaction was stirred under a nitrogen atmosphere at room temperature for approximately 5 minutes then cooled to 0 C. Diphenylphosphoryl azide (0.5 ml, 2.320 mmol) was slowly added to the reaction over 10 minutes. The reaction was stirred at 0 C under a nitrogen atmosphere and allowed to slowly warm to room temperature overnight. Dilute reaction with 100 ml of benzene/ethyl acetate (1:1) and wash with water. Back extract aqueous layer using ethyl acetate. Combine organic extracts and wash successively with 0.1M aqueous citric acid, saturated aqueous sodium bicarbonate and then brine and dry over magnesium sulfate. Filter and remove volatiles in vacuo. Chromatograph on 43.4 g of silica gel slurry packed in 5% ethyl acetate/dichloromethane. Elute with 5% ethyl acetate/dichloromethane. Combination of pure product fractions and removal of volatiles in vacuo yielded 215 mg of an amorphous yellow solid. Combination of less pure fractions yielded an additional 189 mg of product with purity greater than 92%. 1H NMR (500 MHz, CHLOROFORM-D) δ ppm 1.11-1.29 (m, 2H) 1.30-1.48 (m, 3H) 1.57 (s, 2H) 1.61 (s, 10H) 1.69-1.80 (m, 2H) 1.86-1.98 (m, 1H) 1.99-2.13 (m, 4H) 2.76-2.90 (m, 1H) 3.92 (s, 3H) 3.98 (s, 3H) 4.47 (d, J=12.82 Hz, 1H) 5.84 (d, J=14.65 Hz, 1H) 7.02 (d, J=2.44 Hz, 1H) 7.07 (dd, J=8.55, 2.75 Hz, 1H) 7.53 (d, J=8.55 Hz, 1H) 7.65-7.71 (m, 1H) 7.82 (d, J=8.24 Hz, 1H) 7.87 (s, 1H) 8.08 (s, 1H) 8.16 (s, 1H). LC-MS retention time 2.75 min; m/z (MH+). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 0 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

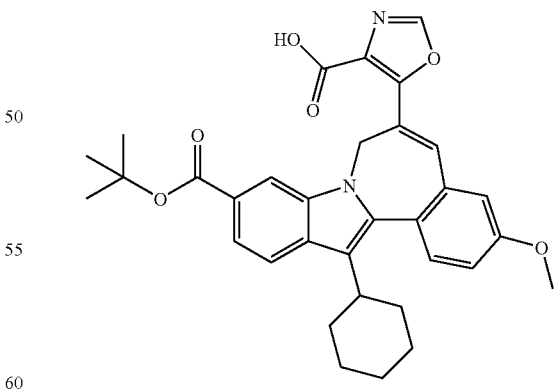

5-(10-(tert-Butoxycarbonyl)-13-cyclohexyl-3-methoxy-7H-indolo[2,1-a][2]benzazepin-6-yl)-1,3-oxazole-4-carboxylic acid. tert-Butyl 13-cyclohexyl-3-methoxy-6-(4-(methoxycarbonyl)-1,3-oxazol-5-yl)-7H-indolo[2,1-a][2]benzazepine-10-carboxylate (205 mg, 0.360 mmol) was dissolved in THF (3.0 ml) and tetrabutylammonium hydroxide (1.1 mL, 1.100 mmol) (1.0M in methanol) was added to the reaction. The reaction was capped and stirred at room temperature for 2 hrs. A 0.1M aqueous solution of NaH2PO4 was added to the reaction followed by 0.1N aqueous hydrochloric acid. The product was extracted into ethyl acetate and the organic phase washed sequentially with 0.1N aqueous hydrochloric acid, 0.1M aqueous NaH2PO4, brine and dried over magnesium sulfate. The product solution was filtered, solvent removed and product dried in vacuo to yield 191 mg of a yellow solid. 1H NMR (500 MHz, CHLOROFORM-D) δ ppm 0.77-0.94 (m, 1H) 1.12-1.31 (m, 3H) 1.30-1.59 (m, 5H) 1.62 (s, 9H) 1.76 (d, J=11.29 Hz, 2H) 1.87-2.18 (m, 4H) 2.76-2.90 (m, 1H) 3.91 (s, 3H) 4.45 (d, J=14.04 Hz, 1H) 6.03 (d, J=12.21 Hz, 1H) 7.03 (d, J=2.44 Hz, 1H) 7.08 (dd, J=8.55, 2.75 Hz, 1H) 7.53 (d, J=8.85 Hz, 1H) 7.68 (d, J=8.24 Hz, 1H) 7.82 (d, J=8.55 Hz, 1H) 7.91 (s, 1H) 8.21 (d, J=5.80 Hz, 2H). LC-MS retention time 1.86 min; m/z 553 (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

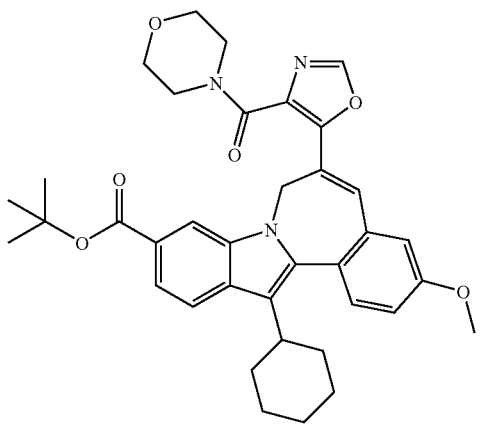

tert-Butyl 13-cyclohexyl-3-methoxy-6-(4-(4-morpholinylcarbonyl)-1,3-oxazol-5-yl)-7H-indolo[2,1-a][2]benzazepine-10-carboxylate 5-(10-(tert-Butoxycarbonyl)-13-cyclohexyl-3-methoxy-7H-indolo[2,1-a][2]benzazepin-6-yl)-1,3-oxazole-4-carboxylic acid (185 mg, 0.334 mmol) was dissolved in DMF (3.2 ml), and O-benzotriazol-1-yl-N,N,N',N'-tetra-methyluronium tetrafluoroborate (193 mg, 0.600 mmol) was added. The reaction was stirred capped at room temperature for 25 minutes and DMAP (163 mg, 1.334 mmol) was dissolved in the reaction then morpholine (0.058 ml, 0.667 mmol) was added. The reaction was capped and stirred at room temperature overnight. The reaction was poured into 30 ml of water and extracted with dichloromethane. The organic layer was washed sequentially with 0.1M aqueous citric acid, 0.1M aqueous NaH2PO4, then dried over anhydrous sodium sulfate. The sample was filtered, volatiles removed and the sample dried in vacuo to obtain 227 mg of an amorphous orange solid. 1H NMR (500 MHz, CHLOROFORM-D) δ ppm 1.16-1.50 (m, 7H) 1.53-1.61 (m, 6H) 1.62 (s, 10H) 1.76 (d, J=10.38 Hz, 2H) 1.83-2.15 (m, 5H) 3.40-3.84 (m, 7H) 3.83-3.95 (m, 5H) 4.40 (d, J=11.60 Hz, 1H) 5.64 (d, J=12.21 Hz, 1H) 6.97 (d, J=2.75 Hz, 1H) 7.05 (dd, J=8.39, 2.59 Hz, 1H) 7.50 (d, J=8.55 Hz, 1H) 7.53 (s, 1H) 7.65 (d, J=8.24 Hz, 1H) 7.77-7.86 (m, 2H) 7.97-8.04 (m, 1H) 8.10 (s, 1H). LC-MS retention time 2.64 min m/z 624 (MH+). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 2 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

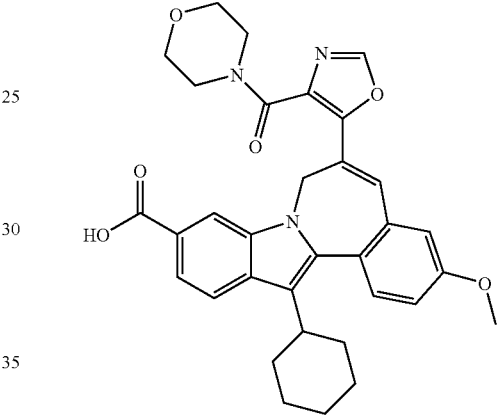

13-Cyclohexyl-3-methoxy-6-(4-(4-morpholinylcarbonyl)-1,3-oxazol-5-yl)-7H-indolo[2,1-a][2]benzazepine-10-carboxylic acid Dissolve tert-Butyl 13-cyclohexyl-3-methoxy-6-(4-(4-morpholinylcarbonyl)-1,3-oxazol-5-yl)-7H-indolo[2,1-a][2] benzazepine-10-carboxylate (203 mg, 0.325 mmol) in 1,2-dichloroethane (3 ml) add TFA (3 ml, 38.9 mmol). The reaction was capped under a nitrogen atmosphere at 25° C. for 2 hrs. Reaction volatiles were removed in vacuo and the residue dissolved in 80 mL of ethyl acetate with heating. The solution was washed with 1N aqueous hydrochloric acid (2×40 mL), brine and dried over magnesium sulfate. The product solution was filtered, volatiles removed and the sample dried in vacuo at room temperature overnight to give 179 mg (97%) of a yellow solid. 1H NMR (500 MHz, CHLOROFORM-D) δ ppm 0.74-1.03 (m, 4H) 1.06-1.31 (m, 6H) 1.32-1.50 (m, 3H) 1.56 (d, J=9.16 Hz, 2H) 1.77 (d, J=8.85 Hz, 2H) 1.86-2.18 (m, 5H) 2.83-2.91 (m, 1H) 3.60 (s, 3H) 3.64-3.89 (m, 4H) 3.88-3.93 (m, 4H) 3.95-4.08 (m, 1H) 4.43 (d, J=15.56 Hz, 1H) 5.64 (d, J=14.95 Hz, 1H) 6.99 (d, J=2.75 Hz, 1H) 7.07 (dd, J=8.70, 2.59 Hz, 1H) 7.48-7.56 (m, 2H) 7.85-7.94 (m, 2H) 8.15 (s, 1H). LC-MS retention time 1.65 min; 568 m/z (MH+). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

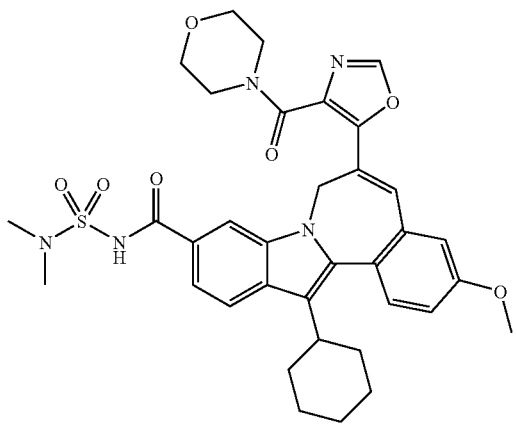

13-Cyclohexyl-N-(dimethylsulfamoyl)-3-methoxy-6-(4-(4-morpholinylcarbonyl)-1,3-oxazol-5-yl)-7H-indolo[2,1-a][2]benzazepine-10-carboxamide In a 2 dram vial, 13-Cyclohexyl-3-methoxy-6-(4-(4-morpholinylcarbonyl)-1,3-oxazol-5-yl)-7H-indolo[2,1-a][2]benzazepine-10-carboxylic acid (40 mg, 0.070 mmol) in THF (1 ml) and CDI (23.8 mg, 0.147 mmol) was added to the reaction. The reaction was capped under a nitrogen atmosphere and stirred at room temperature for 1 hr. The reaction was then heated at 60 C for 1 hr, cooled and N,N-Dimethylsulfamide (46.5 mg, 0.375 mmol) was added to the reaction followed by DBU (0.014 ml, 0.092 mmol). The reaction was capped under a nitrogen atmosphere and heated overnight (16 hrs) at 60 C. The reaction was monitored by HPLC and additional N,N-Dimethylsulfamide (22.9 mg, 0.184 mmol) and DBU (0.015 ml, 0.099 mmol) was added and the reaction heated to 70 C under a nitrogen atmosphere for 5 hrs. The reaction mixture was partitioned between 1N aqueous hydrochloric acid and dichloromethane. The organic phase was washed sequentially with 1N aqueous hydrochloric acid and 0.1M aqueous NaH2PO4 and dried over sodium sulfate. Solvent was removed in vacuo to yield 46 mg of crude product. The title compound was purified on a Shimadzu high pressure liquid chromatography system employing Discovery VP software and interfaced with a SCL-10A controller, SIL-10A autosampler and FRC-10A fraction collector. The sample was dissolved in acetonitrile/DMF (1:1) and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 12 minutes with a run time of 20 minutes using % A=10% acetonitrile, 90% water, 0.1% TFA % B=90% acetonitrile, 10% water, 0.1% TFA solvent system. 1H NMR (500 MHz, CHLOROFORM-D) δ ppm 1.05-1.28 (m, 1.2H) 1.29-1.62 (m, 3.7H) 1.64-1.84 (m, 4.0H) 1.84-2.20 (m, 4.6H) 2.47 (d, J=14.04 Hz, 0.1H) 2.78-2.88 (m, 1.1H) 3.04 (s, 5.9H) 3.10 (s, 0.9H) 3.35-3.89 (m, 9.0H) 3.91 (s, 3.0H) 4.09 (s, 0.4H) 4.18 (d, J=1.83 Hz, 0.9H) 4.41 (d, J=15.56 Hz, 0.9H) 4.55 (d, J=16.48 Hz, 0.1H) 5.59 (d, J=14.95 Hz, 0.9H) 6.62 (d, J=14.34 Hz, 0.1H) 6.97 (d, J=2.44 Hz, 1.0H) 7.07 (dd, J=8.70, 2.59 Hz, 1.0H) 7.27-7.36 (m, 0.3H) 7.46-7.54 (m, 1.9H) 7.59 (d, J=8.55 Hz, 0.9H) 7.75 (d, J=7.93 Hz, 0.1H) 7.82 (s, 1.0H) 7.87 (d, J=8.54 Hz, 0.9H) 8.15 (s, 0.1H) 8.28-8.35 (m, 0.2H) 8.44 (s, 0.9H) 8.94 (d, J=9.16 Hz, 0.1H) 9.43 (s, 0.9H) 9.88 (s, 0.1H) 12.11 (s, 0.1H). LC-MS retention time 1.40 min; 672 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

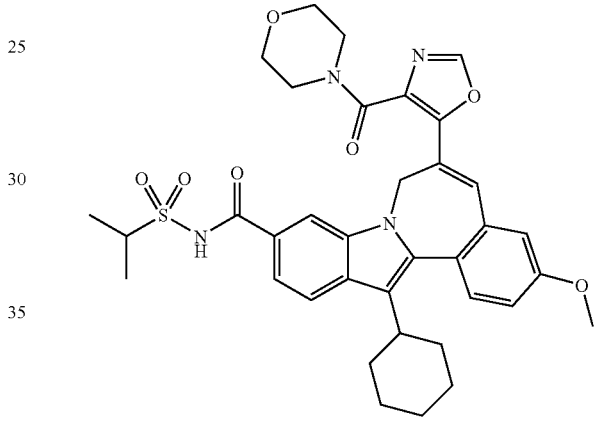

13-cyclohexyl-N-(isopropylsulfonyl)-3-methoxy-6-(4-(4-morpholinylcarbonyl)-1,3-oxazol-5-yl)-7H-indolo[2,1-a][2]benzazepine-10-carboxamide 13-Cyclohexyl-3-methoxy-6-(4-(4-morpholinylcarbonyl)-1,3-oxazol-5-yl)-7H-indolo[2,1-a][2]benzazepine-10-carboxylic acid (40.8 mg, 0.072 mmol) was dissolved in THF (1 ml) and CDI (26 mg, 0.160 mmol) added to the reaction. The reaction was capped under a nitrogen atmosphere and stirred at room temperature for 50 min then heated in an oil bath at 60 C for 1.5 hrs. The reaction was cooled and propane-2-sulfonamide (46 mg, 0.373 mmol) was added to the reaction followed by DBU (0.022 ml, 0.144 mmol). The reaction was capped under a nitrogen atmosphere and heated at 65 C overnight (16 hr). The reaction was partitioned between dichloromethane and 1.0N aqueous hydrochloric acid. The organic layer was washed sequentially with 1N aqueous hydrochloric acid, 0.1M aqueous NaH2PO4. The organic layer was dried over sodium sulfate and solvent removed in vacuo to yield 50 mg of an amorphous yellow solid. The title was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 12 minutes with a run time of 15 minutes using % A=10% acetonitrile, 90% water, 0.1% TFA % B=90% acetonitrile, 10% water, 0.1% TFA solvent system. Removal of solvents and drying in vacuo yielded 28.3 mg of a yellow solid. 1H NMR (500 MHz, CHLOROFORM-D) δ ppm 1.15-1.28 (m, 1.2H) 1.29-1.60 (m, 10.9H) 1.59-1.85 (m, 6.7H) 1.86-2.15 (m, 4.7H) 2.78-2.87 (m, 1.0H) 3.37-3.50 (m, 1.4H) 3.51-3.89 (m, 7.3H) 3.91 (s, 3.3H) 4.02-4.12 (m, 1.5H) 4.15-4.26 (m, 0.9H) 4.42 (d, J=13.73 Hz, 0.9H) 4.54 (d, J=15.26 Hz, 0.1H) 5.54 (d, J=14.65 Hz, 0.9H) 6.57 (d, J=14.04 Hz, 0.1H) 6.97 (d, J=2.44 Hz, 0.9H) 7.07 (dd, J=8.55, 2.44 Hz, 1.0H) 7.28-7.35 (m, 0.3H) 7.48-7.54 (m, 2.0H) 7.62-7.67 (m, 1.0H) 7.75 (d, J=7.93 Hz, 0.1H) 7.82 (s, 1.0H) 7.87 (d, J=8.55 Hz, 1.0H) 8.21 (s, 0.9H) 8.31 (s, 0.2H) 8.48 (s, 1.0H) 8.94 (d, J=9.15 Hz, 0.1H) 9.46 (s, 0.9H) 9.86 (s, 0.1H). LC-MS retention time 1.26 min; 671 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

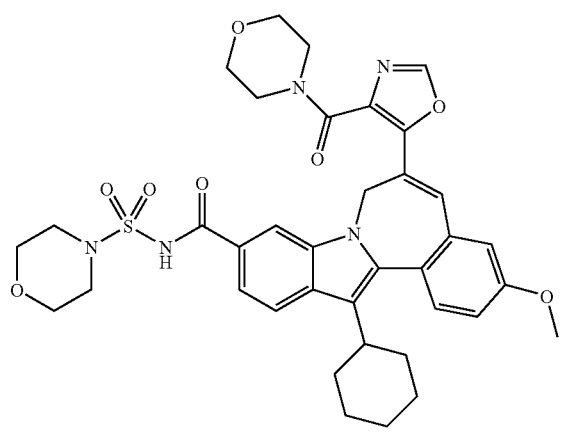

13-cyclohexyl-3-methoxy-6-(4-(4-morpholinylcarbonyl)-1,3-oxazol-5-yl)-N-(4-morpholinylsulfonyl)-7H-indolo[2,1-a][2]benzazepine-10-carboxamide 13-Cyclohexyl-3-methoxy-6-(4-(4-morpholinylcarbonyl)-1,3-oxazol-5-yl)-7H-indolo[2,1-a][2]benzazepine-10-carboxylic acid (40.8 mg, 0.072 mmol) was dissolved in THF (1 ml) and CDI (26 mg, 0.160 mmol) added to the reaction. The reaction was capped under a nitrogen atmosphere and stirred at room temperature for 50 min then heated in an oil bath at 60 C for 1.5 hrs. The reaction was cooled and propane-2-sulfonamide (46 mg, 0.373 mmol) was added to the reaction followed by DBU (0.022 ml, 0.144 mmol). The reaction was capped under a nitrogen atmosphere and heated at 65 C overnight (16 hr). The reaction was partitioned between dichloromethane and 1.0N aqueous hydrochloric acid. The organic layer was washed sequentially with 1N aqueous hydrochloric acid, 0.1M aqueous NaH2PO4. The organic layer was dried over sodium sulfate and solvent removed in vacuo to yield 50 mg of an amorphous yellow solid. The title was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 12 minutes with a run time of 15 minutes using % A=10% acetonitrile, 90% water, 0.1% TFA % B=90% acetonitrile, 10% water, 0.1% TFA solvent system. Removal of solvents and drying in vacuo yielded 28.3 mg of a yellow solid. 1H NMR (500 MHz, CHLOROFORM-D) δ ppm 1.15-1.28 (m, 1.3H) 1.30-1.46 (m, 2.4H) 1.48-1.61 (m, J=16.48 Hz, 1.2H) 1.77 (d, J=9.77 Hz, 2.3H) 1.87-2.15 (m, 4.8H) 2.22-2.52 (m, 4.6H) 2.78-2.90 (m, 1.1H) 3.37-3.72 (m, 8.9H) 3.76 (s, 6.2H) 3.80-3.89 (m, 3.2H) 3.91 (s, 3.6H) 4.08 (s, 0.3H) 4.13-4.23 (m, 1.0H) 4.42 (d, J=13.73 Hz, 0.9H) 4.65 (d, J=14.95 Hz, 0.1H) 5.55 (d, J=14.04 Hz, 1.0H) 6.97 (d, J=2.44 Hz, 1.0H) 7.07 (dd, J=8.70, 2.59 Hz, 1.0H) 7.27-7.33 (m, 0.2H) 7.38 (s, 0.1H) 7.46-7.55 (m, 2.0H) 7.60 (d, J=9.77 Hz, 1.0H) 7.78 (d, J=8.24 Hz, 0.1H) 7.83 (s, 1.0H) 7.87 (d, J=8.55 Hz, 1H) 8.07 (s, 0.1H) 8.10 (d, J=4.27 Hz, 0.1H) 8.31 (d, J=8.54 Hz, 0.1H) 8.42 (s, 0.9H) 8.94 (d, J=9.16 Hz, 0.1H) 9.55 (s, 0.9H) 9.60 (s, 0.1H). LC-MS retention time 1.63 min; 714 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

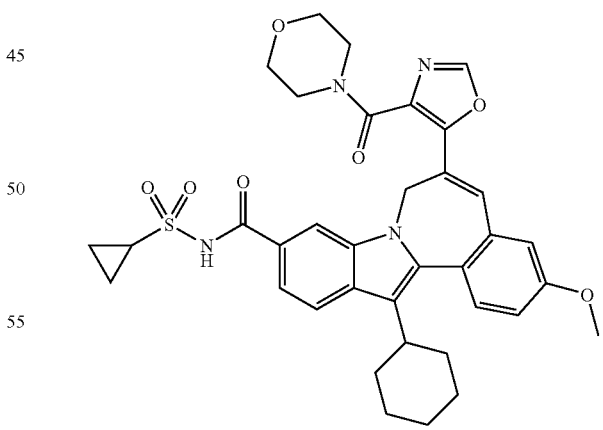

13-cyclohexyl-N-(cyclopropylsulfonyl)-3-methoxy-6-(4-(4-morpholinylcarbonyl)-1,3-oxazol-5-yl)-7H-indolo[2,1-a][2]benzazepine-10-carboxamide 13-Cyclohexyl-3-methoxy-6-(4-(4-morpholinylcarbonyl)-1,3-oxazol-5-yl)-7H-indolo[2,1-a][2]benzazepine-10- carboxylic acid (40 mg, 0.070 mmol) was dissolved in THF (1 ml) and CDI (26 mg, 0.160 mmol) added to the reaction. The reaction was capped under a nitrogen atmosphere and stirred at room temperature for 1 hr 50 min then heated in an oil bath at 65 C for 1 hr 10 min. The reaction was cooled and cyclopropanesulfonamide (48 mg, 0.396 mmol) then DBU (0.022 ml, 0.146 mmol) was added to the reaction. The reaction was capped under a nitrogen atmosphere and heated at 68 C overnight (18 hr). The reaction was partitioned between dichloromethane and 1.0N aqueous hydrochloric acid. The organic layer was washed sequentially with 1N aqueous hydrochloric acid, 0.1M aqueous NaH2PO4. The organic layer was dried over sodium sulfate and solvent removed in vacuo to yield 62 mg of an amorphous yellow solid. The title was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. Removal of solvents and drying in vacuo yielded 30.8 mg of the title compound as a yellow amorphous solid. 1H NMR (500 MHz, CHLOROFORM-D) δ ppm 0.99-1.28 (m, 4.0H) 1.29-1.45 (m, 3.9H) 1.47-1.68 (m, 7.9H) 1.75 (m, 2.3H) 1.84-2.17 (m, 4.5H) 2.77-2.88 (m, 1.0H) 3.14-3.23 (m, 1.2H) 3.33-3.89 (m, 8.3H) 3.91 (s, 3.3H) 4.09 (s, 0.5H) 4.17 (s, 0.9H) 4.42 (d, J=14.34 Hz, 0.9H) 5.54 (d, J=15.56 Hz, 0.9H) 6.60 (d, 0.1H) 6.97 (d, J=2.44 Hz, 1.0H) 7.07 (dd, J=8.55, 2.75 Hz, 1.0H) 7.27-7.35 (m, 0.3H) 7.49 (s, 1.0H) 7.52 (d, J=8.85 Hz, 1.0H) 7.64 (dd, J=8.55, 1.53 Hz, 1.0H) 7.75 (d, J=7.94 Hz, 0.2H) 7.82 (s, 1.0H) 7.87 (d, J=8.55 Hz, 1.0H) 8.21 (s, 0.1H) 8.31-8.36 (m, 0.3H) 8.43 (d, J=1.53 Hz, 1.0H) 8.95 (d, J=9.16 Hz, 0.2H) 9.61 (s, 1.0H) 9.82 (s, 0.1H). LC-MS retention time 1.59 min; 669 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The scheme depicted below is illustrative of methods that can be used to make intermediates and compounds.

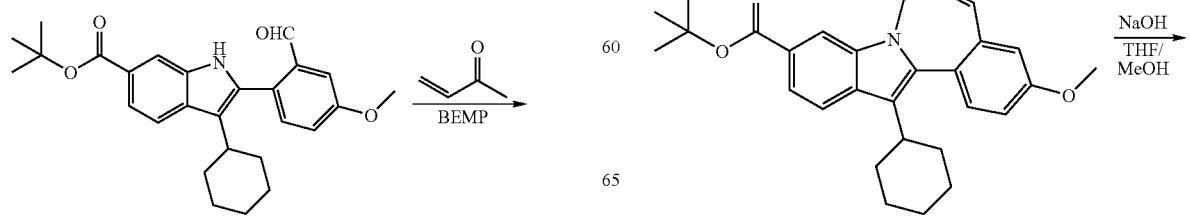

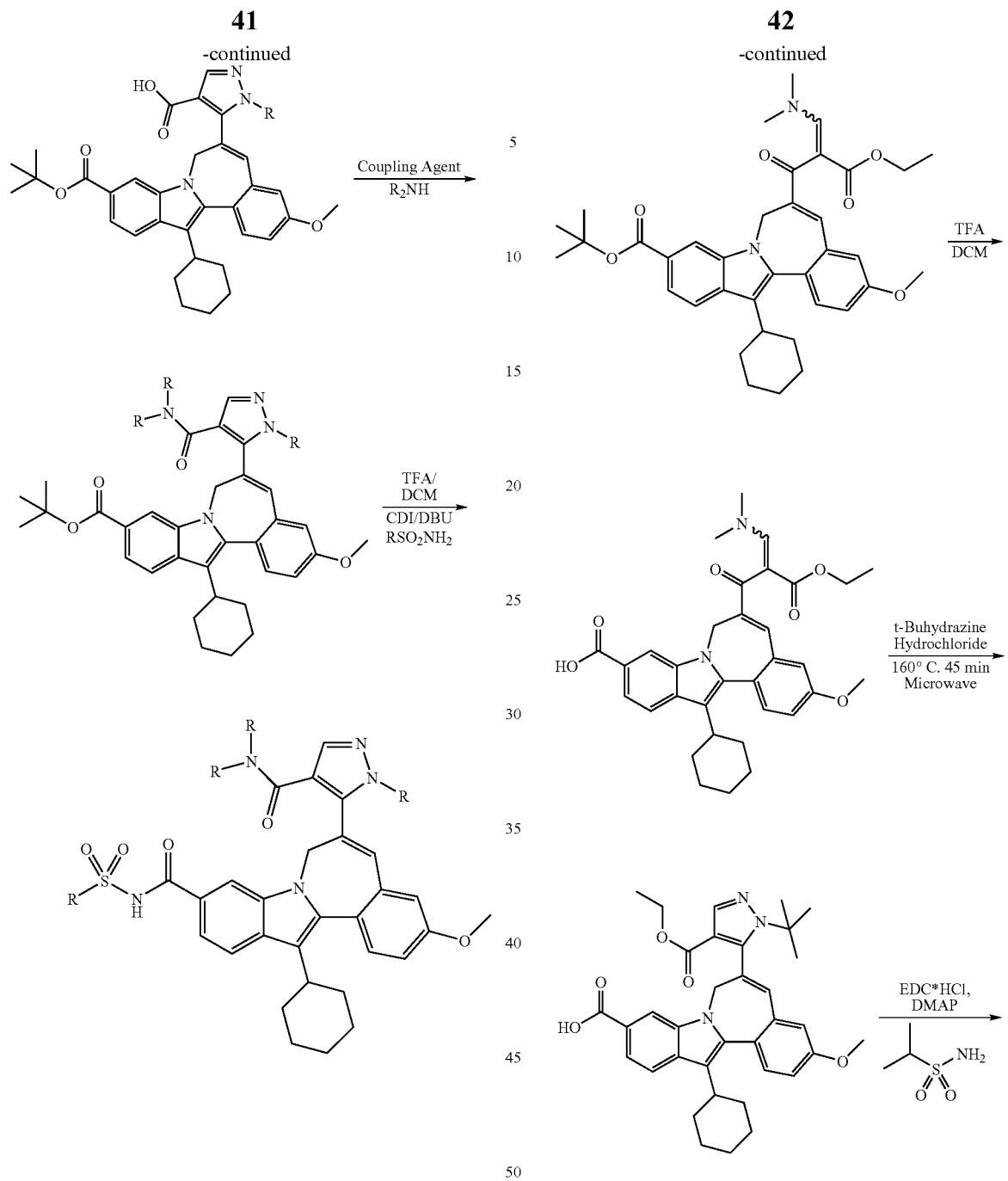
An additional variation in the methodology that can be employed for the synthesis of intermediates and compounds is shown in the following scheme.
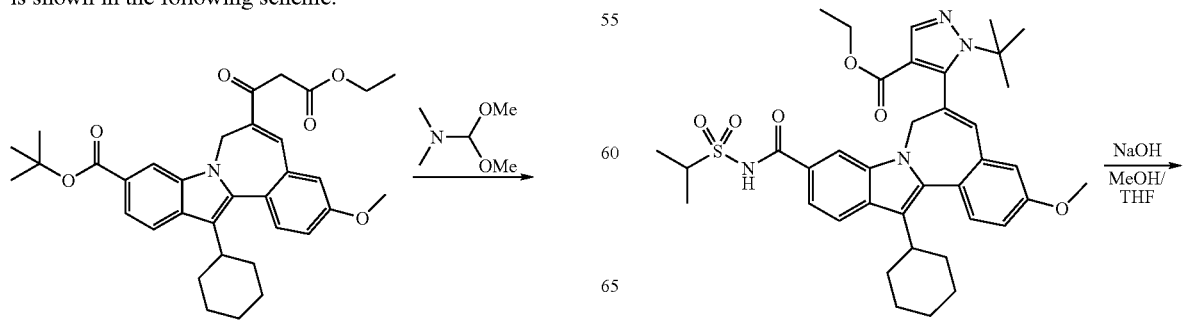

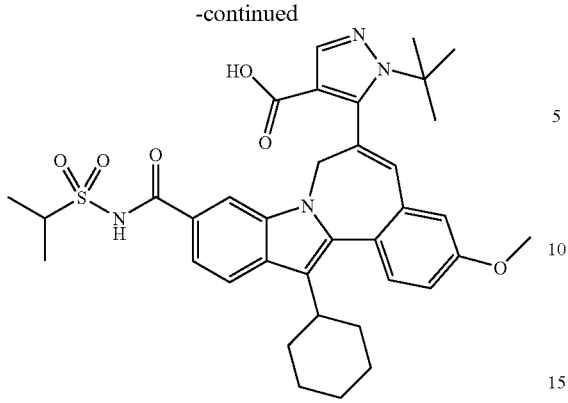

A further variation of the methodology that can be used for the synthesis of further intermediates and compounds is depicted the scheme shown below.

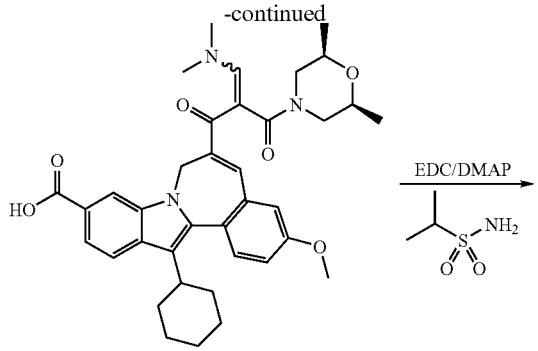

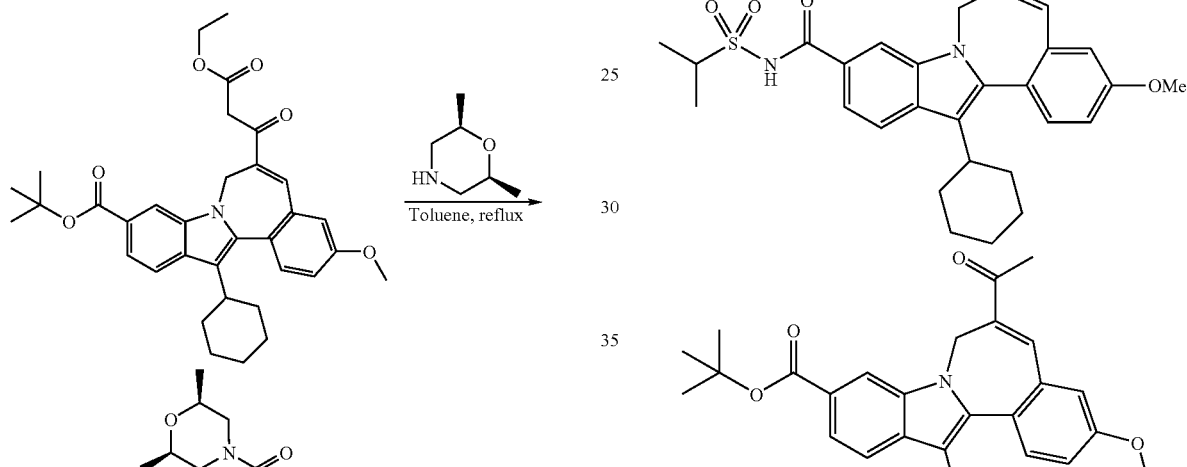

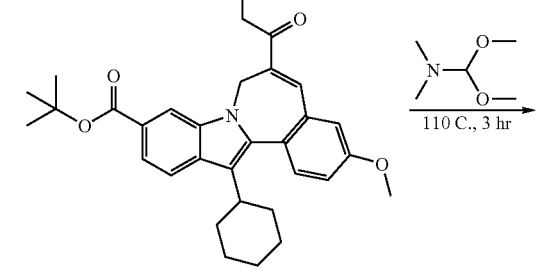

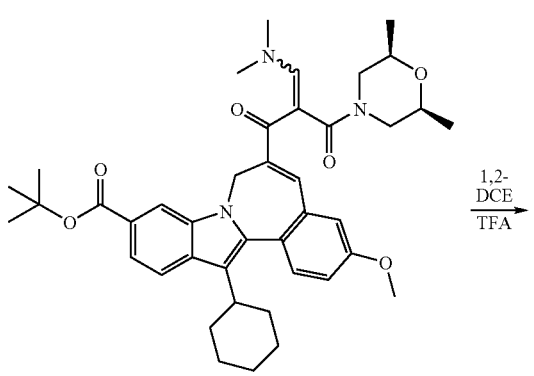

tert-Butyl 6-acetyl-13-cyclohexyl-3-methoxy-7H-indolo[2,1-a][2]benzazepine-10-carboxylate To a suspension of tert-butyl 3-cyclohexyl-2-(2-formyl-4-methoxyphenyl)-1H-indole-6-carboxylate (2 g, 4.61 mmol) in dioxane (9.2 mL) add 2-tert-butylimino-2-diethylamino-1,3-di-methylperhydrodiazaphosphorine (2.00 mL, 6.92 mmol) then but-3-en-2-one (0.756 mL, 9.23 mmol) in a 20 ml microwave vessel. Cap the heterogenous reaction under nitrogen and heat in the microwave at 120 C for 40 minutes. This reaction was repeated two more times on the above scale and one last time with tert-butyl 3-cyclohexyl-2-(2-formyl-4-methoxyphenyl)-1H-indole-6-carboxylate (2.51 g, 5.79 mmol) dissolved in dioxane (11.5 ml), add BEMP (2.5 ml, 8.64 mmol) followed by but-3-en-2-one (0.95 ml, 11.46 mmol). Each reaction segment was worked up while the next sequence was running in the microwave. Work up consisted of partitioning the reaction between ethyl acetate and 1N aqueous hydrochloric acid in a 250 ml separatory funnel. The aqueous phase was back extracted once with ethyl acetate and the organic phases combined and washed sequentially with 1N aqueous hydrochloric acid, 0.1M NaH2PO4, and brine. The solution was then combined with a previous workup in a 1 L erlenmeyer flask containing magnesium sulfate. Filter and remove volatiles, dry in vacuo at room temperature overnight to obtain 10.67 g of a yellow-orange foam. Adsorb the crude product onto 25 g of silica gel using dichloromethane, removing volatiles in vacuo. Chromatograph on 299 g of silica gel slurry packed in 20% ethyl acetate in hexanes and eluting with 20% ethyl acetate in hexanes. Pure product fractions from the chromatography were combined and solvents removed in vacuo. The residue was dissolved in benzene and removed in vacuo to aid in the removal of trace ethyl acetate. The title compound as a yellow foam/amorphous solid was dried in vacuo overnight at room temperature to yield 6.83 g (71.7%). 1H NMR (500 MHz, CHLOROFORM-D) δ ppm 1.12-1.29 (m, 1H) 1.30-1.61 (m, 4H) 1.64 (s, 10H) 1.67-2.00 (m, 4H) 1.98-2.19 (m, 3H) 2.43 (s, 3H) 2.75-2.87 (m, 1H) 3.85-4.01 (m, 4H) 5.86 (s, 1H) 7.00 (d, J=2.75 Hz, 1H) 7.11 (dd, J=8.55, 2.75 Hz, 1H) 7.35 (s, 1.8H, benzene) 7.69 (dd, J=8.55, 1.53 Hz, 1H) 7.82 (d, J=8.24 Hz, 1H) 8.24 (s, 1H). LC-MS retention time 3.28 min; m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 30% solvent A/70% solvent B to 0% solvent A/100% solvent B, a gradient time of 5 min, a hold time of 1 min, and an analysis time of 6 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

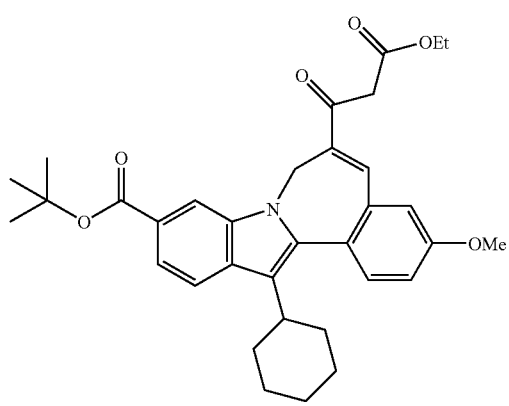

7H-Indolo[2,1-a][2]benzazepine-6-propanoic Acid, 13-cyclohexyl-10-[(1,1-dimethylethoxy)carbonyl]-3-methoxy-beta-oxo-, ethyl ester To a solution of 7H-indolo[2,1-a][2]benzazepine-10-carboxylic acid, 6-acetyl-13-cyclohexyl-3-methoxy-, 1,1-dimethylethyl ester (2.50 g, 5.15 mmol) in THF (15.0 mL) was added a 1M solution of LHMDS (5.41 mL, 5.41 mmol) in THF at −78° C. and stirred for 15 min. Ethyl cyanoformate (0.510 mL, 5.15 mmol) was added at −78° C. to the resulting solution and stirring continued for 30 min. Saturated aqueous NH4Cl (50 mL) was added and the aqueous layer was extracted with CHCl3 (2×50 mL). The organic phase was dried over Na2SO4, filtered, and concentrated under reduced pressure. Silica gel chromatography (2:1 methylene chloride: hexanes) of the concentrate afforded the title compound (1.75 g, 61%) as a yellow oil. MS m/z 558 (MH+). A previous reaction which was run in an analogous fashion to the above reaction and in which starting material 7H-indolo[2,1-a][2]benzazepine-10-carboxylic acid, 6-acetyl-13-cyclohexyl-3-methoxy-, 1,1-dimethylethyl ester was still present was separated under the following conditions: This procedure describes the separation of tert-butyl 13-cyclohexyl-6-(3-ethoxy-3-oxopropanoyl)-3-methoxy-7H-indolo[2,1-a][2]benzazepine-10-carboxylate (desired product) from the starting material ketone, tert-butyl 6-acetyl-13-cyclohexyl-3-methoxy-7H-indolo[2,1-a][2]benzazepine-10-carboxylate. Total weight of materials was estimated to be 2.6 g. 3.9 g of an the sample mixture as an orange oil was dissolved in dichloromethane and adsorbed on 10 g of silica gel. The volatiles were removed in vacuo using a rotary evaporator. The sample adsorbed onto silica gel was applied to a column of 294 g of silica gel which was slurry packed in 30% diethyl ether in hexanes. A bed of sand was placed on top of the adsorbed sample to aid in solvent addition. The approximate size of the silica gel column packing was 75 mm diameter×175 mm in height. The product was eluted using a gradient of 30% diethyl ether in hexanes to 35% diethyl ether in hexanes to 40% diethyl ether in hexanes. Elute with approximately 1 L of 30% Et2O/hexanes, then 1 L of 35% Et2O/hexanes, and finally using 40% Et2O/hexanes. The volumes of fractions collected were approximately 125 ml to 150 ml. The product fractions were combined and volatiles removed and the title keto-ester dried in vacuo to yield 1.63 g of a yellow-orange amorphous solid. 1H NMR (500 MHz, CHLOROFORM-D) δ ppm 1.12 (t, J=7.02 Hz, 2.5H) 1.15-1.28 (m, 1.6H) 1.32 (q, J=7.12 Hz, 1.0H) 1.35-1.43 (m, 1.5H) 1.59 (s, 1.5H) 1.61-1.69 (m, 9.4H) 1.72-1.82 (m, 2.0H) 1.94 (s, 1.2H) 2.04 (s, 2.9H) 2.76-2.85 (m, 1.0H) 3.64-3.79 (m, 0.8H) 3.88 (s, 0.7H) 3.90 (s, 0.7H) 3.92 (s, 2.6H) 3.94-4.06 (m, 0.7H) 4.12 (q, J=7.22 Hz, 1.9H) 4.21-4.33 (m, 0.7H) 4.39 (q, J=7.12 Hz, 0.2H) 5.67 (s, 0.2H) 5.71-5.90 (m, 0.7H) 6.95-7.02 (m, 1.0H) 7.06 (dd, J=8.55, 2.75 Hz, 0.2H) 7.12 (dd, J=8.70, 2.59 Hz, 0.82H) 7.46-7.57 (m, 1.2H) 7.64 (s, 0.8H) 7.69 (d, J=8.55 Hz, 0.9H) 7.76-7.85 (m, 0.9H) 8.14 (s, 0.2H) 8.22 (s, 0.8H) 12.40 (s, 0.1H). LC-MS retention time 2.78 min; 556 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

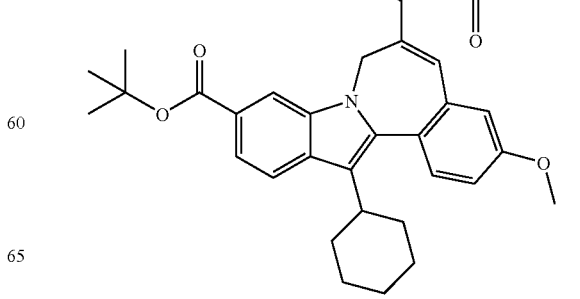

tert-Butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate tert-Butyl 13-cyclohexyl-6-(3-ethoxy-3-oxopropanoyl)-3-methoxy-7H-indolo[2,1-a][2]benzazepine-10-carboxylate (1.63 g, 2.92 mmol) was dissolved in N,N-dimethylformamide dimethyl acetal (7.0 mL, 52.7 mmol) in a 50 ml round bottom flask. The reaction was maintained under a nitrogen atmosphere and heated in oil bath under refluxing conditions (110° C.) for 2.75 hrs. The reaction was then cooled reaction under a nitrogen atmosphere and the volatiles were evaporated in vacuo to give an orange colored foam. TLC analysis (SiO2 plate, elution-50% diethyl ether in hexanes) confirmed that the reaction had gone to completion. This material was dried in vacuo at room temperature overnight to yield 1.87 g of the enamine intermediate as an orange amber foam which was used in the next step without any further purification. LC-MS of intermediate enamine: LC-MS retention time 2.81 min; 613 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 10% MeOH/90% H2O/0.1% trifluoroacetic acid and solvent B was 10% H2O/90% MeOH/0.1% trifluoroacetic acid. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-methyl-1H-pyrazol-5-yl]-3-methoxy-, 1,1-Dimethylethyl ester and 7H-indolo[2,1-a][2]benzazepine-10-carboxylic acid, 13-cyclohexyl-6-[4-(ethoxycarbonyl)-1-methyl-1H-pyrazol-3-yl]-3-methoxy-, 1,1-dimethylethyl ester The intermediate enamine, tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate, (1.83 g, 2.99 mmol) was dissolved in absolute ethanol (10 mL). Within a few minutes of dissolution in ethanol the reaction became heterogeneous with a fine yellow/orange precipitate forming. Methylhydrazine (0.173 mL, 3.29 mmol) was added to the reaction and the reaction was placed under a nitrogen atmosphere with a condenser. The reaction was heated to 80 C and remained heterogeneous at 80 C. An additional 5 ml of absolute ethanol was added and the reaction stirred at 80 C for 15 minutes. The reaction was still heterogeneous and 1,4-dioxane (5 ml) was added and the reaction slowly became homogeneous. The reaction was heated for 2 hours then cooled and the volatiles removed in vacuo to obtain an orange amber foam. The residue was dissolved in benzene and then volatiles removed in vacuo and the sample was dried at room temperature overnight in vacuo to yield 1.79 g of a yellow amorphous solid/foam. LC-MS analysis indicated two possible isomeric products. 102 mg of the crude product was purified by reverse phase prep HPLC. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (4 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system. First eluting product is 7H-indolo[2,1-a][2]benzazepine-10-carboxylic acid, 13-cyclohexyl-6-[4-(ethoxycarbonyl)-1-methyl-1H-pyrazol-5-yl]-3-methoxy-, 1,1-dimethylethyl ester with retention time of 11.7 minutes with the minor component product being 7H-indolo[2,1-a][2]benzazepine-10-carboxylic acid, 13-cyclohexyl-6-[4-(ethoxycarbonyl)-1-methyl-1H-pyrazol-3-yl]-3-methoxy-, 1,1-dimethylethyl ester with a retention of 14.5 minutes.

7H-indolo[2,1-a][2]benzazepine-10-carboxylic acid, 13-cyclohexyl-6-[4-(ethoxycarbonyl)-1-methyl-1H-pyrazol-5-yl]-3-methoxy-, 1,1-dimethylethyl ester. 1H NMR (500 MHz, CHLOROFORM-D) δ ppm 1.13-1.27 (m, 1H) 1.30 (t, J=7.02 Hz, 3H) 1.34-1.55 (m, 3H) 1.58 (s, 9H) 1.61-1.84 (m, 3H) 1.85-2.00 (m, 1H) 1.99-2.18 (m, 3H) 2.86 (t, J=11.75 Hz, 1H) 3.28 (s, 3H) 3.90 (s, 3H) 4.27 (d, J=4.27 Hz, 2H) 4.71 (s, 1H) 4.97 (s, 1H) 6.77 (s, 1H) 6.93 (d, J=2.44 Hz, 1H) 7.07 (dd, J=8.55, 2.44 Hz, 1H) 7.65 (d, J=8.55 Hz, 1H) 7.79-7.88 (m, 2H) 7.97 (s, 1H). LC-MS retention time 3.92 min; 596 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 1 min, and an analysis time of 6 min where solvent A was 5% acetoni-

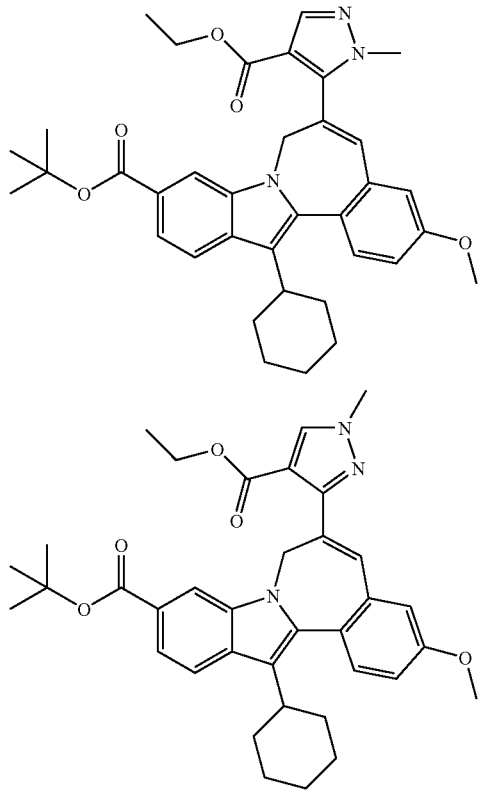

trile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-methyl-1H-pyrazol-3-yl]-3-methoxy-, 1,1-dimethylethyl ester. 1H NMR (500 MHz, CHLOROFORM-D) δ ppm 1.13-1.26 (m, 1H) 1.30 (t, J=7.17 Hz, 3H) 1.33-1.60 (m, 3H) 1.61 (s, 9H) 1.64-1.83 (m, 3H) 1.91 (s, 2H) 1.98-2.16 (m, 3H) 2.82-2.91 (m, 1H) 3.90 (s, 3H) 3.94 (s, 3H) 4.20-4.30 (m, 2H) 4.41 (d, J=14.04 Hz, 1H) 5.76 (d, J=14.04 Hz, 1H) 6.96-7.03 (m, 2H) 7.49-7.54 (m, 1H) 7.64 (dd, J=8.39, 1.37 Hz, 1H) 7.79 (d, J=8.55 Hz, 1H) 7.84 (s, 1H) 7.90 (s, 1H) 8.26 (s, 1H). LC-MS retention time 4.26 min; 596 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 1 min, and an analysis time of 6 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. The remainder of the sample (1.615 g) was adsorbed onto 4 g of silica gel using dichloromethane and chromatographed on 50 g of silica gel slurry packed using 2% ethyl acetate in dichloromethane and eluting with 2% ethyl acetate in dichloromethane. The first component to elute is the minor product, 7H-indolo[2,1-a][2]benzazepine-10-carboxylic acid, 13-cyclohexyl-6-[4-(ethoxycarbonyl)-1-methyl-1H-pyrazol-3-yl]-3-methoxy-, 1,1-dimethylethyl ester, 179 mg isolated. The second component, 7H-indolo[2,1-a][2]benzazepine-10-carboxylic acid, 13-cyclohexyl-6-[4-(ethoxycarbonyl)-1-methyl-1H-pyrazol-5-yl]-3-methoxy-, 1,1-dimethylethyl ester was the major component to elute and yielded 966 mg.

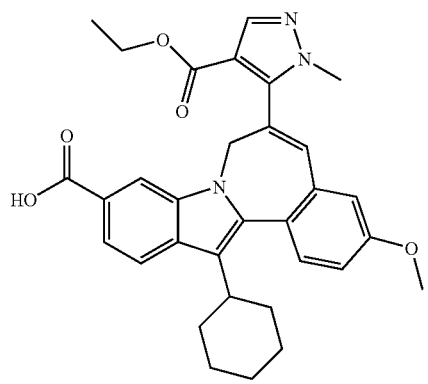

7H-indolo[2,1-a][2]benzazepine-10-carboxylic acid, 13-cyclohexyl-6-[4-(ethoxycarbonyl)-1-methyl-1H-pyrazol-5-yl]-3-methoxy- 7H-indolo[2,1-a][2]benzazepine-10-carboxylic acid, 13-cyclohexyl-6-[4-(ethoxycarbonyl)-1-methyl-1H-pyrazol-5-yl]-3-methoxy-, 1,1-dimethylethyl ester (53 mg, 0.089 mmol) was dissolved in 1,2-dichloroethane (2 mL), under a nitrogen atmosphere. Trifluoroacetic acid was then added (2 ml, 26.0 mmol), and the reaction was stirred at room temperature for 2.5 hours. The volatiles were then removed in vacuo and the residue dissolved in benzene and the resultant solution was evaporated under reduced pressure to remove residual TFA. This process was repeated once. This gave the title compound as a yellow solid, (46.2 mg).

1H NMR (500 MHz, CHLOROFORM-D) δ ppm 1.12-1.26 (m, 1H) 1.31 (t, J=7.02 Hz, 3H) 1.40 (s, 2H) 1.51-1.89 (m, 3H) 1.87-2.23 (m, 4H) 2.87 (t, J=11.29 Hz, 1H) 3.29 (s, 3H) 3.91 (s, 3H) 4.27 (br.s, 2H) 4.73 (br.s, 1H) 4.97 (br.s, 1H) 6.78 (s, 1H) 6.94 (d, J=2.14 Hz, 1H) 7.08 (dd, J=8.55, 2.44 Hz, 1H) 7.54 (d, J=8.85 Hz, 1H) 7.77 (d, J=8.24 Hz, 1H) 7.86-7.95 (m, 2H) 7.98 (s, 1H) 8.36 (br.s, 2H). LC-MS retention time 1.84 min; 538 m/z (MH–). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 0 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

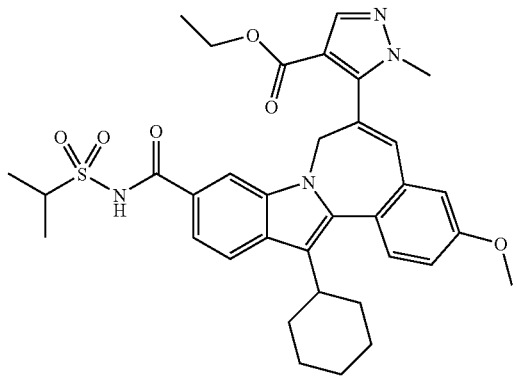

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-, ethyl ester 7H-indolo[2,1-a][2]benzazepine-10-carboxylic acid, 13-cyclohexyl-6-[4-(ethoxycarbonyl)-1-methyl-1H-pyrazol-5-yl]-3-methoxy- (981 mg, 1.818 mmol) was dissolved in THF (18 mL). Carbonyldiimidazole (649 mg, 4.00 mmol) was added to the reaction. The reaction was placed under a nitrogen atmosphere and stirred at room temperature for 45 minutes then heated to reflux for 1 hour. The reaction was cooled under a nitrogen atmosphere and propane-2-sulfonamide (1164 mg, 9.45 mmol) was added to the reaction followed by DBU (0.548 mL, 3.64 mmol). The reaction was then immersed in oil bath at 80° C. under nitrogen atmosphere and heated overnight at 70-80° C. The reaction was then diluted with ethyl acetate and the organic layer washed sequentially with 1.0 N aqueous hydrochloric acid, 0.1M aqueous NaH2PO4 and brine. The organic layer was dried over MgSO4, filtered and volatiles removed in vacuo to yield a yellow foam which was dried in vacuo at room temperature overnight to yield 1.170 g of a yellow amorphous solid. Proton NMR analysis revealed the presence of propane-2-sulfonamide (1.41 ppm, d, 500 MHz, CDCl3) in the sample. The crude sample was dissolved in approximately 200 ml of dichloromethane and washed 2× with 125 ml of water, then sequentially with 1N aqueous hydrochloric acid, 2× with 0.1M NaH2PO4 then again with 1N aqueous hydrochloric acid. The dichloromethane solution was dried over sodium sulfate, filtered and volatiles removed and the product dried in vacuo at room temperature overnight to yield 1.046 g (89%) of the title compound as a yellow amorphous solid. 1H NMR (500 MHz, CHLOROFORM-D) δ ppm 0.80-0.90 (m, 1H) 1.20-1.27 (m, 4H) 1.30 (t, J=7.02 Hz, 4H) 1.32-1.43 (m, 3H) 1.46 (d, J=7.02 Hz, 6H) 1.53-1.64 (m, 3H) 1.79 (d, J=9.77 Hz, 3H) 1.85-2.13 (m, 5H) 2.81-2.91 (m, 1H) 3.90 (s, 3H) 4.00-4.10 (m, 1H) 4.24 (s, 2H) 4.71 (d, J=12.21 Hz, 1H) 4.99 (d, J=16.48 Hz, 1H) 6.77 (s, 1H) 6.94 (d, J=2.44 Hz, 1H) 7.08 (dd, J=8.55, 2.75 Hz, 1H) 7.38 (dd, J=8.55, 1.22 Hz, 1H) 7.52 (d, J=8.85 Hz, 1H) 7.76 (d, J=1.22 Hz, 1H) 7.86-7.92 (m, 2H) 8.26 (br.s, 1H). LC-MS retention time 1.79 min; 643 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

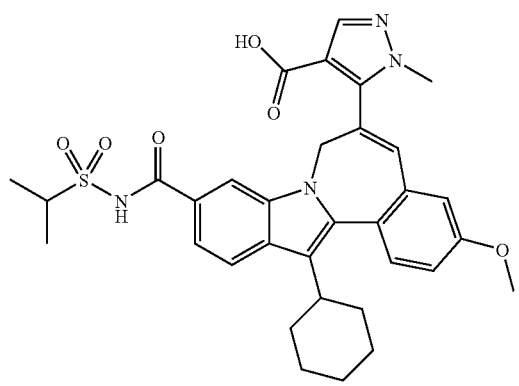

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-, ethyl ester (1.044 g, 1.619 mmol) was dissolved in THF (11 ml) with heating. DMF was then added (5 mL) and the mixture was gently heated to ensure dissolution. The mixture was then cooled to room temperature and tetrabutylammonium hydroxide (6.5 ml, 6.50 mmol) (1.0M in methanol) was added. The resultant mixture was then stirred at room temperature under nitrogen for 2.5 hrs and progress was monidered by LC-MS. Results showed predominately methyl and ethyl esters. The mixture was then stirred for an additional 3 hrs, after which a further 2.0 mL (2 mmol) of tetrabutylammonium hydroxide (1.0M in methanol) was added and the reaction was stirred at room temperature under nitrogen for a further 2 days. Subsequent analysis shows reaction had proceeded to approximately 22% conversion to the desired acid product. Volatiles (methanol, ethanol, THF) were removed from the reaction in vacuo (30° C.) using a rotary evaporator. To the reaction was added 200 uL of 10N aqueous sodium hydroxide and 4 ml of THF. The reaction was mixed by placing on rotary evaporator, gently heated (25° C., 3 hrs) then add approximately 6 ml of DMF and heat at 35 C for 3 hrs and using house vacuum to remove volatiles generated from hydrolysis. Analysis of the reaction by LC-MS indicated approximately 83% conversion to acid product. The reaction was stirred overnight at room temperature and subsequent analysis showed no additional conversion to product. An additional 4.0 ml of 1.0M tetrabutylammonium hydroxide in methanol was added to the reaction. The reaction was placed on a rotary evaporator and volatiles removed in vacuo and the reaction continued to heat at 40-45 C for approximately 6 hours. The reaction was then worked up by adding 1N aqueous hydrochloric acid (100 ml) into the reaction and then the mixture was rinsed into a 500 ml separatory funnel using ethyl acetate bring the organic volume to approx. 200 ml. Partition the reaction between ethyl acetate and 1.0N aqueous hydrochloric acid. The organic layer was wash 3× (~300 ml each) with 1.0N aqueous hydrochloric acid, then brine and dried over MgSO4, filtered and the volatiles removed in vacuo to yield 1.03 g of a yellow film foam. The sample was dried in vacuo at room temperature to 0.92 g (92%) of the title compound. LC-MS retention time 1.48 min; 615 m/z (MH−). LC data was recorded on a Shimadzu LC-10AS liquid chromatograph equipped with a Phenomenex-Luna 10 u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

An alternative procedure for the preparation of the title compound is described below.

Dissolve 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-, ethyl ester (1.044 g, 1.619 mmol) in a pre-mixed solution of THF (20 mL), MeOH (20 mL) and sodium hydroxide (20 mL, 20.00 mmol). The reaction was homogenous and was stirred at room temperature under a nitrogen atmosphere for 26 hrs then concentrated in vacuo using a rotary evaporator with a bath temperature at 20 C. The reaction was poured into 1N aqueous hydrochloric acid and extract using ethyl acetate. The combined organic layers were washed sequentially with 1N aqueous hydrochloric acid and brine, then dried over magnesium sulfate, filtered and solvent removed in vacuo. The crude product dried in vacuo at room temperature to yield 1.68 g of an orange amorphous solid. The crude product was dissolved in chloroform (approximately 50 mL) with heating and hexanes were added until some material starts to precipitate but re-dissolves on swirling (approximately 10-12 ml of hexanes). The mixture was allowed to slowly cool to room temperature and then allowed to stand at room temperature for a few hours. The very fine particulate yellow precipitate was filtered using a Buchner funnel and dried in vacuo at room temperature to yield 819 mg (45%) of purified product as a bright yellow amorphous solid. The title compound 4.6 mg was dissolved in CDCl3 (2 ml) with the addition of approximately 5 drops of CD3OD to aid in dissolution for 1H NMR acquisition.

1H NMR (500 MHz, CHLOROFORM-D/CD3OD) δ ppm 1.11-1.39 (m, 3H) 1.41 (d, J=7.02 Hz, 6H) 1.47-1.65 (m, 1H) 1.75 (d, J=8.85 Hz, 2H) 1.82-2.27 (m, 13H) 2.77-2.90 (m, 1H) 3.28 (s, 3H) 3.88 (s, 3H) 3.97-4.06 (m, 1H) 4.66 (s, 1H) 5.01 (s, 1H) 6.76 (s, 1H) 6.92 (d, J=2.75 Hz, 1H) 7.04 (dd, J=8.70, 2.59 Hz, 1H) 7.47-7.54 (m, 2H) 7.81 (d, J=1.22 Hz, 1H) 7.86 (d, J=8.54 Hz, 1H) 7.91 (s, 1H).

LC-MS retention time 1.39 min; 615 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

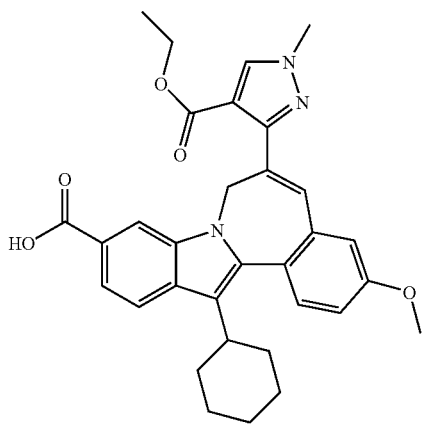

7H-indolo[2,1-a][2]benzazepine-10-carboxylic acid, 13-cyclohexyl-6-[4-(ethoxycarbonyl)-1-methyl-1H-pyrazol-3-yl]-3-methoxy- Dissolve 7H-indolo[2,1-a][2]benzazepine-10-carboxylic acid, 13-cyclohexyl-6-[4-(ethoxycarbonyl)-1-methyl-1H-pyrazol-3-yl]-3-methoxy-, 1,1-dimethylethyl ester (176 mg, 0.295 mmol) in 1,2-dichloroethane (3 mL), place reaction under a nitrogen atmosphere, then add trifluoroacetic acid (3 ml, 38.9 mmol). Stir the reaction at room temperature under a nitrogen atmosphere for 2 hr 20 min then remove volatiles in vacuo. Dissolve product in a mixture of benzene and dichloromethane then remove volatiles in vacuo. Repeat dissolution in benzene and dichloromethane and remove volatiles to aid in removal of trace trifluoroacetic acid. The title compound was dried in vacuo at room temperature to yield 164 mg of a yellow amorphous solid. 1H NMR (500 MHz, CHLOROFORM-D) δ ppm 1.01-1.29 (m, 3H) 1.32 (t, J=7.17 Hz, 3H) 1.35-1.53 (m, 2H) 1.52-1.85 (m, 3H) 1.86-2.20 (m, 4H) 2.79-2.95 (m, 1H) 3.91 (s, 3H) 3.97 (s, 3H) 4.27 (q, J=7.22 Hz, 2H) 4.41 (d, J=14.34 Hz, 1H) 5.84 (d, J=14.34 Hz, 1H) 6.97-7.08 (m, 2H) 7.54 (d, J=8.24 Hz, 1H) 7.76 (d, J=8.55 Hz, 1H) 7.85 (d, J=8.54 Hz, 1H) 7.91 (s, 1H) 7.95 (s, 1H) 8.50 (s, 1H). LC-MS retention time 2.08 min; 538 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 1 min, and an analysis time of 6 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

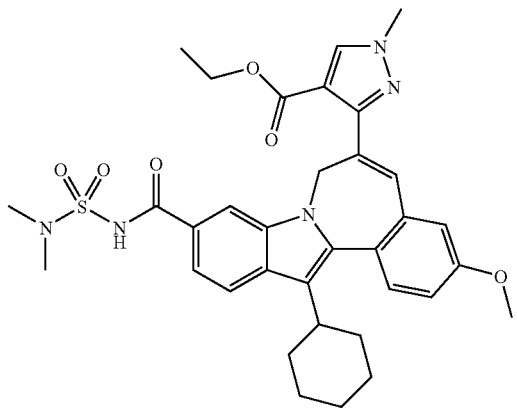

1H-pyrazole-4-carboxylic acid, 3-[13-cyclohexyl-10-[[[(dimethylamino)sulfonyl]amino]carbonyl]-3-methoxy-7H-indolo[2,1-a][2]benzazepin-6-yl]-1-methyl-, ethyl ester Dissolve 7H-indolo[2,1-a][2]benzazepine-10-carboxylic acid, 13-cyclohexyl-6-[4-(ethoxycarbonyl)-1-methyl-1H-pyrazol-3-yl]-3-methoxy- (60 mg, 0.111 mmol) in THF (1.0 mL), then add carbonyl diimidazole (42 mg, 0.259 mmol) to the reaction. The reaction was stirred under a nitrogen atmosphere for 1 hour at room temperature. The reaction was then heated at 70 C for 1 hour then cooled and N,N-dimethylsulfamide (70 mg, 0.564 mmol) was added to the reaction followed by DBU (0.034 mL, 0.222 mmol). The reaction was again capped under a nitrogen atmosphere and heated at 70 C for 16.5 hours. The reaction was diluted with ethyl acetate and washed sequentially with 1.0N aqueous hydrochloric acid, 0.1M aqueous NaH2PO4 and again with 1.0N aqueous hydrochloric acid, and finally with brine. The organic phase was dried over magnesium sulfate, filtered, solvent removed and the product dried in vacuo at room temperature to yield 70 mg of an amorphous yellow solid. 1H NMR (500 MHz, CHLOROFORM-D) δ ppm 0.76-0.95 (m, 2H) 1.12-1.26 (m, 5H) 1.32 (t, J=7.17 Hz, 3H) 1.38 (s, 2H) 1.51-1.61 (m, 4H) 1.67-1.81 (m, 3H) 1.87-2.01 (m, 2H) 2.01-2.11 (m, 3H) 2.82-2.92 (m, 1H) 3.06 (s, 6H) 3.91 (s, 3H) 3.96 (s, 3H) 4.26 (d, J=7.02 Hz, 2H) 4.42 (d, J=14.34 Hz, 1H) 5.75 (d, J=14.04 Hz, 1H) 6.99-7.05 (m, 2H) 7.38 (d, J=8.24 Hz, 1H) 7.52 (d, J=8.24 Hz, 1H) 7.85 (d, J=8.55 Hz, 1H) 7.89-7.96 (m, 2H) 8.18 (s, 1H) 8.36 (br.s, 1H). LC-MS retention time 2.34 min; 644 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient

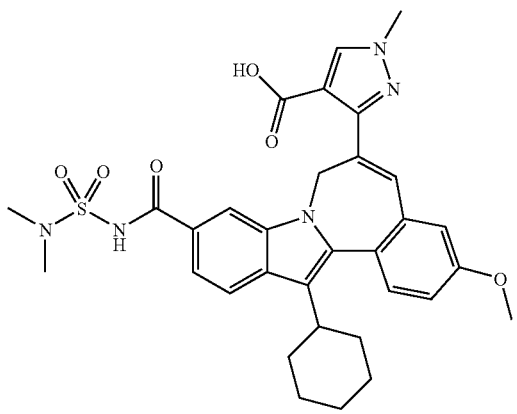

1H-pyrazole-4-carboxylic acid, 3-[13-cyclohexyl-10-
[[[(dimethylamino)sulfonyl]amino]carbonyl]-3-
methoxy-7H-indolo[2,1-a][2]benzazepin-6-yl]-1-
methyl- 1H-pyrazole-4-carboxylic acid, 3-[13-cyclohexyl-10-[[[(dimethylamino)sulfonyl]amino]carbonyl]-3-methoxy-7H-indolo[2,1-a][2]benzazepin-6-yl]-1-methyl-, ethyl ester (66 mg, 0.102 mmol) was dissolved in THF (1 mL) and a 1.0M solution of tetrabutylammonium hydroxide (0.41 mL, 0.410 mmol) in methanol was added to the reaction. The reaction was stirred at room temperature under a nitrogen atmosphere for 4 hrs then analyzed by LC-MS. The reaction was concentrated in vacuo on a rotary evaporator then 1 ml of THF was added to the reaction and the reaction once again capped under a nitrogen atmosphere. The reaction was placed in a water bath at 40 C and allowed to stir overnight. Sometime overnight the heating element on the water bath failed and the reaction was observed to at room temperature the next morning. LC-MS analysis of the reaction indicated the reaction was complete. The reaction was diluted with ethyl acetate and washed sequentially with 1.0N aqueous hydrochloric acid, then again with 1.0N aqueous hydrochloric acid and finally with brine. The organic layer was dried over magnesium sulfate, filtered and solvent removed in vacuo. The title compound was dried in vacuo to yield 63 mg of an amorphous yellow solid. 1H NMR (500 MHz, CHLOROFORM-D) δ ppm 0.81-0.97 (m, 3H) 1.18-1.30 (m, 4H) 1.30-1.65 (m, 6H) 1.66-1.83 (m, 3H) 1.84-2.10 (m, 6H) 2.84-2.92 (m, 3H) 3.04 (s, 6H) 3.88 (s, 3H) 3.97 (s, 3H) 4.43 (d, J=14.34 Hz, 1H) 5.68 (d, J=13.73 Hz, 1H) 6.99 (d, J=2.75 Hz, 1H) 7.02 (dd, J=8.55, 2.44 Hz, 1H) 7.35 (d, J=8.24 Hz, 1H) 7.52 (d, J=8.55 Hz, 1H) 7.77 (s, 1H) 7.83 (d, J=8.24 Hz, 1H) 7.98 (s, 1H) 8.15 (s, 1H) 8.71 (s, 1H). LC-MS retention time 1.58 min; 616 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

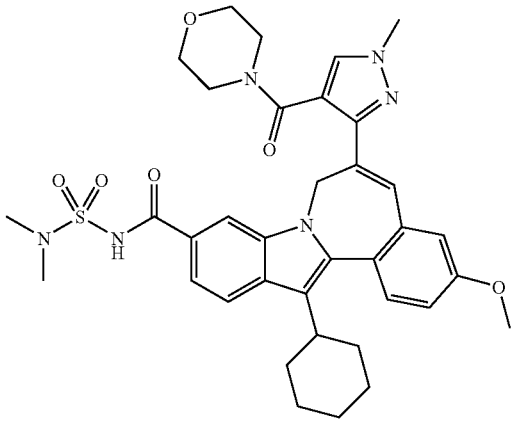

7H-indolo[2,1-a][2]benzazepine-10-carboxamide,
13-cyclohexyl-N-[(dimethylamino)sulfonyl]-3-methoxy-6-[1-methyl-4-(4-morpholinylcarbonyl)-1H-
pyrazol-3-yl]-

1H-pyrazole-4-carboxylic acid, 3-[13-cyclohexyl-10-[[[(dimethylamino)sulfonyl]amino]carbonyl]-3-methoxy-7H-indolo[2,1-a][2]benzazepin-6-yl]-1-methyl- (57 mg, 0.092 mmol) was dissolved in DMF (1.0 ml) and TBTU (55.8 mg, 0.174 mmol) added to the reaction. The reaction was capped under a nitrogen atmosphere and stir at room temperature for 1 hour then DMAP (47 mg, 0.385 mmol) was added to the reaction followed by morpholine (16 μL, 0.184 mmol). The reaction was capped under a nitrogen atmosphere and stirred at room temperature overnight. The reaction was diluted with ethyl acetate and washed sequentially with 1.0N aqueous hydrochloric acid, 0.1M aqueous NaH2PO4 and brine. The organic phase was dried over magnesium sulfate, filtered and solvent removed in vacuo. The title compound was dried overnight in vacuo at room temperature to yield 63 mg of a yellow amorphous solid. The title compound was further purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (total volume 2 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 60% solvent A/40% solvent B to 0% solvent A/100% solvent B, a gradient time of 12 minutes with a run time of 25 minutes using % A=10% acetonitrile, 90% water, 0.1% TFA % B=90% acetonitrile, 10% water, 0.1% TFA solvent system. The sample was run as two 1 ml injections. The run time of the second Prep HPLC run was truncated to 15 minutes base on data from the first run. The product fractions (retention time=8.75 min.) were combined and solvent removed in vacuo. The compound was dried at room temperature in vacuo to yield 38 mg of the title compound as a yellow amorphous solid. 1H NMR (500 MHz, CHLOROFORM-D) δ ppm 1.23 (q, J=12.21 Hz, 1H) 1.30-1.56 (m, 3H) 1.77 (d, J=10.38 Hz, 2H) 1.90-2.14 (m, 4H) 2.54-2.81 (m, 4H) 2.82-2.95 (m, 2H) 2.95-3.05 (m, 2H) 3.07 (s, 6H) 3.09-3.39 (m, 5H) 3.90 (s, 3H) 3.97 (s, 3H) 4.45 (d, J=14.65 Hz, 1H) 5.45 (d, J=14.65 Hz, 1H) 6.95 (d, J=2.75 Hz, 1H) 6.97 (s, 1H) 7.04 (dd, J=8.70, 2.59 Hz, 1H) 7.46 (dd, J=8.55, 1.53 Hz, 1H) 7.52 (d, J=8.55 Hz, 1H) 7.55 (s, 1H) 7.89 (d, J=8.55 Hz, 1H) 7.94 (d, J=1.22 Hz, 1H) 9.13 (br.s, 1H). LC-MS retention time 1.82 min; 685 m/z (MH−). LC data was recorded on a Shimadzu LC-10AS liquid chromatograph equipped with a Phenomenex-Luna 10u C18 3.0× 50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

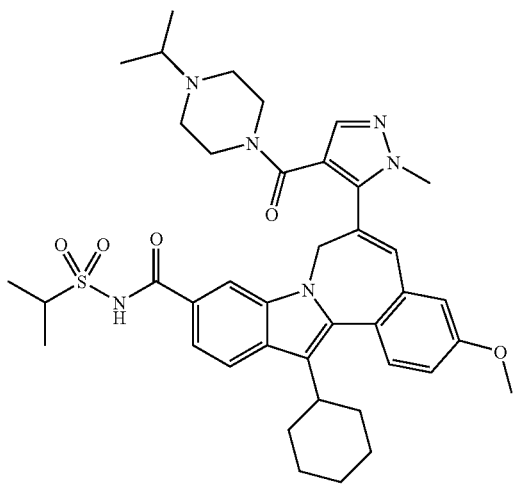

7H-indolo[2,1-a][2]benzazepine-10-carboxamide, 13-cyclohexyl-3-methoxy-N-[(1-methylethyl)sulfonyl]-6-[1-methyl-4-[[4-(1-methylethyl)-1-piperazinyl]carbonyl]-1H-pyrazol-5-yl]-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.92 g, 1.5 mmol) was dissolved in DMF (25 ml) and HATU (1141 mg, 3.0 mmol) was added followed by diisopropylethylamine (1306 uL, 7.5 mmol). A 1 mL solution of the reaction solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-/HATU/DIEA was transferred a 16×100 mm wheaton vial containing 1-isopropylpiperazine (36.9 mg, 0.288 mmol). The reaction was capped and shaken at room temperature overnight. The reaction was transferred into a 96 well plate and the reaction vial rinsed with DMF (800 uL) to bring the final reaction volume to 1.800 mL. The reaction mixture was purified by reverse phase HPLC under the following conditions. The Prep HPLC was controlled by Dionex Chromeleon 6.70 sp1 LC software using Varian a prostar binary pump with 50 mL/min pump head and detection using a Sedex 75 ELS detector for fraction collection. A Dionex UVD340U UV spectrometer was used to observe the UV trace of the HPLC run. A Waters Sunfire C18 19 mm×25 mm 10u was employed for the isolation using a solvent system of A=water and 20 mM ammonium acetate, B=acetonitrile. The following gradient was used: 80% A and 20% B hold for 3 minutes followed by a 19 minute gradient to 5% A and 95% B with a final hold at 5% A and 95% B of 5 minutes. The flow rate for purification was 20 ml/min. The fractions of interest were collected and concentrated to dryness using a Zymark Turbo Vap Evaporator. NMR analysis was performed on the peaks of interest (analytical retention time 5.69 minutes and 6.30 minutes). The title compound was determined to be the peak with analytical retention time of 6.30 minutes by NMR analysis (rotamers). 1H NMR (500 MHz, CHLOROFORM-D) δ ppm 0.17 (s, 0.5H) 0.91 (t, J=6.87 Hz, 3.3H) 1.10 (t, J=14.95 Hz, 1.2H) 1.17-1.32 (m, 2.6H) 1.33-1.59 (m, 13.1H) 1.68-1.83 (m, 3.5H) 1.88-2.18 (m, 8.7H) 2.20-2.67 (m, 7.8H) 2.76-3.05 (m, 3.3H) 3.23 (d, J=10.99 Hz, 1.3H) 3.29-3.53 (m, 1.6H) 3.63-3.86 (m, 2.7H) 3.88-3.98 (m, 6.0H) 4.02-4.10 (m, 1.0H) 4.61 (d, J=14.65 Hz, 1.3H) 4.89 (d, J=14.95 Hz, 0.9H) 6.76-6.86 (m, 0.8H) 6.91-7.00 (m, 1.9H) 7.06-7.13 (m, 1.3H) 7.51-7.57 (m, 1.4H) 7.57-7.66 (m, 1.6H) 7.66-7.75 (m, 1.9H) 7.89 (d, J=8.55 Hz, 1.5H). LCMS analysis using MassLynx 4.0 SP4 LC-MS software, a CTC-Leap HTS-PAL autosampler, with an Agilent 1100 binary pump, Agilent 1100 photodiode array UV detector, Polymer Lab 2100 ELS detector (Temp=45 C, nebulizer temp 35 C) and a Waters ZQ With ESCi mass spectrometer. The analysis was performed using a Phenomenex Gemini 4.6×150 mm C18 3u column with a mobile phase solvent system of A=water and 20 mM ammonium acetate, B=acetonitrile with a flow rate of 1.0 ml/min and a gradient starting at 70% A and 30% B and a final composition 5% A and 95% B, gradient time of 11 minutes and a hold time of 2 minutes to give an analysis runtime of 13 minutes.

Retention time=6.63 minutes, m/z=725 (MH+).

The following compounds were synthesized by an analogous method as described above for 7H-indolo[2,1-a][2]benzazepine-10-carboxamide, 13-cyclohexyl-N-[(dimethylamino)sulfonyl]-3-methoxy-6-[1-methyl-4-(4-morpholinylcarbonyl-1H-pyrazol-3-yl]- and 7H-indolo[2,1-a][2]benzazepine-10-carboxamide, 13-cyclohexyl-3-methoxy-N-[(1-methylethyl)sulfonyl]-6-[1-methyl-4-[[4-(1-methylethyl)-1-piperazinyl]carbonyl]-1H-pyrazol-5-yl]-. Analytical LCMS data on the following examples were acquired using the following columns and conditions. Method 1: Gradient: 3 minutes; Flow rate: 5 mL/min; Stop time: Gradient time+1 minute; Eluent A: 5% CH3CN/95% H2O with 10 mM NH4OAc; Eluent B: 95% CH3CN/5% H2O with 10 mM NH4OAc; Initial % B=30; Final % B=100; Column: Waters Xterra, 3 mm×50 mm, S7. Method 2: Gradient: 3 minutes; Flow rate: 5 mL/min; Stop time: Gradient time+1 minute; Eluent A=10% methanol, 90% water, 0.1% trifluoroacetic acid; % B=90% methanol, 10% water, 0.1% trifluoroacetic acid; Initial % B=40; Final % B=100; Column: Phenomenex Luna 3.0 mm×50 mm S10.

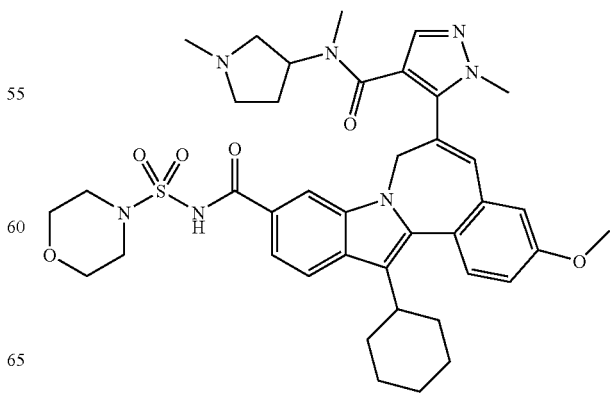

7H-indolo[2,1-a][2]benzazepine-10-carboxamide, 13-cyclohexyl-3-methoxy-6-[1-methyl-4-[[methyl(1-methyl-3-pyrrolidinyl)amino]carbonyl]-1H-pyrazol-5-yl]-N-(4-morpholinylsulfonyl)-. LCMS: m/e 756 (M+H), ret time 2.30 min.

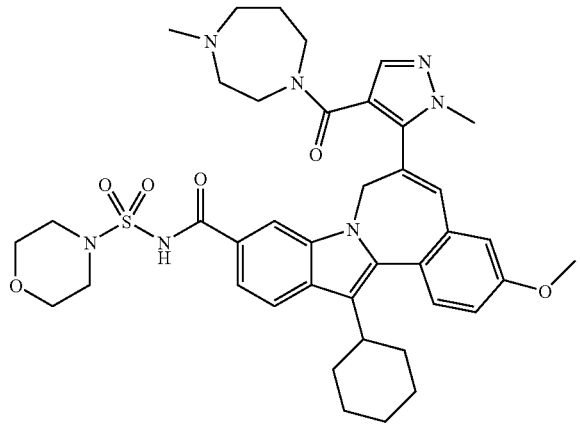

7H-indolo[2,1-a][2]benzazepine-10-carboxamide, 13-cyclohexyl-6-[4-[(hexahydro-4-methyl-1H-1,4-diazepin-1-yl)carbonyl]-1-methyl-1H-pyrazol-5-yl]-3-methoxy-N-(4-morpholinylsulfonyl)-. LCMS: m/e 756 (M+H), ret time 2.10 min.

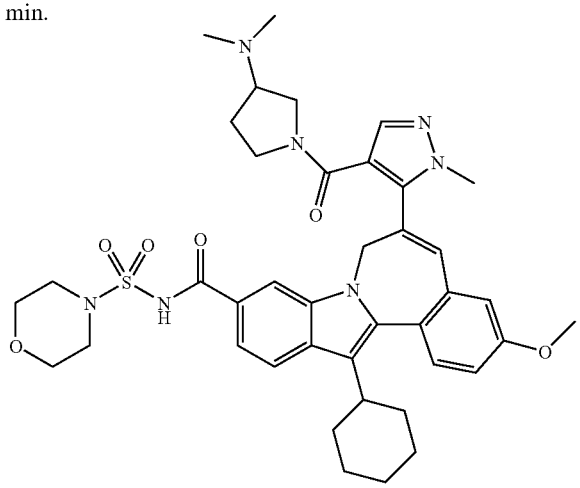

7H-indolo[2,1-a][2]benzazepine-10-carboxamide, 13-cyclohexyl-6-[4-[[3-(dimethylamino)-1-pyrrolidinyl]carbonyl]-1-methyl-1H-pyrazol-5-yl]-3-methoxy-N-(4-morpholinylsulfonyl)-. LCMS: m/e 756 (M+H), ret time 2.40 min.

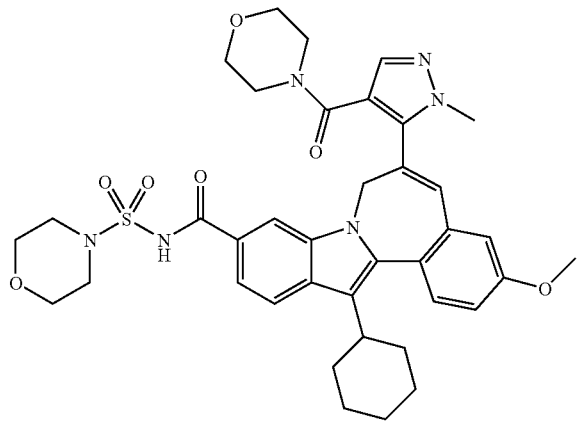

7H-indolo[2,1-a][2]benzazepine-10-carboxamide, 13-cyclohexyl-3-methoxy-6-[1-methyl-4-(4-morpholinylcarbonyl)-1H-pyrazol-5-yl]-N-(4-morpholinylsulfonyl)-. LCMS: m/e 729 (M+H), ret time 2.60 min.

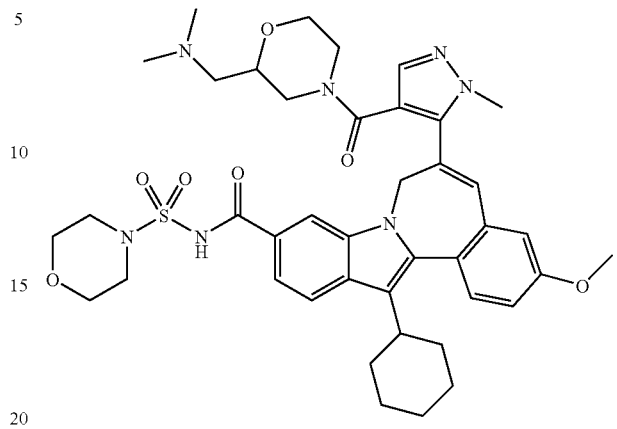

7H-indolo[2,1-a][2]benzazepine-10-carboxamide, 13-cyclohexyl-6-[4-[[2-[(dimethylamino)methyl]-4-morpholinyl]carbonyl]-1-methyl-1H-pyrazol-5-yl]-3-methoxy-N-(4-morpholinylsulfonyl)-. LCMS: m/e 787 (M+H), ret time 2.40 min.

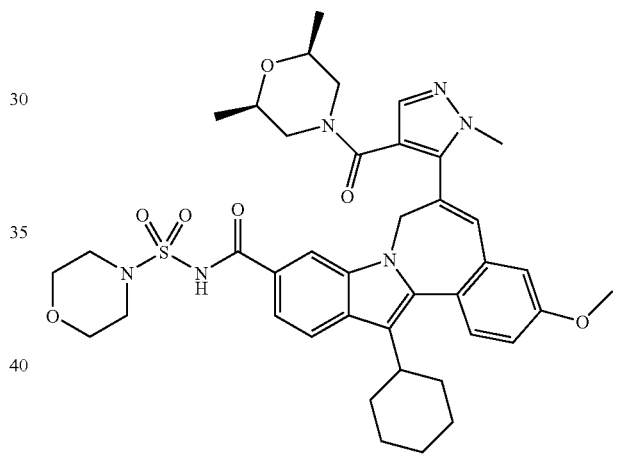

7H-indolo[2,1-a][2]benzazepine-10-carboxamide, 13-cyclohexyl-6-[4-[[(2R,6S)-2,6-dimethyl-4-morpholinyl]carbonyl]-1-methyl-1H-pyrazol-5-yl]-3-methoxy-N-(4-morpholinylsulfonyl)-. LCMS: m/e 757 (M+H), ret time 2.80 min.

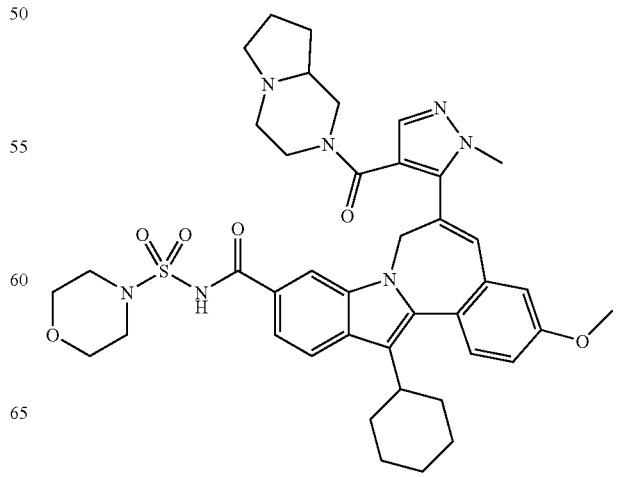

61

7H-indolo[2,1-a][2]benzazepine-10-carboxamide, 13-cyclohexyl-6-[4-[(hexahydropyrrolo[1,2-a]pyrazin-2(1H)-yl)carbonyl]-1-methyl-1H-pyrazol-5-yl]-3-methoxy-N-(4-morpholinylsulfonyl)-. LCMS: m/e 768 (M+H), ret time 2.40 min.

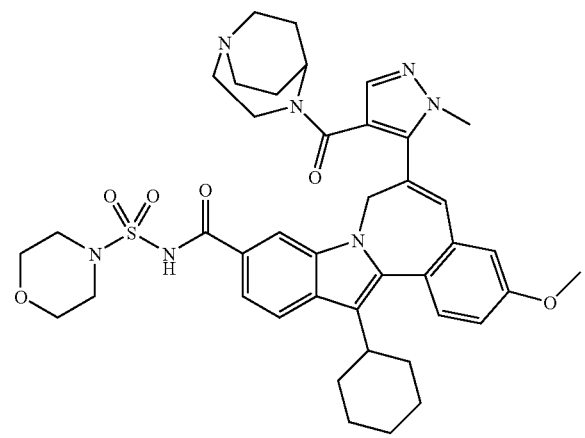

7H-indolo[2,1-a][2]benzazepine-10-carboxamide, 13-cyclohexyl-6-[4-(1,4-diazabicyclo[3.2.2]non-4-ylcarbonyl)-1-methyl-1H-pyrazol-5-yl]-3-methoxy-N-(4-morpholinylsulfonyl)-. LCMS: m/e 768 (M+H), ret time 2.10 min.

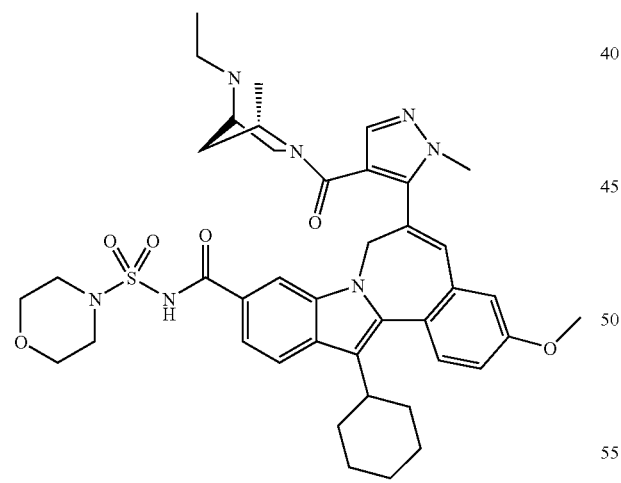

7H-indolo[2,1-a][2]benzazepine-10-carboxamide, 13-cyclohexyl-6-[4-[[(1R,4R)-5-ethyl-2,5-diazabicyclo[2.2.1]hept-2-yl]carbonyl]-1-methyl-1H-pyrazol-5-yl]-3-methoxy-N-(4-morpholinylsulfonyl)-. LCMS: m/e 768 (M+H), ret time 2.30 min.

62

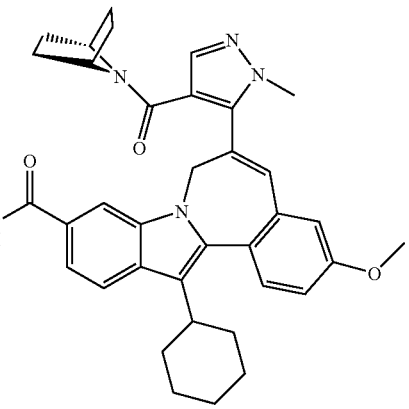

7H-indolo[2,1-a][2]benzazepine-10-carboxamide, 6-[4-(7-azabicyclo[2.2.1]hept-7-ylcarbonyl)-1-methyl-1H-pyrazol-5-yl]-13-cyclohexyl-3-methoxy-N-(4-morpholinylsulfonyl)-. LCMS: m/e 739 (M+H), ret time 3.10 min.

7H-indolo[2,1-a][2]benzazepine-10-carboxamide, 13-cyclohexyl-3-methoxy-6-[1-methyl-4-[(4-methyl-1-piperazinyl)carbonyl]-1H-pyrazol-5-yl]-N-(4-morpholinylsulfonyl)-. LCMS: m/e 742 (M+H), ret time 2.30 min.

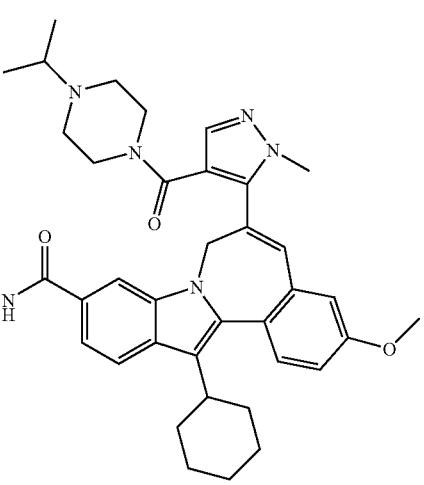

63

7H-indolo[2,1-a][2]benzazepine-10-carboxamide, 13-cyclohexyl-3-methoxy-6-[1-methyl-4-[[4-(1-methylethyl)-1-piperazinyl]carbonyl]-1H-pyrazol-5-yl]-N-(4-morpholinylsulfonyl)-. LCMS: m/e 771 (M+H), ret time 2.40 min.

64

7H-indolo[2,1-a][2]benzazepine-10-carboxamide, 13-cyclohexyl-3-methoxy-6-[1-methyl-4-[[(1R,5S)-3-methyl-3,8-diazabicyclo[3.2.1]oct-8-yl]carbonyl]-1H-pyrazol-5-yl]-N-(4-morpholinylsulfonyl)-. LCMS: m/e 768 (M+H), ret time 2.60 min.

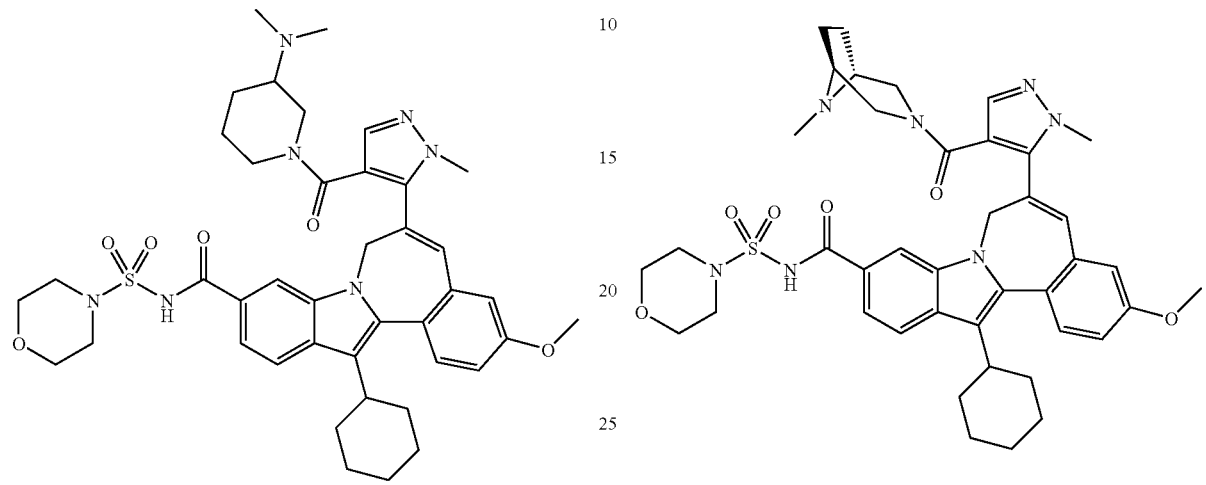

7H-indolo[2,1-a][2]benzazepine-10-carboxamide, 13-cyclohexyl-6-[4-[[3-(dimethylamino)-1-piperidinyl]carbonyl]-1-methyl-1H-pyrazol-5-yl]-3-methoxy-N-(4-morpholinylsulfonyl)-. LCMS: m/e 771 (M+H), ret time 2.20 min.

7H-indolo[2,1-a][2]benzazepine-10-carboxamide, 13-cyclohexyl-3-methoxy-6-[1-methyl-4-[[(1R,5S)-8-methyl-3,8-diazabicyclo[3.2.1]oct-3-yl]carbonyl]-1H-pyrazol-5-yl]-N-(4-morpholinylsulfonyl)-. LCMS: m/e 768 (M+H), ret time 2.60 min.

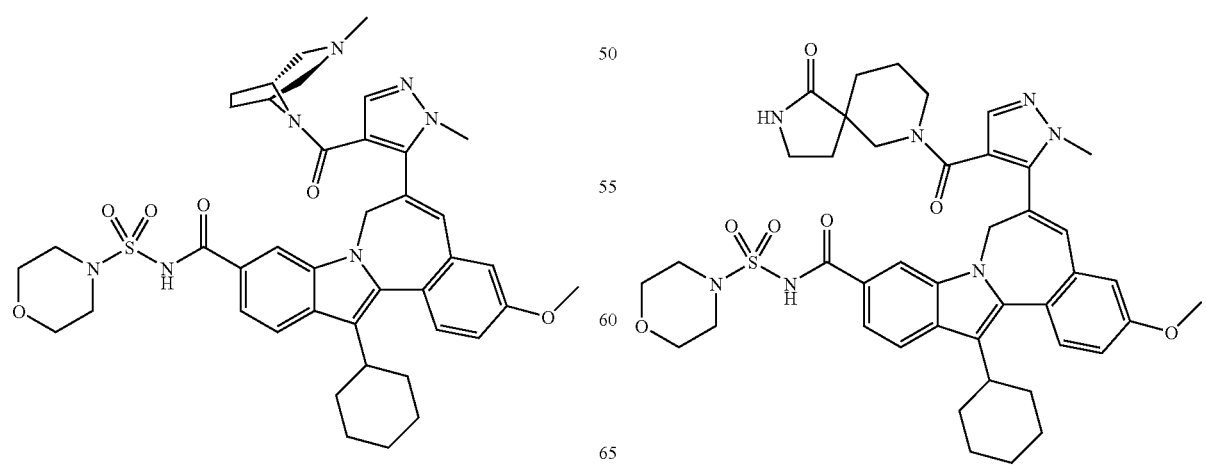

7H-indolo[2,1-a][2]benzazepine-10-carboxamide, 13-cyclohexyl-3-methoxy-6-[1-methyl-4-[(1-oxo-2,7-diazaspiro[4.5]dec-7-yl)carbonyl]-1H-pyrazol-5-yl]-N-(4-morpholinylsulfonyl)-. LCMS: m/e 797 (M+H), ret time 2.40 min.

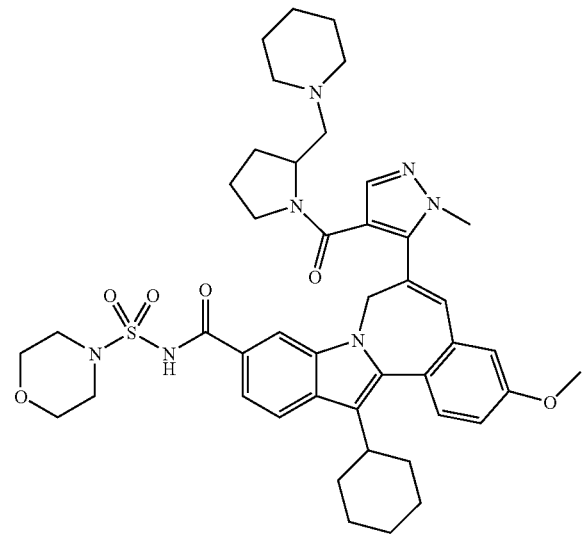

7H-indolo[2,1-a][2]benzazepine-10-carboxamide, 13-cyclohexyl-3-methoxy-6-[1-methyl-4-[[2-(1-piperidinylmethyl)-1-pyrrolidinyl]carbonyl]-1H-pyrazol-5-yl]-N-(4-morpholinylsulfonyl)-. LCMS: m/e 811 (M+H), ret time 2.50 min.

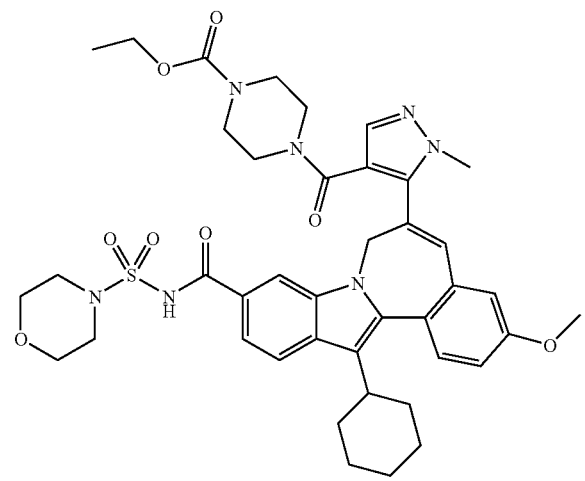

1-piperazinecarboxylic acid, 4-[[5-[13-cyclohexyl-3-methoxy-10-[[(4-morpholinylsulfonyl)amino]carbonyl]-7H-indolo[2,1-a][2]benzazepin-6-yl]-1-methyl-1H-pyrazol-4-yl]carbonyl]-, ethyl ester. LCMS: m/e 800 (M+H), ret time 2.60 min.

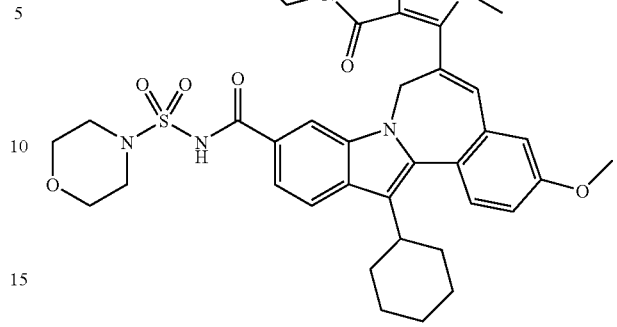

7H-indolo[2,1-a][2]benzazepine-10-carboxamide, 13-cyclohexyl-3-methoxy-6-[4-[[(2-methoxyethyl)(1-methylethyl)amino]carbonyl]-1-methyl-1H-pyrazol-5-yl]-N-(4-morpholinylsulfonyl)-. LCMS: m/e 759 (M+H), ret time 2.80 min.

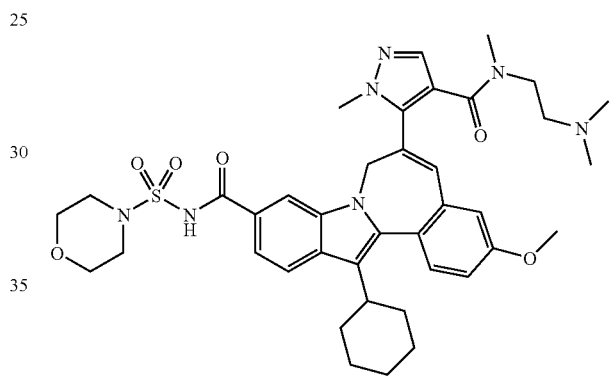

7H-indolo[2,1-a][2]benzazepine-10-carboxamide, 13-cyclohexyl-6-[4-[[[2-(dimethylamino)ethyl]methylamino]carbonyl]-1-methyl-1H-pyrazol-5-yl]-3-methoxy-N-(4-morpholinylsulfonyl)-. LCMS: m/e 744 (M+H), ret time 2.20 min.

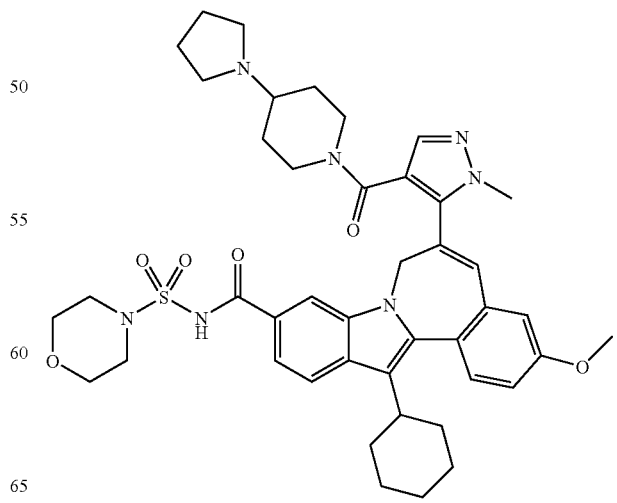

7H-indolo[2,1-a][2]benzazepine-10-carboxamide, 13-cyclohexyl-3-methoxy-6-[1-methyl-4-[[4-(1-pyrrolidinyl)-1-piperidinyl]carbonyl]-1H-pyrazol-5-yl]-N-(4-morpholinylsulfonyl)-. LCMS: m/e 797 (M+H), ret time 2.30 min.

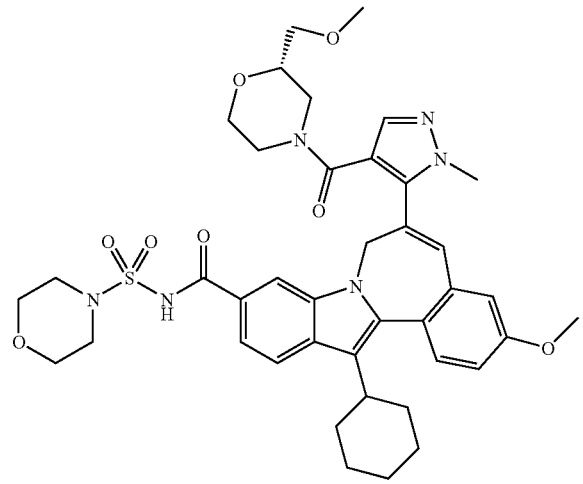

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-methyl-1H-pyrazol-5-yl]-N-(4-morpholinylsulfonyl)-. LCMS: m/e 773 (M+H), ret time 2.60 min.

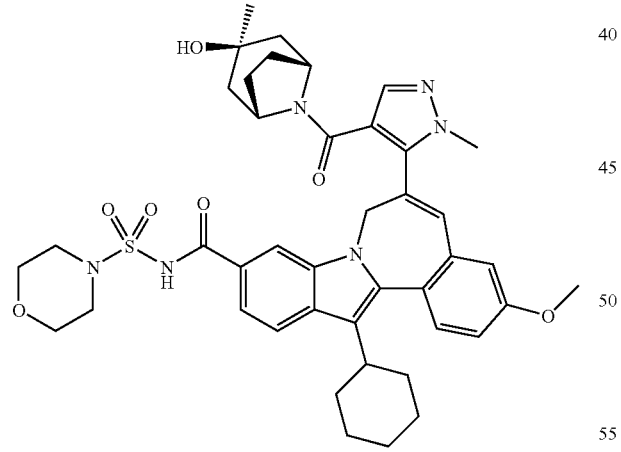

7H-indolo[2,1-a][2]benzazepine-10-carboxamide, 13-cyclohexyl-6-[4-[[(3-endo)-3-hydroxy-3-methyl-8-azabicyclo[3.2.1]oct-8-yl]carbonyl]-1-methyl-1H-pyrazol-5-yl]-3-methoxy-N-(4-morpholinylsulfonyl)-. LCMS: m/e 784 (M+H), ret time 2.70 min.

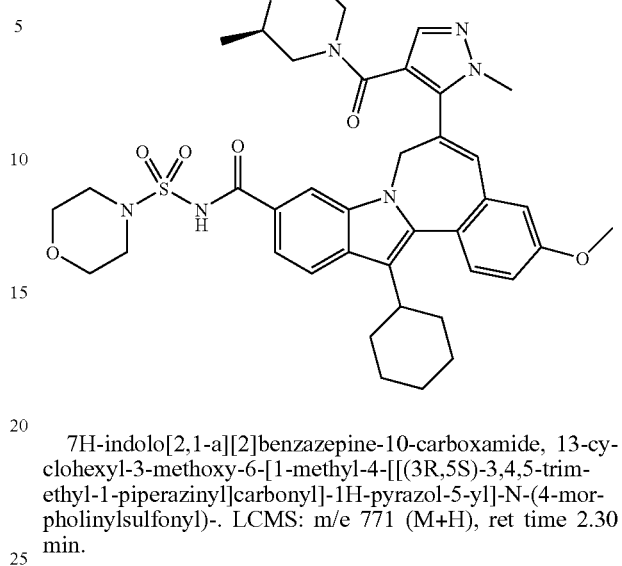

7H-indolo[2,1-a][2]benzazepine-10-carboxamide, 13-cyclohexyl-3-methoxy-6-[1-methyl-4-[[(3R,5S)-3,4,5-trimethyl-1-piperazinyl]carbonyl]-1H-pyrazol-5-yl]-N-(4-morpholinylsulfonyl)-. LCMS: m/e 771 (M+H), ret time 2.30 min.

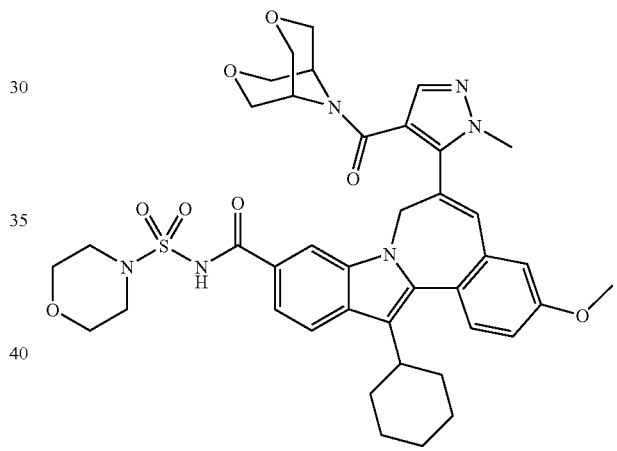

7H-indolo[2,1-a][2]benzazepine-10-carboxamide, 13-cyclohexyl-6-[4-(3,7-dioxa-9-azabicyclo[3.3.1]non-9-ylcarbonyl)-1-methyl-1H-pyrazol-5-yl]-3-methoxy-N-(4-morpholinylsulfonyl)-. LCMS: m/e 771 (M+H), ret time 2.60 min.

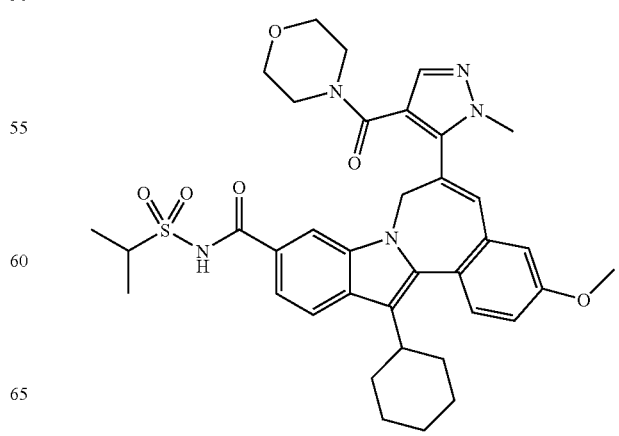

7H-indolo[2,1-a][2]benzazepine-10-carboxamide, 13-cyclohexyl-3-methoxy-N-[(1-methylethyl)sulfonyl]-6-[1-methyl-4-(4-morpholinylcarbonyl)-1H-pyrazol-5-yl]-: LCMS: m/e 686 (M+H), ret time 3.49 min (method 2).

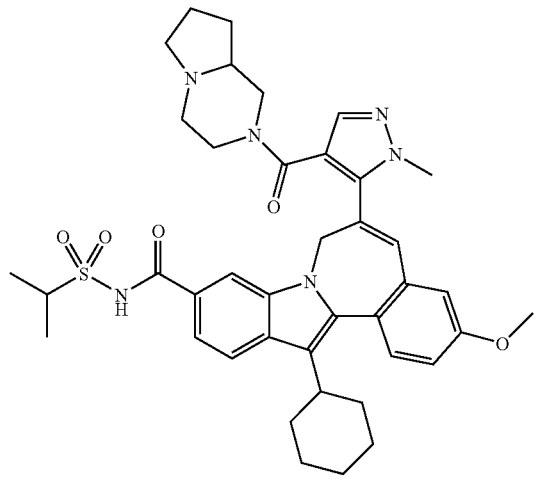

7H-indolo[2,1-a][2]benzazepine-10-carboxamide, 13-cyclohexyl-6-[4-[(hexahydropyrrolo[1,2-a]pyrazin-2(1H)-yl)carbonyl]-1-methyl-1H-pyrazol-5-yl]-3-methoxy-N-[(1-methylethyl)sulfonyl]-: LCMS: m/e 725 (M+H), ret time 2.99 min (method 2).

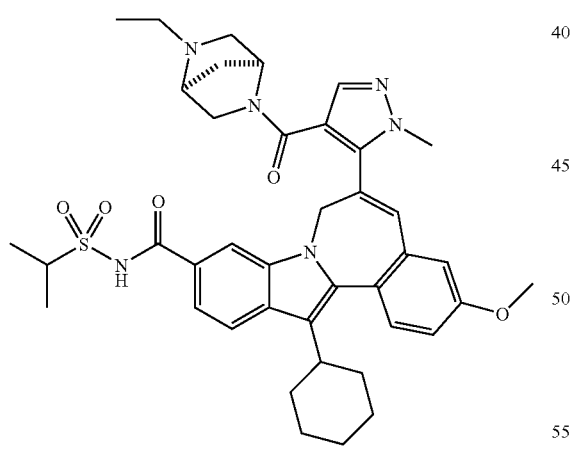

7H-indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-methyl-1H-pyrazol-5-yl]-3-methoxy-N-[(1-methylethyl)sulfonyl]-: LCMS: m/e 725 (M+H), ret time 3.11 min (method 2).

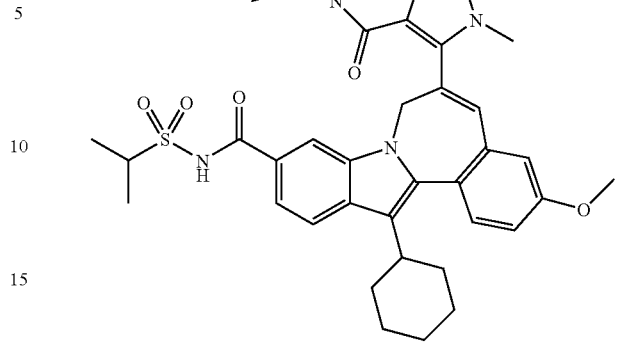

7H-indolo[2,1-a][2]benzazepine-10-carboxamide, 6-[4-(7-azabicyclo[2.2.1]hept-7-ylcarbonyl)-1-methyl-1H-pyrazol-5-yl]-13-cyclohexyl-3-methoxy-N-[(1-methylethyl)sulfonyl]-: LCMS: m/e 696 (M+H), ret time 3.32 min (method 2).

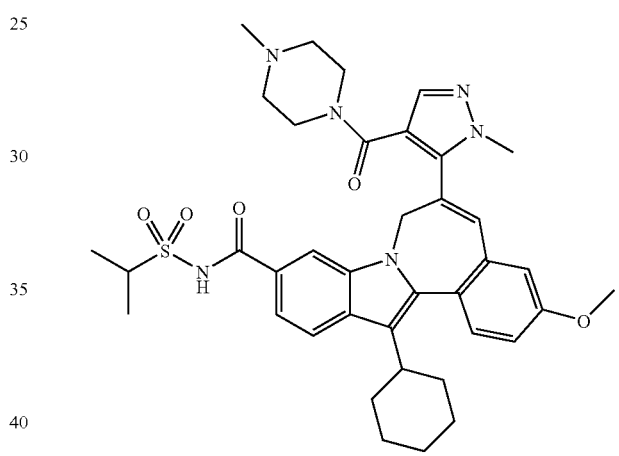

7H-indolo[2,1-a][2]benzazepine-10-carboxamide, 13-cyclohexyl-3-methoxy-N-[(1-methylethyl)sulfonyl]-6-[1-methyl-4-[(4-methyl-1-piperazinyl)carbonyl]-1H-pyrazol-5-yl]-: LCMS: m/e 699 (M+H), ret time 3.05 min (method 2).

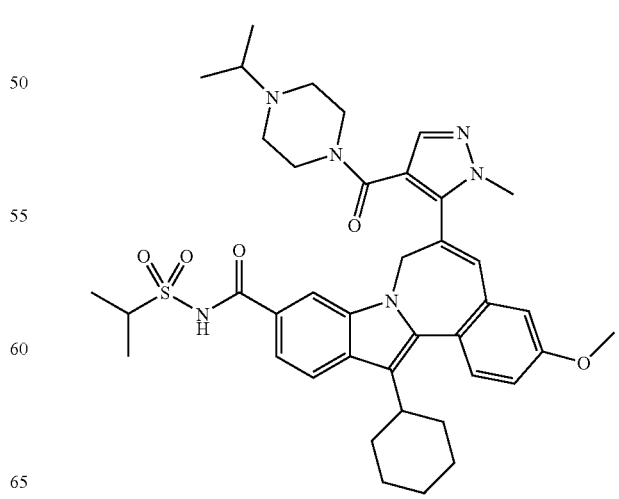

7H-indolo[2,1-a][2]benzazepine-10-carboxamide, 13-cyclohexyl-3-methoxy-N-[(1-methylethyl)sulfonyl]-6-[1-methyl-4-[[4-(1-methylethyl)-1-piperazinyl]carbonyl]-1H-pyrazol-5-yl]-: LCMS: m/e 727 (M+H), ret time 3.19 min (method 2).

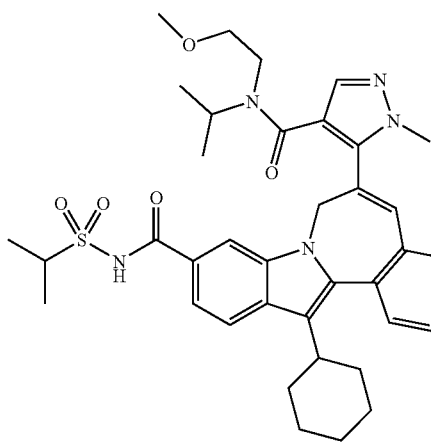

7H-indolo[2,1-a][2]benzazepine-10-carboxamide, 13-cyclohexyl-3-methoxy-6-[4-[[(2-methoxyethyl)(1-methylethyl)amino]carbonyl]-1-methyl-1H-pyrazol-5-yl]-N-[(1-methylethyl)sulfonyl]-: LCMS: m/e 716 (M+H), ret time 3.37 min (method 2).

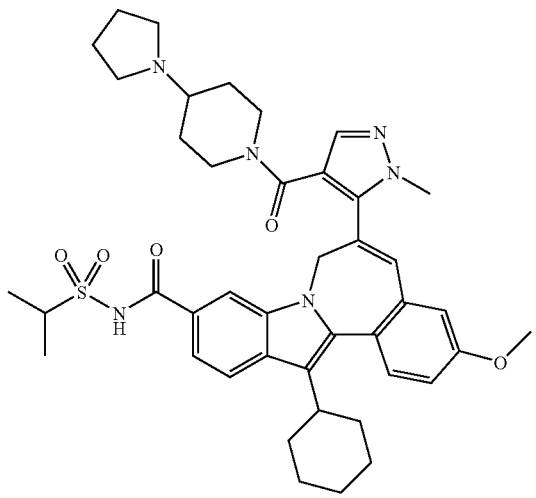

7H-indolo[2,1-a][2]benzazepine-10-carboxamide, 13-cyclohexyl-3-methoxy-N-[(1-methylethyl)sulfonyl]-6-[1-methyl-4-[[4-(1-pyrrolidinyl)-1-piperidinyl]carbonyl]-1H-pyrazol-5-yl]-: LCMS: m/e 753 (M+H), ret time 3.22 min (method 2).

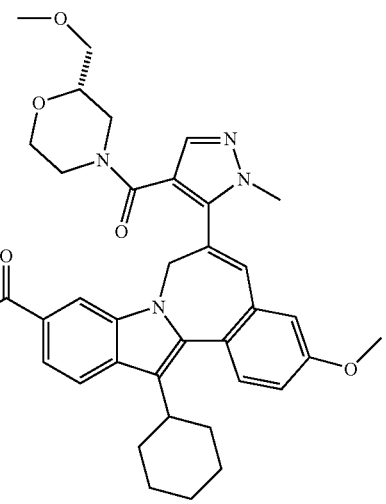

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-methyl-1H-pyrazol-5-yl]-N-[(1-methylethyl)sulfonyl]-: LCMS: m/e 730 (M+H), ret time 3.51 min (method 2).

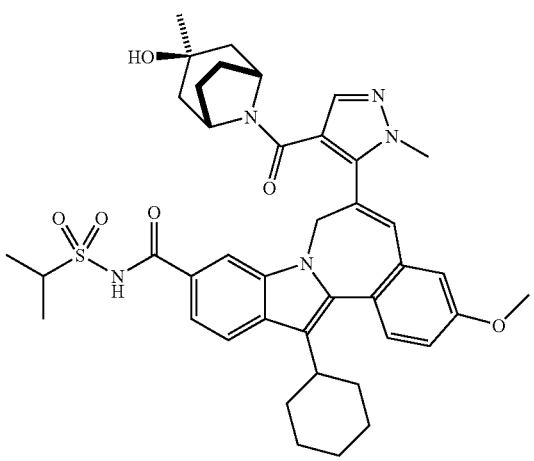

7H-indolo[2,1-a][2]benzazepine-10-carboxamide, 13-cyclohexyl-6-[4-[[(3-endo)-3-hydroxy-3-methyl-8-azabicyclo[3.2.1]oct-8-yl]carbonyl]-1-methyl-1H-pyrazol-5-yl]-3-methoxy-N-[(1-methylethyl)sulfonyl]-: LCMS: m/e 740 (M+H), ret time 2.53 min (method 2).

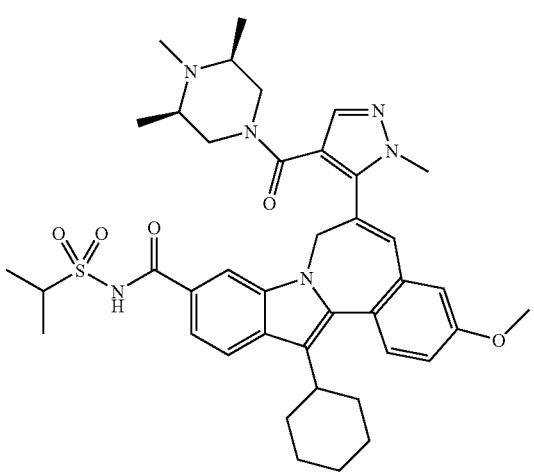

7H-indolo[2,1-a][2]benzazepine-10-carboxamide, 13-cyclohexyl-3-methoxy-N-[(1-methylethyl)sulfonyl]-6-[1-methyl-4-[[(3R,5S)-3,4,5-trimethyl-1-piperazinyl]carbonyl]-1H-pyrazol-5-yl]-: LCMS: m/e 727 (M+H), ret time 2.26 min (method 2).

7H-indolo[2,1-a][2]benzazepine-10-carboxamide, 13-cyclohexyl-N-(cyclopentylsulfonyl)-6-[4-[[(2R,6S)-2,6-dimethyl-4-morpholinyl]carbonyl]-1-methyl-1H-pyrazol-5-yl]-3-methoxy-: LCMS: m/e 740 (M+H), ret time 2.84 min (method 1).

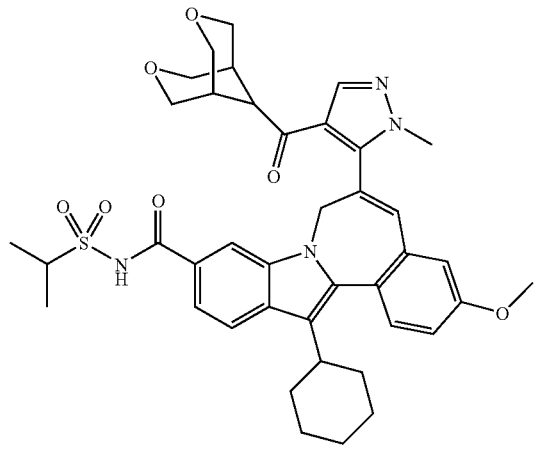

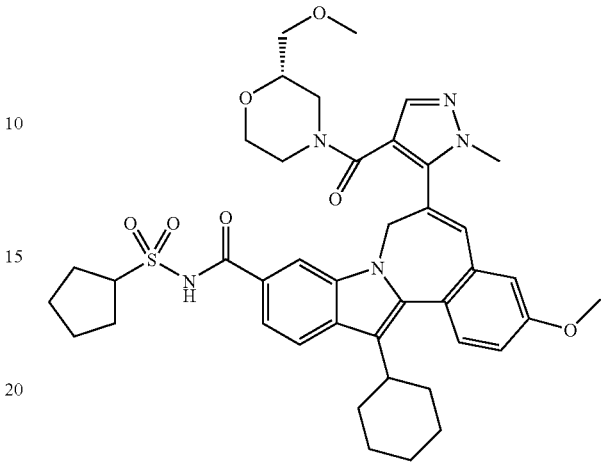

7H-indolo[2,1-a][2]benzazepine-10-carboxamide, 13-cyclohexyl-6-[4-(3,7-dioxa-9-azabicyclo[3.3.1]non-9-ylcarbonyl)-1-methyl-1H-pyrazol-5-yl]-3-methoxy-N-[(1-methylethyl)sulfonyl]-: LCMS: m/e 727 (M+H), ret time 3.50 min (method 2).

7H-indolo[2,1-a][2]benzazepine-10-carboxamide, 13-cyclohexyl-N-(cyclopentylsulfonyl)-3-methoxy-6-[4-[[(2S)-2-(methoxymethyl)-4-morpholinyl]carbonyl]-1-methyl-1H-pyrazol-5-yl]-: LCMS: m/e 756 (M+H), ret time 2.79 min (method 1).

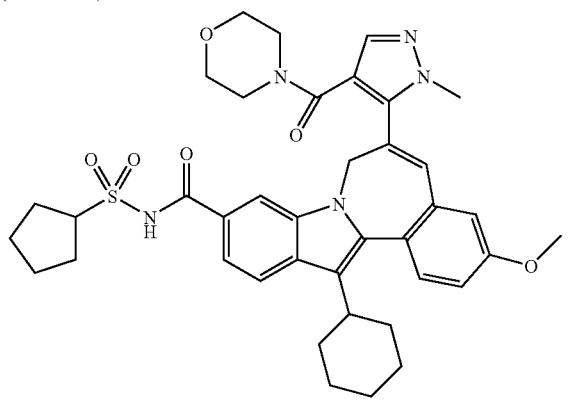

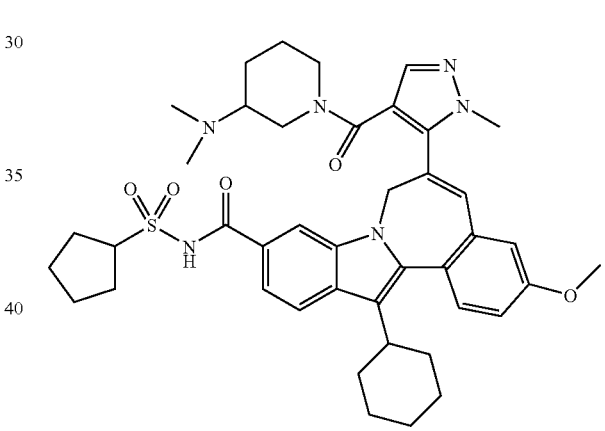

7H-indolo[2,1-a][2]benzazepine-10-carboxamide, 13-cyclohexyl-N-(cyclopentylsulfonyl)-3-methoxy-6-[1-methyl-4-(4-morpholinylcarbonyl)-1H-pyrazol-5-yl]-: LCMS: m/e 712 (M+H), ret time 2.65 min (method 1).

7H-indolo[2,1-a][2]benzazepine-10-carboxamide, 13-cyclohexyl-N-(cyclopentylsulfonyl)-6-[4-[[3-(dimethylamino)-1-piperidinyl]carbonyl]-1-methyl-1H-pyrazol-5-yl]-3-methoxy-: LCMS: m/e 753 (M+H), ret time 2.41 min (method 1).

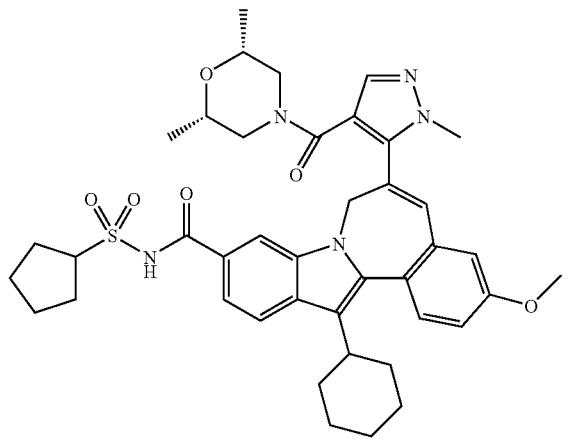

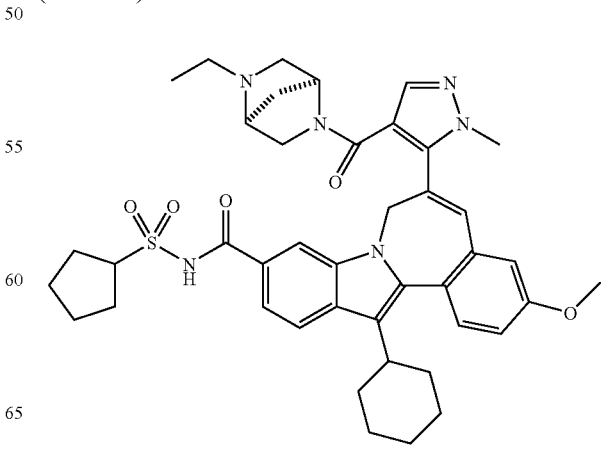

7H-indolo[2,1-a][2]benzazepine-10-carboxamide, 13-cyclohexyl-N-(cyclopentylsulfonyl)-6-[4-[[(1S,4S)-5-ethyl-2,5-diazabicyclo[2.2.1]hept-2-yl]carbonyl]-1-methyl-1H-pyrazol-5-yl]-3-methoxy-: LCMS: m/e 751 (M+H), ret time 2.51 min (method 1).

7H-indolo[2,1-a][2]benzazepine-10-carboxamide, 13-cyclohexyl-N-(cyclopentylsulfonyl)-3-methoxy-6-[1-methyl-4-[(3-methyl-3,8-diazabicyclo[3.2.1]oct-8-yl)carbonyl]-1H-pyrazol-5-yl]-: LCMS: m/e 751 (M+H), ret time 2.36 min (method 1).

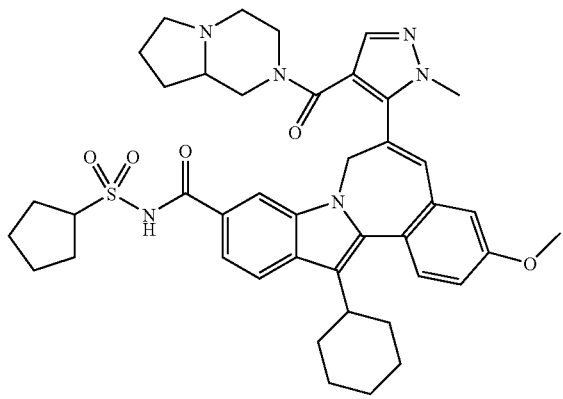

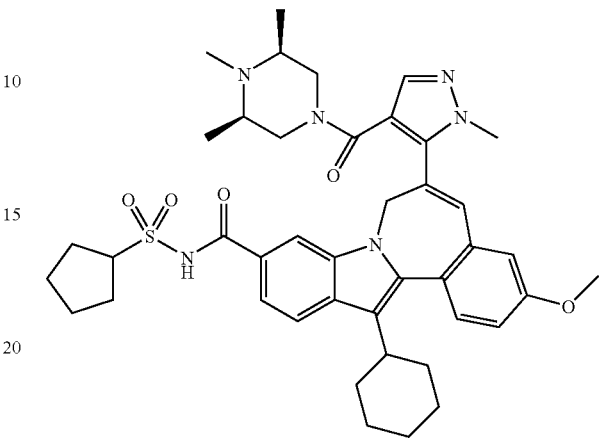

7H-indolo[2,1-a][2]benzazepine-10-carboxamide, 13-cyclohexyl-N-(cyclopentylsulfonyl)-6-[4-[(hexahydropyrrolo[1,2-a]pyrazin-2(1H)-yl)carbonyl]-1-methyl-1H-pyrazol-5-yl]-3-methoxy-: LCMS: m/e 751 (M+H), ret time 2.29 min (method 1).

7H-indolo[2,1-a][2]benzazepine-10-carboxamide, 13-cyclohexyl-N-(cyclopentylsulfonyl)-3-methoxy-6-[1-methyl-4-[[(3R,5S)-3,4,5-trimethyl-1-piperazinyl]carbonyl]-1H-pyrazol-5-yl]-: LCMS: m/e 753 (M+H), ret time 2.39 min (method 1).

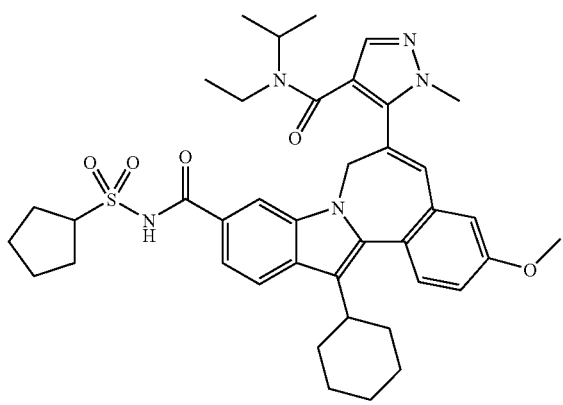

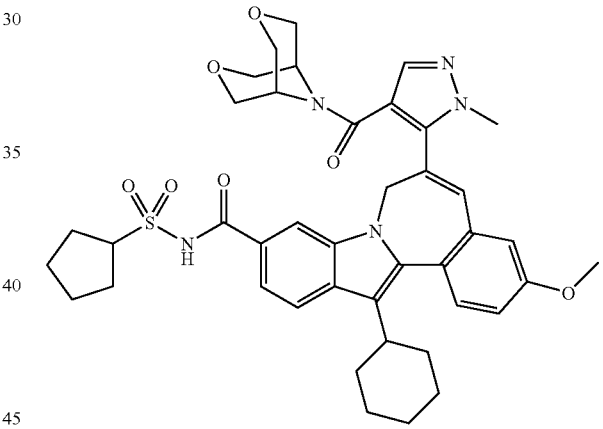

7H-indolo[2,1-a][2]benzazepine-10-carboxamide, 13-cyclohexyl-N-(cyclopentylsulfonyl)-6-[4-[[ethyl(1-methylethyl)amino]carbonyl]-1-methyl-1H-pyrazol-5-yl]-3-methoxy-: LCMS: m/e 712 (M+H), ret time 2.45 min (method 1).

7H-indolo[2,1-a][2]benzazepine-10-carboxamide, 13-cyclohexyl-N-(cyclopentylsulfonyl)-6-[4-(3,7-dioxa-9-azabicyclo[3.3.1]non-9-ylcarbonyl)-1-methyl-1H-pyrazol-5-yl]-3-methoxy-: LCMS: m/e 754 (M+H), ret time 2.87 min (method 1).

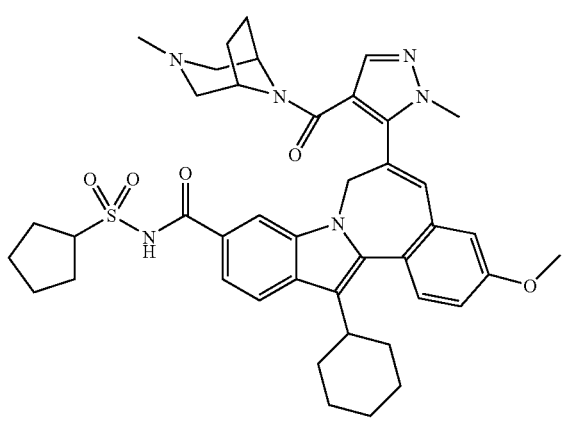

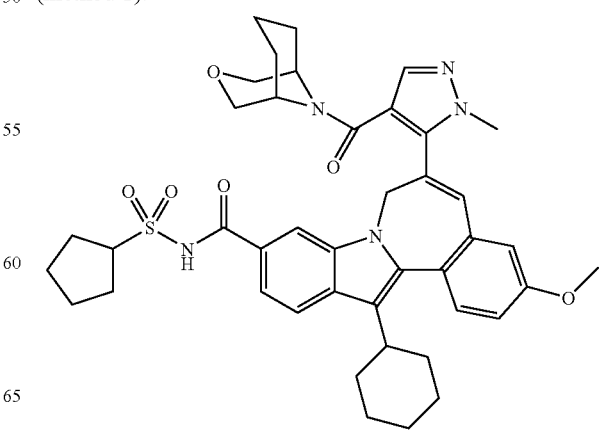

7H-indolo[2,1-a][2]benzazepine-10-carboxamide, 13-cyclohexyl-N-(cyclopentylsulfonyl)-3-methoxy-6-[1-methyl-4-(3-oxa-9-azabicyclo[3.3.1]non-9-ylcarbonyl)-1H-pyrazol-5-yl]-: LCMS: m/e 752 (M+H), ret time 2.92 min (method 1).

The following compounds were synthesized by an analogous method as described above for 7H-indolo[2,1-a][2]benzazepine-10-carboxamide, 13-cyclohexyl-N-[(dimethylamino)sulfonyl]-3-methoxy-6-[1-methyl-4-(4-morpholinylcarbonyl)-1H-pyrazol-3-yl]- and 7H-indolo[2,1-a][2]benzazepine-10-carboxamide, 13-cyclohexyl-3-methoxy-N-[(1-methylethyl)sulfonyl]-6-[1-methyl-4-[[4-(1-methylethyl)-1-piperazinyl]carbonyl]-1H-pyrazol-5-yl]-. Analytical LCMS data on the following examples were acquired using the following column and conditions: Gradient: 6 minutes; Flow rate: 4 mL/min; Stop time: 6 minutes; Eluent A: 5% CH₃CN/95% H₂O with 10 mM NH₄OAc; Eluent B: 95% CH₃CN/5% H₂O with 10 mM NH₄OAc; Initial % B=0; Final % B=100; Column: Phenomenex Luna 4.6 mm×50 mm S5.

13-cyclohexyl-6-(1-ethyl-4-(((2R)-2-(methoxymethyl)-4-morpholinyl)carbonyl)-1H-pyrazol-5-yl)-N-(isopropylsulfonyl)-3-methoxy-7H-indolo[2,1-a][2]benzazepine-10-carboxamide LCMS: m/e 745 (M+H), ret time 4.90 min.

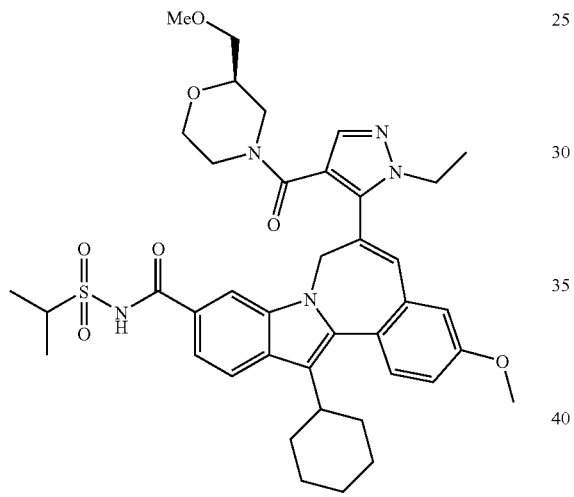

7H-indolo[2,1-a][2]benzazepine-10-carboxamide, 13-cyclohexyl-6-[1-ethyl-4-(3-oxa-9-azabicyclo[3.3.1]non-9-ylcarbonyl)-1H-pyrazol-5-yl]-3-methoxy-N-[(1-methylethyl)sulfonyl]-

LCMS: m/e 741 (M+H), ret time 5.80 min.

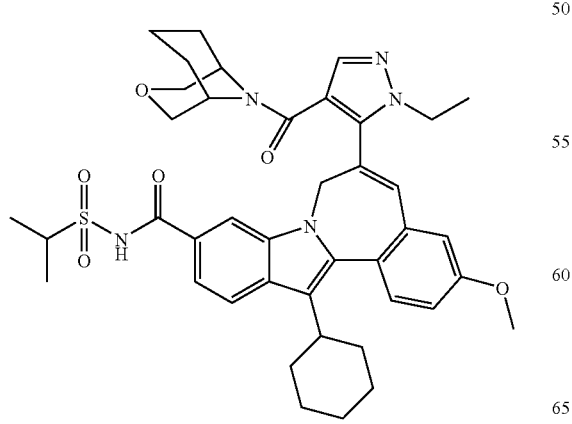

7H-indolo[2,1-a][2]benzazepine-10-carboxamide, 13-cyclohexyl-6-[1-ethyl-4-(2-oxa-5-azabicyclo[2.2.1]hept-5-ylcarbonyl)-1H-pyrazol-5-yl]-3-methoxy-N-[(1-methylethyl)sulfonyl]-

LCMS: m/e 713 (M+H), ret time 4.81 min.

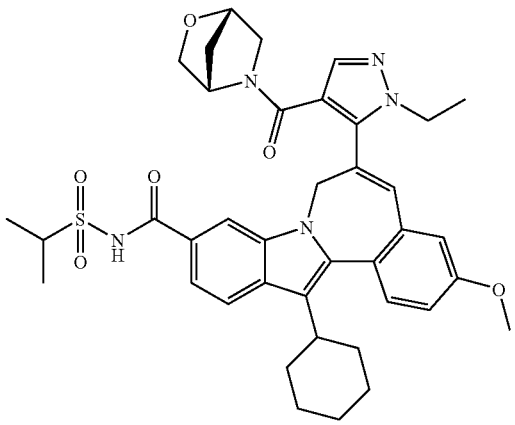

7H-indolo[2,1-a][2]benzazepine-10-carboxamide, 13-cyclohexyl-6-[1-ethyl-4-[[(3R,5S)-3,4,5-trimethyl-1-piperazinyl]carbonyl]-1H-pyrazol-5-yl]-3-methoxy-N-[(1-methylethyl)sulfonyl]-

LCMS: m/e 742 (M+H), ret time 4.64 min.

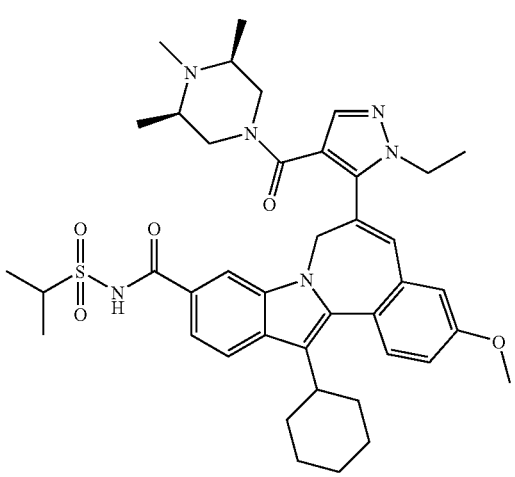

79

7H-indolo[2,1-a][2]benzazepine-10-carboxamide, 13-cyclohexyl-6-[1-ethyl-4-[(3-methyl-3,8-diazabicyclo[3.2.1]oct-8-yl)carbonyl]-1H-pyrazol-5-yl]-3-methoxy-N-[(1-methylethyl)sulfonyl]-

LCMS: m/e 740 (M+H), ret time 5.25 min.

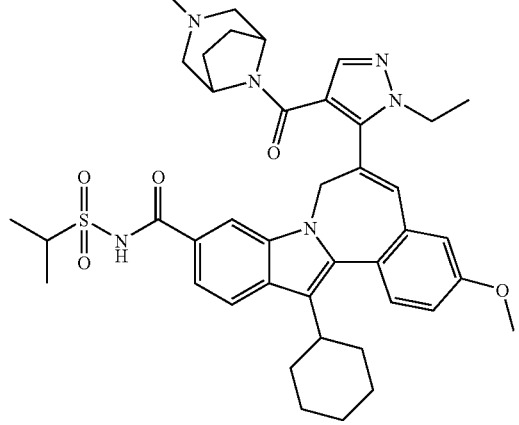

7H-indolo[2,1-a][2]benzazepine-10-carboxamide, 13-cyclohexyl-6-[1-ethyl-4-[(5-ethyl-2,5-diazabicyclo[2.2.1]hept-2-yl)carbonyl]-1H-pyrazol-5-yl]-3-methoxy-N-[(1-methylethyl)sulfonyl]-

LCMS: m/e 740 (M+H), ret time 4.44 min.

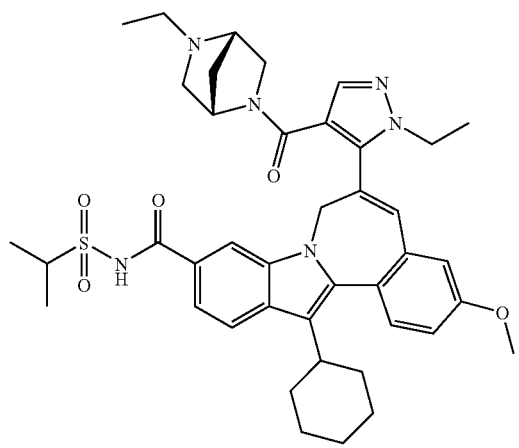

7H-indolo[2,1-a][2]benzazepine-10-carboxamide, 13-cyclohexyl-3-methoxy-N-[(1-methylethyl)sulfonyl]-6-[4-(8-oxa-3-azabicyclo[3.2.1]oct-3-ylcarbonyl)-1-(2,2,2-trifluoroethyl)-1H-pyrazol-5-yl]-

LCMS: m/e 780 (M+H), ret time 5.49 min.

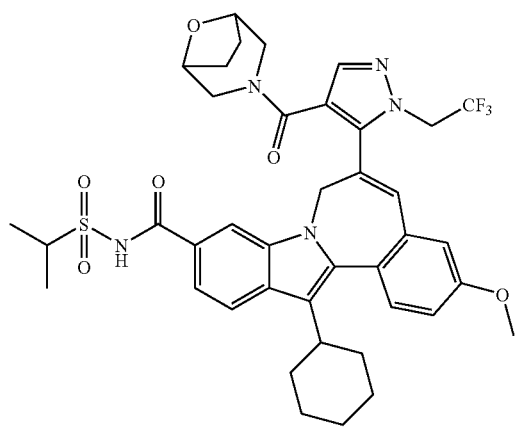

80

7H-indolo[2,1-a][2]benzazepine-10-carboxamide, 13-cyclohexyl-3-methoxy-N-[(1-methylethyl)sulfonyl]-6-[1-methyl-4-[[4-(1-pyrrolidinyl)-1-piperidinyl]carbonyl]-1H-pyrazol-5-yl]-

LCMS: m/e 796 (M+H), ret time 5.12 min.

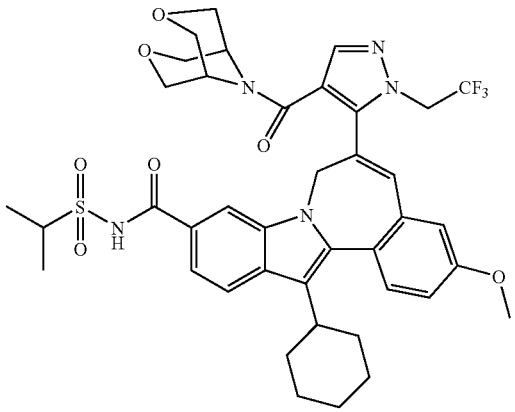

7H-indolo[2,1-a][2]benzazepine-10-carboxamide, 13-cyclohexyl-3-methoxy-N-[(1-methylethyl)sulfonyl]-6-[1-methyl-4-[[4-(1-pyrrolidinyl)-1-piperidinyl]carbonyl]-1H-pyrazol-5-yl]-

LCMS: m/e 766 (M+H), ret time 5.40 min.

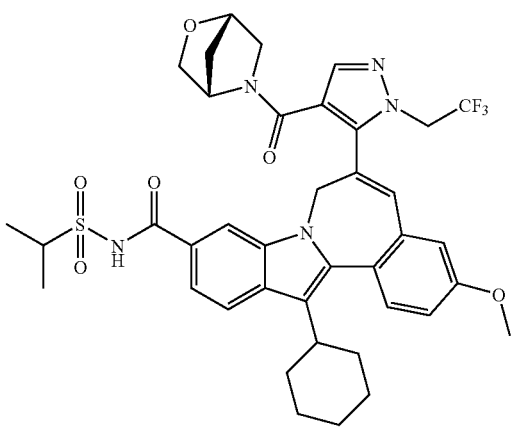

81

7H-indolo[2,1-a][2]benzazepine-10-carboxamide, 13-cyclohexyl-3-methoxy-N-[(1-methylethyl)sulfonyl]-6-[1-methyl-4-[[4-(1-pyrrolidinyl)-1-piperidinyl]carbonyl]-1H-pyrazol-5-yl]-

LCMS: m/e 767 (M+H), ret time 4.86 min.

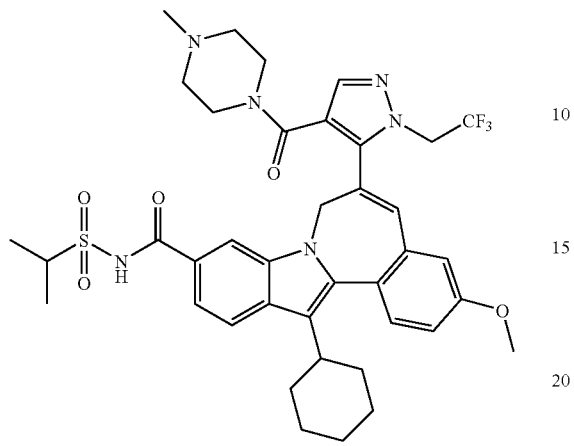

13-cyclohexyl-6-(1-isopropyl-4-(8-oxa-3-azabicyclo[3.2.1]oct-3-ylcarbonyl)-1H-pyrazol-5-yl)-N-(isopropylsulfonyl)-3-methoxy-7H-indolo[2,1-a][2]benzazepine-10-carboxamide LCMS: m/e 740 (M+H), ret time 5.17 min.

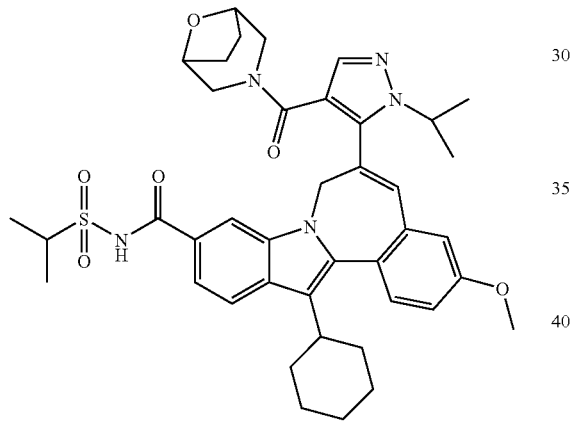

13-cyclohexyl-6-(1-isopropyl-4-(3-oxa-9-azabicyclo[3.3.1]non-9-ylcarbonyl)-1H-pyrazol-5-yl)-N-(isopropylsulfonyl)-3-methoxy-7H-indolo[2,1-a][2]benzazepine-10-carboxamide LCMS: m/e 754 (M+H), ret time 5.94 min.

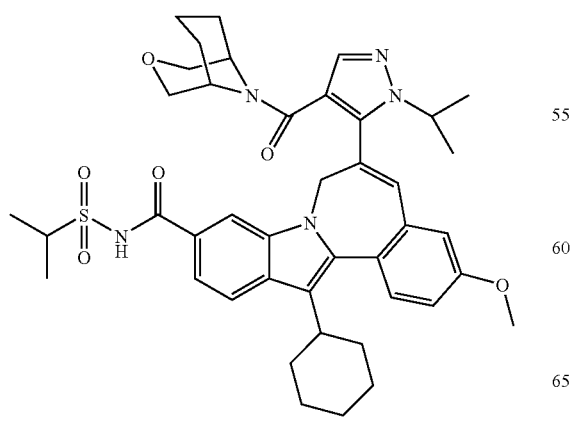

82

13-cyclohexyl-6-(1-isopropyl-4-(2-oxa-5-azabicyclo[2.2.1]hept-5-ylcarbonyl)-1H-pyrazol-5-yl)-N-(isopropylsulfonyl)-3-methoxy-7H-indolo[2,1-a][2]benzazepine-10-carboxamide LCMS: m/e 726 (M+H), ret time 4.96 min.

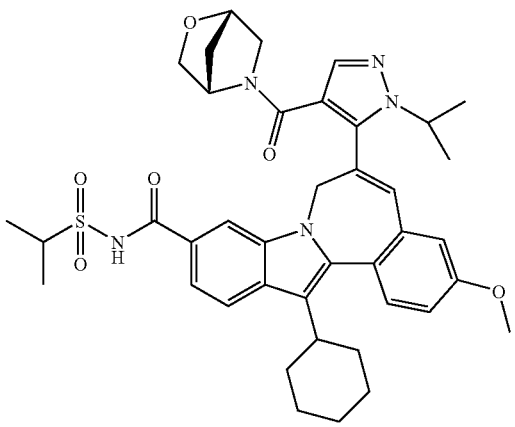

13-cyclohexyl-6-(1-isopropyl-4-((4-methyl-1-piperazinyl)carbonyl)-1H-pyrazol-5-yl)-N-(isopropylsulfonyl)-3-methoxy-7H-indolo[2,1-a][2]benzazepine-10-carboxamide LCMS: m/e 727 (M+H), ret time 4.61 min.

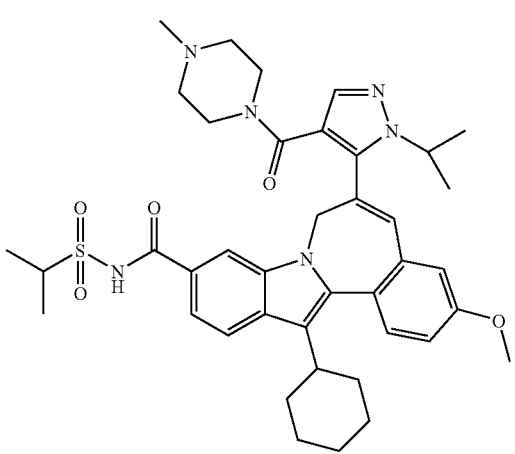

13-cyclohexyl-6-(1-isopropyl-3-methyl-4-(8-oxa-3-azabicyclo[3.2.1]oct-3-ylcarbonyl)-1H-pyrazol-5-yl)-N-(isopropylsulfonyl)-3-methoxy-7H-indolo[2,1-a][2]benzazepine-10-carboxamide LCMS: m/e 754 (M+H), ret time 5.20 min.

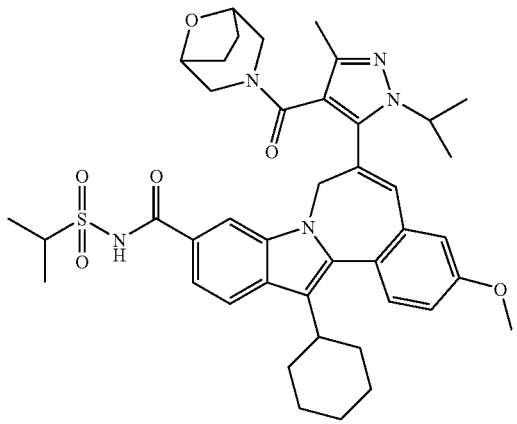

13-cyclohexyl-6-(1-isopropyl-3-methyl-4-(2-oxa-5-azabicyclo[2.2.1]hept-5-ylcarbonyl)-1H-pyrazol-5-yl)-N-(isopropylsulfonyl)-3-methoxy-7H-indolo[2,1-a][2]benzazepine-10-carboxamide LCMS: m/e 740 (M+H), ret time 5.10 min.

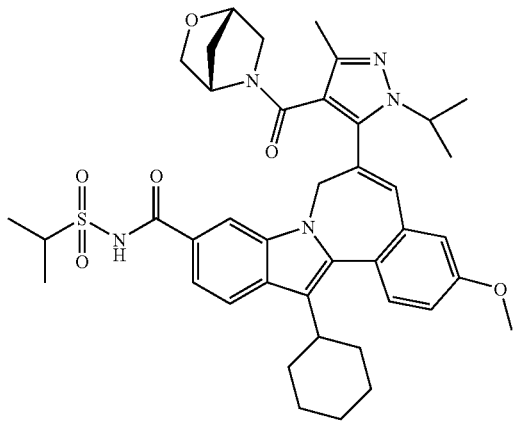

13-cyclohexyl-6-(1-isopropyl-3-methyl-4-(2-oxa-5-azabicyclo[2.2.1]hept-5-ylcarbonyl)-1H-pyrazol-5-yl)-N-(isopropylsulfonyl)-3-methoxy-7H-indolo[2,1-a][2]benzazepine-10-carboxamide LCMS: m/e 767 (M+H), ret time 5.70 min. 1H NMR (500 MHz, DMSO/CHLOROFORM-D) δ ppm 1.10-1.57 (m, 17H) 1.75-2.16 (m, 9H) 2.35 (s, 3H) 2.65 (m, 2H) 2.91 (m, 1H) 2.96 (s, 3H) 3.24 (m, 4H) 3.92-3.95 (m, 5H) 4.67 (br d, 1H) 5.02 (br d, 1H) 7.10 (br m, 1H) 7.16 (s, 1H) 7.25 (m, 1H) 7.59 (d, J=8.24 Hz, 1H) 7.67 (d, J=8.55 Hz, 1H) 7.94 (d, J=8.24 Hz, 1H) 8.00 (s, 1H) 8.17 (s, 1H).

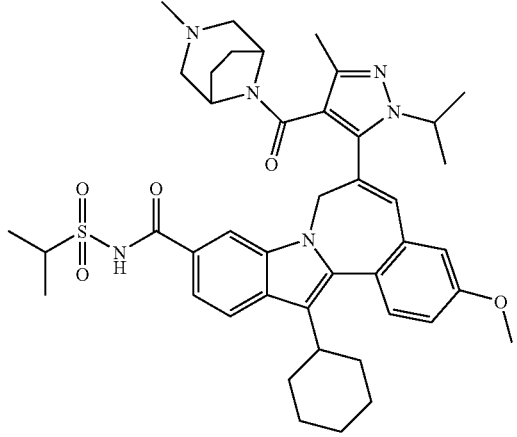

13-cyclohexyl-6-(4-((5-ethyl-2,5-diazabicyclo[2.2.1]hept-2-yl)carbonyl)-1-isopropyl-3-methyl-1H-pyrazol-5-yl)-N-(isopropylsulfonyl)-3-methoxy-7H-indolo[2,1-a][2]benzazepine-10-carboxamide LCMS: m/e 767 (M+H), ret time 4.44 min. 1H NMR (500 MHz, DMSO/CHLOROFORM-D) δ ppm 1.10-1.57 (m, 18H) 1.75-2.16 (m, 9H) 2.29 (m, 4H) 2.91 (m, 1H) 2.96 (s, 3H) 3.24 (m, 4H) 3.92-3.96 (m, 5H) 4.66 (br d, 1H) 5.05 (br d, 1H) 7.10 (br m, 1H) 7.30 (m, 2H) 7.58 (d, J=8.24 Hz, 1H) 7.67 (br m, 1H) 7.95 (br d, 1H) 8.00 (s, 1H) 8.14 (br s, 1H).

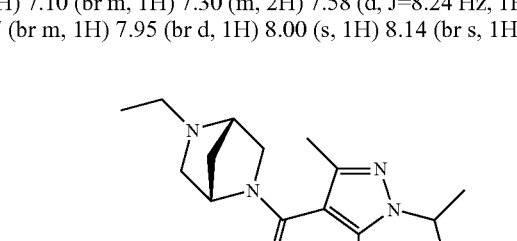
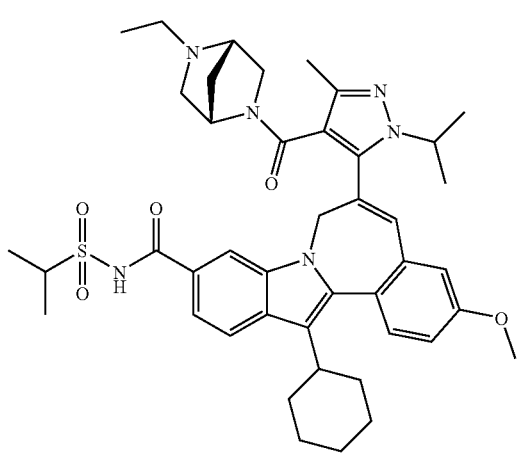
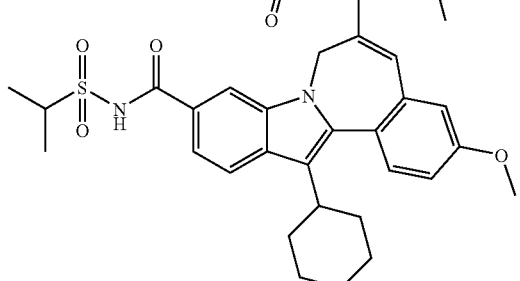

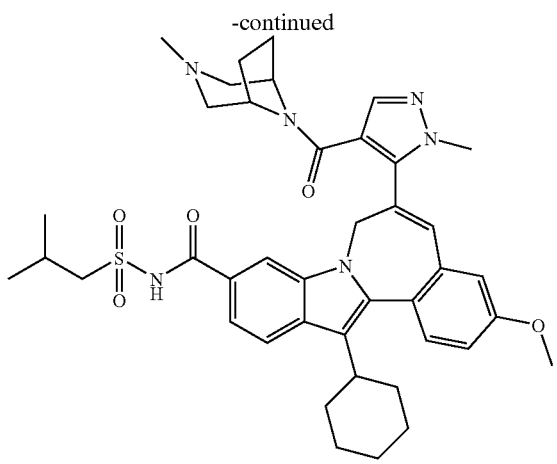

7H-indolo[2,1-a][2]benzazepine-10-carboxamide, 13-cyclohexyl-3-methoxy-6-[1-methyl-4-[(3-methyl-3,8-diazabicyclo[3.2.1]oct-8-yl)carbonyl]-1H-pyrazol-5-yl]-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. 3-methyl-3,8-diazabicyclo[3.2.1]octane, 2HCl (14.21 mg, 0.071 mmol) was then added and the solution was stirred at RT overnight. The reaction mixture was then purified by preparative HPLC using CH₃CN—H₂O-TFA as solvent system. Homogeneous fractions were combined and concentrated to afford the title compound as a brown colored solid, (36.3 mg, 0.043 mmol, 89% yield).

MS m/z 739 (MH⁺), Retention time: 2.070 min. (basic).

1H NMR (500 MHz, MeOD) δ ppm 1.12 (d, J=6.71 Hz, 6H) 1.18-2.19 (m, 14H) 2.24-2.37 (m, 1H) 2.75 (s, 3H) 2.81-3.28 (m, 7H) 3.45-3.52 (m, 2H) 3.63-3.83 (s, br, 3H) 3.91 (s, 3H) 4.61 (d, J=14.65 Hz, 1H) 4.90-4.94 (m, 1H) 7.07-7.19 (m, 3H) 7.54-7.60 (m, 2H) 7.81 (s, br, 2H) 7.93 (d, J=8.54 Hz, 1H).

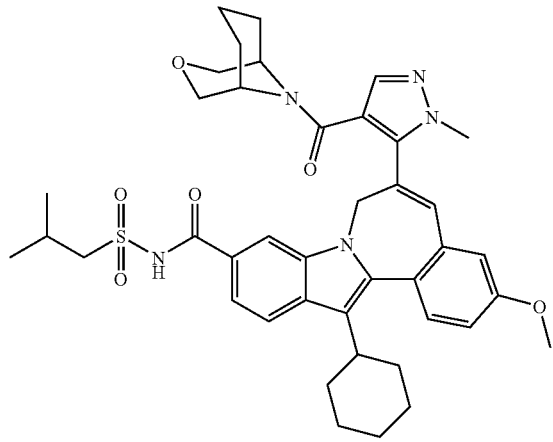

7H-indolo[2,1-a][2]benzazepine-10-carboxamide, 13-cyclohexyl-3-methoxy-6-[1-methyl-4-(3-oxa-9-azabicyclo[3.3.1]non-9-ylcarbonyl)-1H-pyrazol-5-yl]-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. 3-oxa-9-azabicyclo[3.3.1]nonane, HCl (11.67 mg, 0.071 mmol) was then added and the solution was stirred at RT overnight. The reaction mixture was then purified by preparative HPLC using CH₃CN—H₂O-TFA as solvent system. Homogeneous fractions were combined and concentrated under vacuum. The title compound was obtained as a brownish solid, (29.5 mg, 0.040 mmol, 84% yield).

MS m/z 738 (M–H⁻), Retention time: 1.928 min. (basic).

1H NMR (500 MHz, MeOD) δ ppm 1.04-2.40 (m, 23H) 2.72-3.05 (m, 3H) 3.41-4.02 (m, 12H) 4.61-4.69 (m, br, 1H) 4.99-5.08 (m, br, 1H) 7.09-7.25 (m, 3H) 7.55-7.66 (m, 2H) 7.66-7.73 (m, 1H) 7.85-8.03 (m, 2H).

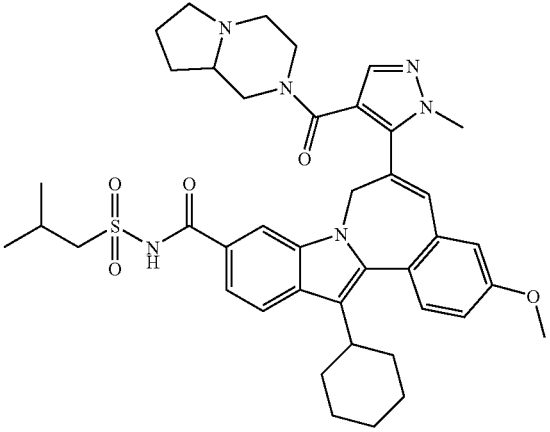

7H-indolo[2,1-a][2]benzazepine-10-carboxamide, 13-cyclohexyl-6-[4-[(hexahydropyrrolo[1,2-a]pyrazin-2(1H)-yl)carbonyl]-1-methyl-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. Octahydropyrrolo[1,2-a]pyrazine (9.00 mg, 0.071 mmol) was then added and the solution was stirred at RT overnight. The reaction mixture was then purified by preparative HPLC column using CH₃CN—H₂O-TFA as solvent system. Homogeneous fractions were combined and concentrated under speed vacuum. The TFA salt of the title compound was obtained as a brownish solid, (35.5 mg, 0.042 mmol, 88% yield).

MS m/z 737 (M–H⁻), Retention time: 1.722 min. (basic).

1H NMR (500 MHz, MeOD) δ ppm 1.15 (d, J=6.71 Hz, 6H) 1.19-2.23 (m, 14H) 2.26-2.40 (m, 1H) 2.88-3.05 (m, 1H) 3.11-3.58 (m, 11H) 3.72 (s, 3H) 3.95 (s, 3H) 4.60-4.70 (m, br, 1H) 5.00-5.16 (m, br, 1H) 7.11 (s, 1H) 7.16 (d, J=2.44 Hz, 1H) 7.20 (dd, J=8.54, 2.75 Hz, 1H) 7.58-7.64 (m, 2H) 7.76 (s, 1H) 7.91 (s, 1H) 7.99 (d, J=8.55 Hz, 1H).

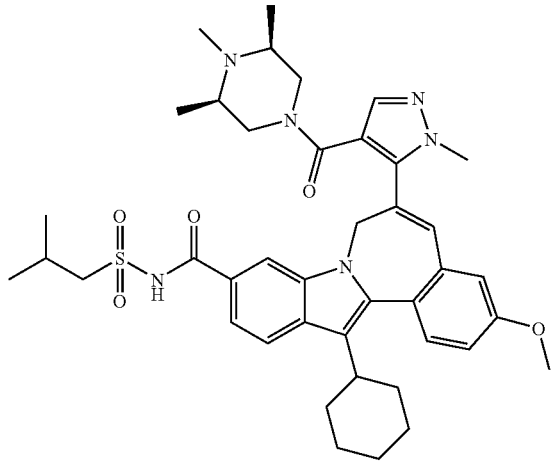

7H-indolo[2,1-a][2]benzazepine-10-carboxamide, 13-cyclohexyl-3-methoxy-N-[(2-methylpropyl)sulfonyl]-6-[1-methyl-4-[[cis-3,4,5-trimethyl-1-piperazinyl]carbonyl]-1H-pyrazol-5-yl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. Cis-1,2,6-trimethylpiperazine (9.15 mg, 0.071 mmol) was then added and the solution was stirred at RT overnight. The reaction mixture was then purified by preparative HPLC using CH₃CN—H₂O-TFA as solvent system. Homogeneous fractions were combined and concentrated under vacuum. The TFA salt of the title compound was obtained as a brownish solid, (39.1 mg, 0.046 mmol, 96% yield).

MS m/z 739 (M−H⁻), Retention time: 1.723 min. (basic).

1H NMR (500 MHz, MeOD) δ ppm 1.15 (d, J=7.02 Hz, 6H) 1.21-1.65 (m, 10H) 1.77-2.22 (m, 6H) 2.28-2.40 (m, 1H) 2.54-3.05 (m, 8H) 3.51 (d, J=6.41 Hz, 2H) 3.74 (s, 3H) 3.95 (s, 3H) 4.03-4.42 (m, br, 2H) 4.59-4.70 (m, br, 1H) 5.01-5.12 (m, br, 1H) 7.13 (s, 1H) 7.16 (d, J=2.75 Hz, 1H) 7.21 (dd, J=8.85, 2.75 Hz, 1H) 7.59-7.66 (m, 2H) 7.74 (s, 1H) 7.93 (s, 1H) 8.00 (d, J=8.55 Hz, 1H).

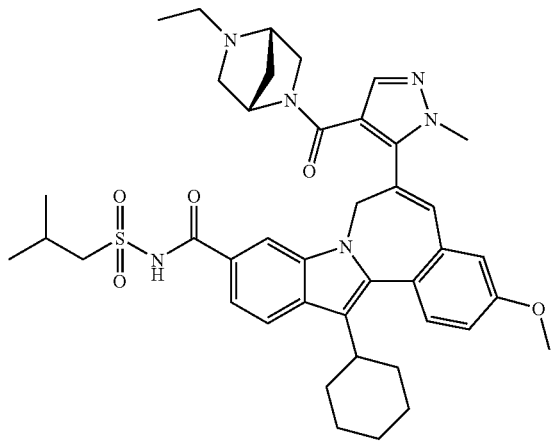

7H-indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-methyl-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. (1S,4S)-2-ethyl-2,5-diazabicyclo[2.2.1]heptane, 2TFA (25.3 mg, 0.071 mmol) was then added and the resultant solution was stirred at RT for 3 hours. LC/MS analysis showed that the reaction had progressed to completion. The reaction mixture was then purified by preparative HPLC using CH₃CN—H₂O-TFA as solvent system. Homogeneous fractions were collected and concentrated under vacuum. The TFA of the title compound was obtained as a brown colored solid, (35.30 mg, 0.041 mmol, 87% yield).

MS m/z 737 (M−H⁻), Retention time: 1.850 min. (basic).

1H NMR (500 MHz, MeOD) δ ppm 1.15 (d, J=6.71 Hz, 6H) 1.21-2.22 (m, 15H) 2.25-2.39 (m, 1H) 2.89-3.02 (m, 1H) 3.05-3.80 (m, 12H) 3.95 (s, 3H) 4.09-4.48 (m, 1H) 4.57-4.70 (m, 1H) 4.99-5.12 (m, 1H) 6.97-7.08 (s, br, 1H) 7.14 (s, 1H) 7.20 (dd, J=8.55, 2.44 Hz, 1H) 7.61 (d, J=8.85 Hz, 2H) 7.82 (s, 1H) 7.88 (s, 1H) 7.97 (d, J=8.55 Hz, 1H).

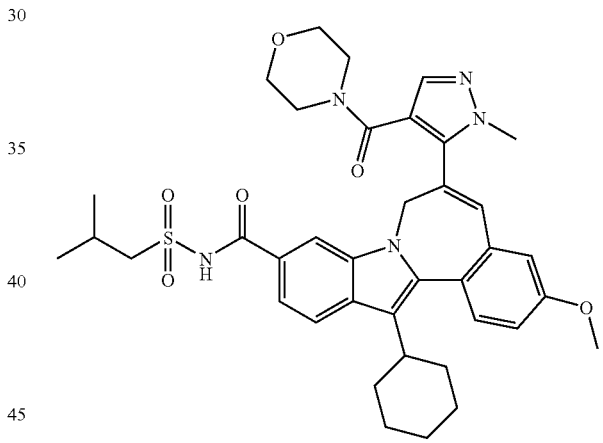

7H-indolo[2,1-a][2]benzazepine-10-carboxamide, 13-cyclohexyl-3-methoxy-6-[1-methyl-4-(4-morpholinylcarbonyl)-1H-pyrazol-5-yl]-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. Morpholine (6.22 mg, 0.071 mmol) was then added and the resultant solution was stirred at RT for 3 hours. LC/MS analysis showed the reaction had progressed to completion. The reaction mixture was then purified by preparative HPLC using CH₃CN—H₂O-TFA as solvent system. Homogeneous fractions were combined and concentrated under vacuum. The title compound was obtained as a yellow solid, (28.4 mg, 0.041 mmol, 85% yield).

MS m/z 698 (M−H⁻), Retention time: 1.618 min. (basic).
1H NMR (500 MHz, MeOD) δ ppm 1.16 (d, J=6.71 Hz, 6H) 1.21-1.36 (m, 1H) 1.40-1.64 (m, 3H) 1.75-1.87 (m, 2H) 1.94-2.25 (m, 4H) 2.27-2.41 (m, 1H) 2.70-3.12 (m, 9H) 3.49-3.55 (m, 2H) 3.85 (s, 3H) 3.95 (s, 3H) 4.69 (d, J=14.34 Hz, 1H) 5.10 (d, J=14.95 Hz, 1H) 7.09 (s, 1H) 7.16 (d, J=2.44 Hz, 1H) 7.20 (dd, J=8.55, 2.44 Hz, 1H) 7.62 (d, J=8.54 Hz, 2H) 7.66 (s, 1H) 7.94 (s, 1H) 7.99 (d, J=8.55 Hz, 1H).

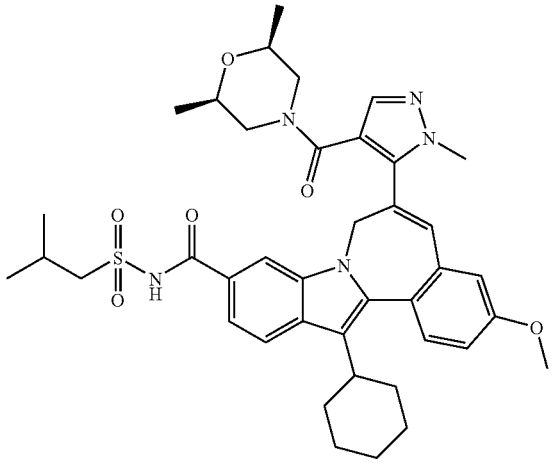

7H-indolo[2,1-a][2]benzazepine-10-carboxamide, 13-cyclohexyl-6-[4-[[cis-2,6-dimethyl-4-morpholinyl]carbonyl]-1-methyl-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. Cis-2,6-dimethylmorpholine (8.22 mg, 0.071 mmol) was then added and the resultant solution was stirred at RT for 3 hours. LC/MS then showed that the reaction had progressed to completion. The reaction mixture was then purified by preparative HPLC using CH₃CN—H₂O-TFA as solvent system. Homogeneous fractions were collected and concentrated under vacuum. The title compound was obtained as a yellow colored solid, (29.6 mg, 0.041 mmol, 85% yield).

MS m/z 726 (M−H⁻), Retention time: 1.753 min. (basic).
1H NMR (500 MHz, MeOD) δ ppm 0.50-2.56 (m, 23H) 2.68-3.06 (m, 2H) 3.21-3.63 (m, 7H) 3.83-4.02 (m, 6H) 4.67 (d, J=14.34 Hz, 1H) 5.04 (d, J=14.65 Hz, 1H) 7.11-7.25 (m, 3H) 7.56-7.69 (m, 3H) 7.93 (s, 1H) 7.99 (d, J=8.24 Hz, 1H).

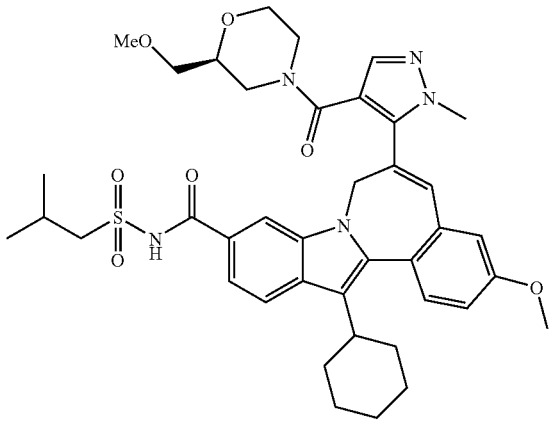

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-methyl-1H-pyrazol-5-yl]-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. (S)-2-(methoxymethyl)morpholine, HCl (11.96 mg, 0.071 mmol) was then added and the resultant solution was stirred at RT for 3 hours. LC/MS analysis then showed the reaction had progressed to completion. The reaction mixture was then purified by preparative HPLC using CH₃CN—H₂O-TFA as solvent system. Homogeneous fractions were combined and concentrated under vacuum. The title compound was obtained as a yellow colored solid, (28.6 mg, 0.038 mmol, 81% yield).

MS m/z 742 (M−H⁻), Retention time: 1.598 min. (basic).
1H NMR (500 MHz, MeOD) δ ppm 1.16 (d, J=6.71 Hz, 6H) 1.22-1.65 (m, 4H) 1.75-2.24 (m, 6H) 2.28-2.42 (m, 1H) 2.88-3.63 (m, 15H) 3.81 (s, 3H) 3.95 (s, 3H) 4.61-4.72 (m, 1H) 5.02-5.14 (m, 1H) 7.11 (s, 1H) 7.17 (d, J=2.44 Hz, 1H) 7.20 (dd, J=8.55, 2.44 Hz, 1H) 7.56-7.65 (m, 2H) 7.66 (s, 1H) 7.93 (s, 1H) 7.96-8.03 (m, 1H).

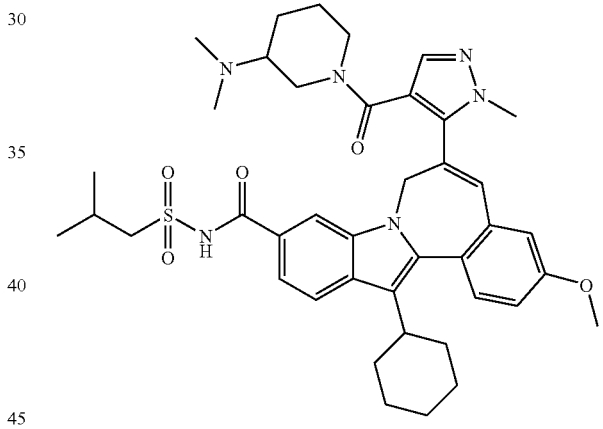

7H-indolo[2,1-a][2]benzazepine-10-carboxamide, 13-cyclohexyl-6-[4-[[3-(dimethylamino)-1-piperidinyl]carbonyl]-1-methyl-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. N,N-dimethylpiperidin-3-amine, 2HCl (14.35 mg, 0.071 mmol) was then added and the resultant solution was stirred at RT for 3 hours. LC/MS then showed the reaction had progressed to completion. The reaction mixture was then purified by preparative HPLC using CH₃CN—H₂O-TFA as solvent system. Homogeneous fractions were collected and concentrated under vacuum. The TFA salt of the title compound was obtained as a yellow colored solid, (36.3 mg, 0.042 mmol, 89% yield).

MS m/z 739 (M−H⁻), Retention time: 1.810 min. (basic).

1H NMR (500 MHz, MeOD) δ ppm 1.16 (d, J=6.71 Hz, 6H) 1.22-1.64 (m, 6H) 1.75-2.24 (m, 8H) 2.29-2.39 (m, 1H) 2.46-3.13 (m, 11H) 3.51 (d, J=6.41 Hz, 2H) 3.83 (s, 3H) 3.95 (s, 3H) 4.16 (s, br, 1H) 4.61-4.73 (m, br, 1H) 5.00-5.12 (m, br, 1H) 7.09 (s, 1H) 7.16 (d, J=2.44 Hz, 1H) 7.20 (dd, J=8.70, 2.59 Hz, 1H) 7.60 (d, J=8.85 Hz, 1H) 7.64 (dd, J=8.55, 1.22 Hz, 1H) 7.69 (s, 1H) 7.94 (s, 1H) 8.01 (d, J=8.24 Hz, 1H).

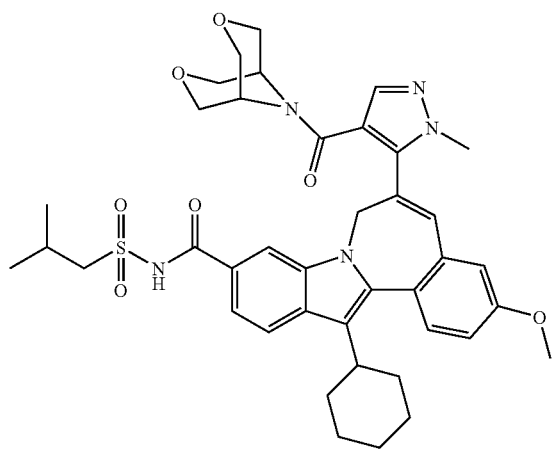

7H-indolo[2,1-a][2]benzazepine-10-carboxamide, 13-cyclohexyl-6-[4-(3,7-dioxa-9-azabicyclo[3.3.1] non-9-ylcarbonyl)-1-methyl-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl] amino]carbonyl]-7H-indolo[2,1-a][2]benzazepin-6-yl]-1-methyl- (30 mg, 0.048 mmol) in DMSO (1 mL), TBTU (22.91 mg, 0.071 mmol) and DIPEA (0.042 mL, 0.238 mmol) were added. The reaction mixture was stirred at RT for 15 min. 3,7-dioxa-9-azabicyclo[3.3.1]nonane (9.21 mg, 0.071 mmol) was then added and the solution was stirred at RT overnight. LC/MS then showed that only 40% SM had reacted. Two more equivalents of TBTU were then added and the reaction mixture was stirred at RT overnight. LC/MS then showed that the reaction had progressed to completion. The reaction mixture was then purified by preparative HPLC using CH₃CN—H₂O-TFA as solvent system. Homogeneous fractions were combined and evaporated under vacuum to give the title compound as a light-yellow colored solid, (26.7 mg, 0.036 mmol, 76% yield).

MS m/z 740 (M−H⁻), Retention time: 1.887 min. (basic).

1H NMR (500 MHz, MeOD) δ ppm 1.16 (d, J=6.71 Hz, 6H) 1.21-1.64 (m, 4H) 1.71-3.15 (m, 10H) 3.43-3.88 (m, 13H) 3.96 (s, 3H) 4.63-4.72 (m, 1H) 5.01-5.11 (m, 1H) 7.13-7.18 (m, 2H) 7.22 (dd, J=8.70, 2.59 Hz, 1H) 7.61 (d, J=8.55 Hz, 1H) 7.64 (d, J=8.85 Hz, 1H) 7.74 (s, 1H) 7.91 (s, 1H) 7.98 (d, J=8.55 Hz, 1H).

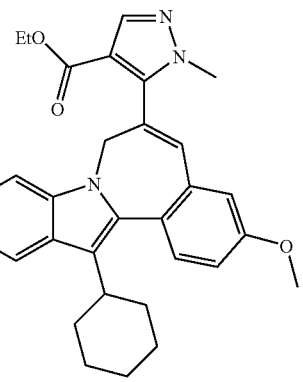

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl)-, ethyl ester CDI (451 mg, 2.78 mmol) was added to a THF (10 mL) solution of 7H-indolo[2,1-a][2]benzazepine-10-carboxylic acid, 13-cyclohexyl-6-[4-(ethoxycarbonyl)-1-methyl-1H-pyrazol-5-yl]-3-methoxy-(750 mg, 1.39 mmol) and the resultant mixture was stirred at 60° C. for 1 h. The reaction was then cooled to r.t. and butane-2-sulfonamide (572 mg, 4.17 mmol) and DBU (0.419 mL, 2.78 mmol) were added. The mixture was then heated at 60° C. overnight, after which the solvent was removed and the residue dissolved in EtOAc. The organic layer was washed with sequentially with 1N HCl solution (3×20 mL), and Brine (3×20 mL) and then dried over Na₂SO₄. The mixture was then filtered and the filtrate was evaporated in vacuo. The residue was purified using a Shimadzu preparative HPLC employing ACN/water and 0.1% TFA buffer with a Xterra column, 30 mm×100 mm, Gradient over 15 min; Starting conc: 10% B; Ending conc: 100% B. Homogeneous fractions were combined and evaporated under reduced pressure to afford the title compound as light yellow solid, (450 mg, 49%). ESI-MS m/e 659 (MH⁺).

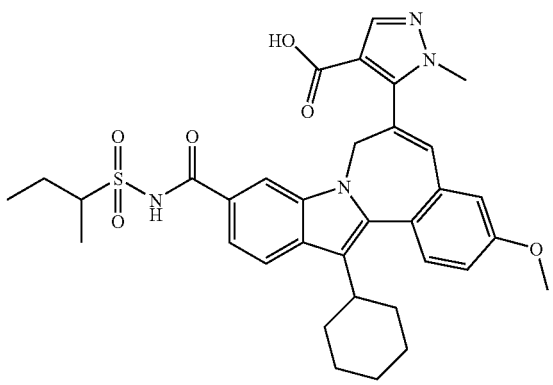

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- NaOH (1N, 5 mL) was added to a solution of 1H-pyrazole-4-carboxylic acid, 5-[13-cyclohexyl-3-methoxy-10-[[[(1- methylethyl)sulfonyl]amino]carbonyl]-7H-indolo[2,1-a][2]benzazepin-6-yl]-1-methyl-, ethyl ester (250 mg, 0.379 mmol) in a 1:1 mixture of THF:MeOH (10 mL) and the resultant solution was agitated at r.t. for 48 h. HCl (1N, 5 mL) was then added and the resultant mixture was evaporated under reduced pressure. The residue was dissolved in EtOAc and washed with brine (3×20 mL) and then dried over Na$_2$SO$_4$. The mixture was then filtered and the filtrate was evaporated in vacuo to afford the title product as yellow solid, (235 mg, 98%). ESI-MS m/e 631 (MH$^+$).

Using the standard amide coupling conditions described for related examples, the following examples can be prepared.

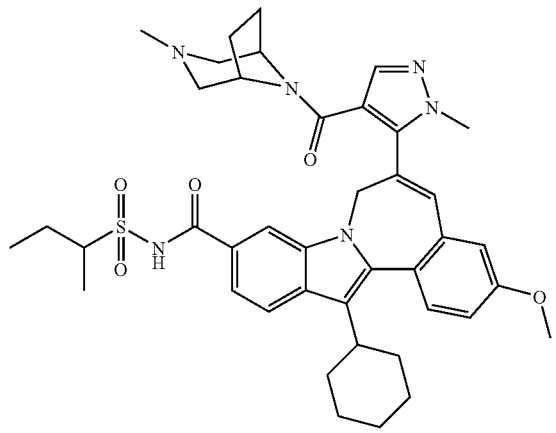

7H-indolo[2,1-a][2]benzazepine-10-carboxamide, 13-cyclohexyl-3-methoxy-6-[1-methyl-4-[(3-methyl-3,8-diazabicyclo[3.2.1]oct-8-yl)carbonyl]-1H-pyrazol-5-yl]-N-[(1-methylpropyl)sulfonyl]-

ESI-MS m/e 739 (MH$^+$). 1H NMR (500 MHz, CHLOROFORM-D) δ ppm 1.08 (t, J=7.32 Hz, 3H) 1.16-1.56 (m, 9H) 1.58-1.85 (m, 4H) 1.90-2.24 (m, 6H) 2.48-2.62 (m, 3H) 2.81-2.99 (m, 3H) 3.15-3.45 (m, 3H) 3.73-4.05 (m, 5H) 3.94 (s, 3H) 4.58-4.69 (m, 1H) 4.80-5.02 (m, 1H) 6.92-7.01 (m, 2H) 7.13 (dd, J=8.70, 2.29 Hz, 1H) 7.53-7.82 (m, 4H) 7.92 (d, J=8.24 Hz, 1H) 10.14 (s, 1H).

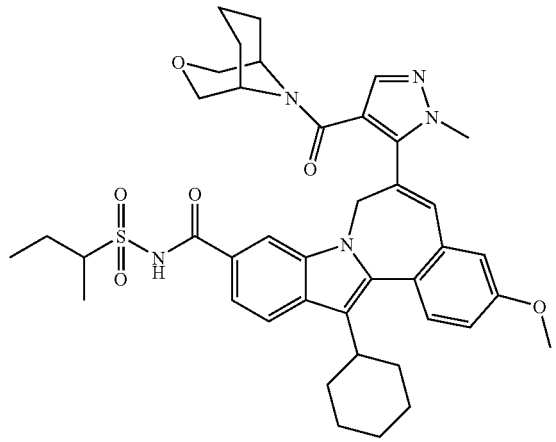

7H-indolo[2,1-a][2]benzazepine-10-carboxamide, 13-cyclohexyl-3-methoxy-6-[1-methyl-4-(3-oxa-9-azabicyclo[3.3.1]non-9-ylcarbonyl)-1H-pyrazol-5-yl]-N-[(1-methylpropyl)sulfonyl]-

ESI-MS m/e 740 (MH$^+$). 1H NMR (500 MHz, CHLOROFORM-D) δ ppm 1.00-1.57 (m, 12H) 1.68-1.84 (m, 3H) 1.91-2.48 (m, 9H) 2.81-2.94 (m, 1H) 3.03-3.16 (m, 1H) 3.18-3.72 (m, 5H) 3.76-4.02 (m, 7H) 4.53-4.68 (m, 1H) 4.94 (d, J=15.87 Hz, 1H) 6.81-6.91 (m, 1H) 6.94 (d, J=2.44 Hz, 1H) 7.13 (d, J=8.54 Hz, 1H) 7.54-7.62 (m, 1H) 7.62-7.85 (m, 3H) 7.87-7.96 (m, 1H).

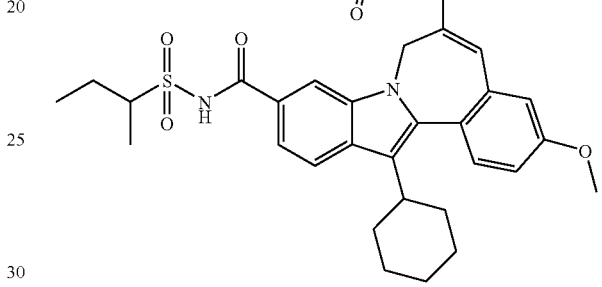

7H-indolo[2,1-a][2]benzazepine-10-carboxamide, 13-cyclohexyl-6-[4-(3,7-dioxa-9-azabicyclo[3.3.1]non-9-ylcarbonyl)-1-methyl-1H-pyrazol-5-yl]-3-methoxy-N-[(1-methylpropyl)sulfonyl]-

ESI-MS m/e 742 (MH$^+$). 1H NMR (500 MHz, CHLOROFORM-D) δ ppm 1.02-1.13 (m, 3H) 1.15-1.27 (m, 1H) 1.31-1.56 (m, 6H) 1.69-1.84 (m, 2H) 1.92-2.39 (m, 6H) 2.62-2.70 (m, 1H) 2.83-2.93 (m, 1H) 3.25 (s, 1H) 3.30-3.49 (m, 3H) 3.52-3.59 (m, 1H) 3.66-3.76 (m, 3H) 3.80-3.86 (m, 2H) 3.89 (s, 3H) 3.94 (s, 3H) 4.63 (d, J=15.26 Hz, 1H) 4.93 (d, J=15.56 Hz, 1H) 6.86 (s, 1H) 6.95 (d, J=2.44 Hz, 1H) 7.13 (dd, J=8.70, 2.59 Hz, 1H) 7.59 (d, J=8.55 Hz, 1H) 7.63 (d, J=8.54 Hz, 1H) 7.72 (d, J=5.49 Hz, 2H) 7.94 (d, J=8.55 Hz, 1H) 10.08-10.26 (m, 1H).

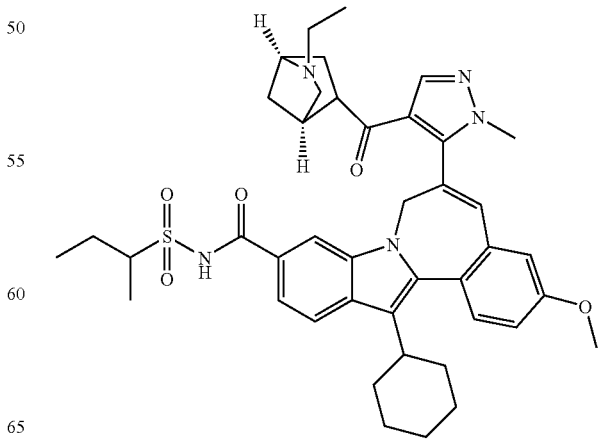

7H-indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-methyl-1H-pyrazol-5-yl]-3-methoxy-N-[(1-methylpropyl)sulfonyl]-

ESI-MS m/e 739 (MH⁺). 1H NMR (500 MHz, CHLOROFORM-D) δ ppm 0.85-1.56 (m, 15H) 1.58-2.39 (m, 8H) 2.68-2.96 (m, 4H) 3.03-3.38 (m, 3H) 3.55 (d, J=5.19 Hz, 1H) 3.72-4.03 (m, 5H) 4.05-4.43 (m, 2H) 4.51-5.04 (m, 3H) 6.68-6.86 (m, 1H) 6.88-7.18 (m, 2H) 7.49-7.97 (m, 5H) 8.17-8.28 (m, 1H).

7H-indolo[2,1-a][2]benzazepine-10-carboxamide, 13-cyclohexyl-3-methoxy-6-[1-methyl-4-(4-morpholinylcarbonyl)-1H-pyrazol-5-yl]-N-[(1-methylpropyl)sulfonyl]-

ESI-MS m/e 700 (MH⁺) 1H NMR (500 MHz, CHLOROFORM-D) δ ppm 1.02-1.14 (m, 3H) 1.16-1.30 (m, 1H) 1.49 (dd, J=20.91, 6.87 Hz, 6H) 1.34-1.45 (m, 1H) 1.93-2.40 (m, 7H) 2.58-2.71 (m, 1H) 2.77-2.97 (m, 4H) 3.04-3.25 (m, 2H) 3.35-3.65 (m, 2H) 3.79-3.88 (m, 1H) 3.90 (s, 3H) 3.94 (s, 3H) 4.61 (d, J=15.87 Hz, 1H) 4.90 (d, J=15.56 Hz, 1H) 6.86 (s, 1H) 6.96 (d, J=2.44 Hz, 1H) 7.13 (dd, J=8.55, 2.44 Hz, 1H) 7.58 (d, J=8.55 Hz, 1H) 7.61 (d, J=7.93 Hz, 1H) 7.65-7.74 (m, 2H) 7.94 (d, J=8.54 Hz, 1H) 10.20-10.44 (m, 1H).

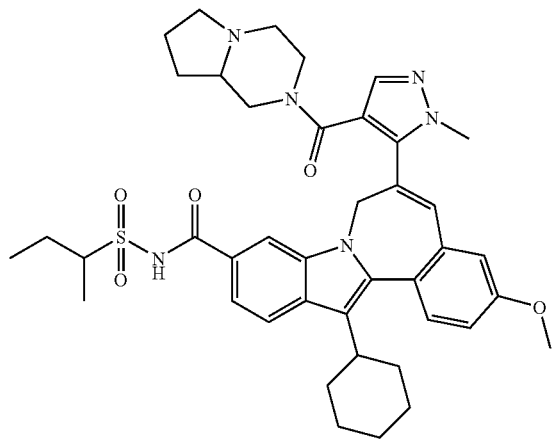

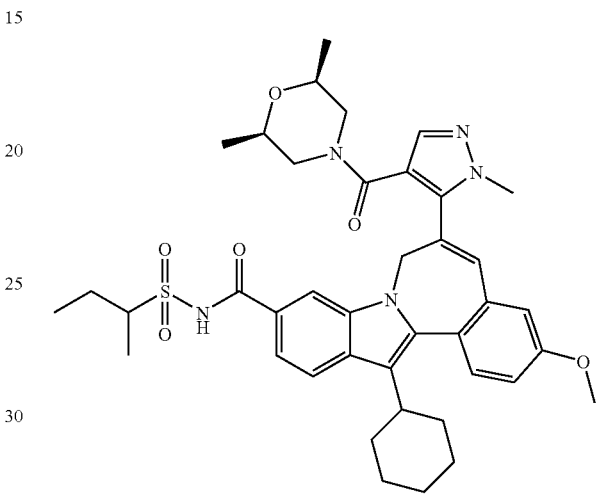

7H-indolo[2,1-a][2]benzazepine-10-carboxamide, 13-cyclohexyl-6-[4-[(hexahydropyrrolo[1,2-a]pyrazin-2(1H)-yl)carbonyl]-1-methyl-1H-pyrazol-5-yl]-3-methoxy-N-[(1-methylpropyl)sulfonyl]-

ESI-MS m/e 739 (MH⁺) 1H NMR (500 MHz, CHLOROFORM-D) δ ppm 1.00-1.13 (m, 3H) 1.21-1.58 (m, 7H) 1.59-1.85 (m, 4H) 1.90-2.49 (m, 11H) 2.80-2.99 (m, 2H) 3.34-3.88 (m, 9H) 3.92 (s, 3H) 4.54-4.69 (m, 1H) 4.76-5.00 (m, 1H) 6.83-6.94 (m, 1H) 6.97 (s, 1H) 7.06-7.15 (m, 1H) 7.48-7.68 (m, J=35.71 Hz, 3H) 7.75 (s, 1H) 7.89 (s, 1H).

7H-indolo[2,1-a][2]benzazepine-10-carboxamide, 13-cyclohexyl-6-[4-[[(2R,6S)-2,6-dimethyl-4-morpholinyl]carbonyl]-1-methyl-1H-pyrazol-5-yl]-3-methoxy-N-[(1-methylpropyl)sulfonyl]-

ESI-MS m/e 728 (MH⁺) 1H NMR (500 MHz, CHLOROFORM-D) δ ppm 0.98-1.13 (m, 3H) 1.14-1.31 (m, 2H) 1.34-1.59 (m, 6H) 1.70-1.86 (m, 3H) 1.88-2.32 (m, 12H) 2.81-2.98 (m, 1H) 2.95-3.14 (m, 1H) 3.13-3.34 (m, 2H) 3.36-3.67 (m, 1H) 3.83-3.93 (m, 3H) 3.92 (s, 3H) 3.95 (s, 3H) 4.61 (d, J=14.34 Hz, 1H) 4.91 (d, J=15.56 Hz, 1H) 6.83 (s, 1H) 6.96 (s, 1H) 7.13 (d, J=8.55 Hz, 1H) 7.51-7.81 (m, 4H) 7.92 (d, J=7.32 Hz, 1H) 10.33-10.59 (m, 1H).

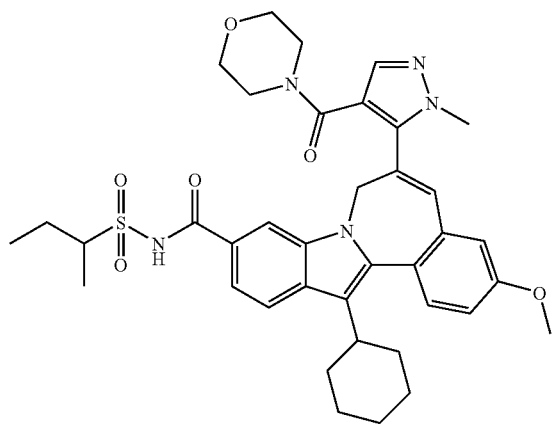

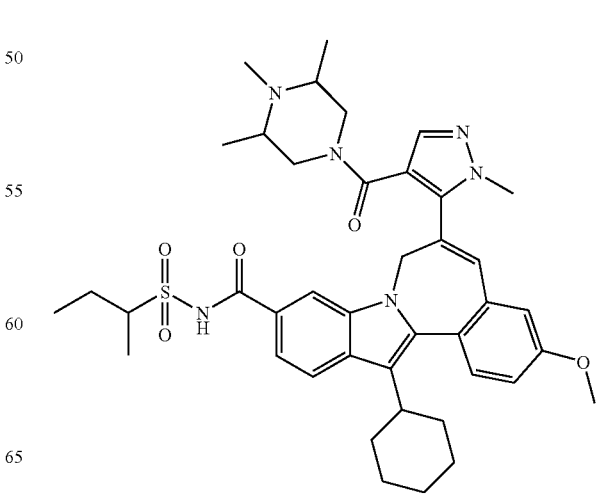

7H-indolo[2,1-a][2]benzazepine-10-carboxamide, 13-cyclohexyl-3-methoxy-N-[(1-methylpropyl)sulfonyl]-6-[1-methyl-4-[(3,4,5-trimethyl-1-piperazinyl)carbonyl]-1H-pyrazol-5-yl]-

ESI-MS m/e 741 (MH$^+$). 1H NMR (500 MHz, CHLOROFORM-D) δ ppm 0.85-2.25 (m, 25H) 2.27-2.64 (m, 3H) 2.93 (s, 1H) 3.28-3.69 (m, 4H) 3.71-3.87 (m, 5H) 3.94 (s, 3H) 4.53-4.69 (m, 1H) 4.83-5.01 (m, 1H) 6.90 (s, 1H) 6.97 (d, J=2.44 Hz, 1H) 7.08-7.15 (m, 1H) 7.50-7.66 (m, 3H) 7.79 (d, J=1.53 Hz, 1H) 7.93 (d, 1H).

7H-indolo[2,1-a][2]benzazepine-10-carboxamide, 13-cyclohexyl-3-methoxy-6-[4-[[2-(methoxymethyl)-4-morpholinyl]carbonyl]-1-methyl-1H-pyrazol-5-yl]-N-[(1-methylpropyl)sulfonyl]-

ESI-MS m/e 744 (MH$^+$) 1H NMR (500 MHz, CHLOROFORM-D) δ ppm 1.01-1.15 (m, 2H) 1.23 (d, J=15.26 Hz, 1H) 1.33-1.59 (m, 5H) 1.70-2.31 (m, 13H) 2.36-2.53 (m, 1H) 2.83-3.49 (m, 10H) 3.81-3.93 (m, 3H) 3.94 (s, 3H) 4.60 (d, J=15.26 Hz, 1H) 4.79-5.00 (m, 1H) 6.85 (s, 1H) 6.95 (s, 1H) 7.12 (dd, J=8.55, 2.75 Hz, 1H) 7.50-7.81 (m, 4H) 7.86-7.99 (m, 1H) 10.29-10.54 (m, 1H).

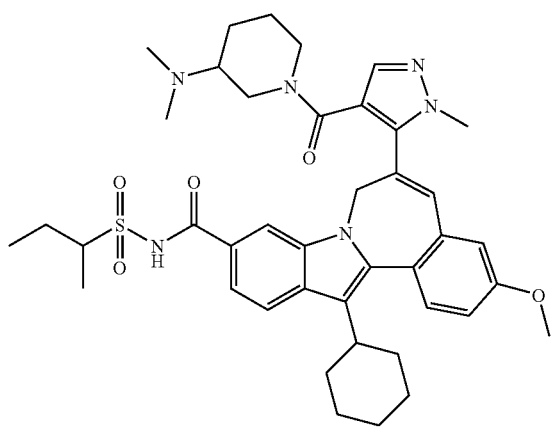

7H-indolo[2,1-a][2]benzazepine-10-carboxamide, 13-cyclohexyl-6-[4-[[3-(dimethylamino)-1-piperidinyl]carbonyl]-1-methyl-1H-pyrazol-5-yl]-3-methoxy-N-[(1-methylpropyl)sulfonyl]-

ESI-MS m/e 741 (MH$^+$). 1H NMR (500 MHz, CHLOROFORM-D) δ ppm 1.01-1.15 (m, 3H) 1.19-1.61 (m, 7H) 1.64-2.28 (m, 15H) 2.41-2.76 (m, 5H) 2.82-2.96 (m, 1H) 3.35-3.83 (m, 3H) 3.78-3.91 (m, 3H) 3.90-3.98 (m, 3H) 4.19-4.40 (m, 1H) 4.54-4.71 (m, 1H) 4.78-4.98 (m, 1H) 6.84-6.96 (m, 1H) 6.95-7.01 (m, 1H) 7.07-7.15 (m, 1H) 7.50-7.58 (m, 1H) 7.59-7.87 (m, 3H) 7.90-7.99 (m, 1H) 10.02-10.36 (m, 1H).

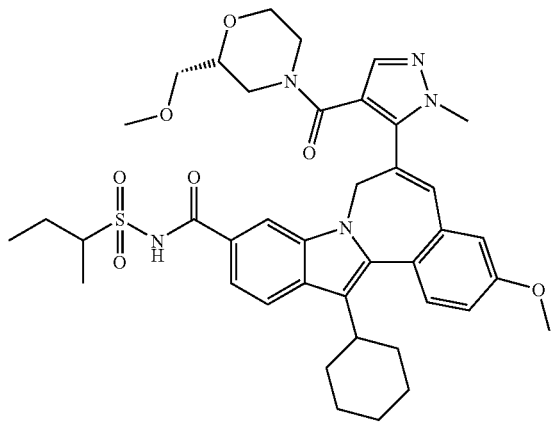

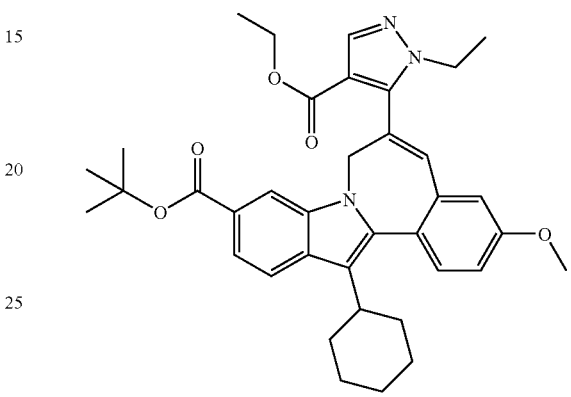

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester. tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (370 mg, 0.604 mmol) was dissolved in ethanol (1.7 ml) and the oxylate salt of ethyl hydrazine (100 mg, 0.664 mg) was added to the reaction at room temperature. The reaction was heated to 80 deg C. for 3 hrs. The reaction was diluted with chloroform and washed with water. The organic phase was concentrated under reduced pressure and purified by prep HPLC under the following conditions: Shimadzu preparative HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (265 mg, 72%) as a yellow paste. MS m/z 610 (MH$^+$).

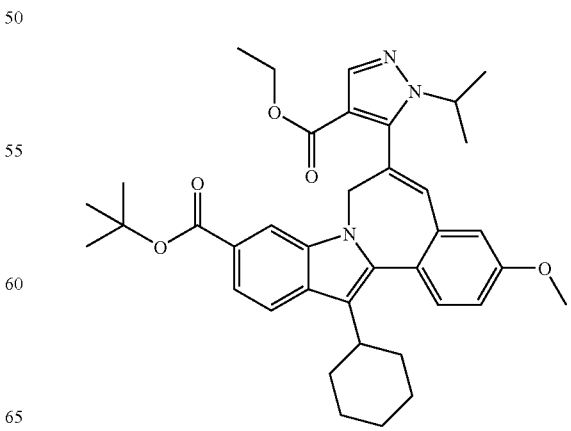

7H-indolo[2,1-a][2]benzazepine-10-carboxylic acid, 13-cyclohexyl-6-[4-(ethoxycarbonyl)-1-(1-methylethyl)-1H-pyrazol-5-yl]-3-methoxy-, 1,1-dimethylethyl ester tert-Butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (180 mg, 0.294 mmol) was dissolved in a solution of ethanol (1 ml), triethyl amine (82.0 uL, 0.588 mmol) and the hydrochloride salt of 2-propyl hydrazine (36 mg, 0.323 mmol). The reaction was heated in a microwave at 160° C. for 2 hours and then concentrated. The resulting solid was purified by preparative HPLC under the following conditions: Shimadzu preparative HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. Homogeneous fractions were combined and evaporated in vacuo to afford the title compound (127 mg, 69%) as a yellow paste. MS m/z 624 (MH$^+$).

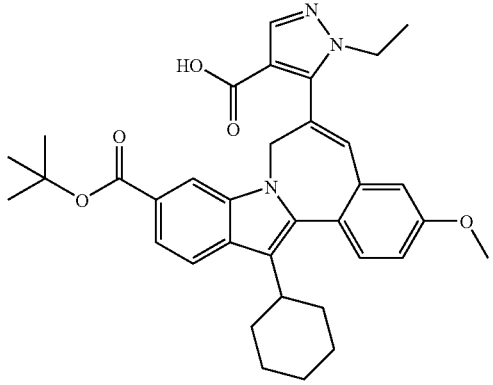

7H-indolo[2,1-a][2]benzazepine-10-carboxylic acid, 6-(4-carboxy-1-ethyl-1H-pyrazol-5-yl)-13-cyclohexyl-3-methoxy-, 10-(1,1-dimethylethyl) ester 7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester (250 mg, 0.410 mmol) was dissolved in 12 mL of methanol/THF (1:1, v/v) and 1M aqueous sodium hydroxide (6 ml, 6 mmol) was added to the reaction. The resulting mixture was stirred at room temperature for 18 hr, and then diluted with 1M aqueous hydrochloric acid and the product was extracted with chloroform. The organic phase was dried over Na$_2$SO$_4$, filtered and the filtrate concentrated in vacuo to give the title compound (251 mg, 100%) that was used in subsequent steps without further purification. MS m/z 612 (MH$^+$).

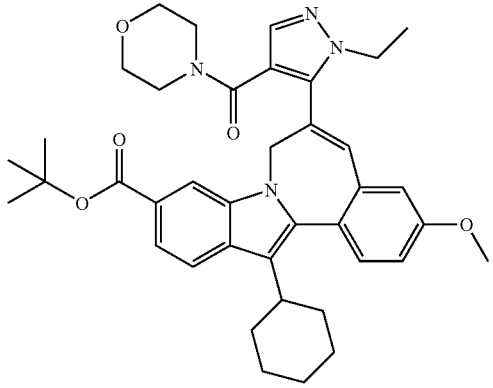

7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy-, 1,1-dimethylethyl ester To a solution of 7H-indolo[2,1-a][2]benzazepine-10-carboxylic acid, 6-(4-carboxy-1-ethyl-1H-pyrazol-5-yl)-13-cyclohexyl-3-methoxy-, 10-(1,1-dimethylethyl) ester (120 mg, 0.206 mmol) in THF (1 mL) at 60° C. was added carbonyldiimidazole (47 mg, 0.288 mmol) and the solution stirred for 1 hour. Morpholine (36 mg, 0.412 mmol) and DBU (33 mg, 0.268 mmol) were then added and the reaction was heated for a further 1 hr and was then allowed to stir to room temperature overnight. The reaction was then diluted with 1M aqueous hydrochloric acid and the resultant mixture was extracted with chloroform. The extracts were dried over Na$_2$SO$_4$, filtered and then concentrated in vacuo to provide the title compound in quantitative yield. MS m/z 651 (MH$^+$).

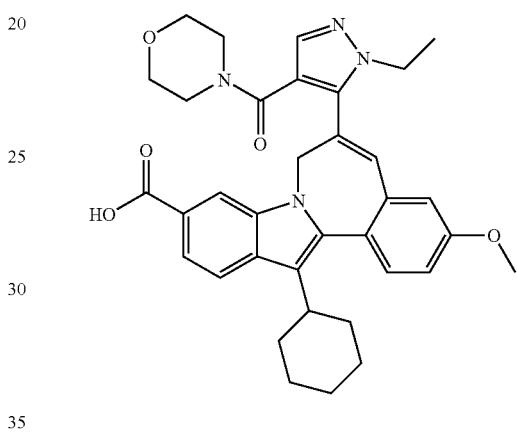

7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy- 7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy-, 1,1-dimethylethyl ester (61 mg, 0.094 mmol) was dissolved in trifluoroacetic acid (2 mL) and stirred at room temperature for 3 hours and the mixture was then concentrated in vacuo. Residual trifluoroacetic acid was removed by azeotroping with benzene and the final product was dried in vacuo to provide the title compound, (56 mg, 100%) that was used without further purification. MS m/z 595 (MH$^+$).

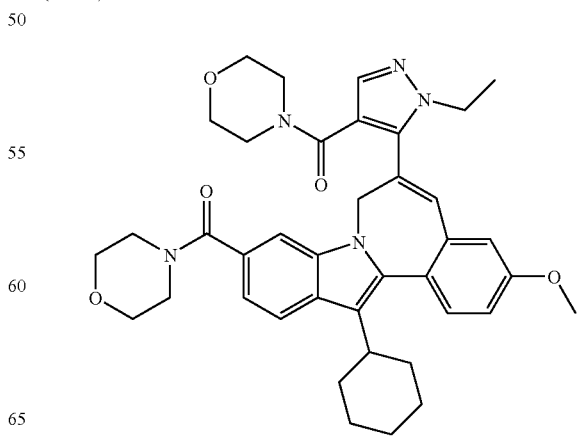

Morpholine, 4-[[13-cyclohexyl-6-[1-ethyl-4-(4-morpholinylcarbonyl)-1H-pyrazol-5-yl]-3-methoxy-7H-indolo[2,1-a][2]benzazepin-10-yl]carbonyl]-

7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy-, (60 mg, 0.092 mmol) was dissolved in THF (0.9 mL) and carbonyldiimidazole (21 mg, 0.130 mmol) was added. The resultant mixture was then stirred at 60° C. for 1 hr. Upon cooling to room temperature under a nitrogen atmosphere, morpholine (40 mg, 0.460 mmol) and DBU (0.012 mL, 0.120 mmol) were added. The reaction was heated for 1 hr then allowed to stir to room temperature overnight. The resulting mixture was filtered and the resultant filtrate was purified by preparative HPLC under the following conditions: Shimadzu preparative HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 mL/min; Column=Waters Sunfire 30×100 mm S5. This afforded the title compound (31 mg, 51%) as a yellow paste. MS m/z 664 (MH$^+$).

The following compounds were synthesized by an analogous sequence as described above for 7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy-:

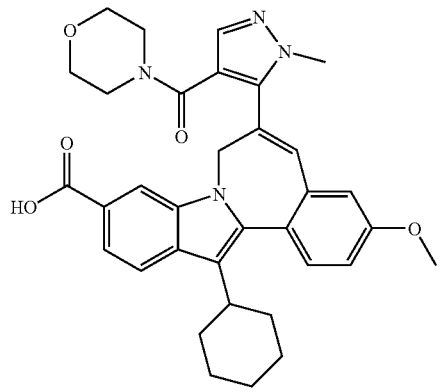

7H-indolo[2,1-a][2]benzazepine-10-carboxylic acid, 13-cyclohexyl-3-methoxy-6-[1-methyl-4-(4-morpholinylcarbonyl)-1H-pyrazol-5-yl]-. MS m/z 581 (MH$^+$).

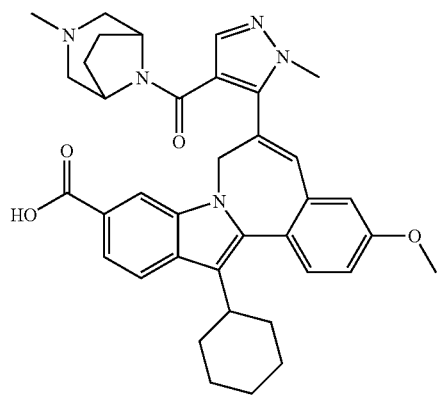

7H-indolo[2,1-a][2]benzazepine-10-carboxylic acid, 13-cyclohexyl-3-methoxy-6-[1-methyl-4-[(3-methyl-3,8-diazabicyclo[3.2.1]oct-8-yl)carbonyl]-1H-pyrazol-5-yl]-. MS m/z 620 (MH$^+$).

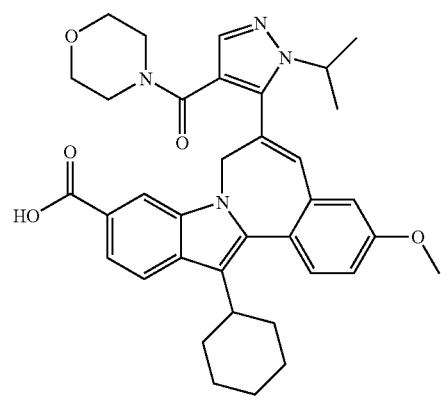

7H-indolo[2,1-a][2]benzazepine-10-carboxylic acid, 13-cyclohexyl-3-methoxy-6-[1-(1-methylethyl)-4-(4-morpholinylcarbonyl)-1H-pyrazol-5-yl]-. MS m/z 609 (MH$^+$).

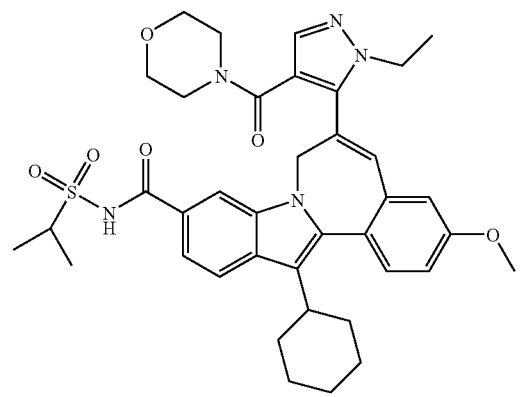

7H-indolo[2,1-a][2]benzazepine-10-carboxamide, 13-cyclohexyl-6-[1-ethyl-4-(4-morpholinylcarbonyl)-1H-pyrazol-5-yl]-3-methoxy-N-[(1-methylethyl)sulfonyl]-

7H-indolo[2,1-a][2]benzazepine-10-carboxylic acid, 13-cyclohexyl-6-[1-ethyl-4-(4-morpholinylcarbonyl)-1H-pyrazol-5-yl]-3-methoxy-, (56 mg, 0.094 mmol) was dissolved in THF (0.9 mL) and carbonyldiimidazole (21 mg, 0.129 mmol) added to the reaction at 60° C. and the resultant mixture was stirred for 1 hr. Propane-2-sulfonamide (57 mg, 0.246 mmol) and DBU (15 mg, 0.120 mmol) were then added to the reaction and the mixture was heated for a further 1 hour, then allowed to stir to room temperature for 18 hours. The resulting mixture was filtered and the filtrate purified by prep HPLC under the following conditions: Shimadzu preparative HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 mL/min; Column=Waters Sunfire 30×100 mm S5. This afforded the title compound (40 mg, 61%) as a yellow paste. MS m/z 700 (MH$^+$).

The following compounds were synthesized by an analogous method as described above for 7H-indolo[2,1-a][2]benzazepine-10-carboxamide, 13-cyclohexyl-6-[1-ethyl-4-(4-morpholinylcarbonyl)-1H-pyrazol-5-yl]-3-methoxy-N-[(1-methylethyl)sulfonyl]-:

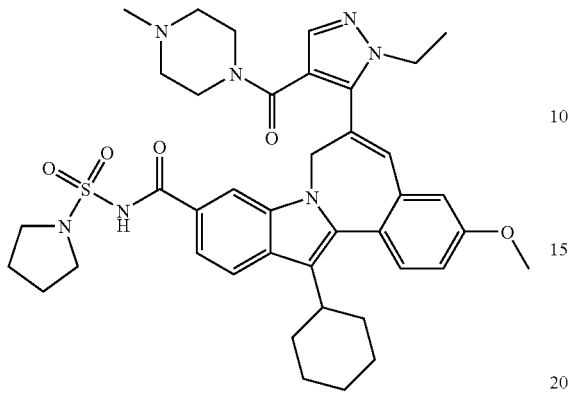

7H-indolo[2,1-a][2]benzazepine-10-carboxamide, 13-cyclohexyl-6-[1-ethyl-4-[(4-methyl-1-piperazinyl)carbonyl]-1H-pyrazol-5-yl]-3-methoxy-N-(1-pyrrolidinylsulfonyl)-. MS m/z 740 (MH+).

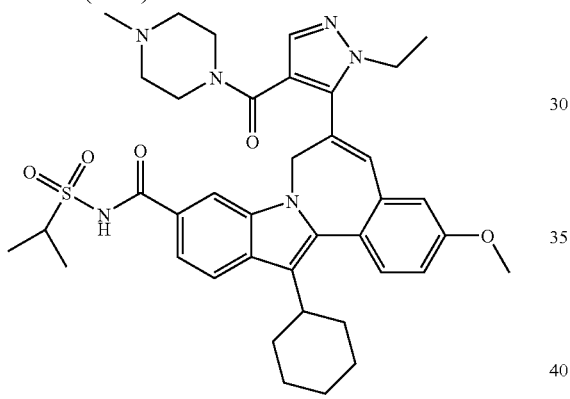

7H-indolo[2,1-a][2]benzazepine-10-carboxamide, 13-cyclohexyl-6-[1-ethyl-4-[(4-methyl-1-piperazinyl)carbonyl]-1H-pyrazol-5-yl]-3-methoxy-N-[(1-methylethyl)sulfonyl]-. MS m/z 713 (MH+).

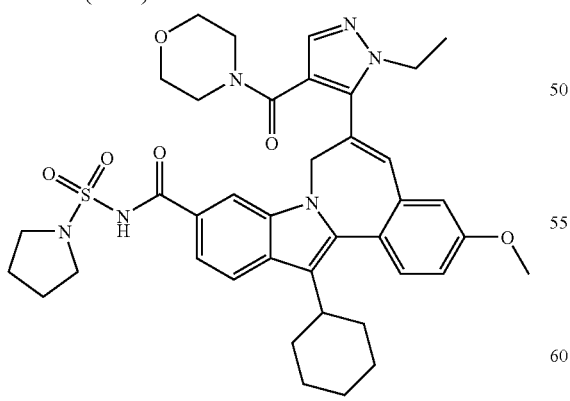

7H-indolo[2,1-a][2]benzazepine-10-carboxamide, 13-cyclohexyl-6-[1-ethyl-4-(4-morpholinylcarbonyl)-1H-pyrazol-5-yl]-3-methoxy-N-(1-pyrrolidinylsulfonyl)-. MS m/z 727 (MH+).

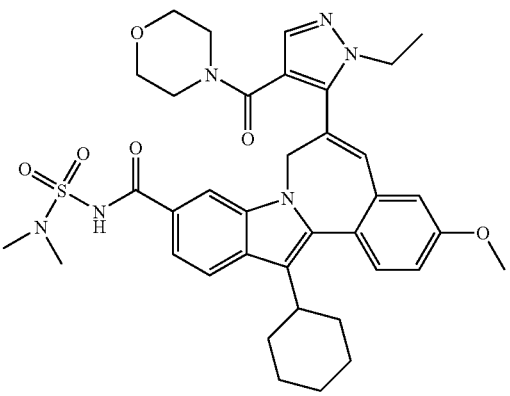

7H-indolo[2,1-a][2]benzazepine-10-carboxamide, 13-cyclohexyl-N-[(dimethylamino)sulfonyl]-6-[1-ethyl-4-(4-morpholinylcarbonyl)-1H-pyrazol-5-yl]-3-methoxy-. MS m/z 701 (MH+).

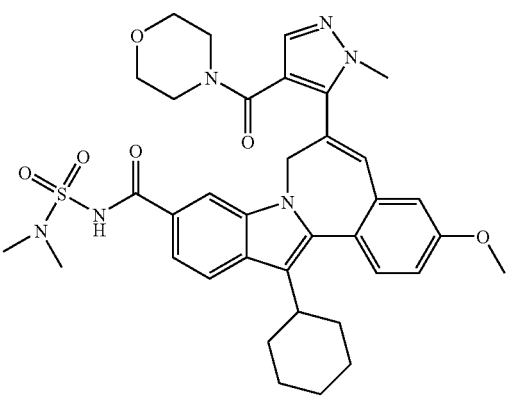

7H-indolo[2,1-a][2]benzazepine-10-carboxamide, 13-cyclohexyl-N-[(dimethylamino)sulfonyl]-3-methoxy-6-[1-methyl-4-(4-morpholinylcarbonyl)-1H-pyrazol-5-yl]-. MS m/z 687 (MH+).

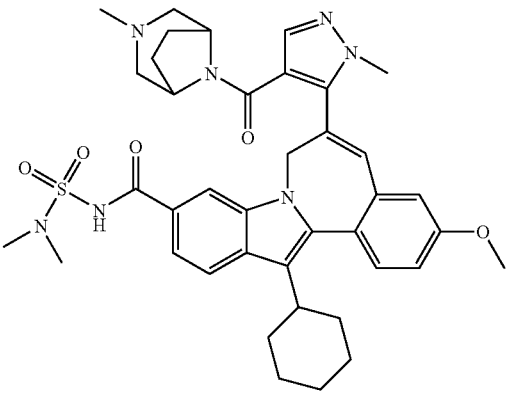

7H-indolo[2,1-a][2]benzazepine-10-carboxamide, 13-cyclohexyl-N-[(dimethylamino)sulfonyl]-3-methoxy-6-[1-methyl-4-[(3-methyl-3,8-diazabicyclo[3.2.1]oct-8-yl)carbonyl]-1H-pyrazol-5-yl]-. MS m/z 726 (MH+).

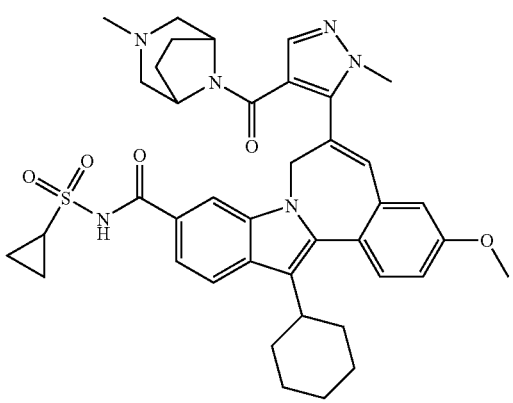

7H-indolo[2,1-a][2]benzazepine-10-carboxamide, 13-cyclohexyl-N-(cyclopropylsulfonyl)-3-methoxy-6-[1-methyl-4-[(3-methyl-3,8-diazabicyclo[3.2.1]oct-8-yl)carbonyl]-1H-pyrazol-5-yl]-. MS m/z 723 (MH+).

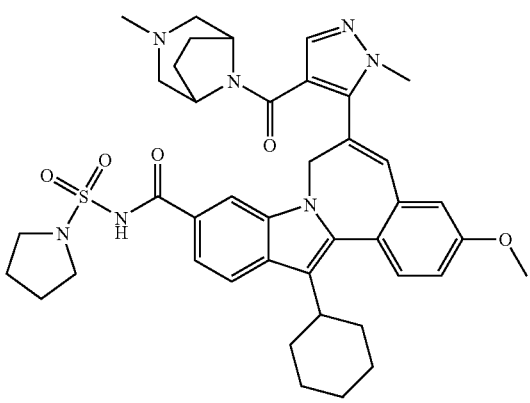

7H-indolo[2,1-a][2]benzazepine-10-carboxamide, 13-cyclohexyl-3-methoxy-6-[1-methyl-4-[(3-methyl-3,8-diazabicyclo[3.2.1]oct-8-yl)carbonyl]-1H-pyrazol-5-yl]-N-(1-pyrrolidinylsulfonyl)-. MS m/z 752 (MH+).

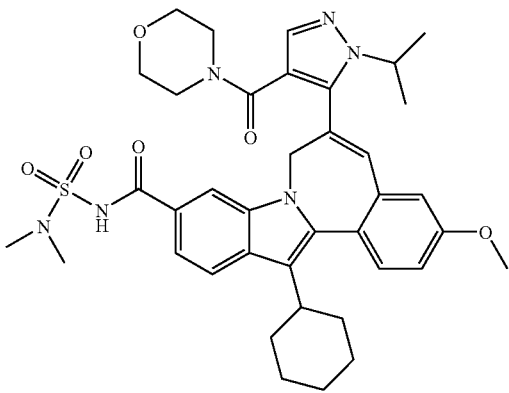

7H-indolo[2,1-a][2]benzazepine-10-carboxamide, 13-cyclohexyl-N-[(dimethylamino)sulfonyl]-3-methoxy-6-[1-(1-methylethyl)-4-(4-morpholinylcarbonyl)-1H-pyrazol-5-yl]-. MS m/z 715 (MH+).

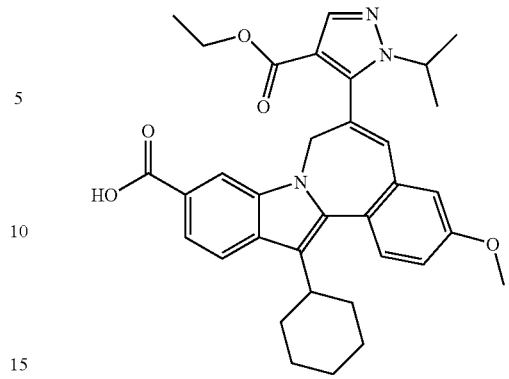

7H-indolo[2,1-a][2]benzazepine-10-carboxylic acid, 13-cyclohexyl-6-[4-(ethoxycarbonyl)-1-1-(1-methylethyl)-1H-pyrazol-5-yl]-3-methoxy-. Dissolve 7H-indolo[2,1-a][2]benzazepine-10-carboxylic acid, 13-cyclohexyl-6-[4-(ethoxycarbonyl)-1-(1-methylethyl)-1H-pyrazol-5-yl]-3-methoxy-, 1,1-dimethylethyl ester (2.00 g, 3.21 mmol) in 1,2-dichloroethane (6.41 mL), place reaction under a nitrogen atmosphere, then add trifluoroacetic acid (6.41 ml). Stir reaction at room temperature under a nitrogen atmosphere for 2 hours. Remove volatiles in vacuo and dissolve the reaction product in benzene and remove in vacuo to aid in removal of trace TFA. Repeat dissolution in benzene and removal in vacuo. Dry sample at room temperature in vacuo to obtain the title compound (1.92 g, 100% yield) as a yellow solid. 1H NMR (500 MHz, CHLOROFORM-D) δ ppm 0.48 (br s, 3H) 1.12-1.65 (m, 9H) 1.72-2.19 (m, 7H) 2.87 (t, J=11.29 Hz, 1H) 3.91 (s, 3H) 4.22 (m, 1H) 4.32 (br.s, 2H) 4.73 (br.s, 1H) 4.97 (br.s, 1H) 6.70 (s, 1H) 6.94 (d, J=2.14 Hz, 1H) 7.08 (dd, J=8.55, 2.44 Hz, 1H) 7.52 (m, 2H) 7.64 (d, J=8.24 Hz, 1H) 7.82 (d, J=8.24 Hz, 1H) 7.96 (s, 1H). LCMS 566 m/z (MH−).

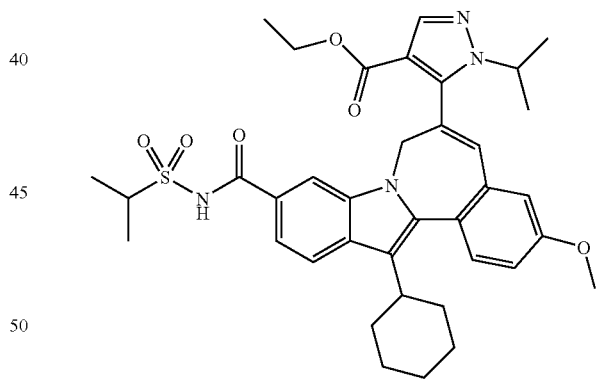

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-1-(1-methylethyl)-, ethyl ester. Dissolve 7H-indolo[2,1-a][2]benzazepine-10-carboxylic acid, 13-cyclohexyl-6-[4-(ethoxycarbonyl)-1-(1-methylethyl)-1H-pyrazol-5-yl]-3-methoxy- (1.00 g, 1.76 mmol) in THF (5.87 mL). Carbonyldiimidazole (857 mg, 5.28 mmol) was added to the reaction. The reaction was placed under a nitrogen atmosphere and stirred at room temperature for 45 minutes then heated to reflux for 1 hour. The reaction was cooled under a nitrogen atmosphere and propane-2-sulfonamide (868 mg, 7.05 mmol) was added to the reaction followed by DBU (0.797 mL, 5.28 mmol). The reaction was immerse in oil bath at 80 deg C. under nitrogen atmosphere and heated overnight at 70-80 deg C. The reaction was diluted with ethyl acetate (50 mL) and the organic layer washed sequentially with 1.0N aqueous hydrochloric acid (50 mL), 0.1M aqueous NaH2PO4 (50 mL) and brine (25 mL). The organic layer was dried over MgSO4, filtered and volatiles removed in vacuo to yield a yellow foam which was dried in vacuo at room temperature overnight to yield 1.03 g (1.57 mmol, 87%) of the title compound as a yellow amorphous solid. 1H NMR (500 MHz, CHLOROFORM-D) δ ppm 0.40 (br s, 3H) 1.12-1.70 (m, 15H) 1.72-2.18 (m, 7H) 2.84 (t, J=11.29 Hz, 1H) 3.90 (s, 3H) 4.11 (m, 1H) 4.26 (m, 3H) 4.66 (br.s, 1H) 4.97 (br.s, 1H) 6.68 (s, 1H) 6.94 (d, J=2.14 Hz, 1H) 7.08 (m, 2H) 7.52 (d, J=8.24 Hz, 1H) 7.67 (d, J=8.24 Hz, 1H) 7.80 (d, J=8.24 Hz, 1H) 7.89 (s, 1H). LCMS 671 m/z (MH−).

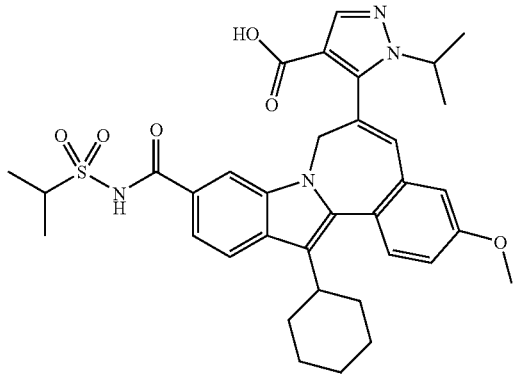

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methylethyl)-. Dissolve 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methylethyl)-, ethyl ester (1.20 g, 1.78 mmol) was dissolved in THF (15.0 mL) and methanol (15.0 mL) was added to the reaction followed by 1N aqueous sodium hydroxide (15.0 mL). The reaction was capped under a nitrogen atmosphere and stirred at room temperature for 18 hrs. The reaction was diluted with ethyl acetate (25.0 mL) and washed with 1.0N aqueous hydrochloric acid (2×20 mL). The organic layer was concentrated in vacuo using a rotary evaporator to yield the title compound as a yellow solid (1.15 g, 100%).

MS m/z 645 (MH+).

1H NMR (500 MHz, CHLOROFORM-D) δ ppm 0.46 (br s, 3H) 1.12-1.70 (m, 12H) 1.72-2.15 (m, 7H) 2.85 (t, J=11.29 Hz, 1H) 3.90 (s, 3H) 4.26 (m, 1H) 4.62 (br.s, 1H) 4.99 (br.s, 1H) 6.69 (s, 1H) 6.96 (d, J=2.14 Hz, 1H) 7.06 (dd, J=8.55, 2.44 Hz, 1H) 7.50 (m, 2H) 7.80 (m, 2H) 7.85 (s, 1H) 9.09 (br s, 1H).

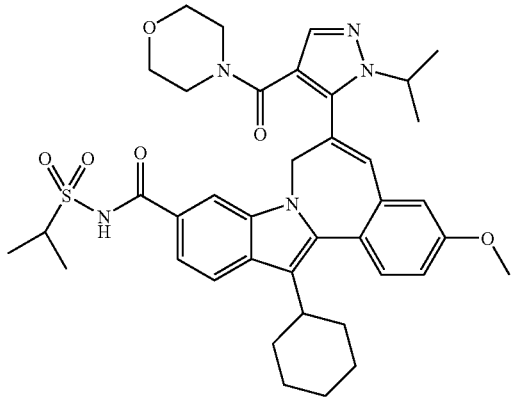

7H-indolo[2,1-a][2]benzazepine-10-carboxamide, 13-cyclohexyl-3-methoxy-6-[1-(1-methylethyl)-4-(4-morpholinylcarbonyl)-1H-pyrazol-5-yl]-N-[(1-methylethyl)sulfonyl]-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methylethyl)- (125 mg, 0.194 mmol) in DMSO (1.94 mL), TBTU (124 mg, 0.388 mmol) and DIPEA (0.100 mg, 0.775 mmol) were added. The reaction mixture was stirred at RT for 15 min. Then morpholine (68 mg, 0.775 mmol) was added. The solution was stirred at RT for overnight. The reaction mixture was purified by prep HPLC column using CH3CN/H2O/TFA as solvent system. Fractions were collected and concentrated under speedvac overnight to yield the title compound as a yellow solid (82 mg, 0.114 mmol, 59% yield). MS m/z 714 (M−H+). 1H NMR (500 MHz, CDCl3) δ ppm 1.20 (m, 1H) 1.32-1.65 (m, 15H) 1.73-2.20 (m, 6H) 2.63-3.24 (m, 7H) 3.50 (br m, 2H) 3.93 (s, 3H) 4.07 (m, 1H) 4.58 (m, 2H) 4.90 (m, br, 1H) 6.78 (s, 1H) 6.93 (d, J=2.44 Hz, 1H) 7.13 (dd, J=8.55, 2.75 Hz, 1H) 7.53-7.64 (m, 2H) 7.71 (m, 2H) 7.93 (d, J=8.55 Hz, 1H) 10.15 (s, br, 1H).

The following compounds were synthesized by an analogous method as described above for 7H-indolo[2,1-a][2]benzazepine-10-carboxamide, 13-cyclohexyl-3-methoxy-6-[1-(1-methylethyl)-4-(4-morpholinylcarbonyl)-1H-pyrazol-5-yl]-N-[(1-methylethyl)sulfonyl]-:

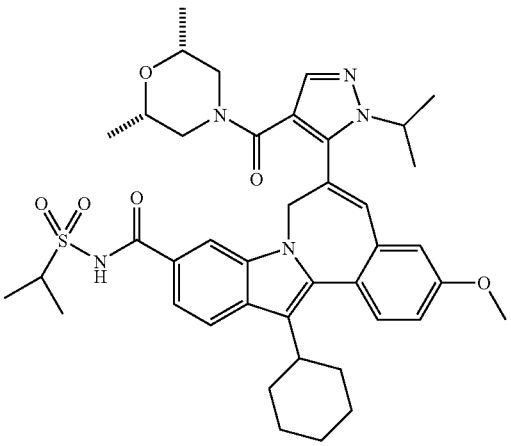

7H-indolo[2,1-a][2]benzazepine-10-carboxamide, 13-cyclohexyl-6-[4-[(2,6-dimethyl-4-morpholinyl)carbonyl]-1-(1-methylethyl)-1H-pyrazol-5-yl]-3-methoxy-N-[(1-methylethyl)sulfonyl]-: 1H NMR (500 MHz, CDCl3) δ ppm 0.61-0.92 (m, 6H) 1.23 (m, 1H) 1.35-1.70 (m, 15H) 1.73-2.20 (m, 6H) 2.88 (m, 1H) 3.12-3.70 (m, 6H) 3.92 (s, 3H) 4.09 (m, 1H) 4.58 (m, 2H) 4.91 (m, br, 1H) 6.75 (s, 1H) 6.92 (d, J=2.44 Hz, 1H) 7.12 (dd, J=8.55, 2.75 Hz, 1H) 7.53-7.68 (m, 2H) 7.75 (m, 2H) 7.92 (d, J=8.55 Hz, 1H) 10.10 (s, br, 1H). LCMS: m/e 742 (M+H).

109

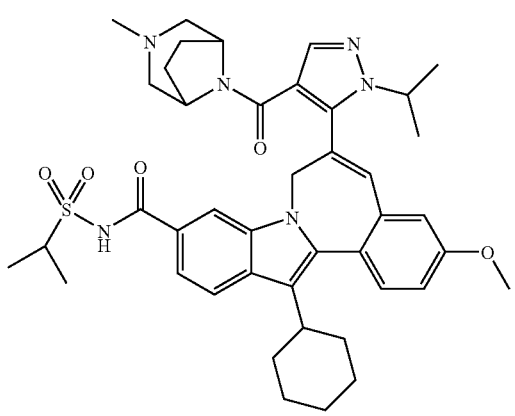

7H-indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(1-methylethyl)-1H-pyrazol-5-yl]-N-[(1-methylethyl)sulfonyl]-: 1H NMR (500 MHz, CDCl3) δ ppm 0.02 (m, 2H) 0.82 (m, 2H) 1.20-1.82 (m, 16H) 1.91-2.18 (m, 6H) 2.39-2.70 (m, 4H) 2.88 (m, 1H) 2.96-3.59 (m, 5H) 3.94 (s, 3H) 4.06 (m, 1H) 4.62 (m, 2H) 4.85 (m, br, 1H) 6.92 (m, 2H) 7.12 (dd, J=8.55, 2.75 Hz, 1H) 7.53-7.69 (m, 3H) 7.86 (br s, 1H) 7.92 (d, J=8.55 Hz, 1H) 10.10 (s, br, 1H). LCMS: m/e 753 (M+H).

110

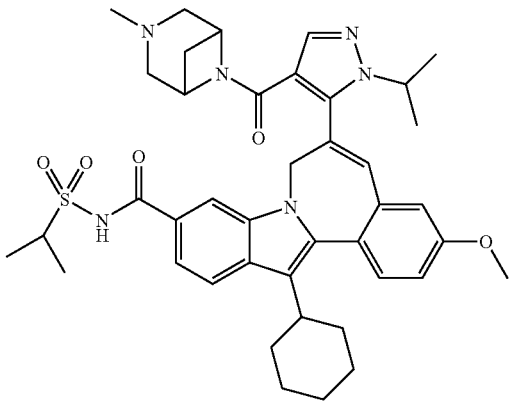

7H-indolo[2,1-a][2]benzazepine-10-carboxamide, 13-cyclohexyl-3-methoxy-6-[4-[(3-methyl-3,6-diazabicyclo[3.1.1]hept-6-yl)carbonyl]-1-(1-methylethyl)-1H-pyrazol-5-yl]-N-[(1-methylethyl)sulfonyl]-: 1H NMR (500 MHz, CDCl3) δ ppm 1.17-1.85 (m, 15H) 1.90-2.18 (m, 9H) 2.59-2.99 (m, 6H) 3.35-4.10 (m, 8H) 4.66-5.00 (m, 3H) 6.92 (m, 2H) 7.12 (dd, J=8.55, 2.75 Hz, 1H) 7.50-7.69 (m, 3H) 7.75-8.01 (m, 2H) 10.00 (s, br, 1H). LCMS: m/e 739 (M+H).

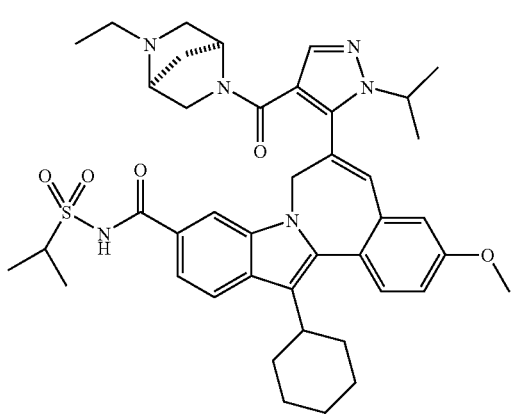

7H-indolo[2,1-a][2]benzazepine-10-carboxamide, 13-cyclohexyl-6-[4-[[(1S)-5-ethyl-2,5-diazabicyclo[2.2.1]hept-2-yl]carbonyl]-1-(1-methylethyl)-1H-pyrazol-5-yl]-3-methoxy-N-[(1-methylethyl)sulfonyl]-: 1H NMR (500 MHz, CDCl3) δ ppm 0.02 (m, 1H) 1.10-1.59 (m, 19H) 1.91-2.49 (m, 8H) 2.80-3.69 (m, 4H) 2.88 (m, 1H) 3.81-4.41 (s, 7H) 4.62 (m, 2H) 4.90 (m, br, 1H) 6.97 (m, 2H) 7.10 (m, 1H) 7.53-7.67 (m, 2H) 7.71-7.95 (m, 3H) 10.20 (s, br, 1H). LCMS: m/e 753 (M+H).

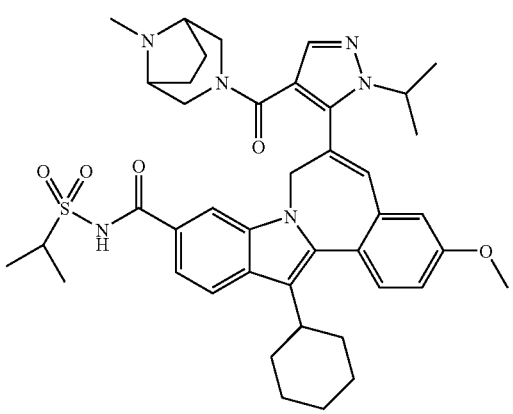

7H-indolo[2,1-a][2]benzazepine-10-carboxamide, 13-cyclohexyl-3-methoxy-6-[4-[(8-methyl-3,8-diazabicyclo[3.2.1]oct-3-yl)carbonyl]-1-(1-methylethyl)-1H-pyrazol-5-yl]-N-[(1-methylethyl)sulfonyl]-: 1H NMR (500 MHz, CDCl3) δ ppm 0.021 (m, 2H) 0.81 (m, 2H) 1.20-1.86 (m, 16H) 1.91-2.17 (m, 6H) 2.41-2.71 (m, 4H) 2.88 (m, 1H) 2.97-3.70 (m, 5H) 3.94 (s, 3H) 4.08 (m, 1H) 4.62 (m, 2H) 4.85 (m, br, 1H) 6.94 (m, 2H) 7.12 (dd, J=8.55, 2.75 Hz, 1H) 7.52-7.69 (m, 3H) 7.80-7.95 (m, 2H) 10.10 (s, br, 1H). LCMS: m/e 753 (M+H).

111

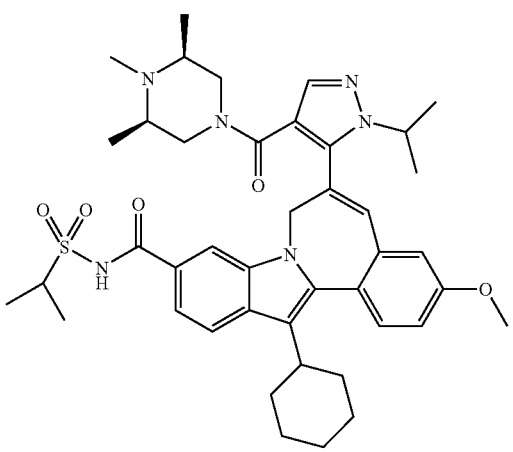

7H-indolo[2,1-a][2]benzazepine-10-carboxamide, 13-cyclohexyl-3-methoxy-N-[(1-methylethyl)sulfonyl]-6-[1-(1-methylethyl)-4-[(3,4,5-trimethyl-1-piperazinyl)carbonyl]-1H-pyrazol-5-yl]-: 1H NMR (500 MHz, CDCl3) δ ppm 1.20-1.82 (m, 22H) 1.91-2.18 (m, 6H) 2.50 (br s, 3H) 2.90 (m, 1H) 3.35-3.69 (m, 7H) 3.92 (s, 3H) 4.02 (m, 1H) 4.61 (br m, 1H) 4.93 (br m, 1H) 6.80 (br s, 1H) 6.95 (s, 1H) 7.11 (dd, J=8.55, 2.75 Hz, 1H) 7.51-7.65 (m, 3H) 7.80 (br s, 1H) 7.90 (d, J=8.55 Hz, 1H) 10.20 (s, br, 1H). LCMS: m/e 755 (M+H).

112

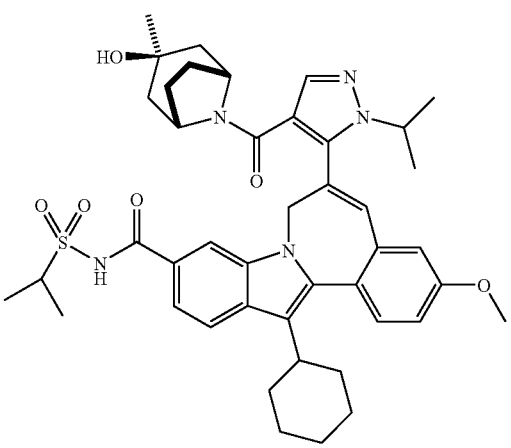

7H-indolo[2,1-a][2]benzazepine-10-carboxamide, 13-cyclohexyl-6-[4-[[(3-endo)-3-hydroxy-3-methyl-8-azabicyclo[3.2.1]oct-8-yl]carbonyl]-1-(1-methylethyl)-1H-pyrazol-5-yl]-3-methoxy-N-[(1-methylethyl)sulfonyl]-: 1H NMR (500 MHz, CDCl3) δ ppm −0.25 (m, 1H) 0.52 (m, 1H) 1.04 (s, 3H) 1.15-1.82 (m, 24H) 1.91-2.18 (m, 4H) 2.89 (m, 1H) 3.29 (m, 1H) 3.62 (m, 1H) 3.92 (s, 3H) 4.06 (m, 1H) 4.54-4.71 (m, 2H) 5.00 (br d, 1H) 6.82 (br s, 1H) 6.91 (d, J=2.75 Hz, 1H) 7.12 (dd, J=8.55, 2.75 Hz, 1H) 7.50-7.60 (m, 2H) 7.70 (m, 1H) 7.80-7.95 (m, 2H) 10.20 (s, br, 1H). LCMS: m/e 768 (M+H), ret time 2.75 min (method 1).

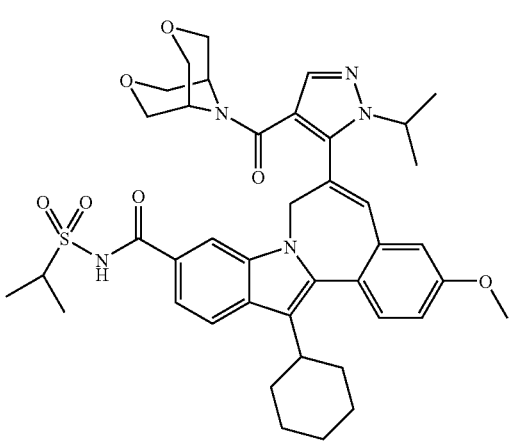

7H-indolo[2,1-a][2]benzazepine-10-carboxamide, 13-cyclohexyl-6-[4-(3,7-dioxa-9-azabicyclo[3.3.1]non-9-ylcarbonyl)-1-(1-methylethyl)-1H-pyrazol-5-yl]-3-methoxy-N-[(1-methylethyl)sulfonyl]-: 1H NMR (500 MHz, CDCl3) δ ppm 1.15-1.82 (m, 19H) 1.91-2.18 (m, 3H) 2.88 (m, 1H) 3.12-3.80 (m, 9H) 3.92 (s, 3H) 4.05 (m, 1H) 4.40 (m, 2H) 4.61 (br d, 1H) 4.92 (br d, 1H) 6.78 (s, 1H) 6.91 (d, J=2.44 Hz, 1H) 7.13 (dd, J=8.55, 2.75 Hz, 1H) 7.59-7.65 (m, 2H) 7.77 (m, 2H) 7.93 (d, J=8.55 Hz, 1H) 10.10 (s, br, 1H). LCMS: m/e 756 (M+H).

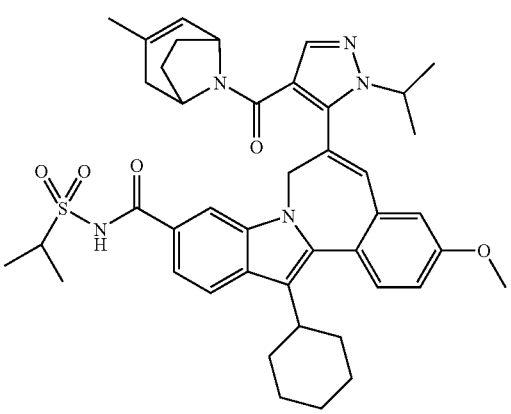

7H-indolo[2,1-a][2]benzazepine-10-carboxamide, 13-cyclohexyl-3-methoxy-6-[4-[(3-methyl-8-azabicyclo[3.2.1]oct-2-en-8-yl)carbonyl]-1-(1-methylethyl)-1H-pyrazol-5-yl]-N-[(1-methylethyl)sulfonyl]-: m/e 750 (M+H), ret time 2.89 min (method 1).

113

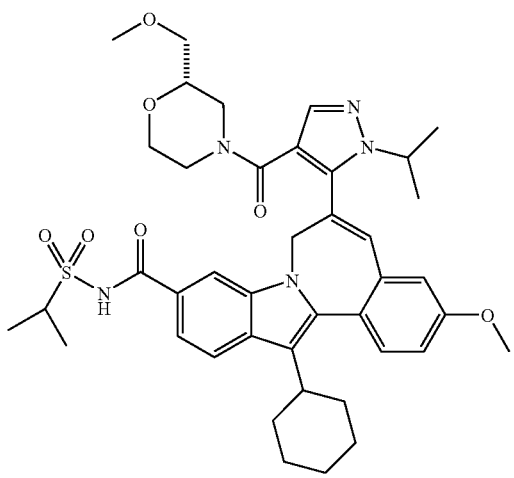

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-(1-methylethyl)-1H-pyrazol-5-yl]-N-[(1-methylethyl)sulfonyl]-: 1H NMR (500 MHz, CDCl3) δ ppm 1.21 (m, 1H) 1.32-1.70 (m, 15H) 1.73-2.20 (m, 6H) 2.72-3.47 (m, 8H) 3.88-4.17 (m, 10H) 4.61 (m, 1H) 4.95 (m, br, 1H) 6.80 (br d, 1H) 6.93 (br s, 1H) 7.12 (dd, J=8.55, 2.75 Hz, 1H) 7.53-7.64 (m, 2H) 7.71-7.96 (m, 3H) 10.15 (s, br, 1H). LCMS: m/e 758 (M+H).

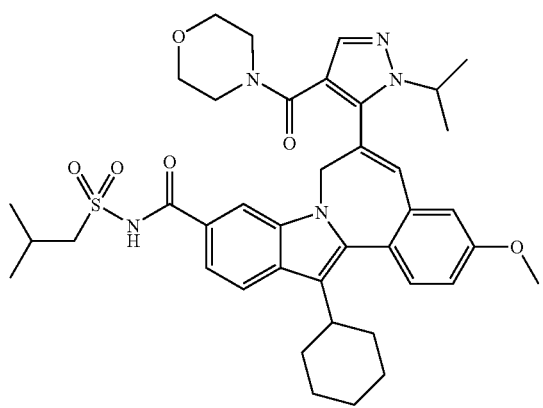

7H-indolo[2,1-a][2]benzazepine-10-carboxamide, 13-cyclohexyl-3-methoxy-6-[1-(1-methylethyl)-4-(4-morpholinylcarbonyl)-1H-pyrazol-5-yl]-N-[(2-methylpropyl)sulfonyl]-: LCMS: m/e 728 (M+H), ret time 3.59 min (method 2).

114

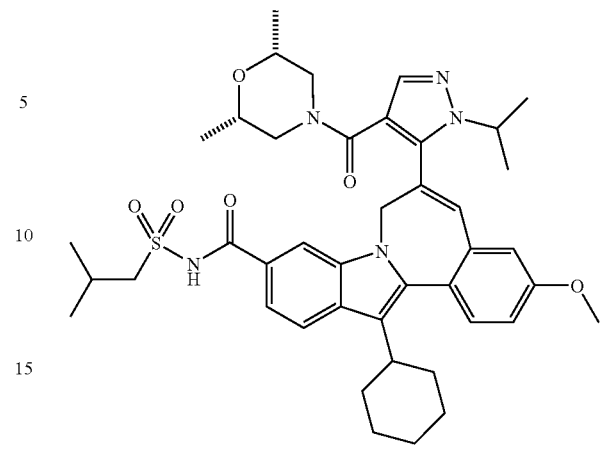

7H-indolo[2,1-a][2]benzazepine-10-carboxamide, 13-cyclohexyl-6-[4-[(2,6-dimethyl-4-morpholinyl)carbonyl]-1-(1-methylethyl)-1H-pyrazol-5-yl]-3-methoxy-N-[(2-methylpropyl)sulfonyl]-: LCMS: m/e 756 (M+H), ret time 3.71 min (method 2).

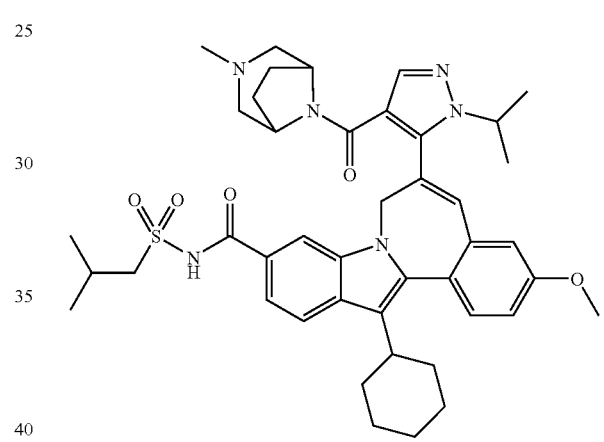

7H-indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(1-methylethyl)-1H-pyrazol-5-yl]-N-[(2-methylpropyl)sulfonyl]-: LCMS: m/e 767 (M+H), ret time 3.35 min (method 2).

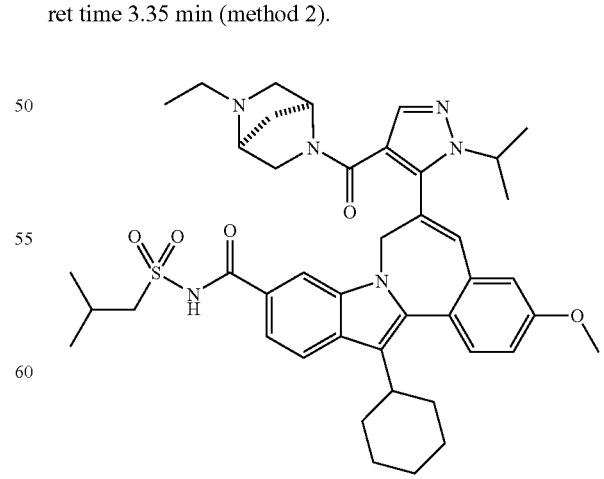

7H-indolo[2,1-a][2]benzazepine-10-carboxamide, 13-cyclohexyl-6-[4-[[(1S)-5-ethyl-2,5-diazabicyclo[2.2.1]hept-2- yl]carbonyl]-1-(1-methylethyl)-1H-pyrazol-5-yl]-3-methoxy-N-[(2-methylpropyl)sulfonyl]-: LCMS: m/e 767 (M+H), ret time 3.31 min (method 2).

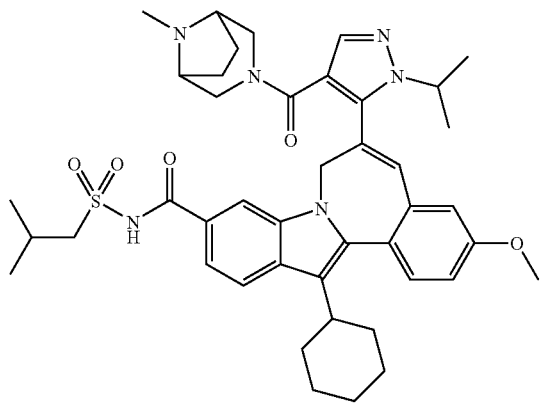

7H-indolo[2,1-a][2]benzazepine-10-carboxamide, 13-cyclohexyl-3-methoxy-6-[4-[(8-methyl-3,8-diazabicyclo[3.2.1]oct-3-yl)carbonyl]-1-(1-methylethyl)-1H-pyrazol-5-yl]-N-[(2-methylpropyl)sulfonyl]-: LCMS: m/e 767 (M+H), ret time 3.38 min (method 2).

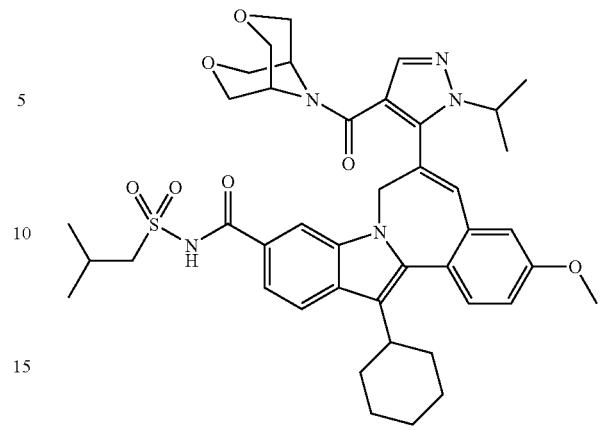

7H-indolo[2,1-a][2]benzazepine-10-carboxamide, 13-cyclohexyl-6-[4-(3,7-dioxa-9-azabicyclo[3.3.1]non-9-ylcarbonyl)-1-(1-methylethyl)-1H-pyrazol-5-yl]-3-methoxy-N-[(2-methylpropyl)sulfonyl]-: LCMS: m/e 770 (M+H), ret time 3.65 min (method 2).

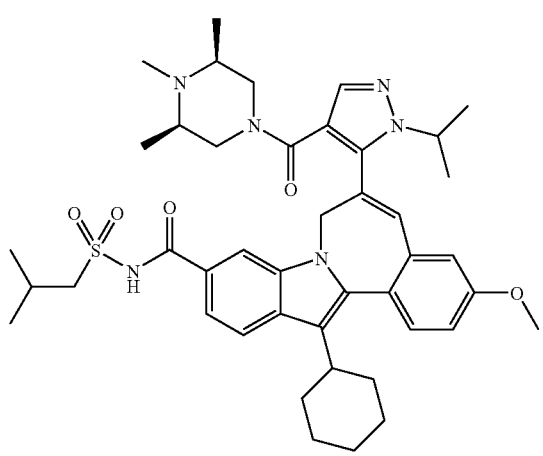

7H-indolo[2,1-a][2]benzazepine-10-carboxamide, 13-cyclohexyl-3-methoxy-N-[(2-methylpropyl)sulfonyl]-6-[1-(1-methylethyl)-4-[(3,4,5-trimethyl-1-piperazinyl)carbonyl]-1H-pyrazol-5-yl]-: LCMS: m/e 769 (M+H), ret time 3.32 min (method 2).

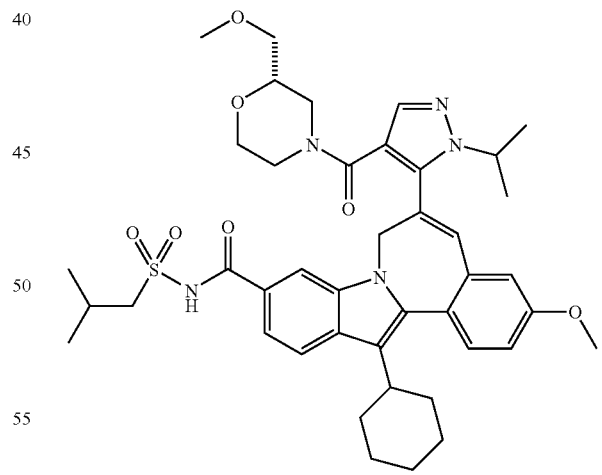

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-(1-methylethyl)-1H-pyrazol-5-yl]-N-[(2-methylpropyl)sulfonyl]-: LCMS: m/e 772 (M+H), ret time 3.61 min (method 2).

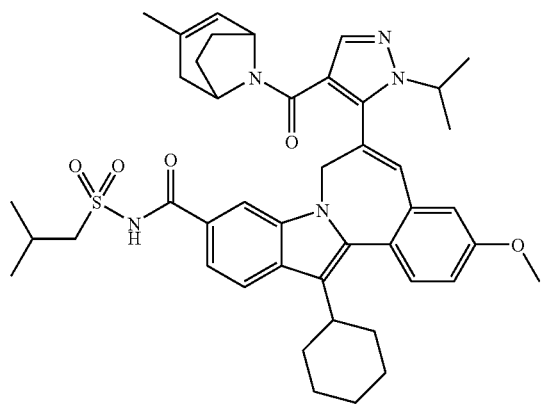

7H-indolo[2,1-a][2]benzazepine-10-carboxamide, 13-cyclohexyl-3-methoxy-6-[4-[(3-methyl-8-azabicyclo[3.2.1]oct-2-en-8-yl)carbonyl]-1-(1-methylethyl)-1H-pyrazol-5-yl]-N-[(2-methylpropyl)sulfonyl]-: LCMS: m/e 764 (M+H), ret time 3.69 min (method 2).

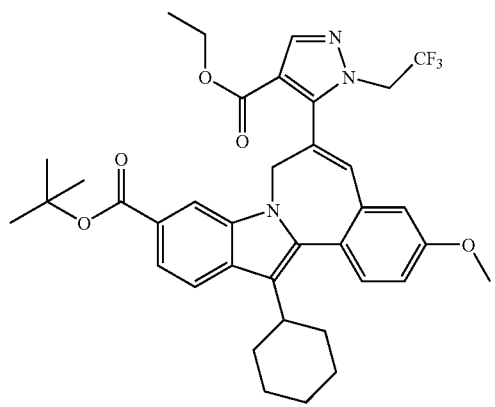

7H-indolo[2,1-a][2]benzazepine-10-carboxylic acid, 13-cyclohexyl-6-[4-(ethoxycarbonyl)-1-(2,2,2-trifluoroethyl)-1H-pyrazol-5-yl]-3-methoxy-, 1,1-dimethylethyl ester. tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (1.20 g, 1.96 mmol) was dissolved in a solution of ethanol (6.53 mL), triethyl amine (0.396 g, 3.92 mmol), and (2,2,2-trifluoroethyl)hydrazine (0.246 g, 2.15 mmol). The reaction was heated in a microwave at 160 deg C. for 2 hours and concentrated. The resulting solid was purified by prep HPLC under the following conditions: Shimadzu prep. HPLC using Discovery VP software: % A=10% acetonitrile, 90% water, 0.1% TFA; % B=90% acetonitrile, 10% water, 0.1% TFA; Initial % B=30; Final % B=100; Gradient=12 min; Runtime=20 min; Flow rate=40 ml/min; Column=Waters Sunfire 30×100 mm S5. This afforded the title compound (1.09 g, 84%) as a yellow paste. MS m/z 664 (MH+).

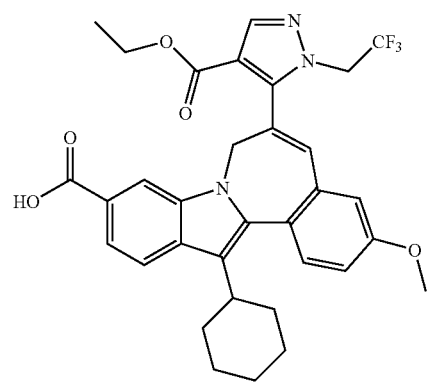

7H-indolo[2,1-a][2]benzazepine-10-carboxylic acid, 13-cyclohexyl-6-[4-(ethoxycarbonyl)-1-1-(2,2,2-trifluoroethyl)-1H-pyrazol-5-yl]-3-methoxy-. Dissolve 7H-indolo[2,1-a][2]benzazepine-10-carboxylic acid, 13-cyclohexyl-6-[4-(ethoxycarbonyl)-1-(2,2,2-trifluoroethyl)-1H-pyrazol-5-yl]-3-methoxy-, 1,1-dimethylethyl ester (1.20 g, 1.81 mmol) in 1,2-dichloroethane (3.62 mL), place reaction under a nitrogen atmosphere, then add trifluoroacetic acid (3.62 mL). Stir reaction at room temperature under a nitrogen atmosphere for 2 hours. Remove volatiles in vacuo and dissolve the reaction product in benzene and remove in vacuo to aid in removal of trace TFA. Repeat dissolution in benzene and removal in vacuo. Dried sample at room temperature in vacuo to obtain the title compound (0.923 g, 100% yield) as a yellow solid. 1H NMR (500 MHz, CHLOROFORM-D) δ ppm 1.20-1.62 (m, 7H) 1.70-2.19 (m, 6H) 2.87 (m, 1H) 3.91 (s, 3H) 4.12-4.45 (m, 4H) 4.76 (br.s, 1H) 4.97 (br.s, 1H) 6.82 (s, 1H) 6.96 (d, J=2.14 Hz, 1H) 7.10 (dd, J=8.55, 2.44 Hz, 1H) 7.56 (d, J=8.85 Hz, 1H) 7.78 (d, J=8.24 Hz, 1H) 7.90 (m, 2H) 8.11 (s, 1H). LCMS 608 m/z (MH+).

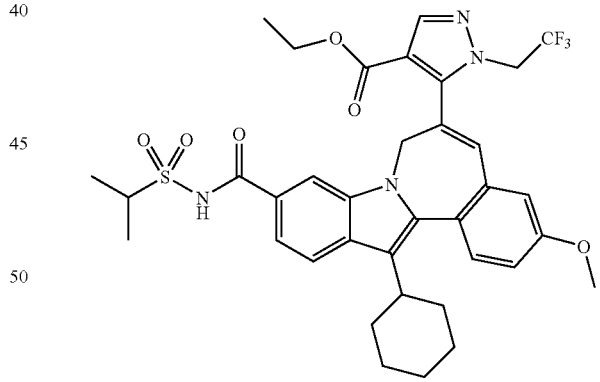

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(2,2,2-trifluoroethyl), ethyl ester. Dissolve 7H-indolo[2,1-a][2]benzazepine-10-carboxylic acid, 13-cyclohexyl-6-[4-(ethoxycarbonyl)-1-1-(2,2,2-trifluoroethyl)-1H-pyrazol-5-yl]-3-methoxy- (800 mg, 1.32 mmol) in THF (4.39 mL). Carbonyldiimidazole (640 mg, 3.95 mmol) was added to the reaction. The reaction was placed under a nitrogen atmosphere and stirred at room temperature for 45 minutes then heated to reflux for 1 hour. The reaction was cooled under a nitrogen atmosphere and propane-2-sulfonamide (649 mg, 5.27 mmol) was added to the reaction followed by DBU (0.595 mL, 3.95 mmol). The reaction was immerse in oil bath at 80 deg C. under nitrogen atmosphere and heated overnight at 70-80 deg C. The reaction was diluted with ethyl acetate (50 mL) and the organic layer washed sequentially with 1.0N aqueous hydrochloric acid (50 mL), 0.1M aqueous NaH2PO4 (50 mL) and brine (25 mL). The organic layer was dried over MgSO4, filtered and volatiles removed in vacuo to yield a yellow foam which was dried in vacuo at room temperature overnight to yield the title compound (949 mg, 100%) as a yellow amorphous solid. 1H NMR (500 MHz, CHLOROFORM-D) δ ppm 1.20-1.62 (m, 13H) 1.70-2.18 (m, 6H) 2.87 (m, 1H) 3.90 (s, 3H) 4.05 (m, 1H) 4.10-4.40 (m, 4H) 4.73 (br.s, 1H) 4.99 (br.s, 1H) 6.82 (s, 1H) 6.93 (d, J=2.14 Hz, 1H) 7.10 (dd, J=8.55, 2.44 Hz, 1H) 7.45 (br d, 1H) 7.52 (d, J=8.85 Hz, 1H) 7.80 (br s, 1H) 7.88 (d, J=8.85 Hz, 1H) 8.02 (s, 1H) 8.60 (br s, 1H). LCMS 713 m/z (MH+).

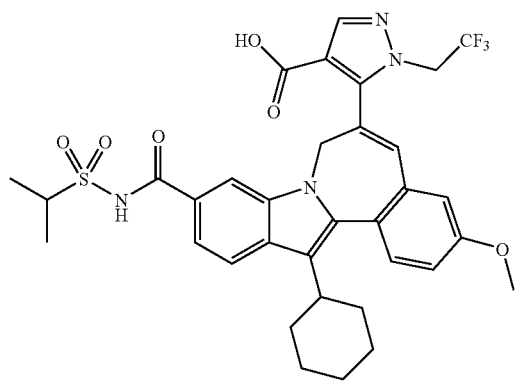

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(2,2,2-trifluoroethyl). Dissolve 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(2,2,2-trifluoroethyl), ethyl ester (0.816 g, 1.15 mmol) in THF (2.86 mL) and methanol (2.86 mL) was added to the reaction followed by 1N aqueous sodium hydroxide (2.29 mL). The reaction was capped under a nitrogen atmosphere and stirred at room temperature for 18 hrs. The reaction was diluted with ethyl acetate (25.0 mL) and washed with 1.0N aqueous hydrochloric acid (2×20 mL). The organic layer was concentrated in vacuo using a rotary evaporator to yield the title compound as a yellow solid (0.784 g, 100%). 1H NMR (500 MHz, CHLOROFORM-D) δ ppm 1.20-1.62 (m, 10H) 1.70-2.18 (m, 6H) 2.87 (m, 1H) 3.90 (s, 3H) 4.05 (m, 1H) 4.27 (br m, 2H) 4.73 (br.s, 1H) 4.99 (br.s, 1H) 6.82 (s, 1H) 6.93 (d, J=2.14 Hz, 1H) 7.10 (dd, J=8.55, 2.44 Hz, 1H) 7.45 (br d, 1H) 7.52 (d, J=8.85 Hz, 1H) 7.80 (br s, 1H) 7.88 (d, J=8.85 Hz, 1H) 8.02 (s, 1H) 8.60 (br s, 1H). LCMS 685 m/z (MH+).

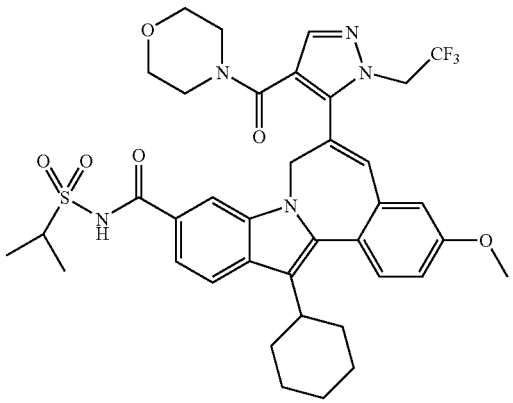

7H-indolo[2,1-a][2]benzazepine-10-carboxamide, 13-cyclohexyl-3-methoxy-N-[(1-methylethyl)sulfonyl]-6-[4-(4-morpholinylcarbonyl)-1-(2,2,2-trifluoroethyl)-1H-pyrazol-5-yl]-: 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(2,2,2-trifluoroethyl) (90 mg, 0.131 mmol) in DMSO (1.31 mL), TBTU (84 mg, 0.263 mmol) and DIPEA (68 mg, 0.526 mmol) were added. The reaction mixture was stirred at RT for 15 min. Then morpholine (46 mg, 0.526 mmol) was added. The solution was stirred at RT for overnight. The reaction mixture was purified by prep HPLC column using CH3CN/H2O/TFA as solvent system. Fractions were collected and concentrated under speedvac overnight to yield the title compound as a yellow solid (53 mg, 0.070 mmol, 53% yield). MS m/z 754 (M−H+); 1H NMR (500 MHz, CHLOROFORM-D) δ ppm 1.22 (m, 1H) 1.33-1.57 (m, 9H) 1.70-2.18 (m, 6H) 2.59 (br m, 1H) 2.70-2.95 (m, 6H) 3.05-3.21 (m, 2H) 3.92 (s, 3H) 4.07 (m, 1H) 4.73 (br.d, 1H) 4.76 (br m, 2H) 4.86 (br.d, 1H) 6.90 (s, 1H) 6.94 (d, J=2.14 Hz, 1H) 7.15 (dd, J=8.55, 2.44 Hz, 1H) 7.60 (d, J=8.85 Hz, 1H) 7.63 (d, J=8.24 Hz, 1H) 7.67 (s, 1H) 7.80 (s, 1H) 7.93 (d, J=8.85 Hz, 1H).

The following compounds were synthesized by an analogous method as described above for 7H-indolo[2,1-a][2]benzazepine-10-carboxamide, 13-cyclohexyl-3-methoxy-N-[(1-methylethyl)sulfonyl]-6-[4-(4-morpholinylcarbonyl)-1-(2,2,2-trifluoroethyl)-1H-pyrazol-5-yl]-:

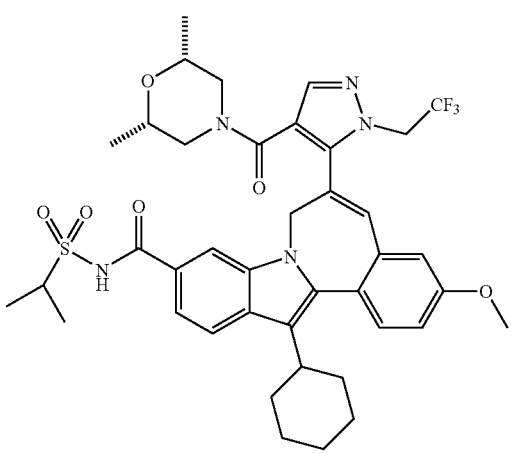

7H-indolo[2,1-a][2]benzazepine-10-carboxamide, 13-cyclohexyl-6-[4-[[(2R,6S)-2,6-dimethyl-4-morpholinyl]carbonyl]-1-(2,2,2-trifluoroethyl)-1H-pyrazol-5-yl]-3-methoxy-N-[(1-methylethyl)sulfonyl]-: 1H NMR (500 MHz, CHLOROFORM-D) δ ppm 0.64-0.90 (m, 5H) 1.16-1.28 (m, 2H) 1.33-1.57 (m, 9H) 1.73-2.18 (m, 8H) 2.30 (br m, 1H) 2.87 (m, 2H) 3.05-3.29 (m, 3H) 3.94 (s, 3H) 4.07 (m, 1H) 4.58 (br.d, 1H) 4.72 (br m, 2H) 4.93 (br.d, 1H) 6.87-6.96 (m, 1H) 7.15 (dd, J=8.55, 2.44 Hz, 1H) 7.52-7.68 (m, 2H) 7.72-7.85 (m, 2H) 7.93 (m, 1H) 8.48 (br s, 1H). LCMS: m/e 782 (M+H).

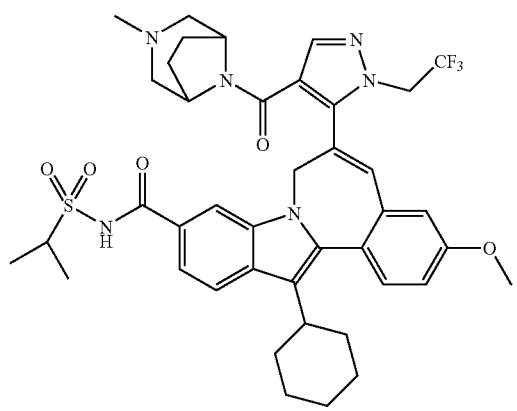

7H-indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(2,2,2-trifluoroethyl)-1H-pyrazol-5-yl]-N-[(1-methylethyl)sulfonyl]-: 1H NMR (500 MHz, CHLOROFORM-D) δ ppm 0.19 (br s, 1H) 0.80 (br s, 1H) 1.25-1.62 (m, 11H) 1.76-2.18 (m, 7H) 2.48 (br m, 1H) 2.62 (br s, 3H) 2.88 (m, 2H) 2.95-3.50 (m, 4H) 3.92 (s, 3H) 4.06 (m, 1H) 4.59 (br.d, 1H) 4.86 (br m, 3H) 6.93 (s, 1H) 7.05 (br s, 1H) 7.17 (dd, J=8.55, 2.44 Hz, 1H) 7.60 (d, J=8.85 Hz, 1H) 7.65 (d, J=8.24 Hz, 1H) 7.86 (br s, 1H) 7.96 (m, 2H) 10.0 (br s, 1H). LCMS: m/e 793 (M+H).

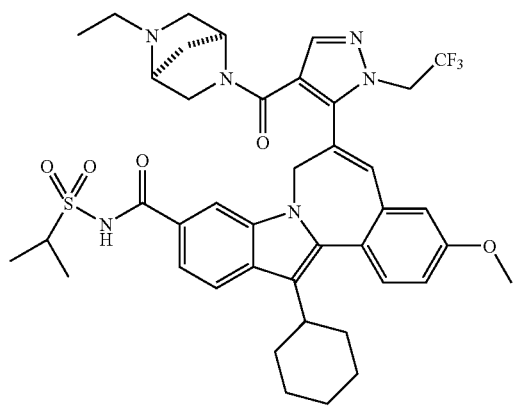

7H-indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-(2,2,2-trifluoroethyl)-1H-pyrazol-5-yl]-3-methoxy-N-[(1-methylethyl)sulfonyl]-: 1H NMR (500 MHz, CHLOROFORM-D) δ ppm 1.10-1.59 (m, 14H) 1.70-2.18 (m, 7H) 2.38 (m, 1H) 2.80-3.85 (m, 8H) 3.95 (s, 3H) 4.03 (m, 1H) 4.58 (br.d, 1H) 4.98 (br.m, 3H) 6.87-6.96 (m, 1H) 7.15 (dd, J=8.55, 2.44 Hz, 1H) 7.52-7.68 (m, 2H) 7.72-7.85 (m, 2H) 7.93 (m, 1H) 8.48 (br s, 1H). LCMS: m/e 793 (M+H).

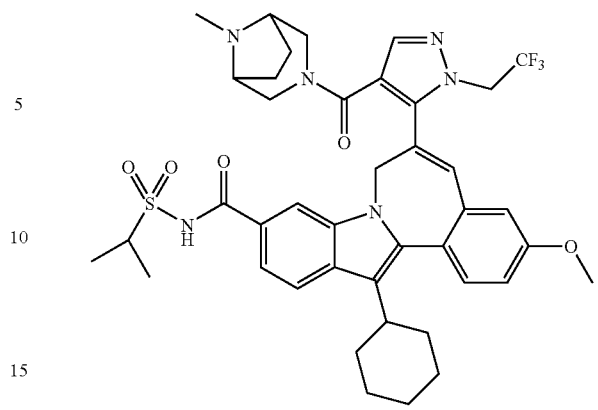

7H-indolo[2,1-a][2]benzazepine-10-carboxamide, 13-cyclohexyl-3-methoxy-6-[4-[[(8-methyl-3,8-diazabicyclo[3.2.1]oct-3-yl)carbonyl]-1-(2,2,2-trifluoroethyl)-1H-pyrazol-5-yl]-N-[(1-methylethyl)sulfonyl]-: 1H NMR (500 MHz, CHLOROFORM-D) δ ppm 0.18 (br s, 1H) 0.81 (br s, 1H) 1.26-1.62 (m, 11H) 1.80 (m, 2H) 1.94-2.18 (m, 5H) 2.44 (br m, 1H) 2.62 (br s, 3H) 2.90 (m, 2H) 2.95-3.55 (m, 4H) 3.92 (s, 3H) 4.06 (m, 1H) 4.59 (br.d, 1H) 4.86 (br m, 3H) 6.92 (s, 1H) 7.03 (br s, 1H) 7.17 (dd, J=8.55, 2.44 Hz, 1H) 7.58-7.65 (m, 1H) 7.86 (br s, 1H) 7.96 (m, 2H) 10.0 (br s, 1H). LCMS: m/e 793 (M+H).

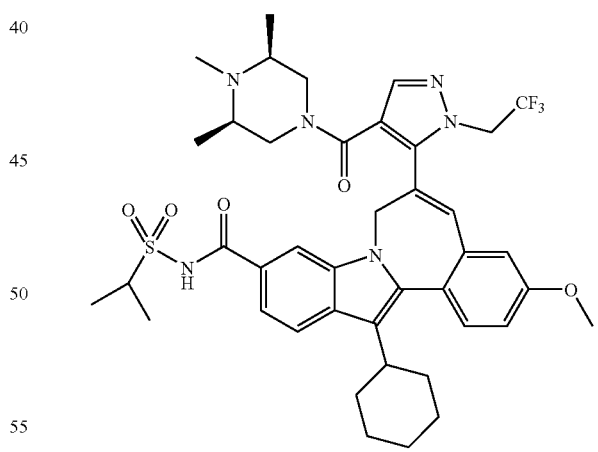

7H-indolo[2,1-a][2]benzazepine-10-carboxamide, 13-cyclohexyl-3-methoxy-N-[(1-methylethyl)sulfonyl]-6-[1-(2,2,2-trifluoroethyl)-4-[[(3R,5S)-3,4,5-trimethyl-1-piperazinyl]carbonyl]-1H-pyrazol-5-yl]-: 1H NMR (500 MHz, CHLOROFORM-D) δ ppm 1.05-1.57 (m, 15H) 1.70-2.12 (m, 7H) 2.30-2.99 (m, 6H) 3.20-3.65 (m, 4H) 3.92 (s, 3H) 4.03 (m, 1H) 4.60 (br.d, 1H) 4.65-4.98 (br.m, 3H) 6.95 (m, 2H) 7.15 (dd, J=8.55, 2.44 Hz, 1H) 7.57 (m, 2H) 7.71 (s, 1H) 7.82 (br s, 1H) 7.93 (d, J=8.85 Hz, 1H). LCMS: m/e 795 (M+H).

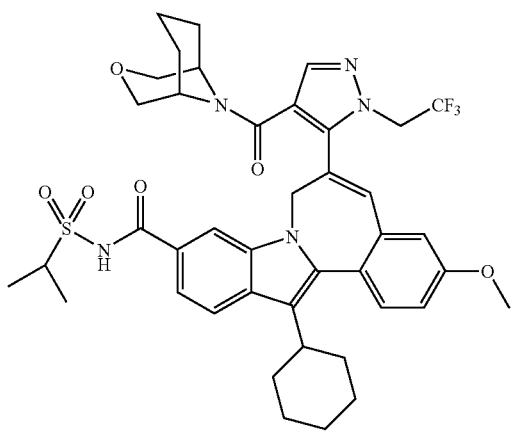

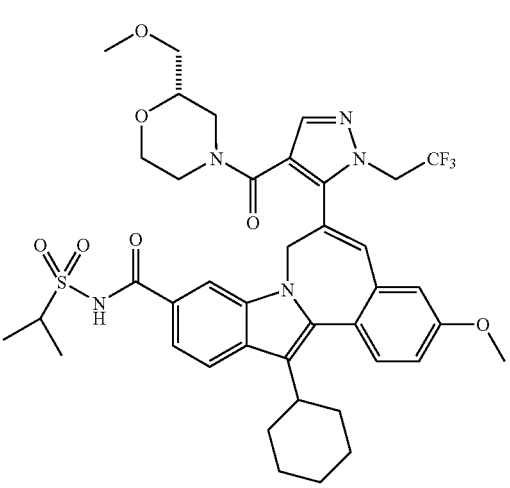

7H-indolo[2,1-a][2]benzazepine-10-carboxamide, 13-cyclohexyl-3-methoxy-N-[(1-methylethyl)sulfonyl]-6-[4-(3-oxa-9-azabicyclo[3.3.1]non-9-ylcarbonyl)-1-(2,2,2-trifluoroethyl)-1H-pyrazol-5-yl]-: 1H NMR (500 MHz, CHLOROFORM-D) δ ppm 1.12-1.53 (m, 13H) 1.70-2.40 (m, 9H) 2.87 (m, 1H) 3.03-3.62 (m, 6H) 3.92 (s, 3H) 4.07 (m, 1H) 4.73 (br.d, 1H) 4.76 (br m, 2H) 4.86 (br.d, 1H) 6.90 (s, 1H) 6.94 (d, J=2.14 Hz, 1H) 7.15 (dd, J=8.55, 2.44 Hz, 1H) 7.60 (d, J=8.85 Hz, 1H) 7.63 (d, J=8.24 Hz, 1H) 7.67 (s, 1H) 7.80 (s, 1H) 7.93 (d, J=8.85 Hz, 1H). LCMS: m/e 794 (M+H).

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-(2,2,2-trifluoroethyl)-1H-pyrazol-5-yl]-N-[(1-methylethyl)sulfonyl]-: 1H NMR (500 MHz, CDCl3) δ ppm 1.21 (m, 1H) 1.32-1.70 (m, 9H) 1.73-2.20 (m, 6H) 2.72-3.40 (m, 13H) 3.92 (m, 3H) 4.10 (m, 1H) 4.60 (m, 1H) 4.82 (m, br, 3H) 6.85-6.96 (m, 2H) 7.17 (dd, J=8.55, 2.75 Hz, 1H) 7.53-7.72 (m, 3H) 7.80-7.96 (m, 2H). LCMS: m/e 798 (M+H).

Methyl 5-chloro-1-methyl-3-(trifluoromethyl)-1H-pyrazole-4-carboxylate. To a solution of 5-chloro-1-methyl-3-(trifluoromethyl)-1H-pyrazole-4-carboxylic acid (1.00 g, 4.38 mmol) in benzene (5.83 mL) and methanol (2.92 mL) at room temperature was added 2M trimethylsilyldiazomethane (8.75 mL). The resulting solution was stirred at room temperature for 3 hours. Solvent was removed at reduced pressure on a rotary evaporator to yield the title compound (1.06 g, 4.38 mmol, 100% yield) as a white solid. MS m/z 243 (MH+). 1H NMR (500 MHz, CHLOROFORM-D) δ ppm 3.82 (s, 3H) 3.89 (s, 3H).

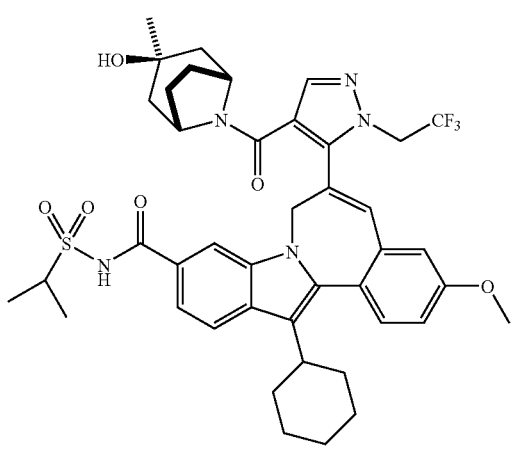

7H-indolo[2,1-a][2]benzazepine-10-carboxamide, 13-cyclohexyl-6-[4-[(3-hydroxy-3-methyl-8-azabicyclo[3.2.1]oct-8-yl)carbonyl]-1-(2,2,2-trifluoroethyl)-1H-pyrazol-5-yl]-3-methoxy-N-[(1-methylethyl)sulfonyl]-: 1H NMR (500 MHz, CDCl3) δ ppm −0.25 (m, 1H) 0.52 (m, 1H) 1.06 (s, 3H) 1.15-1.82 (m, 18H) 1.91-2.18 (m, 4H) 2.88 (m, 1H) 3.32 (m, 1H) 3.60 (m, 1H) 3.93 (s, 3H) 4.07 (m, 1H) 4.56 (br d, 1H) 4.82 (m, 2H) 4.97 (br d, 1H) 6.82 (br s, 2H) 7.16 (dd, J=8.55, 2.75 Hz, 1H) 7.60 (d, J=8.55 Hz, 1H) 7.70 (d, J=8.24 Hz, 1H) 7.84-7.92 (m, 3H). LCMS: m/e 808 (M+H).

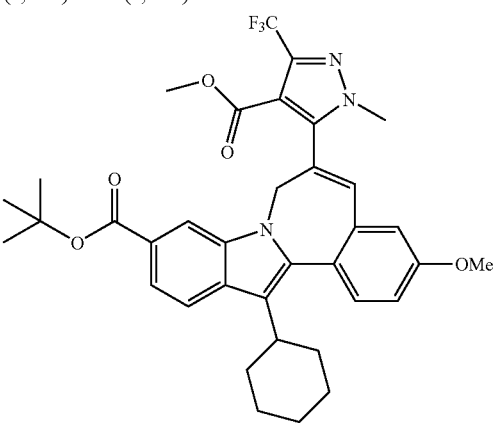

7H-indolo[2,1-a][2]benzazepine-10-carboxylic acid, 13-cyclohexyl-3-methoxy-6-[4-(methoxycarbonyl)-1-methyl-3-(trifluoromethyl)-1H-pyrazol-5-yl]-, 1,1-dimethylethyl ester. In a microwave tube, 7H-indolo[2,1-a][2]benzazepine-10-carboxylic acid, 13-cyclohexyl-3-methoxy-6-(tributylstannyl)-, 1,1-dimethylethyl ester (1.00 g, 1.37 mmol), methyl 5-chloro-1-methyl-3-(trifluoromethyl)-1H-pyrazole-4-carboxylate (497 mg, 2.05 mmol) and bis(dibenzylideneacetone) palladium (78 mg, 0.136 mmol) were added. It was then sealed, degassed and flushed with nitrogen. 1,4-dioxane (6.83 mL) was added. The reaction mixture was heated at 160° C. under microwave condition for 3 hours. It was then filtered and the filtrate was concentrated. The residue was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (8 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system. The product-containing fractions were collected and concentrated to give title compound as a yellow solid (547 mg, 0.842 mmol, 61% yield). MS m/z 650 (MH$^+$). 1H NMR (500 MHz, CHLOROFORM-D) δ ppm 1.06-2.29 (m, 19H) 2.85 (m, 1H) 3.30 (s, br, 3H) 3.78 (s, br, 3H) 3.91 (s, 3H) 4.76 (m, br, 1H) 4.97 (m, br, 1H) 6.80 (s, 1H) 6.93 (d, J=2.44 Hz, 1H) 7.11 (dd, J=8.55, 2.75 Hz, 1H) 7.56 (d, J=8.54 Hz, 1H) 7.82 (dd, J=8.24, 1.22 Hz, 1H) 7.91 (dd, J=8.24, 1.22 Hz, 1H) 7.98 (s, 1H).

mL) was added. The reaction mixture was stirred at RT for 4 hours. Volatiles were removed on a rotary evaporator to give the title compound as a brownish thick oil as crude product (500 mg, 0.842 mmol, 100% yield). MS m/z 594 (MH$^+$). 1H NMR (500 MHz, CHLOROFORM-D) δ ppm 1.06-2.28 (m, 10H) 2.86 (m, 1H) 3.30 (s, br, 3H) 3.78 (s, br, 3H) 3.91 (s, 3H) 4.75 (m, br, 1H) 4.96 (m, br, 1H) 6.80 (s, 1H) 6.93 (d, J=2.44 Hz, 1H) 7.10 (dd, J=8.55, 2.75 Hz, 1H) 7.54 (d, J=8.54 Hz, 1H) 7.81 (dd, J=8.24, 1.22 Hz, 1H) 7.91 (dd, J=8.24, 1.22 Hz, 1H) 7.97 (s, 1H).

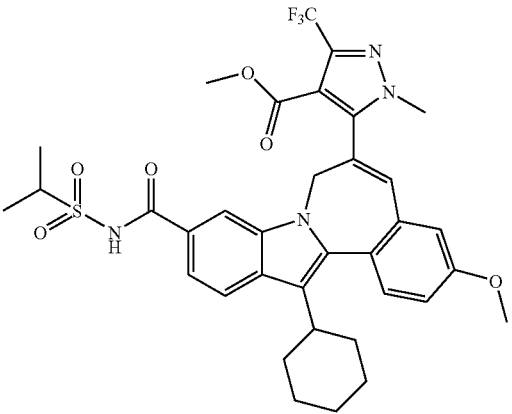

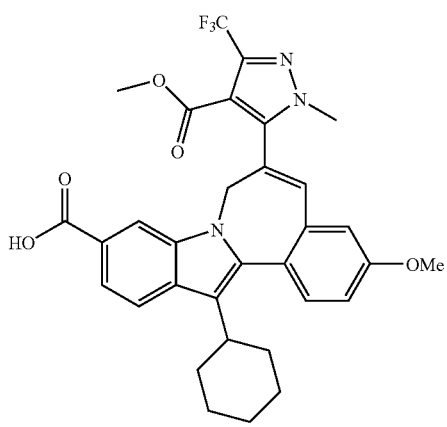

7H-indolo[2,1-a][2]benzazepine-10-carboxylic acid, 13-cyclohexyl-3-methoxy-6-[4-(methoxycarbonyl)-1-methyl-3-(trifluoromethyl)-1H-pyrazol-5-yl]-. To a solution of 7H-indolo[2,1-a][2]benzazepine-10-carboxylic acid, 13-cyclohexyl-3-methoxy-6-[4-(methoxycarbonyl)-1-methyl-3-(trifluoromethyl)-1H-pyrazol-5-yl]-, 1,1-dimethylethyl ester (547 mg, 0.842 mmol) in 1,2-dichloroethane (5 mL), TFA (5

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(trifluoromethyl)-, methyl ester. To a solution of 7H-indolo[2,1-a][2]benzazepine-10-carboxylic acid, 13-cyclohexyl-3-methoxy-6-[4-(methoxycarbonyl)-1-methyl-3-(trifluoromethyl)-1H-pyrazol-5-yl]-(480 mg, 0.809 mmol) in tetrahydrofuran (2.70 mL) was added carbonyldiimidazole (393 mg, 2.43 mmol). The reaction mixture was heated at 60° C. for one hour and then allowed to cool. Propane-2-sulfonamide (398 mg, 3.23 mmol) and DBU (0.366 mL, 2.43 mmol) were added at room temperature, and the reaction mixture was then heated at 60° C. for 4 hours. The resultant mixture was then diluted with 1N HCl (50 mL) solution and extracted with ethyl acetate (2×40 mL). The organic layers were combined and concentrated on a rotary evaporator to give the product as an orange colored oil. This material was then purified by preparative HPLC column using CH$_3$CN/H$_2$O/TFA as solvent system. Homogeneous fractions were collected and concentrated under reduced pressure. The title compound was obtained as a yellow solid, (492 mg, 0.704 mmol, 87% yield). MS m/z 699 (MH$^+$). 1H NMR (500 MHz, CHLOROFORM-D) δ ppm 1.16-1.61 (m, 10H) 1.69-2.21 (m, 6H) 2.86 (m, 1H) 3.34 (s, br, 3H) 3.67 (s, br, 3H) 3.91 (s, 3H) 4.01-4.19 (m, 1H) 4.70 (m, br, 1H) 4.97 (m, br, 1H) 6.70 (s, 1H) 6.94 (d, J=2.75 Hz, 1H) 7.09 (dd, J=8.55, 2.75 Hz, 1H) 7.51 (dd, J=8.55, 1.22 Hz, 1H) 7.81 (d, J=1.22 Hz, 1H) 7.88 (d, J=8.55 Hz, 1H) 7.92 (d, J=8.55 Hz, 1H) 8.68 (s, 1H).

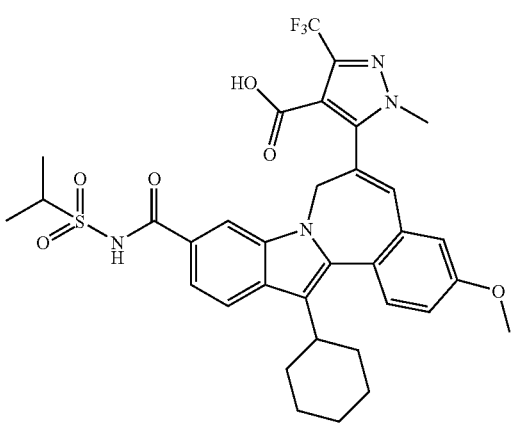

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(trifluoromethyl)-. 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(trifluoromethyl)-, methyl ester (0.300 g, 0.429 mmol) was dissolved in THF (1.07 mL) and methanol (1.07 mL) was added followed by 1N aqueous sodium hydroxide (0.900 mL). The reaction was then placed under a nitrogen atmosphere and stirred at room temperature for 18 hrs. The mixture was then diluted with ethyl acetate (50.0 mL) and washed with 1.0 N aqueous hydrochloric acid (2×50 ml). The organic layer was concentrated in vacuo using a rotary evaporator to yield the title compound as a yellow solid (282 mg, 0.412 mmol, 96%). MS m/z 685 (MH+). 1H NMR (500 MHz, CHLOROFORM-D) δ ppm 1.16-1.61 (m, 10H) 1.69-2.21 (m, 6H) 2.86 (m, 1H) 3.34 (s, br, 3H) 3.91 (s, 3H) 4.01-4.19 (m, 1H) 4.70 (m, br, 1H) 4.99 (m, br, 1H) 6.70 (s, 1H) 6.94 (d, J=2.75 Hz, 1H) 7.10 (dd, J=8.55, 2.75 Hz, 1H) 7.51 (dd, J=8.55, 1.22 Hz, 1H) 7.81 (d, J=1.22 Hz, 1H) 7.88 (d, J=8.55 Hz, 1H) 7.92 (d, J=8.55 Hz, 1H) 9.00 (s, 1H).

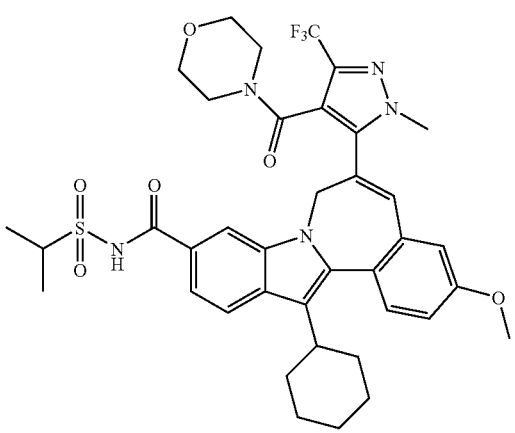

7H-indolo[2,1-a][2]benzazepine-10-carboxamide, 13-cyclohexyl-3-methoxy-N-[(1-methylethyl)sulfonyl]-6-[1-methyl-4-(4-morpholinylcarbonyl)-3-(trifluoromethyl)-1H-pyrazol-5-yl]-. To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(trifluoromethyl)- (75 mg, 0.11 mmol) in DMSO (1.1 mL), TBTU (70 mg, 0.22 mmol) and DIPEA (0.057 mL, 0.4444 mmol) were added. The reaction mixture was stirred at RT for 15 min. Then morpholine (38 mg, 0.44 mmol) was added. The solution was stirred at RT overnight. The reaction mixture was then purified by preparative HPLC using $CH_3CN/H_2O$/TFA as solvent system. Homogeneous fractions were collected and concentrated under reduced pressure to yield the title compound as a yellow solid, (67 mg, 0.089 mmol, 81% yield). MS m/z 754 (M–H+). 1H NMR (500 MHz, MeOD) δ ppm 1.18-1.52 (m, 10H) 1.75-2.25 (m, 6H) 2.63-3.26 (m, 9H) 3.50 (s, br, 3H) 3.95 (s, 3H) 3.96-4.03 (m, 1H) 4.64 (d, br, 1H) 4.98 (m, br, 1H) 6.88 (s, 1H) 6.94 (d, J=2.44 Hz, 1H) 7.15 (dd, J=8.55, 2.75 Hz, 1H) 7.55-7.65 (m, 2H) 7.80 (s, br, 1H) 7.93 (d, J=8.55 Hz, 1H) 10.30 (s, br, 1H).

The following compounds were synthesized by an analogous method as described above for 7H-indolo[2,1-a][2]benzazepine-10-carboxamide, 13-cyclohexyl-3-methoxy-N-[(1-methylethyl)sulfonyl]-6-[1-methyl-4-(4-morpholinylcarbonyl)-3-(trifluoromethyl)-1H-pyrazol-5-yl]-:

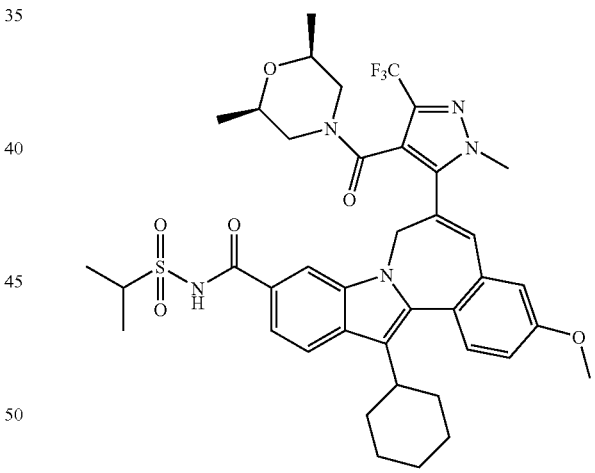

7H-indolo[2,1-a][2]benzazepine-10-carboxamide, 13-cyclohexyl-6-[4-[[(2R,6S)-2,6-dimethyl-4-morpholinyl]carbonyl]-1-methyl-3-(trifluoromethyl)-1H-pyrazol-5-yl]-3-methoxy-N-[(1-methylethyl)sulfonyl]-. MS m/z 782 (M–H+). 1H NMR (500 MHz, MeOD) δ ppm 0.71 (s, br, 3H), 0.75 (s, br, 3H) 1.18-1.52 (m, 10H) 1.75-2.21 (m, 9H) 2.35 (m, 1H) 2.83-3.21 (m, 3H) 3.50 (s, br, 3H) 3.95 (s, 3H) 3.96-4.03 (m, 1H) 4.64 (d, br, 1H) 5.02 (d, br, 1H) 6.81 (s, 1H) 6.94 (d, J=2.44 Hz, 1H) 7.13 (dd, J=8.55, 2.75 Hz, 1H) 7.55-7.65 (m, 2H) 7.80 (s, br, 1H) 7.93 (d, J=8.55 Hz, 1H) 10.50 (s, br, 1H).

129

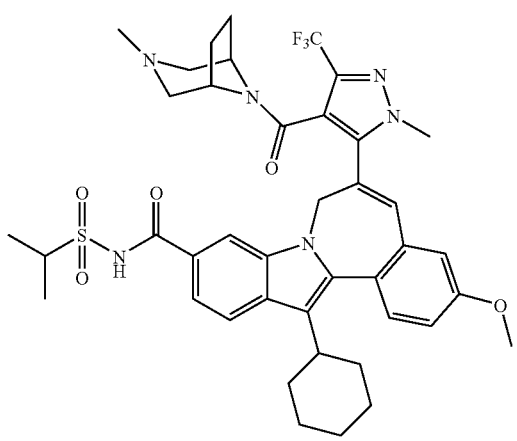

7H-indolo[2,1-a][2]benzazepine-10-carboxamide, 13-cyclohexyl-3-methoxy-N-[(1-methylethyl)sulfonyl]-6-[1-methyl-4-[(3-methyl-3,8-diazabicyclo[3.2.1]oct-8-yl)carbonyl]-3-(trifluoromethyl)-1H-pyrazol-5-yl]-. MS m/z 793 (M–H+). 1H NMR (500 MHz, MeOD) δ ppm 1.16-2.20 (m, 20H) 2.40-2.99 (m, 7H) 3.22-3.71 (m, 3H) 3.90-4.11 (m, 7H) 4.63 (m, br, 1H) 4.98 (m, br, 1H) 6.98 (m, 1H) 7.03 (m, 1H) 7.23 (m, 1H) 7.52-7.73 (m, 3H) 7.82 (s, br, 1H) 10.10 (s, br, 1H).

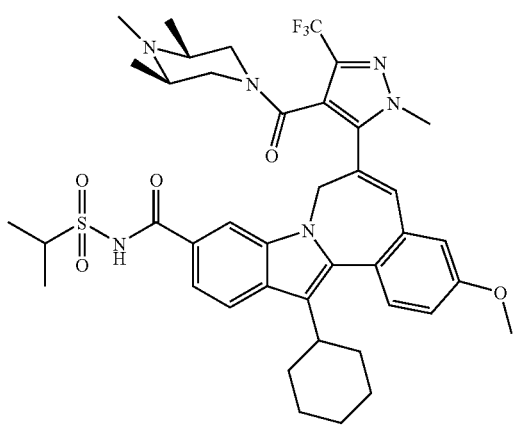

1p;1p7H-indolo[2,1-a][2]benzazepine-10-carboxamide, 13-cyclohexyl-3-methoxy-N-[(1-methylethyl)sulfonyl]-6-[1-methyl-3-(trifluoromethyl)-4-[[(3R,5S)-3,4,5-trimethyl-1-piperazinyl]carbonyl]-1H-pyrazol-5-yl]-. MS m/z 795 (M–H+). 1H NMR (500 MHz, MeOD) δ ppm 1.10-1.51 (m, 16H) 1.71-2.50 (m, 11H) 2.59-2.94 (m, 5H) 3.50 (s, br, 3H) 3.96 (s, 3H) 4.63 (m, br, 2H) 4.95 (m, br, 1H) 6.93 (m, 2H) 7.13 (m, 1H) 7.49-7.65 (m, 2H) 7.82 (s, br, 1H) 7.93 (m, 1H) 10.10 (s, br, 1H).

130

7H-indolo[2,1-a][2]benzazepine-10-carboxamide, 13-cyclohexyl-3-methoxy-N-[(1-methylethyl)sulfonyl]-6-[1-methyl-4-(8-oxa-3-azabicyclo[3.2.1]oct-3-ylcarbonyl)-3-(trifluoromethyl)-1H-pyrazol-5-yl]-

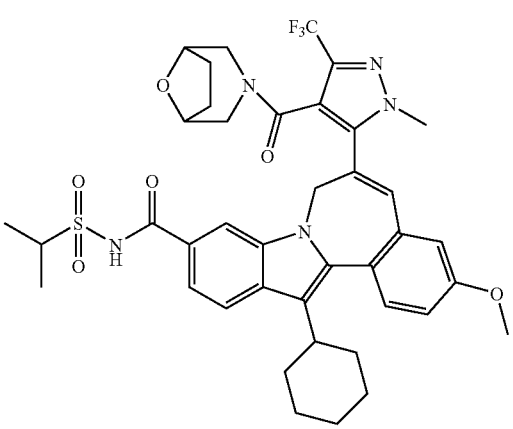

MS m/z 780 (M–H+)

1H NMR (500 MHz, CDCl3) δ ppm 0.70 (m, 1H) 1.21-1.52 (m, 13H) 1.75-2.20 (m, 8H) 2.30 (m, 1H) 2.79-2.98 (m, 3H) 3.11 (m, 1H) 3.87 (m, 1H) 3.98 (s, br, 3H) 4.05 (s, 3H) 4.61 (d, br, 1H) 4.89 (m, br, 1H) 6.85-6.98 (m, 2H) 7.17 (dd, J=8.55, 2.75 Hz, 1H) 7.55-7.70 (m, 2H) 7.84-8.03 (m, 1H) 7.93 (d, J=8.55 Hz, 1H) 10.45 (s, br, 1H).

7H-indolo[2,1-a][2]benzazepine-10-carboxamide, 13-cyclohexyl-3-methoxy-6-[4-[[(2S)-2-(methoxymethyl)-4-morpholinyl]carbonyl]-1-methyl-3-(trifluoromethyl)-1H-pyrazol-5-yl]-N-[(1-methylethyl)sulfonyl]-

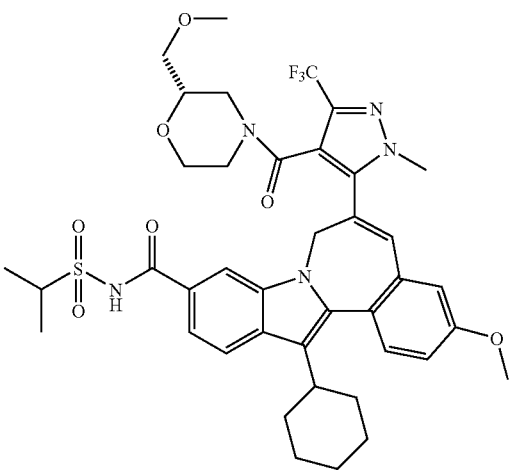

MS m/z 798 (M–H+)

1H NMR (500 MHz, CDCl3) δ ppm 1.11-1.61 (m, 10H) 1.75-2.52 (m, 10H) 2.81-3.60 (m, 9H) 3.95 (s, br, 3H) 4.03 (s, 3H) 3.95-4.03 (m, 1H) 4.65 (d, br, 1H) 5.01 (m, br, 1H) 6.85 (br s, 1H) 6.97 (s, 1H) 7.15 (dd, J=8.55, 2.75 Hz, 1H) 7.50-7.71 (m, 2H) 7.79-7.93 (m, 2H) 10.40 (s, br, 1H).

131

7H-indolo[2,1-a][2]benzazepine-10-carboxamide, 13-cyclohexyl-3-methoxy-N-[(1-methylethyl)sulfonyl]-6-[1-methyl-4-[(4-methyl-1-piperazinyl)carbonyl]-3-(trifluoromethyl)-1H-pyrazol-5-yl]-

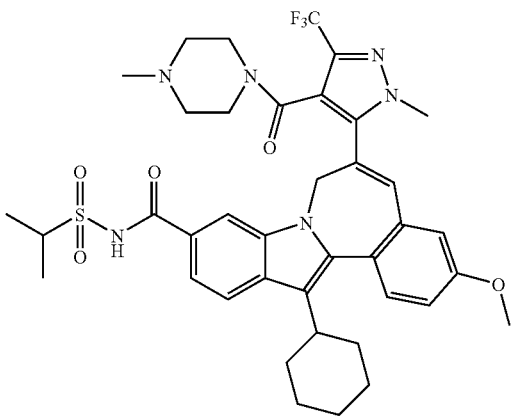

MS m/z 767 (M−H⁺)

1H NMR (500 MHz, CDCl3) δ ppm 1.13-1.58 (m, 10H) 1.75-2.12 (m, 6H) 2.20-2.97 (m, 5H) 3.19-3.79 (m, 7H) 3.95 (s, 3H) 3.99 (br s, 3H) 3.95-4.03 (m, 1H) 4.50 (m, br, 1H) 4.92 (m, br, 1H) 6.87-7.01 (m, 2H) 7.11 (dd, J=8.55, 2.75 Hz, 1H) 7.50 (dd, J=8.55, 2.75 Hz, 1H) 7.59-7.80 (m, 2H) 7.91 (br s, 1H) 10.50 (s, br, 1H).

7H-indolo[2,1-a][2]benzazepine-10-carboxamide, 13-cyclohexyl-3-methoxy-N-[(1-methylethyl)sulfonyl]-6-[1-methyl-4-[(8-methyl-3,8-diazabicyclo[3.2.1]oct-3-yl)carbonyl]-3-(trifluoromethyl)-1H-pyrazol-5-yl]-

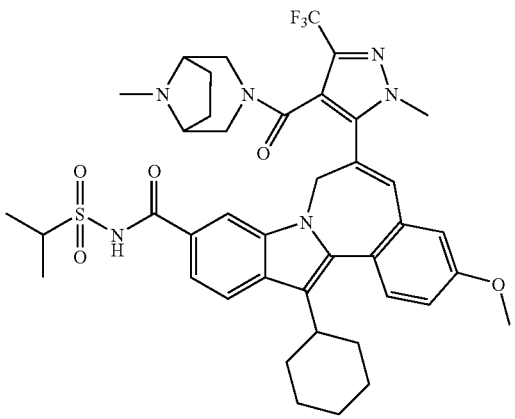

MS m/z 793 (M−H⁺)

1H NMR (500 MHz, CDCl3) δ ppm 0.37 (br m, 1H) 0.83 (br m, 1H) 1.14-1.70 (m, 11H) 1.75-2.16 (m, 7H) 2.35-2.70 (m, 4H) 2.86 (m, 2H) 3.20-3.79 (m, 4H) 3.90-4.11 (m, 7H) 4.63 (d, br, 1H) 4.94 (m, br, 1H) 6.95-7.10 (m, 2H) 7.15 (dd, J=8.55, 2.75 Hz, 1H) 7.53-7.70 (m, 3H) 7.81 (s, br, 1H) 10.10 (s, br, 1H).

132

7H-indolo[2,1-a][2]benzazepine-10-carboxamide, 13-cyclohexyl-6-[4-[[(1S,4S)-5-ethyl-2,5-diazabicyclo[2.2.1]hept-2-yl]carbonyl]-1-methyl-3-(trifluoromethyl)-1H-pyrazol-5-yl]-3-methoxy-N-[(1-methylethyl)sulfonyl]-

MS m/z 793 (M−H⁺)

1H NMR (500 MHz, CDCl3) δ ppm 0.55 (br m, 1H) 1.14-1.70 (m, 13H) 1.75-2.16 (m, 7H) 2.52-3.70 (m, 9H) 3.89-4.11 (m, 7H) 4.69 (d, br, 1H) 5.00 (m, br, 1H) 6.95-7.15 (m, 3H) 7.50-7.81 (m, 4H) 10.20 (s, br, 1H).

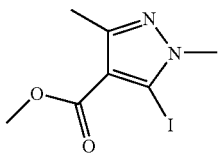

Methyl 5-iodo-1,3-dimethyl-1H-pyrazole-4-carboxylate

To a solution of methyl 1,3-dimethyl-1H-pyrazole-4-carboxylate (154 mg, 1 mmol) in dry tetrahydrofuran (10 mL) at −78° C., 2 M solution of BuLi (0.550 mL, 1.100 mmol) in pentane was added dropwise. The reaction mixture was then warmed to −45° C. and stirred for 1 h. It was then cooled to −78° C. and a solution of IODINE (279 mg, 1.100 mmol) in THF (2 mL) was added. The reaction mixture was warmed to RT and stirred for 1 h. It was then quenched with saturated NH₄Cl solution and extracted with ethyl acetate (2×25 mL). The organic layers were combined, washed with brine, dried over MgSO₄, and then concentrated in vacuo. The crude product was obtained as a brown thick oil. This material was then purified by preparative HPLC using CH₃CN/H₂O/TFA as solvent system. Homogeneous fractions were combined and concentrated in vacuo. The concentrate was then extracted with ethyl acetate and the extracts combined and dried over MgSO₄. The suspension was then filtered and the filter and evaporated under reduced pressure to give the title compound as a white solid, (137 mg, 0.460 mmol, 46.0% yield). MS m/z 281 (MH⁺), Retention time: 1.107 min. (basic). 1H NMR (500 MHz, CHLOROFORM-D) δ ppm 2.45 (s, 3H) 3.84 (s, 3H) 3.91 (s, 3H).

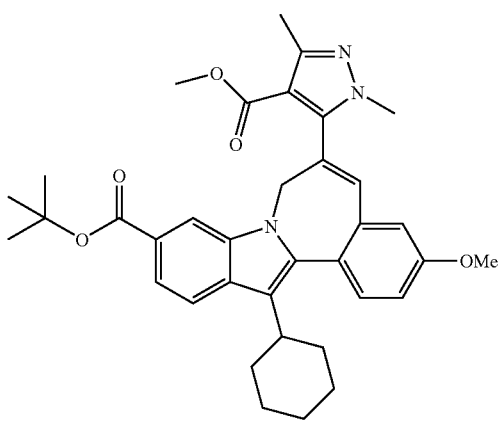

7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-, 1,1-dimethylethyl ester 7H-indolo[2,1-a][2]benzazepine-10-carboxylic acid, 13-cyclohexyl-3-methoxy-6-(tributylstannyl)-, 1,1-dimethylethyl ester (50 mg, 0.068 mmol), methyl 5-iodo-1,3-dimethyl-1H-pyrazole-4-carboxylate (38.2 mg, 0.136 mmol) and Bis(triphenylphosphine)-palladium(II) chloride (4.79 mg, 6.82 μmol) were added to a standard microwave tube. The vessel was then sealed, degassed and flushed with nitrogen. 1,4-Dioxane (2.0 mL) was added and the resultant mixture was heated at 120° C. under microwave conditions for 2 h. It was then filtered and the filtrate concentrated. The residue was purified by preparative. HPLC using $CH_3CN$—$H_2O$-TFA as solvent system. Homogeneous fractions were collected and concentrated in vacuo to give the title compound as an orange colored solid, (9.1 mg, 0.015 mmol, 21.26% yield). MS m/z 596 (MH$^+$), Retention time: 2.893 min. (basic). 1H NMR (500 MHz, CHLOROFORM-D) δ ppm 1.06-2.28 (m, 19H) 2.47 (s, 3H) 2.77-2.93 (m, 1H) 3.19 (s, 3H) 3.53-3.83 (s, br, 3H) 3.90 (s, 3H) 4.58-4.73 (m, br, 1H) 4.86-5.03 (m, br, 1H) 6.71 (s, 1H) 6.92 (d, J=2.44 Hz, 1H) 7.06 (dd, J=8.55, 2.75 Hz, 1H) 7.52 (d, J=8.54 Hz, 1H) 7.65 (dd, J=8.24, 1.22 Hz, 1H) 7.80-7.85 (m, 2H).

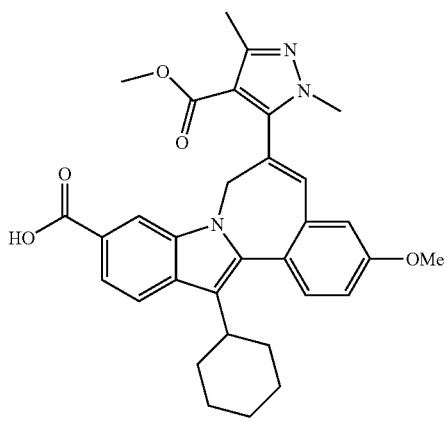

7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-

To a solution of 7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-, 1,1-dimethylethyl ester (601 mg, 1.009 mmol) in 1,2-Dichloroethane (10 mL), TFA (5 mL, 64.9 mmol) was added. The reaction mixture was stirred at RT for 4 hours. Solvent and TFA were then evaporated to give a brownish thick oil, (650 mg, 1.144 mmol, 113% yield). 10 mg of this crude product was purified by preparative HPLC using $CH_3CN$—$H_2O$-TFA as solvent system. Homogeneous fractions were combined and concentrated under reduced pressure to give the title compound as a yellow solid, (3.5 mg, 35% recovery). MS m/z 540 (MH$^+$), Retention time: 1.925 min. (basic). 1H NMR (500 MHz, MeOD) δ ppm 1.15-1.59 (m, 4H) 1.68-2.24 (m, 6H) 2.41 (s, 3H) 2.84-2.97 (m, 1H) 3.11-3.50 (m, br, 6H) 3.90 (s, 3H) 4.55-4.69 (m, br, 1H) 4.94-5.06 (m, br, 1H) 6.88 (s, 1H) 7.07 (d, J=2.44 Hz, 1H) 7.14 (dd, J=8.70, 2.59 Hz, 1H) 7.57 (d, J=8.55 Hz, 1H) 7.67 (dd, J=8.55, 1.22 Hz, 1H) 7.87 (d, J=8.54 Hz, 1H) 7.89 (s, 1H).

Note: The remaining crude product was used in the subsequent steps without further purification.

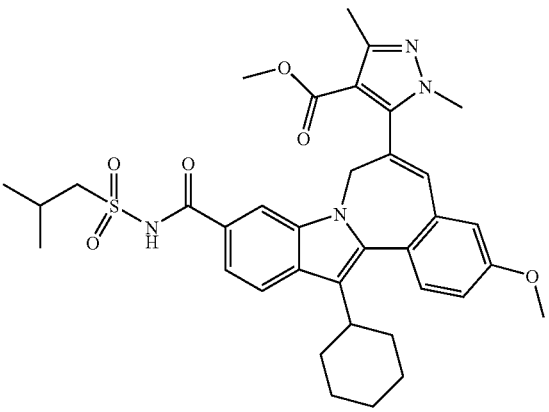

1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1,3-dimethyl-, methyl ester To a solution of 7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-(225 mg, 0.417 mmol) in tetrahydrofuran (10 mL), CDI (101 mg, 0.625 mmol) was added. The reaction mixture was heated at 60° C. for one hour and then allowed to cool to RT. 2-Methylpropane-1-sulfonamide (172 mg, 1.251 mmol) and DBU (0.126 mL, 0.834 mmol) were then added and the resultant mixture was heated at 60° C. for 4 hours. The reaction was then quenched with 1N HCl solution and the product extracted with ethyl acetate (2×40 mL). The organic layers were combined, washed with 1N HCl solution, brine, dried (MgSO$_4$) and then filtered. Evaporation of the filtrate gave the product as an orange colored oil. This material was then purified by preparative HPLC using $CH_3CN$—$H_2O$-TFA as solvent system. Homogeneous fractions were combined and concentrated in vacuo, to provide the title compound as a yellow colored solid, (46.6 mg, 0.067 mmol, 16.12% yield). MS m/z 659 (MH+), Retention time: 2.197 min. (basic). 1H NMR (500 MHz, CHLOROFORM-D) δ ppm 1.14 (d, J=6.71 Hz, 6H) 1.19-1.60 (m, 4H) 1.70-2.15 (m, 6H) 2.34-2.43 (m, 1H) 2.49 (s, 3H) 2.80-2.92 (m, 1H) 3.12-3.75 (m, 8H) 3.91 (s, 3H) 4.63-4.74 (m, br, 1H) 4.85-4.99 (m, br, 1H) 6.75 (s, 1H) 6.94 (d, J=2.75 Hz, 1H) 7.09 (dd, J=8.55, 2.75 Hz, 1H) 7.39 (dd, J=8.55, 1.53 Hz, 1H) 7.53 (d, J=8.55 Hz, 1H) 7.75 (d, J=1.22 Hz, 1H) 7.90 (d, J=8.55 Hz, 1H) 8.52 (s, 1H).

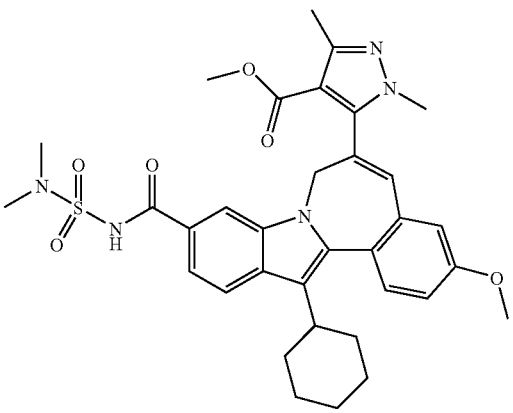

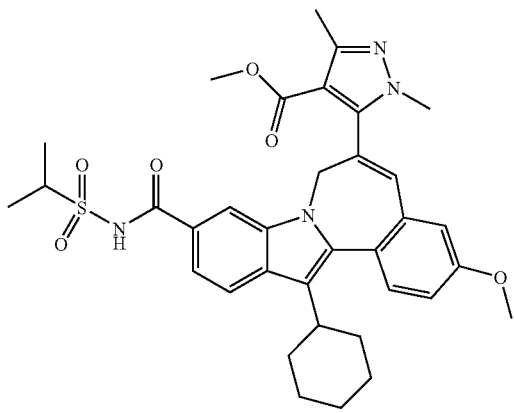

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl-, methyl ester To a solution of 7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-(225 mg, 0.417 mmol) in tetrahydrofuran (10 mL), CDI (101 mg, 0.625 mmol) was added. The reaction mixture was heated at 60° C. for one hour and was then allowed to cool to room temperature. Propane-2-sulfonamide (154 mg, 1.251 mmol) and DBU (0.126 mL, 0.834 mmol) were then added and the resultant mixture was heated at 60° C. for 4 hours. The reaction was then quenched with 1N HCl solution and the product extracted with ethyl acetate (2×40 mL). The organic layers were combined, washed with 1N HCl solution, brine, then dried (MgSO4) and filtered. Evaporation of solvents gave the product as an orange colored thick oil. This material was then purified by preparative HPLC using CH3CN—H2O-TFA as solvent system. Homogeneous fractions were combined and concentrated in vacuo to provide the title compound as a yellow colored solid, (42.5 mg, 0.066 mmol, 15.81% yield). MS m/z 645 (MH+), Retention time: 2.105 min. (basic). 1H NMR (500 MHz, CHLOROFORM-D) δ ppm 1.16-1.61 (m, 10H) 1.69-2.21 (m, 6H) 2.48 (s, 3H) 2.81-2.92 (m, 1H) 3.24 (s, 3H) 3.66 (s, br, 3H) 3.91 (s, 3H) 4.01-4.10 (m, 1H) 4.63-4.75 (m, br, 1H) 4.84-4.98 (m, br, 1H) 6.74 (s, 1H) 6.94 (d, J=2.75 Hz, 1H) 7.08 (dd, J=8.55, 2.75 Hz, 1H) 7.39 (dd, J=8.55, 1.22 Hz, 1H) 7.53 (d, J=8.55 Hz, 1H) 7.74 (d, J=1.22 Hz, 1H) 7.90 (d, J=8.55 Hz, 1H) 8.28 (s, 1H).

1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1,3-dimethyl-, methyl ester To a solution of 7H-indolo[2,1-a][2]benzazepine-10-carboxylic acid, 13-cyclohexyl-3-methoxy-6-[4-(methoxycarbonyl)-1,3-dimethyl-1H-pyrazol-5-yl]-(120 mg, 0.222 mmol) in THF (5 mL), CDI (54.1 mg, 0.334 mmol) was added. The reaction mixture was heated at 60° C. for one hour, and then allowed to cool to room temperature. N,N-dimethylsulfamide (83 mg, 0.667 mmol) and DBU (0.067 mL, 0.445 mmol) were then added and the resultant mixture was heated at 60° C. overnight. The reaction was then quenched with 1N HCl solution and the product extracted with ethyl acetate (2×30 mL). The organic layers were combined, washed with 1N HCl solution, brine, dried (MgSO4) and then filtered. Evaporation of solvents gave the crude product as an orange colored thick oil. This material was then purified by preparative HPLC using CH3CN—H2O-TFA as a solvent system. Homogeneous fractions were combined and concentrated under vacuum to provide the title compound as an orange colored solid, (31.4 mg, 0.049 mmol, 21.87% yield). MS m/z 646 (MH+), Retention time: 2.245 min. (basic). 1H NMR (500 MHz, CHLOROFORM-D) δ ppm 1.18-1.60 (m, 4H) 1.70-2.14 (m, 6H) 2.49 (s, 3H) 2.80-2.91 (m, 1H) 3.05 (s, 6H) 3.24 (s, 3H) 3.68 (s, br, 3H) 3.91 (s, 3H) 4.64-4.74 (m, br, 1H) 4.86-5.00 (m, br, 1H) 6.74 (s, 1H) 6.94 (d, J=2.75 Hz, 1H) 7.08 (dd, J=8.85, 2.75 Hz, 1H) 7.35 (dd, J=8.55, 1.53 Hz, 1H) 7.53 (d, J=8.55 Hz, 1H) 7.75 (d, J=1.22 Hz, 1H) 7.89 (d, J=8.54 Hz, 1H) 8.44 (s, 1H).

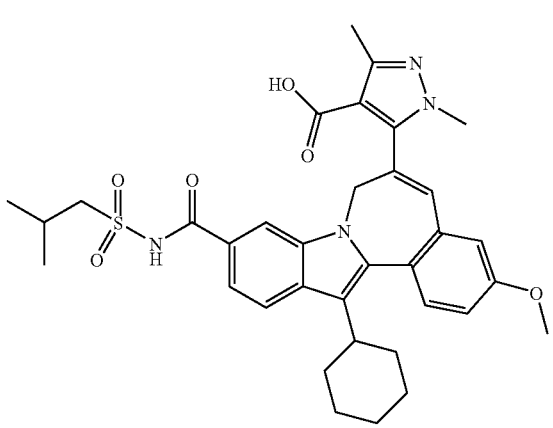

1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1,3-dimethyl- To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1,3-dimethyl-, methyl ester (44.2 mg, 0.067 mmol) in tetrahydrofuran (2.0 mL) and MeOH (2.000 mL), 1N NaOH (0.537 mL, 0.537 mmol) solution was added. The reaction mixture was stirred at RT for 4 days. LC/MS showed that only ~25% of the starting ester was hydrolyzed. 0.5 mL of more 1N NaOH solution was added. The reaction mixture was then stirred at RT for three more days. The reaction mixture was concentrated, and the residue was acidified using 1N HCl solution. The resultant mixture was then extracted with ethyl acetate (2×20 mL) and the organic layers were combined, washed with brine, dried (MgSO$_4$) and then filtered. Evaporation of filtrate gave the crude product as a viscous orange-colored oil. This material was then purified by preparative HPLC using CH$_3$CN—H$_2$O-TFA as a solvent system. Homogeneous fractions were collected concentrated under reduced pressure to give the title compound as a light yellow colored solid, (12.2 mg, 0.019 mmol, 28.2% yield). MS m/z 645 (MH$^+$), Retention time: 1.847 min. (basic). 1H NMR (500 MHz, DMSO-D6) δ ppm 1.02 (d, J=6.71 Hz, 6H) 1.08-1.53 (m, 4H) 1.64-2.09 (m, 6H) 2.08-2.20 (m, 1H) 2.36 (s, 3H) 2.71-2.85 (m, 1H) 3.09 (s, 3H) 3.45 (d, J=6.71 Hz, 2H) 3.88 (s, 3H) 4.42-4.62 (m, br, 1H) 4.96-5.18 (m, br, 1H) 6.97 (s, 1H) 7.15 (d, J=2.75 Hz, 1H) 7.21 (dd, J=8.85, 2.75 Hz, 1H) 7.54 (d, J=8.85 Hz, 1H) 7.60 (dd, J=8.39, 1.37 Hz, 1H) 7.90 (d, J=8.54 Hz, 1H) 8.14 (s, 1H) 11.76 (s, 1H) 12.37 (s, br, 1H).

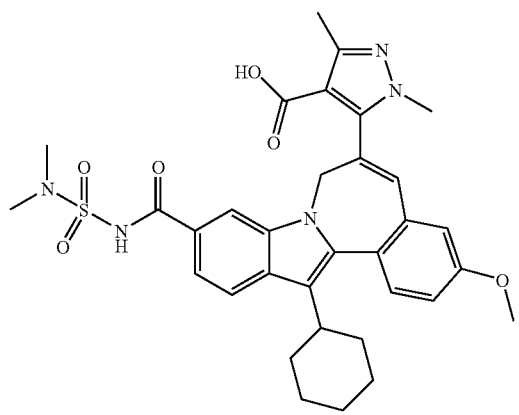

1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1,3-dimethyl- To a solution of 1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1,3-dimethyl-, methyl ester (29.4 mg, 0.046 mmol) in THF (1.5 mL) and MeOH (1.500 mL), 1N NaOH (0.364 mL, 0.364 mmol) solution was added. The reaction mixture was stirred at RT for 4 days. LC/MS showed that only 40% ester was hydrolyzed. 0.5 mL of more 1N NaOH solution was added. The reaction mixture was then stirred at RT for three more days. The reaction mixture was concentrated and the residue acidified using 1N HCl solution. The product was then extracted with ethyl acetate (2×20 mL). The organic layers were combined, washed with brine, dried (MgSO$_4$) and then filtered. Evaporation of filtrate gave the crude product as an orange colored oil. This material was then purified by preparative HPLC using CH$_3$CN—H$_2$O-TFA as a solvent system. Homogeneous fractions were combined and concentrated in vacuo to give the title compound as a light yellow colored solid, (9.5 mg, 0.015 mmol, 33.0% yield). MS m/z 632 (MH$^+$), Retention time: 1.853 min. (basic). 1H NMR (500 MHz, DMSO-D6) δ ppm 1.06-1.53 (m, 4H) 1.58-2.07 (m, 6H) 2.35 (s, 3H) 2.74-2.83 (m, 1H) 2.87 (s, 6H) 3.02-3.16 (s, br, 3H) 3.88 (s, 3H) 4.41-4.61 (m, br, 1H) 4.96-5.20 (m, br, 1H) 6.97 (s, 1H) 7.15 (d, J=2.75 Hz, 1H) 7.20 (dd, J=8.55, 2.75 Hz, 1H) 7.54 (d, J=8.55 Hz, 1H) 7.60 (dd, J=8.55, 1.53 Hz, 1H) 7.89 (d, J=8.54 Hz, 1H) 8.14 (s, 1H) 11.51 (s, 1H) 12.35 (s, br, 1H).

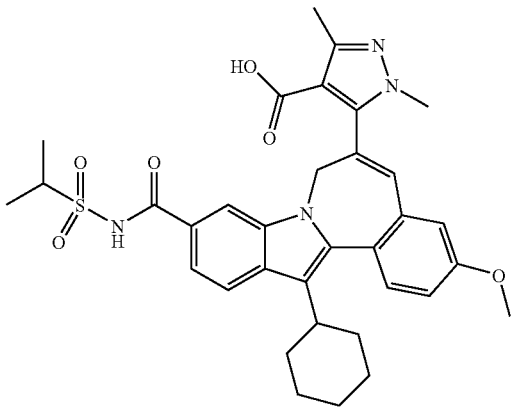

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl- To a mixture of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl-, methyl ester (80 mg, 0.124 mmol) and potassium trimethylsilanolate (TMSOK) (31.8 mg, 0.248 mmol) in a round-bottomed flask, Tetrahydrofuran (8 mL) was added. The resultant mixture was then stirred at RT overnight. LC/MS showed that only 40% of SM reacted. Two more equivalents of TMSOK were added and stirring was continued for 48 hrs. The reaction mixture was then concentrated and 1N HCl solution was added. A yellow solid separated (85 mg), and 10 mg of the material was then purified by preparative HPLC using CH$_3$CN—H$_2$O-TFA as solvent system. Homogeneous fractions were combined and evaporated under vacuum to give the title compound as a yellow colored solid, (7.6 mg, 76% recovery). MS m/z 631 (MH$^+$), Retention time: 1.648 min. (basic). 1H NMR (500 MHz, Acetone) δ ppm 1.11-1.61 (m, 10H) 1.63-2.21 (m, 6H) 2.38 (s, 3H) 2.85-3.00 (m, 1H) 3.17 (s, 3H) 3.83-3.97 (m, 4H) 4.54-4.72 (m, br, 1H) 5.09-5.29 (m, br, 1H) 6.93 (s, 1H) 7.11 (d, J=2.75 Hz, 1H) 7.17 (dd, J=8.55, 2.75 Hz, 1H) 7.61 (d, J=8.55 Hz, 1H) 7.68 (dd, J=8.55, 1.53 Hz, 1H) 7.96 (d, J=8.55 Hz, 1H) 8.21 (s, 1H) 9.96 (s, 1H). Note: The crude product describe above can be used without further purification for the preparation of carboxamide examples of the current invention.

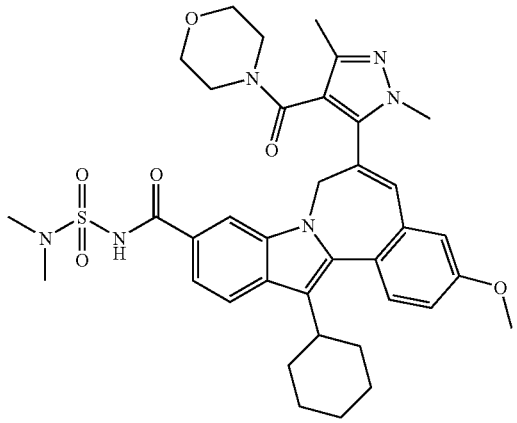

7H-indolo[2,1-a][2]benzazepine-10-carboxamide, 13-cyclohexyl-N-[(dimethylamino)sulfonyl]-6-[1,3-dimethyl-4-(4-morpholinylcarbonyl)-1H-pyrazol- To a solution of 1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1,3-dimethyl- (9.5 mg, 0.015 mmol) in DMSO (1 mL), TBTU (9.66 mg, 0.030 mmol) and DIPEA (0.013 mL, 0.075 mmol) were added. The reaction mixture was stirred at RT for 15 min. Morpholine (1.965 mg, 0.023 mmol) was then added and the resultant solution was stirred at RT for 48 hours. The reaction mixture was then purified by preparative HPLC using $CH_3CN$—$H_2O$-TFA as a solvent system. Homogeneous fractions were combined and concentrated under vacuum. The title compound was obtained as a yellow colored solid, (8.0 mg, 0.011 mmol, 74.4% yield). MS m/z 699 (M−H⁻), Retention time: 1.990 min. (basic). 1H NMR (500 MHz, MeOD) δ ppm 1.18-1.64 (m, 4H) 1.73-2.26 (m, 9H) 2.59-3.09 (m, 15H) 3.85 (s, 3H) 3.95 (s, 3H) 4.67 (d, J=14.96 Hz, 1H) 5.02-5.15 (m, 1H) 7.07 (s, 1H) 7.15 (d, J=2.44 Hz, 1H) 7.20 (dd, J=8.55, 2.75 Hz, 1H) 7.56-7.64 (m, 2H) 7.92 (s, 1H) 7.98 (d, J=8.55 Hz, 1H).

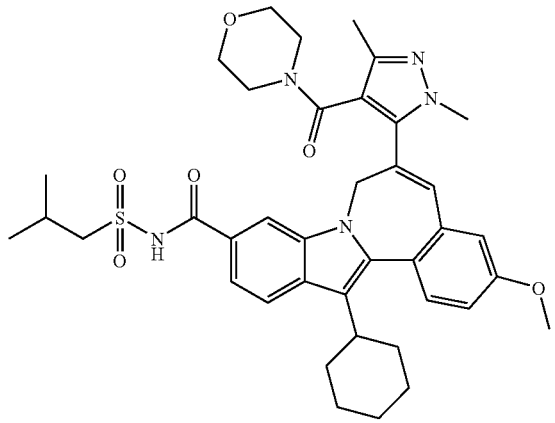

7H-indolo[2,1-a][2]benzazepine-10-carboxamide, 13-cyclohexyl-6-[1,3-dimethyl-4-(4-morpholinylcarbonyl)-1H-pyrazol-5-yl]-3-methoxy-N-[(2-methylpropyl)sulfonyl]-

To a solution of 1H-pyrazole-4-carboxylic acid, 5-[13-cyclohexyl-3-methoxy-10-[[[(2-methylpropyl)sulfonyl]amino]carbonyl]-7H-indolo[2,1-a][2]benzazepin-6-yl]-1,3-dimethyl- (10 mg, 0.016 mmol) in DMSO (1 mL), TBTU (9.96 mg, 0.031 mmol) and DIPEA (0.014 mL, 0.078 mmol) were added. The reaction mixture was stirred at RT for 15 min. Morpholine (1.351 mg, 0.016 mmol) was then added and the resultant solution was stirred at RT overnight. The reaction mixture was then purified by preparative HPLC using $CH_3CN$—$H_2O$-TFA as a solvent system. Homogeneous fractions were collected and concentrated under vacuum, to provide the title compound as a yellow colored solid, (10.7 mg, 0.015 mmol, 95% yield). MS m/z 712 (M−H⁻), Retention time: 1.895 min. (basic). 1H NMR (500 MHz, MeOD) δ ppm 1.16 (d, J=6.71 Hz, 6H) 1.20-1.64 (m, 4H) 1.73-2.27 (m, 9H) 2.29-2.43 (m, 1H) 2.56-3.14 (m, 9H) 3.49-3.55 (m, 2H) 3.85 (s, 3H) 3.95 (s, 3H) 4.67 (d, J=14.96 Hz, 1H) 4.98-5.16 (m, br, 1H) 7.07 (s, 1H) 7.15 (d, J=2.44 Hz, 1H) 7.20 (dd, J=8.70, 2.59 Hz, 1H) 7.55-7.66 (m, 2H) 7.95 (s, 1H) 7.98 (d, J=8.55 Hz, 1H).

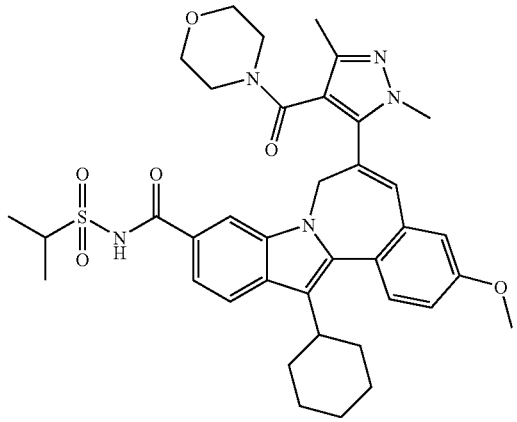

7H-indolo[2,1-a][2]benzazepine-10-carboxamide, 13-cyclohexyl-6-[1,3-dimethyl-4-(4-morpholinylcarbonyl)-1H-pyrazol-5-yl]-3-methoxy-N-[(1-methylethyl)sulfonyl]-

To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl- (20 mg, 0.032 mmol) in DMSO (1 mL), TBTU (20.36 mg, 0.063 mmol) and DIPEA (0.028 mL, 0.159 mmol) were added. The reaction mixture was stirred at RT for 15 min. Morpholine (4.14 mg, 0.048 mmol) was then added and the resultant solution was stirred at RT overnight. The reaction mixture was then purified by preparative HPLC using $CH_3CN$—$H_2O$-TFA as a solvent system. Homogeneous fractions were combined and concentrated under vacuum. The title compound was obtained as a yellow colored solid, (16.8 mg, 0.024 mmol, 74.2% yield). MS m/z 698 (M−H⁻), Retention time: 1.798 min. (basic). 1H NMR (500 MHz, MeOD) δ ppm 1.18-1.62 (m, 10H) 1.72-2.25 (m, 9H) 2.53-3.23 (m, 9H) 3.84 (s, 3H) 3.95 (s, 3H) 3.96-4.03 (m, 1H) 4.64 (d, J=14.95

Hz, 1H) 5.00-5.15 (m, br, 1H) 7.06 (s, 1H) 7.14 (d, J=2.44 Hz, 1H) 7.19 (dd, J=8.55, 2.75 Hz, 1H) 7.55-7.65 (m, 2H) 7.94 (s, 1H) 7.98 (d, J=8.55 Hz, 1H).

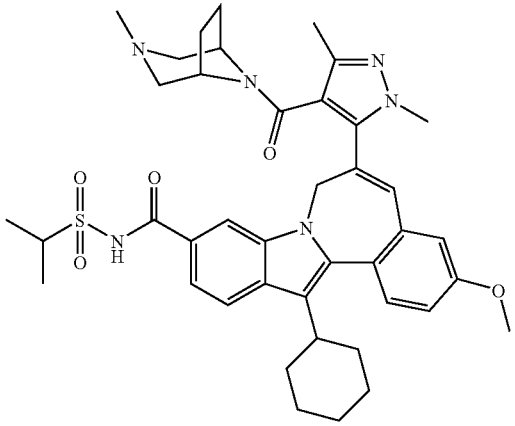

7H-indolo[2,1-a][2]benzazepine-10-carboxamide, 13-cyclohexyl-6-[1,3-dimethyl-4-[(3-methyl-3,8-diazabicyclo[3.2.1]oct-8-yl)carbonyl]-1H-pyrazol-5-yl]-3-methoxy-N-[(1-methylethyl)sulfonyl To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl- (20 mg, 0.032 mmol) in DMSO (1 mL), TBTU (20.36 mg, 0.063 mmol) and DIPEA (0.028 mL, 0.159 mmol) were added. The reaction mixture was stirred at RT for 15 min. Then 3-methyl-3,8-diazabicyclo[3.2.1]octane.2HCl (9.47 mg, 0.048 mmol) was added. The solution was then stirred at RT overnight. The crude reaction mixture was then purified by preparative HPLC using CH₃CN—H₂O-TFA as solvent system. Homogeneous fractions were combined and concentrated under vacuum to afford the title compound as a yellow solid, (19.7 mg, 0.023 mmol, 71.4% yield) as TFA salt. MS m/z 737 (M−H⁻), Retention time: 2.040 min. (basic). 1H NMR (500 MHz, MeOD) δ ppm 1.16-1.67 (m, 14H) 1.74-2.25 (m, 6H) 2.38 (s, 3H) 2.51-2.66 (m, 1H) 2.72 (s, 3H) 2.94-3.05 (m, 1H) 3.16-3.39 (m, 5H) 3.84 (s, 3H) 3.96 (s, 3H) 3.98-4.05 (m, 1H) 4.59-4.71 (m, br, 1H) 4.94-5.05 (m, br, 1H) 7.14-7.28 (m, 3H) 7.62-7.66 (m, 2H) 7.91 (s, 1H) 8.00 (d, J=8.54 Hz, 1H).

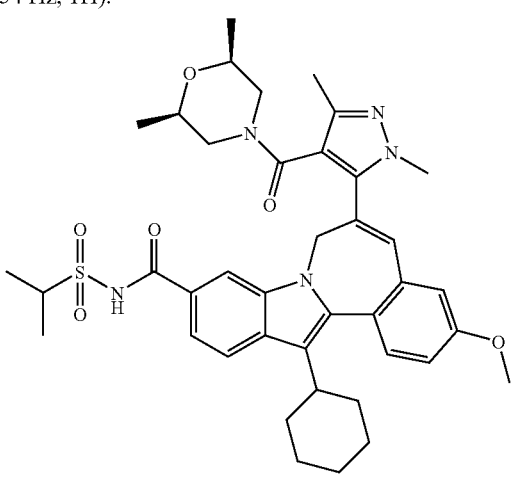

7H-indolo[2,1-a][2]benzazepine-10-carboxamide, 13-cyclohexyl-6-[1,3-dimethyl-4-[[cis-2,6-dimethyl-4-morpholinyl]carbonyl]-1H-pyrazol-5-yl]-3-methoxy-N-[(1-methylethyl)sulfonyl]-. To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1,3-dimethyl- (13 mg, 0.021 mmol) in DMSO (1 mL), TBTU (13.24 mg, 0.041 mmol) and DIPEA (0.018 mL, 0.103 mmol) were added. The reaction mixture was stirred at RT for 15 min. Then cis-2,6-dimethylmorpholine (3.56 mg, 0.048 mmol) was added and the resultant mixture was stirred at RT overnight. The crude reaction mixture was purified by preparative HPLC using CH₃CN—H₂O-TFA as a solvent system. Homogeneous fractions were combined and concentrated under vacuum to afford the title compound as a yellow colored solid, (10.1 mg, 0.014 mmol, 67.3% yield). MS m/z 326 (M−H⁻), Retention time: 1.958 min. (basic). 1H NMR (500 MHz, CHLOROFORM-D) δ ppm 0.57-2.33 (m, 25H) 2.81-3.60 (m, 5H) 3.77-3.99 (m, 8H) 4.03-4.12 (m, 1H) 4.57 (d, J=15.26 Hz, 1H) 4.76-4.94 (m, 1H) 6.75-6.88 (m, 1H) 6.95 (s, 1H) 7.12 (dd, J=8.55, 2.14 Hz, 1H) 7.50-7.67 (m, 2H) 7.71 (s, 1H) 7.91 (d, J=8.24 Hz, 1H). The following compounds were synthesized by an analogous method as described above for 7H-indolo[2,1-a][2]benzazepine-10-carboxamide, 13-cyclohexyl-6-[1,3-dimethyl-4-[[cis-2,6-dimethyl-4-morpholinyl]carbonyl]-1H-pyrazol-5-yl]-3-methoxy-N-[(1-methylethyl)sulfonyl]-:

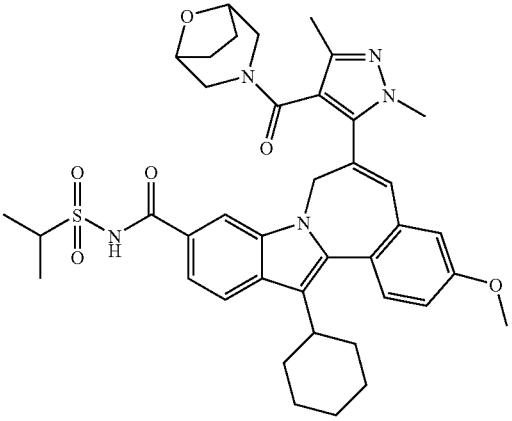

7H-indolo[2,1-a][2]benzazepine-10-carboxamide, 13-cyclohexyl-6-[1,3-dimethyl-4-(8-oxa-3-azabicyclo[3.2.1]oct-3-ylcarbonyl)-1H-pyrazol-5-yl]-3-methoxy-N-[(1-methylethyl)sulfonyl]-

MS m/z 726 (M+H). 1H NMR (500 MHz, CHLOROFORM-D) δ ppm 0.70-2.32 (m, 23H) 2.75-3.69 (m, 5H) 3.81-3.99 (m, 8H) 4.03 (m, 1H) 4.55 (br d, 1H) 4.90 (br d, 1H) 6.75 (s, 1H) 6.96 (s, 1H) 7.14 (m, 1H) 7.51-7.65 (m, 2H) 7.72 (s, 1H) 7.87 (d, J=8.24 Hz, 1H) 10.12 (br s, 1H).

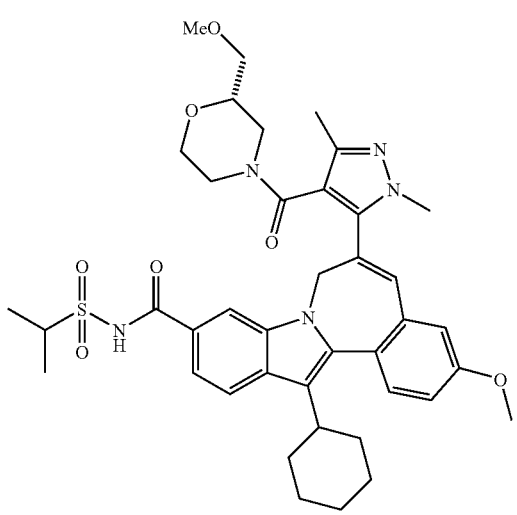

7H-indolo[2,1-a][2]benzazepine-10-carboxamide, 13-cyclohexyl-3-methoxy-6-[4-[[(2S)-2-(methoxymethyl)-4-morpholinyl]carbonyl]-1,3-dimethyl-1H-pyrazol-5-yl]-N-[(1-methylethyl)sulfonyl]-

MS m/z 744 (M+H). 1H NMR (500 MHz, CHLOROFORM-D) δ ppm 1.19-2.52 (m, 21H) 2.85-3.59 (m, 11H) 3.85-3.95 (m, 6H) 4.07 (m, 1H) 4.60 (br d, 1H) 4.93 (br d, 1H) 6.86 (br s, 1H) 6.97 (s, 1H) 7.16 (m, 1H) 7.53-7.69 (br m, 2H) 7.22 (br m, 1H) 7.94 (br m, 1H) 10.20 (br s, 1H).

7H-indolo[2,1-a][2]benzazepine-10-carboxamide, 13-cyclohexyl-6-[1,3-dimethyl-4-[(4-methyl-1-piperazinyl)carbonyl]-1H-pyrazol-5-yl]-3-methoxy-N-[(1-methylethyl)sulfonyl]-

MS m/z 713 (M+H). 1H NMR (500 MHz, CHLOROFORM-D) δ ppm 1.13-2.26 (m, 19H) 2.39-3.71 (m, 12H) 3.75-3.86 (m, 6H) 4.03 (m, 1H) 4.61 (br d, 1H) 4.83 (br d, 1H) 6.96 (m, 2H) 7.13 (m, 1H) 7.53 (d, J=8.24 Hz, 1H) 7.61-7.82 (m, 2H) 7.92 (d, J=8.24 Hz, 1H) 10.20 (br s, 1H).

Methyl 1-(1-methylethyl)-3-methyl-1H-pyrazole-4-carboxylate

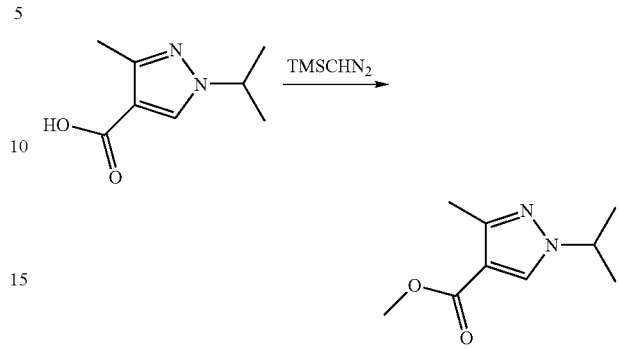

To a solution of 1-(1-methylethyl)-3-methyl-1H-pyrazole-4-carboxylic acid (2.00 g, 11.9 mmol) in benzene (15.9 mL) and methanol (7.93 mL) at room temperature was added 2M trimethylsilyldiazomethane (23.8 mL). The resulting solution was stirred at room temperature for 3 hours. Solvent was removed at reduced pressure on a rotary evaporator to yield the title compound (2.17 g, 111.89 mmol, 100% yield) as a white solid.

MS m/z 183 (MH+).

1H NMR (500 MHz, CHLOROFORM-D) δ ppm 1.49 (d, 6H) 2.48 (s, 3H) 3.81 (s, 3H) 4.42 (m, 1H) 7.86 (s, 1H).

Methyl 5-iodo-1-(1-methylethyl)-3-methyl-1H-pyrazole-4-carboxylate

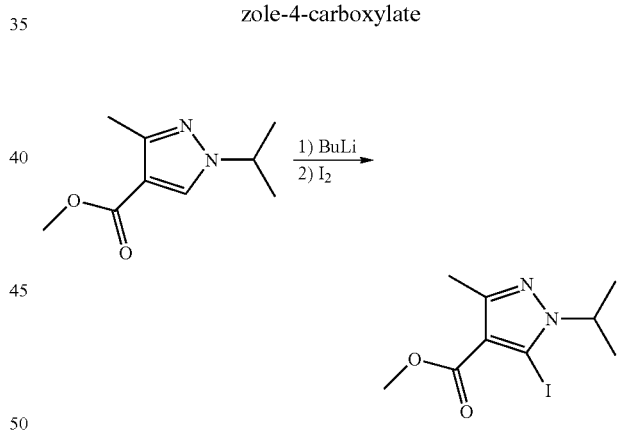

To a solution of methyl 1-(1-methylethyl)-3-methyl-1H-pyrazole-4-carboxylate (2.00 g, 11.0 mmol) in dry tetrahydrofuran (22.0 mL) at −78° C., 2 M solution of butyllithium (6.04 mL, 12.1 mmol) in pentane was added dropwise. The reaction mixture was then warmed to −45° C. and stirred for 1 h. It was then cooled to −78° C. and a solution of iodine (3.06 g, 12.1 mmol) in THF (11.0 mL) was added. The reaction mixture was warmed to RT and stirred for 1 h. Then it was quenched with saturated NH4Cl solution and extracted with ethyl acetate (2×25 mL). The organic layers were combined, washed with brine and dried (MgSO4). Evaporation of solvent gave a tan solid as title compound (3.38 g, 11.0 mmol, 100% crude yield). MS m/z 309 (MH+); 1H NMR (500 MHz, CHLOROFORM-D) δ ppm 1.41 (d, 6H) 2.47 (s, 3H) 3.82 (s, 3H) 4.77 (m, 1H).

145

7H-indolo[2,1-a][2]benzazepine-10-carboxylic acid, 13-cyclohexyl-3-methoxy-6-[4-(methoxycarbonyl)-1-(1-methylethyl)-3-methyl-1H-pyrazol-1-yl]-, 1,1-dimethylethyl ester

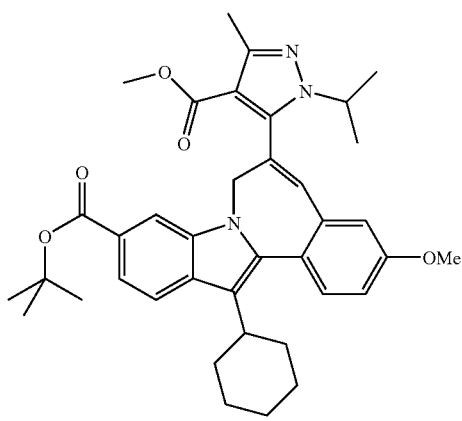

In a microwave tube, 7H-indolo[2,1-a][2]benzazepine-10-carboxylic acid, 13-cyclohexyl-3-methoxy-6-(tributylstannyl)-, 1,1-dimethylethyl ester (611 mg, 0.834 mmol), methyl 5-iodo-1-(1-methylethyl)-3-methyl-1H-pyrazole-4-carboxylate (360 mg, 1.17 mmol) and bis(triphenylphosphine)palladium II chloride (58.5 mg, 0.083 mmol) were added. It was then sealed, degassed and flushed with nitrogen. 1,4-Dioxane (4.17 mL) was added. The reaction mixture was heated at 160° C. under microwave condition for 1 hour. It was then filtered and the filtrate was concentrated. The residue was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (8 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system.

The product-containing fractions were collected and concentrated to give title compound as a yellow solid (156 mg, 0.250 mmol, 30% yield).

MS m/z 624 (MH$^+$); 1H NMR (500 MHz, CHLOROFORM-D) δ ppm 0.41 (br s, 3H) 1.18-1.59 (m, 16H) 1.72-2.20 (m, 6H) 2.49 (s, 3H) 2.86 (m, 1H) 3.68 (m, 1H) 3.85 (br s, 3H) 3.92 (s, 3H) 4.69 (br.d, 1H) 4.97 (br.d, 1H) 6.68 (s, 1H) 6.92 (d, J=2.14 Hz, 1H) 7.06 (dd, J=8.55, 2.44 Hz, 1H) 7.51 (d, J=8.55 Hz 1H) 7.73 (d, J=8.24 Hz, 1H) 7.81 (d, J=8.24 Hz, 1H) 7.87 (s, 1H).

146

7H-indolo[2,1-a][2]benzazepine-10-carboxylic acid, 13-cyclohexyl-3-methoxy-6-[4-(methoxycarbonyl)-1 (1-methylethyl)-3-trifluoromethyl-1H-pyrazol-5-yl]-

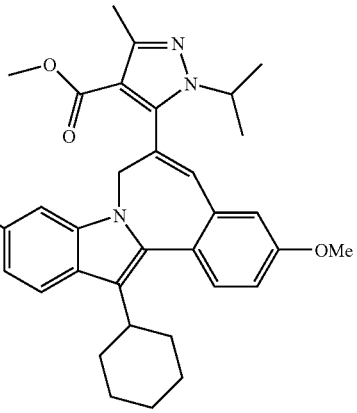

To a solution of 7H-indolo[2,1-a][2]benzazepine-10-carboxylic acid, 13-cyclohexyl-3-methoxy-6-[4-(methoxycarbonyl)-1-(1-methylethyl)-3-methyl-1H-pyrazol-5-yl]-, 1,1-dimethylethyl ester (156 mg, 0.250 mmol) in 1,2-dichloroethane (4 mL), TFA (4 mL) was added. The reaction mixture was stirred at RT for 2 hours. Volatiles were removed on a rotary evaporator to give the title compound as a brownish thick oil as crude product (142 mg, 0.8250 mmol, 100% yield).

MS m/z 568 (MH$^+$).

1H NMR (500 MHz, CHLOROFORM-D) δ ppm 0.41 (br s, 3H) 1.18-1.59 (m, 7H) 1.72-2.20 (m, 6H) 2.52 (s, 3H) 2.87 (m, 1H) 3.63 (m, 1H) 3.85 (br s, 3H) 3.91 (s, 3H) 4.71 (br.d, 1H) 4.96 (br.d, 1H) 6.68 (s, 1H) 6.96 (d, J=2.14 Hz, 1H) 7.08 (dd, J=8.55, 2.44 Hz, 1H) 7.52 (d, J=8.55 Hz 1H) 7.77 (d, J=8.24 Hz, 1H) 7.87 (d, J=8.24 Hz, 1H) 7.97 (s, 1H).

7H-indolo[2,1-a][2]benzazepine-10-carboxylic acid, 13-cyclohexyl-3-methoxy-6-[4-(methoxycarbonyl)-1 (1-methylethyl)-3-trifluoromethyl-1H-pyrazol-5-yl]-

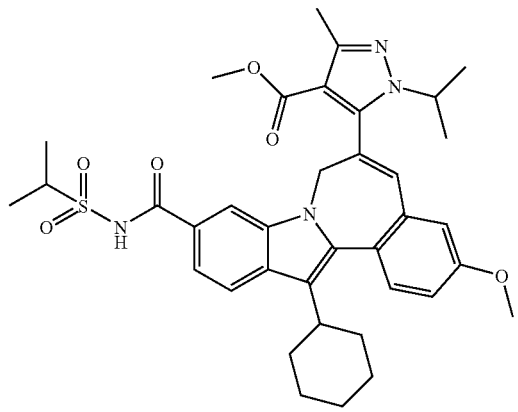

To a solution of 7H-indolo[2,1-a][2]benzazepine-10-carboxylic acid, 13-cyclohexyl-3-methoxy-6-[4-(methoxycarbonyl)-1(1-methylethyl)-3-trifluoromethyl-1H-pyrazol-5-yl]-(110 mg, 0.194 mmol) in tetrahydrofuran (0.646 mL) was added carbonyldiimidazole (94.0 mg, 0.581 mmol). The reaction mixture was heated at 60° C. for one hour. Propane-2-sulfonamide (95 mg, 0.775 mmol) and DBU (0.088 mL, 0.581 mmol) were added at room temperature. The reaction mixture was then heated at 60° C. for 4 hours. The reaction mixture was diluted with 1N HCl (50 mL) solution and extracted with ethyl acetate (2×40 mL). The organic layers were combined and concentrated on a rotary evaporator to give an orange oil as crude product. It was then purified by prep HPLC column using $CH_3CN/H_2O$/TFA as solvent system. Fractions were collected and concentrated under speedvac for 16 h. A yellow solid was obtained as title compound (114 mg, 0.169 mmol, 87% yield).

MS m/z 673 (MH$^+$).

1H NMR (500 MHz, CHLOROFORM-D) δ ppm 0.41 (br s, 3H) 1.18-1.52 (m, 13H) 1.70-2.20 (m, 6H) 2.51 (s, 3H) 2.85 (m, 1H) 3.59 (m, 1H) 3.87 (s, 3H) 3.92 (s, 3H) 4.02 (m, 1H) 4.73 (br.d, 1H) 4.97 (br.d, 1H) 6.67 (s, 1H) 6.96 (d, J=2.14 Hz, 1H) 7.08 (dd, J=8.55, 2.44 Hz, 1H) 7.40-7.62 (m, 2H) 7.78-7.84 (m, 2H), 9.00 (br s, 1H).

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methylethyl)-3-methyl-

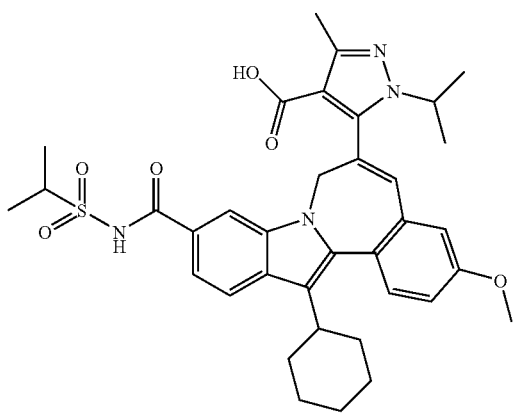

To a mixture of 7H-indolo[2,1-a][2]benzazepine-10-carboxylic acid, 13-cyclohexyl-3-methoxy-6-[4-(methoxycarbonyl)-1(1-methylethyl)-3-trifluoromethyl-1H-pyrazol-5-yl]-(110 mg, 0.163 mmol) was dissolved in THF (0.272 mL) and methanol (0.272 mL) was added to the reaction followed by 1N aqueous sodium hydroxide (0.600 mL). The reaction was capped under a nitrogen atmosphere and stirred at room temperature for 18 hrs. The reaction was diluted with ethyl acetate (25.0 mL) and washed with 1.0N aqueous hydrochloric acid (2×20 ml). The organic layer was concentrated in vacuo using a rotary evaporator to yield the title compound as a yellow solid (107 mg, 0.163 mmol, 100%).

MS m/z 659 (MH$^+$)

1H NMR (500 MHz, CHLOROFORM-D) δ ppm 0.39 (br s, 3H) 1.18-1.52 (m, 13H) 1.70-2.20 (m, 6H) 2.48 (s, 3H) 2.83 (m, 1H) 3.51 (m, 1H) 3.87 (s, 3H) 4.02 (m, 1H) 4.72 (br.d, 1H) 4.98 (br.d, 1H) 6.65 (s, 1H) 6.95 (d, J=2.14 Hz, 1H) 7.08 (dd, J=8.55, 2.44 Hz, 1H) 7.41-7.60 (m, 2H) 7.79-7.83 (m, 2H), 8.96 (br s, 1H).

7H-indolo[2,1-a][2]benzazepine-10-carboxamide, 13-cyclohexyl-3-methoxy-N-[(1-methylethyl)sulfonyl]-6-[3-methyl-1-(1-methylethyl)-4-(4-morpholinylcarbonyl)-1H-pyrazol-5-yl]-

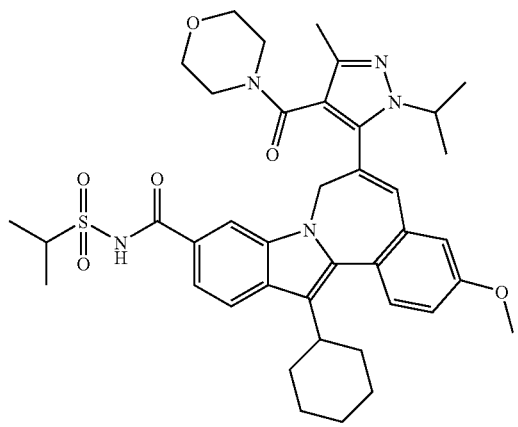

To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1-methylethyl)-3-methyl- (25 mg, 0.038 mmol) in DMSO (0.38 mL), TBTU (24 mg, 0.076 mmol) and DIPEA (0.020 mg, 0.44 mmol) were added. The reaction mixture was stirred at RT for 15 min. Then morpholine (38 mg, 0.15 mmol) was added. The solution was stirred at RT for overnight. The reaction mixture was purified by prep HPLC column using $CH_3CN/H_2O$/TFA as solvent system. Fractions were collected and concentrated under speedvac overnight to yield the title compound as a yellow solid (24 mg, 0.031 mmol, 81% yield).

MS m/z 728 (M–H$^+$)

1H NMR (500 MHz, CHLOROFORM-D) δ ppm 1.18-1.70 (m, 16H) 1.75-2.16 (m, 6H) 2.30 (s, 3H) 2.60-3.31 (m, 9H) 3.94 (m, 3H) 4.04 (m, 1H) 4.56 (br.m, 2H) 4.93 (br.d, 1H) 6.79 (br s, 1H) 6.94 (s, 1H) 7.12 (dd, J=8.55, 2.44 Hz, 1H) 7.57 (d, J=8.55 Hz 1H) 7.66 (br s, 1H) 7.82 (s, 1H) 7.97 (d, J=8.55 Hz, 1H), 10.20 (br s, 1H).

The following compounds were synthesized by an analogous method as described above for 7H-indolo[2,1-a][2]benzazepine-10-carboxamide, 13-cyclohexyl-3-methoxy-N-[(1methylethyl)sulfonyl]-6-[3-methyl-1-(1-methylethyl)-4-(4-morpholinylcarbonyl)-1H-pyrazol-5-yl]-:

7H-indolo[2,1-a][2]benzazepine-10-carboxamide, 13-cyclohexyl-6-[4-[[(2R,6S)-2,6-dimethyl-4-morpholinyl]carbonyl]-3-methyl-1-(1-methylethyl)-1H-pyrazol-5-yl]-3-methoxy-N-[(1-methylethyl)sulfonyl]-

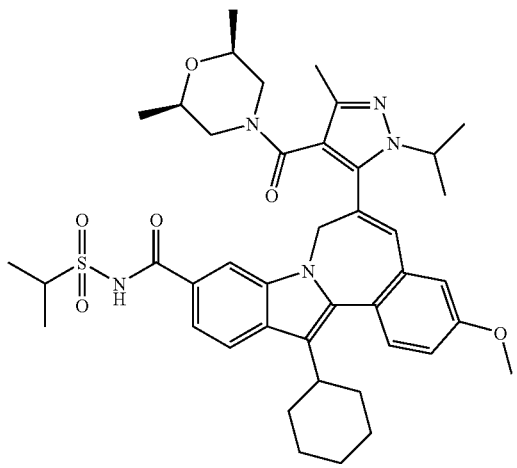

MS m/z 756 (M–H⁺)

1H NMR (500 MHz, CHLOROFORM-D) δ ppm 0.70-0.91 (br m, 6H) 1.02-1.81 (m, 16H) 1.86-2.16 (m, 6H) 2.28 (s, 3H) 2.85-3.29 (m, 5H) 3.96 (s, 3H) 4.12 (br m, 3H) 4.55 (br.m, 2H) 4.92 (br.d, 1H) 6.73 (br s, 1H) 6.94 (br s, 1H) 7.16 (dd, J=8.55, 2.44 Hz, 1H) 7.51-7.72 (m, 2H) 7.76-7.98 (m, 2H), 10.50 (br s, 1H).

7H-indolo[2,1-a][2]benzazepine-10-carboxamide, 13-cyclohexyl-3-methoxy-N-[(1-methylethyl)sulfonyl]-6-[3-methyl-1-(1-methylethyl)-4-[(4-methyl-1-piperazinyl)carbonyl]-1H-pyrazol-5-yl]-

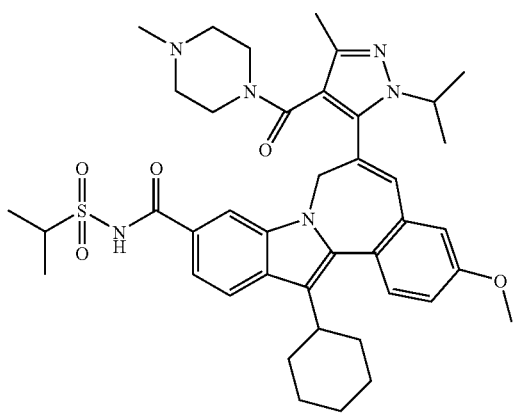

MS m/z 741 (M–H⁺)

1H NMR (500 MHz, CHLOROFORM-D) δ ppm 1.15-1.81 (m, 18H) 1.86-2.12 (m, 4H) 2.21-2.45 (m, 5H) 2.61-3.05 (m, 6H) 3.10-3.75 (m, 4H) 3.93 (s, 3H) 4.04 (m, 1H) 4.61 (br.m, 2H) 4.90 (br.d, 1H) 6.86 (br s, 1H) 6.96 (s, 1H) 7.14 (br m, 1H) 7.59-7.83 (m, 3H) 7.93 (br s, 1H), 10.10 (br s, 1H).

7H-indolo[2,1-a][2]benzazepine-10-carboxamide, 13-cyclohexyl-3-methoxy-N-[(1-methylethyl)sulfonyl]-6-[3-methyl-1-(1-methylethyl)-4-[[(3R,5S)-3,4,5-trimethyl-1-piperazinyl]carbonyl]-1H-pyrazol-5-yl]-

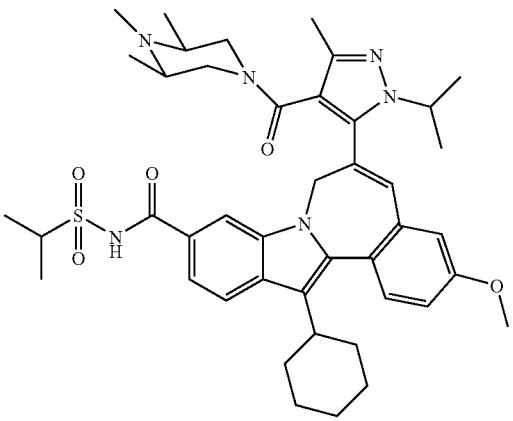

MS m/z 769 (M–H⁺)

1H NMR (500 MHz, CHLOROFORM-D) δ ppm 0.21 (br s, 1H) 1.02 (br s, 3H) 1.15-1.60 (m, 17H) 1.69-2.12 (m, 8H) 2.28 (m, 4H) 2.69-3.60 (m, 6H) 3.96 (s, 3H) 4.08 (br m, 3H) 4.60 (br.m, 2H) 4.88 (br.m, 1H) 6.82 (br s, 1H) 6.95 (s, 1H) 7.15 (br m, 1H) 7.55-7.74 (m, 2H) 7.78-7.99 (m, 2H), 10.12 (br s, 1H).

1H-pyrazole-4-carboxylic acid, 1-methyl-3-(1-methylethyl)-, ethyl ester

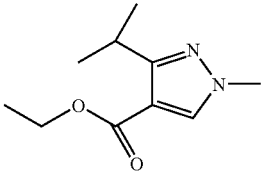

To ethyl 4-methyl-3-oxopentanoate (5.00 g, 31.6 mmol) was added N,N-dimethylformamide dimethyl acetal (37.7 g, 316 mmol). The resulting solution was stirred at 100° C. for 3 hours. Solvent was removed at reduced pressure on a rotary evaporator to yield an orange oil. 3.00 grams of this oil was redissolved in ethanol (46.9 mL). Triethylamine (2.85 g, 28.1 mmol) and methylhydrazine (0.713 g, 15.5 mmol) was added at room temperature, the resulting solution was stirred for 2 hours, diluted with 1M HCl (100 mL) and extracted with chloroform (100 mL). The resulting oil was purified through a column of silica gel using 5:1 hexanes/ethyl acetate as the eluent to yield a yellow oil (2.40 g, 12.1 mmol). MS m/z 197 (MH⁺).

1H-pyrazole-4-carboxylic acid, 5-iodo-1-methyl-3-(1-methylethyl)-, ethyl ester

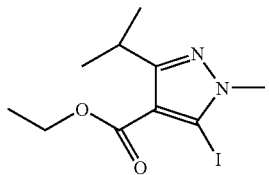

To a solution of 1H-pyrazole-4-carboxylic acid, 1-methyl-3-(1-methylethyl)-, ethyl ester (2.14 g, 10.9 mmol) in dry tetrahydrofuran (21.8 mL) at −78° C., 1.4 M solution of sec-butyllithium (8.57 mL, 12.0 mmol) in pentane was added dropwise. The reaction mixture was then warmed to −45° C. and stirred for 1 h. It was then cooled to −78° C. and iodine (3.04 g, 12.0 mmol) was added. The reaction mixture was warmed to RT and stirred for 1 h. Then it was quenched with saturated NH$_4$Cl solution and extracted with ethyl acetate (2×25 mL). The organic layers were combined, washed with brine and dried (MgSO$_4$). Evaporation of solvent gave a solid that was purified by prep HPLC column using CH$_3$CN/H$_2$O/TFA as solvent system. Fractions were collected and concentrated under speedvac overnight to yield a title compound (0.843 g, 2.62 mmol, 24% crude yield) as a beige solid.

MS m/z 323 (MH$^+$)

1H NMR (500 MHz, CHLOROFORM-D) δ ppm 1.25 (d, 6H) 1.37 (t, 3H) 3.52 (m, 1H) 3.91 (s, 3H) 4.31 (q, 2H).

7H-indolo[2,1-a][2]benzazepine-10-carboxylic acid, 13-cyclohexyl-6-[4-(ethoxycarbonyl)-1-methyl-3-(1-methylethyl)-1H-pyrazol-5-yl]-3-methoxy-, 1,1-dimethylethyl ester

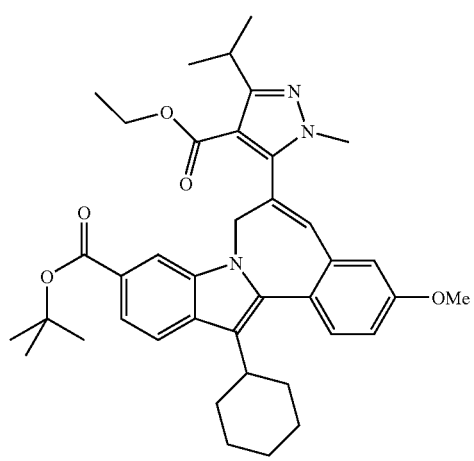

In a microwave tube, 7H-indolo[2,1-a][2]benzazepine-10-carboxylic acid, 13-cyclohexyl-3-methoxy-6-(tributylstannyl)-, 1,1-dimethylethyl ester (800 mg, 1.09 mmol), 1H-pyrazole-4-carboxylic acid, 5-iodo-1-methyl-3-(1-methylethyl)-, ethyl ester (422 mg, 1.31 mmol), LiCl (231 mg, 5.46 mmol), CuCl (454 mg, 4.59 mmol) and bis(triphenylphosphine)palladium II chloride (77.0 mg, 0.109 mmol) were added. It was then sealed, degassed and flushed with nitrogen. 1,4-Dioxane (5.46 mL) was added. The reaction mixture was heated at 160° C. under microwave condition for 1 hour. It was then filtered and the filtrate was concentrated. The residue was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (8 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system. The product-containing fractions were collected and concentrated to give title compound as a yellow solid (286 mg, 0.448 mmol, 41% yield).

MS m/z 638 (MH$^+$)

7H-indolo[2,1-a][2]benzazepine-10-carboxylic acid, 13-cyclohexyl-6-[4-(ethoxycarbonyl)-1-methyl-3-(1-methylethyl)-1H-pyrazol-5-yl]-3-methoxy-

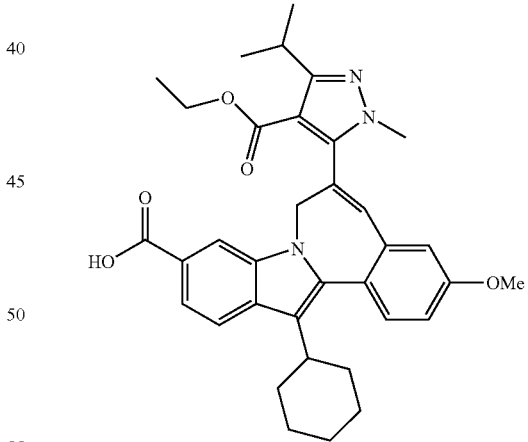

To a solution of 7H-indolo[2,1-a][2]benzazepine-10-carboxylic acid, 13-cyclohexyl-6-[4-(ethoxycarbonyl)-1-methyl-3-(1-methylethyl)-1H-pyrazol-5-yl]-3-methoxy-, 1,1-dimethylethyl ester (286 mg, 0.448 mmol) in 1,2-dichloroethane (4 mL), TFA (4 mL) was added. The reaction mixture was stirred at RT for 2 hours. Volatiles were removed on a rotary evaporator to give the title compound as a brownish thick oil as crude product (260 mg, 0.448 mmol, 100% yield).

MS m/z 582 (MH$^+$)

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(1-methylethyl)-, ethyl ester

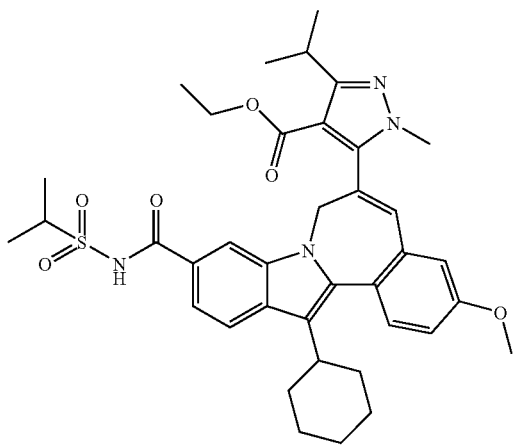

To a solution of 7H-indolo[2,1-a][2]benzazepine-10-carboxylic acid, 13-cyclohexyl-6-[4-(ethoxycarbonyl)-1-methyl-3-(1-methylethyl)-1H-pyrazol-5-yl]-3-methoxy- (140 mg, 0.241 mmol) in tetrahydrofuran (0.802 mL) was added carbonyldiimidazole (117 mg, 0.722 mmol). The reaction mixture was heated at 60° C. for one hour. Propane-2-sulfonamide 119 mg, 0.963 mmol) and DBU (0.109 mL, 0.722 mmol) were added at room temperature. The reaction mixture was then heated at 60° C. for 2 hours. The reaction mixture was diluted with 1N HCl (50 mL) solution and extracted with chloroform (50 mL). The organic layers were combined and concentrated on a rotary evaporator to give an orange oil as crude product. It was purified through silica gel using 90/9/1 methylene chloride/MeOH/AcOH as the eluent to give the title compound (160 mg, 0.233 mmol, 97% yield) as a yellow oil. MS m/z 687 (MH⁺)

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(1-methylethyl)-

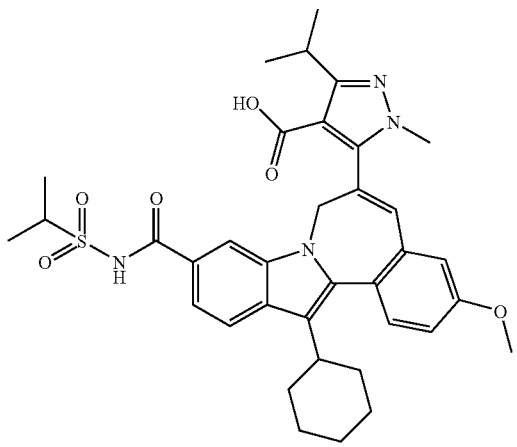

To a mixture of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(1-methylethyl)-, ethyl ester (160 mg, 0.233 mmol) was dissolved in THF (0.582 mL) and methanol (0.582 mL) was added to the reaction followed by 1N aqueous sodium hydroxide (2.32 mL). The reaction was capped under a nitrogen atmosphere and stirred at room temperature for 120 hrs. The reaction was diluted with chloroform (50 mL) and washed with 1.0N aqueous hydrochloric acid (50 mL). The organic layer was concentrated in vacuo using a rotary evaporator to yield the title compound as a yellow solid (153 mg, 0.233 mmol, 100%).

MS m/z 659 (MH⁺)

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-(4-morpholinylcarbonyl)-1H-pyrazol-5-yl]-

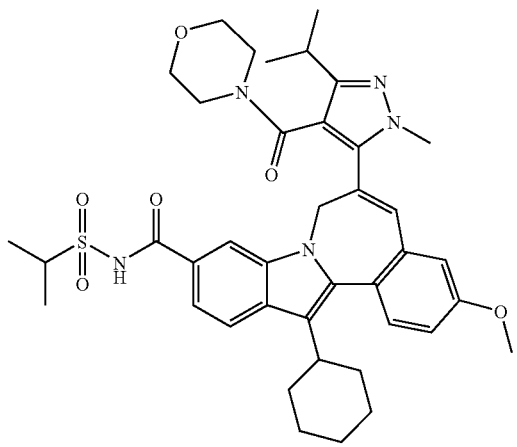

To a solution of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-3-(1-methylethyl)- (50 mg, 0.076 mmol) in DMSO (0.760 mL), TBTU (49 mg, 0.152 mmol) and DIPEA (0.039 mg, 0.30 mmol) were added. The reaction mixture was stirred at RT for 15 min. Then morpholine (26 mg, 0.304 mmol) was added. The solution was stirred at RT for overnight. The reaction mixture was purified by prep HPLC column using $CH_3CN/H_2O$/TFA as solvent system. Fractions were collected and concentrated under speedvac overnight to yield the title compound as a yellow solid (26 mg, 0.035 mmol, 47% yield).

MS m/z 728 (M–H⁺)

1H NMR (500 MHz, CHLOROFORM-D) δ ppm 1.15-1.62 (m, 16H) 1.72-2.25 (m, 7H) 2.53-3.36 (m, 9H) 3.90 (s, 3H) 3.94 (s, 3H) 4.07 (m, 1H) 4.60 (br d, 1H) 4.94 (br d, 1H) 6.82 (d, J=2.44 Hz, 1H) 6.96 (s, 1H) 7.14 (dd, J=8.55, 2.75 Hz, 1H) 7.57 (d, J=8.55 Hz, 1H) 7.64 (m, 1H) 7.76 (s, 1H) 7.96 (d, J=8.55 Hz, 1H) 10.56 (br s, 1H).

The following compounds were synthesized by an analogous method as described above for 7H-indolo[2,1-a][2]benzazepine-10-carboxamide, 13-cyclohexyl-3-methoxy-N-[(1methylethyl)sulfonyl]-6-[1-methyl-3-(1-methylethyl)-4-(4-morpholinylcarbonyl)-1H-pyrazol-5-yl]-:

methylethyl)sulfonyl]-6-[1-methyl-3-(1-methylethyl)-4-(4-morpholinylcarbonyl)-1H-pyrazol-5-yl]-:

7H-indolo[2,1-a][2]benzazepine-10-carboxamide, 13-cyclohexyl-6-[4-[[(2R,6S)-2,6-dimethyl-4-morpholinyl]carbonyl]-1-methyl-3-(1-methylethyl)-1H-pyrazol-5-yl]-3-methoxy-N-[(1-methylethyl)sulfonyl]-

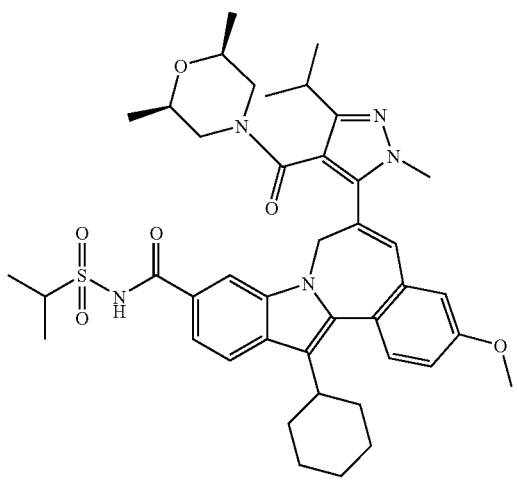

MS m/z 756 (MH$^+$). 1H NMR (500 MHz, CHLOROFORM-D) δ ppm 0.70 (m, 6H) 1.05-1.62 (m, 16H) 1.72-2.28 (m, 7H) 2.83-3.21 (m, 5H) 3.90-3.94 (m, 8H) 4.08 (m, 1H) 4.59 (br d, 1H) 4.96 (br d, 1H) 6.79 (d, J=2.44 Hz, 1H) 6.96 (s, 1H) 7.14 (dd, J=8.55, 2.75 Hz, 1H) 7.58 (d, J=8.55 Hz, 1H) 7.69 (m, 1H) 7.81 (s, 1H) 7.96 (d, J=8.55 Hz, 1H) 10.70 (br s, 1H).

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-[(4-methyl-1-piperazinyl)carbonyl]-1H-pyrazol-5-yl]-

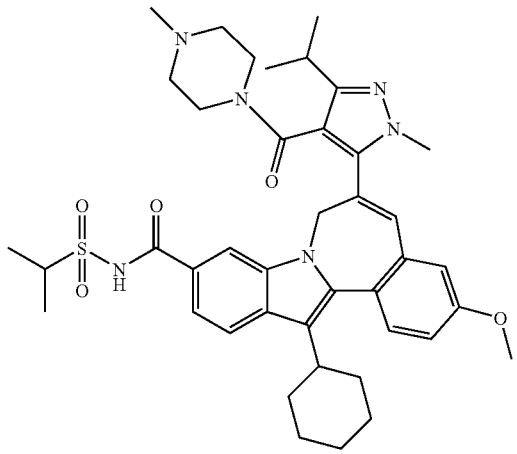

MS m/z 741 (MH$^+$). 1H NMR (500 MHz, CHLOROFORM-D) δ ppm 1.12-1.70 (m, 16H) 1.70-2.12 (m, 7H) 2.33 (br s, 3H) 2.70-3.32 (m, 7H) 3.45-4.07 (m, 9H) 4.61 (br s, 1H) 4.97 (br s, 1H) 6.89 (br s, 1H) 7.96 (s, 1H) 7.13 (br m, 1H) 7.50-7.86 (br m, 3H) 7.94 (d, J=8.55 Hz, 1H) 10.30 (br s, 1H).

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-[[(3R,5S)-3,4,5-trimethyl-1-piperazinyl]carbonyl]-1H-pyrazol-5-yl]-

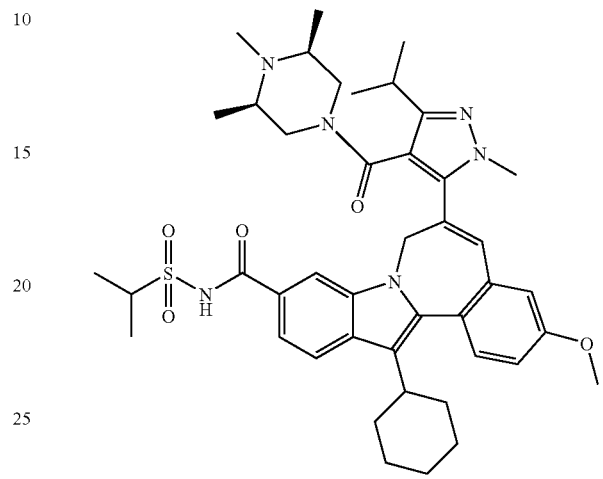

MS m/z 769 (MH$^+$). 1H NMR (500 MHz, CHLOROFORM-D) δ ppm 1.05 (m, 6H) 1.05-1.62 (m, 16H) 1.72-2.13 (m, 7H) 2.28 (br s, 3H) 2.83-3.48 (m, 5H) 3.79-4.11 (m, 9H) 4.62 (br d, 1H) 4.99 (br d, 1H) 6.86 (br s, 1H) 6.97 (s, 1H) 7.18 (br s, 1H) 7.60-7.81 (br m, 3H) 7.95 (d, J=8.55 Hz, 1H) 10.32 (br s, 1H).

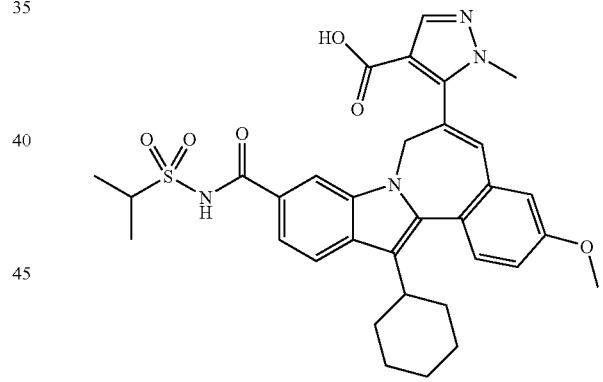

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- Dissolve 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl-, ethyl ester (1.044 g, 1.619 mmol) in a pre-mixed solution of THF (20 mL), MeOH (20 mL) and sodium hydroxide (20 mL, 20.00 mmol). The reaction was homogenous and was stirred at room temperature under a nitrogen atmosphere for 26 hrs then concentrated in vacuo using a rotary evaporator with a bath temperature at 20 C. The reaction was poured into 1N aqueous hydrochloric acid and extract using ethyl acetate. The combined organic layers were washed sequentially with 1N aqueous hydrochloric acid and brine, then dried over magnesium sulfate, filtered and solvent removed in vacuo. The crude product dried in vacuo at room temperature to yield 1.68 g of an orange amorphous solid. The crude product was dissolved in chloroform (approximately 50 mL) with heating and hexanes were added until some material starts to precipitate but re-dissolves on swirling (approximately 10-12 ml of hexanes). The mixture was allowed to slowly cool to room temperature and then allowed to stand at room temperature for a few hours. The very fine particulate yellow precipitate was filtered using a Buchner funnel and dried in vacuo at room temperature to yield 819 mg (45%) of purified product as a bright yellow amorphous solid. The title compound 4.6 mg was dissolved in CDCl3 (2 ml) with the addition of approximately 5 drops of CD3OD to aid in dissolution for 1H NMR acquisition.

1H NMR (500 MHz, CHLOROFORM-D/CD3OD) δ ppm 1.11-1.39 (m, 3H) 1.41 (d, J=7.02 Hz, 6H) 1.47-1.65 (m, 1H) 1.75 (d, J=8.85 Hz, 2H) 1.82-2.27 (m, 13H) 2.77-2.90 (m, 1H) 3.28 (s, 3H) 3.88 (s, 3H) 3.97-4.06 (m, 1H) 4.66 (s, 1H) 5.01 (s, 1H) 6.76 (s, 1H) 6.92 (d, J=2.75 Hz, 1H) 7.04 (dd, J=8.70, 2.59 Hz, 1H) 7.47-7.54 (m, 2H) 7.81 (d, J=1.22 Hz, 1H) 7.86 (d, J=8.54 Hz, 1H) 7.91 (s, 1H).

LC-MS retention time 1.39 min; 615 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

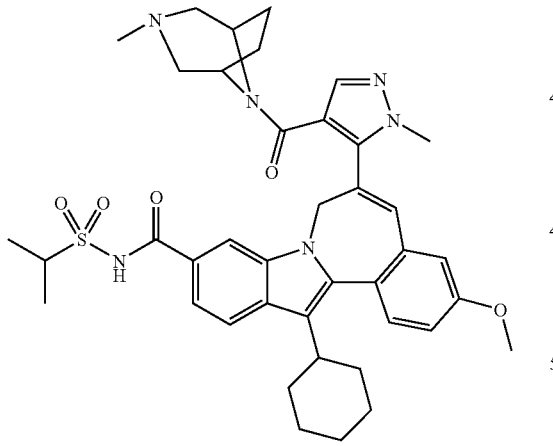

7H-indolo[2,1-a][2]benzazepine-10-carboxamide, 13-cyclohexyl-3-methoxy-N-[(1-methylethyl)sulfonyl]-6-[1-methyl-4-[(3-methyl-3,8-diazabicyclo[3.2.1]oct-8-yl)carbonyl]-1H-pyrazol-5-yl]-

In a 2 dram vial, 900 uL of a stock solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.09M, 0.081 mmol) and TBTU (0.19M, 0.171 mmol) in DMF was stirred under a nitrogen atmosphere for 1 hour at room temperature. DMAP (40 mg, 0.327 mmol) was added to the reaction and stirred until dissolved then the amine reagent, 3-methyl-3,8-diazabicyclo[3.2.1]octane dihydrochloride (35 mg, 0.176 mmol), was added and the reaction capped under nitrogen and stirred at room temperature overnight. The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 63 mg of an amorphous yellow film/foam. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. Sample was purified in two HPLC injections, and the product fractions combined (retention time=5.5 min) and volatiles removed in vacuo. The sample was dried in vacuo at room temperature to yield 44.4 mg of the title compound as a TFA salt.

1H NMR (500 MHz, CHLOROFORM-D) δ ppm 1.10-1.31 (m, 1H) 1.33-1.57 (m, 10H) 1.80 (s, 2H) 1.89-2.16 (m, 5H) 2.57 (s, 4H) 2.74 (s, 9H) 2.84-3.12 (m, 4H) 3.27 (s, 2H) 3.32-3.72 (m, 4H) 3.88 (s, 3H) 3.94 (s, 4H) 4.00-4.14 (m, 1H) 4.63 (d, J=15.56 Hz, 1H) 4.89 (d, J=12.21 Hz, 1H) 6.96 (d, J=2.14 Hz, 2H) 7.13 (dd, J=8.55, 2.44 Hz, 1H) 7.57 (d, J=8.85 Hz, 1H) 7.63 (d, J=7.63 Hz, 2H) 7.76 (s, 1H) 7.93 (d, J=8.55 Hz, 1H).

LC-MS retention time 1.81 min; 723 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

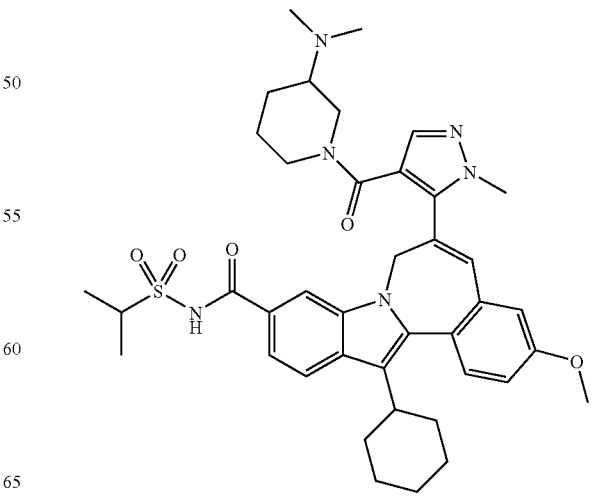

7H-indolo[2,1-a][2]benzazepine-10-carboxamide, 13-cyclohexyl-6-[4-[[3-(dimethylamino)-1-piperidinyl]carbonyl]-1-methyl-1H-pyrazol-5-yl]-3-methoxy-N-[(1-methylethyl)sulfonyl]-

In a 2 dram vial, 900 uL of a stock solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.09M, 0.081 mmol) and TBTU (0.19M, 0.171 mmol) in DMF was stirred under a nitrogen atmosphere for 1 hour at room temperature. DMAP (42 mg, 0.344 mmol) was added to the reaction and stirred until dissolved then the amine reagent, N,N-dimethylpiperidin-3-amine dihydrochloride (34 mg, 0.169 mmol) was added and the reaction capped under nitrogen and stirred at room temperature overnight. The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 67 mg as a yellow film. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA.

Combine product fractions, retention time=5.03 min, remove volatiles in vacuo and dry at room temperature in vacuo to yield 26.2 mg of the title compound as an amorphous yellow solid.

1H NMR (500 MHz, CHLOROFORM-D) δ ppm 1.04-1.18 (m, 1H) 1.18-1.45 (m, 6H) 1.48 (d, J=6.71 Hz, 7H) 1.80 (d, J=8.55 Hz, 3H) 1.86-2.26 (m, 5H) 2.37-2.99 (m, 20H) 3.12-3.72 (m, 4H) 3.85 (s, 4H) 3.93 (s, 3H) 3.98-4.08 (m, 1H) 4.23 (s, 0.4H) 4.60 (d, J=14.34 Hz, 1H) 4.86 (d, J=11.90 Hz, 1H) 6.82-7.02 (m, 2H) 7.11 (d, J=7.02 Hz, 1H) 7.53 (d, J=8.55 Hz, 1H) 7.58-7.88 (m, 3H) 7.94 (d, J=8.24 Hz, 1H) 10.05 (s, 0.6H).

LC-MS retention time 1.54 min; 725 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

13-cyclohexyl-6-(4-(((2R,6S)-2,6-dimethyl-4-morpholinyl)carbonyl)-1-methyl-1H-pyrazol-5-yl)-N-(isopropylsulfonyl)-3-methoxy-7H-indolo[2,1-a][2]benzazepine-10-carboxamide In a 2 dram vial, 932 uL of a stock solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.087M, 0.081 mmol) and TBTU (0.18M, 0.168 mmol), in DMF was stirred under a nitrogen atmosphere for 1.75 hours at room temperature. DMAP (40 mg, 0.327 mmol) was added to the reaction and stirred until dissolved then the amine reagent, (2R,6S)-2,6-dimethylmorpholine (0.030 mL, 0.243 mmol), was added and the reaction capped under nitrogen and stirred at room temperature overnight (19 hrs). The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 65 mg of a yellow film. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA Retention time of product=12.83 minutes. The sample was purified in two 1 ml injections, the second run was cut to a runtime of 20 minutes with the same 15 min gradient. Combine product fractions and remove volatiles in vacuo using a rotary evaporator then dry sample in vacuo at room temperature to yield 26.1 mg of the title compound as an opaque yellow solid/amorphous film.

1H NMR (500 MHz, CHLOROFORM-D) δ ppm 0.60-0.93 (m, 6H) 1.16-1.29 (m, 2H) 1.30-1.58 (m, 9H) 1.79 (d, J=10.68 Hz, 2H) 1.92 (s, 14H) 2.05-2.27 (m, 3H) 2.88 (t, J=11.44 Hz, 1H) 3.13-3.31 (m, 2H) 3.46 (br.s, 1H) 3.91 (s, 3H) 3.94 (s, 3H) 4.02-4.13 (m, 1H) 4.60 (d, J=15.56 Hz, 1H) 4.90 (d, J=15.56 Hz, 1H) 6.83 (br, s, 1H) 6.95 (d, J=2.14 Hz, 1H) 7.06-7.17 (m, 1H) 7.49-7.80 (m, 4H) 7.93 (s, 1H) 10.12 (br.s, 0.2H) 10.47 (br.s, 0.6H).

LC-MS retention time 1.90 min; 712 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

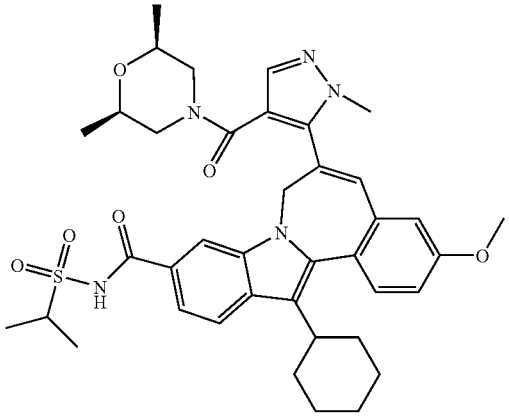

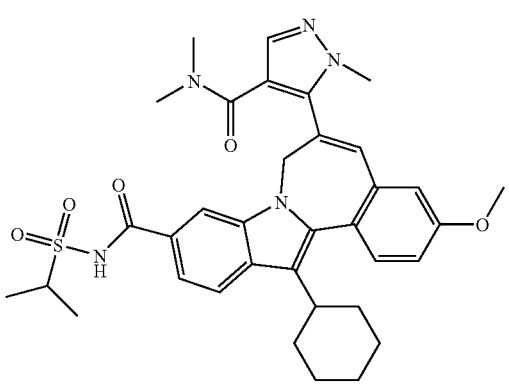

13-cyclohexyl-6-(4-(dimethylcarbamoyl)-1-methyl-1H-pyrazol-5-yl)-N-(isopropylsulfonyl)-3-methoxy-7H-indolo[2,1-a][2]benzazepine-10-carboxamide In a 2 dram vial, 932 uL of a stock solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.087M, 0.081 mmol) and TBTU (0.18M, 0.168 mmol), in DMF was stirred under a nitrogen atmosphere for 1.75 hours at room temperature. DMAP (41.8 mg, 0.342 mmol) was added to the reaction and stirred until dissolved then the amine reagent, dimethylamine hydrochloride (17.5 mg, 0.215 mmol), was added and the reaction capped under nitrogen and stirred at room temperature overnight (19 hrs). The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 57 mg as a yellow foam/amorphous solid/film.

The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA Retention time of product=12.05 minutes. The sample was purified in two 1 ml injections. Combine product fractions and remove volatiles in vacuo using a rotary evaporator then dry sample in vacuo at room temperature to yield 37.6 mg (68%) as an amorphous yellow solid.

1H NMR (500 MHz, CHLOROFORM-D) δ ppm 1.15-1.30 (m, 1H) 1.33-1.45 (m, 2H) 1.49 (br.s, 7H) 1.79 (d, J=8.55 Hz, 2H) 1.91-2.17 (m, 7H) 2.32 (br.s, 9H) 2.45 (br.s, 3H) 2.78-2.91 (m, 1H) 3.50 (br.s, 1H) 3.82 (s, 3H) 3.93 (s, 3H) 4.01-4.10 (m, 1H) 4.60 (d, J=14.34 Hz, 1H) 4.93 (d, J=14.65 Hz, 1H) 6.86 (s, 1H) 6.96 (d, J=2.75 Hz, 1H) 7.10 (dd, J=8.70, 2.59 Hz, 1H) 7.53 (d, J=8.55 Hz, 1H) 7.58 (d, J=8.55 Hz, 1H) 7.66 (s, 1H) 7.75 (s, 1H) 7.91 (d, J=8.55 Hz, 1H) 9.99 (br.s, 1H).

LC-MS retention time 1.74 min; 642 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

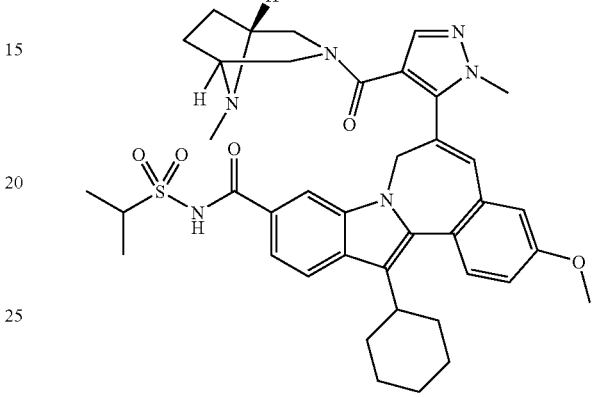

7H-indolo[2,1-a][2]benzazepine-10-carboxamide, 13-cyclohexyl-3-methoxy-N-[(1-methylethyl)sulfonyl]-6-[1-methyl-4-[[(1R,5S)-8-methyl-3,8-diazabicyclo[3.2.1]oct-3-yl]carbonyl]-1H-pyrazol-5-yl]-

In a 2 dram vial, 900 uL of a stock solution containing 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (0.09M, 0.081 mmol) and TBTU (0.19M, 0.171 mmol) in DMF was stirred under a nitrogen atmosphere for 1 hour at room temperature. DMAP (41 mg, 0.336 mmol) was added to the reaction and stirred until dissolved then the amine reagent, (1R,5S)-8-methyl-3,8-diazabicyclo[3.2.1]octane dihydrochloride (30 mg, 0.151 mmol), was added and the reaction capped under nitrogen and stirred at room temperature overnight. The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 70 mg. The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA.

Retention time of product was 5.56 minutes and remove volatiles/solvent in vacuo. HPLC analysis of the first Prep HPLC purification using % A=10 mM Ammonium Acetate, pH=6.8 in Water/Acetonitrile (95%/5%) % B=10 mM Ammonium Acetate, pH=6.8 in Water/Acetonitrile (5%/95%) solvent system show impurities in the sample. The sample was further purified on a Shimadzu high pressure liquid chromatography system employing Discovery VP software interfaced with a SCL-10A controller, SIL-10A autosampler and FRC-10A fraction collector. The sample was dissolved in 0.5 ml DMF/1.5 ml acetonitrile and purified using a Phenonemex Gemini 30 mm×100 mm column and monitored using a SPD-10AV UV-Vis detector at a detector wave length of 220 nM. The elution conditions employed a flow rate of 40 mL/min, a gradient of 70 solvent A/30% solvent B to 0% solvent A/100% solvent B, a gradient time of 20 minutes with a run time of 30 minutes using % A=10 mM Ammonium Acetate, pH=6.8 in Water/Acetonitrile (95%/5%) % B=10 mM Ammonium Acetate, pH=6.8 in Water/Acetonitrile (5%/95%) solvent system. Product elution time is from 9.7 minutes to 11.7 minutes. Combine product fractions and remove volatiles and dry in vacuo. The trifluoroacetic acid salt of the title compound was made by dissolving the purified product in dichloromethane and adding 10 uL of trifluoroacetic acid then removing volatiles in vacuo. Drying in vacuo at room temperature yielded 23.6 mg (35%) of the trifluoroacetic acid salt of the title compound as a yellow amorphous solid.

1H NMR (500 MHz, CHLOROFORM-D) δ ppm 1.11-1.29 (m, 1H) 1.32-1.45 (m, 3H) 1.49 (dd, J=11.14, 6.87 Hz, 6H) 1.79 (d, J=10.68 Hz, 2H) 1.89-2.13 (m, 4H) 2.28-2.73 (m, 15H) 2.84-2.95 (m, 1H) 3.25 (s, 2H) 3.39 (s, 2H) 3.76-3.92 (m, 3H) 3.94 (s, 3H) 4.01-4.12 (m, 1H) 4.63 (d, J=15.87 Hz, 1H) 4.87 (s, 1H) 6.96 (d, J=2.14 Hz, 2H) 7.13 (dd, J=8.85, 2.44 Hz, 1H) 7.57 (d, J=8.55 Hz, 1H) 7.63 (s, 1H) 7.77 (s, 1H) 7.92 (d, J=8.55 Hz, 1H) 10.06 (s, 1H).

LC-MS retention time 1.73 min; 723 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 6-[4-[[[2-[bis(1-methylethyl)amino]ethyl](1-methylethyl)amino]carbonyl]-1-methyl-1H-pyrazol-5-yl]-13-cyclohexyl-3-methoxy-N-[(1-methylethyl)sulfonyl]-

In a 2 dram vial, 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (52.1 mg, 0.084 mmol) was dissolved in DMF (0.9 ml) and TBTU (56.2 mg, 0.175 mmol) was added and the reaction stirred under a nitrogen atmosphere for 1 hour at room temperature. DMAP (46 mg, 0.377 mmol) was added to the reaction and stirred until dissolved then the amine reagent, N,N,N'-triisopropylethylenediamine (55 mg, 0.295 mmol), was added and the reaction capped under nitrogen and stirred at room temperature overnight. The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 84 mg as a yellow glass/film.

The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA. The retention time of product=6 minutes. Combine product fractions and remove volatiles in vacuo using a rotary evaporator then dry sample in vacuo at room temperature to yield 36.0 mg (47%) as a yellow amorphous solid.

1H NMR (500 MHz, CHLOROFORM-D) δ ppm 1.05 (s, 6H) 1.18-1.43 (m, 15H) 1.46 (d, J=7.02 Hz, 8H) 1.78 (d, J=8.55 Hz, 2H) 1.87-2.12 (m, 4H) 2.62 (s, 14H) 2.80-2.90 (m, 1H) 3.12 (s, 2H) 3.24-3.70 (m, 9H) 3.92 (s, 3H) 3.97-4.06 (m, 1H) 4.19 (s, 1H) 4.55 (s, 1H) 4.99 (s, 1H) 6.86 (s, 1H) 6.94 (d, J=2.44 Hz, 1H) 7.09 (dd, J=8.55, 2.75 Hz, 1H) 7.48-7.57 (m, 3H) 7.85 (s, 1H) 7.90 (d, J=8.54 Hz, 1H) 9.33 (s, 1H) 10.12 (s, 1H).

LC-MS retention time 1.80 min; 783 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

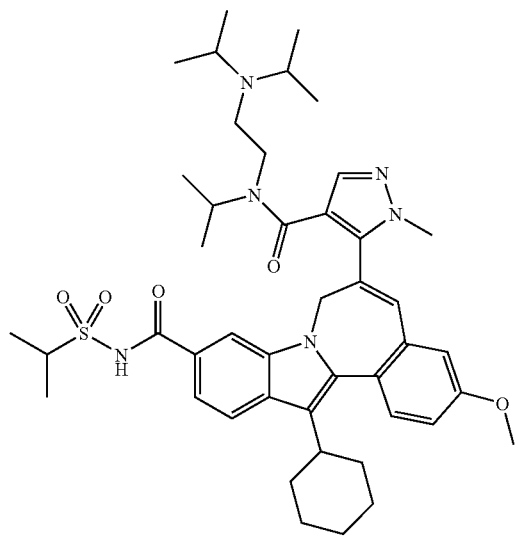

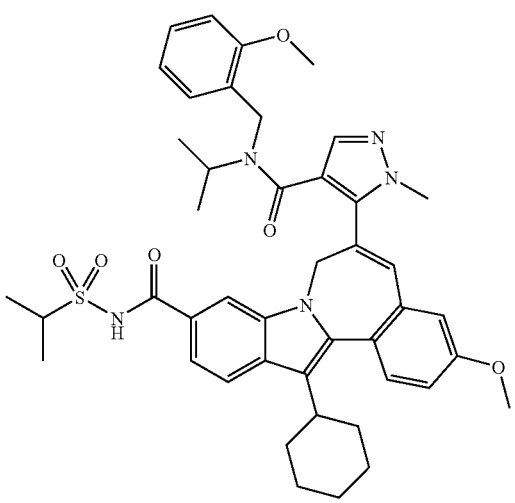

7H-indolo[2,1-a][2]benzazepine-10-carboxamide, 13-cyclohexyl-3-methoxy-6-[4-[[[(2-methoxyphenyl)methyl](1-methylethyl)amino]carbonyl]-1-methyl-1H-pyrazol-5-yl]-N-[(1-methylethyl)sulfonyl]-

In a 2 dram vial, 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (50 mg, 0.081 mmol) was dissolved in DMF (811 μL) and TBTU (51.5 mg, 0.160 mmol) was added and the reaction stirred under a nitrogen atmosphere for 1.3 hour at room temperature. DMAP (52 mg, 0.426 mmol) was added to the reaction and stirred until dissolved then the amine reagent, N-(2-methoxybenzyl)propan-2-amine hydrochloride (36 mg, 0.167 mmol), was added and the reaction capped under nitrogen and stirred at room temperature overnight. The reaction was diluted with ethyl acetate and washed sequentially with 1.0N aqueous hydrochloric acid and brine. The organic phase was dried over MgSO4, filtered and solvent removed in vacuo. The crude product was dried in vacuo at room temperature to yield 75 mg as a yellow film.

The sample was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 mL) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA Retention time of product=14.7 minutes. Remove volatiles from product fraction in vacuo using a rotary evaporator then dry sample in vacuo at room temperature to yield 45.4 mg (72%) as a amorphous yellow solid. Proton NMR exhibits rotomeric characteristics.

1H NMR (500 MHz, CHLOROFORM-D) δ ppm 0.34-1.03 (m, 6.3H) 1.04-1.32 (m, 3.4H) 1.29-1.66 (m, 7.6H) 1.78 (d, 2.2H) 1.90-2.24 (m, 4.3H) 2.52 (s, 3.6H) 2.87 (s, 1.1H) 3.36-3.71 (m, 2.1H) 3.71-3.88 (m, 5.5H) 3.92 (s, 3.4H) 4.00-4.06 (m, 0.8H) 4.13-4.39 (m, 1.1H) 4.63 (d, J=12.21 Hz, 1.0H) 5.08 (d, J=14.04 Hz, 0.9H) 6.54-6.83 (m, 2.5H) 6.86-6.99 (m, 2.6H) 7.02-7.20 (m, 2.1H) 7.34-7.71 (m, 3.1H) 7.74-7.99 (m, 2.0H) 9.39 (br.s, 0.4H) 9.85 (br.s, 0.5H).

LC-MS retention time 1.99 min; 776 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 2 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[4-[[[(5-ethyl-1,3,4-oxadiazol-2-yl)methyl](1-methylethyl)amino]carbonyl]-1-methyl-1H-pyrazol-5-yl]-3-methoxy-N-[(1-methylethyl)sulfonyl]-

In a 2 dram vial, 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (50 mg, 0.081 mmol) was dissolved in DMF (811 μL) and TBTU (51.5 mg, 0.160 mmol) was added and the reaction stirred under a nitrogen atmosphere for 1 hour at room temperature. DMAP (43.2 mg, 0.354 mmol) was added to the reaction and stirred until dissolved then the amine reagent, N-((5-ethyl-1,3,4-oxadiazol-2-yl)methyl)propan-2-amine (47.3 mg, 0.280 mmol) dissolved in 0.2 ml of DMF, was added to the reaction. The reaction was capped under nitrogen and stirred at room temperature overnight.

The reaction was purified on a Shimadzu high pressure liquid chromatography system employing Discovery VP software interfaced with a SCL-10A controller, SIL-10A autosampler and FRC-10A fraction collector. The reaction was diluted to 2 ml volume with acetonitrile and the reaction was purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. Retention time of product is 11.45 minutes. Combine product fractions and remove volatiles in vacuo using a rotary evaporator then dry sample in vacuo at room temperature to yield 47.8 mg as a yellow amorphous solid/film.

1H NMR (500 MHz, CHLOROFORM-D) δ ppm 1.07-1.24 (m, 5H) 1.27 (t, J=7.48 Hz, 4H) 1.38 (d, J=5.49 Hz, 8H) 1.56 (d, J=9.46 Hz, 1H) 1.78 (d, J=9.46 Hz, 2H) 1.88-1.99 (m, 1H) 2.00-2.17 (m, 3H) 2.55-2.82 (m, 4H) 2.83-2.94 (m, 1H) 3.73 (s, 3H) 3.89 (s, 3H) 3.97-4.08 (m, 1H) 4.15-4.80 (m, 4H) 5.22 (d, J=16.79 Hz, 1H) 6.88 (s, 1H) 6.94 (d, J=2.75 Hz, 1H) 7.04 (dd, J=8.55, 2.44 Hz, 1H) 7.46 (d, J=8.85 Hz, 1H) 7.59-7.67 (m, 2H) 7.91 (d, J=8.55 Hz, 1H) 8.31 (br.s, 1H) 9.62 (br.s, 1H).

LC-MS retention time 1.75 min; 766 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

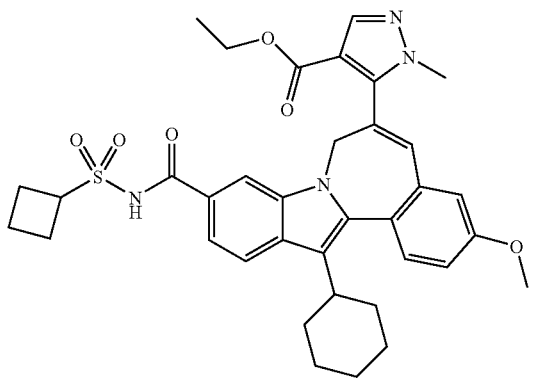

1H-pyrazole-4-carboxylic acid, 5-[10-[[(cyclobutyl-sulfonyl)amino]carbonyl]-13-cyclohexyl-3-methoxy-7H-indolo[2,1-a][2]benzazepin-6-yl]-1-methyl-, ethyl ester Dissolve 7H-indolo[2,1-a][2]benzazepine-10-carboxylic acid, 13-cyclohexyl-6-[4-(ethoxycarbonyl)-1-methyl-1H-pyrazol-5-yl]-3-methoxy-(653 mg, 1.210 mmol) in THF (12 ml) in a 50 ml RB flask. Carbonyldiimidazole (1.308 g, 8.07 mmol) was added to the reaction. The flask fitted with a condenser was placed under a nitrogen atmosphere and the reaction allowed to stir at room temperature for 1 hr then refluxed for 50 minutes. The reaction was cooled under a nitrogen atmosphere and cyclobutanesulfonamide (825 mg, 6.10 mmol) was added to the reaction followed by DBU (0.383 ml, 2.54 mmol). The reaction was heated overnight at 70 C under a nitrogen atmosphere. LC-MS analysis indicated primarily imidazolide but an insignificant amount of product, therefore cyclobutylsulfonamide (700 mg, 5.17 mmol) was added to the reaction followed by DBU (0.383 ml, 2.54 mmol). The reaction was heated to reflux under a nitrogen atmosphere for 3.5 hours and progress rechecked by LCMS. Additional cyclobutylsulfonamide (357 mg, 2.64 mmol) and DBU (0.383 ml, 2.54 mmol) was added to the reaction and the reaction heated to reflux for 3.25 hrs. The reaction was cooled and ethyl acetate and washed two times with 1.0N aqueous hydrochloric acid. The aqueous layer was back extracted with ethyl acetate. The organic layers were combined and wash sequentially with 1.0N aqueous hydrochloric acid, 0.1M NaH2PO4, and again with 1.0N aqueous hydrochloric acid and finally brine. The organic phase was dried over magnesium sulfate, filtered and solvent removed in vacuo to yield 949 mg of a crude product as a yellow solid. The crude product was adsorbed onto 2.6 g of silica gel and chromatographed on 28.7 g of silica gel slurry packed using 2% methanol in dichloromethane and eluted using 2% methanol in dichloromethane. Pure product fractions were combined and the volatiles removed in vacuo using a rotary evaporator to yield 465 mg (59%) of the title compound as an amorphous yellow solid.

1H NMR (500 MHz, CHLOROFORM-D) δ ppm 1.20 (m, 1H) 1.30 (t, J=7.17 Hz, 3H) 1.33-1.48 (m, 2H) 1.55 (br.s, 4H) 1.78 (d, J=9.46 Hz, 2H) 1.87-2.14 (m, 6H) 2.32-2.42 (m, 2H) 2.55-2.69 (m, 2H) 2.79-2.92 (m, 1H) 3.28 (s, 3H) 3.90 (s, 3H) 4.25 (br.s, 2H) 4.53-4.63 (m, 1H) 4.71 (d, J=10.68 Hz, 1H) 4.97 (d, J=14.34 Hz, 1H) 6.77 (s, 1H) 6.94 (d, J=2.44 Hz, 1H) 7.07 (dd, J=8.55, 2.75 Hz, 1H) 7.35 (dd, J=8.39, 1.37 Hz, 1H) 7.52 (d, J=8.85 Hz, 1H) 7.73 (d, J=1.22 Hz, 1H) 7.88 (d, J=8.55 Hz, 1H) 7.91 (s, 1H) 8.24 (s, 1H).

LC-MS retention time 1.78 min; 655 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

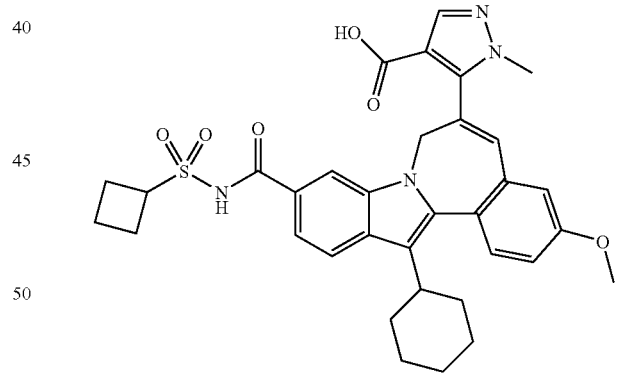

1H-pyrazole-4-carboxylic acid, 5-[10-[[(cyclobutyl-sulfonyl)amino]carbonyl]-13-cyclohexyl-3-methoxy-7H-indolo[2,1-a][2]benzazepin-6-yl]-1-methyl- 1H-pyrazole-4-carboxylic acid, 5-[10-[[(cyclobutylsulfo-nyl)amino]carbonyl]-13-cyclohexyl-3-methoxy-7H-indolo[2,1-a][2]benzazepin-6-yl]-1-methyl-, ethyl ester (463 mg, 0.705 mmol) was dissolved in THF (6.8 mL), then diluted using methanol (6.8 mL) with heating and the mixture cooled to room temperature. To the reaction suspension in THF/methanol was added 1.0N aqueous sodium hydroxide (6.8 mL, 6.8 mmol). Upon addition of the sodium hydroxide solution the reaction became a clear homogeneous solution. The reaction was stirred at room temperature under a nitrogen atmosphere for 20 hrs. Concentrate reaction in vacuo using a rotary evaporator with room temperature bath (20 C). Partition the reaction between 200 ml of ethyl acetate and 1.0N aqueous hydrochloric acid. Extract aqueous phase using ethyl acetate. Combine organic phases and wash sequentially with 1.0N aqueous hydrochloric acid and brine. Dry the organic layer over magnesium sulfate, filter and remove volatiles from the filtrate in vacuo to yield 457 mg of the title compound as a light yellow colored solid.

1H NMR (500 MHz, MeOD) δ ppm 0.83 (br.s, 1H) 1.11-1.29 (m, 3H) 1.30-1.60 (m, 4H) 1.74 (d, J=7.93 Hz, 2H) 1.87 (br.s, 1H) 1.94-2.07 (m, 5H) 2.25-2.35 (m, 2H) 2.50-2.60 (m, 2H) 2.78-2.87 (m, 1H) 3.24 (s, 3H) 3.87 (s, 3H) 4.46-4.55 (m, 1H) 4.67 (br.s, 1H) 4.99 (br.s, 1H) 6.78 (s, 1H) 6.93 (d, J=2.44 Hz, 1H) 7.05 (dd, J=8.55, 2.75 Hz, 1H) 7.49 (d, J=8.55 Hz, 1H) 7.52 (dd, J=8.55, 1.53 Hz, 1H) 7.81 (d, J=1.53 Hz, 1H) 7.84 (d, J=8.55 Hz, 1H) 7.89 (s, 1H).

LC-MS retention time 1.42 min; 627 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. General Procedure for Amide Couplings on:

1H-pyrazole-4-carboxylic acid, 5-[10-[[(cyclobutylsulfonyl)amino]carbonyl]-13-cyclohexyl-3-methoxy-7H-indolo[2,1-a][2]benzazepin-6-yl]-1-methyl-

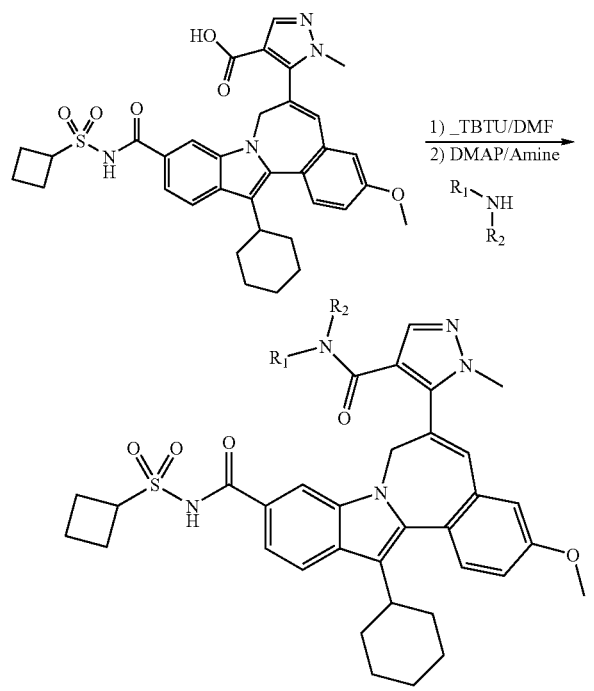

Into a 2 dram vial place 639 ul of a stock solution containing 1H-pyrazole-4-carboxylic acid, 5-[10-[[(cyclobutylsulfonyl)amino]carbonyl]-13-cyclohexyl-3-methoxy-7H-indolo[2,1-a][2]benzazepin-6-yl]-1-methyl- (0.639 mL, 0.072 mmol) and TBTU (0.639 mL, 0.138 mmol) which was premixed for 1.25 hr at room temperature. To the reaction mixture add 239 ul of a stock solution containing DMAP (0.239 mL, 0.358 mmol), then add the amine reagent (0.159 mmol). Cap the reaction under a nitrogen atmosphere and stir at room temperature overnight. The sample was purified on a Shimadzu high pressure liquid chromatography system employing Discovery VP software interfaced with a SCL-10A controller, SIL-10A autosampler and FRC-10A fraction collector. The sample was diluted to 2 ml (or 4 ml) using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes (or 25 minutes) using % A=10% acetonitrile, 90% water, 0.1% TFA % B=90% acetonitrile, 10% water, 0.1% TFA solvent system. Volatiles from the product fraction(s) are removed in vacuo using a speed vac overnight with heating.

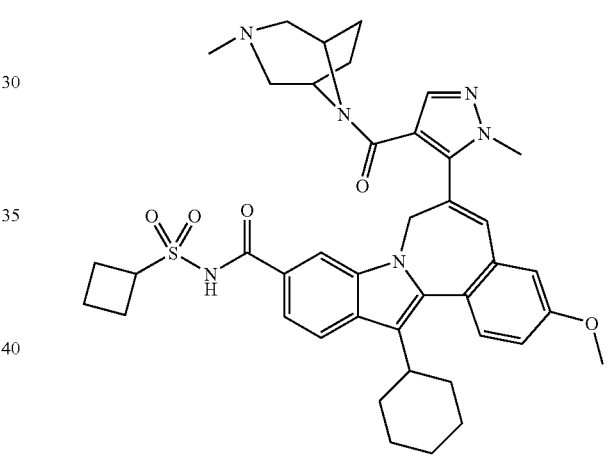

7H-indolo[2,1-a][2]benzazepine-10-carboxamide, N-(cyclobutylsulfonyl)-13-cyclohexyl-3-methoxy-6-[1-methyl-4-[(3-methyl-3,8-diazabicyclo[3.2.1]oct-8-yl)carbonyl]-1H-pyrazol-5-yl]-

1H NMR (500 MHz, CHLOROFORM-D) δ ppm 1.13-1.30 (m, 1H) 1.31-1.56 (m, 4H) 1.79 (d, J=10.68 Hz, 2H) 1.88-2.15 (m, 7H) 2.37 (s, 4H) 2.54 (s, 4H) 2.67 (d, J=9.16 Hz, 4H) 2.83-2.96 (m, 2H) 3.05-3.64 (m, 5H) 3.89 (s, 3H) 3.93 (s, 3H) 4.54-4.69 (m, 2H) 4.88 (s, 1H) 6.95 (t, J=2.14 Hz, 1H) 7.13 (dd, J=8.70, 2.59 Hz, 1H) 7.57 (d, J=8.55 Hz, 1H) 7.60 (d, J=6.71 Hz, 1H) 7.77 (s, 1H) 7.91 (d, J=8.24 Hz, 1H) 10.17 (s, 1H).

LC-MS retention time 1.55 min; 735 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

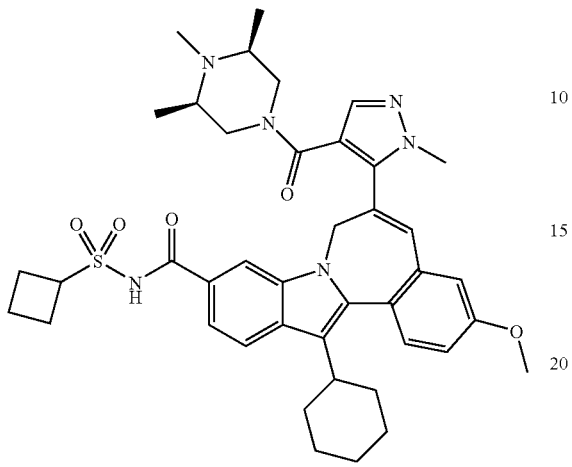

7H-indolo[2,1-a][2]benzazepine-10-carboxamide, N-(cyclobutylsulfonyl)-13-cyclohexyl-3-methoxy-6-[1-methyl-4-[[(3R,5S)-3,4,5-trimethyl-1-piperazinyl]carbonyl]-1H-pyrazol-5-yl]-

See procedure for general amide coupling. The sample was purified on a Shimadzu high pressure liquid chromatography system employing Discovery VP software interfaced with a SCL-10A controller, SIL-10A autosampler and FRC-10A fraction collector. The sample was solubilized by diluting to 2 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 90% solvent A/10% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. Retention time of product=8.3 minutes.

1H NMR (500 MHz, CHLOROFORM-D) d ppm 0.99-1.32 (m, 7H) 1.32-1.66 (m, 3H) 1.80 (d, J=8.55 Hz, 2H) 1.88-2.13 (m, 6H) 2.35 (s, 2H) 2.54 (s, 2H) 2.66 (s, 2H) 2.92 (s, 2H) 3.02-3.71 (m, 10H) 3.80 (s, 3H) 3.93 (s, 3H) 4.08 (s, 1H) 4.49-4.67 (m, 2H) 4.92 (d, J=12.21 Hz, 1H) 6.91 (s, 1H) 6.97 (d, J=2.44 Hz, 1H) 7.11 (dd, J=8.39, 2.29 Hz, 1H) 7.54 (d, J=8.54 Hz, 1H) 7.56-7.65 (m, 2H) 7.78 (s, 1H) 7.92 (d, J=8.55 Hz, 1H) 9.71 (s, 1H).

LC-MS retention time 1.49 min; 737 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

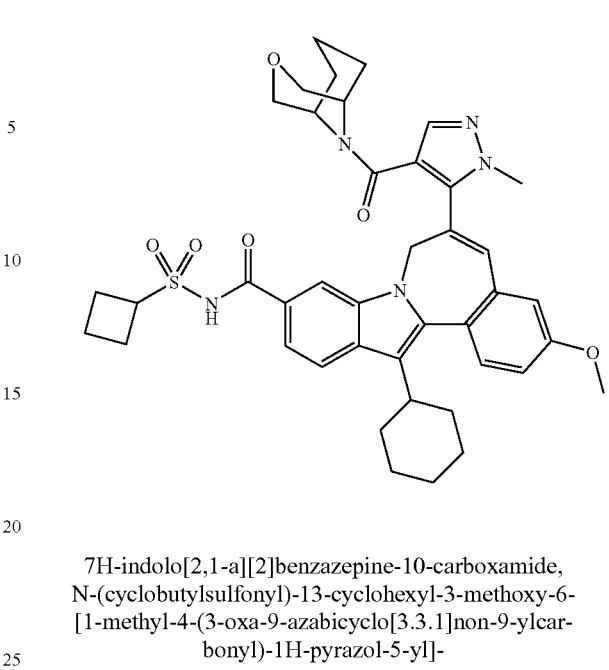

7H-indolo[2,1-a][2]benzazepine-10-carboxamide, N-(cyclobutylsulfonyl)-13-cyclohexyl-3-methoxy-6-[1-methyl-4-(3-oxa-9-azabicyclo[3.3.1]non-9-ylcarbonyl)-1H-pyrazol-5-yl]-

See procedure for general amide coupling.

Sample was diluted to 4 ml using acetonitrile. The sample needed more than 2 ml volume to completely solubilize in acetonitrile indicating lower solubility than previous run samples.

The sample was purified on a Shimadzu high pressure liquid chromatography system employing Discovery VP software interfaced with a SCL-10A controller, SIL-10A autosampler and FRC-10A fraction collector. The sample was diluted to 4 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. The purification was performed as two 2 ml injections. Retention time of product was 13.9 minutes.

Volatiles from the product fractions were removed in vacuo using a speed vac overnight with heating. Weight of isolated title compound was 38.6 mg.

1H NMR (500 MHz, CHLOROFORM-D) δ ppm 0.85 (m, 1H) 1.21 (m, 2H) 1.31-1.57 (m, 6H) 1.77 (d, J=8.24 Hz, 3H) 1.89-2.14 (m, 6H) 2.15-2.24 (m, 1H) 2.30 (d, J=11.29 Hz, 1H) 2.34-2.43 (m, 2H) 2.57-2.79 (m, 2H) 2.86 (t, J=10.53 Hz, 1H) 2.94-3.41 (m, 9H) 3.51 (d, J=14.65 Hz, 1H) 3.62 (d, J=10.68 Hz, 1H) 3.86 (s, 1H) 3.93 (s, 5H) 4.51-4.68 (m, 2H) 4.83-5.06 (m, 1H) 6.78-6.89 (m, 1H) 6.94 (d, J=2.44 Hz, 1H) 7.08-7.17 (m, 1H) 7.58 (d, J=8.54 Hz, 1H) 7.63 (d, J=7.93 Hz, 1H) 7.66-7.81 (m, 2H) 7.90 (t, J=9.16 Hz, 1H) 10.19 (s, 0.2H) 10.44 (s, 0.7H).

LC-MS retention time 1.62 min; 736 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min

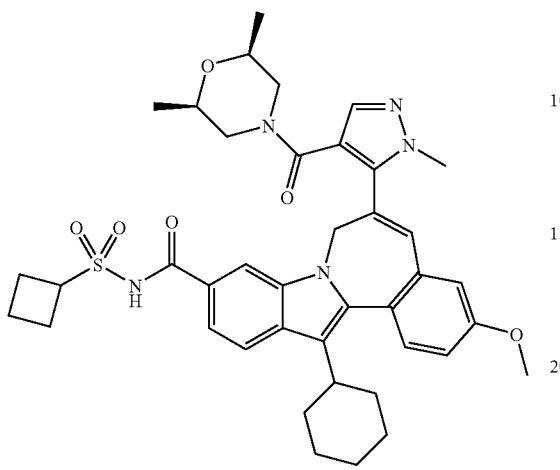

7H-indolo[2,1-a][2]benzazepine-10-carboxamide, N-(cyclobutylsulfonyl)-13-cyclohexyl-6-[4-[[(2R,6S)-2,6-dimethyl-4-morpholinyl]carbonyl]-1-methyl-1H-pyrazol-5-yl]-3-methoxy- See procedure for general amide coupling.

The sample was purified on a Shimadzu high pressure liquid chromatography system employing Discovery VP software interfaced with a SCL-10A controller, SIL-10A autosampler and FRC-10A fraction collector. The sample was diluted to 2 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. Retention time of product=13.5 minutes.

Volatiles from the product fractions were removed in vacuo using a speed vac overnight with heating.

1H NMR (500 MHz, CHLOROFORM-D) δ ppm 0.68 (br.s, 3H) 0.78 (m, 1H) 0.81-0.91 (m, 1H) 1.12-1.32 (m, 2H) 1.32-1.50 (m, 3H) 1.79 (d, J=11.29 Hz, 2H) 1.90-2.01 (m, 3H) 2.01-2.16 (m, 5H) 2.18-2.27 (m, 1H) 2.28-2.36 (m, 1H) 2.35-2.46 (m, 1H) 2.60-2.82 (m, 3H) 2.83-3.11 (m, 5H) 3.12-3.31 (m, 2H) 3.42 (s, 1H) 3.81-3.94 (m, 3H) 3.94 (s, 3H) 4.51-4.70 (m, 2H) 4.90 (d, J=14.34 Hz, 1H) 6.79-6.90 (m, 1H) 6.95 (d, J=1.83 Hz, 1H) 7.13 (dd, J=8.55, 2.14 Hz, 1H) 7.60 (dd, J=24.57, 8.39 Hz, 2H) 7.69 (d, J=16.48 Hz, 1H) 7.91 (d, J=8.24 Hz, 1H) 10.03 (s, 0.3H) 10.42 (s, 0.7H).

LC-MS retention time 1.85 min; 724 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 2 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

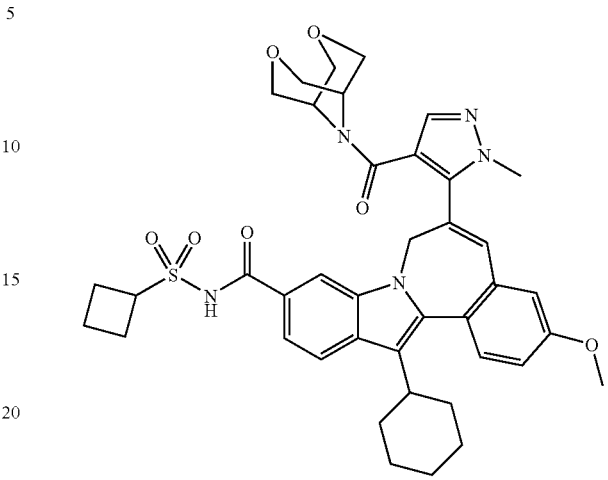

7H-indolo[2,1-a][2]benzazepine-10-carboxamide, N-(cyclobutylsulfonyl)-13-cyclohexyl-6-[4-(3,7-dioxa-9-azabicyclo[3.3.1]non-9-ylcarbonyl)-1-methyl-1H-pyrazol-5-yl]-3-methoxy- Into a 2 dram vial place 639 ul of a stock solution containing 1H-pyrazole-4-carboxylic acid, 5-[10-[[(cyclobutylsulfonyl)amino]carbonyl]-13-cyclohexyl-3-methoxy-7H-indolo[2,1-a][2]benzazepin-6-yl]-1-methyl- (0.639 mL, 0.072 mmol) and TBTU (0.639 mL, 0.138 mmol) which was premixed for 1.25 hr at room temperature. To the reaction mixture add 239 ul of a stock solution containing DMAP (0.239 mL, 0.358 mmol), then add the amine reagent 3,7-dioxa-9-azabicyclo[3.3.1]nonane hydrochloride (38.0 mg, 0.229 mmol). Cap the reaction under a nitrogen atmosphere and stir at room temperature. Analysis of the reaction mixture by LCMS indicated only a trace of product present. The reaction was allowed to sit capped at room temperature for 3 days then HATU (92 mg, 0.242 mmol). The reaction was capped and stirred at room temperature overnight. LCMS indicated a complete reaction. The reaction was allowed to stir at room temperature for 2 more days (weekend).

The sample was purified on a Shimadzu high pressure liquid chromatography system employing Discovery VP software interfaced with a SCL-10A controller, SIL-10A autosampler and FRC-10A fraction collector. The reaction was diluted to 2 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. The retention time of product was observed as split peaks at 10.72 min and 11.03 minutes. Volatiles from the product fractions were removed in vacuo using a speed vac overnight with heating.

1H NMR analysis of each product fraction provided identical NMR spectrums. The product fraction were combined and into a vial and dried in vacuo at room temperature to yield 34.5 mg (65%) of the title compound as a yellow amorphous solid.

1H NMR (500 MHz, CHLOROFORM-D) δ ppm 1.11-1.27 (m, 1H) 1.31-1.52 (m, 3H) 1.71-1.83 (m, J=8.85 Hz, 2H) 1.92-2.15 (m, 6H) 2.31 (s, 1H) 2.38 (s, 1H) 2.55-2.77 (m, 3H) 2.81-2.91 (m, 1H) 3.25 (s, 1H) 3.33 (d, J=9.46 Hz, 1H) 3.42 (s, 2H) 3.55 (d, J=10.07 Hz, 1H) 3.62-3.80 (m, 3H) 3.89 (s, 3H) 3.93 (s, 3H) 4.23 (s, 3H) 4.53-4.66 (m, 2H) 4.93 (d, J=15.26 Hz, 1H) 6.87 (s, 1H) 6.95 (d, J=2.44 Hz, 1H) 7.13 (dd, J=8.54, 2.75 Hz, 1H) 7.58 (d, J=8.55 Hz, 1H) 7.61 (d, J=8.55 Hz, 1H) 7.70 (s, 1H) 7.74 (s, 1H) 7.93 (d, J=8.54 Hz, 1H) 10.09 (s, 1H).

LC-MS retention time 1.50 min; 738 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

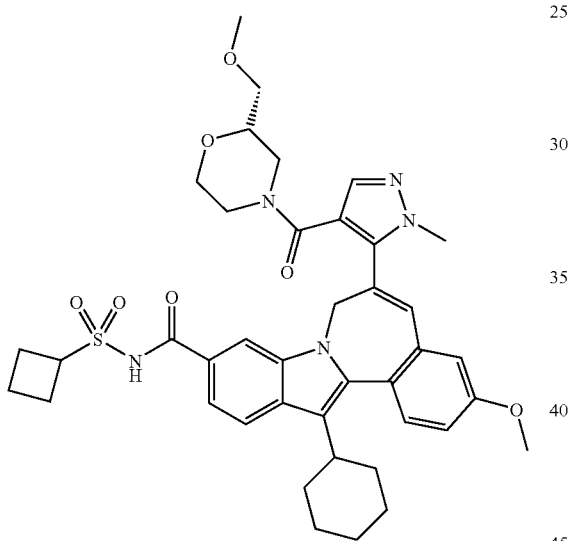

7H-indolo[2,1-a][2]benzazepine-10-carboxamide, N-(cyclobutylsulfonyl)-13-cyclohexyl-3-methoxy-6-[4-[[(2S)-2-(methoxymethyl)-4-morpholinyl]carbonyl]-1-methyl-1H-pyrazol-5-yl]-

Into a 2 dram vial place 787 ul of a stock solution containing 1H-pyrazole-4-carboxylic acid, 5-[10-[[(cyclobutylsulfonyl)amino]carbonyl]-13-cyclohexyl-3-methoxy-7H-indolo[2,1-a][2]benzazepin-6-yl]-1-methyl- (0.091M) (0.787 mL, 0.072 mmol) and TBTU (0.213M) (0.787 mL, 0.168 mmol) which was pre-mixed for 1.25 hr at room temperature. To the reaction mixture add DMAP (48.0 mg, 0.393 mmol), then add the amine reagent then add the amine reagent, in this case, (S)-2-(methoxymethyl)morpholine hydrochloride (30.4 mg, 0.181 mmol). Cap the reaction under a nitrogen atmosphere and stir at room temperature overnight. The reaction is diluted with acetonitrile and purified by reverse phase Prep HPLC.

1H NMR (500 MHz, CHLOROFORM-D) δ ppm 1.19 (m, 1H) 1.31-1.54 (m, 3H) 1.79 (d, J=10.38 Hz, 2H) 1.90-2.20 (m, 7H) 2.23-2.55 (m, 3H) 2.58-2.82 (m, 4H) 2.82-3.13 (m, 6H) 3.11-3.49 (m, 5H) 3.90 (s, 3H) 3.94 (s, 3H) 4.51-4.67 (m, 2H) 4.78-4.96 (m, 1H) 6.85 (s, 1H) 6.95 (s, 1H) 7.12 (dd, J=8.55, 2.44 Hz, 1H) 7.56 (d, J=8.55 Hz, 1H) 7.59 (d, J=7.63 Hz, 1H) 7.63-7.74 (m, 2H) 7.90 (t, J=9.00 Hz, 1H) 10.09 (s, 0.3H) 10.41 (s, 0.6H).

LC-MS retention time 1.62 min; 740 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 2 min, and an analysis time of 5 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The following examples can be prepared in an analogous fashion.

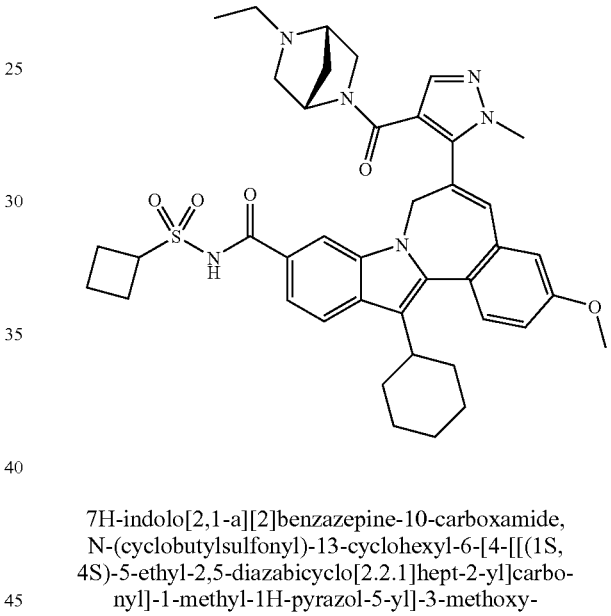

7H-indolo[2,1-a][2]benzazepine-10-carboxamide, N-(cyclobutylsulfonyl)-13-cyclohexyl-6-[4-[[(1S, 4S)-5-ethyl-2,5-diazabicyclo[2.2.1]hept-2-yl]carbonyl]-1-methyl-1H-pyrazol-5-yl]-3-methoxy- HPLC Method: The sample was purified on a Shimadzu high pressure liquid chromatography system employing Discovery VP software interfaced with a SCL-10A controller, SIL-10A autosampler and FRC-10A fraction collector. The reaction mixture was diluted to 2 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. The product retention time is 5.71 minutes. Volatiles from the product fractions were removed in vacuo using a speed vac with a medium heat setting.

The proton NMR of this sample exhibited characteristics of rotomers.

1H NMR (500 MHz, CHLOROFORM-D) δ ppm 0.49 (s, 0.3H) 0.96-1.29 (m, 2.2H) 1.30-1.59 (m, 3.3H) 1.79 (d, J=11.60 Hz, 1.8H) 1.86-2.17 (m, 3.8H) 2.19-2.46 (m, 2.1H)

2.49-3.74 (m, 6.4H) 3.76-4.21 (m, 5.1H) 4.24-4.39 (m, 0.8H) 4.43-4.70 (m, 1.4H) 4.73-5.07 (m, 1.0H) 5.23 (s, 0.1H) 6.73 (d, J=29.30 Hz, 0.4H) 6.88-7.00 (m, 0.8H) 7.04-7.13 (m, 0.7H) 7.44-7.60 (m, 0.9H) 7.58-7.96 (m, 2.0H) 8.19 (s, 0.1H) 10.43 (d, J=81.79 Hz, 0.4H) 11.20 (d, J=87.28 Hz, 0.5H) 12.46 (s, 0.6H).

LC-MS retention time 1.60 min; 737 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

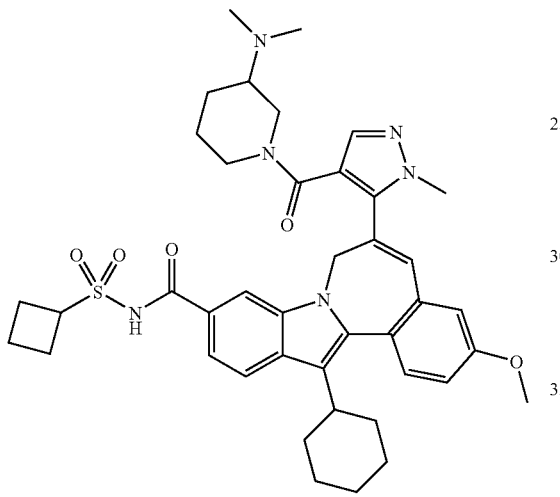

7H-indolo[2,1-a][2]benzazepine-10-carboxamide, N-(cyclobutylsulfonyl)-13-cyclohexyl-6-[4-[[3-(dimethylamino)-1-piperidinyl]carbonyl]-1-methyl-1H-pyrazol-5-yl]-3-methoxy- HPLC Method: The sample was purified on a Shimadzu high pressure liquid chromatography system employing Discovery VP software interfaced with a SCL-10A controller, SIL-10A autosampler and FRC-10A fraction collector. The reaction was diluted to 4 ml using acetonitrile with a very small amount of methanol and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. The retention time of product was 5.37 minutes. The compound was purified as two 2 ml injections.

Peaks in proton NMR spectra are generally broad, characteristic of restricted rotation in molecule.

1H NMR (500 MHz, CHLOROFORM-D) δ ppm 1.13-1.32 (m, 2H) 1.32-1.59 (m, 5H) 1.79 (s, 3H) 1.89-2.18 (m, 7H) 2.36 (s, 2H) 2.48-2.76 (m, 8H) 2.88 (s, 1H) 3.51 (s, 1H) 3.60-3.91 (m, 7H) 3.93 (s, 3H) 4.24 (s, 0.6H) 4.47-4.68 (m, 2H) 4.84 (d, J=13.43 Hz, 1H) 6.86-6.98 (m, 1H) 7.07-7.17 (m, 1H) 7.53 (d, J=8.55 Hz, 1H) 7.58-7.84 (m, 2H) 7.93 (d, J=7.93 Hz, 1H) 10.07 (s, 1H).

LC-MS retention time 1.56 min; 739 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

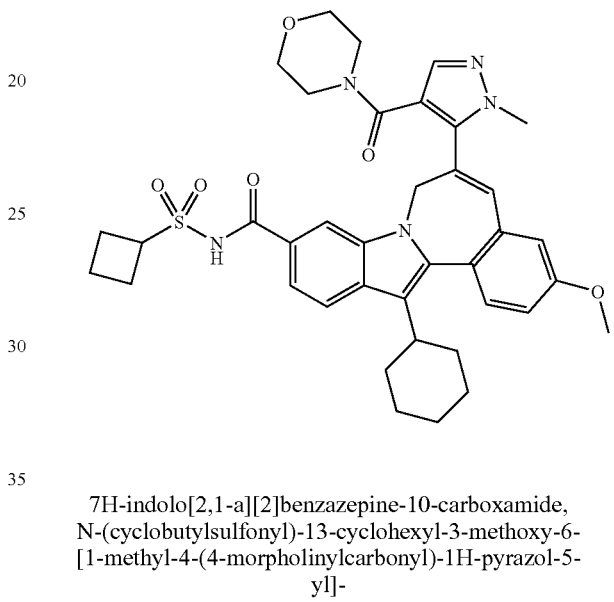

7H-indolo[2,1-a][2]benzazepine-10-carboxamide, N-(cyclobutylsulfonyl)-13-cyclohexyl-3-methoxy-6-[1-methyl-4-(4-morpholinylcarbonyl)-1H-pyrazol-5-yl]-

HPLC Method: The sample was purified on a Shimadzu high pressure liquid chromatography system employing Discovery VP software interfaced with a SCL-10A controller, SIL-10A autosampler and FRC-10A fraction collector. The reaction mixture was diluted to 4 ml using acetonitrile and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 50% solvent A/50% solvent B to 0% solvent A/100% solvent B, a gradient time of 15 minutes with a run time of 20 minutes using % A=10% acetonitrile, 90% water, 0.1% TFA % B=90% acetonitrile, 10% water, 0.1% TFA solvent system. The compound was purified as two 2 ml injections.

Volatiles from the product fractions were removed in vacuo using a speed vac overnight with heating. The product fractions were combined using dichloromethane and solvent removed in vacuo to give 35.4 mg (71%) of the title compound as a yellow amorphous solid.

1H NMR (500 MHz, CHLOROFORM-D) δ ppm 1.22 (m, 1H) 1.33-1.55 (m, 3H) 1.79 (d, J=10.68 Hz, 2H) 1.91-2.21 (m, 7H) 2.37 (d, J=29.60 Hz, 3H) 2.56-2.79 (m, 4H) 2.78-2.96 (m, 4H) 3.12 (s, 3H) 3.90 (s, 3H) 3.94 (s, 3H) 4.53-4.65 (m, 2H) 4.89 (d, J=14.95 Hz, 1H) 6.86 (s, 1H) 6.95 (d, J=2.44 Hz, 1H) 7.12 (dd, J=8.70, 2.59 Hz, 1H) 7.57 (d, J=8.85 Hz, 1H) 7.59 (d, J=8.55 Hz, 1H) 7.67 (s, 1H) 7.69 (s, 1H) 7.93 (d, J=8.54 Hz, 1H) 10.24 (s, 1H).

LCMS for 74814-024-a: LC-MS retention time 1.61 min; 696 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

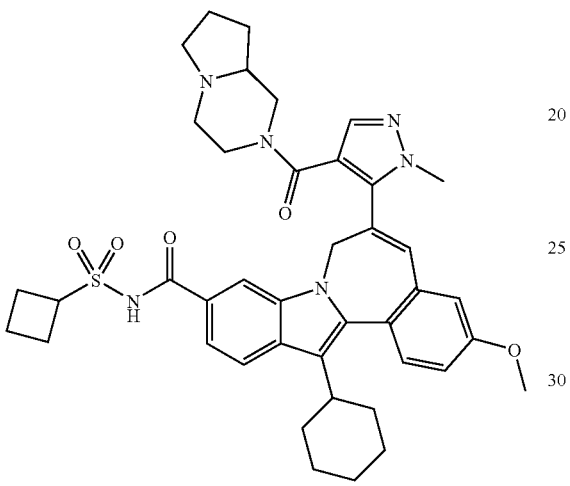

7H-indolo[2,1-a][2]benzazepine-10-carboxamide, N-(cyclobutylsulfonyl)-13-cyclohexyl-6-[4-[(hexahydropyrrolo[1,2-a]pyrazin-2(1H)-yl)carbonyl]-1-methyl-1H-pyrazol-5-yl]-3-methoxy- HPLC Method: The sample was purified on a Shimadzu high pressure liquid chromatography system employing Discovery VP software interfaced with a SCL-10A controller, SIL-10A autosampler and FRC-10A fraction collector. The reaction was diluted to 4 ml using acetonitrile and a trace of methanol and in purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. Retention time of product=5.72 minutes.

The compound was purified as two 2 ml injections. Volatiles were removed from the product fractions in vacuo overnight using a speed-vac set at medium heating.

1H NMR (500 MHz, CHLOROFORM-D) δ ppm 1.24 (s, 1H) 1.30-1.45 (m, 2H) 1.31-1.45 (m, 2H) 1.58 (none, 2H) 1.78 (s, 4H) 1.88-2.24 (m, 9H) 2.34 (s, 2H) 2.65 (s, 3H) 2.74-3.18 (m, 3H) 3.18-3.87 (m, 9H) 3.89-3.96 (m, 3H) 3.96-4.35 (m, 3H) 4.45-4.68 (m, 2H) 4.76-5.00 (m, 1H) 6.80-6.95 (m, 1H) 6.96 (s, 1H) 7.05-7.15 (m, J=8.24 Hz, 1H) 7.47-7.68 (m, 3H) 7.68-7.81 (m, 1H) 7.88 (s, 1H) 9.94 (s, 1H) 12.54 (s, 1H).

LC-MS retention time 1.61 min; 735 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

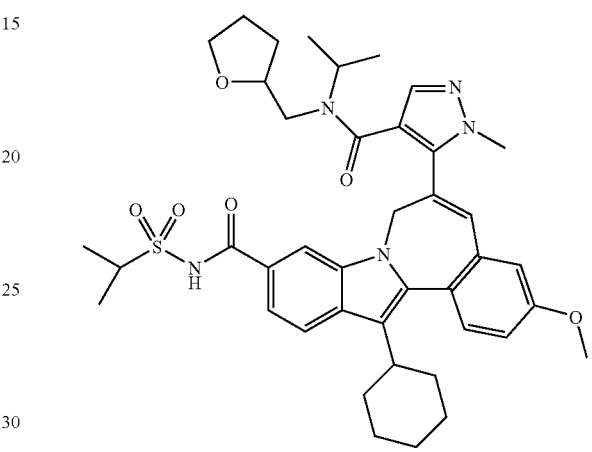

7H-indolo[2,1-a][2]benzazepine-10-carboxamide, 13-cyclohexyl-3-methoxy-N-[(1-methylethyl)sulfonyl]-6-[1-methyl-4-[[(1-methylethyl)[(tetrahydro-2-furanyl)methyl]amino]carbonyl]-1H-pyrazol-5-yl]-

In a 2 dram vial, 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (51.1 mg, 0.083 mmol) was dissolved in DMF (829 μl) and HATU (66.3 mg, 0.174 mmol) was added to the reaction. The reaction was stirred under a nitrogen atmosphere for 1.2 hours at room temperature. DMAP (41.5 mg, 0.340 mmol) was added to the reaction and stirred until dissolved then the amine reagent, Isopropyl-(tetrahydro-furan-2-ylmethyl)-amine (36 μl, 0.251 mmol), was added and the reaction capped under nitrogen and stirred at room temperature for 17 hours. Note-assume density of amine reagent is 1 g/cc, important aspect is not exact stoichiometry but excess amine present. The product was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (2 ml) and purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 15 minutes with a run time of 25 minutes using % A=10% acetonitrile, 90% water, 0.1% TFA % B=90% acetonitrile, 10% water, 0.1% TFA solvent system. Retention time of product is 13.3 minutes. Take product fraction and remove volatiles in vacuo using a rotary evaporator. The title compound was isolated (47.4 mg, 77%) as an amorphous yellow solid. Proton NMR spectra exhibits characteristics of restricted rotation (broad and rotomeric peaks).

1H NMR (500 MHz, CHLOROFORM-D) d ppm 0.61 (s, 1.6H) 0.80-1.11 (m, 5.1H) 1.23 (s, 2.7H) 1.31-1.57 (m, 10.7H) 1.76 (s, 4.0H) 1.87-2.13 (m, 5.9H) 2.20 (s, 2.4H) 2.38-2.75 (m, 0.7H) 2.78-2.92 (m, 1.2H) 3.06-3.25 (m, 1.3H) 3.37-3.82 (m, 6.9H) 3.91 (s, 3.9H) 3.97-4.27 (m, 2.0H) 4.56 (d, J=12.82 Hz, 0.9H) 4.93-5.23 (m, 0.9H) 6.87 (s, 1.0H) 6.94 (d, J=2.44 Hz, 1.0H) 7.07 (d, J=7.93 Hz, 1.0H) 7.51 (d, J=7.93 Hz, 1.1H) 7.57 (s, 2.2H) 7.81-8.01 (m, 2.1H) 9.48-9.81 (m, 0.6H) 9.98 (s, 0.5H).

LC-MS retention time 1.76 min; 740 m/z (MH−). LC data was recorded on a Shimadzu LC-10AS liquid chromatograph equipped with a Waters Xterra MS 7u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

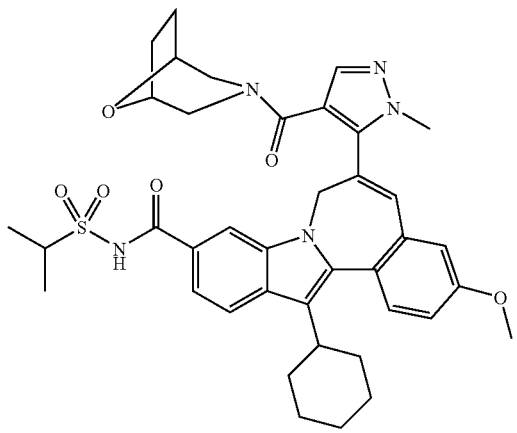

7H-indolo[2,1-a][2]benzazepine-10-carboxamide, 13-cyclohexyl-3-methoxy-N-[(1-methylethyl)sulfonyl]-6-[1-methyl-4-(8-oxa-3-azabicyclo[3.2.1]oct-3-ylcarbonyl)-1H-pyrazol-5-yl]-

In a 2 dram vial, 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-methyl- (50.8 mg, 0.082 mmol) was dissolved in DMF (824 μL) and HATU (72.2 mg, 0.190 mmol) was added and the reaction stirred under a nitrogen atmosphere for 1 hour at room temperature. DMAP (41.8 mg, 0.342 mmol) was added to the reaction and stirred until dissolved then the amine reagent, 8-oxa-3-azabicyclo[3.2.1]octane hydrochloride (30.6 mg, 0.205 mmol). The reaction capped under nitrogen and stirred at room temperature overnight. The product was purified on a Shimadzu high pressure liquid chromatography system employing Discovery VP software interfaced with a SCL-10A controller, SIL-10A autosampler and FRC-10A fraction collector. The reaction was acidified with aqueous acetic acid then diluted to 2 ml with acetonitrile and filtered using a 0.45 uM syringe filter. The filtrate was purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 25 minutes using % A=10% acetonitrile, 90% water, 0.1% TFA % B=90% acetonitrile, 10% water, 0.1% TFA solvent system. The product was collected as a single fraction from 13.99 to 14.70 minutes. Volatiles from the product fraction were removed in vacuo using a speed vac at medium heat setting.

The title compound was isolated (46.0 mg, 78% yield) as a yellow amorphous solid.

1H NMR (500 MHz, CHLOROFORM-D) δ ppm 0.26-1.05 (m, 1.2H) 1.14-1.32 (m, 1.9H) 1.33-1.45 (m, 2.3H) 1.49 (dd, J=14.04, 6.71 Hz, 7.1H) 1.53-1.72 (m, 3.4H) 1.79 (d, J=9.77 Hz, 2.2H) 1.97 (d, J=10.99 Hz, 1.2H) 2.02-2.15 (m, 3.1H) 2.27 (d, J=11.29 Hz, 0.7H) 2.86 (t, J=11.60 Hz, 1.6H) 3.02 (d, J=8.85 Hz, 1.5H) 3.16 (s, 3.9H) 3.32 (d, J=11.60 Hz, 1.1H) 3.73-3.87 (m, 2.1H) 3.90 (s, 2.8H) 3.92-3.97 (m, 3.4H) 4.00-4.11 (m, 1.4H) 4.59 (d, J=15.26 Hz, 1.0H) 4.86 (d, J=14.34 Hz, 0.8H) 5.04 (s, 0.3H) 6.86 (s, 1.0H) 6.95 (s, 1.0H) 7.11 (dd, J=8.55, 2.44 Hz, 1.0H) 7.54 (d, J=8.85 Hz, 1.2H) 7.57-7.77 (m, 2.7H) 7.80-8.02 (m, 1.3H) 9.74 (s, 0.2H) 10.11 (s, 0.7H).

LC-MS retention time 1.61 min; 710 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

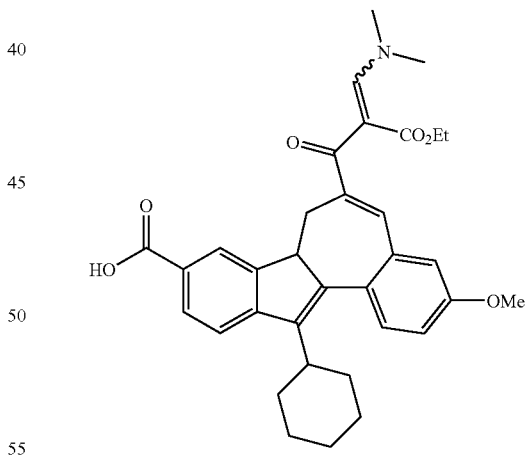

13-cyclohexyl-6-((2E,Z)-3-(dimethylamino)-2-(ethoxycarbonyl)-2-propenoyl)-3-methoxy-7H-indolo[2,1-a][2]benzazepine-10-carboxylic acid In a 50 ml round bottom flask dissolve tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (538 mg, 0.879 mmol) in 1,2-dichloroethane (5 mL) then add TFA (5 mL). The reaction mixture turned a darker reddish color upon addition of TFA. Place the reaction under a nitrogen atmosphere and stir at room temperature for 2.25 hrs. Remove volatiles in vacuo using a rotary evaporator, dissolve oily red residue in dichloromethane/benzene and remove volatiles in vacuo on rotary evaporator. Take resulting red oil dissolve in ethyl acetate wash with 1.0N aqueous hydrochloric acid. The aqueous layer was back extracted with ethyl acetate. The organic layers were combined and sequentially washed with 1.0N aqueous hydrochloric acid and brine. The organic layer was dried over MgSO4, filtered and the solvents removed in vacuo to give a reddish-orange oil which was dissolved in benzene and volatiles removed in vacuo to yield 519 mg of the title compound a red-orange foam. The compound was used without further purification.

LC-MS retention time 1.86 min; 555 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

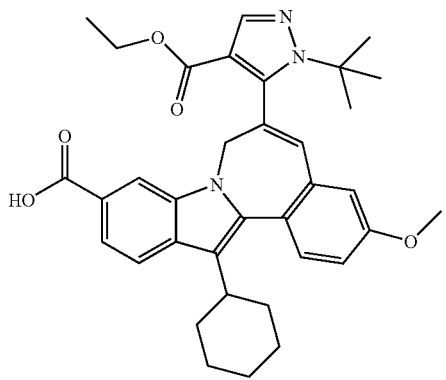

7H-indolo[2,1-a][2]benzazepine-10-carboxylic acid, 13-cyclohexyl-6-[1-(1,1-dimethylethyl)-4-(ethoxycarbonyl)-1H-pyrazol-5-yl]-3-methoxy- 7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy- (101 mg, 0.181 mmol) was dissolved in ethanol (726 μL) and dioxane (181 μL). Triethyl amine (59 μL, 0.423 mmol) was added to the reaction followed by the hydrazine reagent, tert-butylhydrazine hydrochloride (23.6 mg, 0.189 mmol). The reaction was capped under a nitrogen atmosphere and heated in a microwave to 160 C for 45 minutes. The reaction was concentrated in vacuo using a rotary evaporator and the residue was dissolved in ethyl acetate and washed sequentially with 1.0N aqueous hydrochloric acid then brine. The organic layer was dried over magnesium sulfate, filtered and volatiles removed in vacuo to give 91 mg of a yellow amorphous solid. The product was purified on a Shimadzu high pressure liquid chromatography system employing Discovery VP software interfaced with a SCL-10A controller, SIL-10A autosampler and FRC-10A fraction collector. The sample was dissolved in acetonitrile/DMF mixture purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system.

The above isomeric major product retention time was 18.54 minutes. The minor region-isomeric alkylated pyrazole was collected with retention time of 20.54 minutes.

The volatiles were removed from product fractions in vacuo to obtain 29.8 mg of the title compound as a yellow amorphous solid.

1H NMR (500 MHz, CHLOROFORM-D) δ ppm 1.09 (s, 9H) 1.18-1.56 (m, 8H) 1.63 (d, 1H) 1.78 (d, J=8.55 Hz, 2H) 1.88-2.22 (m, 5H) 2.89 (t, J=11.75 Hz, 1H) 3.89 (s, 3H) 4.27 (s, 2H) 4.84 (d, J=14.65 Hz, 1H) 4.96 (d, J=14.95 Hz, 1H) 6.81 (s, 1H) 6.90 (d, J=2.14 Hz, 1H) 7.05 (dd, J=8.70, 2.59 Hz, 1H) 7.52 (d, J=8.54 Hz, 1H) 7.76 (dd, J=8.55, 1.22 Hz, 1H) 7.88 (d, J=8.55 Hz, 1H) 7.92 (s, 1H) 8.01 (s, 1H).

LC-MS retention time 2.20 min; 580 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

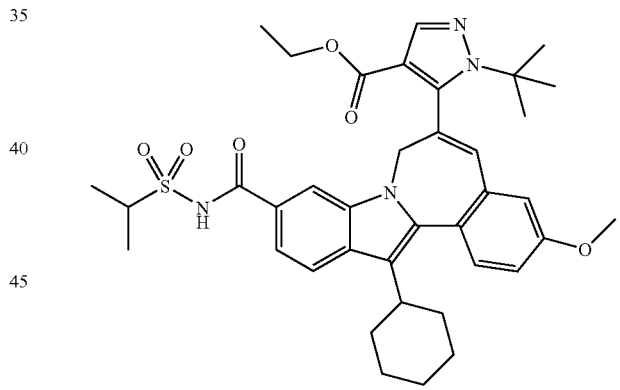

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1,1-dimethylethyl)-, ethyl ester In a 2 dram vial, 7H-indolo[2,1-a][2]benzazepine-10-carboxylic acid, 13-cyclohexyl-6-[1-(1,1-dimethylethyl)-4-(ethoxycarbonyl)-1H-pyrazol-5-yl]-3-methoxy- (139 mg, 0.239 mmol) was dissolved in dichloromethane (2.4 ml) and propane-2-sulfonamide (98 mg, 0.796 mmol) and DMAP (90 mg, 0.737 mmol) were added to the reaction followed by EDC (70.3 mg, 0.367 mmol). The reaction was capped under a nitrogen atmosphere and stirred at room temperature for 18 hrs. The reaction was monitored by HPLC then allowed to continue stirring under a nitrogen atmosphere at room temperature for 24 hrs.

Subsequent HPLC analysis revealed no discernable change in reaction composition over the last 24 hrs. Volatiles were removed from the reaction in vacuo using a rotary evaporator and the reaction residue was diluted with ethyl acetate and washed sequentially with 1.0N aqueous hydrochloric acid, 0.1M aqueous NaH2PO4 and 1.0N aqueous hydrochloric acid then brine. The organic phase was dried over MgSO4, filtered and solvent removed in vacuo. The product was dried in vacuo at room temperature to give 165 mg of product as an amorphous yellow solid. The product was used without any further purification.

LC-MS retention time 2.03 min; 685 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

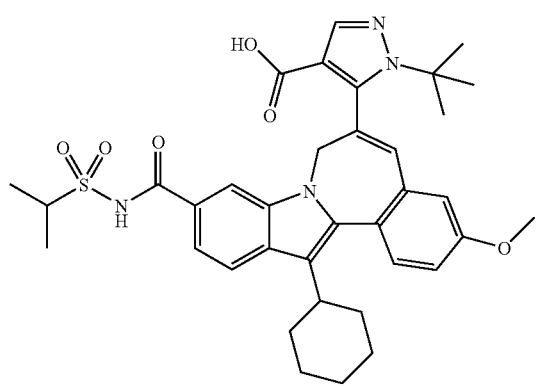

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1,1-dimethylethyl)-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1,1-dimethylethyl)-, ethyl ester (164 mg, 0.239 mmol) was dissolved in THF (3 mL) and methanol (3.00 mL) then 1.0 N aqueous sodium hydroxide (3.00 mL) was added to the reaction and the reaction was placed under a nitrogen atmosphere and stirred at room temperature for 25 hrs. The reaction was concentrated in vacuo using a rotary evaporator without heating then partitioned between ethyl acetate and 1.0N aqueous hydrochloric acid. Wash ethyl acetate with 1N aqueous hydrochloric acid, combine aqueous layers and back extract with ethyl acetate. The organic layers were combined and wash with brine, dry over magnesium sulfate and solvent removed in vacuo using a rotary evaporator. The product was dried in vacuo at room temperature to give 158.4 mg as a yellow amorphous solid. The product was carried on without any further purification.

LC-MS retention time 1.54 min; 657 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

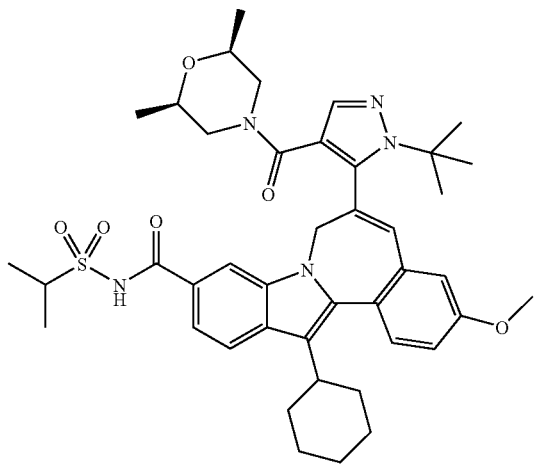

7H-indolo[2,1-a][2]benzazepine-10-carboxamide, 13-cyclohexyl-6-[1-(1,1-dimethylethyl)-4-[[(2R,6S)-2,6-dimethyl-4-morpholinyl]carbonyl]-1H-pyrazol-5-yl]-3-methoxy-N-[(1-methylethyl)sulfonyl]-

1H-pyrazole-4carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1,1-dimethylethyl)- (60 mg, 0.091 mmol) was dissolved in DMF (911 μL). HATU (81.5 mg, 0.214 mmol) was added to the reaction and the reaction was capped under a nitrogen atmosphere and stir at room temperature for 1.25 hrs. DMAP (45.9 mg, 0.376 mmol) was added to reaction followed by amine reagent, (2R,6S)-2,6-dimethylmorpholine (34 μL, 0.275 mmol). The reaction was capped under a nitrogen atmosphere and stir at room temperature for 18 hr. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile and a couple of drops of aqueous acetic acid then purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. Retention time of product was 18.5 minutes. Product fractions were combined and volatiles removed in vacuo using a rotary evaporator. The sample was dried in vacuo at room temperature to give 32.5 mg as a yellow amorphous film. 1H NMR results are characteristic of restricted rotation with broadening and splitting of peaks.

1H NMR (500 MHz, CHLOROFORM-D) δ ppm 0.66 (d, J=6.10 Hz, 2.4H) 0.71 (d, J=6.10 Hz, 2.3H) 0.78 (dd, J=11.29, 6.10 Hz, 1.8H) 1.10 (s, 1.2H) 1.25 (dd, J=13.73, 6.71 Hz, 3.0H) 1.35-1.44 (m, 2.5H) 1.46 (t, J=7.02 Hz, 4.7H) 1.54 (d, J=6.71 Hz, 3.7H) 1.67 (s, 0.6H) 1.71 (s, 6.8H) 1.72-1.75 (m, 2.7H) 1.79 (d, J=11.90 Hz, 2.5H) 1.83-1.92 (m, 1.0H) 1.98 (d, J=12.51 Hz, 2.2H) 2.02-2.21 (m, 7.9H) 2.21-2.30 (m, 1.4H) 2.80-2.95 (m, 2.3H) 3.04 (d, J=42.42 Hz, 0.6H) 3.23 (d, J=13.73 Hz, 0.3H) 3.34 (d, J=12.82 Hz, 0.8H) 3.92 (d, J=4.88 Hz, 0.5H) 3.95 (s, 3.0H) 4.04-4.13 (m, 1.1H) 4.49-4.58 (m, 1.0H) 4.79 (d, J=14.65 Hz, 0.3H) 4.86 (d, J=15.26 Hz, 0.7H) 6.78 (s, 0.8H) 6.85 (s, 0.3H) 6.87 (d, J=2.75 Hz, 0.8H) 6.91 (s, 0.3H) 7.14 (dd, J=8.55, 2.44 Hz, 1.0H) 7.55-7.60 (m, 0.9H) 7.60-7.64 (m, 2.3H) 7.64-7.68 (m, 1.0H) 7.83-7.95 (m, 1.3H) 10.32 (s, 0.3H) 10.60 (s, 0.7H).

LC-MS retention time 2.10 min; 754 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

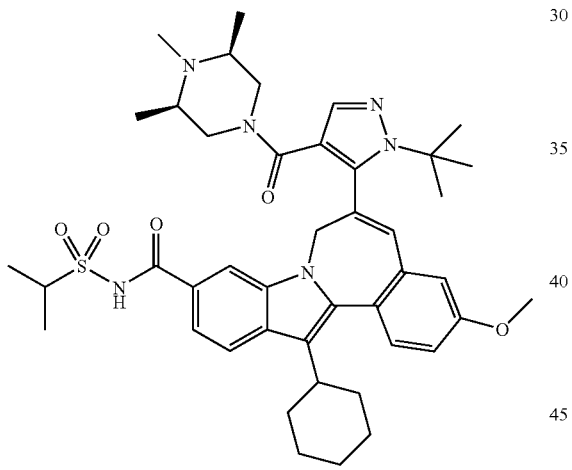

7H-indolo[2,1-a][2]benzazepine-10-carboxamide, 13-cyclohexyl-6-[1-(1,1-dimethylethyl)-4-[[(3R,5S)-3,4,5-trimethyl-1-piperazinyl]carbonyl]-1H-pyrazol-5-yl]-3-methoxy-N-[(1-methylethyl)sulfonyl]-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-(1,1-dimethylethyl)- (48.8 mg, 0.074 mmol) was dissolved in DMF (741 μL). HATU (65.3 mg, 0.172 mmol) was added to the reaction and the reaction was capped under a nitrogen atmosphere and stir at room temperature for 1 hrs. DMAP (53.8 mg, 0.440 mmol) was added to reaction followed by amine reagent, (2R,6S)-1,2,6-trimethylpiperazine dihydrochloride (34.5 mg, 0.172 mmol). The reaction was capped under a nitrogen atmosphere and stir at room temperature for 18 hr. The product was purified on a Shimadzu high pressure liquid chromatography system employing Discovery VP software interfaced with a SCL-10A controller, SIL-10A autosampler and FRC-10A fraction collector. The reaction was acidified with a few drops of aqueous acetic acid and diluted to 2 ml with acetonitrile then purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 25 minutes using % A=10% acetonitrile, 90% water, 0.1% TFA % B=90% acetonitrile, 10% water, 0.1% TFA solvent system. Product was collected from 8.14 minutes to 9.45 minutes. Volatiles were removed in vacuo from the combined product fractions to ultimately yield 11.1 mg of the title compound as a yellow amorphous film.

1H NMR (500 MHz, CHLOROFORM-D) δ ppm 0.93-1.34 (m, 9.7H) 1.37-1.52 (m, 9.5H) 1.56-1.68 (m, 1.6H) 1.68-1.83 (m, 9.2H) 1.87-2.20 (m, 5.4H) 2.28-2.52 (m, 2.0H) 2.55-3.01 (m, 9.4H) 3.19 (d, J=40.59 Hz, 0.8H) 3.63 (d, J=134.28 Hz, 2.4H) 3.83-4.04 (m, 4.0H) 4.54 (d, J=14.65 Hz, 0.8H) 4.76 (d, J=14.34 Hz, 0.8H) 6.72-6.97 (m, 2.0H) 7.08 (d, J=7.32 Hz, 1.0H) 7.36-7.76 (m, 3.4H) 7.88 (s, 1.2H) 10.86 (s, 0.5H) 11.26 (s, 0.4H).

LC-MS retention time 1.81 min; 767 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

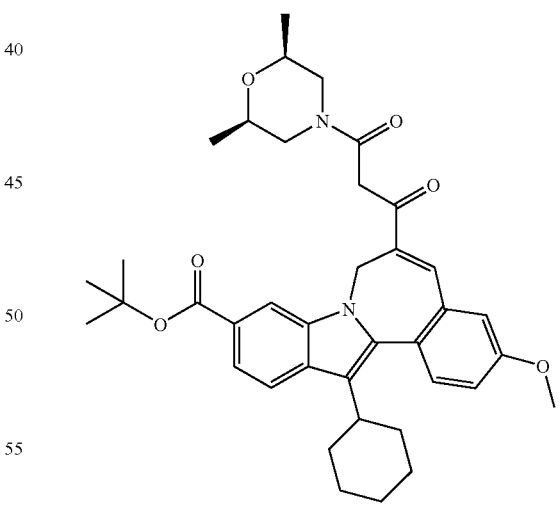

7H-indolo[2,1-a][2]benzazepine-10-carboxylic acid, 13-cyclohexyl-6-[3-[(2R,6S)-2,6-dimethyl-4-morpholinyl]-1,3-dioxopropyl]-3-methoxy-, 1,1-dimethylethyl ester In a 250 ml round bottom flask dissolve tert-butyl 13-cyclohexyl-6-(3-ethoxy-3-oxopropanoyl)-3-methoxy-7H-indolo[2,1-a][2]benzazepine-10-carboxylate (3.13 g, 5.61 mmol) in toluene (56 mL) and add cis-2,6-Dimethylmorpholine (2.6 mL, 20.99 mmol) to the reaction. Place reaction under a nitrogen atmosphere and heat to reflux for 9 hours. The reaction was partitioned between ethyl acetate and 1.0M aqueous citric acid. The organic layer was washed sequentially with 1.0M aqueous citric acid, 0.1M NaH2PO4, and brine. Dry organic phase over magnesium sulfate, filter and remove solvent in vacuo to give 3.01 g of crude product as a orange-amber foam. Dissolve the crude product in dichloromethane and adsorb onto 8.2 g of silica gel. Chromatograph crude product on 90 g of silica gel slurry packed in 5% ethyl acetate in dichloromethane, elute with gradient of 5% ethyl acetate in dichloromethane to 10% ethyl acetate in dichloromethane. Pure product fractions were combined and solvent removed in vacuo using a rotary evaporator to yield a yellow amorphous solid which was further dried in vacuo at room temperature to yield 1.28 g of the title compound. Less pure fractions yielded another 0.48 g of product. LCMS analysis gave two peaks of equivalent mass to that of the desired product. Resolution of the two peaks by Prep HPLC under the following conditions yielded peaks which interconverted when analyzed after isolation: Shimadzu high pressure liquid chromatography system employing Discovery VP software interfaced with a SCL-10A controller, SIL-10A autosampler and FRC-10A fraction collector. The sample 76816-035-a (63 mg) was dissolved in acetonitrile/DMF mixture (2:1, 2 ml) purified using a Phenonmenex Luna C18 30×100 mm 10u column and monitored using a SPD-10AV UV-Vis detector at a detector wave length of 220 nM. The elution conditions employed a flow rate of 40 mL/min, a gradient of 60% solvent A/40% solvent B to 0% solvent A/100% solvent B, a gradient time of 15 minutes with a run time of 25 minutes using % A=10 mM Ammonium Acetate in 95:5 Water/Acetonitrile % B=10 mM Ammonium Acetate in 5:95 Water/Acetonitrile solvent system. Two peaks were isolated from the sample: First peak at RT=16.3 minutes. Both samples exhibited identical HPLC spectra after isolation indicating inter-conversion.

1H NMR (500 MHz, CHLOROFORM-D) δ ppm 0.89 (s, 2.0H) 1.01 (s, 3.3H) 1.19 (d, J=26.25 Hz, 3.5H) 1.30-1.47 (m, 4.5H) 1.55 (s, 4.2H) 1.60 (s, 3.6H) 1.63 (s, 9.0H) 1.76 (d, J=8.24 Hz, 3.1H) 1.93 (d, J=9.46 Hz, 1.9H) 1.98-2.15 (m, 4.2H) 2.23 (s, 1.2H) 2.39 (s, 0.4H) 2.56-2.72 (m, 1.6H) 2.74-2.86 (m, 1.6H) 2.91 (s, 0.8H) 3.47-3.65 (m, 2.8H) 3.74-3.85 (m, 1.6H) 3.90 (s, 1.4H) 3.91 (s, 3.1H) 3.93-4.04 (m, 1.8H) 4.19 (d, J=12.82 Hz, 0.5H) 4.26 (d, J=14.65 Hz, 0.5H) 4.39 (s, 0.5H) 4.47 (d, J=11.29 Hz, 0.4H) 5.18 (s, 0.3H) 5.71-5.92 (m, 1.1H) 7.01 (d, J=2.75 Hz, 0.4H) 7.03-7.06 (m, 1.4H) 7.11 (dd, J=8.70, 2.59 Hz, 1.0H) 7.47-7.51 (m, 0.9H) 7.52 (s, 0.5H) 7.57 (s, 0.4H) 7.65 (d, J=1.53 Hz, 0.2H) 7.68 (dd, J=8.55, 1.22 Hz, 1.2H) 7.80 (s, 0.6H) 7.80-7.82 (m, 0.7H) 7.84 (s, 0.2H) 7.91 (s, 0.4H) 8.04 (s, 0.5H) 8.19 (s, 0.3H) 8.21 (d, J=1.22 Hz, 1.0H) 15.15 (d, J=23.80 Hz, 0.4H).

LC-MS retention time 4.21 min (88%); 625 m/z (MH−) and 5.23 min (12%); 625 m/z (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 5 min, a hold time of 2 min, and an analysis time of 7 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray.

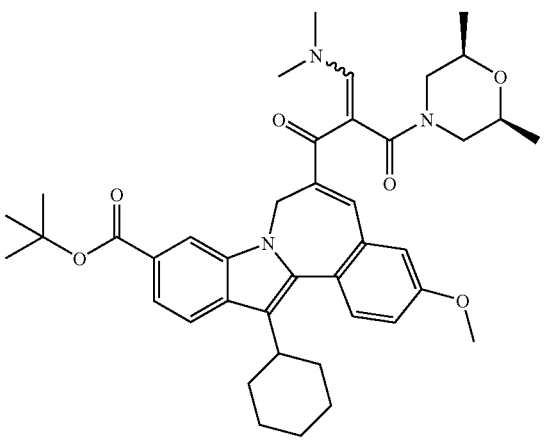

7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-, 1,1-dimethylethyl ester 7H-indolo[2,1-a][2]benzazepine-10-carboxylic acid, 13-cyclohexyl-6-[3-[(2R,6S)-2,6-dimethyl-4-morpholinyl]-1,3-dioxopropyl]-3-methoxy-, 1,1-dimethylethyl ester was dissolved in N,N-Dimethylformamide dimethyl acetal (10 mL,). The reaction was fitted with a condenser and placed under a nitrogen atmosphere. The reaction was heated to reflux for 3 hrs, cooled then the volatiles were removed in vacuo using a rotary evaporator, then dry in vacuo at room temperature to obtain the product as an amorphous orange solid (517 mg, 86%).

LC-MS retention time 4.60 min; 682 m/z (MH+). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode. The intermediate was used without further purification.

191

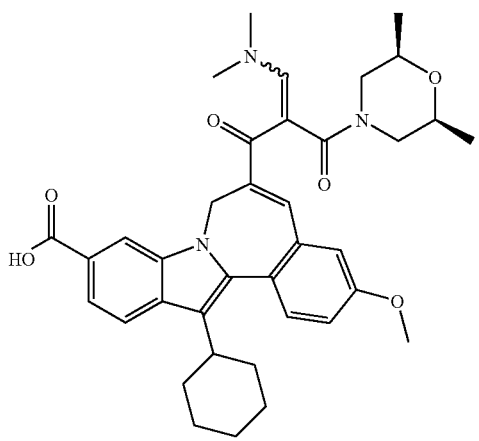

7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy- 7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-, 1,1-dimethylethyl ester was dissolved in 1,2-dichloroethane (5 mL) and TFA (5 mL) was added to the reaction. The reaction was placed under a nitrogen atmosphere and stirred for 2.5 hrs. Volatiles were removed in vacuo from the reaction using a rotary evaporator to give a reddish oil. The product was dissolved in benzene/dichloromethane and the volatiles again removed in vacuo to give a red foam. The product was dissolved in ethyl acetate and washed with 1.0N aqueous hydrochloric acid. The aqueous layer was back extracted with ethyl acetate. The organic extracts were combined, washed with brine and dried over magnesium sulfate. The organic solution was filtered and the volatiles removed in vacuo using a rotary evaporator to give a amber-orange foam. The product was dried in vacuo at room temperature to give 388 mg of amorphous amber-orange solid.

LC-MS retention time 2.83 min; 624 m/z (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

192

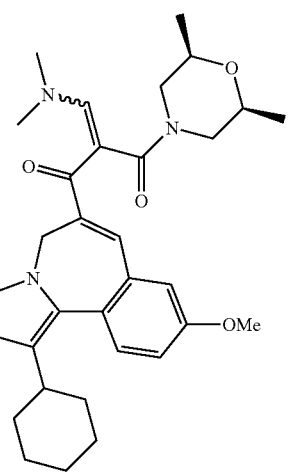

7H-indolo[2,1-a][2]benzazepine-10-carboxamide, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-N-[(1-methylethyl)sulfonyl]-

In a 25 ml rb flask, dissolve 7H-indolo[2,1-a][2]benzazepine-10-carboxylic acid, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy- (385 mg, 0.616 mmol) in dichloromethane (6.2 mL), add propane-2-sulfonamide (233 mg, 1.892 mmol) and DMAP (230 mg, 1.880 mmol) to the reaction followed by EDC (177 mg, 0.924 mmol). The reaction was placed under a nitrogen atmosphere and stirred at room temperature for 18.5 hrs. The reaction was diluted with ethyl acetate and washed with 1.0N aqueous hydrochloric acid. The aqueous phases were combined and back extracted with ethyl acetate. The organic layers were combined and sequentially washed with 1.0N aqueous hydrochloric acid and brine. The organic solution was dried over magnesium sulfate, filtered and the solvent removed in vacuo using a rotary evaporator to give an amorphous orange solid/foam which was dried in vacuo to give 415 mg of crude product.

LC-MS retention time 3.00 min; 729 m/z (MH−). LC data was recorded on a Shimadzu LC-10AS liquid chromatograph equipped with a Phenomenex-Luna 10u C18 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 5 min, a hold time of 2 min, and an analysis time of 7 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The crude product was used without any further purification in subsequent pyrazole synthesis.

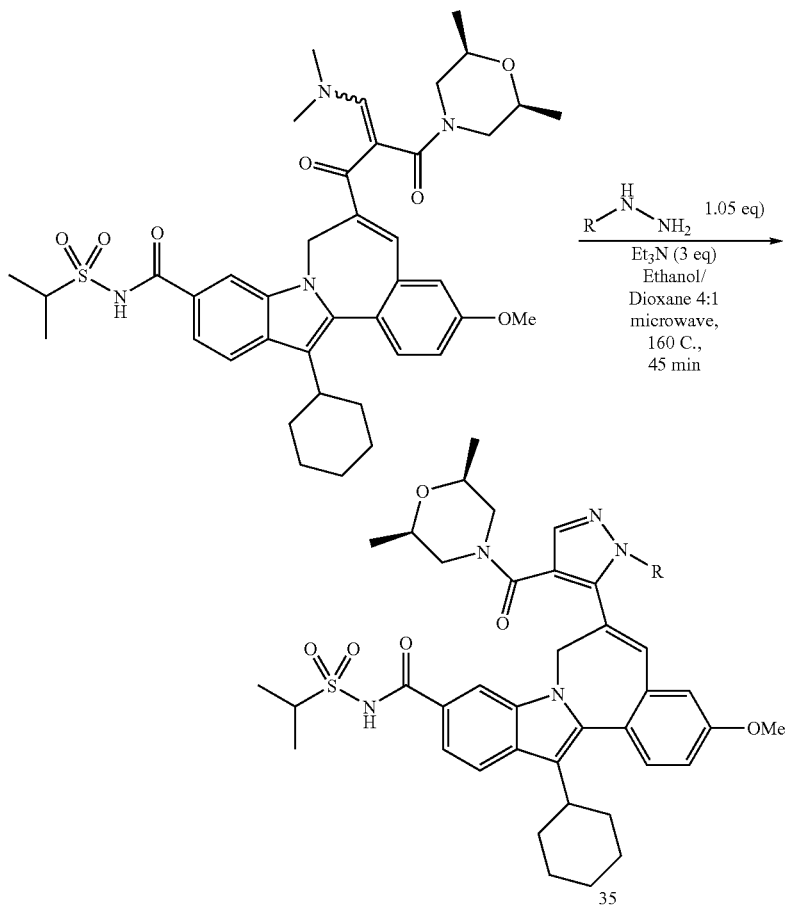

The following analog can be prepared using the general methodology described below.

7H-indolo[2,1-a][2]benzazepine-10-carboxamide, 13-cyclohexyl-6-[(2E,Z)-3-(dimethylamino)-2-[[(2R,6S)-2,6-dimethyl-4-morpholinyl]carbonyl]-1-oxo-2-propenyl]-3-methoxy-N-[(1-methylethyl)sulfonyl]-(100 mg, 0.137 mmol) in ethanol (547 µL) and dioxane (137 µL). Add the hydrazine reagent (0.146 mmol) followed by TEA (58.2 µL, 0.417 mmol) to the reaction in a 0.5-2 mL microwave reaction vessel. The vessel was capped under a nitrogen atmosphere and heated at 160 C for 45 minutes. The reaction was diluted in DMF/Acetonitrile and product compound purified by reverse phase HPLC.

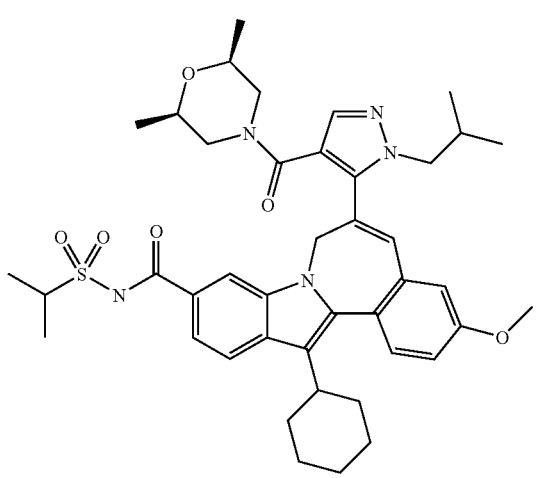

7H-indolo[2,1-a][2]benzazepine-10-carboxamide, 13-cyclohexyl-6-[4-[[(2R,6S)-2,6-dimethyl-4-morpholinyl]carbonyl]-1-(2-methylpropyl)-1H-pyrazol-5-yl]-3-methoxy-N-[(1-methylethyl)sulfonyl]-

This compound was isolated using reverse phase HPLC with the instrumentation listed below using gradient method Bin# 16. Dionex APS-3000: Chromeleon 6.70 sp1 LC software; Thermo-Finnigan Xcalibur MS software; Dionex P680 binary pump for analytical; Dionex PP150 binary pump prep; Dionex UVD340U UV spectrometer; Polymer Labs PL-ELS1000 ELS detector; Thermo-Finnigen MSQ Surveyor Plus mass spectrometer. LC Conditions: Column; Waters Xbridge 19×200 mm 5 um C18; Guard Column; Waters Xbridge 19×10 mm 5 um C18; Mobile Phase; A=Water, 20 mM NH4OH; B=CAN. LC-MS retention time 5.47 min; 756.87 m/z (MH+). LC data was recorded using Masslynx 4.0 SP4 with a system equipped with: CTC-Leap HTS-PAL autosampler with Harney 4-port injection module, Waters 1525 binary pump, Waters 2488 UV detector at 220 nm, Polymer Lab 1000 ELS detector (evap. Temp.=90 C, Neb. Temp.=80 C) and a Waters LCT mass spectrometer with 4 way MUX source. The sample was analyzed using an Ascentis 4.6×50 mm 5 uM C18 column. The elution conditions employed a flow rate of 2 ml/min, a gradient of 100% solvent A/0% solvent B to 0% solvent A/100% solvent B, a gradient time of 8 min, a hold time of 1 min, and an analysis time of 9 min where solvent A was 5% acetonitrile/95% H2O/10 mM ammonium acetate and solvent B was 5% H2O/

95% acetonitrile/10 mM ammonium acetate. MS ionization using a Waters LCT mass spectrometer in ESI positive mode.

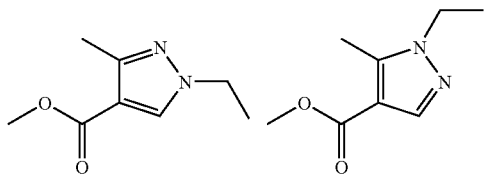

Methyl 1-ethyl-3-methyl-1H-pyrazole-4-carboxylate, and Methyl 1-ethyl-5-methyl-1H-pyrazole-4-carboxylate Methyl 2-((dimethylamino)methylene)-3-oxobutanoate (1.712 g, 10 mmol) in was suspended in diethyl ether (50 mL), under a nitrogen atmosphere to 0° C. Ethylhydrazine oxalate (1.651 g, 11 mmol) in diethyl ether (13 mL), triethyl amine (7.0 mL, 50.2 mmol) and ethanol (6 mL) were then added. The resultant mixture slowly became more homogeneous and stirring was continued 0° C. for 40 min, after which the ice bath was removed and the mixture stirred for an additional 1.5 hours. The reaction was then partitioned between ethyl acetate and 1.0N aqueous hydrochloric acid. Extract aqueous phase with ethyl acetate. Combine the organic layers and wash sequentially with 1.0N aqueous hydrochloric acid, saturated aqueous sodium bicarbonate and brine. Dry organic layer over magnesium sulfate, filter and remove volatiles in vacuo to yield a yellow oil, transfer to a small pear shaped flask in benzene, remove volatiles in vacuo using rotary evaporator. The sample was briefly dried in vacuo on a rotary evaporator to yield 1.549 g of a yellow liquid/oil.

1H NMR analysis indicated an mixture of isomers of 53:46 ratio.

1H NMR (500 MHz, CHLOROFORM-D) δ ppm 1.40 (t, J=7.32 Hz, 3.01H) 1.46 (t, J=7.32 Hz, 3.56H) 2.44 (s, 3.45H) 2.52 (s, 2.99H) 3.79 (s, 3.49H) 3.79 (s, 2.79H) 4.05-4.13 (m, 4.44H) 7.80 (s, 1.09H) 7.82 (s, 0.86H).

LC-MS retention time 0.80 min; 169 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

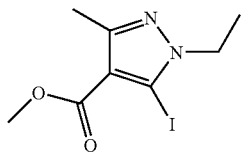

Methyl 1-ethyl-5-iodo-3-methyl-1H-pyrazole-4-carboxylate

In a 100 ml RB a mixture of methyl 1-ethyl-3-methyl-1H-pyrazole-4-carboxylate, and methyl 1-ethyl-5-methyl-1H-pyrazole-4-carboxylate mixture (1.539 g, 9.15 mmol) was dissolved in anhydrous THF (44 mL). The reaction was placed under a nitrogen atmosphere and cooled to −78 C, then n-butyl lithium (5.49 mL, 10.98 mmol) 2.0M in pentane was added in a dropwise fashion. The orange solution at −78 C was then immersed in a acetonitrile/CO2 bath at −44 C and stirred for 1 hour. The reaction was cooled to −78 C and a solution of iodine (2.55 g, 10.07 mmol) in tetrahydrofuran (10 mL) was added by cannula over approximately 10 minutes. The reaction was stirred at −78 C for 10 minutes after the addition of iodine then the cold bath removed and the reaction allowed to warm to room temperature over 1 hr. The reaction was quenched with a saturated aqueous solution of ammonium chloride and extracted into ethyl acetate. The reaction was partitioned between ethyl acetate and aqueous saturated ammonium chloride, washed with aqueous sodium sulfite and again with saturated aqueous ammonium chloride and brine. The product solution was dried over magnesium sulfate and volatiles removed in vacuo using rotary evaporator. The crude product was isolated as an amber oil (approx 2.1 g). The title compound (Rf=0.66 in 50% ethyl acetate/hexanes on Analtech Uniplate silica gel GHLF 250 micron TLC plate) was isolated by silica gel chromatography. The crude reaction was adsorbed onto 5.5 g of silica gel using dichloromethane and chromatographed on 55.9 g of silica gel slurry packed in a column using 10% ethyl acetate in hexanes. Elution with 10% ethyl acetate in hexanes then a step gradient of 15%, 20%, 25%, 30%, 40%, 50% and finally to 70% ethyl acetate in hexanes yielded the purified product and separation of crude reaction components.

The title compound (424 mg, 30%) was isolated as a nearly colorless solid.

1H NMR (500 MHz, CHLOROFORM-D) δ ppm 1.40 (t, J=7.17 Hz, 3H) 2.45 (s, 3H) 3.84 (s, 3H) 4.24 (q, J=7.32 Hz, 2H).

LC-MS retention time 1.19 min; 295 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

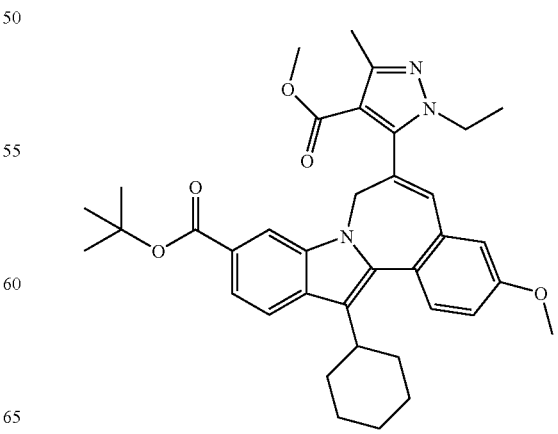

7H-indolo[2,1-a][2]benzazepine-10-carboxylic acid, 13-cyclohexyl-6-[1-ethyl-4-(methoxycarbonyl)-3-methyl-1H-pyrazol-5-yl]-3-methoxy-, 1,1-dimethylethyl ester Into a 20 ml microwave vessel charge, 7H-indolo[2,1-a][2]benzazepine-10-carboxylic acid, 13-cyclohexyl-3-methoxy-6-(tributylstannyl)-, 1,1-dimethylethyl ester (300 mg, 0.409 mmol), methyl 1-ethyl-5-iodo-3-methyl-1H-pyrazole-4-carboxylate (169 mg, 0.573 mmol), bis(triphenylphosphine)palladium(II) dichloride (29.6 mg, 0.042 mmol) and 1 g of activated 3 A molecular sieves. Cap reaction vessel and evacuate and fill with nitrogen through three cycles. Dioxane was added to the reaction and the reagents dissolved at room temperature. The sealed reaction was heated at 120 C for 17 hrs. Ethyl acetate was added to the reaction and the reaction filtered through a 0.45 uM Whatman autovial filter. The filter cake was rinsed with ethyl acetate and the volatiles were removed from the filtrate in vacuo to give a 508 mg of yellow oil. The crude product with an odor of tin was dissolved in 13 ml of dioxane and stirred for 2 hrs with a aqueous solution of potassium fluoride. An attempt to filter the solution was unsuccessful and the aqueous/organic suspension was poured into a separatory funnel and ethyl acetate added and the aqueous layer extracted with ethyl acetate. The organic layer was washed with brine and dried over magnesium sulfate, filtered and volatiles removed in vacuo to obtain 446 mg of amber oil that still has an odor of tin. The crude product was adsorbed onto 1.1 g of silica gel using dichloromethane and purified on a 15.0 g of silica gel column slurry loaded in dichloromethane. The column was eluted with a step gradient of dichloromethane to 2% ethyl acetate in dichloromethane and finally flushed with 5% ethyl acetate in dichloromethane. The product fraction were combined and solvent removed in vacuo to give the title compound (152 mg, 61%) as a amorphous yellow solid. The compound had a faint odor indicating trace amount of tin may be present. The product was used in subsequent steps without further purification.

1H NMR shows sample probably contains a butyl tin impurity. 1H NMR (500 MHz, CHLOROFORM-D) δ ppm 0.64 (s, 3H) 0.81-0.89 (m, 2H) 0.91 (t, J=7.32 Hz, 2.5H, Sn compound?) 1.20-1.31 (m, 7H) 1.31-1.41 (m, 3H) 1.43-1.55 (m, 3H) 1.56 (s, 5H) 1.58 (s, 8H) 1.60-1.68 (m, 2H) 1.77 (d, J=9.46 Hz, 2H) 1.94 (d, J=7.63 Hz, 1H) 2.03 (s, 0.9H, EtOAc) 2.07 (s, 2H) 2.45 (s, 0.4H) 2.47 (s, 3H) 2.53 (s, 0.3H) 2.85 (t, J=11.90 Hz, 1H) 3.50 (d, J=54.93 Hz, 3H) 3.73-3.85 (m, 3H) 3.90 (s, 3H) 4.08-4.14 (m, 0.8H, EtOAc and impurity) 4.59 (q, J=7.22 Hz, 1H) 4.66 (d, J=13.43 Hz, 1H) 4.95 (d, J=14.04 Hz, 1H) 6.72 (s, 1H) 6.92 (d, J=2.44 Hz, 1H) 7.05 (dd, J=8.70, 2.59 Hz, 1H) 7.51 (d, J=8.54 Hz, 1H) 7.63 (dd, J=8.55, 1.53 Hz, 1H) 7.78-7.83 (m, 1H) 7.85 (s, 1H).

LC-MS retention time 2.74 min; 610 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

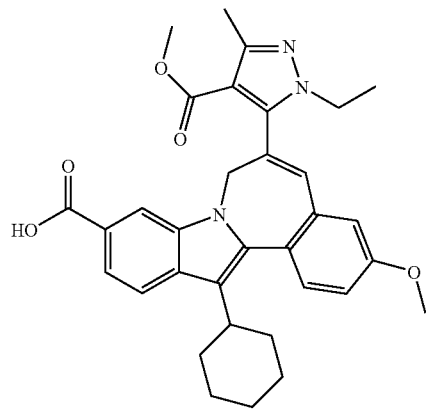

7H-indolo[2,1-a][2]benzazepine-10-carboxylic acid, 13-cyclohexyl-6-[1-ethyl-4-(methoxycarbonyl)-3-methyl-1H-pyrazol-5-yl]-3-methoxy- 7H-indolo[2,1-a][2]benzazepine-10-carboxylic acid, 13-cyclohexyl-6-[1-ethyl-4-(methoxycarbonyl)-3-methyl-1H-pyrazol-5-yl]-3-methoxy-, 1,1-dimethylethyl ester (151 mg, 0.248 mmol) was dissolved in 1,2-dichloroethane (2 ml) and TFA (2.000 ml) added. The reaction was stirred under a nitrogen atmosphere at room temperature for 2.5 hrs. Volatiles from the reaction were removed in vacuo using a rotary evaporator to give a orange/amber oil. The oily product was dissolved in a mixture of dichloromethane and benzene and the volatiles were removed in vacuo to obtain a yellow amorphous solid. The solid was suspended in benzene-dichloromethane and again volatiles removed in vacuo. The product was dried in vacuo at room temperature to give 151 mg of a yellow solid with a trace odor of tin. The product was triturated with the addition of 1.5 to 2 mls of dichloromethane and several milliliters of hexanes. The suspension was heated to reflux then allowed to cool. The product as a pale yellow amorphous solid was filtered and rinsed with hexanes and dried in vacuo at room temperature to yield 114.7 mg of the title compound.

1H NMR (500 MHz, CHLOROFORM-D) δ ppm 0.60 (s, 3H) 0.88 (t, J=7.02 Hz, 1H) 1.19-1.33 (m, 3H) 1.34-1.58 (m, 3H) 1.79 (d, J=8.85 Hz, 2H) 1.96 (s, 1H) 2.08 (s, 3H) 2.51 (s, 3H) 2.86 (t, J=11.60 Hz, 1H) 3.41-3.71 (m, 3H) 3.73-3.89 (m, 2H) 3.91 (s, 3H) 4.49 (s, 6H) 4.70 (d, J=12.21 Hz, 1H) 4.96 (d, J=12.21 Hz, 1H) 6.76 (s, 1H) 6.94 (d, J=2.44 Hz, 1H) 7.08 (dd, J=8.70, 2.59 Hz, 1H) 7.54 (d, J=8.54 Hz, 1H) 7.76 (dd, J=8.39, 1.37 Hz, 1H) 7.89 (d, J=8.54 Hz, 1H) 7.95 (s, 1H).

LC-MS retention time 1.87 min; 552 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

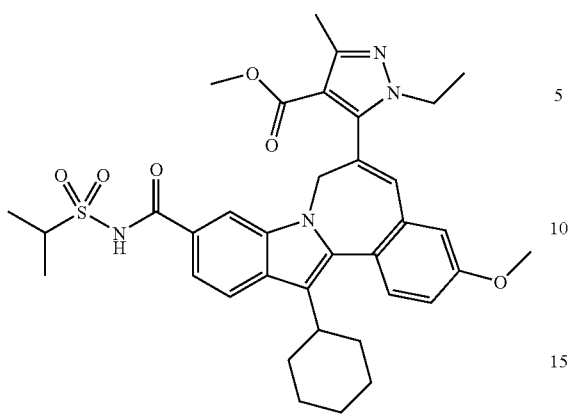

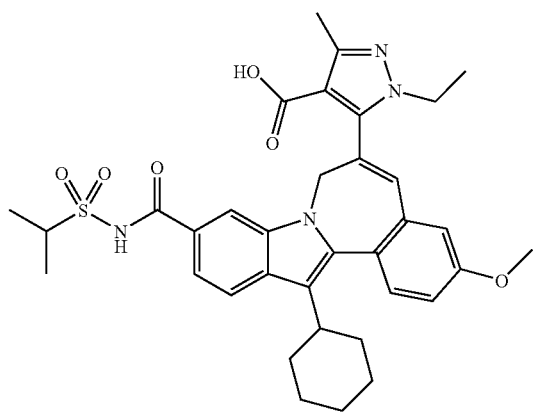

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, methyl ester 7H-indolo[2,1-a][2]benzazepine-10-carboxylic acid, 13-cyclohexyl-6-[1-ethyl-4-(methoxycarbonyl)-3-methyl-1H-pyrazol-5-yl]-3-methoxy- (109.4 mg, 0.198 mmol) was suspended in dichloromethane (2 ml) and propane-2-sulfonamide (82 mg, 0.666 mmol) and DMAP (77.8 mg, 0.637 mmol) were added to the reaction. Upon addition of DMAP the reaction became a homogeneous yellow solution. EDC (57.7 mg, 0.301 mmol) was added to the reaction and the reaction was capped under a nitrogen atmosphere and stir at room temperature for 2 days. The reaction was diluted with ethyl acetate and washed sequentially with 1.0N aqueous hydrochloric acid and brine. The organic phase was dried over MgSO4, filtered and solvent removed in vacuo to obtain 128 mg of product as a yellow foam.

1H NMR analysis shows the presence of ethyl acetate and approximately 0.24 equivalents of propane-2-sulfonamide reagent. The material was used without further purification.

LC-MS retention time 1.84 min; 657 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

1H NMR (500 MHz, CHLOROFORM-D) δ ppm 0.66 (s, 2H) 0.79-0.94 (m, 2H) 1.28-1.39 (m, 2H) 1.45-1.49 (m, 6H) 1.50-1.56 (m, 1H) 1.79 (d, J=8.85 Hz, 2H) 1.96 (s, 2H) 2.05-2.11 (m, 2H) 2.26 (s, 7H, H2O peak) 2.49 (s, 3H) 2.81-2.91 (m, 1H) 3.38-3.71 (m, 4H) 3.74-3.88 (m, 2H) 3.91 (s, 3H) 4.01-4.08 (m, 1H) 4.69 (d, J=15.26 Hz, 1H) 4.94 (d, J=12.51 Hz, 1H) 6.76 (s, 1H) 6.94 (d, J=2.75 Hz, 1H) 7.08 (dd, J=8.70, 2.59 Hz, 1H) 7.38 (d, J=8.55 Hz, 1H) 7.53 (d, J=8.55 Hz, 1H) 7.76 (s, 1H) 7.89 (d, J=8.54 Hz, 1H) 8.30 (s, 1H).

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, methyl ester (127 mg, 0.193 mmol) was dissolved in THF (3 ml) and methanol (3 ml) added to the solution. Sodium hydroxide (3 ml, 3.00 mmol, 1.0N aqueous solution) was added to the homogeneous yellow solution reaction. The reaction turned to a rose-reddish cloudy color after complete addition of sodium hydroxide solution. The reaction was stirred at room temperature under a nitrogen atmosphere and eventually became a clear rose colored solution. The reaction was stirred at room temperature under a nitrogen atmosphere. HPLC analysis after 40 hours revealed 78% conversion to product. Sodium hydroxide (1.0 ml, 1.00 mmol, 1.0N aqueous solution) was added to the reaction and the reaction stirred under a nitrogen atmosphere for an additional 24 hrs. The reaction was concentrated to dryness in vacuo using a rotary evaporator with bath at ambient temperature. The pink solid residue was partitioned between ethyl acetate and 1.0N aqueous hydrochloric acid. The aqueous phase was extracted with ethyl acetate and the organic layers combined and washed sequentially with 1.0N aqueous hydrochloric acid and brine. The organic layer was dried over magnesium sulfate, filtered and solvents removed in vacuo to give a yellow solid which was dried in vacuo at room temperature to give 108 mg of the title compound as a amorphous yellow solid.

1H NMR (500 MHz, CHLOROFORM-D) δ ppm 0.71 (s, 3H) 0.81-0.94 (m, 2H) 0.96-1.20 (m, 3H) 1.23-1.27 (m, 3H) 1.27-1.37 (m, 3H) 1.41 (t, J=7.17 Hz, 6H) 1.45-1.53 (m, 2H) 1.60-1.73 (m, 1H) 1.77 (d, J=11.90 Hz, 2H) 1.86-2.02 (m, 2H) 2.04-2.08 (m, 1H) 2.47 (s, 2H) 2.77-2.89 (m, 1H) 3.43-3.69 (m, 4H) 3.70-3.86 (m, 2H) 3.99-4.06 (m, 2H) 4.61 (d, J=10.07 Hz, 1H) 4.95 (d, J=13.73 Hz, 1H) 6.75 (s, 1H) 6.94 (d, J=2.44 Hz, 1H) 7.03-7.10 (m, 1H) 7.42 (d, J=8.24 Hz, 1H) 7.47-7.54 (m, 1H) 7.79-7.91 (m, 2H) 8.76 (s, 1H).

LC-MS retention time 1.50 min; 643 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

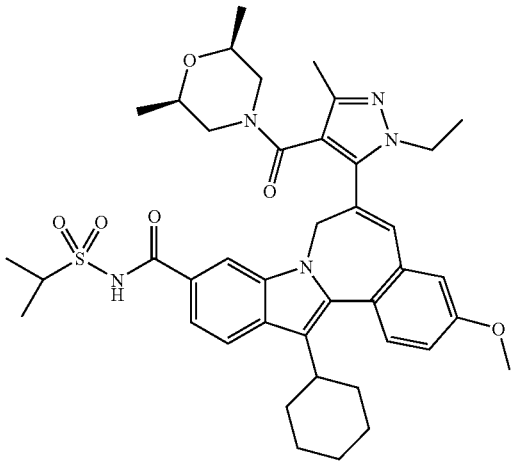

7H-indolo[2,1-a][2]benzazepine-10-carboxamide, 13-cyclohexyl-6-[4-[[(2R,6S)-2,6-dimethyl-4-morpholinyl]carbonyl]-1-ethyl-3-methyl-1H-pyrazol-5-yl]-3-methoxy-N-[(1-methylethyl)sulfonyl]-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- (61.1 mg, 0.095 mmol) was dissolved in DMF (948 µL) and HATU (80 mg, 0.210 mmol) added to the reaction. The reaction was capped under a nitrogen atmosphere and stirred at room temperature for 1 hr. DMAP (36.7 mg, 0.300 mmol) was added to the reaction followed by the amine reagent, (2R,6S)-2,6-dimethylmorpholine (35.2 µL, 0.284 mmol). The clear yellow reaction solution was capped under a nitrogen atmosphere and the reaction stirred at room temperature for 42 hours. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 50% solvent A/50% solvent B to 0% solvent A/100% solvent B, a gradient time of 25 minutes with a run time of 30 minutes using % A=10% acetonitrile, 90% water, 0.1% TFA % B=90% acetonitrile, 10% water, 0.1% TFA solvent system. Retention time of product was from 16.16 to 17.47 minutes. The product fractions were combined and volatiles removed in vacuo using a rotary evaporator. The title compound was dried in vacuo at room temperature to yield 36.3 mg as a yellow amorphous solid.

1H NMR (500 MHz, CHLOROFORM-D) δ ppm 0.68 (s, 4H) 0.75-0.93 (m, 2H) 1.05 (s, 1H) 1.30-1.45 (m, 6H) 1.51 (dd, J=21.82, 6.26 Hz, 7H) 1.79 (d, J=10.68 Hz, 2H) 1.89-2.02 (m, 3H) 2.03-2.16 (m, 3H) 2.26 (s, 12H) 2.88 (t, J=10.68 Hz, 1H) 2.95-3.31 (m, 3H) 3.34-3.75 (m, 1H) 3.94 (s, 3H) 4.03-4.11 (m, 1H) 4.17 (s, 2H) 4.57 (d, J=14.65 Hz, 1H) 4.87 (d, J=15.56 Hz, 1H) 6.74-6.86 (m, 1H) 6.93 (s, 1H) 7.12 (d, J=7.02 Hz, 1H) 7.58 (d, J=8.54 Hz, 1H) 7.66 (s, 1H) 7.73 (s, 1H) 7.90 (d, J=8.24 Hz, 1H) 10.66 (s, 1H).

LC-MS retention time 1.93 min; 740 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

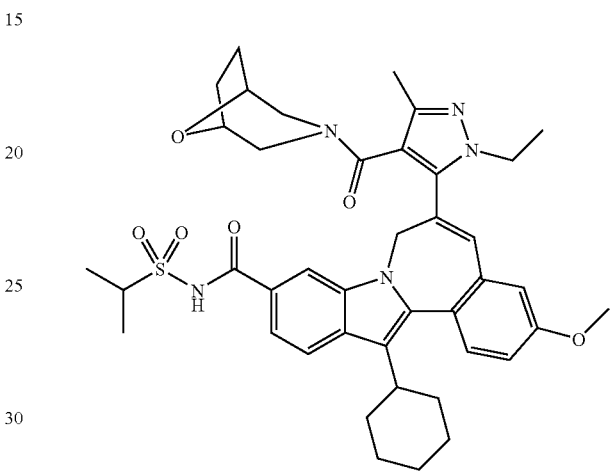

7H-indolo[2,1-a][2]benzazepine-10-carboxamide, 13-cyclohexyl-6-[1-ethyl-3-methyl-4-(8-oxa-3-azabicyclo[3.2.1]oct-3-ylcarbonyl)-1H-pyrazol-5-yl]-3-methoxy-N-[(1-methylethyl)sulfonyl]-

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- (45.8 mg, 0.071 mmol) was dissolved DMF (710 µL) and HATU (62.7 mg, 0.165 mmol) was added to the reaction. The reaction was capped under a nitrogen atmosphere and stirred for 1 hr at room temperature. DMAP (37.1 mg, 0.304 mmol), was added to the reaction followed by the amine reagent 8-oxa-3-azabicyclo[3.2.1]octane hydrochloride (23.3 mg, 0.156 mmol). The reaction was again capped under a nitrogen atmosphere and stirred at room temperature for 42 hrs. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 50% solvent A/50% solvent B to 0% solvent A/100% solvent B, a gradient time of 25 minutes with a run time of 35 minutes using % A=10% acetonitrile, 90% water, 0.1% TFA % B=90% acetonitrile, 10% water, 0.1% TFA solvent system. Retention time of product was from 14.77 to 15.57 minutes. Volatiles were removed from the product fraction in vacuo using a rotary evaporator. The title compound was dried in vacuo at room temperature to yield 28.2 mg of a yellow amorphous solid.

1H NMR (500 MHz, CHLOROFORM-D) δ ppm 0.68 (s, 1H) 1.14-1.30 (m, 2H) 1.32-1.55 (m, 11H) 1.55-1.72 (m, 3H) 1.80 (t, J=10.68 Hz, 2H) 1.90-2.02 (m, 2H) 2.11 (s, 12H) 2.19-2.34 (m, 4H) 2.85 (t, J=11.75 Hz, 1H) 2.98 (d, J=11.90 Hz, 1H) 3.13 (s, 1H) 3.25-3.68 (m, 2H) 3.74-3.91 (m, 2H) 3.94 (s, 3H) 4.00-4.10 (m, 1H) 4.19 (d, J=27.77 Hz, 2H) 4.55 (d, J=14.95 Hz, 1H) 4.80 (d, J=14.65 Hz, 1H) 5.03 (s, 0.15H) 6.82 (s, 1H) 6.93 (s, 1H) 7.11 (dd, J=8.70, 2.59 Hz, 1H) 7.54 (d, J=8.55 Hz, 1H) 7.62 (d, J=7.63 Hz, 2H) 7.81-8.01 (m, 1H) 10.51 (s, 1H).

LC-MS retention time 1.79 min; 738 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy-, 1,1-dimethylethyl ester

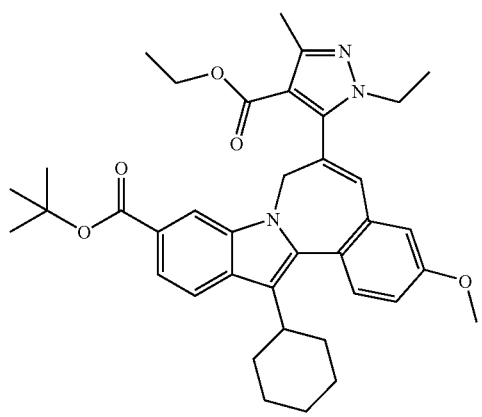

7H-indolo[2,1-a][2]benzazepine-10-carboxylic acid, 13-cyclohexyl-3-methoxy-6-(tributylstannyl)-, 1,1-dimethylethyl ester (2.025 g, 2.764 mmol) was charged into a 20 ml microwave reaction vessel with a magnetic stir bar along with copper (I) chloride (1.368 g, 13.82 mmol), tetrakis(triphenylphosphine)palladium (0) (0.319 g, 0.276 mmol) and lithium chloride (0.926 g, 21.84 mmol) (LiCl, flame dried then vacuum overnight). The reaction vessel was capped and evacuated/filled with nitrogen three times. To the reaction vessel was added a solution of 1-ethyl-5-iodo-3-methyl-1H-pyrazole-4-carboxylate (1.022 g, 3.32 mmol) in DMSO (13.5 mL). Sparge the reaction for approx 3 minutes with nitrogen then heat to 120 C in oil bath. The initial solution was dark in color and became light green color of CuCl during sparging with nitrogen. The reaction was heated for 4 hrs at 120 C Dilute reaction with approximately 400 mL of ethyl acetate, and wash with 5% aqueous ammonium hydroxide solution. Back extract deep blue aqueous layer with diethyl ether. Combine organic phases and wash with brine, filter through ceilite plug and rinse ceilite with ethyl acetate. Dry filtrate over magnesium sulfate, filter and remove solvent in vacuo using a rotary evaporator. Reaction produced 2.83 g of crude product as a yellow oil. The crude product was combined with 2.04 g of a previous reaction and adsorbed onto 14.8 g of silica gel and purified by column chromatography on 186 g of silica gel slurry packed in dichloromethane. The column was eluted with 1500 ml of dichloromethane then 2% ethyl acetate in dichloromethane (>3 L) and then 5% ethyl acetate in dichloromethane and finally eluted with 10% ethyl acetate in dichloromethane.

Product fractions indicated pure by TLC (2% ethyl acetate in dichloromethane) were combined and solvent removed in vacuo using a rotary evaporator to give a yellow amorphous solid when dried in vacuo at room temperature yielded 2.149 g (71% yield) of pure product 1H NMR (500 MHz, CHLOROFORM-D) δ ppm 0.65 (s, 3H) 1.21-1.44 (m, 7H) 1.44-1.54 (m, 2H) 1.56 (s, 3H) 1.58 (s, 9H) 1.77 (d, J=10.07 Hz, 2H) 1.94 (s, 1H) 1.99-2.15 (m, 3H) 2.48 (s, 3H) 2.80-2.90 (m, 1H) 3.43 (s, 1H) 3.54 (s, 1H) 3.90 (s, 3H) 4.19-4.36 (m, 2H) 4.65 (d, J=12.21 Hz, 1H) 4.96 (d, J=14.95 Hz, 1H) 6.72 (s, 1H) 6.92 (d, J=2.75 Hz, 1H) 7.05 (dd, J=8.70, 2.59 Hz, 1H) 7.51 (d, J=8.85 Hz, 1H) 7.63 (d, J=8.55 Hz, 1H) 7.81 (d, J=8.24 Hz, 1H) 7.85 (s, 1H) LC-MS retention time 2.98 min; 624 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy-

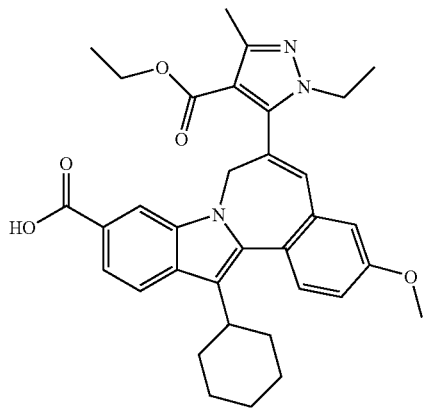

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy-, 1,1-dimethylethyl ester (2.134 g, 3.42 mmol) was dissolved in 1,2-dichloroethane (17 mL) then TFA (17 mL) was added and the reaction stirred at room temperature under a nitrogen atmosphere for 2 hrs. Volatiles were removed from the reaction in vacuo using a rotary evaporator. The orange-amber reaction residue was dissolved in dichloromethane and benzene added. The solvents and residual TFA was removed in vacuo using the rotary evaporator. The product was dried in vacuo at room temperature to give 2.309 g of an amorphous yellow solid. Analysis of the product by 1H NMR and 19F NMR indicated TFA still present. The product was then dissolved in ethyl acetate and washed with 1.0N aqueous hydrochloric acid. The aqueous phases were combined and back extracted with ethyl acetate. The organic extracts were combined and washed with brine, dried over magnesium sulfate, filtered and volatiles removed in vacuo to yield to give a yellow foam which was dissolved in dichloromethane and benzene and volatiles again removed in vacuo using the rotary evaporator. The product, as a light yellow amorphous solid, was dried in vacuo to give 1.962 g of product. The product was sufficiently pure to use without further purification.

1H NMR showed a broad baseline shift (4.5 to 5 ppm, water, H+ from acid function group) causing larger integration values for the bridge methylene protons.

1H NMR (500 MHz, CHLOROFORM-D) δ ppm 0.63 (s, 3H) 1.12-1.60 (m, 9H) 1.78 (d, J=9.16 Hz, 2H) 1.95 (s, 1H) 2.00-2.19 (m, 3H) 2.50 (s, 3H) 2.86 (t, J=11.90 Hz, 1H) 3.51 (d, J=34.79 Hz, 2H) 3.90 (s, 3H) 4.19-4.40 (m, 2H) 4.68 (d, J=14.65 Hz, 2H) 4.96 (d, J=12.21 Hz, 2H) 6.73 (s, 1H) 6.93 (d, J=2.14 Hz, 1H) 7.07 (dd, J=8.55, 2.14 Hz, 1H) 7.53 (d, J=8.85 Hz, 1H) 7.76 (d, J=8.55 Hz, 1H) 7.88 (d, J=8.55 Hz, 1H) 7.96 (s, 1H).

LC-MS retention time 2.94 min; 568 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 2 min, and an analysis time of 5 min where solvent A was 10% acetonitrile/90% H2O/0.1% TFA and solvent B was 90% H2O/10% acetonitrile/0.1% TFA. MS data was determined using a Micromass Platform for LC in electrospray mode.

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, ethyl ester

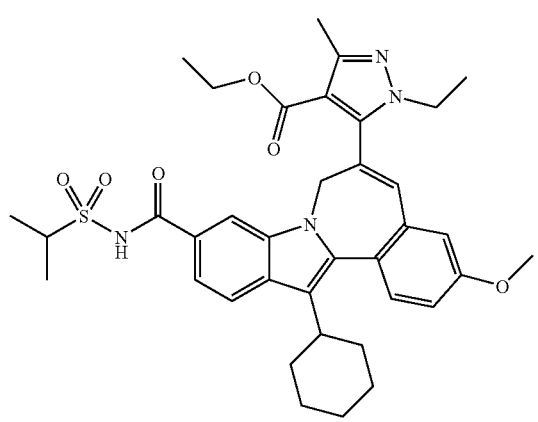

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy- (1.965 g, 3.46 mmol) was dissolved in dichloromethane (35 mL). Propane-2-sulfonamide (1.415 g, 11.49 mmol) and DMAP (1.355 g, 11.09 mmol) were added to the reaction followed by EDC (1.046 g, 5.46 mmol). The reaction was stirred under a nitrogen atmosphere for 2 days.

Remove volatiles/solvent from reaction in vacuo using a rotary evaporator.

Partition the reaction between ethyl acetate and 1.0N aqueous hydrochloric acid.

Wash organic layer sequentially with 1.0N aqueous hydrochloric acid, 0.1N aqueous NaH2PO4 and brine. Dry organic layer over magnesium sulfate, filter and remove solvent in vacuo to obtain a yellow foam which was dried in vacuo at room temperature to give 2.12 g of crude product as an amber-orange amorphous foam. Dissolve the crude product in dichloromethane and adsorb onto 5.3 g of silica gel. The product was purified by column chromatography on 71 g of silica gel slurry loaded in 2% methanol in dichloromethane. The product was eluted with 2% methanol in dichloromethane and after collecting 40 18×150 mm fraction tubes 3% methanol in dichloromethane. The pure product fractions were combined and solvent removed in vacuo using a rotary evaporator. The title compound (1.482 g) was obtained as a amorphous yellow solid.

1H NMR (500 MHz, CHLOROFORM-D) δ ppm 0.66 (s, 3H) 1.12-1.44 (m, 6H) 1.46 (d, J=7.02 Hz, 6H) 1.49-1.55 (m, J=19.99, 6.56 Hz, 1H) 1.55-1.63 (m, 4H) 1.78 (d, J=9.16 Hz, 2H) 1.87-2.17 (m, 4H) 2.48 (s, 3H) 2.80-2.92 (m, 1H) 3.37-3.66 (m, 2H) 3.90 (s, 3H) 3.99-4.09 (m, 1H) 4.15-4.35 (m, 1H) 4.68 (d, J=14.04 Hz, 1H) 4.95 (d, J=13.73 Hz, 1H) 6.74 (s, 1H) 6.94 (d, J=2.44 Hz, 1H) 7.07 (dd, J=8.55, 2.44 Hz, 1H) 7.37 (d, J=8.24 Hz, 1H) 7.51 (d, J=8.54 Hz, 1H) 7.77 (s, 1H) 7.88 (d, J=8.24 Hz, 1H) 8.29 (s, 1H).

LC-MS retention time 2.02 min; 671 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

1H-pyrazole-4-carboxylic acid, 5-[10-(aminocarbonyl)-13-cyclohexyl-3-methoxy-7H-indolo[2,1-a][2]benzazepin-6-yl]-1-ethyl-3-methyl-, ethyl ester

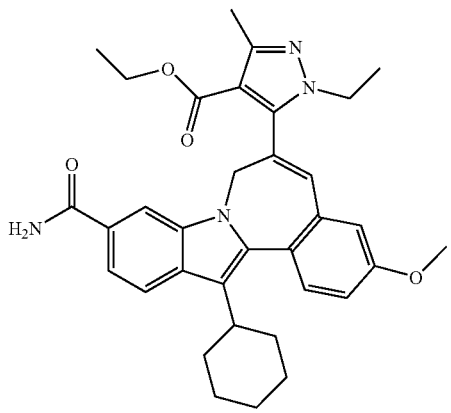

The title compound was isolated as a minor impurity in the purification of 1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, ethyl ester in the above example. 1H NMR had indicated that ammonium chloride as an impurity contained in reactant propane-2-sulfonamide was most likely responsible for the formation to the title compound. The title compound, 1H-pyrazole-4-carboxylic acid, 5-[10-(aminocarbonyl)-13-cyclohexyl-3-methoxy-7H-indolo[2,1-a][2]benzazepin-6-yl]-1-ethyl-3-methyl-, ethyl ester, trailed the major product, 4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, ethyl ester of the reaction in the above chromatography conditions. The title compound (153 mg) was isolated as a light yellow solid.

1H NMR (500 MHz, CHLOROFORM-D) δ ppm 0.64 (s, 2H) 0.80-0.97 (m, 1H) 1.13-1.57 (m, 7H) 1.60 (s, 3H) 1.78 (d, J=10.07 Hz, 2H) 1.95 (s, 1H) 2.08 (s, 3H) 2.47 (s, 3H) 2.80-2.92 (m, 1H) 3.50 (d, J=39.67 Hz, 2H) 3.90 (s, 3H) 4.28 (s, 2H) 4.67 (d, J=13.43 Hz, 1H) 4.98 (d, J=12.21 Hz, 1H) 5.58 (s, 1H) 6.01 (s, 1H) 6.72 (s, 1H) 6.93 (d, J=2.14 Hz, 1H) 7.06 (dd, J=8.55, 2.44 Hz, 1H) 7.34 (d, J=8.24 Hz, 1H) 7.52 (d, J=8.85 Hz, 1H) 7.80 (s, 1H) 7.85 (d, J=8.55 Hz, 1H).

NMR results for sample in DMSO were not satisfactory. All peaks were broad (including solvent peak). Likewise NMR taken in acetonitrile exhibited broad peak shape.

1H NMR (500 MHz, ACETONITRILE-D3) δ ppm 0.55 (s, 2H) 0.78-1.00 (m, 1H) 1.10-1.35 (m, 4H) 1.38-1.58 (m, 3H) 1.69-1.83 (m, 2H) 2.03-2.13 (m, 5H) 2.15 (s, 3H) 2.41 (s, 3H) 2.78-2.92 (m, 1H) 3.48 (s, 2H) 3.90 (s, 3H) 4.21 (d, J=30.21 Hz, 2H) 4.62 (s, 1H) 5.01 (s, 1H) 5.82 (s, 1H) 6.67 (s, 1H) 6.84 (s, 1H) 7.05 (d, J=2.75 Hz, 1H) 7.13 (dd, J=8.55, 2.75 Hz, 1H) 7.47 (dd, J=8.39, 1.37 Hz, 1H) 7.59 (d, J=8.55 Hz, 1H) 7.74 (s, 1H) 7.89 (d, J=8.24 Hz, 1H).

LC-MS retention time 2.19 min; 567 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-[(3-methyl-3,8-diazabicyclo[3.2.1]oct-8-yl)carbonyl]-1H-pyrazol-5-yl]-3-methoxy-N-[(1-methylethyl)sulfonyl]-

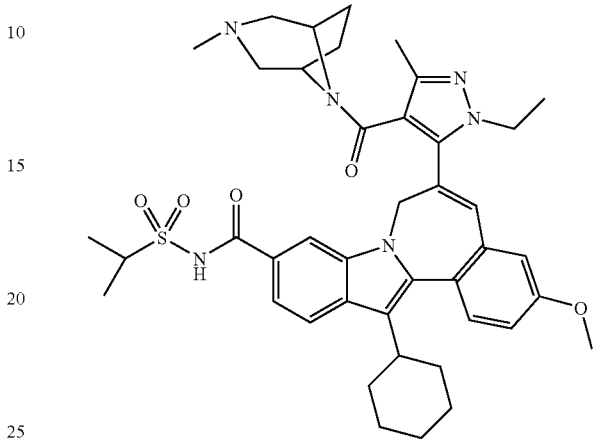

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- (40.8 mg, 0.063 mmol) was dissolved in DMF (633 μL) and HATU (49.2 mg, 0.129 mmol) added to the reaction. The reaction was stirred for 1 hr at room temperature under a nitrogen atmosphere then DMAP (39.2 mg, 0.321 mmol) was added to the reaction followed by the amine reagent, 3-methyl-3,8-diazabicyclo[3.2.1]octane dihydrochloride (29.5 mg, 0.148 mmol). The reaction was capped under a nitrogen atmosphere and stirred at room temperature for 19 hr. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 50% solvent A/50% solvent B to 0% solvent A/100% solvent B, a gradient time of 25 minutes with a run time of 30 minutes using % A=10% acetonitrile, 90% water, 0.1% TFA % B=90% acetonitrile, 10% water, 0.1% TFA solvent system. Retention time of product was 4.34 min. Volatiles were removed from the product fraction in vacuo using a Speed-vac using a medium heat setting. The product was transferred to a vial in acetonitrile, solvent removed using a nitrogen sweep then the sample was dried in vacuo at room temperature to yield 32.3 mg of the title compound as a yellow amorphous solid. 1H NMR exhibits broad peaks characteristic of salt formation and/or restricted rotation.

1H NMR (500 MHz, CHLOROFORM-D) δ ppm 0.87 (s, 0.2H) 1.24 (s, 2H) 1.32-1.63 (m, 9H) 1.79 (d, J=10.99 Hz, 2H) 1.88-2.15 (m, 4H) 2.19-2.75 (m, 12H) 2.80-2.99 (m, 2H) 3.11 (s, 2H) 3.42 (d, J=70.19 Hz, 3H) 3.80-3.90 (m, 1H) 3.94 (s, 3H) 4.03 (s, 1H) 4.20 (s, 2H) 4.57 (d, J=15.56 Hz, 1H) 4.81 (s, 1H) 6.98 (s, 1H) 7.12 (d, J=8.55 Hz, 1H) 7.54 (d, J=7.93 Hz, 1H) 7.63 (s, 1H) 7.91 (d, J=8.24 Hz, 1H) 10.16 (s, 1H).

LC-MS retention time 2.04 min; 75 μm/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-[[(3R,5S)-3,4,5-trimethyl-1-piperazinyl]carbonyl]-1H-pyrazol-5-yl]-3-methoxy-N-[(1-methylethyl)sulfonyl]-

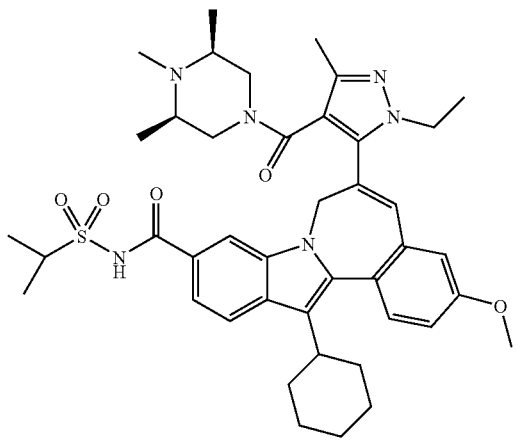

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- (39.8 mg, 0.062 mmol) was dissolved in DMF (617 µL) and HATU (47.9 mg, 0.126 mmol) added to the reaction. The reaction was stirred for 1 hr at room temperature under a nitrogen atmosphere then DMAP (47.7 mg, 0.390 mmol) was added to the reaction followed by the amine reagent, (2R,6S)-1,2,6-trimethylpiperazine dihydrochloride (29.4 mg, 0.146 mmol). The reaction was capped under a nitrogen atmosphere and stirred at room temperature for 19 hr. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 25 minutes with a run time of 30 minutes using % A=10% acetonitrile, 90% water, 0.1% TFA % B=90% acetonitrile, 10% water, 0.1% TFA solvent system.

Retention time of product is 8.08 min, Remove volatiles from product fractions in vacuo overnight using speed-vac at medium heating setting. The product fraction were combined in acetonitrile, transferred into a vial and solvent removed using a nitrogen sweep. The product was dried overnight at room temperature to yield 32.5 mg of the title compound as a yellow amorphous solid.

1H NMR (500 MHz, CHLOROFORM-D) δ ppm 0.27 (s, 1.5H) 1.04 (s, 6H) 1.21-1.46 (m, 6H) 1.50 (s, 6H) 1.81 (d, J=9.77 Hz, 2H) 1.90-2.13 (m, 4H) 2.25 (s, 3H) 2.36 (s, 2H) 2.92 (s, 8H) 3.08-3.65 (m, 5H) 3.84 (s, 1H) 3.94 (s, 3H) 4.00-4.10 (m, 1H) 4.15 (s, 2H) 4.60 (d, J=14.34 Hz, 1H) 4.72-4.98 (m, 2H) 6.89 (s, 1H) 6.95 (d, J=2.44 Hz, 1H) 7.13 (d, J=7.63 Hz, 1H) 7.56 (d, J=7.32 Hz, 1H) 7.61-7.88 (m, 2H) 7.94 (d, J=8.55 Hz, 1H) 10.19 (s, 1H).

LC-MS retention time 1.26 min; 753 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 2 min, a hold time of 1 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-[(1S,4S)-2-oxa-5-azabicyclo[2.2.1]hept-5-ylcarbonyl]-1H-pyrazol-5-yl]-3-methoxy-N-[(1-methylethyl)sulfonyl]-

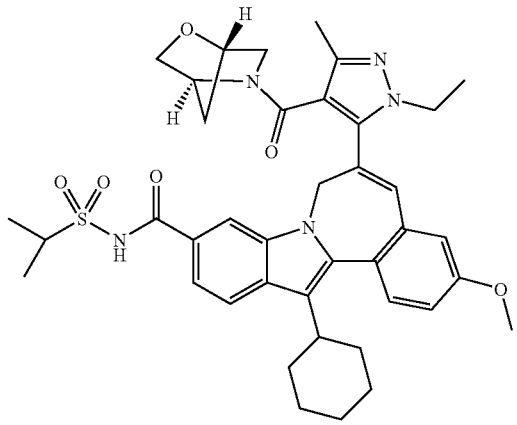

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-41.7 mg, 0.065 mmol) was dissolved in DMF (647 µL) and HATU (49.8 mg, 0.131 mmol) added to the reaction. The reaction was stirred for 1 hr at room temperature under a nitrogen atmosphere then DMAP (53.5 mg, 0.438 mmol) was added to the reaction followed by the amine reagent, (1S,4S)-(+)-2-Aza-5-oxabicyclo(2.2.1)-heptane hydrochloride (22.6 mg, 0.167 mmol). The reaction was capped under a nitrogen atmosphere and stirred at room temperature for 19 hr. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile and a few drops of water purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 25 minutes with a run time of 35 minutes using % A=10% acetonitrile, 90% water, 0.1% TFA % B=90% acetonitrile, 10% water, 0.1% TFA solvent system. Retention time of product is 18.9 min. Remove volatiles from product fractions in vacuo overnight using speed-vac at medium heating setting. The product fraction was dissolved in dichloromethane and transferred into a vial and solvent removed using a nitrogen sweep. The product was dried overnight at room temperature to yield 31.0 mg of the title compound as a yellow amorphous solid.

1H NMR data shows characteristics of restricted rotation with broadening and splitting of some peaks.

1H NMR (500 MHz, CHLOROFORM-D) δ ppm 0.15 (s, 0.6H) 0.94 (s, 0.4H) 1.08-1.34 (m, 2.6H) 1.34-1.60 (m, 12.4H) 1.79 (d, J=10.38 Hz, 2.1H) 1.97 (d, J=9.77 Hz, 1.3H) 2.00-2.16 (m, 3.0H) 2.29 (s, 3.0H) 2.71 (d, J=6.71 Hz, 0.2H) 2.81-2.94 (m, 1.4H) 3.03 (d, J=11.90 Hz, 1.0H) 3.09-3.67 (m, 8.7H) 3.83-4.02 (m, 4.4H) 4.01-4.11 (m, 1.4H) 4.13-4.31 (m, 2.2H) 4.53-4.65 (m, 1.0H) 4.92 (dd, J=15.26, 5.49 Hz, 0.9H) 6.84 (d, J=18.62 Hz, 0.6H) 6.89-6.97 (m, 1.5H) 7.12 (t, J=8.09 Hz, 1.0H) 7.55 (q, J=7.73 Hz, 1.0H) 7.59-7.66 (m, 0.8H) 7.67-7.76 (m, 0.9H) 7.83 (s, 0.3H) 7.86-7.99 (m, 1.0H) 10.41-10.82 (m, 0.8H).

LC-MS retention time 1.71 min; 724 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The compounds below were synthesized by identical coupling methodology used in the above examples.

7H-indolo[2,1-a][2]benzazepine-10-carboxamide, 13-cyclohexyl-6-[1-ethyl-4-[(5-ethyl-2,5-diazabicyclo[2.2.1]hept-2-yl)carbonyl]-3-methyl-1H-pyrazol-5-yl]-3-methoxy-N-[(1-methylethyl)sulfonyl]-

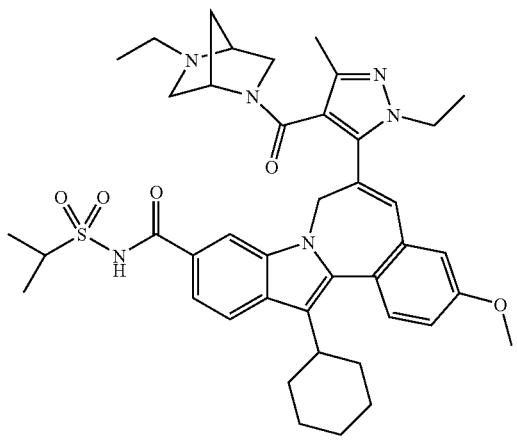

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with a couple drops of TFA and water, filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. The product was collected between 6.62 minutes and 8.81 minutes.

The title compound was isolated (86.7 mg) as a yellow amorphous solid.

1H NMR is characteristic of restricted rotation and/or salt formation with splitting/broadening of peaks-appears rotomeric.

1H NMR (500 MHz, CHLOROFORM-D) δ ppm 0.29-0.58 (m, 0.5H) 0.87 (s, 0.2H) 0.96-1.07 (m, 0.2H) 1.17 (s, 2.1H) 1.23-1.34 (m, 1.2H) 1.34-1.57 (m, 10.7H) 1.58-1.74 (m, 1.0H) 1.81 (d, J=9.46 Hz, 1.9H) 1.96 (d, J=14.34 Hz, 1.1H) 2.04 (d, J=8.55 Hz, 2.8H) 2.19-2.34 (m, 3.1H) 2.60-2.98 (m, 8.3H) 3.03-3.57 (m, 3.7H) 3.59-3.87 (m, 1.9H) 3.94 (s, 3.0H) 4.03 (s, 0.8H) 4.09-4.36 (m, 2.3H) 4.58 (t, J=15.26 Hz, 1.0H) 4.78 (d, J=14.34 Hz, 0.9H) 6.90-7.23 (m, 3.0H) 7.45-7.67 (m, 2.6H) 7.92 (d, J=7.63 Hz, 0.9H) 8.32 (s, 0.1H) 9.29 (s, 0.1H) 9.92-10.87 (m, 0.95H).

LC-MS retention time 1.73 min; 751 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-[(8-methyl-3,8-diazabicyclo[3.2.1]oct-3-yl)carbonyl]-1H-pyrazol-5-yl]-3-methoxy-N-[(1-methylethyl)sulfonyl]-

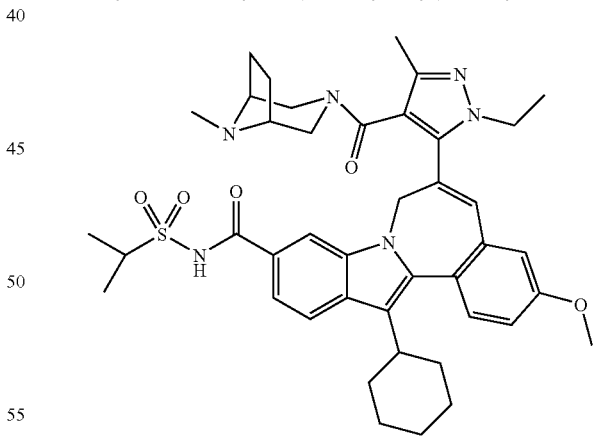

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with a couple drops of TFA and water then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system. The product fractions were collected between 6.79 and 8.69 minutes.

The title compound was isolated (80.0 mg) as a yellow amorphous solid. 1NMR exhibits characteristics of restricted rotation and/or salt formation.

1H NMR (500 MHz, CHLOROFORM-D) δ ppm 0.87 (s, 2.0H) 1.23 (s, 2.2H) 1.30-1.62 (m, 10.5H) 1.76 (s, 2.7H) 1.86-2.10 (m, 5.5H) 2.14-2.47 (m, 4.6H) 2.55-2.93 (m, 7.7H) 3.14-3.86 (m, 5.2H) 3.85-3.94 (m, 3.6H) 3.98 (dd, J=12.67, 6.56 Hz, 1.8H) 4.08-4.40 (m, 1.4H) 4.44-5.09 (m, 2.0H) 6.95 (s, 1.5H) 7.01-7.14 (m, 1.2H) 7.50 (d, J=7.63 Hz, 1.0H) 7.58 (d, J=7.93 Hz, 1.0H) 7.66-7.82 (m, 0.7H) 7.87 (d, J=8.55 Hz, 1.0H) 8.24 (s, 0.1H) 8.67 (s, 0.1H) 10.18 (s, 0.6H)

LC-MS retention time 1.80 min; 751 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-(4-morpholinylcarbonyl)-1H-pyrazol-5-yl]-3-methoxy-N-[(1-methylethyl)sulfonyl]-

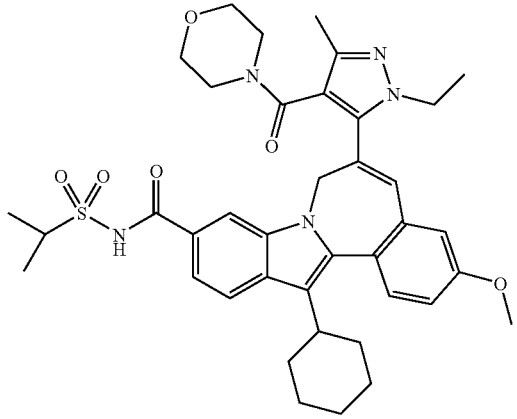

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with a few drops of TFA and water, then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. The product fractions were collected between 15.62 and 16.66 minutes.

The title compound was isolated (67.0 mg) as a yellow amorphous solid.

1H NMR (500 MHz, CHLOROFORM-D) δ ppm 1.14-1.29 (m, 1H) 1.34-1.46 (m, 5H) 1.51 (dd, J=22.89, 6.71 Hz, 7H) 1.79 (d, J=10.38 Hz, 2H) 1.91-2.01 (m, 2H) 2.02-2.20 (m, 7H) 2.27 (s, 3H) 2.50-2.77 (m, 2H) 2.78-2.93 (m, 3H) 3.08 (s, 2H) 3.94 (s, 3H) 4.01-4.09 (m, 1H) 4.11-4.24 (m, 2H) 4.57 (d, J=15.26 Hz, 1H) 4.84 (d, J=14.95 Hz, 1H) 6.81 (s, 1H) 6.93 (d, J=2.44 Hz, 1H) 7.12 (dd, J=8.70, 2.59 Hz, 1H) 7.57 (d, J=8.55 Hz, 1H) 7.62 (d, J=8.24 Hz, 1H) 7.67 (s, 1H) 7.92 (d, J=8.24 Hz, 1H) 10.60 (s, 1H).

LC-MS retention time 1.83 min; 712 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-3-methyl-4-(3-oxa-9-azabicyclo[3.3.1]non-9-ylcarbonyl)-1H-pyrazol-5-yl]-3-methoxy-N-[(1-methylethyl)sulfonyl]-

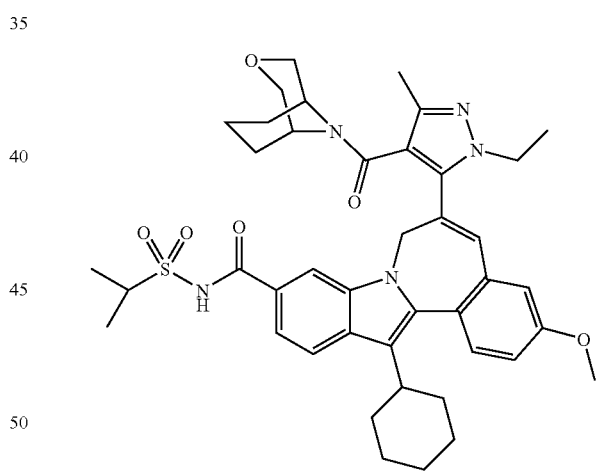

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with a few drops of TFA and water, then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA %

B=90% acetonitrile, 10% water, 0.1% TFA solvent system. The product fractions were collected between 18.65 and 19.75 minutes.

The title compound was isolated (63.2 mg) as a yellow amorphous solid.

1H NMR exhibits some charasteristics of restricted rotation with the splitting of some peaks-rotomeric.

1H NMR (500 MHz, CHLOROFORM-D) δ ppm 1.14-1.27 (m, 2.0H) 1.28-1.51 (m, 12.8H) 1.51-1.58 (m, J=6.56, 6.56 Hz, 3.3H) 1.68 (t, J=13.73 Hz, 0.9H) 1.77 (d, J=10.38 Hz, 2.0H) 1.90-2.27 (m, 8.6H) 2.30 (s, 3.2H) 2.32-2.45 (m, 1.1H) 2.83-2.92 (m, 1.0H) 3.05 (d, J=9.16 Hz, 0.7H) 3.16 (s, 0.8H) 3.23 (s, 0.8H) 3.32 (d, J=10.99 Hz, 1.2H) 3.43-3.80 (m, 1.2H) 3.94 (s, 3.0H) 3.99-4.09 (m, 1.1H) 4.10-4.26 (m, 2.0H) 4.58 (d, J=15.26 Hz, 1.0H) 4.89 (d, J=14.95 Hz, 0.7H) 4.95 (d, J=14.65 Hz, 0.3H) 6.75-6.85 (m, 1.0H) 6.91 (d, J=2.14 Hz, 1.0H) 7.08-7.14 (m, 1.0H) 7.57 (t, J=8.70 Hz, 1.0H) 7.65 (d, J=8.24 Hz, 1.0H) 7.74 (s, 0.7H) 7.81 (s, 0.3H) 7.89 (t, J=8.24 Hz, 1.0H) 10.86 (s, 0.8H).

LC-MS retention time 2.15 min; 752 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-4-[[(2S)-2-(methoxymethyl)-4-morpholinyl]carbonyl]-3-methyl-1H-pyrazol-5-yl]-3-methoxy-N-[(1-methylethyl)sulfonyl]-

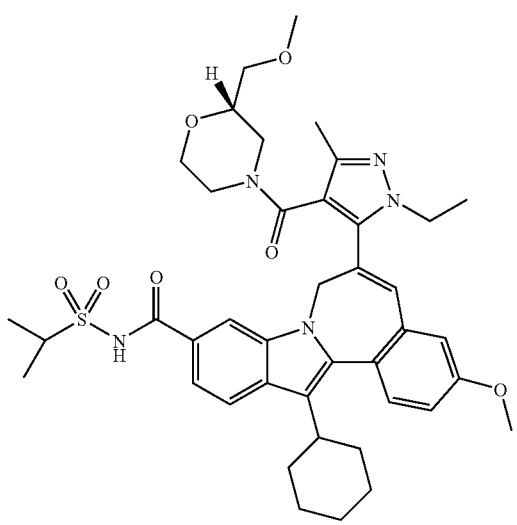

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with a few drops of TFA and water, then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. The product fractions were collected between 15.58 and 16.76 minutes.

The title compound was isolated (65.1 mg) as a yellow amorphous solid.

1H NMR exhibits some charasteristics of restricted rotation with the splitting of some peaks-rotomeric.

1H NMR (500 MHz, CHLOROFORM-D) δ ppm 1.15-1.30 (m, 1.3H) 1.31-1.46 (m, 4.9H) 1.49 (d, J=6.41 Hz, 3.9H) 1.53 (d, J=6.41 Hz, 3.3H) 1.79 (d, J=9.77 Hz, 2.4H) 1.83-2.03 (m, 4.9H) 2.02-2.18 (m, 3.1H) 2.26 (s, 3.0H) 2.29-2.52 (m, 1.3H) 2.68 (s, 0.5H) 2.80-3.02 (m, 3.8H) 3.05 (s, 1.9H) 3.12-3.30 (m, 3.3H) 3.29-3.51 (m, 1.4H) 3.94 (s, 2.9H) 4.00-4.10 (m, 1.1H) 4.10-4.24 (m, 1.9H) 4.56 (d, J=15.26 Hz, 1.0H) 4.74-4.92 (m, 0.9H) 6.81 (d, J=17.09 Hz, 1.0H) 6.92 (s, 1.0H) 7.11 (dd, J=8.55, 2.14 Hz, 1.0H) 7.50-7.77 (m, 3.0H) 7.89 (t, J=9.00 Hz, 1.0H) 10.74 (s, 0.6H).

LC-MS retention time 1.88 min; 756 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester

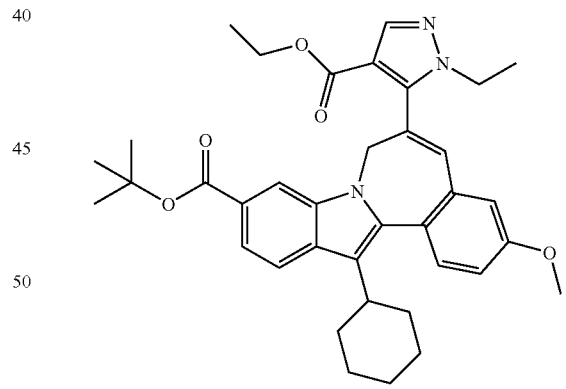

In a 20 ml microwave vessel suspend tert-butyl 13-cyclohexyl-6-((2E,Z)-3-(dimethylamino)-2-(ethoxycarbonyl)-2-propenoyl)-3-methoxy-7H-indolo[2,1-a][2]benzazepine-10-carboxylate (2.056 g, 3.36 mmol) in ethanol (9 mL) and dioxane (2.2 mL). To the reaction was added ethylhydrazine oxalate (0.533 g, 3.55 mmol) followed by triethyl amine (1.4 mL, 10.04 mmol). The reaction was capped under a nitrogen atmosphere and heated using microwave to 160 C for 40 min. The reaction was diluted with ethyl acetate and washed with 1.0N aqueous hydrochloric acid and the aqueous layer extracted with ethyl acetate. The organic extracts were combined and washed sequentially with saturated aqueous sodium bicarbonate and then 1.0N aqueous hydrochloric acid and brine. The organic phase was dried over magnesium sulfate, filtered and solvent removed in vacuo using a rotary evaporator to give 2.02 g of crude product. The crude product was combined with 500 mg of crude product from an analogous reaction in dichloromethane and adsorbed onto 6.3 g of silica gel. The title compound was purified by silica column chromatography (89 g slurry loaded in dichloromethane), eluting with dichloromethane then 2% ethyl acetate in dichloromethane. Note the first major UV adsorbing spot is that of the regio-ethyl pyrazole isomer and the second larger spot on TLC is that of the title compound.

The pure product fractions were collected and solvent removed in vacuo to give 1.006 g of the title compound as a yellow amorphous solid.

1H NMR (500 MHz, CHLOROFORM-D) δ ppm 0.70 (s, 3H) 1.28-1.51 (m, 7H) 1.57 (s, 9H) 1.77 (d, J=9.16 Hz, 2H) 1.94 (s, 1H) 2.07 (s, 3H) 2.79-2.94 (m, 1H) 3.53-3.71 (m, 2H) 3.90 (s, 3H) 4.21-4.33 (m, 2H) 4.69 (d, J=11.90 Hz, 1H) 4.99 (d, J=12.51 Hz, 1H) 6.76 (s, 1H) 6.93 (d, J=2.44 Hz, 1H) 7.06 (dd, J=8.55, 2.44 Hz, 1H) 7.52 (d, J=8.85 Hz, 1H) 7.63 (d, J=8.55 Hz, 1H) 7.79-7.84 (m, 2H) 7.93 (s, 1H).

LC-MS retention time 2.91 min; 610 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-ethyl-1H-pyrazol-3-yl]-3-methoxy-, 1,1-dimethylethyl ester

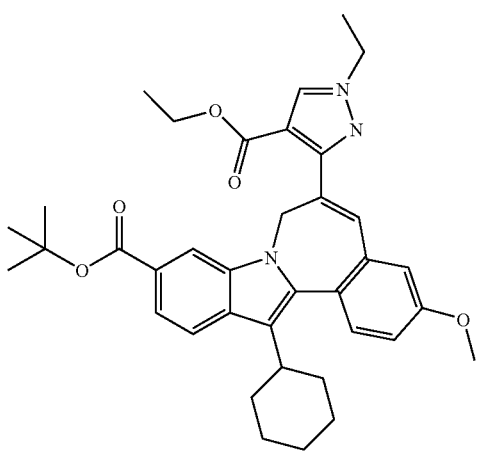

The above compound was isolated as a minor component of the reaction mixture for the above experimental for 7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester and is described in the text as the regio-ethyl pyrazole isomer.

1H NMR (500 MHz, CHLOROFORM-D) δ ppm 1.17-1.27 (m, 2H) 1.31 (t, J=7.17 Hz, 3H) 1.34-1.51 (m, 3H) 1.51-1.57 (m, 7H) 1.61 (s, 9H) 1.61-1.66 (m, 1H) 1.75 (d, J=11.29 Hz, 2H) 1.93 (d, J=7.02 Hz, 1H) 1.97-2.16 (m, 3H) 2.81-2.91 (m, 1H) 3.90 (s, 3H) 4.13-4.31 (m, 4H) 4.39 (d, J=14.34 Hz, 1H) 5.84 (d, J=14.04 Hz, 1H) 6.96-7.06 (m, 2H) 7.51 (d, J=8.24 Hz, 1H) 7.64 (d, J=8.24 Hz, 1H) 7.79 (d, J=8.55 Hz, 1H) 7.94 (d, J=7.32 Hz, 1H) 8.29 (s, 1H).

LC-MS retention time 3.06 min; 610 m/z (MH+). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-

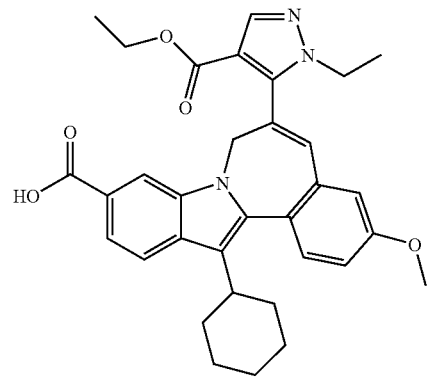

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester (0.984 g, 1.614 mmol) was dissolved in 1,2-dichloroethane (10 mL) and TFA (10.00 mL) added to the reaction. The reaction was placed under a nitrogen atmosphere and stirred at room temperature for 3.5 hours. Volatiles were removed from the reaction in vacuo using a rotary evaporator. Dissolve product in ethyl acetate and wash sequentially with 1.0N aqueous hydrochloric acid and brine, dry over magnesium sulfate, filter and remove solvents in vacuo. The title compound was dried in vacuo to yield 978 mg as a amorphous yellow solid.

1H NMR (500 MHz, CHLOROFORM-D) δ ppm 0.69 (s, 3H) 1.14-1.28 (m, 2H) 1.28-1.39 (m, 4H) 1.37-1.61 (m, 3H) 1.78 (d, J=9.46 Hz, 2H) 1.95 (s, 1H) 2.08 (s, 3H) 2.80-2.95 (m, 1H) 3.65 (s, 2H) 3.91 (s, 3H) 4.19-4.36 (m, 2H) 4.73 (d, J=12.21 Hz, 1H) 4.99 (d, J=10.38 Hz, 1H) 6.78 (s, 1H) 6.94 (d, J=2.75 Hz, 1H) 7.08 (dd, J=8.55, 2.75 Hz, 1H) 7.53 (d, J=8.55 Hz, 1H) 7.75 (dd, J=8.55, 1.22 Hz, 1H) 7.88 (d, J=8.55 Hz, 1H) 7.93 (s, 1H) 7.99 (s, 1H).

LC-MS retention time 2.03 min; 552 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM Ethyl 5-(13-cyclohexyl-10-((isopropylsulfonyl)car-
bamoyl)-3-methoxy-7H-indolo[2,1-a][2]benzazepin-
6-yl)-1-ethyl-1H-pyrazole-4-carboxylate

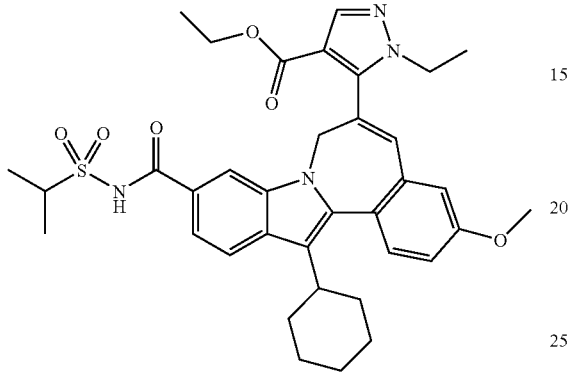

In a 100 ml round bottom flask dissolve 13-cyclohexyl-6-(4-(ethoxycarbonyl)-1-ethyl-1H-pyrazol-5-yl)-3-methoxy-7H-indolo[2,1-a][2]benzazepine-10-carboxylic acid (950 mg, 1.680 mmol), propane-2-sulfonamide (652 mg, 5.29 mmol) and DMAP (655 mg, 5.36 mmol) in dichloromethane (16.8 mL). To the reaction add EDC (508 mg, 2.65 mmol). Place the reaction under a nitrogen atmosphere and stir a room temperature for 64 hours.

Remove solvent in vacuo using a rotary evaporator and partition the reaction between ethyl acetate and 1.0N aqueous hydrochloric acid. Wash the organic extract sequentially with 1.0N aqueous hydrochloric acid and brine then dry over magnesium sulfate. Filter off the magnesium sulfate from the organic extract rinsing with ethyl acetate then remove the solvent in vacuo from the filtrate using a rotary evaporator. The product was dried in vacuo at room temperature to yield 1.009 g of the title compound as a yellow amorphous solid.

1H NMR (500 MHz, CHLOROFORM-D) δ ppm 0.69 (s, 3H) 1.18-1.36 (m, 6H) 1.41 (d, J=6.71 Hz, 2H) 1.45 (d, J=6.71 Hz, 6H) 1.48-1.61 (m, 2H) 1.79 (d, J=9.46 Hz, 2H) 1.90-2.15 (m, 4H) 2.46 (s, 4H) 2.82-2.93 (m, 1H) 3.66 (s, 2H) 3.90 (s, 3H) 4.00-4.08 (m, 1H) 4.26 (dd, J=13.73, 6.71 Hz, 2H) 4.72 (d, J=13.73 Hz, 1H) 4.99 (d, J=12.21 Hz, 1H) 6.79 (s, 1H) 6.94 (d, J=1.83 Hz, 1H) 7.08 (dd, J=8.39, 1.98 Hz, 1H) 7.37 (d, J=8.55 Hz, 1H) 7.52 (d, J=8.55 Hz, 1H) 7.76 (s, 1H) 7.88 (d, J=8.55 Hz, 1H) 7.95 (s, 1H) 8.31 (s, 1H).

LC-MS retention time 1.95 min; 657 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

5-(13-cyclohexyl-10-((isopropylsulfonyl)carbam-
oyl)-3-methoxy-7H-indolo[2,1-a][2]benzazepin-6-
yl)-1-ethyl-1H-pyrazole-4-carboxylic acid

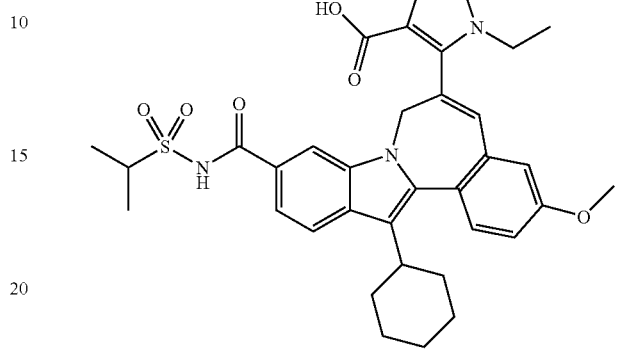

Ethyl 5-(13-cyclohexyl-10-((isopropylsulfonyl)carbamoyl)-3-methoxy-7H-indolo[2,1-a][2]benzazepin-6-yl)-1-ethyl-1H-pyrazole-4-carboxylate was dissolved in THF (14 mL) and methanol (14 mL) then sodium hydroxide (15 mL, 15.00 mmol) (1.0N aqueous) was added to the reaction. The reaction was placed under a nitrogen atmosphere and stirred at room temperature for 16.5 hrs. The reaction was concentrated in vacuo using a rotary evaporator (bath temp equal to less than 26 C) then partitioned between ethyl acetate and 1.0N aqueous hydrochloric acid. The aqueous layer was extracted with ethyl acetate and the organic extracts combined, washed with brine and dried over magnesium sulfate. The organic solution was filtered and solvents removed in vacuo to give amorphous amber-orange solid (902 mg) after drying at room temperature in vacuo.

1H NMR (500 MHz, CHLOROFORM-D) δ ppm 0.79 (s, 3H) 1.12-1.21 (m, 1H) 1.28-1.38 (m, 2H) 1.41 (d, J=6.71 Hz, 6H) 1.43-1.57 (m, 2H) 1.66-1.83 (m, 2H) 1.87-2.07 (m, 4H) 2.77-2.89 (m, 1H) 3.71 (s, 3H) 3.90 (s, 3H) 3.98-4.07 (m, 1H) 4.63 (d, J=13.43 Hz, 1H) 4.99 (d, J=12.82 Hz, 1H) 6.79 (s, 1H) 6.94 (d, J=2.44 Hz, 1H) 7.07 (dd, J=8.70, 2.29 Hz, 1H) 7.43 (d, J=8.24 Hz, 1H) 7.51 (d, J=8.85 Hz, 1H) 7.80-7.87 (m, 2H) 7.95 (s, 1H) 8.86 (s, 1H).

LC-MS retention time 1.35 min; 629 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

13-cyclohexyl-6-(4-(((2R,6S)-2,6-dimethyl-4-morpholinyl)carbonyl)-1-ethyl-1H-pyrazol-5-yl)-N-(isopropylsulfonyl)-3-methoxy-7H-indolo[2,1-a][2]benzazepine-10-carboxamide

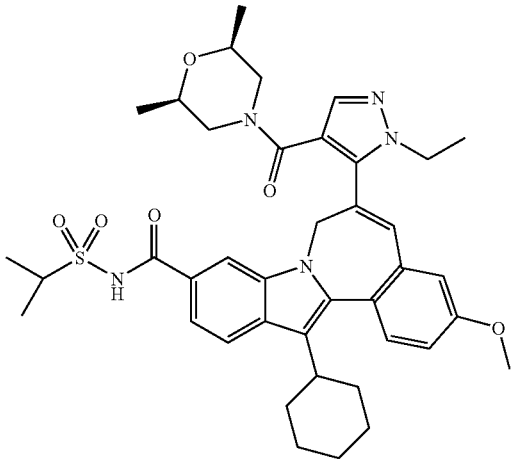

5-(13-cyclohexyl-10-((isopropylsulfonyl)carbamoyl)-3-methoxy-7H-indolo[2,1-a][2]benzazepin-6-yl)-1-ethyl-1H-pyrazole-4-carboxylic acid (75 mg, 0.119 mmol) was dissolved in DMF (1.2 ml) and HATU (103 mg, 0.271 mmol) added to the reaction. The reaction was capped and stirred at room temperature for 1.5 hrs then DMAP (44.3 mg, 0.363 mmol) and the amine reagent (2R,6S)-2,6-dimethylmorpholine (0.044 ml, 0.357 mmol) were added to the reaction. The reaction was capped under a nitrogen atmosphere and stirred at room temperature for 2 days. The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with 2 drops of water added to aid solubility then purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. Product eluted between 17.39 and 18.20 minutes. Volatiles from the product fraction were removed in vacuo overnight using a Speed-Vac set at medium heat. The title compound (54.3 mg) was isolated as a yellow amorphous solid.

1H NMR (500 MHz, CHLOROFORM-D) δ ppm 0.69 (s, 4H) 0.82 (d, J=33.57 Hz, 2H) 1.15-1.31 (m, 1H) 1.31-1.59 (m, 12H) 1.79 (d, J=10.68 Hz, 2H) 1.88-2.32 (m, 13H) 2.88 (t, J=11.14 Hz, 1H) 2.96-3.31 (m, 2H) 3.95 (s, 3H) 4.04-4.12 (m, 1H) 4.22 (s, 2H) 4.60 (d, J=14.95 Hz, 1H) 4.90 (d, J=15.56 Hz, 1H) 6.77-6.86 (m, 1H) 6.94 (s, 1H) 7.10-7.17 (m, 1H) 7.61 (dd, J=27.62, 7.17 Hz, 2H) 7.70 (d, J=19.23 Hz, 2H) 7.92 (d, J=7.93 Hz, 1H) 10.49 (s, 1H).

LC-MS retention time 1.93 min; 726 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

The following compounds were prepared from 5-(13-cyclohexyl-10-((isopropylsulfonyl)carbamoyl)-3-methoxy-7H-indolo[2,1-a][2]benzazepin-6-yl)-1-ethyl-1H-pyrazole-4-carboxylic acid by identical coupling methodology used in the above example for 13-cyclohexyl-6-(4-(((2R,6S)-2,6-dimethyl-4-morpholinyl)carbonyl)-1-ethyl-1H-pyrazol-5-yl)-N-(isopropylsulfonyl)-3-methoxy-7H-indolo[2,1-a][2]benzazepine-10-carboxamide.

7H-indolo[2,1-a][2]benzazepine-10-carboxamide, 13-cyclohexyl-6-[1-ethyl-4-(8-oxa-3-azabicyclo[3.2.1]oct-3-ylcarbonyl)-1H-pyrazol-5-yl]-3-methoxy-N-[(1-methylethyl)sulfonyl]-

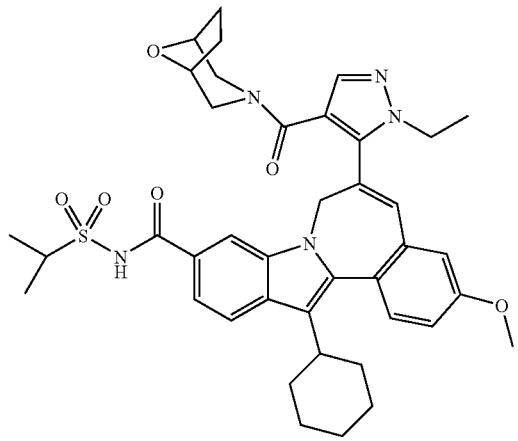

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile and a few drops of water added to solubilize. The sample was then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. The product fraction was collected between 16.30 min and 17.11 min.

The title compound was isolated (61.7 mg) as a yellow amorphous solid.

1H NMR (500 MHz, CHLOROFORM-D) δ ppm 1.24 (dd, J=21.67, 10.38 Hz, 2H) 1.39 (s, 4H) 1.46 (d, J=5.80 Hz, 6H) 1.52-1.72 (m, 4H) 1.78 (d, J=8.85 Hz, 2H) 1.90-2.03 (m, 2H) 2.08 (s, 3H) 2.27 (s, 1H) 2.85 (t, J=11.60 Hz, 1H) 2.97-3.13 (m, 1H) 3.31 (s, 1H) 3.86 (s, 1H) 3.93 (s, 3H) 3.98-4.09 (m, 2H) 4.22 (s, 2H) 4.57 (d, J=15.26 Hz, 1H) 4.81-5.07 (m, 1H) 6.71-6.92 (m, 3H) 6.94 (s, 1H) 7.11 (d, J=7.93 Hz, 1H) 7.54 (d, J=8.55 Hz, 1H) 7.72 (s, 1H) 7.82-8.02 (m, 1H) 9.63-10.11 (m, 1H).

LC-MS retention time 1.80 min; 724 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-6-[1-ethyl-4-[(8-methyl-3,8-diazabicyclo[3.2.1]oct-3-yl)carbonyl]-1H-pyrazol-5-yl]-3-methoxy-N-[(1-methylethyl)sulfonyl]-

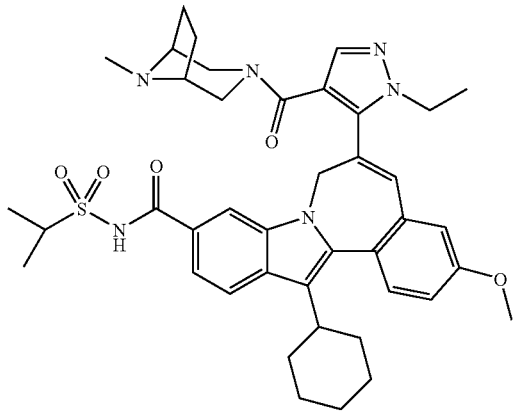

HPLC Purification Method:

The product was purified on a Shimadzu high pressure liquid chromatography system employing Discovery VP software interfaced with a SCL-10A controller, SIL-10A autosampler and FRC-10A fraction collector. The reaction was diluted to 4 ml with acetonitrile/DMF (1:1) and a couple drops of TFA added, the sample was filtered through a 0.45 uM syringe filter and the filtrate injected in two injections and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 20 minutes using % A=10% methanol, 90% water, 0.1% trifluoroacetic acid % B=90% methanol, 10% water, 0.1% trifluoroacetic acid solvent system.

The title compound was isolated (55.5 mg) as a yellow-greenish amorphous solid.

1H NMR (500 MHz, CHLOROFORM-D) d ppm 0.74 (s, 3H) 1.12-1.29 (m, 2H) 1.30-1.41 (m, 4H) 1.42-1.57 (m, 4H) 1.77 (d, J=8.55 Hz, 2H) 1.86-2.10 (m, 4H) 2.18 (s, 1H) 2.24-2.50 (m, 2H) 2.78-2.95 (m, 4H) 3.03 (s, 5H) 3.73 (s, 1H) 3.81-3.88 (m, 1H) 3.90 (s, 3H) 3.93 (s, 1H) 3.99-4.08 (m, 2H) 4.10-4.37 (m, 3H) 4.40-4.69 (m, 3H) 6.90 (s, 1H) 6.96 (d, J=2.44 Hz, 1H) 7.07 (dd, J=8.70, 2.29 Hz, 1H) 7.49-7.55 (m, 2H) 7.57-7.65 (m, 1H) 7.67 (s, 1H) 7.86 (d, J=8.24 Hz, 1H) 10.64 (s, 1H) 11.24 (s, 1H).

LC-MS retention time 1.74 min; 737 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Ethyl 5-(13-cyclohexyl-10-((dimethylsulfamoyl)carbamoyl)-3-methoxy-7H-indolo[2,1-a][2]benzazepin-6-yl)-1-ethyl-3-methyl-1H-pyrazole-4-carboxylate

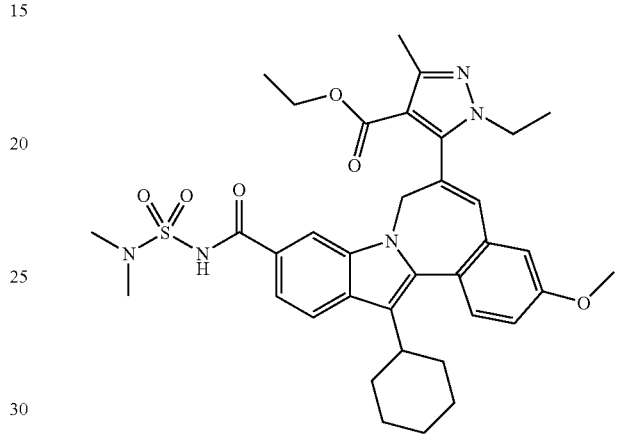

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy- (0.603 g, 1.062 mmol) was dissolved in dichloromethane (10.6 mL) with DMAP (0.417 g, 3.41 mmol) and N,N-dimethylsulfamide (0.394 g, 3.17 mmol). EDC (0.336 g, 1.753 mmol) was added to the reaction and the reaction was stirred under a nitrogen atmosphere at room temperature for 40 hours. Solvent was removed from the reaction in vacuo using a rotary evaporator. The residue was partitioned between ethyl acetate and 1.0N aqueous hydrochloric acid. The organic phase was sequentially washed with 1.0N aqueous hydrochloric acid, a mixture of 0.1M aqueous NaH2P04/1.0N aqueous hydrochloric acid and again with 1.0N aqueous hydrochloric acid and finally with brine. The organic phase was dried over magnesium sulfate, filtered and solvent removed in vacuo using a rotary evaporator. The yellow amorphous solid was dried in vacuo at room temperature to yield 669 mg of the title compound.

1H NMR (500 MHz, CHLOROFORM-D) δ ppm 0.53-0.90 (m, 3H) 1.15-1.46 (m, 7H) 1.47-1.66 (m, 4H) 1.78 (d, J=8.85 Hz, 2H) 1.91-2.15 (m, 4H) 2.48 (s, 3H) 2.86 (t, J=16.02 Hz, 1H) 3.04 (s, 6H) 3.52 (d, J=38.76 Hz, 2H) 3.90 (s, 3H) 4.26 (s, 2H) 4.67 (d, J=14.34 Hz, 1H) 4.95 (d, J=13.73 Hz, 1H) 6.73 (s, 1H) 6.93 (d, J=2.44 Hz, 1H) 7.06 (dd, J=8.55, 2.44 Hz, 1H) 7.33 (d, J=8.55 Hz, 1H) 7.51 (d, J=8.55 Hz, 1H) 7.78 (s, 1H) 7.87 (d, J=8.55 Hz, 1H) 8.46 (s, 1H)

LC-MS retention time 2.23 min; 672 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM 1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1-ethyl-3-methyl-

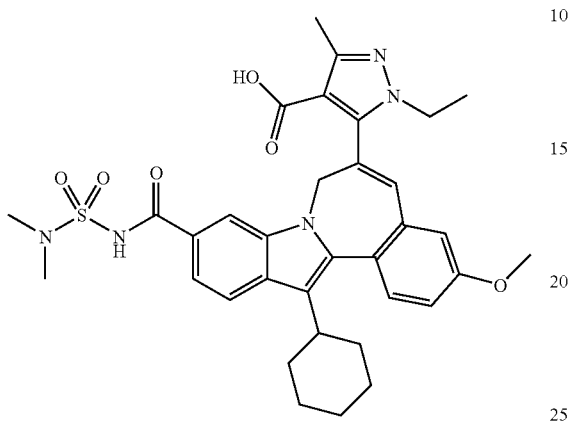

In a 100 ml rb flask dissolve 1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1-ethyl-3-methyl-, ethyl ester (652 mg, 0.968 mmol) in THF (10 mL) and methanol (10.00 mL). Sodium hydroxide (10 mL, 10.00 mmol), 1.0N aqueous solution was added to the reaction and the reaction was stirred under a nitrogen atmosphere at room temperature for 7 days.

The reaction was concentrated using rotary evaporator keeping the water heating bath temperature at or below 25 C. The remaining reaction solution was partitioned between ethyl acetate and 1.0N aqueous hydrochloric acid. Extract aqueous phase with ethyl acetate and combine the organic extracts and wash with brine, dry over magnesium sulfate, filter and remove solvent in vacuo using a rotary evaporator. The amorphous film residue was dissolved in dichloromethane and the solvent and volatiles were removed in vacuo using a rotary evaporator. The yellow amorphous solid was broken up into a more finely divided solid and dried in vacuo at room temperature to yield 600 mg of the title compound as a yellow amorphous solid.

1H NMR (500 MHz, CHLOROFORM-D) δ ppm 0.71 (s, 3H) 0.86 (s, 1H) 1.10-1.58 (m, 6H) 1.69 (s, 1H) 1.76 (d, J=10.99 Hz, 1H) 1.86-2.15 (m, 5H) 2.47 (s, 3H) 2.84 (t, J=11.90 Hz, 1H) 3.00 (s, 6H) 3.59 (s, 2H) 3.90 (s, 3H) 4.64 (d, J=13.43 Hz, 1H) 4.97 (d, J=13.73 Hz, 1H) 6.75 (s, 1H) 6.95 (d, J=2.75 Hz, 1H) 7.06 (dd, J=8.55, 2.44 Hz, 1H) 7.35 (d, J=8.24 Hz, 1H) 7.50 (d, J=8.54 Hz, 1H) 7.77-7.86 (m, 2H) 8.68 (s, 1H).

LC-MS retention time 1.75 min; 644 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

13-cyclohexyl-6-(4-(((2R,6S)-2,6-dimethyl-4-morpholinyl)carbonyl)-1-ethyl-3-methyl-1H-pyrazol-5-yl)-N-(dimethylsulfamoyl)-3-methoxy-7H-indolo[2,1-a][2]benzazepine-10-carboxamide

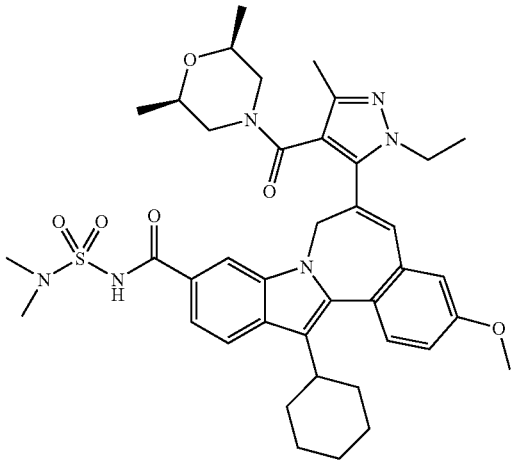

CAS Name for 77778-062 (126 mg, 0.195 mmol) was dissolved in DMF (1.951 mL) and

HATU (167 mg, 0.439 mmol) was added to the reaction. The reaction was capped and stirred at room temperature for 1.5 hrs then DMAP (72.1 mg, 0.590 mmol) was added to the reaction followed by the amine reagent, (2R,6S)-2,6-dimethylmorpholine (72.5 µL, 0.585 mmol). The reaction was capped under a nitrogen atmosphere and stirred at room temperature for 2 days. The product was purified on a Shimadzu high pressure liquid chromatography system employing Discovery VP software interfaced with a SCL-10A controller, SIL-10A autosampler and FRC-10A fraction collector. The reaction was diluted to 4 ml with acetonitrile with a few drops of water to dissolve then filtered through a 0.45 uM syringe filter and purified (2×2 ml injections) using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. The product fractions were collected and volatiles removed in vacuo overnight using a speed-vac set on medium heating. The product fractions were analyzed by LCMS and the pure fractions were combined in dichloromethane and transferred to a vial. The solvent was removed using a nitrogen sweep and the product dried in vacuo at room temperature to yield 89.2 mg of the title compound as amorphous yellow solid.

1H NMR (500 MHz, CHLOROFORM-D) δ ppm 0.68 (s, 3H) 0.73-1.08 (m, 3H) 1.15-1.29 (m, 1H) 1.31-1.54 (m, 6H) 1.79 (d, J=10.99 Hz, 2H) 1.88-2.18 (m, 6H) 2.26 (s, 3H) 2.58-2.99 (m, 7H) 3.07 (s, 5H) 3.10-3.27 (m, 2H) 3.94 (s, 3H) 4.19 (s, 2H) 4.57 (d, J=14.95 Hz, 1H) 4.90 (d, J=15.26 Hz, 1H) 6.70-6.88 (m, 1H) 6.93 (s, 1H) 7.12 (d, J=7.63 Hz, 1H) 7.45-7.67 (m, 2H) 7.73 (s, 1H) 7.91 (d, J=8.24 Hz, 1H) 10.61 (s, 1H)

LC-MS retention time 2.13 min; 741 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

1H-pyrazole-4-carboxylic acid, 5-[13-cyclohexyl-10-[[(cyclopropylsulfonyl)amino]carbonyl]-3-methoxy-7H-indolo[2,1-a][2]benzazepin-6-yl]-1-ethyl-3-methyl-, ethyl ester

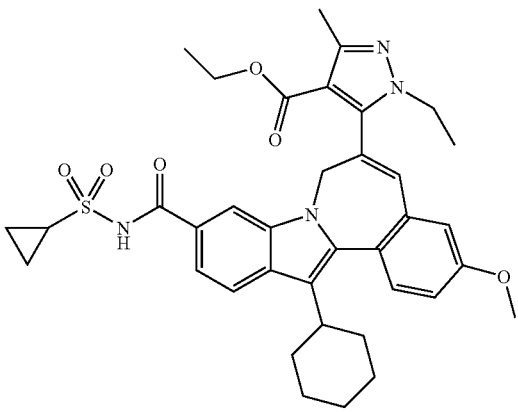

Dissolve 7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy- (110 mg, 0.194 mmol) in THF (0.646 mL). Carbonyldiimidazole (94 mg, 0.581 mmol) was added to the reaction. The reaction was placed under a nitrogen atmosphere and heated to 60 deg C. for 1 hour. The reaction was cooled under a nitrogen atmosphere and cyclopropanesulfonamide (94 mg, 0.775 mmol) was added to the reaction followed by DBU (0.088 mL, 0.581 mmol). The reaction was immerse in oil bath at 60 deg C. under nitrogen atmosphere and heated overnight at 60 deg C. The reaction was diluted with chloroform (50 mL) and the organic layer washed sequentially with 1.0N aqueous hydrochloric acid (50 mL), 0.1M aqueous NaH2PO4 (50 mL) and brine (25 mL). The organic layer was dried over MgSO4, filtered and volatiles removed in vacuo to yield a yellow foam which was dried in vacuo at room temperature overnight to yield 130 mg (0.194 mmol, 90% crude) of the title compound as a yellow amorphous solid. 1H NMR (500 MHz, CHLOROFORM-D) δ ppm 0.67 (br.m, 3H) 1.12-1.59 (m, 9H) 1.62-2.16 (m, 8H) 2.49 (s, 3H) 2.87 (m, 1H) 3.91 (s, 3H) 4.11 (m, 2H) 4.27 (m, 3H) 4.69 (br.d, 1H) 4.97 (br.d, 1H) 6.72 (s, 1H) 6.94 (s, 1H) 7.07 (dd, J=8.55, 2.14 Hz, 1H) 7.37 (dd, J=8.55, 2.14 Hz, 1H) 7.51 (d, J=8.24 Hz, 1H) 7.82 (d, J=2.14 Hz, 1H) 7.89 (d, J=8.24 Hz, 1H) 8.59 (br, s, 1H).

LCMS 671 m/z (MH+).

1H-pyrazole-4-carboxylic acid, 5-[13-cyclohexyl-10-[[(cyclopropylsulfonyl)amino]carbonyl]-3-methoxy-7H-indolo[2,1-a][2]benzazepin-6-yl]-1-ethyl-3-methyl-

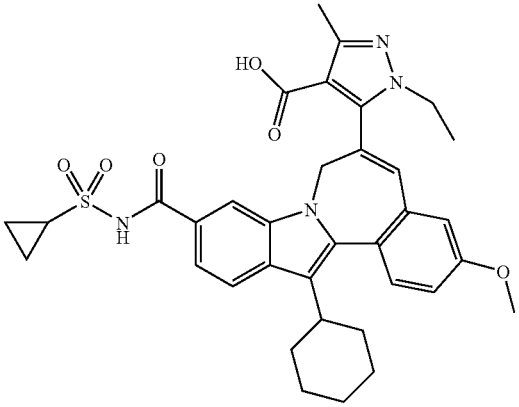

Dissolve 1H-pyrazole-4-carboxylic acid, 5-[13-cyclohexyl-10-[[(cyclopropylsulfonyl)amino]carbonyl]-3-methoxy-7H-indolo[2,1-a][2]benzazepin-6-yl]-1-ethyl-3-methyl-, ethyl ester (130 mg, 0.194 mmol) was dissolved in dioxane (0.969 mL) and methanol (0.969 mL) was added to the reaction followed by 1N aqueous sodium hydroxide (1.94 mL). The reaction was capped under a nitrogen atmosphere and stirred at room temperature for 72 hrs. The reaction was diluted with chloroform (50 mL) and washed with 1.0N aqueous hydrochloric acid (50 mL). The organic layer was concentrated in vacuo using a rotary evaporator to yield the title compound as a yellow solid (125 mg, 100% crude). 1H NMR (500 MHz, CHLOROFORM-D) δ ppm 0.72 (br.m, 3H) 1.12-1.59 (m, 6H) 1.62-2.16 (m, 8H) 2.51 (s, 3H) 2.87 (m, 3H) 3.91 (s, 3H) 4.12 (m, 1H) 4.69 (br.d, 1H) 5.01 (br.d, 1H) 6.74 (s, 1H) 6.96 (s, 1H) 7.08 (dd, J=8.55, 2.14 Hz, 1H) 7.41 (dd, J=8.55, 2.14 Hz, 1H) 7.52 (d, J=8.24 Hz, 1H) 7.88 (m, 2H) 8.92 (br, s, 1H). MS m/z 643 (MH+).

7H-indolo[2,1-a][2]benzazepine-10-carboxamide, 13-cyclohexyl-N-(cyclopropylsulfonyl)-6-[4-[[(2R,6S)-2,6-dimethyl-4-morpholinyl]carbonyl]-1-ethyl-3-methyl-1H-pyrazol-5-yl]-3-methoxy-

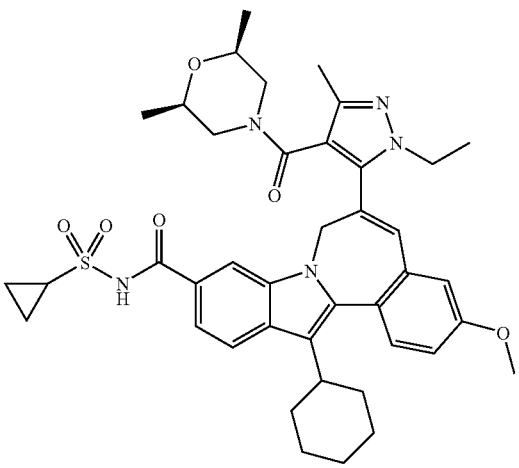

1H-pyrazole-4-carboxylic acid, 5-[13-cyclohexyl-10-[[(cyclopropylsulfonyl)amino]carbonyl]-3-methoxy-7H-indolo[2,1-a][2]benzazepin-6-yl]-1-ethyl-3-methyl- was dissolved in DMF (1.9 mL) and HATU (160 mg, 0.421 mmol) added to the reaction. The reaction was stirred at room temperature for 1.5 hrs then DMAP (70.7 mg, 0.579 mmol) was added to the reaction followed by (2R,6S)-2,6-dimethylmorpholine (71.1 μL, 0.574 mmol). The reaction was capped under a nitrogen atmosphere and stirred at room temperature for 17 hrs. The product was purified on a Shimadzu high pressure liquid chromatography system employing Discovery VP software interfaced with a SCL-10A controller, SIL-10A autosampler and FRC-10A fraction collector. The reaction was diluted to 4 ml with acetonitrile with a few drops of water to dissolve then filtered through a 0.45 uM syringe filter and purified (2×2 ml injections) using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system.

The title compound was dried in vacuo at room temperature to yield 71.8 mg of yellow amorphous solid.

1H NMR (500 MHz, CHLOROFORM-D) δ ppm 0.68 (s, 4H) 0.81 (d, J=33.27 Hz, 2H) 0.93-1.18 (m, 3H) 1.20-1.30 (m, 1H) 1.33-1.48 (m, 6H) 1.50-1.61 (m, 1H) 1.79 (d, J=10.99 Hz, 2H) 1.97 (d, J=9.77 Hz, 3H) 2.04-2.17 (m, 3H) 2.26 (s, 3H) 2.88 (t, J=11.29 Hz, 1H) 3.05-3.29 (m, 3H) 3.53 (s, 5H) 3.95 (s, 3H) 4.20 (s, 2H) 4.57 (d, J=14.95 Hz, 1H) 4.89 (d, J=15.56 Hz, 1H) 6.75-6.87 (m, 1H) 6.93 (s, 1H) 7.13 (d, J=8.24 Hz, 1H) 7.52-7.60 (m, 1H) 7.63-7.77 (m, 2H) 7.86-7.99 (m, 1H) 10.72 (s, 1H)

LC-MS retention time 1.50 min; 738 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 0 min, and an analysis time of 3 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

Methyl 1-isopropyl-5(3)-methyl-1H-pyrazole-4-carboxylate

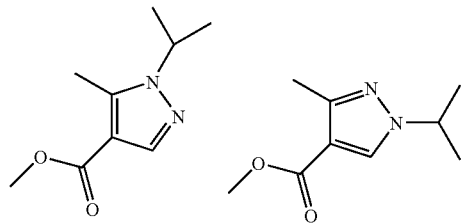

Dissolve methyl 3-methyl-1H-pyrazole-4-carboxylate (2.375 g, 16.95 mmol) in DMF (85 mL), sodium hydride (0.471 g, 18.64 mmol) (95% in mineral oil) was added portion wise under nitrogen. The reaction was stirred for approximately 10 minutes and 2-iodopropane (1.861 mL, 18.64 mmol) was added to the reaction. The reaction was stirred at room temperature under a nitrogen atmosphere overnight (23 hr). Solvent was removed from the reaction in vacuo using a rotary evaporator. The orange residue was partitioned between 1.0N aqueous hydrochloric acid (~30 ml) and ethyl acetate. The yellow colored aqueous solution was extracted with ethyl acetate and the organic extracts were combined and washed 1× with saturated aqueous sodium bicarbonate solution. The aqueous hydrochloric acid washes were neutralized to pH of ~4 with 10N aqueous sodium hydroxide then saturated aqueous sodium bicarbonate added to make the solution basic. The basic aqueous solutions were combined and extracted with ethyl acetate. The organic extracts were combined and washed with brine and dried over magnesium sulfate, filtered and solvent removed in vacuo to yield a yellow oil (4.4 g). The yellow oil was dissolved in benzene and volatiles removed in vacuo using a rotary evaporator (bath temp=40 C) to obtain a yellow oil (weight=2.964 g). The material was dissolved in a small amount of dichloromethane and applied to a silica gel column (105 g) slurry loaded in dichloromethane. The product was eluted with dichloromethane to yield a mixture of isomers as a yellow oil (1.736 g).

1H NMR (500 MHz, CHLOROFORM-D) δ ppm 1.46 (s, 2.29H) 1.47 (s, 5.08H) 1.48 (s, 3.03H) 2.45 (s, 3.00H) 2.54 (s, 1.99H) 3.79 (s, 3.15H) 3.79 (s, 1.91H) 4.34-4.49 (m, 1.80H) 7.83 (s, 1.02H) 7.85 (s, 0.65H).

Methyl 3 (5)-iodo-1-isopropyl-5(3)-methyl-1H-pyrazole-4-carboxylate

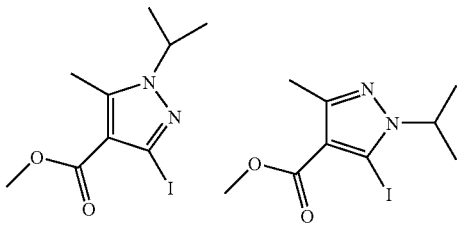

Vasilevskii, S. F.; Gerasimov, V. A.; Shvartsbert, M. S.; Bulletin of the Academy of Sciences of the USSR, Division of Chemical Science (English Translation), 30 (4) 683-685 (1981), ISSN: 0568-5230; Izvestiya Akademii Nauk SSSR, Seriya Khimicheskaya, 4, 902-904 (1981). In a 25 ml flask dissolve methyl 1-isopropyl-3(5)-methyl-1H-pyrazole-4-carboxylate mixture (550 mg, 3.02 mmol) in acetic acid (3.2 ml), then add sulfuric acid (1.22 ml, 6.87 mmol) (30% w/w) followed by iodine (620 mg, 2.443 mmol) and iodic acid (250 mg, 1.421 mmol). The reaction was heated at 95 C under a nitrogen atmosphere for approximately 21 hrs. The reaction was cooled and sodium acetate (750 mg, 9.14 mmol) to the reaction. The reaction was transferred to a sepratory funnel in ethyl acetate and washed with 10% aqueous sodium sulfite. The organic layer was washed in an erlenmeyer with saturated aqueous sodium bicarbonate (Caution: CO2 evolution). The organic phase was decanted and washed with saturated aqueous sodium bicarbonate then brine. The organic extract was dried over magnesium sulfate, filtered and solvent removed in vacuo using a rotary evaporator to give the product as a yellow oil (598 mg). The crude mixture was used without further purification.

LC-MS retention time 1.4 min unresolved peaks; 309 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 95% H2O/5% acetonitrile/10 mM ammonium acetate. MS data was determined using a Micromass Platform for LC in electrospray mode.

7H-indolo[2,1-a][2]benzazepine-10-carboxylic acid, 13-cyclohexyl-3-methoxy-6-[4-(methoxycarbonyl)-5-methyl-1-(1-methylethyl)-1H-pyrazol-3-yl]-, 1,1-dimethylethyl ester

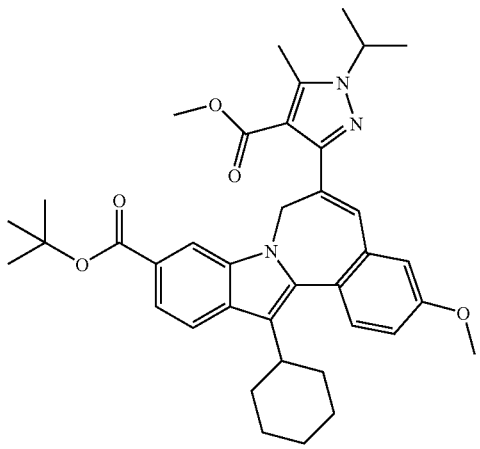

7H-indolo[2,1-a][2]benzazepine-10-carboxylic acid, 13-cyclohexyl-3-methoxy-6-(tributylstannyl)-, 1,1-dimethylethyl ester (679 mg, 0.927 mmol) was charged into a 20 ml microwave vessel with copper(I) chloride (468 mg, 4.73 mmol), tetrakis(triphenylphosphine)palladium(0) (106.8 mg, 0.092 mmol) and lithium chloride (312 mg, 7.36 mmol) (lithium chloride flame dried and stored in vacuum at room temperature overnight). The reaction vessel was capped with a teflon lined septa and evacuated and back filled with nitrogen three times. A mixture containing methyl 3(5)-iodo-1-isopropyl-5(3)-methyl-1H-pyrazole-4-carboxylate (356 mg, 1.155 mmol) in DMSO (6.2 mL) was added to the reaction vessel. The reaction was sparged for approximately 2 minutes with nitrogen and stirred for 5 minutes at room temperature then heated to 120 C in an oil bath for 5 hrs. Dilute reaction with ethyl acetate and wash sequentially with 5% aqueous ammonium hydroxide then brine. Back extract aqueous layer with diethyl ether. Combine organic extracts and wash sequentially with water then brine. Filter off a fine precipitate suspension in the organic layer then dry filtrate using magnesium sulfate. Filter drying agent and remove volatiles to yield the crude reaction products as a yellow oil (825 mg). The crude product was adsorbed onto 2 g of silica gel using dichloromethane and purified by column chromatography using 25.8 g of silica gel slurry loaded in 30% hexanes in dichloromethane. The products were eluted from the column with 30% hexanes in dichloromethane then a gradient to dichloromethane, continued elution with 1% ethyl acetate in dichloromethane and finally a gradient to 5% ethyl acetate in dichloromethane. Pure fractions of the title compound were combined and volatiles removed to yield the title compound (165 mg) a yellow film.

LC-MS retention time 3.91 min; 624 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 5 ml/min, a gradient of 70% solvent A/30% solvent B to 0% solvent A/100% solvent B, a gradient time of 3 min, a hold time of 3 min, and an analysis time of 6 min where solvent A was 10% acetonitrile/90% H2O/0.1% TFA and solvent B was 90% H2O/10% acetonitrile/0.1% TFA. MS data was determined using a Micromass Platform for LC in electrospray mode.

1H NMR indicates some impurities present. The material was used without further purification.

1H NMR (500 MHz, CHLOROFORM-D) δ ppm 0.91 (t, J=7.48 Hz, 1.2H) 1.16-1.41 (m, 5.6H) 1.44 (d, J=6.71 Hz, 2.2H) 1.46-1.53 (m, 4.5H) 1.55 (s, 6.8H) 1.60 (s, 9.2H) 1.61-1.67 (m, 1.7H) 1.69-1.81 (m, 2.3H) 1.93 (d, J=10.99 Hz, 1.2H) 2.06 (s, 3.1H) 2.48-2.50 (s, 0.7H) 2.51 (s, 2.8H) 2.77-2.83 (m, 0.4H) 2.83-2.92 (m, 1.0H) 3.70 (s, 2.9H) 3.80 (s, 0.6H) 3.90 (s, 3.0H) 4.35-4.53 (m, 2.2H) 5.59 (d, J=14.95 Hz, 0.9H) 6.95 (d, J=2.75 Hz, 1.0H) 6.99 (dd, J=8.55, 2.75 Hz, 1.0H) 7.36 (s, 1.0H) 7.50 (d, J=8.55 Hz, 1.1H) 7.64 (dd, J=8.39, 1.37 Hz, 1.0H) 7.80 (d, J=8.55 Hz, 1.0H) 8.19 (s, 0.9H).

7H-indolo[2,1-a][2]benzazepine-10-carboxylic acid, 13-cyclohexyl-3-methoxy-6-[4-(methoxycarbonyl)-5-methyl-1-(1-methylethyl)-1H-pyrazol-3-yl]-

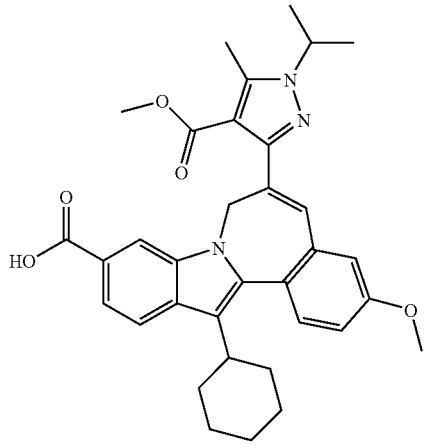

7H-indolo[2,1-a][2]benzazepine-10-carboxylic acid, 13-cyclohexyl-3-methoxy-6-[4-(methoxycarbonyl)-5-methyl-1-(1-methylethyl)-1H-pyrazol-3-yl]-, 1,1-dimethylethyl ester (152 mg, 0.244 mmol) was dissolved in 1,2-dichloroethane (1.2 mL), then TFA (1.2 mL) was added to the reaction. The reaction was stirred at room temperature under a nitrogen atmosphere for 2 hrs. Volatiles were removed from the reaction in vacuo using a rotary evaporator. Dissolve residue in dichloromethane and benzene then remove volatiles in vacuo using a rotary evaporator, repeat sequence. The resulting yellow foam was dissolved in dichloromethane and transferred to a tared round bottom flask. The volatiles were removed in vacuo an the resulting yellow foam was dried in vacuo at room temperature to yield 147 mg of the title compound. The material was used without further purification. LC-MS retention time 2.24 min; 566 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

LC-MS retention time 3.09 min; 568 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 2 min, and an analysis time of 5 min where solvent A was 10% acetonitrile/90% H2O/0.1% TFA and solvent B was 90% H2O/10% acetonitrile/0.1% TFA. MS data was determined using a Micromass Platform for LC in electrospray mode.

1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)-, methyl ester

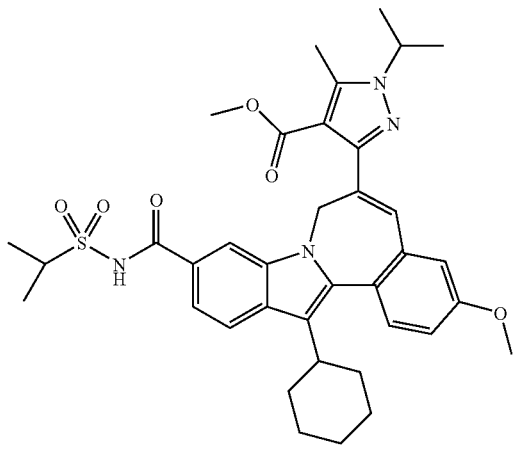

In a 2 dram vial suspend 7H-indolo[2,1-a][2]benzazepine-10-carboxylic acid, 13-cyclohexyl-3-methoxy-6-[4-(methoxycarbonyl)-5-methyl-1-(1-methylethyl)-1H-pyrazol-3-yl]- in dichloromethane (2.5 ml). To the reaction as a fine yellow suspension add propane-2-sulfonamide (96.7 mg, 0.785 mmol) and DMAP (105 mg, 0.859 mmol). Upon addition of DMAP, the reaction became a homogeneous clear yellow solution. EDC (77 mg, 0.402 mmol) was added to the reaction and the reaction was capped under a nitrogen atmosphere and stir at room temperature for 39 hrs. The solvent was removed in vacuo using a rotary evaporator and the reaction residue partitioned between ethyl acetate and 1.0N aqueous hydrochloric acid. The organic layer was washed sequentially with 1.0N aqueous hydrochloric acid, 0.1M aqueous NaH2PO4 and 1.0N aqueous hydrochloric acid then brine. The organic layer was dried over magnesium sulfate, filtered and solvent remove in vacuo to yield a yellow amorphous solid. The product was dried in vacuo at room temperature to give 154 mg of the title compound as an amorphous yellow solid. The product was used without further purification.

LC-MS retention time 3.14 min; 673 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 2 min, and an analysis time of 5 min where solvent A was 10% acetonitrile/90% H2O/0.1% TFA and solvent B was 90% H2O/10% acetonitrile/0.1% TFA. MS data was determined using a Micromass Platform for LC in electrospray mode.

LC-MS retention time 2.16 min; 671 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)-

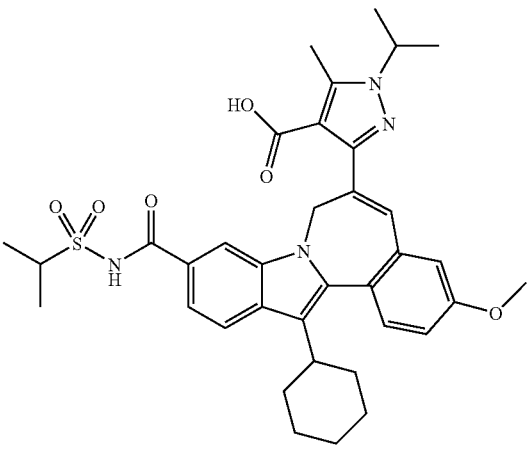

1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)-, methyl ester (153 mg, 0.227 mmol) was dissolved in THF (2.2 mL) and Methanol (2.2 mL). To the clear orange/amber solution aqueous 1.0N sodium hydroxide (2.2 mL, 2.200 mmol) was added. The reaction mixture turned a rose/red color and was slightly cloudy which became clear within 24 hrs. The reaction was stirred under a nitrogen atmosphere at room temperature for 14 days. Progression of the reaction was measured at intervals of every few days by taking a 15 ul aliquot diluting in acetonitrile and adding 1 to 2 drops of water to dissolve salts then analyzing the solution by LCMS.

The reaction was partitioned between 1.0N aqueous hydrochloric acid and ethyl acetate. The aqueous phase was extracted 1× using ethyl acetate and the organic extracts combined and washed with brine and dried over magnesium sulfate. Filtering and removing solvents in vacuo using a rotary evaporator gave a orange amorphous solid. The crude product was dried in vacuo at room temperature to yield 151 mg of amorphous amber-orange solid. The crude product was used without further purification.

LC-MS retention time 2.85 min; 659 m/z (MH+). LC data was recorded on a Shimadzu LC-10AS liquid chromatograph equipped with a Waters Sunfire C18 5u 4.6×50 mm column using a SPD-10AV UV-Vis detector at a detector wave length of 220 nM. The elution conditions employed a flow rate of 4 ml/min, a gradient of 100% solvent A/0% solvent B to 0% solvent A/100% solvent B, a gradient time of 3 min, a hold time of 1 min, and an analysis time of 4 min where solvent A was 10% acetonitrile/90% H2O/0.1% TFA and solvent B was 90% H2O/10% acetonitrile/0.1% TFA. MS data was determined using a Micromass Platform for LC in electrospray mode.

7H-indolo[2,1-a][2]benzazepine-10-carboxamide, 13-cyclohexyl-6-[4-[[(2R,6S)-2,6-dimethyl-4-morpholinyl]carbonyl]-5-methyl-1-(1-methylethyl)-1H-pyrazol-3-yl]-3-methoxy-N-[(1-methylethyl)sulfonyl]-

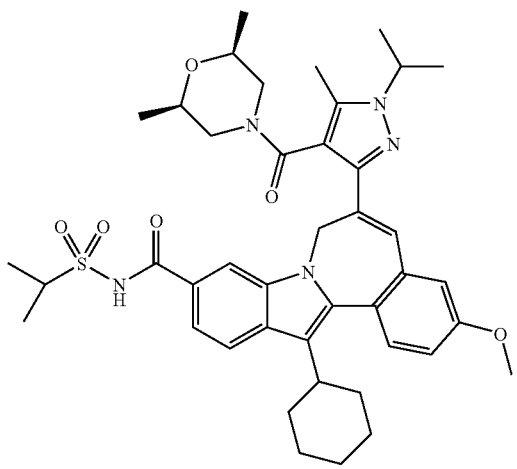

In a 2 dram vial, 1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)- (50 mg, 0.076 mmol) was dissolved in DMF (759 µL) then HATU (66 mg, 0.174 mmol) was added to the reaction. The reaction was stirred at room temperature under a nitrogen atmosphere for 20 minutes and DMAP (30.3 mg, 0.248 mmol) was added to the reaction followed by the amine reagent, (2R,6S)-2,6-dimethylmorpholine (28.2 µL, 0.228 mmol). The reaction was capped under a nitrogen atmosphere and stirred at room temperature overnight (16 hrs).

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 50% solvent A/50% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system. Volatiles from the product fraction at retention time 15.9 minutes were removed in vacuo and the title compound was dried in vacuo at room temperature to yield 25.9 mg of a yellow amorphous solid.

1H NMR of sample shows characteristics of restricted rotation.

1H NMR (500 MHz, CHLOROFORM-D) δ ppm 0.80 (s, 1.2H) 0.96 (d, J=4.58 Hz, 0.4H) 1.07 (d, J=5.80 Hz, 2.3H) 1.17-1.29 (m, 1.2H) 1.31-1.40 (m, 1.1H) 1.39-1.45 (m, 1.1H) 1.46-1.54 (m, 9.9H) 1.56 (d, J=12.51 Hz, 0.6H) 1.61 (d, J=6.41 Hz, 0.8H) 1.65 (d, J=6.10 Hz, 0.5H) 1.72 (t, J=6.41 Hz, 2.0H) 1.78 (d, J=10.99 Hz, 2.0H) 1.89-2.02 (m, 2.0H) 2.02-2.17 (m, 2.8H) 2.20 (s, 0.9H) 2.27 (s, 2.0H) 2.30-2.44 (m, 1.5H) 2.49 (d, J=13.12 Hz, 0.5H) 2.71 (br.s, 4.2H) 2.81-3.01 (m, 2.3H) 3.15 (s, 0.4H) 3.27 (d, J=12.82 Hz, 0.5H) 3.35-3.43 (m, 0.7H) 3.47-3.57 (m, 0.5H) 3.90 (d, J=4.58 Hz, 3.0H) 4.01-4.15 (m, 1.1H) 4.32 (dd, J=20.29, 14.19 Hz, 0.7H) 4.38-4.55 (m, 2.0H) 5.15 (d, J=15.56 Hz, 0.2H) 5.46 (d, J=15.26 Hz, 0.1H) 5.80 (d, J=14.34 Hz, 0.4H) 5.93 (d, J=14.34 Hz, 0.3H) 6.75 (s, 0.4H) 6.83-6.93 (m, 0.6H) 6.94-7.01 (m, J=22.89 Hz, 1.0H) 7.03 (dd, J=8.55, 2.14 Hz, 1.0H) 7.39 (t, J=7.17 Hz, 0.7H) 7.52 (d, J=8.55 Hz, 1.1H) 7.60 (d, J=8.24 Hz, 0.2H) 7.82-7.98 (m, 1.5H) 8.02-8.11 (m, 0.4H) 8.34 (d, J=19.84 Hz, 0.6H) 9.17 (s, 0.1H) 10.02 (s, 0.2H).

LC-MS retention time 1.96 min; 754 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-3-methoxy-N-[(1-methylethyl)sulfonyl]-6-[5-methyl-4-[(3-methyl-3,8-diazabicyclo[3.2.1]oct-8-yl)carbonyl]-1-(1-methylethyl)-1H-pyrazol-3-yl]-

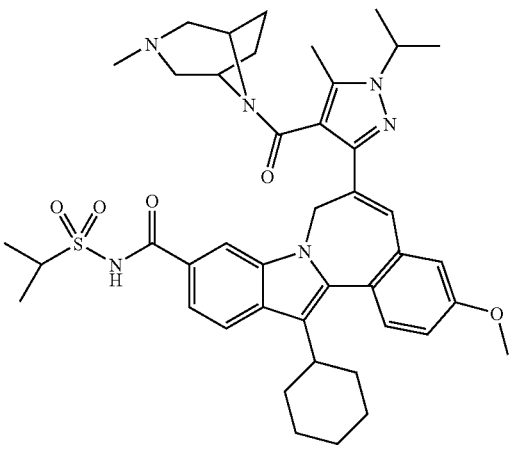

1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)- (50 mg, 0.076 mmol) was dissolved in DMF (759 µL) and HATU (59.6 mg, 0.157 mmol) to the reaction. The reaction was stirred under a nitrogen atmosphere for 55 minutes then DMAP (52.0 mg, 0.426 mmol) was added to the reaction followed by the amine reagent, 3-methyl-3,8-diazabicyclo[3.2.1]octane dihydrochloride (37.8 mg, 0.190 mmol). The reaction was capped under a nitrogen atmosphere and stirred at room temperature for 63 hours.

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile with 2 drops of trifluoroacetic acid added, filtered through a syringe filter and the filtrate purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 30 minutes using % A=10% acetonitrile, 90% water, 0.1% TFA % B=90% acetonitrile, 10% water, 0.1% TFA solvent system.

The retention time of the product was 8.84 min. The volatiles/solvents were removed in vacuo from the product fraction using a rotary evaporator and the product dried in vacuo at room temperature to yield 27.4 mg of the title compound as a yellow solid.

The 1H NMR shows characteristics of restricted rotation and/or salt formation exhibiting broadening of peaks and multiple peak sets, integrals rounded to nearest whole number.

1H NMR (500 MHz, CHLOROFORM-D) δ ppm 0.59 (s, 1H) 0.89 (s, 1H) 1.22 (d, J=20.14 Hz, 1H) 1.29-1.66 (m, 12H) 1.77 (d, J=10.38 Hz, 4H) 1.87-2.14 (m, 5H) 2.16-2.48 (m, 4H) 2.79-3.07 (m, 3H) 3.10-3.81 (m, 7H) 3.90 (s, 3H) 4.04 (d, J=39.06 Hz, 2H) 4.48 (s, 2H) 4.67 (s, 1H) 4.99 (d, J=94.00 Hz, 1H) 5.71 (s, 1H) 5.98 (s, 1H) 6.70-6.97 (m, 2H) 7.04 (d, J=7.63 Hz, 1H) 7.34-7.63 (m, 2H) 7.76-7.94 (m, 2H) 8.06 (s, 1H) 9.34 (s, 1H) 9.70 (s, 1H)

LC-MS retention time 2.01 min; 765 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

7H-indolo[2,1-a][2]benzazepine-10-carboxamide, 13-cyclohexyl-3-methoxy-N-[(1-methylethyl)sulfonyl]-6-[5-methyl-1-(1-methylethyl)-4-[[(3R,5S)-3,4,5-trimethyl-1-piperazinyl]carbonyl]-1H-pyrazol-3-yl]-

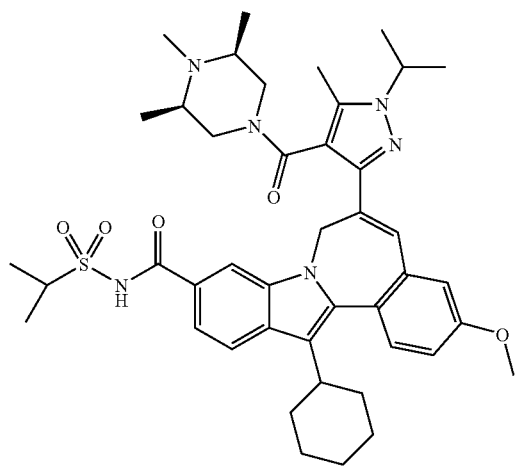

1H-pyrazole-4-carboxylic acid, 3-[13-cyclohexyl-3-methoxy-10-[[[(1-methylethyl)sulfonyl]amino]carbonyl]-7H-indolo[2,1-a][2]benzazepin-6-yl]-5-methyl-1-(1-methylethyl)- (46 mg, 0.070 mmol) was dissolved in DMF (698 μL) and HATU (61.6 mg, 0.162 mmol) was added to the reaction. The reaction was capped and stirred for 68 minutes at room temperature then DMAP (44.5 mg, 0.364 mmol) was added to the reaction followed by (2R,6S)-1,2,6-trimethylpiperazine dihydrochloride (35.9 mg, 0.178 mmol). The reaction was capped under a nitrogen atmosphere and stirred at room temperature for 17 hrs.

The product was purified on a Shimadzu high pressure liquid chromatography system employing Discovery VP software interfaced with a SCL-10A controller, SIL-10A autosampler and FRC-10A fraction collector. The reaction was diluted to 2 ml with acetonitrile and 2 drops of TFA added to ensure protonation then filtered through a 0.45 uM syringe filter and purified using a Waters Sunfire Prep C18 OBD, 5 uM 19 mm×150 mm column and monitored using a SPD-10AV UV-Vis detector at a detector wave length of 220 nM. The elution conditions employed a flow rate of 25 mL/min, a gradient of 70 solvent A/30% solvent B to 0% solvent A/100% solvent B, a gradient time of 20 minutes with a run time of 20 minutes using % A=10% acetonitrile, 90% water, 0.1% TFA % B=90% acetonitrile, 10% water, 0.1% TFA solvent system.

Volatiles were removed from the product fractions in vacuo overnight using a speed-vac on the medium heating setting. The product fraction were combined in dichloromethane then solvent removed in vacuo and the product was dried in vacuo at room temperature to give 27.0 mg of the title compound as a brown-tan amorphous solid.

1H NMR is characteristic of restricted rotation and or salt formation.

1H NMR (500 MHz, CHLOROFORM-D) δ ppm 0-0.61 (m, 2.7H) 0.91 (t, J=7.32 Hz, 0.8H) 0.98-1.14 (m, 2.6H) 1.17-1.44 (m, 5.9H) 1.48 (s, 10.7H) 1.57-1.86 (m, 5.3H) 1.88-2.12 (m, 4.2H) 2.13-2.38 (m, 5.0H) 2.40-2.82 (m, 9.1H) 2.84-3.06 (m, 1.9H) 3.09-3.80 (m, 2.7H) 3.91 (d, J=10.07 Hz, 3.0H) 4.07 (d, J=10.99 Hz, 1.3H) 4.22-4.40 (m, 0.6H) 4.42-4.51 (m, 1.0H) 4.55 (d, J=13.73 Hz, 0.3H) 4.68 (dd, J=30.98, 14.80 Hz, 0.5H) 5.04 (d, J=15.87 Hz, 0.3H) 5.83 (d, J=15.26 Hz, 0.3H) 6.01 (d, J=15.56 Hz, 0.2H) 6.68-6.78 (m, 0.3H) 6.91 (d, J=27.47 Hz, 0.7H) 6.96-7.11 (m, 1.9H) 7.38 (dd, J=15.26, 7.93 Hz, 0.6H) 7.48-7.58 (m, 1.0H) 7.72 (d, J=7.93 Hz, 0.3H) 7.86 (d, J=8.24 Hz, 0.8H) 7.93 (s, 0.9H) 8.08 (s, 0.3H) 8.37 (d, J=33.57 Hz, 0.5H) 9.94 (s, 0.3H) 11.49 (s, 0.4H).

LC-MS retention time 2.04 min; 767 m/z (MH−). LC data was recorded on a Shimadzu LC-10AS liquid chromatograph equipped with a Phenomenex-Luna 10u C18 3.0×50 mm column using a SPD-10AV UV-Vis detector at a detector wave length of 220 nM. The elution conditions employed a flow rate of 5 ml/min, a gradient of 100% solvent A/0% solvent B to 0% solvent A/100% solvent B, a gradient time of 3 min, a hold time of 1 min, and an analysis time of 4 min where solvent A was 5% acetonitrile/95% H2O/10 mM ammonium acetate and solvent B was 5% H2O/95% acetonitrile/10 mM ammonium acetate. MS data was determined using a Micromass Platform for LC in electrospray mode.

239

7H-indolo[2,1-a][2]benzazepine-10-carboxylic acid, 13-cyclohexyl-6-[1-ethyl-5-(methoxycarbonyl)-3-methyl-1H-pyrazol-4-yl]-3-methoxy-, 1,1-dimethylethyl ester

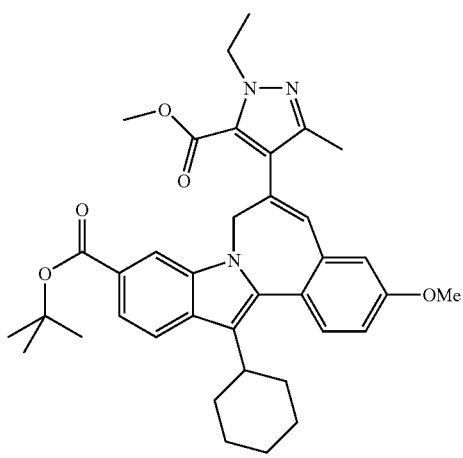

In a microwave tube, 7H-indolo[2,1-a][2]benzazepine-10-carboxylic acid, 13-cyclohexyl-3-methoxy-6-(tributylstannyl)-, 1,1-dimethylethyl ester (1.10 g, 1.50 mmol), methyl 4-bromo-1-ethyl-3-methyl-1H-pyrazole-5-carboxylate (482 mg, 1.92 mmol) and bis(triphenylphosphine)palladium II chloride (105 mg, 0.150 mmol), LiCl (318 mg, 7.51 mmol), CuCl (624 mg, 6.31 mmol) were added. It was then sealed, degassed and flushed with nitrogen. 1,4-Dioxane (7.51 mL) was added. The reaction mixture was heated at 120° C. under microwave condition for 1 hour. It was then filtered and the filtrate was concentrated. The residue was purified on a Shimadzu high pressure liquid chromatography system employing Discovery VP software interfaced with a SCL-10A controller, SIL-10A autosampler and FRC-10A fraction collector. The sample was dissolved in acetonitrile/DMF (1:1) (8 ml) purified using a Waters Sunfire Prep C18 OBD, 5 uM 19 mm×100 mm column and monitored using a SPD-10AV UV-Vis detector at a detector wave length of 220 nM. The elution conditions employed a flow rate of 25 mL/min, a gradient of 25% solvent A/75% solvent B to 0% solvent A/100% solvent B, a gradient time of 10 minutes with a run time of 20 minutes using % A=10% acetonitrile, 90% water, 0.1% TFA % B=90% acetonitrile, 10% water, 0.1% TFA solvent system.

The product-containing fractions were collected and concentrated to give title compound as a yellow oil (916 mg, 0.150 mmol, 40% yield).

MS m/z 610 (MH$^+$).

240

7H-indolo[2,1-a][2]benzazepine-10-carboxylic acid, 13-cyclohexyl-6-[1-ethyl-5-(methoxycarbonyl)-3-methyl-1H-pyrazol-4-yl]-3-methoxy-

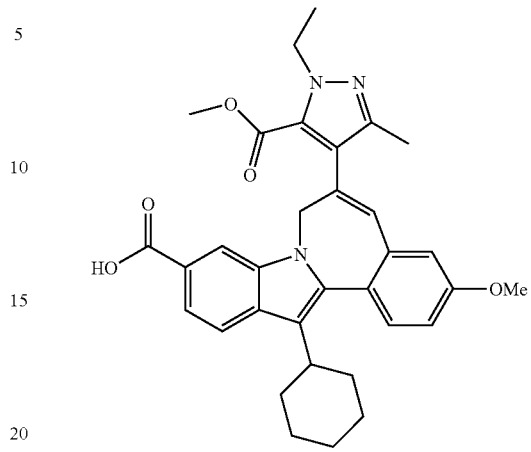

To a solution of 7H-indolo[2,1-a][2]benzazepine-10-carboxylic acid, 13-cyclohexyl-6-[1-ethyl-5-(methoxycarbonyl)-3-methyl-1H-pyrazol-4-yl]-3-methoxy-, 1,1-dimethylethyl ester (290 mg, 0.476 mmol) in 1,2-dichloroethane (0.951 mL), TFA (0.951 mL) was added. The reaction mixture was stirred at RT for 2 hours. Volatiles were removed on a rotary evaporator to give the title compound as a brownish thick oil as crude product (263 mg, 0.476 mmol, 100% yield).

MS m/z 568 (MH$^+$).

1H-pyrazole-5-carboxylic acid, 4-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, methyl ester

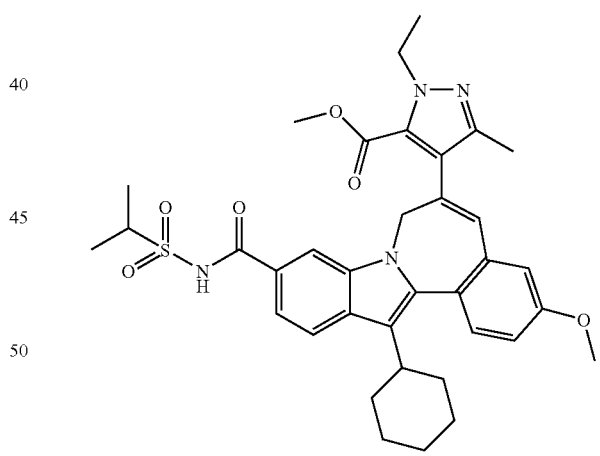

To a solution of 7H-indolo[2,1-a][2]benzazepine-10-carboxylic acid, 13-cyclohexyl-6-[1-ethyl-5-(methoxycarbonyl)-3-methyl-1H-pyrazol-4-yl]-3-methoxy-(260 mg, 0.470 mmol) in tetrahydrofuran (1.57 mL) was added carbonyldiimidazole (228 mg, 1.41 mmol). The reaction mixture was heated at 60° C. for one hour. Propane-2-sulfonamide (231 mg, 1.88 mmol) and DBU (0.212 mL, 1.41 mmol) were added at room temperature. The reaction mixture was then heated at 60° C. for 2 hours. The reaction mixture was diluted with 1N HCl (50 mL) solution and extracted with chloroform (50 mL). The organic layers were combined and concentrated on a rotary evaporator to give an orange oil as crude product. It was purified through silica gel using 90/9/1 methylene chloride/MeOH/AcOH as the eluent to give the title compound (269 mg, 0.409 mmol, 87% yield) as a yellow oil.

MS m/z 659 (MH+).

1H-pyrazole-5-carboxylic acid, 4-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-

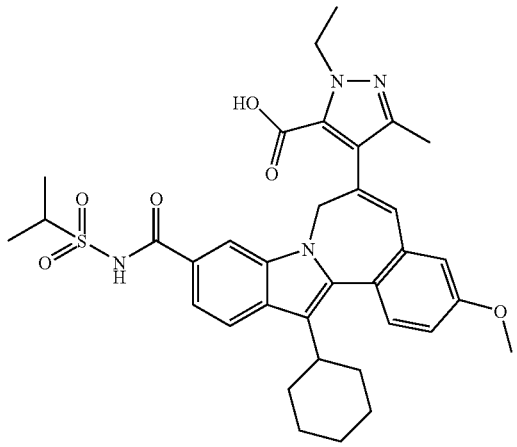

To a mixture of 1H-pyrazole-5-carboxylic acid, 4-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, methyl ester (260 mg, 0.395 mmol) was dissolved in dioxane (1.97 mL) and methanol (1.97 mL) was added to the reaction followed by 1N aqueous sodium hydroxide (3.95 mL). The reaction was capped under a nitrogen atmosphere and stirred at room temperature for 72 hrs. The reaction was diluted with chloroform (50.0 mL) and washed with 1.0N aqueous hydrochloric acid (50 ml). The organic layer was concentrated in vacuo using a rotary evaporator to yield the title compound as a yellow solid (252 mg, 0.391 mmol, 99%).

MS m/z 645 (MH+).

7H-indolo[2,1-a][2]benzazepine-10-carboxamide, 13-cyclohexyl-6-[1-ethyl-3-methyl-5-(4-morpholinylcarbonyl)-1H-pyrazol-4-yl]-3-methoxy-N-[(1-methylethyl)sulfonyl]-

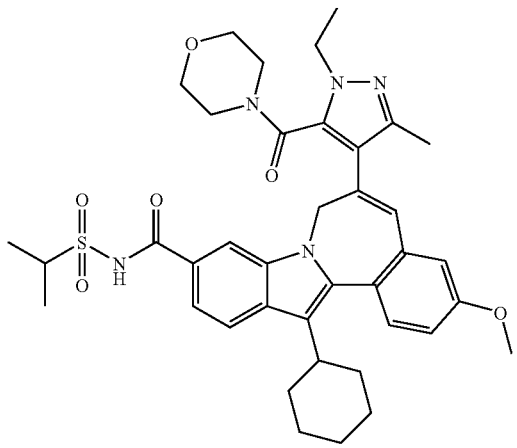

To a solution of 1H-pyrazole-5-carboxylic acid, 4-[13-cyclohexyl-3-methoxy-10-[[[(1-methylethyl)sulfonyl]amino]carbonyl]-7H-indolo[2,1-a][2]benzazepin-6-yl]-1-ethyl-3-methyl- (35 mg, 0.054 mmol) in DMF (0.54 mL), TBTU (35 mg, 0.109 mmol) and DIPEA (0.028 mg, 0.22 mmol) were added. The reaction mixture was stirred at RT for 15 min. Then morpholine (19 mg, 0.22 mmol) was added. The solution was stirred at RT for overnight. The reaction mixture was purified by prep HPLC column using CH3CN/H2O/TFA as solvent system. Fractions were collected and concentrated under speedvac overnight to yield the title compound as a beige solid (26 mg, 0.036 mmol, 81% yield).

MS m/z 714 (MH+)

1H NMR (500 MHz, CHLOROFORM-D) δ ppm 1.19-1.62 (m, 13H) 1.76-2.30 (m, 6H) 2.41 (s, 3H) 2.60 (m, 1H) 2.77-3.22 (m, 8H) 3.94 (s, 3H) 4.13 (m, 2H) 4.30 (m, 1H) 4.63 (br d, 1H) 4.83 (br d, 1H) 6.72 (s, 1H) 6.97 (s, 1H) 7.12 (d, J=8.24 Hz, 1H) 7.65-7.70 (m, 3H) 7.98 (d, J=8.24 Hz, 1H) 10.38 (s, 1H).

The following compounds were synthesized by an analogous method as described above for 7H-indolo[2,1-a][2]benzazepine-10-carboxamide, 13-cyclohexyl-6-[1-ethyl-3-methyl-5-(4-morpholinylcarbonyl)-1H-pyrazol-4-yl]-3-methoxy-N-[(1-methylethyl)sulfonyl]-:

7H-indolo[2,1-a][2]benzazepine-10-carboxamide, 13-cyclohexyl-6-[5-[[(2R,6S)-2,6-dimethyl-4-morpholinyl]carbonyl]-1-ethyl-3-methyl-1H-pyrazol-4-yl]-3-methoxy-N-[(1-methylethyl)sulfonyl]-

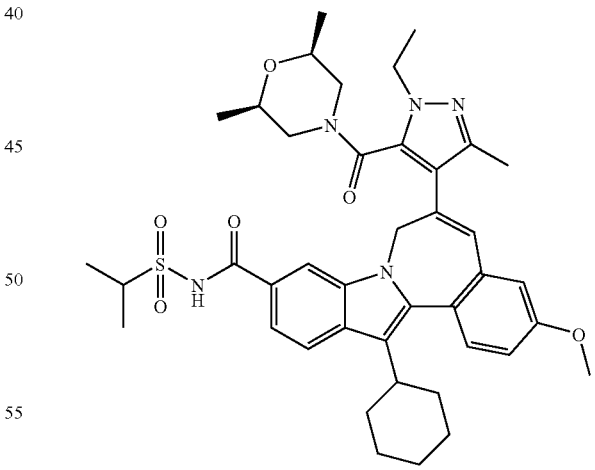

MS m/z 742 (MH+). 1H NMR (500 MHz, CHLOROFORM-D) δ ppm 0.75 (m, 6H) 1.05-1.62 (m, 13H) 1.76-2.26 (m, 6H) 2.33 (m, 1H) 2.39 (s, 3H) 2.81-3.29 (m, 4H) 3.70-4.01 (m, 5H) 4.14 (m, 2H) 4.27 (m, 1H) 4.63 (br d, 1H) 4.83 (br d, 1H) 6.70 (s, 1H) 6.98 (s, 1H) 7.18 (br d, 1H) 7.65-7.81 (m, 3H) 7.96 (d, J=8.24 Hz, 1H) 10.49 (s, 1H).

7H-indolo[2,1-a][2]benzazepine-10-carboxamide, 13-cyclohexyl-6-[1-ethyl-3-methyl-5-[(4-methyl-1-piperazinyl)carbonyl]-1H-pyrazol-4-yl]-3-methoxy-N-[(1-methylethyl)sulfonyl]-

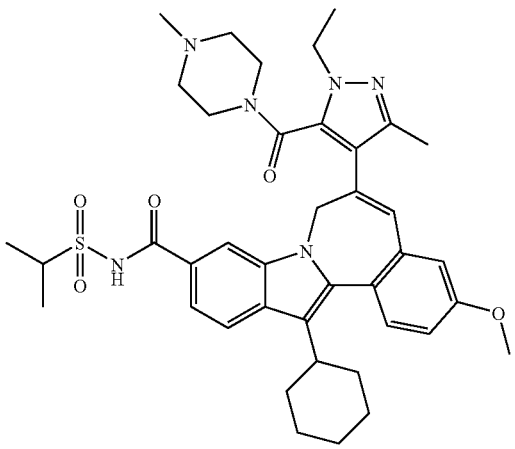

MS m/z 727 (MH+). 1H NMR (500 MHz, CHLOROFORM-D) δ ppm 1.22-1.62 (m, 13H) 1.76-2.20 (m, 6H) 2.39 (br s, 6H) 2.78-3.90 (m, 9H) 3.96 (s, 3H) 4.08-4.25 (m, 3H) 4.63 (br d, 1H) 4.73 (br d, 1H) 6.78 (s, 1H) 6.99 (s, 1H) 7.12 (br d, 1H) 7.62-7.82 (m, 3H) 7.98 (br d, 1H) 10.02 (br s, 1H).

7H-indolo[2,1-a][2]benzazepine-10-carboxamide, 13-cyclohexyl-6-[1-ethyl-3-methyl-5-[[(3R,5S)-3,4,5-trimethyl-1-piperazinyl]carbonyl]-1H-pyrazol-4-yl]-3-methoxy-N-[(1-methylethyl)sulfonyl]-

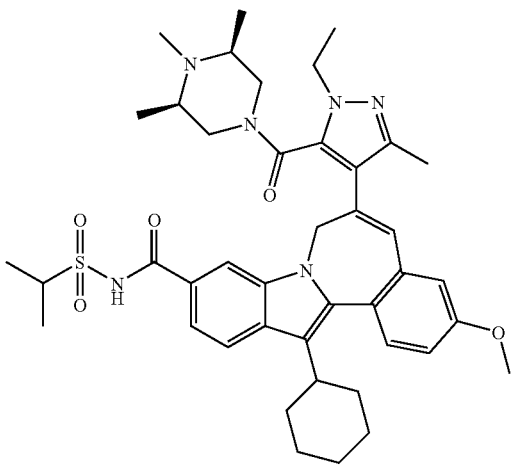

MS m/z 755 (MH+). 1H NMR (500 MHz, CHLOROFORM-D) δ ppm 1.04 (m, 6H) 1.25-1.62 (m, 13H) 1.76-2.13 (m, 6H) 2.31 (br s, 3H) 2.40 (s, 3H) 2.99-3.12 (m, 3H) 3.35-3.52 (m, 2H) 3.90-3.99 (m, 4H) 4.05-4.25 (m, 4H) 4.64 (br d, 1H) 4.85 (br d, 1H) 6.76 (s, 1H) 6.98 (s, 1H) 7.13 (d, J=8.24 Hz, 1H) 7.59 (d, J=8.24 Hz, 1H) 7.82 (m, 2H) 8.00 (d, J=8.24 Hz, 1H) 10.05 (s, 1H).

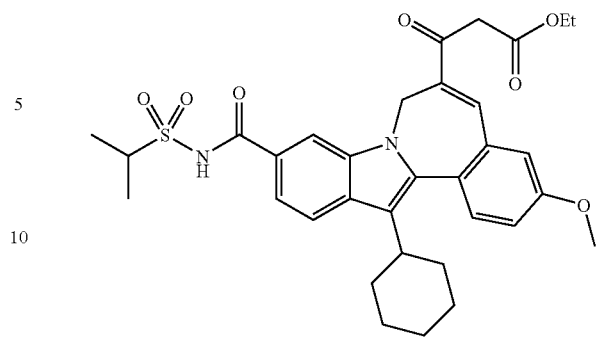

7H-indolo[2,1-a][2]benzazepine-6-propanoic Acid, 13-cyclohexyl-3-methoxy-10-[[[(1-methylethyl)sulfonyl]amino]carbonyl]-beta-oxo-, ethyl ester To a stirred solution of 7H-indolo[2,1-a][2]benzazepine-6-carboxylic acid, 13-cyclohexyl-3-methoxy-10-[[[(1-methylethyl)sulfonyl]amino]carbonyl]-(4 g, 7.45 mmol) in THF (20 mL) was added CDI (1.151 g, 7.10 mmol) and the mixture was heated at 45° C. for 0.5 h and the reaction mixture was cooled and transferred into a suspension of magnesium chloride (1.419 g, 14.91 mmol) and potassium ethyl malonate (2.54 g, 14.91 mmol) in THF (15 mL). Additional THF (40 mL) was added to dissolve the ensuing precipitation. The reaction mixture was stirred for 0.5 h at r. t. and then heated at 60° C. overnight. Rxn mixture was cooled to rt and diluted with EtOAc, washed with 1N HCl, brine and dried (Mg2SO4). Crude product was purified on a Thomson 160 g column (MeOH/DCM: 0 to 25%) to afford the product as a reddish solid (3.8 g, 84%). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H₂O/90% MeOH/0.1% Trifluoroacetic Acid; Column: XBridge 4.6×50 mm S5.

LC/MS: retention time 3.418 min, m/z 607 (MH+).

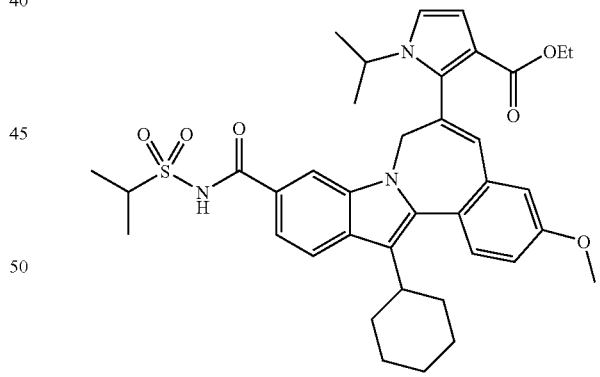

1H-pyrrole-3-carboxylic acid, 2-[13-cyclohexyl-3-methoxy-10-[[[(1-methylethyl)sulfonyl]amino]carbonyl]-7H-indolo[2,1-a][2]benzazepin-6-yl]-1-(1-methylethyl)-, ethyl ester To a solution of 7H-indolo[2,1-a][2]benzazepine-6-propanoic acid, 13-cyclohexyl-3-methoxy-10-[[[(1-methylethyl)sulfonyl]amino]carbonyl]-beta-oxo-, ethyl ester (0.8 g, 1.055 mmol) in THF (3 mL) was added propan-2-amine (0.624 g, 10.55 mmol) and Tosic Acid (10.03 mg, 0.053 mmol). The mixture was stirred at r.t. for 0.5 h and 1,2- dibromoethyl acetate (0.337 g, 1.371 mmol) was added at 0° C. The reaction mixture was stirred at r.t. for 0.5 h and then sodium hydride (0.051 g, 2.110 mmol) was added and stirred for 10 min at r.t. The mixture was heated at 60° C. for 3 h and cooled to r.t., diluted with EtOAc and washed with ice cold HCl (1N), brine and dried (MgSO4). Crude product was purified on a Biotage 25M column, (EtOAc/hexane: 5-100%) to afford the compound as a beige foam (0.26 g, 35%). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.631 min, m/z 672 (MH+).

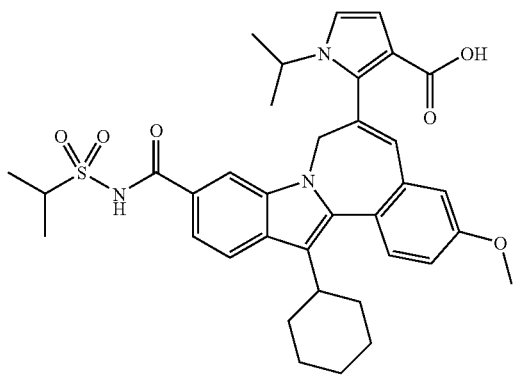

1H-pyrrole-3-carboxylic acid, 2-[13-cyclohexyl-3-methoxy-10-[[[(1-methylethyl)sulfonyl]amino]carbonyl]-7H-indolo[2,1-a][2]benzazepin-6-yl]-1-(1-methylethyl)-

To a solution of 1H-pyrrole-3-carboxylic acid, 2-[13-cyclohexyl-3-methoxy-10-[[[(1-methylethyl)sulfonyl]amino] carbonyl]-7H-indolo[2,1-a][2]benzazepin-6-yl]-1-(1-methylethyl)-, ethyl ester (80 mg, 0.119 mmol) in THF (2 mL) and was added potassium trimethylsilanolate (45.8 mg, 0.357 mmol). The mixture was stirred under nitrogen for 30 min and another portion of potassium trimethylsilanolate (100 mg) was added. The reaction mixture was stirred at r.t. for 2 days and diluted with EtOAc, washed with cold 1 N HCl, brine, dried (MgSO4) and removed the solvent to afford the acid as a beige solid (71 mg, 88%). 1H NMR (400 MHz, CHLOROFORM-d) δ ppm 8.80 (1H, br. s.), 7.81-7.89 (1H, m), 7.76 (1H, s), 7.45-7.52 (1H, m), 7.42 (1H, d, J=6.29 Hz), 7.03 (1H, dd, J=8.69, 2.64 Hz), 6.93 (1H, d, J=2.27 Hz), 6.47-6.76 (3H, m), 4.98 (1H, d, J=13.85 Hz), 4.61 (1H, d, J=14.60 Hz), 3.97-4.07 (1H, m), 3.89 (1H, s), 3.34-3.52 (1H, m), 2.73-2.89 (1H, m), 1.87-2.12 (4H, m), 1.66-1.84 (2H, m), 0.81-1.55 (19H, m). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.503 min, m/z 644 (MH+).

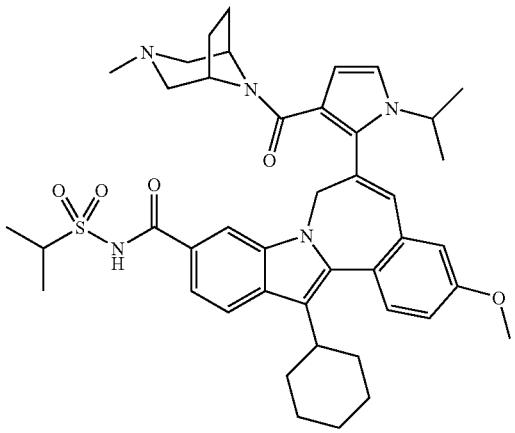

13-Cyclohexyl-6-(1-isopropyl-3-(3-methyl-3,8-diazabicyclo[3.2.1]octane-8-carbonyl)-1H-pyrrol-2-yl)-3-methoxy-N-(isopropylsulfonyl)-7H-indolo[2,1-a][2]benzazepine-10-carboxamide 1H NMR (400 MHz, CHLOROFORM-d) δ ppm 7.87 (1H, d, J=8.56 Hz), 7.78 (1H, s), 7.66 (1H, d, J=8.06 Hz), 7.54 (1H, d, J=8.31 Hz), 7.02-7.09 (1H, m), 6.89 (1H, d, J=2.77 Hz), 6.83 (1H, br. s.), 6.69 (1H, br. s.), 6.48 (1H, br. s.), 4.91 (1H, d, J=15.36 Hz), 4.55 (1H, d, J=15.61 Hz), 4.48 (1H, br. s.), 4.01-4.13 (1H, m), 3.93 (3H, s), 3.58 (1H, br. s.), 3.12 (1H, br. s.), 2.78-2.92 (1H, m), 1.70-2.34 (14H, m), 1.13-1.68 (16H, m), 1.05 (1H, br. s.), 0.52 (1H, br. s.), −0.30 (1H, br. s.). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.331 min, m/z 752 (MH+).

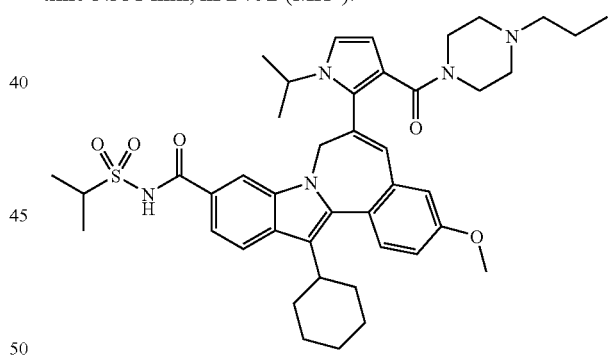

13-Cyclohexyl-6-(1-isopropyl-3-(4-propylpiperazine-1-carbonyl)-1H-pyrrol-2-yl)-3-methoxy-N-(isopropylsulfonyl)-7H-indolo[2,1-a][2]benzazepine-10-carboxamide. 1H NMR (400 MHz, CHLOROFORM-d) δ ppm 7.87 (1H, d, J=8.56 Hz), 7.79 (1H, s), 7.59 (1H, d, J=8.31 Hz), 7.53 (1H, d, J=8.56 Hz), 7.05 (1H, dd, J=8.69, 2.64 Hz), 6.90 (1H, d, J=2.52 Hz), 6.78 (1H, br. s.), 6.68 (1H, s), 6.32 (1H, d, J=2.27 Hz), 4.91 (1H, d, J=14.60 Hz), 4.55 (2H, d, J=14.86 Hz), 3.99-4.50 (2H, m), 3.95-4.32 (1H, m), 3.92 (3H, s), 2.70-3.19 (5H, m), 1.86-2.16 (8H, m), 1.67-1.84 (2H, m), 1.09-1.64 (18H, m), 0.65-0.83 (3H, m). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.330 min, m/z 754 (MH+).

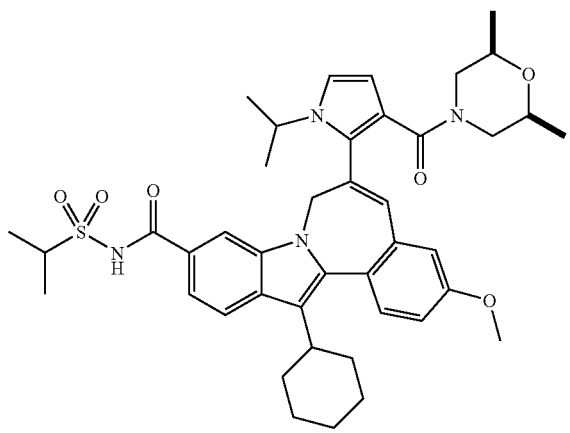

13-Cyclohexyl-6-(3-((2S,6R)-2,6-dimethylmorpholine-4-carbonyl)-1-isopropyl-1H-pyrrol-2-yl)-3-methoxy-N-(isopropylsulfonyl)-7H-indolo[2,1-a][2]benzazepine-10-carboxamide. 1H NMR (400 MHz, CHLOROFORM-d) δ ppm 7.87-7.93 (1H, m), 7.75 (1H, br. s.), 7.44-7.66 (2H, m), 7.01-7.12 (1H, m), 6.90 (1H, br. s.), 6.83 (1H, br. s.), 6.64 (1H, br. s.), 6.37 (1H, br. s.), 4.90 (0H, d, J=14.86 Hz), 4.57 (1H, s), 4.31-4.50 (1H, m), 4.05-4.16 (1H, m), 3.94 (3H, s), 3.85-3.92 (1H, m), 2.70-3.74 (5H, m), 1.84-2.25 (7H, m), 1.66-1.84 (2H, m), 0.97-1.66 (20H, m), 0.53-0.93 (5H, m); LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H$_2$O/90% MeOH/0.1% Trifluoroacetic Acid; Column: XBridge 4.6×50 mm S5.

LC/MS: retention time 3.550 min, m/z 741 (MH$^+$).

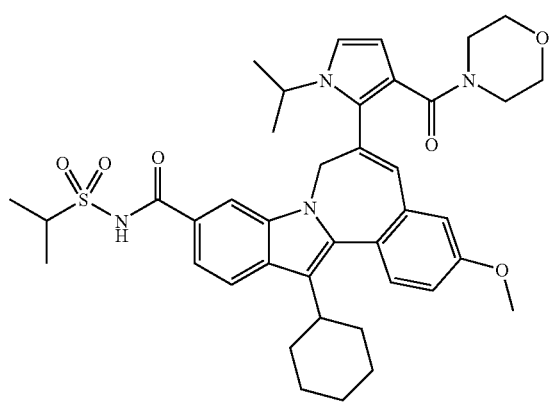

13-Cyclohexyl-6-(1-isopropyl-3-(morpholine-4-carbonyl)-1H-pyrrol-2-yl)-3-methoxy-N-(isopropylsulfonyl)-7H-indolo[2,1-a][2]benzazepine-10-carboxamide. 1H NMR (400 MHz, CHLOROFORM-d) δ ppm 10.21 (1H, br. s.), 7.92 (1H, d, J=8.56 Hz), 7.84 (1H, s), 7.61 (1H, d, J=8.31 Hz), 7.56 (1H, d, J=8.81 Hz), 7.09 (1H, dd, J=8.69, 2.64 Hz), 6.90 (1H, d, J=2.77 Hz), 6.82 (1H, br. s.), 6.69 (1H, s), 6.36 (1H, d, J=2.52 Hz), 4.94 (1H, d, J=14.86 Hz), 4.56 (1H, d, J=15.11 Hz), 4.38 (1H, br. s.), 4.02-4.12 (1H, m), 3.94 (3H, s), 3.58-4.14 (2H, m), 2.53-3.28 (6H, m), 1.95 (1H, br. s.), 1.88-2.30 (4H, m), 1.72-1.85 (2H, m), 1.08-1.64 (16H, m).

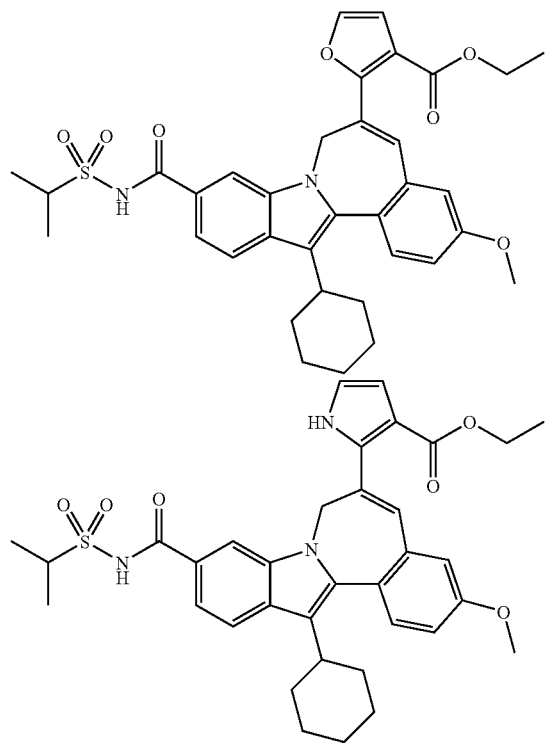

3-Furancarboxylic acid, 2-[13-cyclohexyl-3-methoxy-10-[[[(1-methylethyl)sulfonyl]amino]carbonyl]-7H-indolo[2,1-a][2]benzazepin-6-yl]-, Ethyl ester 1H-pyrrole-3-carboxylic acid, 2-[13-cyclohexyl-3-methoxy-10-[[[(1-methylethyl)sulfonyl]amino]carbonyl]-7H-indolo[2,1-a][2]benzazepin-6-yl]-, Ethyl ester To a solution of starting 7H-indolo[2,1-a][2]benzazepine-6-propanoic acid, 13-cyclohexyl-3-methoxy-10-[[[(1-methylethyl)sulfonyl]amino]carbonyl]-beta-oxo-, ethyl ester (1.200 g, 1.978 mmol) in THF (20 mL) was added 1,2-dibromoethyl acetate in THF (0.26 M, 9.13 mL, 2.373 mmol). NH$_3$ was then bubbled through the mixture for 10 min and the reaction was maintained under ammonia (1 atmosphere) overnight. The mixture was then heated at 60° C. for 2 h and then cooled to room temperature, diluted with EtOAc and washed with cold 0.5 N HCl (3×) and brine. The organic layer was then dried (MgSO$_4$) and filtered and the filtrate evaporated under reduced pressure. The crude product was purified on a Biotage 40M Column (EtOAc/hexane 0% to 100%) to afford a yellow solid which was further purified by preparative HPLC to afford the title furan (65 mg, 5%) and title pyrrole (145 mg, 11%). Furan product: 1H NMR (400 MHz, METHANOL-d$_4$) δ ppm 8.10 (1H, s), 7.90 (1H, d, J=8.56 Hz), 7.81 (1H, s), 7.49-7.63 (3H, m), 7.05-7.18 (2H, m), 6.86 (1H, d, J=2.01 Hz), 5.93 (1H, d, J=14.35 Hz), 4.28-4.47 (3H, m), 3.94-4.02 (1H, m), 3.92 (3H, s), 2.79-2.96 (1H, m), 1.86-2.23 (4H, m), 1.69-1.84 (2H, m), 1.44 (6H, d, J=6.80 Hz), 1.35 (3H, t, J=7.05 Hz), 1.27-1.60 (4H, m). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column:

XBridge 4.6×50 mm S5. LC/MS: retention time 3.736 min, m/z 631 (MH+). Pyrrole product: 1H NMR (400 MHz, MeOD) δ ppm 11.02 (1H, br. s.), 8.03 (1H, br. s.), 7.84 (1H, d, J=8.56 Hz), 7.81 (1H, s), 7.47-7.56 (2H, m), 7.01-7.11 (2H, m), 6.90 (1H, s), 6.58-6.64 (2H, m), 5.44 (1H, d, J=17.63 Hz), 4.51 (1H, d, J=14.10 Hz), 4.18-4.35 (2H, m), 3.87 (3H, s), 3.81-3.97 (1H, m), 2.82-2.95 (1H, m), 1.86-2.20 (4H, m), 1.68-1.84 (2H, m), 1.12-1.55 (13H, m). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.475 min, m/z 630 (MH+).

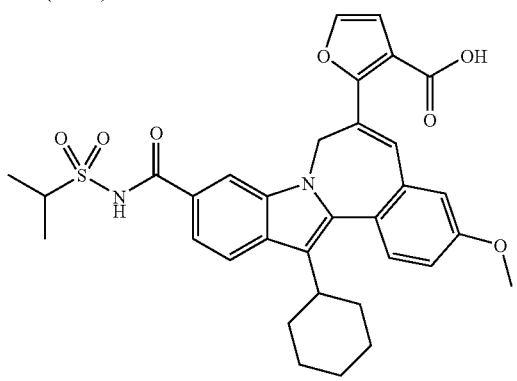

3-Furancarboxylic acid, 2-[13-cyclohexyl-3-methoxy-10-[[[(1-methylethyl)sulfonyl]amino]carbonyl]-7H-indolo[2,1-a][2]benzazepin-6-yl]-

To a mixture of 3-Furancarboxylic acid, 2-[13-cyclohexyl-3-methoxy-10-[[[(1-methylethyl)sulfonyl]amino]carbonyl]-7H-indolo[2,1-a][2]benzazepin-6-yl]-, ethyl ester (63 mg, 0.100 mmol) and potassium trimethylsilanolate (128 mg, 0.999 mmol) was added THF (2 mL). The mixture was stirred at r. t. under nitrogen for 2 h. Diluted with EtOAc and washed with cold 1N HCl and dried (MgSO4), removed the solvents to afford acid (48 mg, 80%). LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5.

LC/MS: retention time 3.558 min, m/z 603 (MH+).

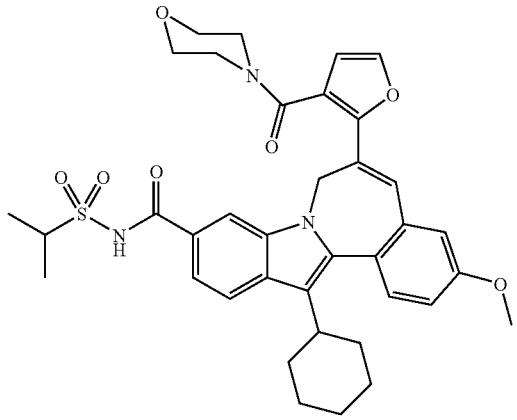

13-cyclohexyl-6-(3-(morpholine-4-carbonyl)furan-2-yl)-3-methoxy-N-(isopropylsulfonyl)-7H-indolo[2,1-a][2]benzazepine-10-carboxamide 1H NMR (400 MHz, CHLOROFORM-d) δ ppm 8.08 (1H, d, J=1.01 Hz), 7.86 (1H, d, J=8.56 Hz), 7.66 (1H, dd, J=8.44, 1.38 Hz), 7.49 (1H, d, J=8.56 Hz), 7.40 (1H, d, J=1.76 Hz), 7.33 (1H, s), 7.04 (1H, dd, J=8.56, 2.77 Hz), 6.96 (1H, d, J=2.52 Hz), 6.48 (1H, d), 5.23 (1H, d), 4.40 (1H, d), 3.99-4.18 (2H, m), 3.90 (3H, s), 3.79-3.95 (1H, m), 3.67-3.78 (2H, m), 3.42-3.51 (2H, m), 3.33-3.41 (1H, m), 3.19-3.31 (1H, m), 2.75-2.88 (1H, m), 1.86-2.13 (4H, m), 1.14-1.83 (12H, m); LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5. LC/MS: retention time 3.276 min, m/z 711 (MH+).

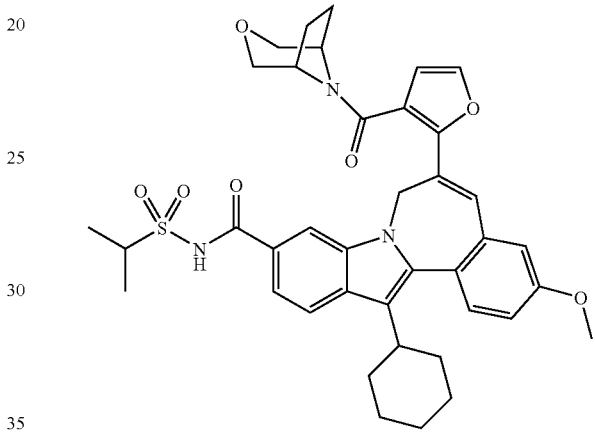

13-cyclohexyl-6-(3-(3-methyl-3,8-diazabicyclo[3.2.1]octane-8-carbonyl)furan-2-yl)-1H-pyrrol-2-yl)-3-methoxy-N-(isopropylsulfonyl)-7H-indolo[2,1-a][2]benzazepine-10-carboxamide. LC/MS method: Start % B: 0; Final % B: 100; Gradient time: 3 min; Stop time: 4 min; Flow rate: 4 mL/min; Wavelength: 220 Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5.

LC/MS: retention time 3.503 min, m/z 644 (MH+).

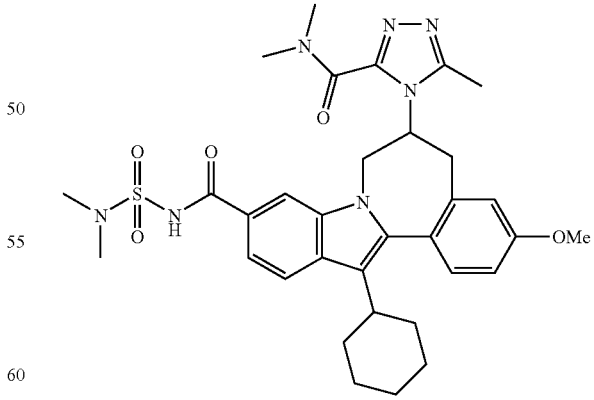

5H-indolo[2,1-a][2]benzazepine-10-carboxamide, 13-cyclohexyl-6-[3-[(dimethylamino)carbonyl]-5-methyl-4H-1,2,4-triazol-4-yl]-N-[(dimethylamino)sulfonyl]-6,7-dihydro-3-methoxy-. To a mixture of ethanediamide, N'-[13-cyclohexyl-10-[[[(dimethylamino)sulfonyl]amino]

carbonyl]-6,7-dihydro-3-methoxy-5H-indolo[2,1-a][2]benzazepin-6-yl]-N,N-dimethyl- (19.9 mg, 0.033 mmol) in CH$_2$Cl$_2$ (1 mL) at 0° C. under N$_2$ was added phosphorus pentachloride (20.4 mg, 0.098 mmol). The mixture was stirred at 0° C. for 2 hours, and then added with acetylhydrazine (7.25 mg, 0.098 mmol). The mixture was stirred at 0° C. for 1 hour, and then at r.t. for 21 hours. The mixture was added another 14.5 mg (0.196 mmol) of acetylhydrazine, evaporated to dryness, added PhCH$_3$ (1 mL), and then stirred at 120° C. for 6 hours. The mixture was cooled to r.t. and then evaporated. The residue was diluted with MeOH and purified by using Shimadzu-VP preparative reverse phase HPLC to obtain the TFA salt of the product using the separation method: Solvent A=10% MeOH-90% H2O-0.1% TFA, Solvent B=90% MeOH-10% H2O-0.1% TFA, Start % B=60, Final % B=90, Gradient time=10 min, Stop time=12 min, Flow Rate=30 mL/min, Column: Xterra Prep MS C18 5u 30×50 mm, Fraction Collection: 7.02-7.62 min. (UV detection at 220 nm). LC/MS were performed by using Shimadzu-VP instrument with UV detection at 220 nm and Waters Micromass. HPLC method: Solvent A=10% MeOH-90% H2O-0.1% TFA, Solvent B=90% MeOH-10% H2O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=648.41, HPLC R$_t$=1.787 min. HPLC method: Solvent A=5% MeCN-95% H2O-10 mM NH$_4$OAc, Solvent B=95% MeCN-5% H2O-10 mM NH$_4$OAc, Start % B=0, Final % B=100, Gradient time=2 min, Stop time=3 min, Flow Rate=5 ml/min, Column: Phenomenex Lina C18 5 um 3.0×50 mm; (ES+) m/z (M+H)$^+$=648.38, HPLC R$_t$=1.260 min. Analytical HPLC were performed by using Shimadzu-VP instrument with UV detection at 254 nm and 256 nm. Analytical HPLC method: Solvent A=5% MeCN-95% H2O-0.1% TFA, Solvent B=95% MeCN-5% H2O-0.1% TFA, Start % B=10, Final % B=100, Gradient time=10 min, Stop time=20 min, Flow Rate=1 ml/min, Column: Waters Sunfire C-18, 4.6×150 mm, 3.5 um; R$_t$=10.46 min; Column: Waters Xbridge Phenyl 4.6×150 mm, 3.5 um; R$_t$=9.42 min.

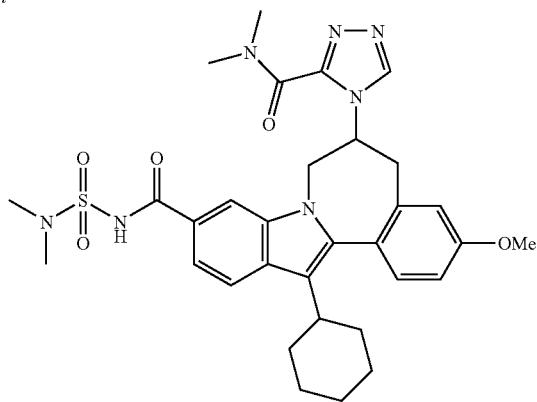

5H-indolo[2,1-a][2]benzazepine-10-carboxamide, 13-cyclohexyl-6-[3-[(dimethylamino)carbonyl]-4H-1,2,4-triazol-4-yl]-N-[(dimethylamino)sulfonyl]-6,7-dihydro-3-methoxy-. This example was prepared in a similar manner as described by using formylhydrazine as the coupling partner. Purification by Shimadzu-VP preparative reverse phase HPLC to obtain the TFA salt of the product using the separation method: Solvent A=10% MeOH-90% H2O-0.1% TFA, Solvent B=90% MeOH-10% H2O-0.1% TFA, Start % B=40, Final % B=90, Gradient time=10 min, Stop time=12 min, Flow Rate=30 mL/min, Column: Xterra Prep MS C18 5u 30×50 mm, Fraction Collection: 9.57-9.99 min. (UV detection at 220 nm).

LC/MS were performed by using Shimadzu-VP instrument with UV detection at 220 nm and Waters Micromass. HPLC method: Solvent A=10% MeOH-90% H2O-0.1% TFA, Solvent B=90% MeOH-10% H2O-0.1% TFA, Start % B=0, Final % B=100, Gradient time=2 min, Stop time=3 min, Flow Rate=5 ml/min, Column: Xterra MS C18 S7 3.0×50 mm; (ES+) m/z (M+H)$^+$=634.45, HPLC R$_t$=1.785 min. Analytical HPLC were performed by using Shimadzu-VP instrument with UV detection at 254 nm and 256 nm. Analytical HPLC method: Solvent A=5% MeCN-95% H2O-0.1% TFA, Solvent B=95% MeCN-5% H2O-0.1% TFA, Start % B=10, Final % B=100, Gradient time=10 min, Stop time=20 min, Flow Rate=1 ml/min, Column: Waters Sunfire C-18, 4.6×150 mm, 3.5 um; R$_t$=10.33 min; Column: Waters Xbridge Phenyl 4.6×150 mm, 3.5 um; R$_t$=9.44 min.

All the Prep HPLC purifications were run at following conditions except for the other conditions that mentioned in individual procedures. Solvent A: 10% MeOH-90% H2O-0.1% TFA; Solvent B: 90% MeOH-10% H2O-0.1% TFA; Column: XTERRA 30×100 mm S5. LCMS methods: All LCMS analysis conditions used method 1 except mentioned in individual procedure. Method 1: Start % B: 0; Final % B: 100; Gradient time: 3 min; Stop time: 4 min; Flow rate: 4 ml/min; Wavelength: 220; Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5; Method 2: Start % B: 0; Final % B: 100; Gradient time: 3 min; Stop time: 5 min; Flow rate: 4 ml/min; Wavelength: 220; Solvent A: 10% MeOH/90% H2O/0.1% Trifluoroacetic Acid; Solvent B: 10% H2O/90% MeOH/0.1% Trifluoroacetic Acid; Column: XBridge 4.6×50 mm S5.

Preparation of Compound 1: 13-cyclohexyl-6-[1-cyclopropyl-4-[[(2R,6S)-2,6-dimethyl-4-morpholinyl]carbonyl]-1H-imidazol-5-yl]-3-methoxy-N-[(1-methylethyl)sulfonyl]-7H-indolo[2,1-a][2]benzazepine-10-carboxamide

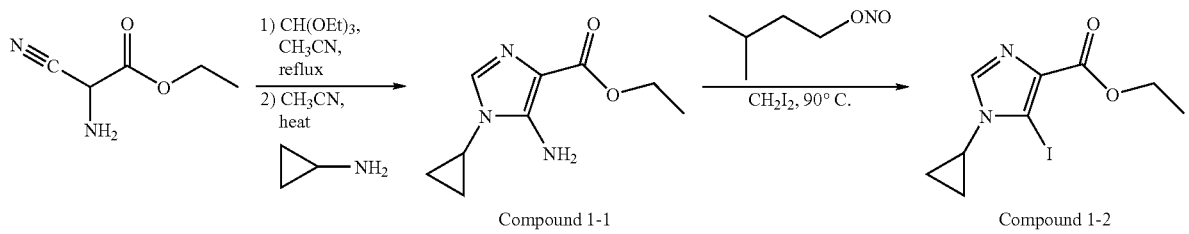

-continued
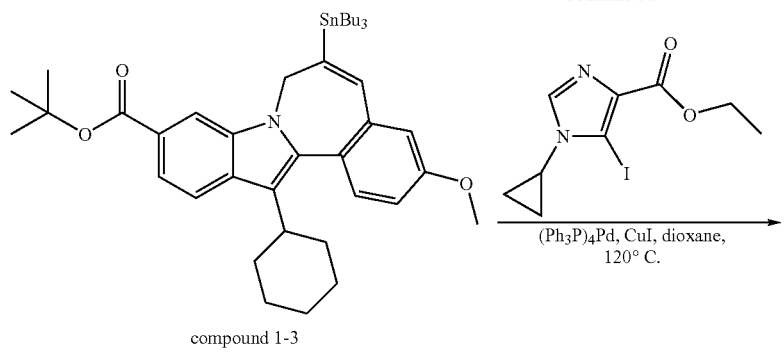
compound 1-3
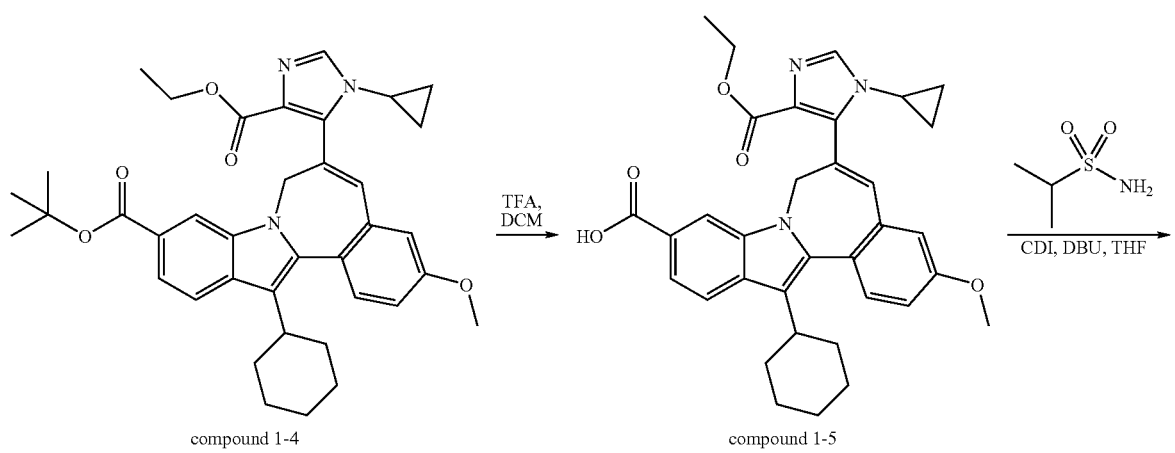
compound 1-4
compound 1-5
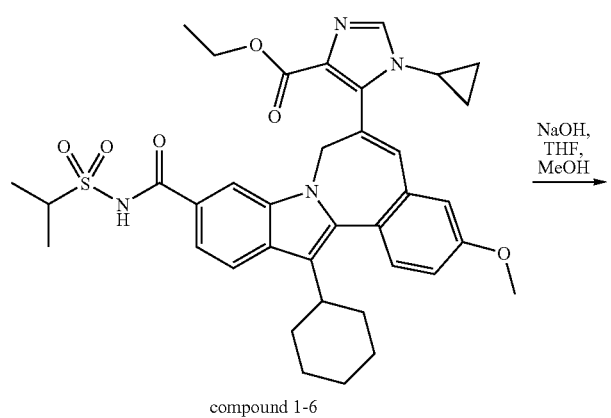
compound 1-6
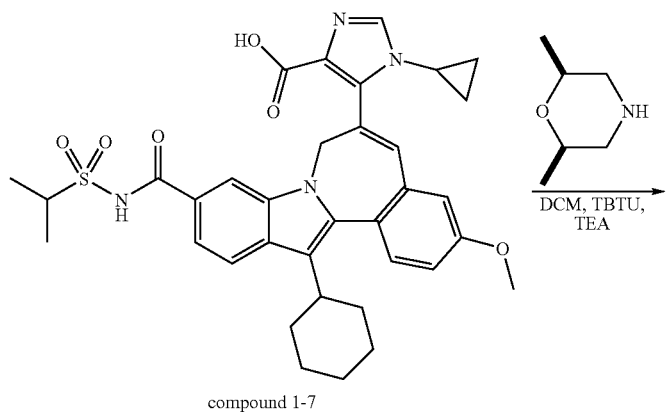
compound 1-7

-continued

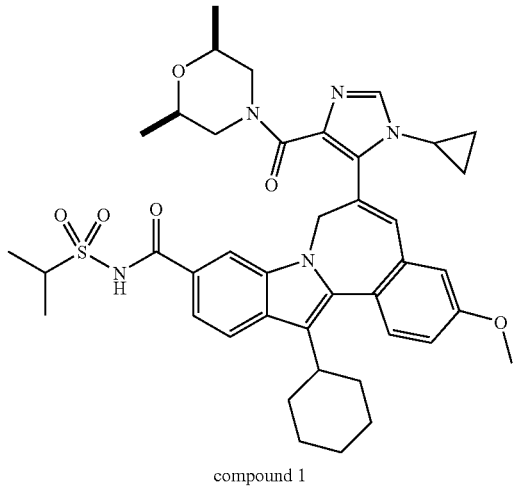

compound 1

Step 1: Preparation of Compound 1-1

To a solution of ethyl 2-amino-2-cyanoacetate (1.8 g, 15 mmol) in Acetonitrile (25 mL) was added triethoxymethane (2.7 mL, 16.3 mmol). The clear brown solution was refluxed for 1 h, removed the solvent in vacuum to afford a residue.

A mixture of the above residue and cyclopropanamine (1.2 mL, 17.32 mmol) in Acetonitrile (15 mL) in a sealed tube was heated at 50° C. for 0.5 h and 85° C. for 3 h, cooled and then removed the solvents. The residue was dissolved in DCM, washed with 2 N NaOH, dried (MgSO4), removed the solvent to afford compound 1-1 as a beige solid (1.8 g, 62%). The crude product was directly used in next reaction.

Step 2: Preparation of Compound 1-2

To a solution of isopentyl nitrite (3.70 mL, 27.7 mmol) in $CH_2I_2$ (10 mL, 124 mmol) was added dropwise a solution of compound 1-1 (1.8 g, 9.22 mmol) in chloroform (10 mL) at 90° C. (bath temperature) over 5 min, 5 ml $CHCl_3$ was used to washed the flask to complete the transfer. After the reaction mixture was stirred for 1 h at 90° C., the solvents were partially removed and the remaining mixture was purified on Thomson 80 g column (EtOAc/hexane: 0 to 100%) to afford compound 1-2 as a reddish semi-solid (0.71 g, 25%). LC-MS retention time: 1.682 min; MS m/z 307 $(M+H)^+$. 1H NMR (400 MHz, CHLOROFORM-d) δ ppm 7.69 (1H, s), 4.39 (2H, q, J=7.05 Hz), 3.12-3.27 (1H, m), 1.41 (3H, t, J=7.18 Hz), 1.16-1.26 (2H, m), 0.96-1.07 (2H, m).

Step 3: Preparation of Compound 1-4

Compound 1-2 (0.6 g, 1.960 mmol), Tetrakis (0.158 g, 0.136 mmol), copper (I) iodide (0.260 g, 1.365 mmol) and compound 1-3 (1 g, 1.365 mmol) was added in a microwave vial. Capped the vessel, evacuated and filled with nitrogen. Dioxane (5 ml) was added and the mixture was evacuated and refilled with nitrogen. The reaction mixture was heated in oil bath at 120° C. for 4 h. Removed the solvent and the residue was purified on Thomson 80 g column (EtOAc/hexane: 0 to 80%) to afford compound 1-4 as a pale yellow solid (0.24 g, 28%). LC-MS retention time: 3.603 min; MS m/z 622 $(M+H)^+$. 1H NMR (400 MHz, CHLOROFORM-d) δ ppm 7.78-7.84 (2H, m), 7.37-7.70 (2H, m), 7.04 (1H, dd, J=8.69, 2.64 Hz), 6.92 (1H, d, J=2.52 Hz), 6.82 (1H, s), 5.09 (1H, d, J=14.35 Hz), 4.70 (1H, d, J=15.61 Hz), 4.38 (1H, q, J=7.05 Hz), 3.89 (3H, s), 2.77-2.91 (2H, m), 1.99-2.17 (2H, m), 1.85-1.98 (1H, m), 1.67-1.83 (2H, m), 1.57 (9H, s), 1.39 (3H, t, J=7.05 Hz), 1.12-1.65 (7H, m), 0.70 (1H, br. s.), 0.59 (1H, br. s.), 0.03 (1H, br. s.), −0.66 (1H, br. s.).

Step 4: Preparation of Compound 1-5

To a solution of compound 1-3 (0.24 g, 0.386 mmol) in DCM (0.5 mL) was added TFA (1 mL, 12.98 mmol). The mixture was stirred at rt for 1.5 h, removed the solvents in vacuum to afford compound 1-5 as a brown foam (0.218 g, 100%). LC-MS retention time: 3.300 min; MS m/z 566 $(M+H)^+$.

Step 5: Preparation of Compound 1-6

A mixture of compound 1-4 (0.218 g, 0.385 mmol) and CDI (0.125 g, 0.771 mmol) in THF (5 ml) was stirred at 50° C. for 0.5 h, cooled down and added propane-2-sulfonamide (0.100 g, 0.812 mmol) and DBU (0.2 ml, 1.327 mmol). The mixture was stirred at ambient temperature for 3 days and diluted with EtOAc and washed with HCl (0.1 N), brine, removed the solvent, purified on Thomson 25 g column (MeOH/DCM: 0 to 25%) to afford compound 1-6 (0.136 g, 53%). LC-MS retention time: 3.208 min; MS m/z 671 $(M+H)^+$. 1H NMR (500 MHz, CHLOROFORM-d) δ ppm 8.12 (1H, br. s.), 7.89 (1H, d, J=8.55 Hz), 7.52 (2H, d, J=8.55 Hz), 7.32 (1H, br. s.), 7.06 (1H, dd, J=8.70, 2.59 Hz), 6.93 (1H, d, J=2.44 Hz), 6.82 (1H, s), 5.23 (1H, d, J=14.65 Hz), 4.71 (1H, d, J=14.34 Hz), 4.29 (2H, br. s.), 3.97-4.06 (1H, m), 3.90 (3H, s), 2.78-2.93 (2H, m), 1.86-2.23 (4H, m), 1.12-1.84 (15H, m), 0.72 (1H, br. s.), 0.59 (1H, br. s.), 0.03 (1H, br. s.), −0.50 (1H, br. s.).

Step 6: Preparation of Compound 1-7

A mixture of compound 1-5 (0.136 g, 0.203 mmol) in THF (3 mL), NaOH (1.5 mL, 1.500 mmol), and MeOH (1.5 mL) was stirred at rt over night, diluted with EtOAc and washed with 0.2 N HCl, brine, dried (MgSO4), removed the solvent to afford compound 1-7 as a yellow solid (0.102 g, 78%). LC-MS retention time: 3.055 min;

MS m/z 643 $(M+H)^+$. 1H NMR (400 MHz, CHLOROFORM-d) δ ppm 8.23 (1H, br. s.), 7.84 (2H, br. s.), 7.37-7.47

(1H, m), 7.08 (1H, br. s.), 6.97 (1H, dd, J=8.69, 2.39 Hz), 6.71-6.84 (1H, m), 5.81 (1H, d, J=14.60 Hz), 4.68 (1H, d, J=15.11 Hz), 3.89-3.97 (1H, m), 3.83 (3H, s), 2.85 (2H, br. s.), 1.12-2.22 (17H, m), 0.74 (1H, br. s.), 0.46 (1H, br. s.), −0.12 (1H, br. s.), −0.30 (1H, br. s.).

Step 7: Preparation of Compound 1

A mixture of compound 1-6 (0.082 g, 0.128 mmol), DCM (1 mL), TEA (0.1 ml, 0.717 mmol), (2R,6S)-2,6-dimethyl-morpholine (0.03 mL, 0.244 mmol), and TBTU (0.060 g, 0.187 mmol) was stirred for 3 h and quenched with MeOH and then removed the solvents. The residue was purified by Prep-HPLC to afford compound 1 and isolated as mono TFA salt (0.0361 g, 31%). LC-MS retention time: 3.170 min; MS m/z 740 (M+H)+; 1H NMR (400 MHz, CHLOROFORM-d) δ ppm 8.88 (1H, br. s.), 7.89-8.11 (2H, m), 7.72 (1H, d, J=8.56 Hz), 7.62 (1H, d, J=8.31 Hz), 7.54-7.65 (1H, m), 7.05-7.19 (2H, m), 7.00 (1H, br. s.), 5.03-5.19 (1H, m), 4.62 (1H, d, J=14.35 Hz), 4.01-4.12 (1H, m), 3.97 (3H, s), 3.02-3.61 (4H, m), 2.85-2.99 (1H, m), 1.65-2.55 (9H, m), 0.97-1.63 (14H, m), 0.89-0.97 (1H, m), 0.73-0.86 (3H, m), 0.66 (2H, br. s.).

Preparation of Compound 2: 13-cyclohexyl-6-[1-cyclopropyl-4-(4-morpholinylcarbonyl)-1H-imidazol-5-yl]-3-methoxy-N-[(1-methylethyl)sulfonyl]-7H-indolo[2,1-a][2]benzazepine-10-carboxamide

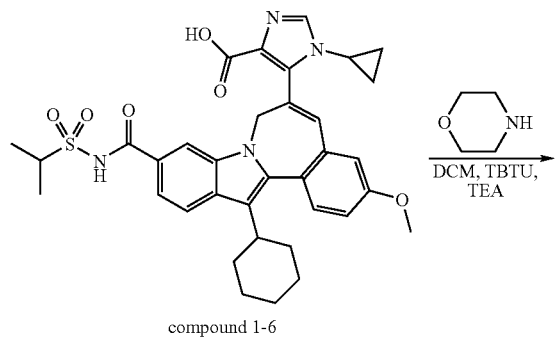

compound 1-6

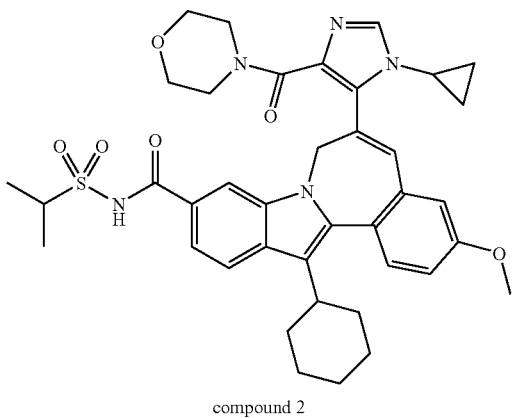

compound 2

A mixture of compound 1-6 (0.020 g, 0.031 mmol), DCM (1 mL), morpholine (0.01 mL, 0.115 mmol), TEA (0.05 ml, 0.359 mmol), and TBTU (0.030 g, 0.093 mmol) was stirred at rt for 3 h and quenched with MeOH, and then removed the solvents. The residue was purified by Prep-HPLC to afford compound 2 and isolated as mono TFA salt (0.0072 g, 28%). LC-MS retention time: 3.071 min; MS m/z 712 (M+H)+; 1H NMR (400 MHz, CHLOROFORM-d) δ ppm 8.69 (1H, br. s.), 7.88-7.97 (2H, m), 7.63 (1H, d, J=8.56 Hz), 7.57 (1H, d, J=8.81 Hz), 7.13 (1H, dd, J=8.56, 2.52 Hz), 7.06 (1H, s), 6.96 (1H, d, J=2.52 Hz), 5.06 (1H, d, J=14.60 Hz), 4.61 (1H, d, J=15.36 Hz), 3.95-4.05 (1H, m), 3.93 (3H, s), 2.71-3.55 (10H, m), 2.44 (1H, br. s.), 1.89-2.21 (4H, m), 1.71-1.85 (2H, m), 1.14-1.63 (10H, m), 0.92-1.11 (4H, m).

Preparation of Compound 3: 6-[1-cyclobutyl-4-[[(2R,6S)-2,6-dimethyl-4-morpholinyl]carbonyl]-1H-imidazol-5-yl]-13-cyclohexyl-3-methoxy-N-[(1-methylethyl)sulfonyl]-7H-indolo[2,1-a][2]benzazepine-10-carboxamide

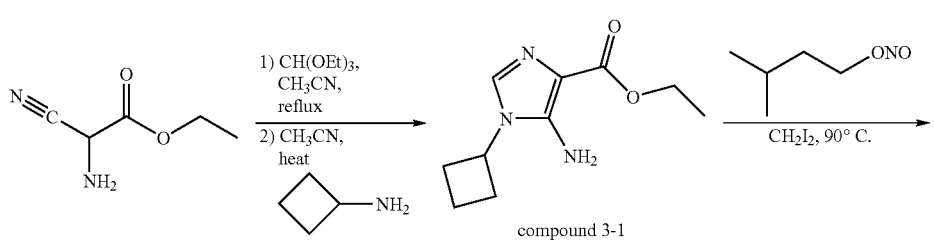

compound 3-1

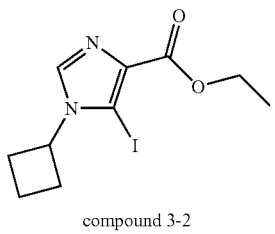

compound 3-2

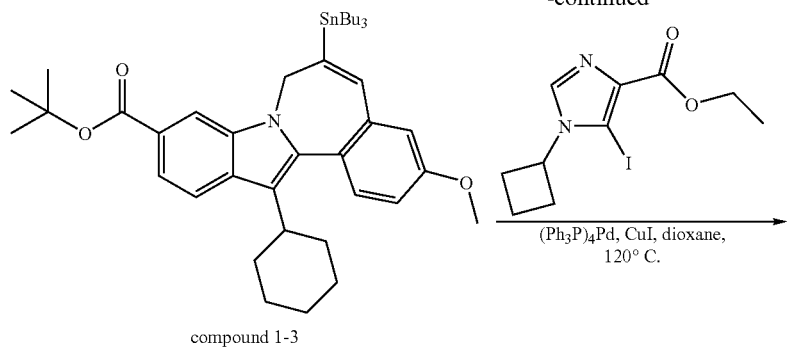
compound 1-3
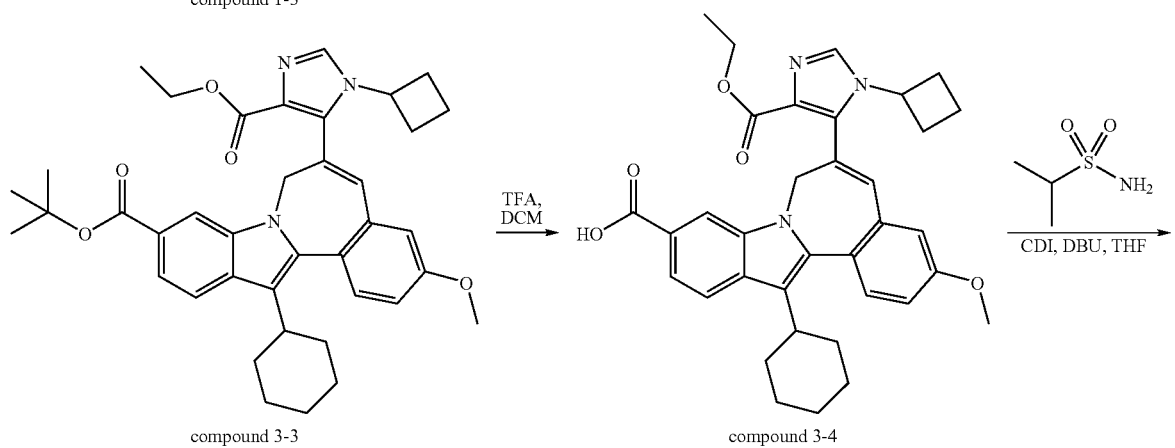
compound 3-3
compound 3-4
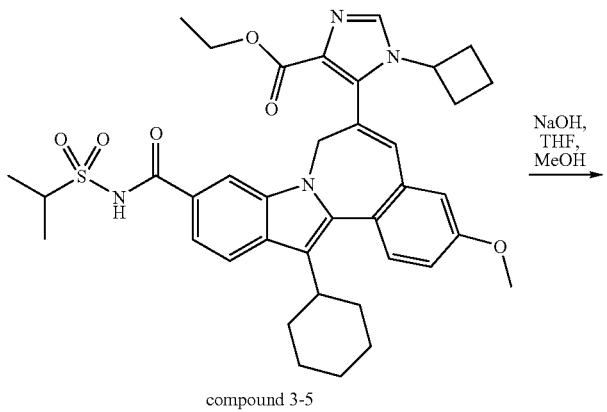
compound 3-5
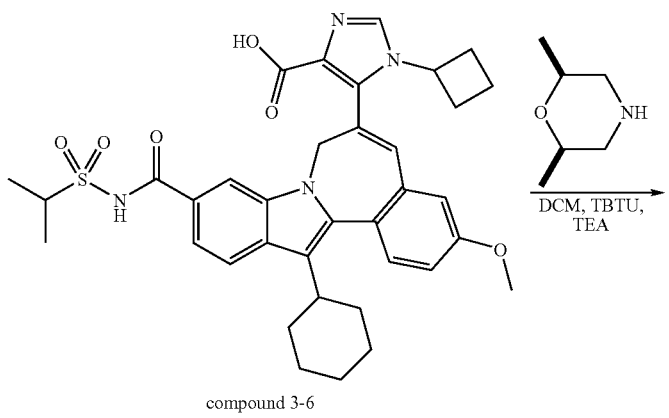
compound 3-6

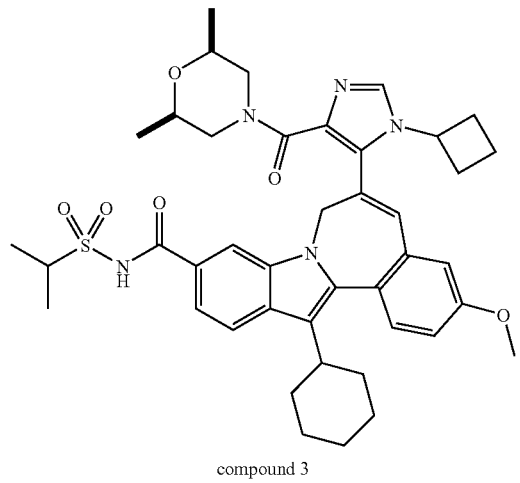

compound 3

Step 1: Preparation of Compound 3-1

Compound 3-1 was prepared by using a similar method as described in synthesis of compound 1-1 except cyclobutanamine (1.4 mL, 16.40 mmol) was used in place of cyclopropanamine (1.8 g, 62%). The crude product was directly used in the next reaction.

Step 2: Preparation of Compound 3-2

To a solution of isopentyl nitrite (3.26 mL, 24.37 mmol) in diiodomethane (10 mL, 124 mmol) was added dropwise a solution of ethyl 5-amino-1-cyclobutyl-1H-imidazole-4-carboxylate (1.7 g, 8.12 mmol) in chloroform (10 mL) at 90° C. (bath temperature) over 5 min, 5 ml CHCl3 was used to washed the flask to complete the transfer. The mixture was stirred for 1 h at the temperature. The solvent was partially removed and then purified on Thomson 110 g column (EtOAc/hexane: 0 to 100%) to afford a reddish oil which was re-purified on Thomson 90 g column (EtOAc/hexane: 0 to 100%) to afford compound 3-2 as a brown solid (0.8 g, 31%). LC-MS retention time: 1.888 min; MS m/z 321 (M+H)$^+$; 1H NMR (400 MHz, CHLOROFORM-d) δ ppm 7.83 (1H, s), 4.58-4.71 (1H, m), 4.37 (2H, q, J=7.22 Hz), 2.56-2.68 (2H, m), 2.25-2.42 (2H, m), 1.88-2.00 (2H, m), 1.39 (3H, t, J=7.18 Hz).

Step 3: Preparation of Compound 3-3

In a microwave vial was added ethyl 1-cyclobutyl-5-iodo-1H-imidazole-4-carboxylate (0.7 g, 2.187 mmol), Tetrakis (0.158 g, 0.136 mmol), copper (I) iodide (0.260 g, 1.365 mmol) and compound 1-3 (1 g, 1.365 mmol). Capped the vessel evacuated and filled with nitrogen. Dioxane (10 ml) was added and the mixture was evacuated and refilled with nitrogen. The reaction mixture was heated in a oil bath at 120° C. for 4 h, concentrated and the residue was purified on Thomson 80 g column (EtOAc/hexane; 0 to 100%) to afford compound 3-3 as a beige solid (0.22 g, 25%).
LC-MS retention time: 3.636 min; MS m/z 636 (M+H)$^+$; 1H NMR (400 MHz, CHLOROFORM-d) δ ppm 7.77-7.83 (2H, m), 7.57-7.70 (1H, m), 7.41-7.56 (1H, m), 7.04 (1H, dd, J=8.56, 2.77 Hz), 6.90 (1H, d, J=2.52 Hz), 6.68 (1H, s), 5.02 (1H, d, J=14.10 Hz), 4.68 (1H, d, J=14.35 Hz), 4.37 (2H, br. s.), 3.89-4.00 (1H, m), 3.89 (3H, s), 2.76-2.93 (1H, m), 2.26-2.43 (1H, m), 1.65-2.21 (9H, m), 1.58 (9H, s), 0.84-1.52 (10H, m).

Step 4: Preparation of Compound 3-4

To a solution of compound 3-3 (0.24 g, 0.377 mmol) in DCM (0.5 mL) was added TFA (1 mL, 12.98 mmol). The mixture was stirred at rt for 2 h, and then removed the solvents in vacuum to afford the compound 3-4 as a brown foam (0.219 g, 100%).
LC-MS retention time: 3.320 min; MS m/z 580 (M+H)$^+$.

Step 5: Preparation of Compound 3-5

A mixture of compound 3-4 (0.219 g, 0.378 mmol) and CDI (0.122 g, 0.752 mmol) in THF (5 ml) was stirred at 50° C. for 0.5 h, cooled and added propane-2-sulfonamide (0.100 g, 0.812 mmol) and DBU (0.2 ml, 1.327 mmol). The mixture was stirred at ambient temperature for 3 days. The reaction mixture was diluted with EtOAc, washed HCl (0.1N), brine and dried (MgSO4). Crude product was purified on a Thomson 25 g column (MeOH/DCM: 0 to 25%) to afford the compound 3-5 (0.087 g, 34%). LC-MS retention time: 3.230 min; MS m/z 685 (M+H)$^+$; 1H NMR (500 MHz, CHLOROFORM-d) δ ppm 8.30 (1H, br. s.), 7.89 (1H, d, J=8.55 Hz), 7.54 (1H, br. s.), 7.52 (1H, d, J=8.85 Hz), 7.28-7.36 (1H, m), 7.06 (1H, dd, J=8.55, 2.44 Hz), 6.92 (1H, d, J=2.44 Hz), 6.70 (1H, s), 5.24 (1H, br. s.), 4.69 (1H, d, J=14.04 Hz), 4.29 (2H, br. s.), 3.91-4.07 (2H, m), 3.91 (3H, s), 2.82-2.94 (1H, m), 1.88-2.24 (6H, m), 1.00-1.85 (19H, m).

Step 6: Preparation of Compound 3-6

A mixture of compound 3-5 (0.087 g, 0.127 mmol) in THF (3 mL), NaOH (1.5 mL, 1.500 mmol), and MeOH (1.5 mL) was stirred at rt overnight, diluted with EtOAc and washed with HCl (0.2N), brine, dried (MgSO4), removed the solvent to afford compound 3-6 as a yellow solid (0.079 g, 95%). LC-MS retention time: 3.108 min;
MS m/z 657 (M+H)$^+$.

Step 7: Preparation of Compound 3

A mixture of compound 3-6 (0.059 g, 0.090 mmol), TEA (0.06 ml, 0.430 mmol), (2R,6S)-2,6-dimethylmorpholine (0.03 mL, 0.244 mmol), DCM (1 mL) and TBTU (0.060 g, 0.187 mmol) was stirred at rt for 5 h and quenched with MeOH (1 mL), removed the solvent, purified by Prep-HPLC to afford compound 3 and isolated as mono TFA salt (0.0311 g, 37%). LC-MS retention time: 3.181 min; MS m/z 754 (M+H)$^+$; 1H NMR (400 MHz, CHLOROFORM-d) δ ppm 9.04 (1H, br. s.), 7.87-8.12 (2H, m), 7.74 (1H, d, J=8.06 Hz), 7.61 (1H, br. s.), 7.18 (1H, d, J=8.56 Hz), 6.98 (2H, br. s.), 5.01-5.17 (1H, m), 3.99 (3H, s), 3.94-4.78 (8H, m), 3.05-3.54 (2H, m), 2.83-2.97 (1H, m), 2.34-2.75 (5H, m), 1.73-2.24 (9H, m), 1.16-1.67 (10H, m), 0.65-1.07 (4H, m).

Preparation of Compound 4: 6-[1-cyclobutyl-4-(4-morpholinylcarbonyl)-1H-imidazol-5-yl]-13-cyclohexyl-3-methoxy-N-[(1-methylethyl)sulfonyl]-7H-indolo[2,1-a][2]benzazepine-10-carboxamide

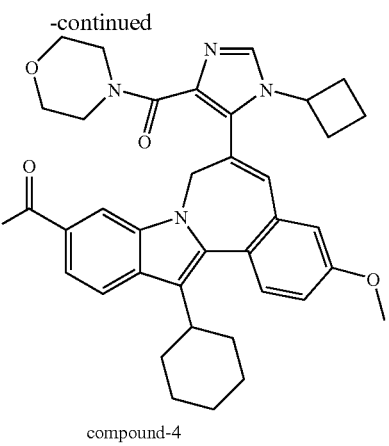

compound-4

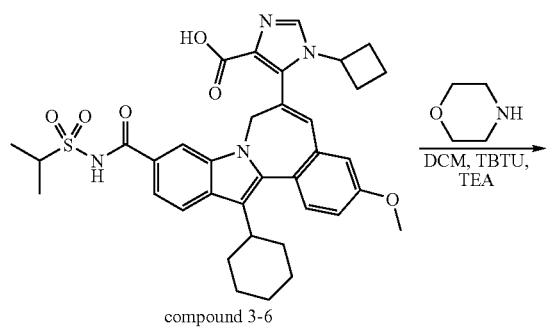

A mixture of compound 3-6 (0.020 g, 0.030 mmol), DCM (1 mL), TEA (0.05 ml, 0.359 mmol), morpholine (0.01 mL, 0.115 mmol), and TBTU (0.030 g, 0.093 mmol) was stirred at rt for 5 h and quenched with MeOH (1 mL), removed the solvents and purified by Prep-HPLC to afford compound 4 and isolated as mono TFA salt (0.0046 g, 17%). LC-MS retention time: 3.100 min; MS m/z 726 (M+H)$^+$; 1H NMR (400 MHz, CHLOROFORM-d) δ ppm 8.87 (1H, br. s.), 8.03 (1H, br. s.), 7.97 (1H, d, J=8.31 Hz), 7.70 (1H, d, J=8.56 Hz), 7.60 (1H, d, J=8.56 Hz), 7.17 (1H, dd, J=8.69, 2.64 Hz), 6.93-7.00 (2H, m), 5.08 (1H, d, J=14.10 Hz), 4.52-4.66 (2H, m), 3.99-4.09 (1H, m), 3.98 (3H, s), 2.27-3.46 (14H, m), 1.73-2.25 (8H, m), 1.13-1.68 (10H, m).

Preparation of Compound 5: 13-cyclohexyl-3-methoxy-6-[1-(1-methylethyl)-4-(4-morpholinylcarbonyl)-1H-imidazol-5-yl]-N-[(1-methylethyl)sulfonyl]-7H-indolo[2,1-a][2]benzazepine-10-carboxamide

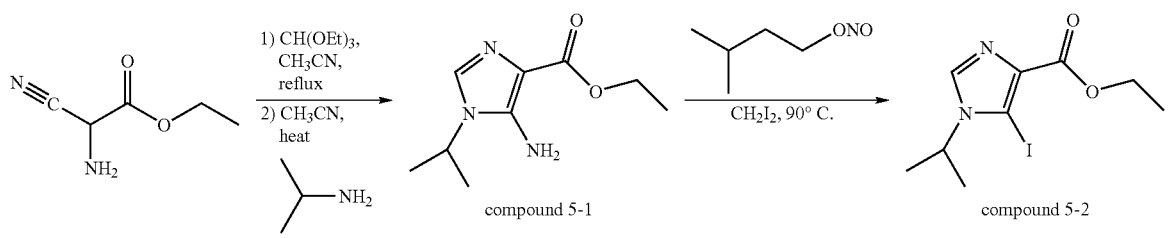

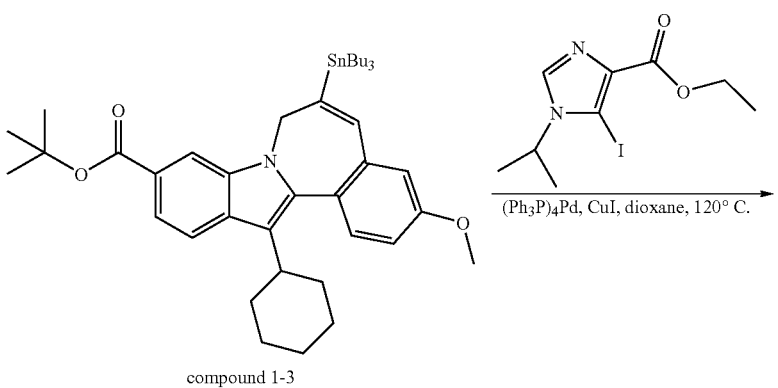

compound 1-3

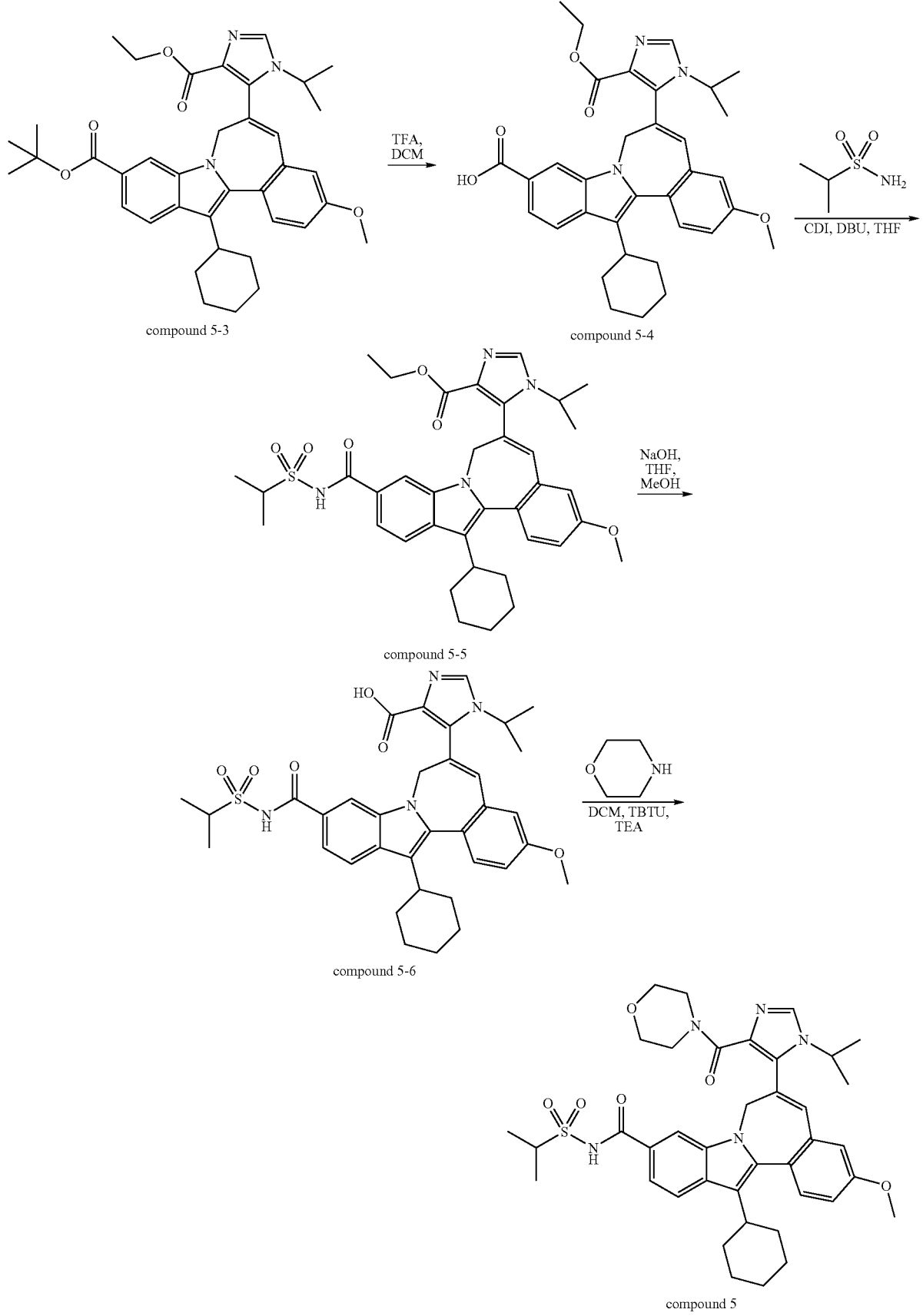

Step 1: Preparation of Compound 5-1

To a solution of ethyl 2-amino-2-cyanoacetate (3.5 g, 27.3 mmol) in Acetonitrile (50 mL) was added triethoxymethane (5.00 mL, 30.0 mmol). The clear brown solution was refluxed for 50 min and then removed the solvent in vacuum to afford a brown residue. The residue and propan-2-amine (2.56 mL, 30.0 mmol) were dissolved in Acetonitrile (50 mL), heated at 50° C. in a seal tube for 30 min, and at 85° C. for 30 min. The reaction mixture was cooled and removed the solvent. The residue was dissolved in DCM and washed with 2 N NaOH, dried (MgSO4), removed the solvent. The resultant residue was dissolved in DCM (~5 ml) and enough hexane was added to precipitate out the product which was filtered to afford the compound 5-1 as a brown solid (1.6 g, 30%). The crude product was directly used in next step.

Step 2: Preparation of Compound 5-2

To a solution of isopentyl nitrite (3.25 mL, 24.34 mmol) in $CH_2I_2$ (30 mL, 372 mmol) was added dropwise a solution of compound 5-1 (1.6 g, 8.11 mmol) in chloroform (8 mL) at 90° C. (bath temperature) over 5 min. The reaction mixture was stirred at 90° C. for 1 h, and concentrated, purified on Thomson 110 g column (EtOAc/hexane: 0 to 100%) and re-purified on Thomson 90 g column (EtOAc/hexane: 0 to 100%) to afford compound 5-2 as a brown solid (1.18 g, 47%). LC-MS retention time: 1.677 min;

MS m/z 309 (M+H)+; 1H NMR (400 MHz, CHLOROFORM-d) δ ppm 7.81 (1H, s), 4.45-4.60 (1H, m), 4.40 (2H, q, J=7.13 Hz), 1.53 (6H, d, J=6.80 Hz), 1.42 (3H, t, J=7.18 Hz).

Step 3: Preparation of Compound 5-3

Compound 5-2 (0.290 g, 0.941 mmol), Tetrakis (0.095 g, 0.082 mmol), compound 1-3 (0.600 g, 0.819 mmol) and CuI (0.03 g) were added in a microwave vial, capped, evacuated and filled with nitrogen. Dioxane (3.5 ml) was added and the mixture was evacuated and refilled with nitrogen and then heated in a oil bath at 120° C. for 2 h. Removed the solvent, and the residue was purified on Thomson 90 g column (EtOAc/hexane: 5 to 100%) to afford compound 5-3 (0.3 µg, 61%). LC-MS retention time: 3.573 min; MS m/z 624 (M+H)+; 1H NMR (400 MHz, CHLOROFORM-d) δ ppm 7.75-7.85 (2H, m), 7.59-7.70 (1H, m), 7.41-7.57 (2H, m), 7.04 (1H, dd, J=8.69, 2.64 Hz), 6.93 (1H, d, J=2.52 Hz), 6.67 (1H, s), 4.98 (1H, d, J=14.10 Hz), 4.67-4.77 (1H, m), 4.31-4.46 (2H, m), 3.89 (3H, s), 3.45-3.61 (1H, m), 2.72-2.90 (1H, m), 1.05-2.23 (25H, m), 0.89-0.93 (3H, m).

Step 4: Preparation of Compound 5-4

A mixture of compound 5-3 (0.430 g, 0.689 mmol) in DCM (1 mL) and TFA (5 ml, 64.9 mmol) was stirred for 0.5 h. The reaction mixture was concentrated in vacuum to afford compound 5-4 (0.391 g, 100%). LC-MS retention time: 3.278 min; MS m/z 568 (M+H)+.

Step 5: Preparation of Compound 5-5

A mixture of compound 5-4 (0.391 g, 0.689 mmol), propane-2-sulfonamide (0.255 g, 2.066 mmol), DMAP (0.589 g, 4.82 mmol), and N-(3-Dimethylaminopropyl)-N'-ethylcarbodiimide hydrochloride (0.180 g, 0.939 mmol) in DCM (1 mL) was stirred at rt for 3 days. MeOH (1 mL) was added and the mixture was stirred for 0.5 h, diluted with EtOAc, washed with satd. NH4Cl, brine, dried (Na2SO4) and purified on Thomson 25 g column (MeOH/DCM: 0 to 25%) to afford the compound 5-5 as a yellow glass (0.255 g, 55%). LC-MS retention time: 3.191 min; MS m/z 673 (M+H)+.

Step 6: Preparation of Compound 5-6

A mixture of compound 5-5 (0.25 g, 0.372 mmol) in THF (3 mL), MeOH (1.5 mL) and NaOH (1.5 mL, 1.500 mmol) was stirred at rt overnight. The reaction mixture was diluted with EtOAc and washed with 0.2 N HCl, brine, dried (MgSO4), removed the solvent to afford compound 5-6 as a yellow solid (0.172 g, 72%). LC-MS retention time: 3.070 min; MS m/z 645 (M+H)+.

Step 7: Preparation of Compound 5

A mixture of compound 5-6 (0.040 g, 0.062 mmol), morpholine (0.04 mL, 0.459 mmol), TBTU (0.0398 g, 0.124 mmol) in DCM (1 mL) was stirred at rt for 1 h. Quenched with MeOH, removed the solvents and purified by prep HPLC to afford the compound 5 as a yellow solid and isolated as mono TFA salt (0.0135 g, 24%).

LC-MS retention time: 3.060 min; MS m/z 714 (M+H)+; 1H NMR (400 MHz, CHLOROFORM-d) δ ppm 8.04 (1H, br. s.), 7.92 (1H, d, J=8.56 Hz), 7.64 (1H, d, J=7.05 Hz), 7.55 (1H, d, J=8.56 Hz), 7.12 (1H, dd, J=8.69, 2.64 Hz), 6.95 (1H, d, J=2.52 Hz), 6.92 (1H, br. s.), 5.08 (1H, d, J=14.86 Hz), 4.58 (1H, d, J=15.36 Hz), 4.26 (1H, br. s.), 3.94-4.03 (1H, m), 3.93 (3H, s), 2.75-3.79 (8H, m), 1.87-2.18 (4H, m), 1.69-1.84 (2H, m), 1.08-1.60 (18H, m).

Preparation of Compound 6

13-cyclohexyl-3-methoxy-6-[4-[(3-methyl-3,8-diazabicyclo[3.2.1]oct-8-yl)carbonyl]-1-(1-methylethyl)-1H-imidazol-5-yl]-N-[(1-methylethyl)sulfonyl]-7H-indolo[2,1-a][2]benzazepine-10-carboxamide

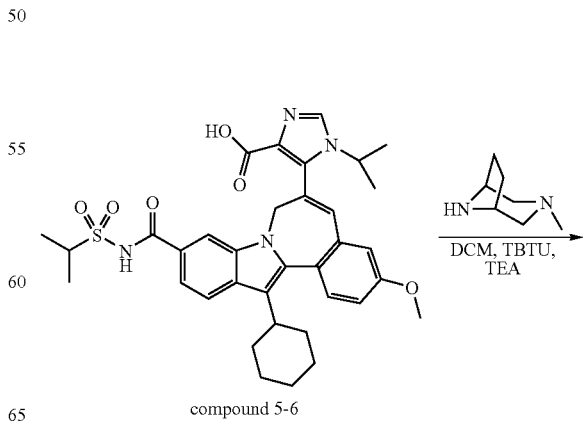

compound 5-6

269

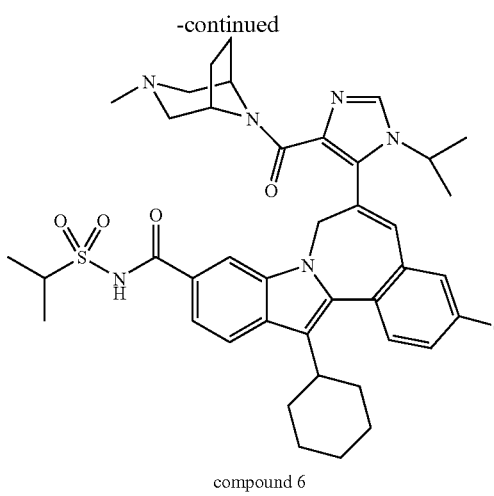

compound 6

The compound 5-6 (0.046 g, 0.071 mmol) was dissolved in DCM (2 ml) and added TEA (0.1 ml, 0.717 mmol), 3-methyl-3,8-diazabicyclo[3.2.1]octane, 2HCl (0.020 g, 0.100 mmol) and TBTU (0.035 g, 0.109 mmol). The mixture was stirred for 1.5 h, quenched with MeOH, removed the solvent and purified by prep HPLC to afford the compound 6 and isolated as bis-TFA salt (0.023 g, 32%). LC-MS retention time: 3.056 min; MS m/z 753 (M+H)$^+$.

Preparation of Compound 7: 13-cyclohexyl-3-methoxy-N-[(1-methylethyl)sulfonyl]-6-[1-(1-methylethyl)-4-[[(3R,5S)-3,4,5-trimethyl-1-piperazinyl]carbonyl]-1H-imidazol-5-yl]-7H-indolo[2,1-a][2]benzazepine-10-carboxamide

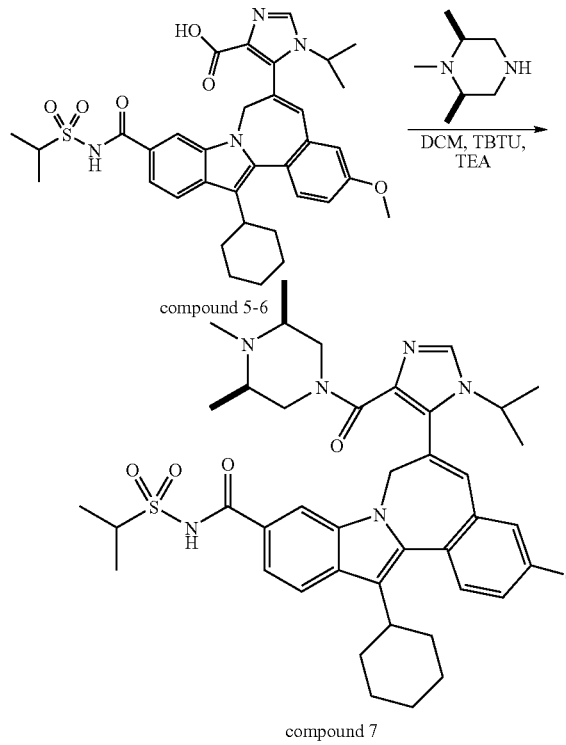

compound 7

The compound 5-6 (0.046 g, 0.071 mmol) was dissolved in 2 ml of DCM and added TEA (0.1 ml, 0.717 mmol), (2R,6S)-

270

1,2,6-trimethylpiperazine, 2HCl (0.030 g, 0.149 mmol) and TBTU (0.035 g, 0.109 mmol). The mixture was stirred for 1.5 h, quenched with MeOH, removed the solvent and purified by prep HPLC to afford the compound 6 and isolated as bis-TFA salt (0.0264 g, 36%). LC-MS retention time: 3.035; MS m/z 755 (M+H)$^+$.

Preparation of Compound 8: 13-cyclohexyl-6-[4-[[(2R,6S)-2,6-dimethyl-4-morpholinyl]carbonyl]-1-(1-methylethyl)-1H-imidazol-5-yl]-3-methoxy-N-[(1-methylethyl)sulfonyl]-7H-indolo[2,1-a][2]benzazepine-10-carboxamide

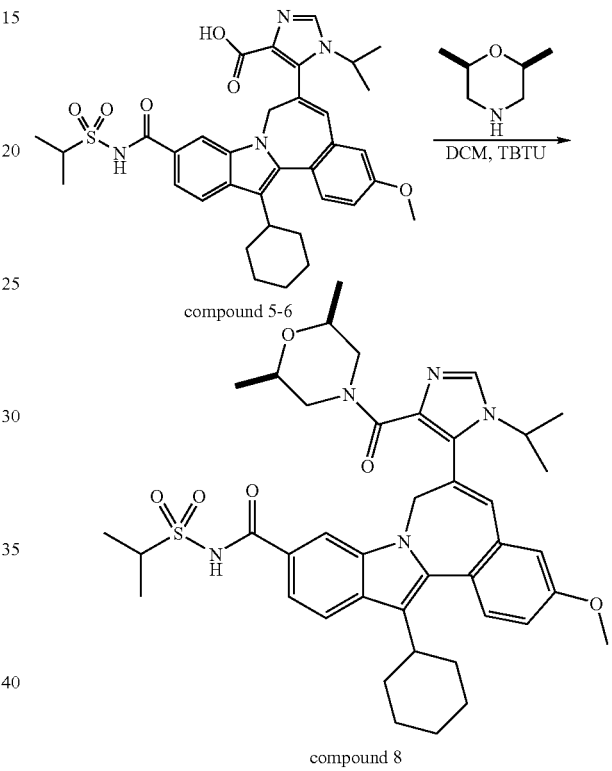

compound 8

To a mixture of compound 5-6 (0.040 g, 0.062 mmol) and (2R,6S)-2,6-dimethylmorpholine (0.04 mL, 0.325 mmol) in DCM was added (2R,6S)-2,6-dimethylmorpholine (0.04 mL, 0.325 mmol) and TBTU (0.0398 g, 0.124 mmol). The reaction mixture was stirred at rt for 1.5 h. Quenched with MeOH, removed the solvent, and purified by prep HPLC to afford the compound 8 as a yellow solid and isolated as mono TFA salt (0.0105 g, 19%).

Preparation of Compound 9: 13-cyclohexyl-N-[(dimethylamino)sulfonyl]-3-methoxy-6-[1-(1-methylethyl)-5-(4-morpholinylcarbonyl)-1H-imidazol-4-yl]-7H-indolo[2,1-a][2]benzazepine-10-carboxamide

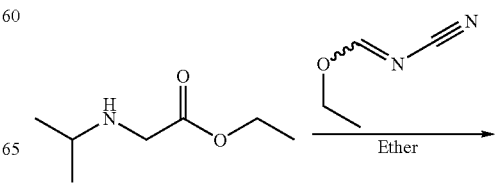

-continued

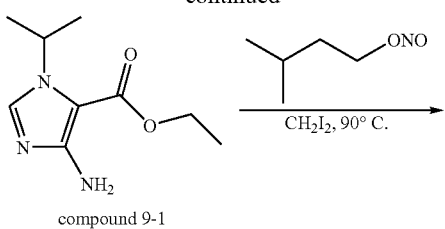
compound 9-1

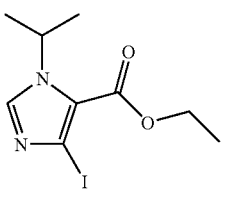
compound 9-2

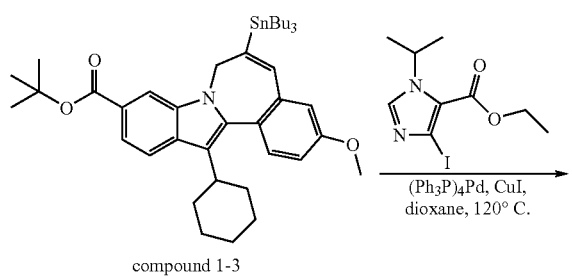
compound 1-3

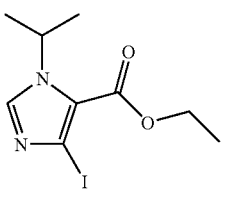
compound 9-3

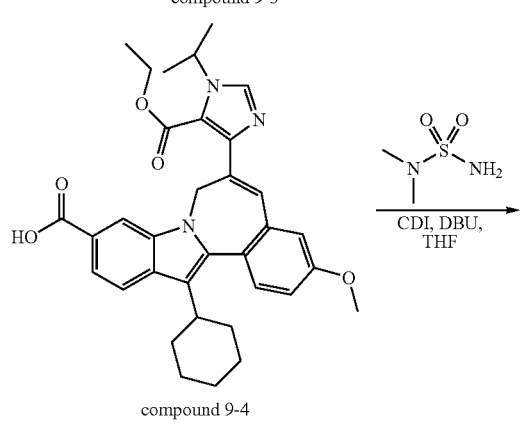
compound 9-4

-continued

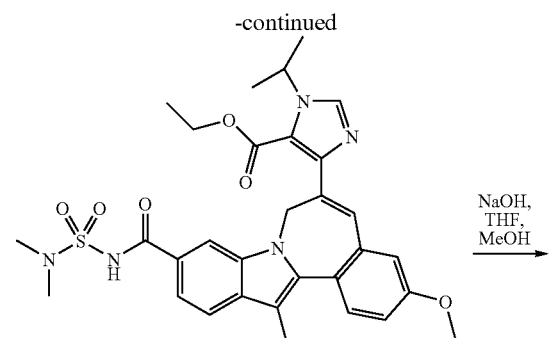
compound 9-5

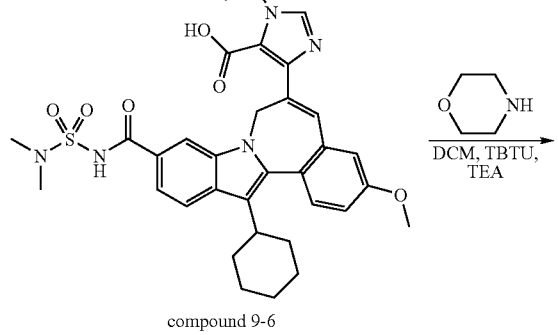
compound 9-6

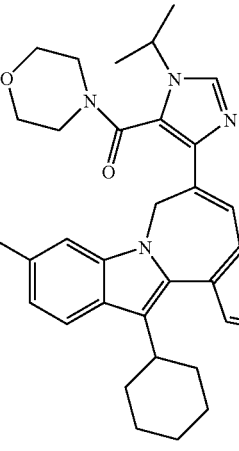
compound 9

Step 1: Preparation of Compound 9-1

A solution of ethyl N-cyanoformimidate (1.095 g, 11.16 mmol) in Ether (5 ml) was added dropwise to a solution of ethyl 2-(isopropylamino)acetate (1.62 g, 111.16 mmol) in ether (5 ml). The reaction mixture was stirred at rt for 1 h and removed the solvent. To the residue was added EtOH (10.00 mL) and potassium ethoxide (1.127 g, 13.39 mmol). The reaction mixture was stirred for 1 h, removed the solvents to afford a tan solid (1.9 g, 86%). The crude product was used in next step.

Step 2: Preparation of Compound 9-2

To a solution of isopentyl nitrite (3.86 mL, 28.9 mmol) in $CH_2I_2$ (20 mL, 248 mmol) was added ethyl 4-amino-1-isopropyl-1H-imidazole-5-carboxylate (1.9 g, 9.63 mmol) in chloroform (8 mL) at 90° C. over 5 min. To complete the addition CHCl3 (10 mL) was used to wash down the solid. After the reaction mixture was stirred for 1 h, the solvent was partially removed and purified on Thomson 90 g column (EtOAc/hexane: 0 to 60%) to afford the compound 9-2 as a brown solid (0.739 g, 25%). LC-MS retention time: 2.098 min; MS m/z 309 (M+H)+; 1H NMR (400 MHz, CHLOROFORM-d) δ ppm 7.65 (1H, s), 5.22-5.30 (1H, m), 4.36 (2H, q, J=7.22 Hz), 1.47 (6H, d, J=6.80 Hz), 1.43 (3H, t, J=7.18 Hz).

Step 3: Preparation of Compound 9-3

In a microwave vial was added ethyl 4-iodo-1-isopropyl-1H-imidazole-5-carboxylate (0.389 g, 1.263 mmol), Tetrakis (0.142 g, 0.123 mmol), CuI (0.03 g) and compound 1-3 (0.9 g, 1.228 mmol). Capped the vial evacuated and filled with nitrogen. Dioxane (3.5 ml) was added and evacuated, filled with nitrogen. The reaction mixture was heated in a oil bath at 120° C. for 2 h. Cooled and removed the solvent and the residue was purified on Thomson 80 g column (EtOAc/hexane: 0 to 80%) to afford compound 9-3 as a pale yellow solid (0.364 g, 47%). LC-MS retention time: 3.588 min; MS m/z 624 (M+H)+.

Step 4: Preparation of Compound 9-4

A mixture of compound 9-3 (0.364 g, 0.584 mmol) and TFA (2 ml, 26.0 mmol) in DCM (1 mL) was stirred at rt for 0.5 h and removed the excess TFa and solvent in vacuum to afford compound the compound 9-4 as a yellow solid (0.331 g, 100%).
LC-MS retention time: 3.265 min; MS m/z 568 (M+H)+.

Step 5: Preparation of Compound 9-5

A mixture of compound 9-4 (0.331 g, 0.583 mmol), N,N-dimethyl sulfamide (0.22 g, 1.772 mmol), DMAP (0.499 g, 4.08 mmol), and N-(3-Dimethylaminopropyl)-N'-ethylcarbodiimide hydrochloride (0.22 g, 1.148 mmol) in DCM (4 mL) was stirred at rt for 3 days and quenched with 1 ml of MeOH, stirred for 5 min, removed the solvents. The residue was purified on Thomson 40 g column (EtOAc/hexane: 5 to 100%) to afford the compound 9-5 as a DMAP salt (0.42 g, 90%). LC-MS retention time: 3.221 min; MS m/z 674 (M+H)+.

Step 6: Preparation of Compound 9-6

A mixture of compound 9-5 (0.42 g, 0.528 mmol) in THF (5 mL), MeOH (3 mL) and sodium hydroxide (3 mL, 3.00 mmol) was stirred at rt for 16 h. The reaction mixture was partially concentrated, diluted with EtOAc, washed with pH 4 buffer, dried (MgSO4), and removed the solvent to afford the compound 9-6 as a yellow solid.
LC-MS retention time: 2.981 min; MS m/z 646 (M+H)+.

Step 7: Preparation of Compound 7

A mixture of compound 9-6 (0.040 g, 0.062 mmol), morpholine (0.03 mL, 0.344 mmol) and TBTU (0.035 g, 0.109 mmol) in DCM (1 mL) was stirred for 1.5 h, and diluted with MeOH (1 ml), removed the solvent and purified by Prep-HPLC to afford the compound 9 as a yellow solid and isolated as mono TFA salt (0.0091 g, 18%).
LC-MS retention time: 3.061 min; MS m/z 715 (M+H)+; 1H NMR (400 MHz, CHLOROFORM-d) δ ppm 8.50 (1H, br. s.), 8.25 (1H, br. s.), 7.88 (1H, d, J=8.31 Hz), 7.67 (1H, br. s.), 7.48-7.56 (1H, m), 7.09 (1H, dd, J=8.56, 2.52 Hz), 7.01 (1H, br. s.), 6.92 (1H, br. s.), 5.51 (1H, d, J=14.35 Hz), 4.59-4.71 (2H, m), 4.53 (1H, d, J=13.35 Hz), 3.89 (3H, s), 3.74-3.83 (1H, m), 3.42 (2H, br. s.), 3.21-3.30 (1H, m), 3.03 (6H, s), 2.83-2.95 (1H, m), 2.28 (1H, br. s.), 1.86-2.20 (7H, m), 1.73-1.83 (2H, m), 1.09-1.72 (9H, m).

Preparation of Compound 10: 13-cyclohexyl-N-[(dimethylamino)sulfonyl]-6-[5-[[(2R,6S)-2,6-dimethyl-4-morpholinyl]carbonyl]-1-(1-methylethyl)-1H-imidazol-4-yl]-3-methoxy-7H-indolo[2,1-a][2]benzazepine-10-carboxamide

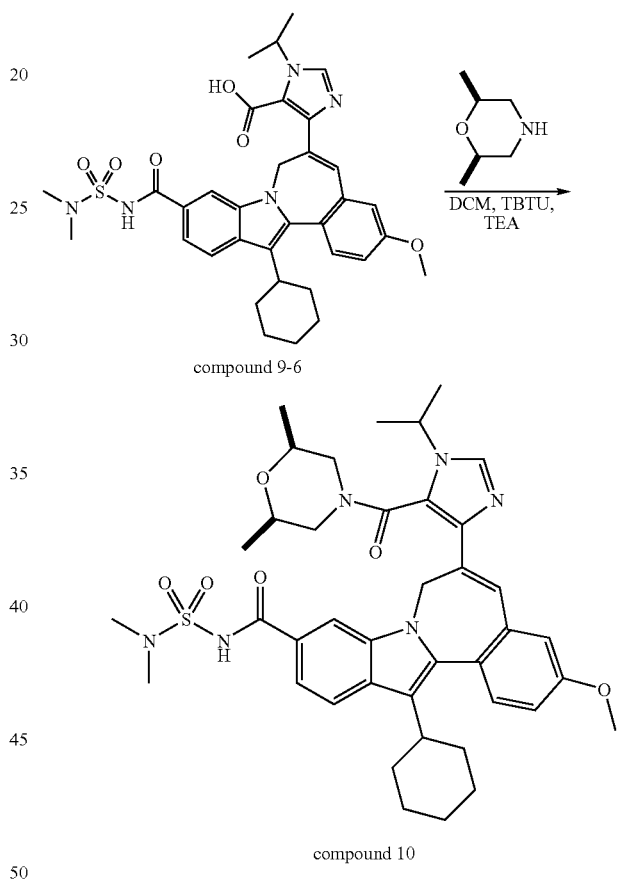

A mixture of compound 9-6 (0.04 g, 0.062 mmol), (2R,6S)-2,6-dimethylmorpholine (0.03 mL, 0.244 mmol), and TBTU (0.035 g, 0.109 mmol) in DCM (1 mL) was stirred for 1 h, quenched with MeOH, removed the solvent and purified by Prep-HPLC to afford compound 10 as a yellow solid and isolated as mono TFA salt (0.011 g, 19%). LC-MS retention time: 3.188 min; MS m/z 743 (M+H)+; compound 10 exists as rotamers as observed by 1H NMR; major rotamer: 1H NMR (400 MHz, CHLOROFORM-d) δ ppm 8.21-8.44 (2H, m), 7.82-7.92 (1H, m), 7.61-7.74 (1H, m), 5.47-5.68 (1H, m), 4.62-4.83 (1H, m), 4.24-4.56 (1H, m), 3.84-3.89 (3H, m), 3.20-3.79 (7H, m), 3.03 (6H, s), 2.74-2.96 (2H, m), 2.28-2.56 (1H, m), 1.89-2.17 (4H, m), 1.11-1.81 (15H, m), 0.63-1.05 (3H, m), −0.04 (1H, d, J=5.79 Hz).

275

Preparation of Compound 11: 13-cyclohexyl-6-[4-[[(2R,6S)-2,6-dimethyl-4-morpholinyl]carbonyl]-1-(1-methylethyl)-1H-1,2,3-triazol-5-yl]-3-methoxy-N-[(1-methylethyl)sulfonyl]-7H-indolo[2,1-a][2]benzazepine-10-carboxamide

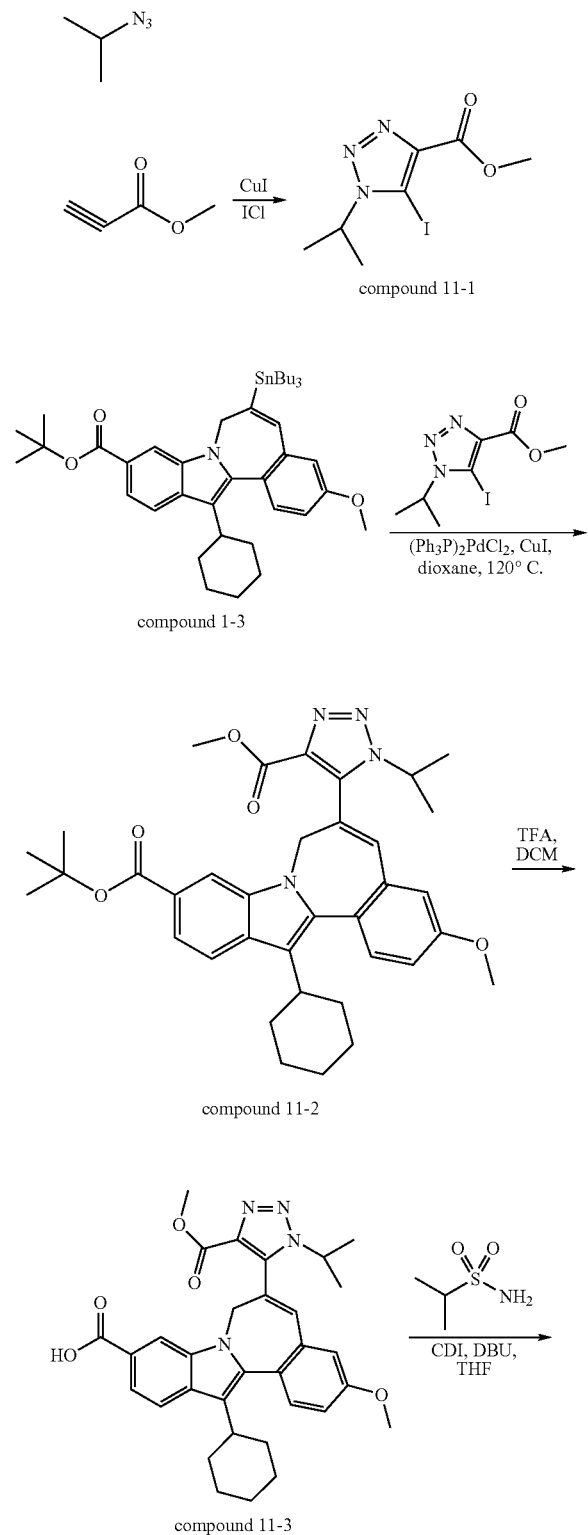

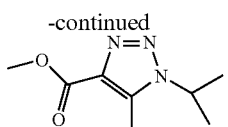

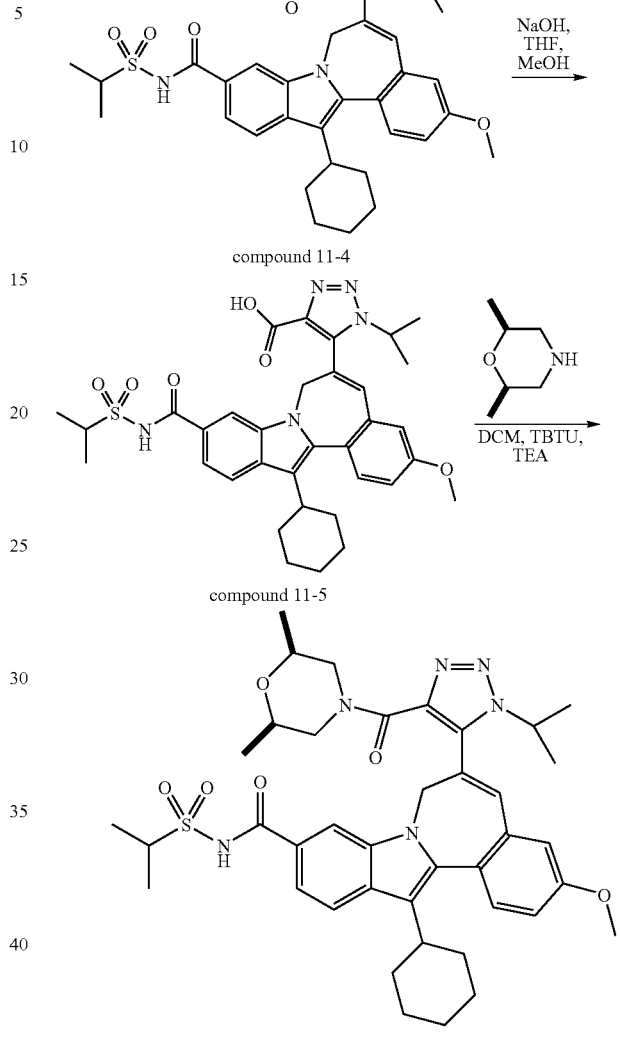

Step 1: Preparation of Compound 11-1

To a solution of 2-azidopropane (0.5 g, 5.87 mmol) in THF (20 mL) was added methyl propiolate (0.631 mL, 7.05 mmol) under N2 and followed by addition of TEA (0.983 mL, 7.05 mmol) dropwise. Iodine monochloride (1.145 g, 7.05 mmol) was added (washed with 3 mL of THF to complete the transfer) and added powdered copper (I) iodide (1.343 g, 7.05 mmol) at −30° C. bath temperature. The reaction mixture was stirred at −30° C. for 5 min, removed the bath and stirred at rt for 20 h. The reaction mixture was concentrated and directly purified on Thomson 80 g column (EtOAc/hexane: 0 to 80%) to afford the compound 10-1 as a yellow solid (0.257 g, 15%). LC-MS retention time: 1.727 min; MS m/z 296 (M+H)$^+$; 1H NMR (400 MHz, CHLOROFORM-d) δ ppm 4.71-4.90 (1H, m), 3.96 (3H, s), 1.63 (6H, d, J=6.80 Hz).

Step 2: Preparation of Compound 11-2

Powdered 3 A molecular sieve (0.75 g) was added into a 20 ml microwave viall, flame dried under vacuum, refilled with N2 and cooled. Compound 1-3 (0.682 g, 0.931 mmol), methyl 5-iodo-1-isopropyl-1H-1,2,3-triazole-4-carboxylate (0.229 g, 0.776 mmol), and Bis(triphenylphosphine)palladium(II) dichloride (0.055 g, 0.078 mmol) were added. Capped the vial, evacuated and filled with nitrogen. Dioxane (5 ml) was added and the mixture was evacuated and filled with nitrogen and heated in a oil bath at 120° C. for 20 h. The reaction mixture was cooled down and filtered through celite, removed the solvent and the residue was purified on Thomson 25 g column (EtOAc/hexane: 0 to 100%) to afford the compound 10-2 as a dark brown solid (0.269 g, 57%). LC-MS retention time: 3.743 min; MS m/z 611 (M+H)⁺; 1H NMR (400 MHz, CHLOROFORM-d) δ ppm 7.81 (1H, d, J=8.31 Hz), 7.74 (1H, s), 7.64 (1H, dd, J=8.56, 1.26 Hz), 7.51 (1H, d, J=8.56 Hz), 7.08 (1H, dd, J=8.56, 2.77 Hz), 6.93 (1H, d, J=2.77 Hz), 4.87-5.00 (1H, m), 4.79-4.87 (1H, m), 4.67-4.78 (1H, m), 3.96 (3H, s), 3.90 (3H, s), 2.76-2.87 (0H, m), 1.98-2.17 (3H, m), 1.86-1.98 (1H, m), 1.69-1.84 (2H, m), 1.63 (6H, d, J=6.80 Hz), 1.56 (9H, s), 1.13-1.70 (6H, m).

Step 3: Preparation of Compound 11-3

A mixture of compound 11-2 (0.269 g, 0.440 mmol), DCM (0.5 mL), and TFA (1 ml, 12.98 mmol) was stirred at rt for 1 h. Removed the solvents in vacuum to afford the compound 10-3 (0.244 g, 100%). LC-MS retention time: 3.575 min; MS m/z 555 (M+H)⁺.

Step 4: Preparation of Compound 11-4

A mixture of compound 11-1 (0.244 g, 0.440 mmol), propane-2-sulfonamide (0.163 g, 1.320 mmol) and DMAP (0.376 g, 3.08 mmol), N-(3-Dimethylaminopropyl)-N'-ethyl-carbodiimide hydrochloride (0.180 g, 0.939 mmol) in DCM (1 mL) was stirred at rt overnight. The reaction mixture was diluted with EtOAc and washed with cold 0.1 N HCl, water, brine, dried (MgSO4), removed the solvent, and purified on Thomson 12 g column [EtOAc-MeOH (9-1)/hexane: 5 to 100%] to afford the compound 10-4 as a glass (0.150 g, 52%). LC-MS retention time: 3.310 min; MS m/z 660 (M+H)⁺.

Step 5: Preparation of Compound 11-5

A mixture of compound 11-4 (0.15 g, 0.227 mmol) in THF (2 mL), NaOH (0.909 mL, 0.909 mmol), and MeOH (1 mL) was stirred at rt for 20 h, diluted with EtOAc and washed with 0.2 N HCl brine, dried (MgSO4), removed the solvent to afford the compound 10-5 as a yellow solid (0.134 g, 91%). LC-MS retention time: 3.233 min;
MS m/z 646 (M+H)⁺.

Step 6: Preparation of Compound 11

A mixture of compound 11-5 (0.0446 g, 0.069 mmol), (2R,6S)-2,6-dimethylmorpholine (0.008 g, 0.069 mmol), TEA (0.03 mL, 0.215 mmol), and TBTU (0.022 g, 0.069 mmol) in DCM was stirred at rt for 2 h. Quenched with MeOH, removed the solvent and purified by prep HPLC to afford the compound 11 as a yellow solid (0.0122 g, 23%). LC-MS retention time: 3.273 min; MS m/z 743 (M+H)⁺; 1H NMR (400 MHz, CHLOROFORM-d) δ ppm 7.89 (1H, d, J=8.56 Hz), 7.41-7.59 (2H, m), 7.08 (1H, d, J=8.56 Hz), 6.94 (1H, d, J=2.27 Hz), 6.74 (1H, s), 4.91-5.13 (1H, m), 4.53-4.74 (1H, m), 3.96-4.35 (2H, m), 3.90 (3H, s), 3.34-3.60 (1H, m), 2.40-2.99 (11H, m), 1.89-2.17 (4H, m), 1.67-1.84 (2H, m), 0.66-1.56 (18H, m).

Preparation of Compound 12: 13-cyclohexyl-3-methoxy-N-[(1-methylethyl)sulfonyl]-6-[1-(1-methylethyl)-4-[[(3R,5S)-3,4,5-trimethyl-1-piperazinyl]carbonyl]-1H-1,2,3-triazol-5-yl]-7H-indolo[2,1-a][2]benzazepine-10-carboxamide

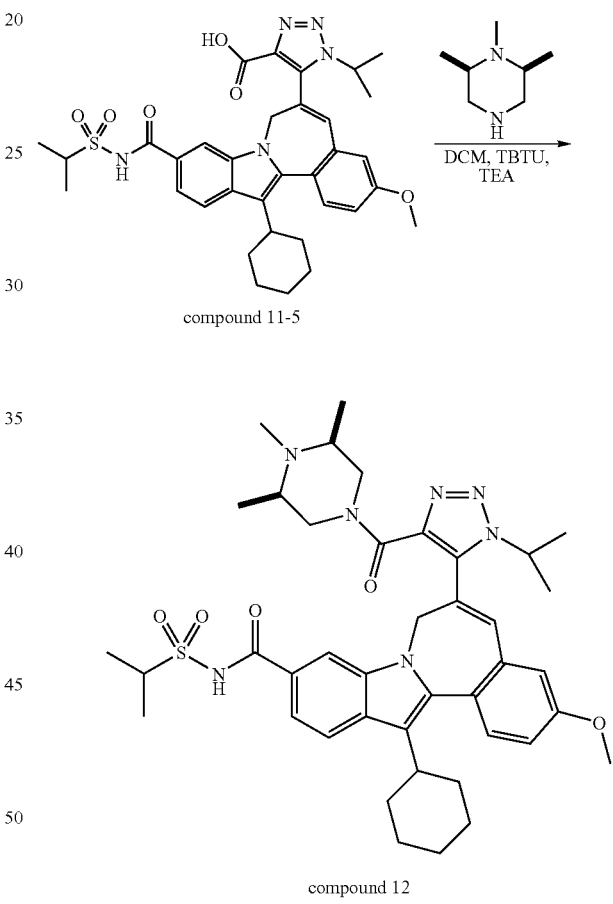

compound 11-5 compound 12

A mixture of compound 11-5 (0.0446 g, 0.069 mmol), (2R,6S)-1,2,6-trimethylpiperazine (0.0124 g, 0.097 mmol), TEA (0.1 mL, 0.717 mmol) and TBTU (0.031 g, 0.097 mmol) in DCM was stirred at rt for 1 h. Quenched with MeOH, removed the solvent and purified by prep HPLC to afford the compound 12 as a yellow solid (0.0129 g, 21%) and isolated as mono TFA salt. LC-MS retention time: 3.081 min; MS m/z 756 (M+H)⁺; 1H NMR (400 MHz, CHLOROFORM-d) δ ppm 7.76-7.92 (2H, m), 7.41-7.56 (2H, m), 7.06 (1H, dd, J=8.69, 2.39 Hz), 6.98 (1H, br. s.), 6.75 (1H, s), 5.33 (1H, br. s.), 5.02 (1H, br. s.), 4.66 (1H, d, J=13.85 Hz), 3.99 (1H, br. s.), 3.89 (3H, s), 2.63-3.78 (10H, m), 1.00-2.21 (28H, m).

Preparation of Compound 13: 13-cyclohexyl-N-[(dimethylamino)sulfonyl]-3-methoxy-6-[1-(1-methylethyl)-4-(4-morpholinylcarbonyl)-1H-1,2,3-triazol-5-yl]-7H-indolo[2,1-a][2]benzazepine-10-carboxamide

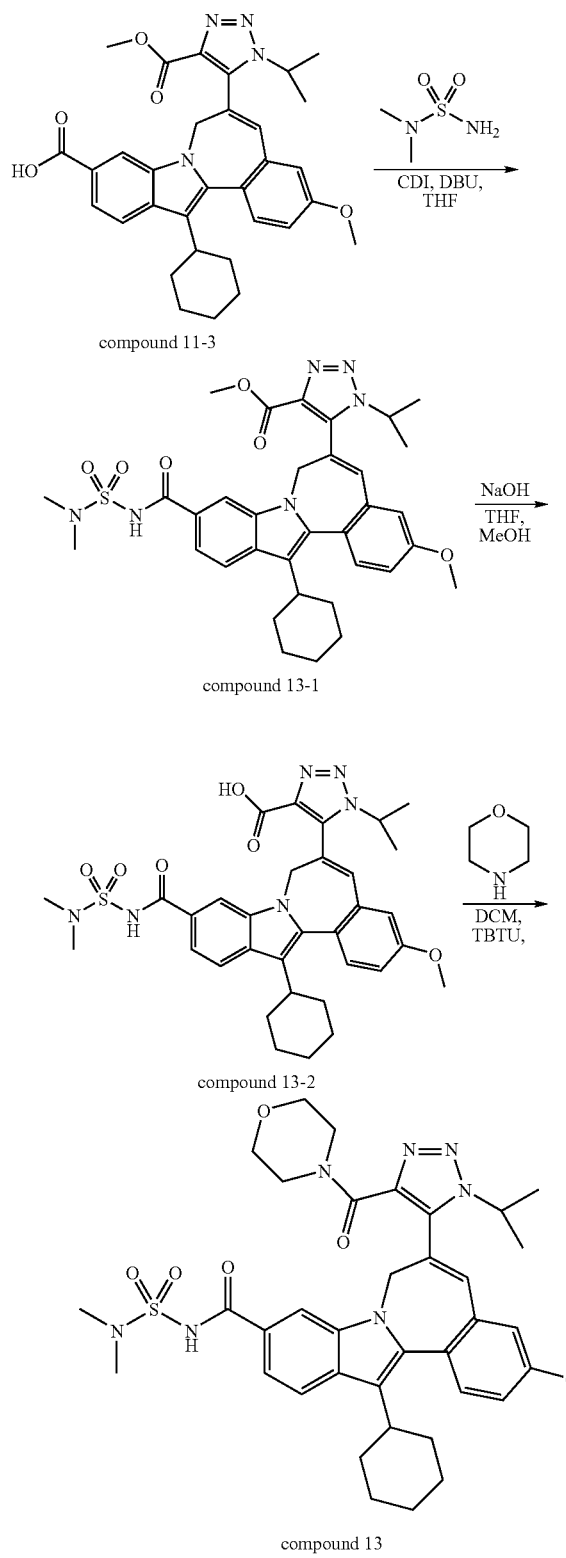

Step 1: Preparation of Compound 13-1

A mixture of compound 11-3 (0.296 g, 0.534 mmol) and CDI (0.169 g, 1.042 mmol) in THF (5 ml) was stirred at 50° C. for 0.5 h, cooled and added N,N-dimethylsulfamide (0.129 g, 1.039 mmol) and DBU (0.4 ml, 2.65 mmol). The mixture was stirred at ambient temperature overnight. Removed the solvent in vacuum and added DCM (5 mL) and DMAP (0.250 g, 2.046 mmol), and 1-(3-Dimethylaminopropyl)-3-ethylcarbodiimide hydrochloride (0.140 g, 0.730 mmol). The reaction mixture was stirred overnight, concentrated and directly loaded on Thomson 40 g column (EtOAc/Hexane: 5 to 100%). The collection was dissolved in EtOAc and washed with cold HCl (1N), brine, dried (MgSO4), removed the solvent to afford compound 13-1 as a yellow solid (0.240 g, 68%). LC-MS retention time: 3.250 min; MS m/z 661 (M+H)$^+$; 1H NMR (400 MHz, CHLOROFORM-d) δ ppm 9.06 (1H, br. s.), 8.21 (1H, br. s.), 7.90 (1H, d, J=8.56 Hz), 7.48-7.57 (1H, m), 7.19 (1H, br. s.), 7.09 (1H, dd, J=8.69, 2.64 Hz), 6.95 (1H, d, J=2.52 Hz), 6.75 (1H, s), 5.21 (1H, br. s.), 4.76 (1H, br. s.), 3.93-4.02 (1H, m), 3.91 (3H, s), 3.77 (3H, s), 2.92 (6H, s), 2.81-2.89 (1H, m), 1.09-2.27 (16H, m).

Step 2: Preparation of Compound 13-2

A mixture of compound 13-1 (0.24 g, 0.363 mmol) in THF (4 mL), NaOH (2 mL, 2.000 mmol) and MeOH (2 mL) was stirred at rt for 20 h. Diluted with EtOAc and washed with 0.2 N HCl, brine, dried (MgSO4), removed the solvent to afford a brown solid. LC-MS retention time: 3.220 min; MS m/z 647 (M+H)$^+$; 1H NMR (400 MHz, CHLOROFORM-d) δ ppm 8.51 (1H, br. s.), 7.89 (1H, d, J=8.56 Hz), 7.65 (1H, d, J=7.81 Hz), 7.43 (1H, d, J=8.56 Hz), 6.99 (1H, d, J=9.32 Hz), 6.93 (1H, d, J=2.52 Hz), 6.77 (1H, s), 5.47 (1H, br. s.), 4.66 (1H, d, J=14.86 Hz), 3.91-4.00 (1H, m), 3.80 (3H, s), 2.83 (6H, s), 1.04-2.24 (16H, m).

Step 3: Preparation of Compound 13

To a mixture of compound 13-2 (0.040 g, 0.062 mmol) and morpholine (0.02 ml, 0.230 mmol) in DCM (1 mL) was added TEA (0.03 ml, 0.215 mmol) and TBTU (0.028 g, 0.087 mmol). The reaction mixture was stirred at rt for 2 h and another portion of morpholine (0.02 ml, 0.230 mmol) and TBTU (0.028 g, 0.087 mmol) was added and stirred for 1 h. Quenched with MeOH, removed the solvents, and the residue was dissolved in MeOH, filtered and purified by prep-HPLC to afford a yellow solid which was re-purified by prep TLC (MeOH/DCM: 2 to 10%) to afford the compound 13 as a glass (0.0028 g, 6%). LC-MS retention time: 3.198 min; MS m/z 716 (M+H)$^+$; 1H NMR (400 MHz, CHLOROFORM-d) δ ppm 7.87 (1H, d, J=8.06 Hz), 7.75 (1H, br. s.), 7.50 (1H, d, J=8.81 Hz), 7.36 (1H, d, J=7.81 Hz), 7.04-7.09 (1H, m), 6.93 (1H, br. s.), 6.70 (1H, s), 5.04 (1H, d, J=18.63 Hz), 4.66-4.78 (1H, m), 4.27 (1H, br. s.), 4.11 (1H, br. s.), 3.90-4.01 (1H, m), 3.89 (3H, s), 3.50-3.75 (4H, m), 3.02 (6H, s), 2.83 (1H, br. s.), 2.67 (2H, br. s.), 1.86-2.14 (4H, m), 0.74-1.82 (12H, m).

281

Preparation of Compound 14: 13-cyclohexyl-6-[4-[(3-methyl-3,8-diazabicyclo[3.2.1]oct-8-yl)carbonyl]-1-(1-methylethyl)-1H-1,2,3-triazol-5-yl]-N-[(dimethylamino)sulfonyl]-3-methoxy-7H-indolo[2,1-a][2]benzazepine-10-carboxamide

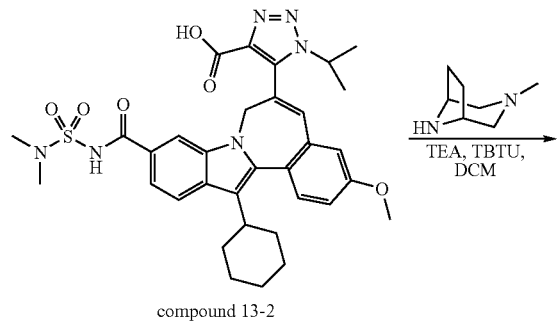

compound 13-2 compound 14

To a mixture of compound 13-2 (0.040 g, 0.062 mmol) and 3-methyl-3,8-diazabicyclo[3.2.1]octane, HCl (0.025 g, 0.154 mmol) in DCM (1 mL) was added TEA (0.10 ml, 0.717 mmol) and TBTU (0.028 g, 0.087 mmol). The reaction mixture was stirred at rt for 2 h and another portion of 3-methyl-3,8-diazabicyclo[3.2.1]octane, HCl (0.025 g, 0.154 mmol) and TBTU (0.028 g, 0.087 mmol) were added and stirred for 1 h. Quenched with MeOH, removed the solvent, and purified by prep HPLC to afford the compound 14 (0.0223 g, 41.5%) as a yellow solid and isolated as mono TFA salt. LC-MS retention time: 3.086 min; MS m/z 755 (M+H)$^+$; 1H NMR (400 MHz, CHLOROFORM-d) δ ppm 8.66 (1H, br. s.), 7.87 (1H, d, J=8.56 Hz), 7.79 (1H, br. s.), 7.46-7.56 (1H, m), 7.32 (1H, d, J=8.31 Hz), 7.08 (1H, dd, J=8.69, 2.64 Hz), 6.92 (1H, br. s.), 6.69 (1H, br. s.), 5.81 (1H, br. s.), 5.10 (1H, d, J=15.36 Hz), 4.82-5.04 (2H, m), 4.71 (1H, d, J=14.86 Hz), 3.89 (3H, s), 3.64-3.84 (3H, m), 3.57 (1H, d, J=11.58 Hz), 3.01 (6H, s), 2.70-3.28 (5H, m), 1.87-2.59 (8H, m), 1.71-1.85 (2H, m), 1.03-1.58 (6H, m), 0.39-0.88 (2H, m).

282

Preparation of Compound 15: 13-cyclohexyl-6-[4-[[(2R,6S)-2,6-dimethyl-4-morpholinyl]carbonyl]-1-1-(1-methylethyl)-1H-1,2,3-triazol-5-yl]-N-[(dimethylamino)sulfonyl]-3-methoxy-7H-indolo[2,1-a][2]benzazepine-10-carboxamide

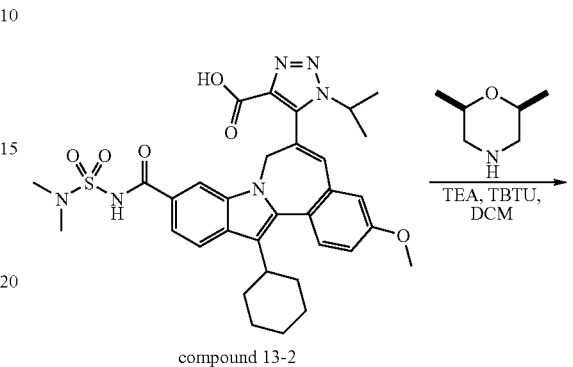

compound 13-2 compound 15

To a mixture of compound 13-2 (0.040 g, 0.062 mmol) and (2R,6S)-2,6-dimethylmorpholine (0.02 ml, 0.163 mmol) in DCM (1 mL) was added TEA (0.03 ml, 0.215 mmol) and TBTU (0.0278 g, 0.087 mmol). The reaction mixture was stirred at rt for 2 h. Quenched with MeOH, removed the solvents. The residue was dissolved in MeOH, filtered, and purified by prep HPLC to afford the compound 15 as a yellow solid (0.0193 g, 41%). LC-MS retention time: 3.253 min; MS m/z 744 (M+H)$^+$; 1H NMR (400 MHz, CHLOROFORM-d) δ ppm 7.89 (1H, d, J=8.56 Hz), 7.78 (1H, br. s.), 7.35-7.56 (2H, m), 7.09 (1H, d, J=8.56 Hz), 6.93 (1H, br. s.), 6.74 (1H, br. s.), 4.94-5.09 (1H, m), 4.67 (1H, d, J=14.60 Hz), 3.94-4.36 (2H, m), 3.90 (3H, s), 3.43-3.64 (1H, m), 3.02 (6H, s), 2.51-3.38 (7H, m), 1.87-2.19 (4H, m), 1.78 (2H, d, J=9.32 Hz), 0.70-1.56 (14H, m).

283

Preparation of Compound 16: 13-cyclohexyl-6-[4-[(6,6-difluorohexahydro-4-methyl-1H-1,4-diazepin-1-yl)carbonyl]-1-(1-methylethyl)-1H-1,2,3-triazol-5-yl]-N-[(dimethylamino)sulfonyl]-3-methoxy-7H-indolo[2,1-a][2]benzazepine-10-carboxamide

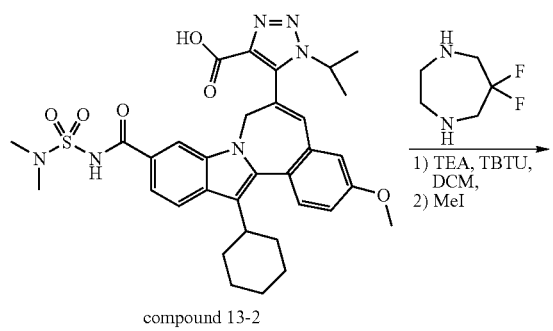

compound 13-2

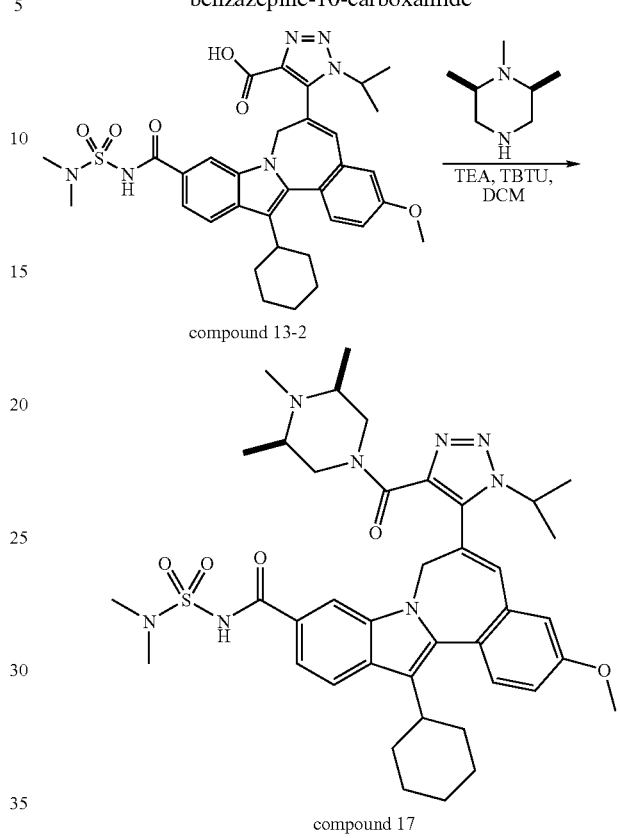

284

Preparation of Compound 17: 13-cyclohexyl-6-[4-[[(3R,5S)-3,4,5-trimethyl-1-piperazinyl]carbonyl]-1-(1-methylethyl)-1H-1,2,3-triazol-5-yl]-N-[(dimethylamino)sulfonyl]-3-methoxy-7H-indolo[2,1-a][2]benzazepine-10-carboxamide compound 16

To a mixture of compound 13-2 (0.040 g, 0.062 mmol) and 6,6-difluoro-1,4-diazepane, hydrobromide (0.0268 g, 0.124 mmol) in DCM (1 mL) was added TEA (0.10 ml, 0.717 mmol) and TBTU (0.0278 g, 0.087 mmol). The reaction mixture was stirred at rt for 1 h. MeI (0.06 ml, 0.960 mmol) was injected to the reaction mixture and stirred at rt for 1.5 h. Quenched with MeOH, removed the solvents, the residue was dissolved in MeOH, filtered, and purified by prep HPLC to afford a yellow solid which was re-purified by prep TLC to afford the compound 16 as a glass (0.0073 g, 15%). LC-MS retention time: 3.076 min; MS m/z 779 (M+H)+.

To a mixture of compound 13-2 (0.040 g, 0.062 mmol) and (2R,6S)-1,2,6-trimethylpiperazine, 2HCl (0.025 g, 0.124 mmol) in DCM (1 mL) was added TEA (0.10 ml, 0.717 mmol) and TBTU (0.028 g, 0.087 mmol). The reaction mixture was stirred at rt for 2 h and another portion of TEA (0.10 ml, 0.717 mmol) and TBTU (0.028 g, 0.087 mmol) were added and stirred for 1 h. Quenched with MeOH, removed the solvents, the residue was dissolved in MeOH, filtered, and purified by prep-HPLC to afford the compound 17 as a yellow solid and isolated as mono TFA salt (0.0293 g, 54%). LC-MS retention time: 3.060 min; MS m/z 757 (M+H)+.

Preparation of Compound 18: 13-cyclohexyl-6-[5-cyclopropyl-3-[[(2R,6S)-2,6-dimethyl-4-morpholinyl]carbonyl]-4-isoxazolyl]-N-[(dimethylamino)sulfonyl]-3-methoxy-7H-indolo[2,1-a][2]benzazepine-10-carboxamide

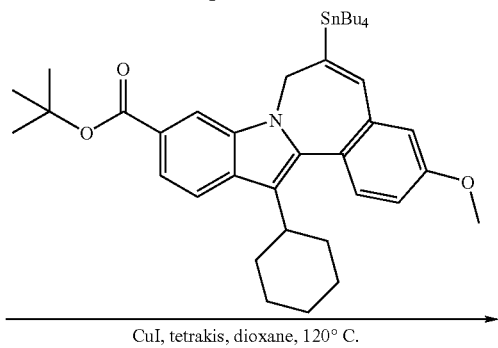

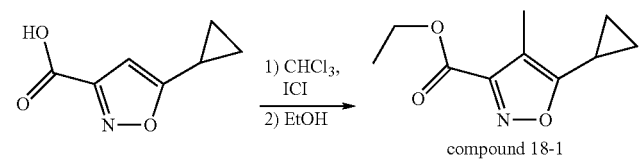

compound 18-1

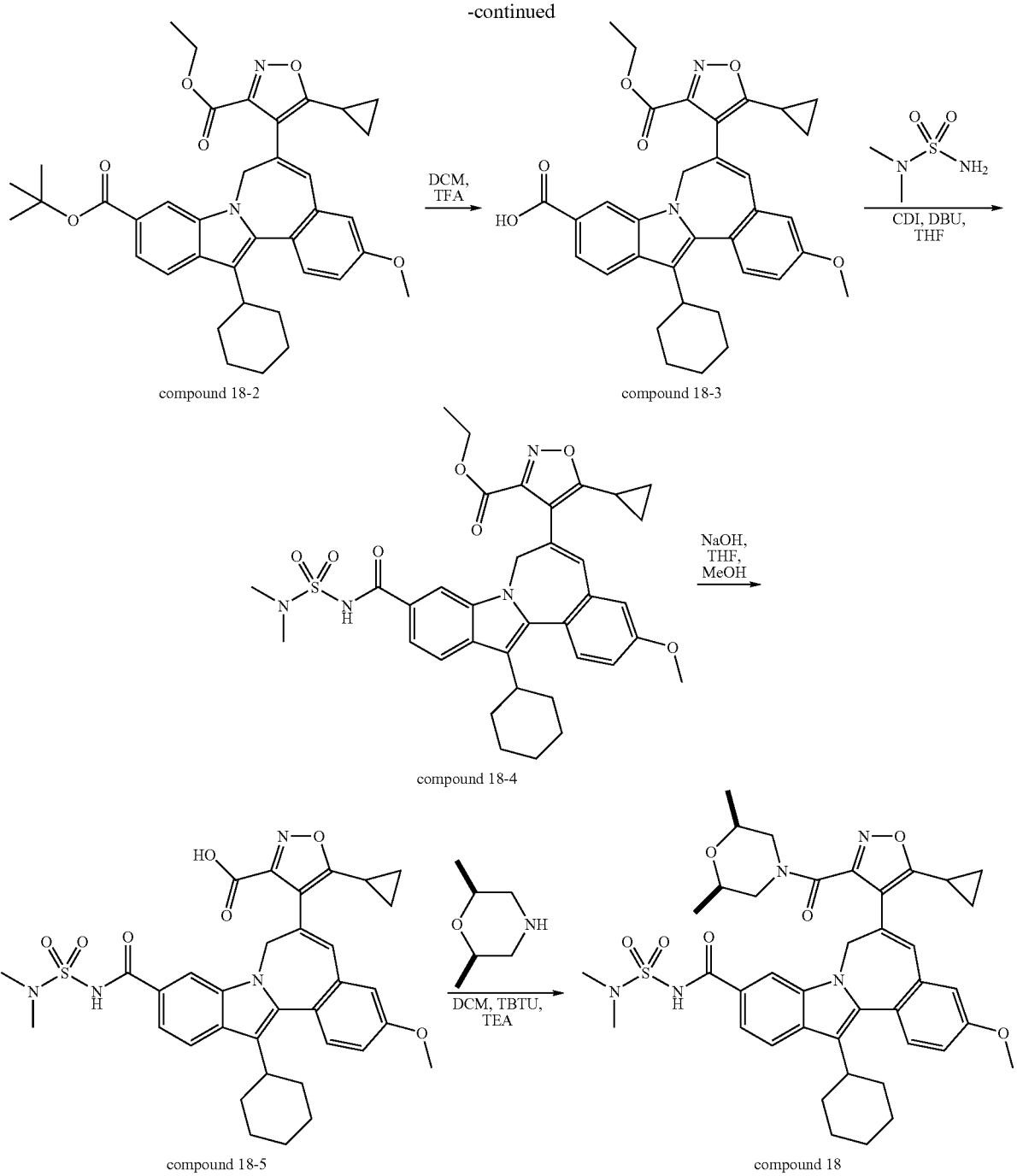

Step 1: Preparation of Compound 18-1

To a solution of 5-cyclopropylisoxazole-3-carboxylic acid (0.5 g, 3.27 mmol) in CHCl3 (3 mL) was added a solution of iodine chloride (0.69 g, 4.25 mmol) in CHCl3 (6 mL) at 0° C. The reaction mixture was stirred at 70° C. for 5 h. Removed the solvent and the residue was dissolved in ethanol (5 mL, 3.27 mmol) was added SOCl2 (0.5 mL, 6.85 mmol). The mixture was stirred at 70° C. for 1 h, cooled, diluted with EtOAc and washed with cold 1N NaOH, brine, dried (MgSO4), and purified by Thomson 25 g column (EtOAc/hexane: 0 to 100%) to afford the compound 18-1 as an oil. LC-MS retention time: 2.502 min; MS m/z 309 (M+H)$^+$; 1H NMR (400 MHz, CHLOROFORM-D) δ ppm 4.43 (2H, q, J=7.22 Hz), 2.10-2.21 (1H, m), 1.41 (3H, t, J=7.05 Hz), 1.11-1.21 (4H, m).

Step 2: Preparation of Compound 18-2

In a microwave vial were added ethyl 5-cyclopropyl-4-iodoisoxazole-3-carboxylate (0.360 g, 0.879 mmol), Tetrakis (0.095 g, 0.082 mmol), CuI (0.03 g) and compound 1-3 (0.600 g, 0.819 mmol). Capped the vial evacuated and filled with nitrogen. Dioxane (3.5 ml) was added and the mixture was evacuated and filled with nitrogen. The reaction mixture was heated in a oil bath at 120° C. for 2 h. Cooled and removed the solvent. The residue was purified on Thomson 40 g column (EtOAc/hexane: 5 to 100%) to afford the compound 18-2 (0.094 g, 18%). LC-MS retention time: 4.04 min; MS m/z 623 (M+H)+ (Method 2); 1H NMR (400 MHz, CHLOROFORM-d) δ ppm 7.85 (1H, d, J=1.26 Hz), 7.81 (1H, d, J=8.31 Hz), 7.64 (1H, dd, J=8.44, 1.38 Hz), 7.50 (1H, d, J=8.56 Hz), 7.02 (1H, dd, J=8.56, 2.77 Hz), 6.90 (1H, d, J=2.77 Hz), 6.74 (1H, s), 4.85-5.02 (1H, m), 4.51-4.65 (1H, m), 4.34-4.42 (2H, m), 3.89 (3H, s), 2.78-2.91 (1H, m), 1.86-2.17 (3H, m), 1.74 (1H, d, J=3.27 Hz), 1.58 (9H, s), 1.37 (3H, t, J=7.05 Hz), 0.49-1.67 (11H, m).

Step 3: Preparation of Compound 18-3

To a solution of compound 18-2 (0.094 g, 0.151 mmol) in DCM (0.5 mL) was added TFA (0.5 mL, 6.49 mmol). The mixture was stirred at rt for 1 h and then removed the solvent in vacuum to afford the compound 18-3 as brown foam (0.086 g, 100%).
LC-MS retention time: 3.548 min; MS m/z 567 (M+H)+.

Step 4: Preparation of Compound 18-4

To a mixture of compound 18-3 (0.086 g, 0.152 mmol) in and THF (1 ml) was added CDI (0.050 g, 0.308 mmol) the mixture was stirred at 50° C. for 0.5 h, cooled down and added N,N-dimethylsulfamide (0.040 g, 0.322 mmol) and DBU (0.1 ml, 0.663 mmol). The mixture was stirred at ambient temperature overnight and directly loaded on Thomson 25 g column (MeOH/DCM: 0 to 25%) to afford the compound 18-4 as a yellow glass (0.086 g, 84%). LC-MS retention time: 3.438 min; MS m/z 673 (M+H)+; 1H NMR (400 MHz, CHLOROFORM-d) δ ppm 8.44 (1H, br. s.), 7.87 (1H, d, J=8.31 Hz), 7.82 (1H, d, J=1.51 Hz), 7.48-7.54 (1H, m), 7.33-7.38 (1H, m), 7.03 (1H, dd, J=8.56, 2.77 Hz), 6.91 (1H, d, J=2.52 Hz), 6.75 (1H, s), 4.92 (1H, br. s.), 4.63 (1H, br. s.), 4.23-4.45 (2H, m), 3.90 (3H, s), 3.03 (6H, s), 2.82-2.90 (1H, m), 1.11-2.16 (14H, m), 0.46-0.94 (4H, m).

Step 5: Preparation of Compound 18-5

A suspension of compound 18-4 (0.086 g, 0.128 mmol) in THF (2 mL), MeOH (1 ml) and NaOH (1 ml, 1.000 mmol) was stirred overnight and diluted with EtOAc, washed with pH 4.0 buffer, brine, dried (MgSO4) removed the solvent to afford compound 18-5 as a yellow solid (0.083 g 100%). LC-MS retention time: 3.331 min;
MS m/z 645 (M+H)+.

Step 6: Preparation of Compound 18

A mixture of compound 18-5 (0.039 g, 0.060 mmol), TEA (0.15 ml, 1.076 mmol), (2R,6S)-2,6-dimethylmorpholine (0.03 mL, 0.244 mmol), TBTU (0.035 g, 0.109 mmol) in 2 ml of DCM was stirred for 3 h and quenched with MeOH, removed the solvent, and purified by Prep-HPLC to afford the compound 18 (0.0159 g, 34%). LC-MS retention time: 3.271 min; MS m/z 742 (M+H)+.

Preparation of Compound 19: 13-cyclohexyl-6-[5-cyclopropyl-3-(4-morpholinylcarbonyl)-4-isoxazolyl]-N-[(dimethylamino)sulfonyl]-3-methoxy-7H-indolo[2,1-a][2]benzazepine-10-carboxamide

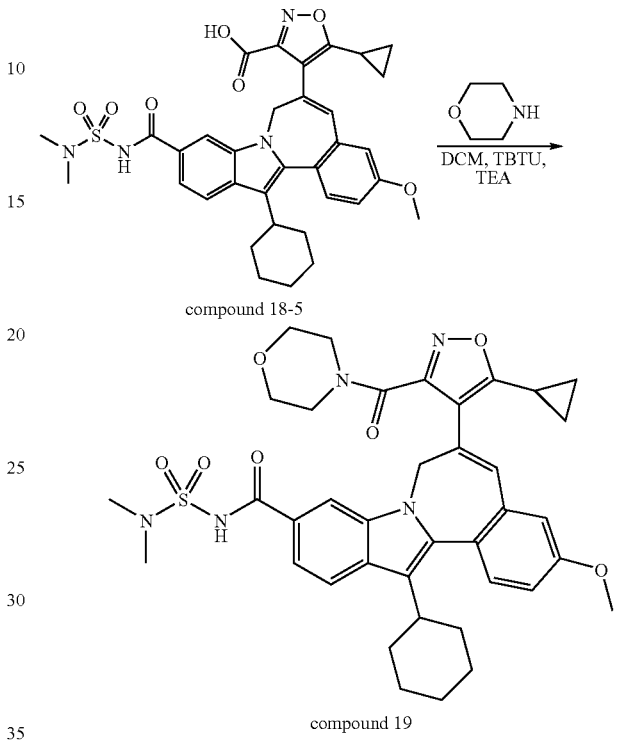

A mixture of compound 18-5 (0.039 g, 0.060 mmol), TEA (0.15 m, 0.1076 mmol), morpholine (0.03 mL, 0.244 mmol), TBTU (0.035 g, 0.109 mmol) in 2 ml of DCM was stirred for 3 h and quenched with MeOH, removed the solvent. The residue was dissolved in MeOH and purified by Prep-HPLC to afford a solid which was re-purified by Prep-HPLC (Solvent A: 10 mM Ammonia Acetate in 95:5 H2O/ACN; 10 mM Ammonia Acetate in 5:95 H2O/ACN; Start B %30 end B % 100, gradient time 16 min; end time 20 min, Column: XTERRA 30×100 mm S5) to afford the compound 19 as a yellow solid (0.0048 g, 11%). LC-MS retention time: 3.190 min; MS m/z 714 (M+H)+; 1H NMR (400 MHz, CHLOROFORM-d) δ ppm 7.91 (1H, d, J=8.56 Hz), 7.80 (1H, d, J=1.51 Hz), 7.55 (1H, dd, J=8.56, 1.51 Hz), 7.51 (1H, d, J=8.81 Hz), 7.05 (1H, dd, J=8.69, 2.64 Hz), 6.89 (1H, d, J=2.77 Hz), 6.86 (1H, s), 4.96 (1H, d, J=15.86 Hz), 4.58 (1H, d, J=14.86 Hz), 3.91 (3H, s), 3.13-3.30 (2H, m), 3.06 (2H, s), 2.78-3.10 (6H, m), 2.66 (1H, br. s.), 1.84-2.28 (7H, m), 1.68-1.82 (2H, m), 1.00-1.55 (10H, m).

Biological Methods

The compounds demonstrated activity against HCV NS5B as determined in the following HCV RdRp assays.
HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The E. coli competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at –80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., Anal. Biochem. 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 µM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for some compounds are reported in Table 1.

TABLE 1
| Structure | IC$_{50}$ (μM) | EC$_{50}$ (μM) |
|---|---|---|
| 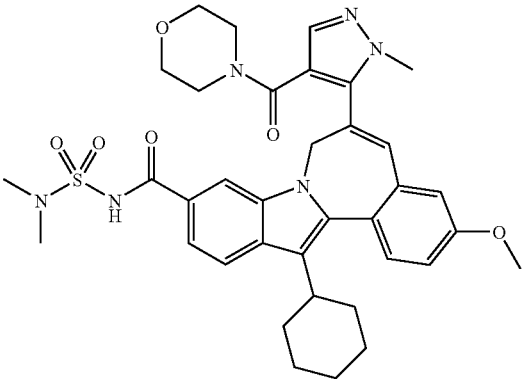 | B | B |
| 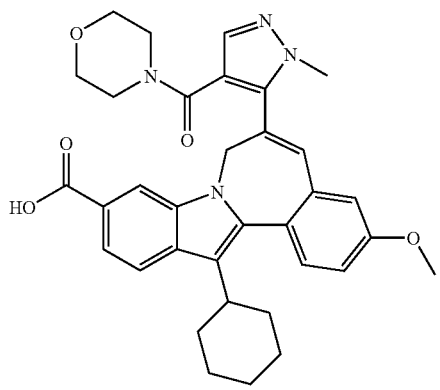 | B | B |
| 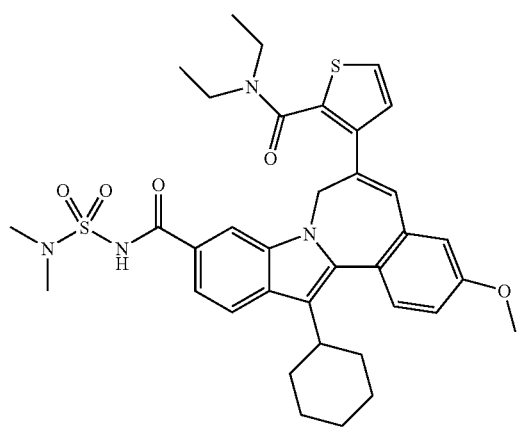 | B | B |
| 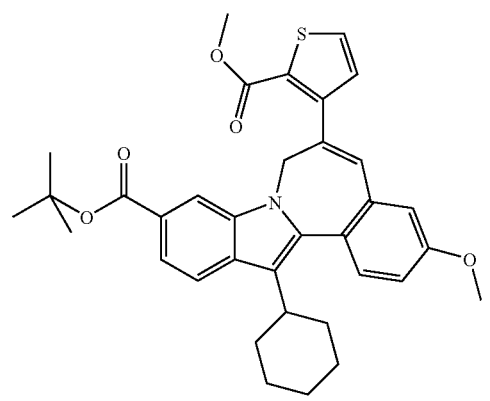 | | |

TABLE 1-continued

| Structure | IC$_{50}$ (μM) | EC$_{50}$ (μM) |
|---|---|---|
| | B | B |
| | B | B |
| 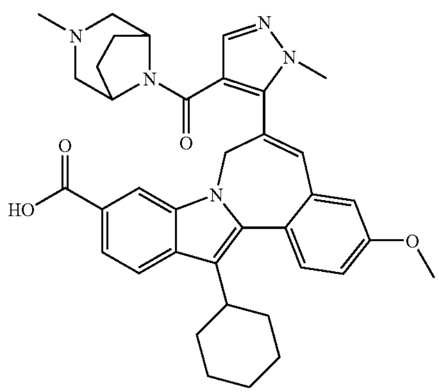 | A | B |
| | B | B |

TABLE 1-continued

| Structure | IC$_{50}$ (μM) | EC$_{50}$ (μM) |
|---|---|---|
| | B | B |
| | D | D |
| | D | D |
| | B | D |

TABLE 1-continued

| Structure | IC$_{50}$ (µM) | EC$_{50}$ (µM) |
|---|---|---|
| | B | B |
| | B | B |
| 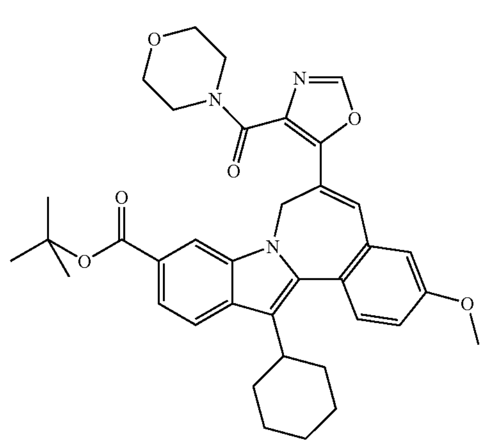 | D | D |

TABLE 1-continued

| Structure | IC$_{50}$ (µM) | EC$_{50}$ (µM) |
|---|---|---|
| | B | B |
| | B | B |
| | B | B |

TABLE 1-continued
| Structure | IC$_{50}$ (μM) | EC$_{50}$ (μM) |
|---|---|---|
| 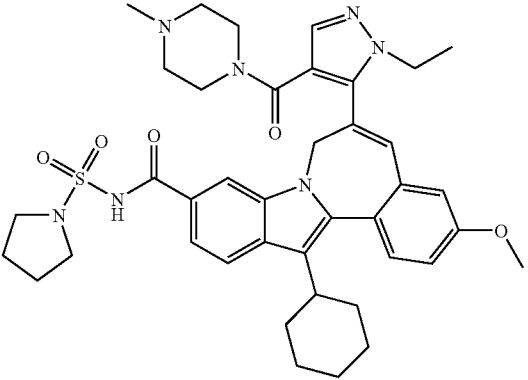 | B | B |
| 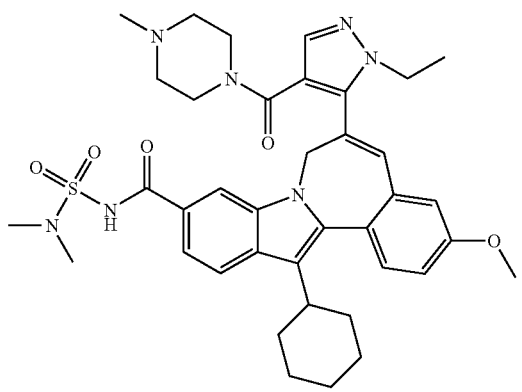 | B | B |
| 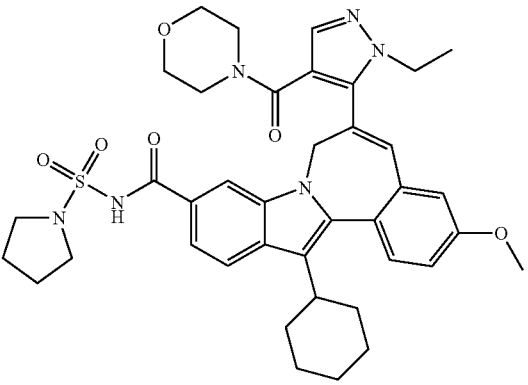 | B | B |
| 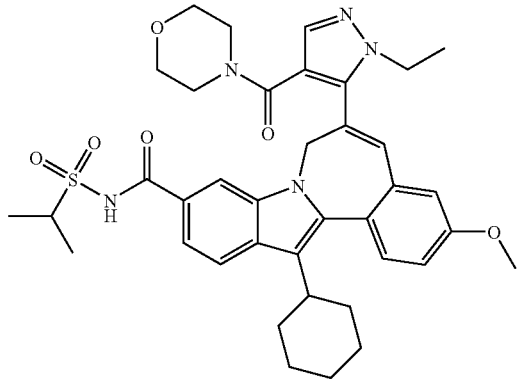 | B | B |

TABLE 1-continued

| Structure | IC$_{50}$ (μM) | EC$_{50}$ (μM) |
|---|---|---|
| | B | B |
| 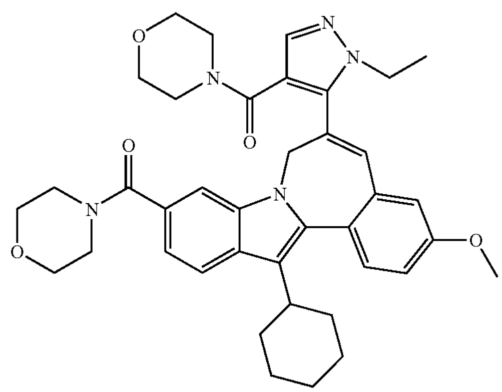 | A | B |
| | B | B |

TABLE 1-continued

| Structure | IC$_{50}$ (μM) | EC$_{50}$ (μM) |
|---|---|---|
| | B | B |
| 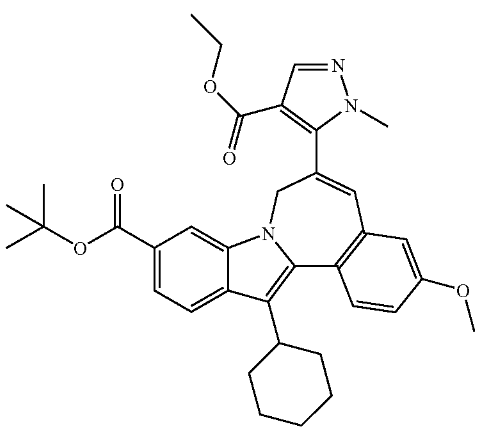 | D | B |
| | B | B |

TABLE 1-continued

| Structure | IC$_{50}$ (μM) | EC$_{50}$ (μM) |
|---|---|---|
| | B | B |
| | B | |
| | B | B |

TABLE 1-continued

| Structure | IC$_{50}$ (μM) | EC$_{50}$ (μM) |
|---|---|---|
| | C | B |
| 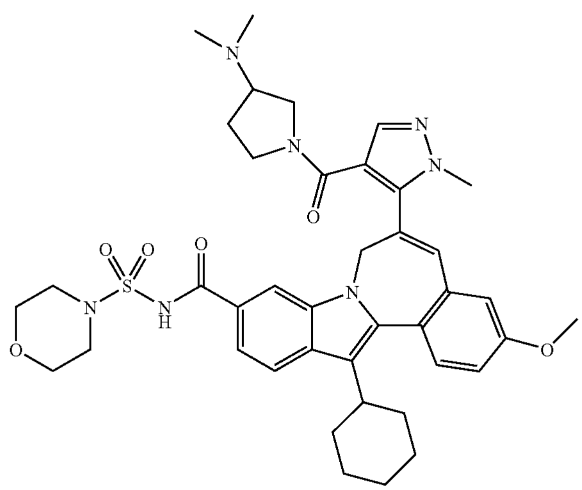 | B | B |
| | C | B |

TABLE 1-continued
| Structure | IC$_{50}$ (μM) | EC$_{50}$ (μM) |
|---|---|---|
| 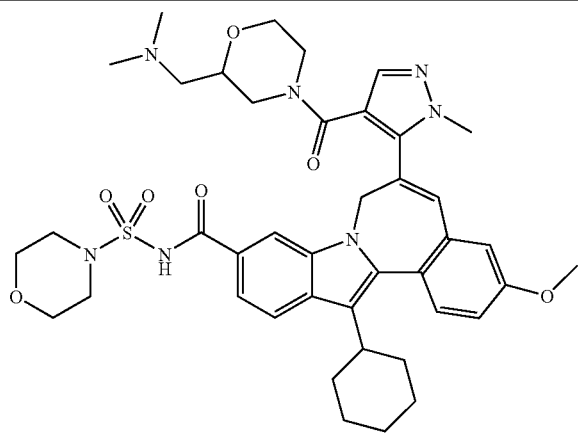 | B | B |
| 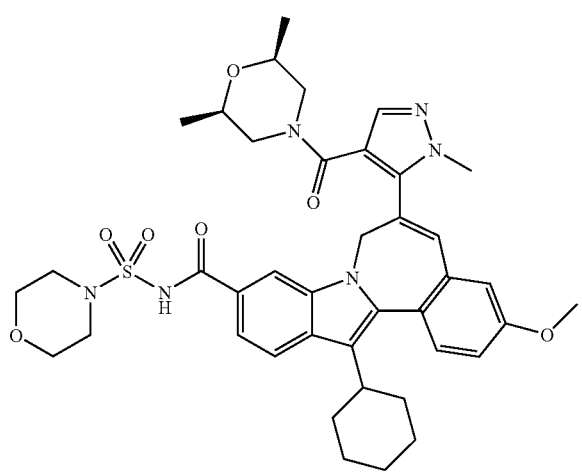 | B | B |
| 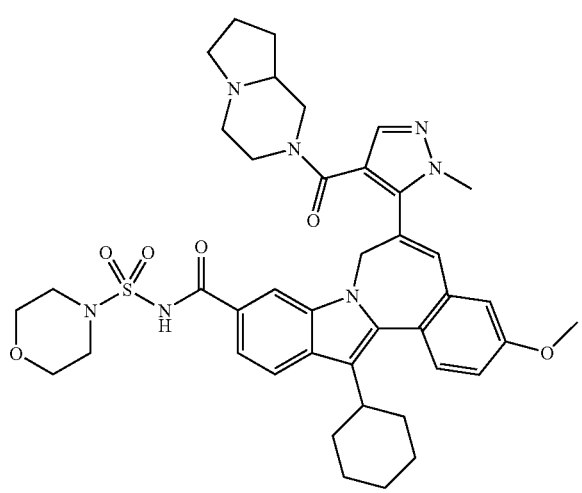 | B | B |

TABLE 1-continued
| Structure | IC$_{50}$ (μM) | EC$_{50}$ (μM) |
|---|---|---|
| 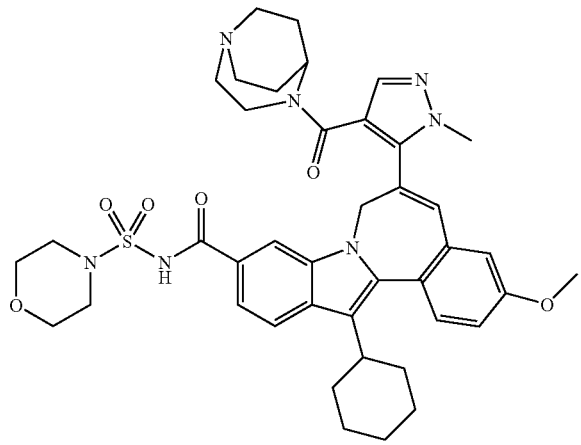 | B | B |
| 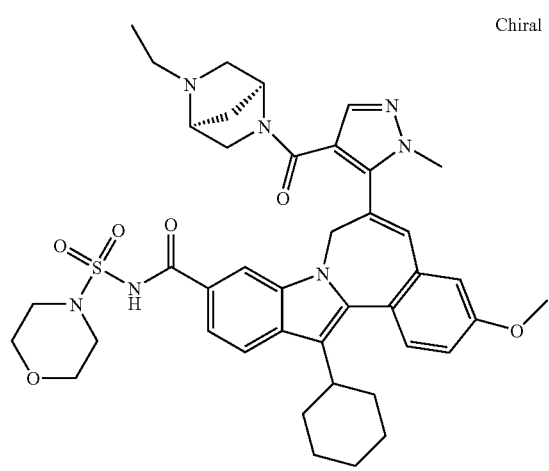 Chiral | B | B |
| 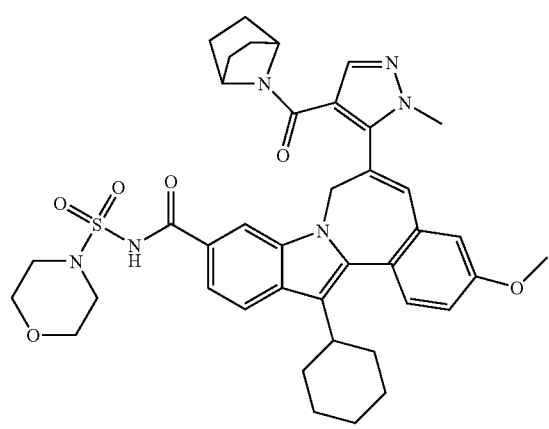 | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued
| Structure | IC$_{50}$ (µM) | EC$_{50}$ (µM) |
|---|---|---|
| 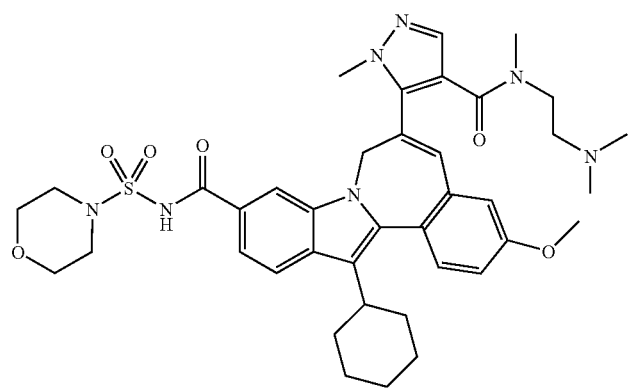 | B | B |
| 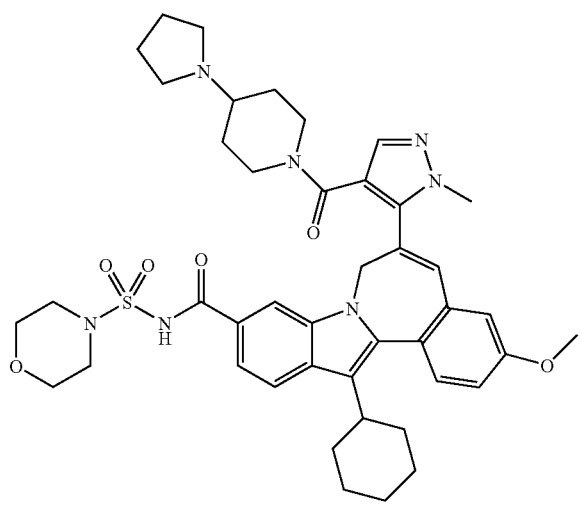 | B | A |
| 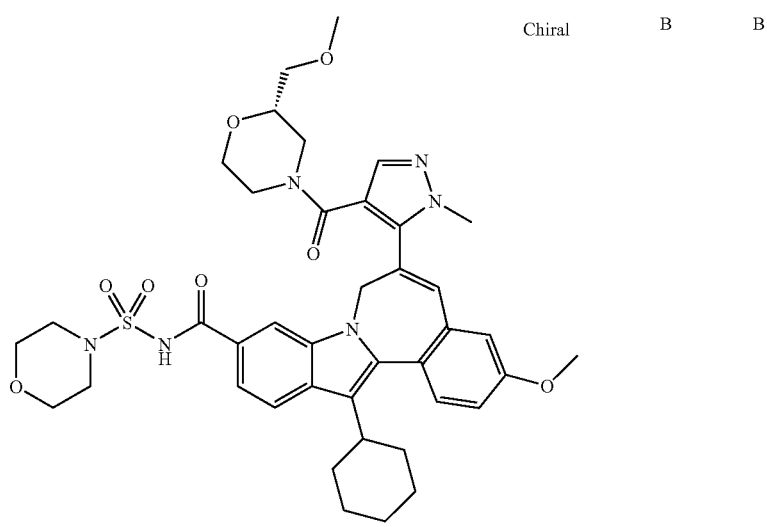 Chiral | B | B |

TABLE 1-continued
| Structure | IC$_{50}$ (μM) | EC$_{50}$ (μM) |
|---|---|---|
| 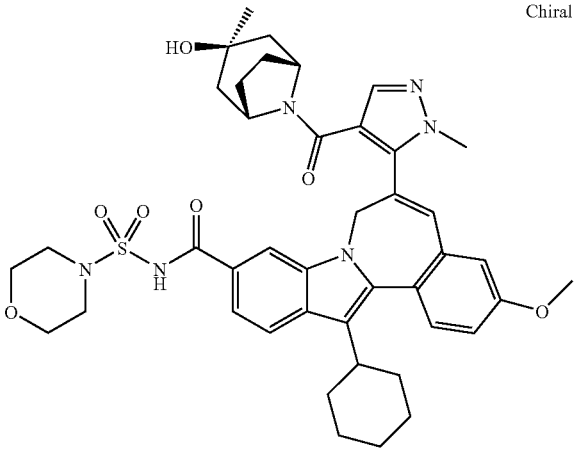 Chiral | B | B |
| 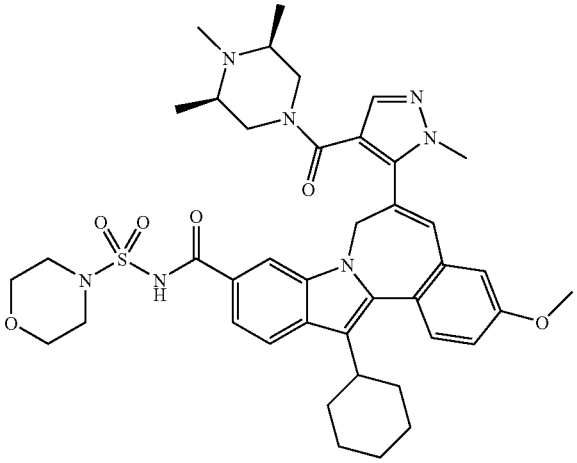 | B | B |
| 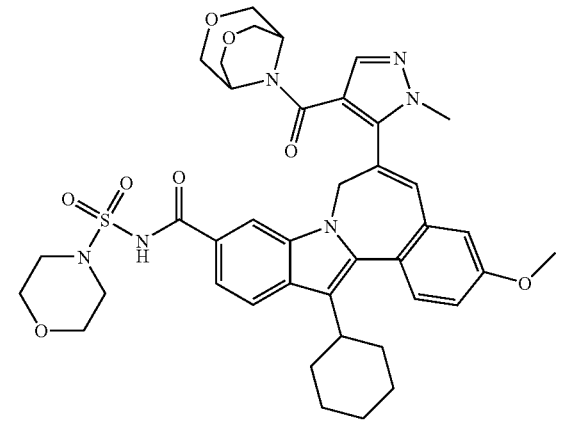 | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | | IC$_{50}$ (μM) | EC$_{50}$ (μM) |
|---|---|---|---|
| | Chiral | B | B |
| | Chiral | B | B |
| | | B | B |
| | | B | B |

TABLE 1-continued
| Structure | IC$_{50}$ (μM) | EC$_{50}$ (μM) |
|---|---|---|
| | B | B |
| | B | B |
| Chiral | B | B |
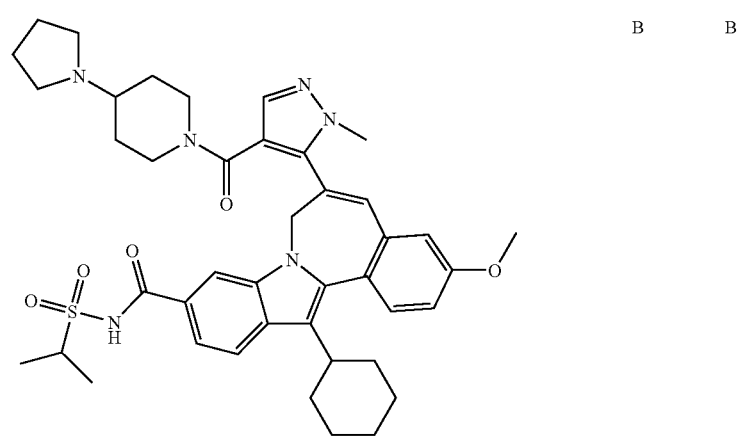
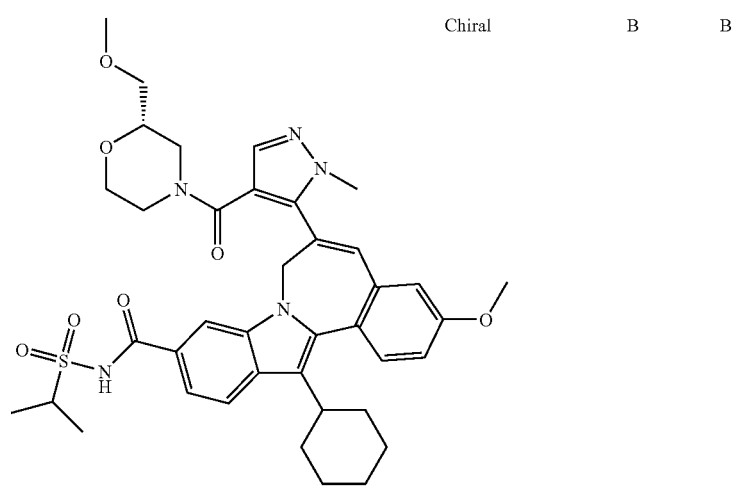

TABLE 1-continued

| Structure | IC$_{50}$ (μM) | EC$_{50}$ (μM) |
|---|---|---|
| | B | B |
| | B | B |
| | B | B |
| | | |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |
| | B | |

TABLE 1-continued
| Structure | IC$_{50}$ (μM) | EC$_{50}$ (μM) |
|---|---|---|
| 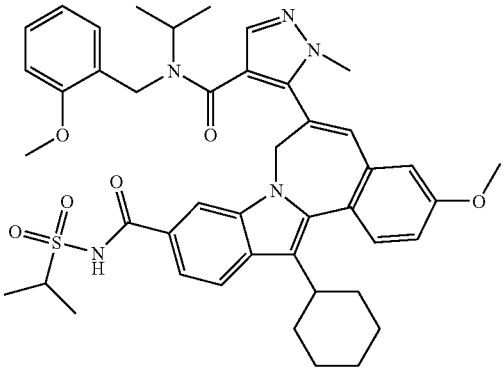 | B | |
| 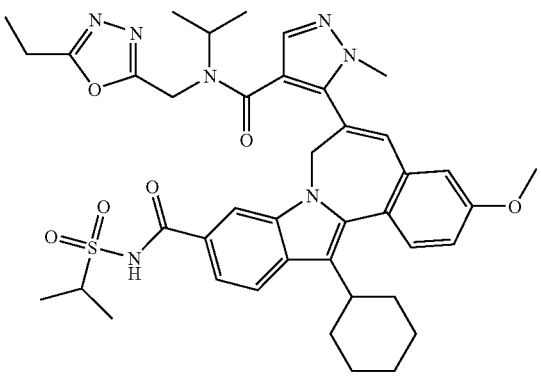 | B | |
| 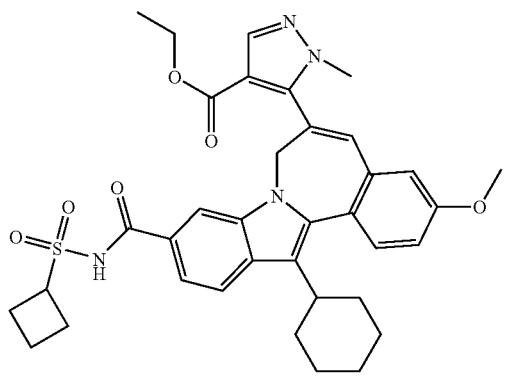 | B | |
| 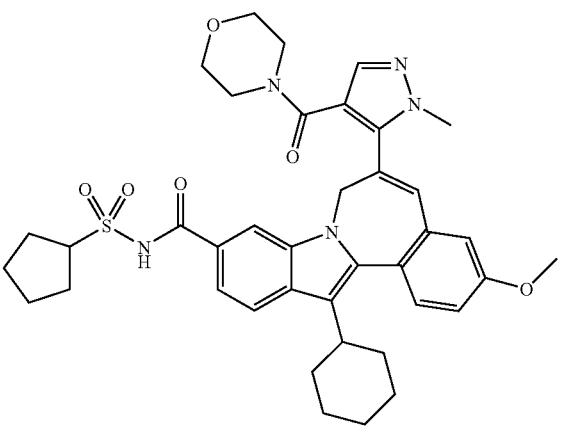 | B | B |

TABLE 1-continued

| Structure | IC$_{50}$ (μM) | EC$_{50}$ (μM) |
|---|---|---|
| | B | |
| | Chiral  B | B |
| | B | |

TABLE 1-continued
| Structure | IC$_{50}$ (μM) | EC$_{50}$ (μM) |
|---|---|---|
| 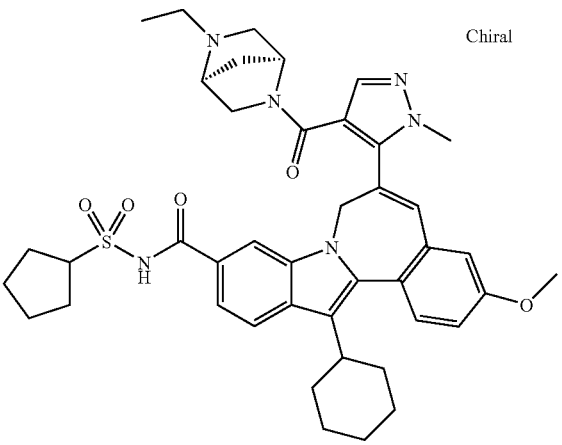 Chiral | B | |
| 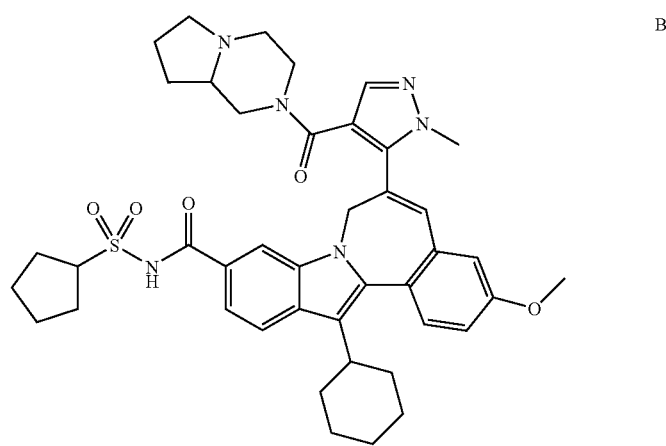 | B | |
| 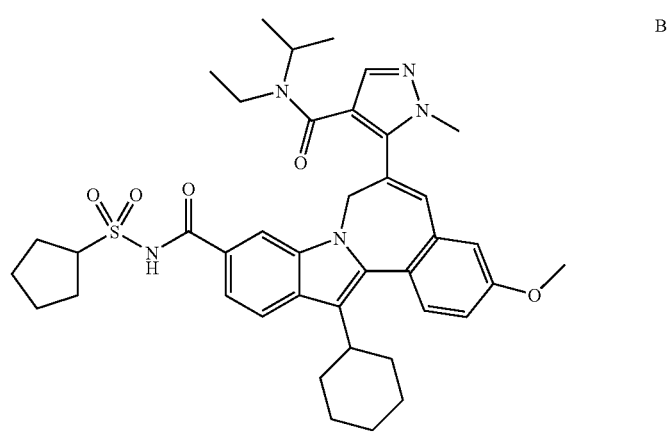 | B | |

TABLE 1-continued
| Structure | IC$_{50}$ (μM) | EC$_{50}$ (μM) |
|---|---|---|
| 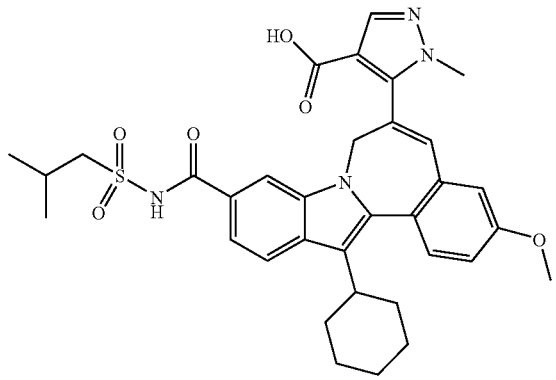 | | |
| 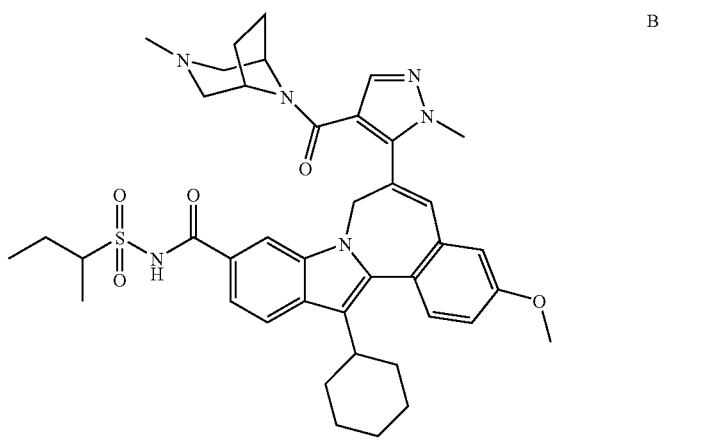 | B | B |
| 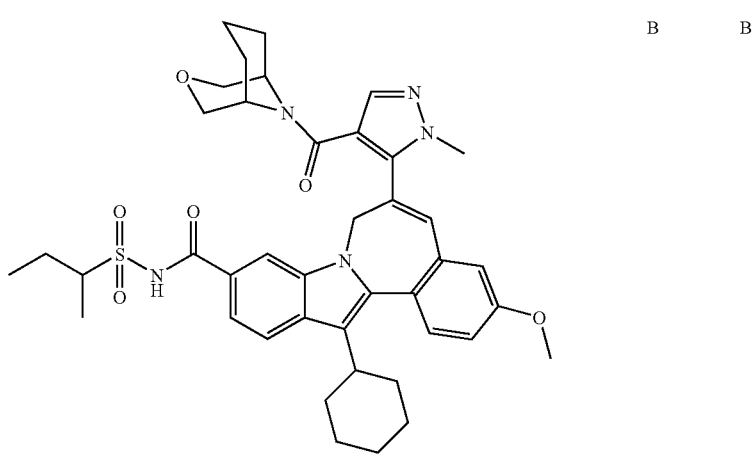 | B | B |

TABLE 1-continued
| Structure | IC$_{50}$ (µM) | EC$_{50}$ (µM) |
|---|---|---|
| 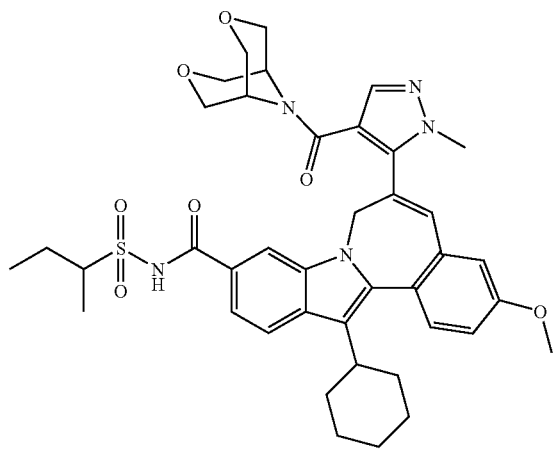 | B | B |
| 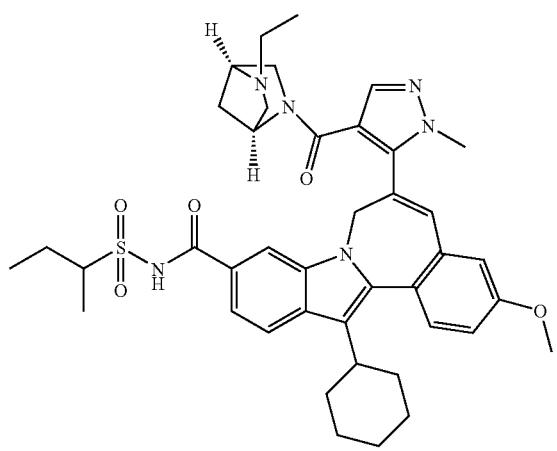 | B | |
| 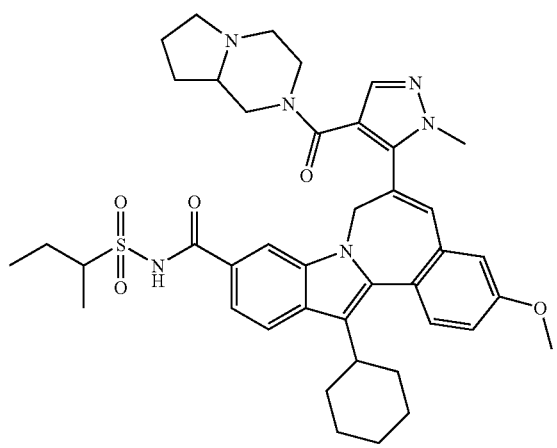 | B | |

| Structure | IC$_{50}$ (μM) | EC$_{50}$ (μM) |
|---|---|---|
| 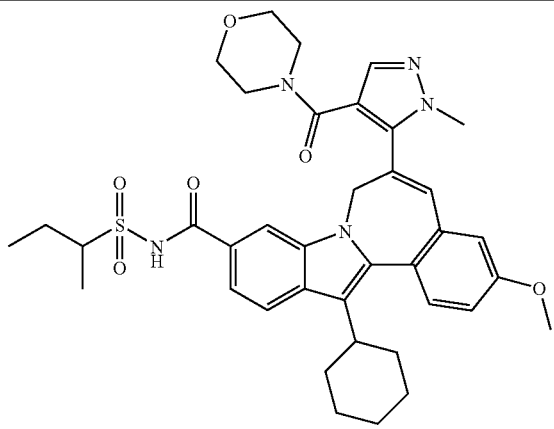 | B | B |
| 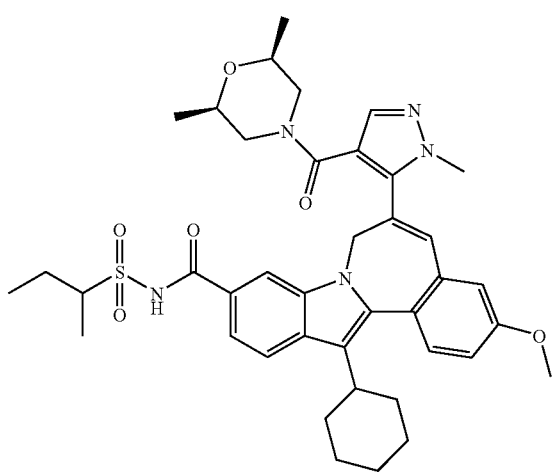 | B | B |
| 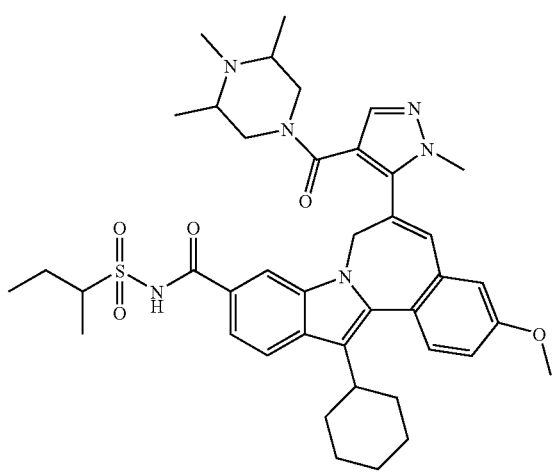 | B | B |

TABLE 1-continued

| Structure | IC$_{50}$ (μM) | EC$_{50}$ (μM) |
|---|---|---|
| | B | B |
| | B | B |
| | B | |

TABLE 1-continued
| Structure | IC$_{50}$ (μM) | EC$_{50}$ (μM) |
|---|---|---|
| 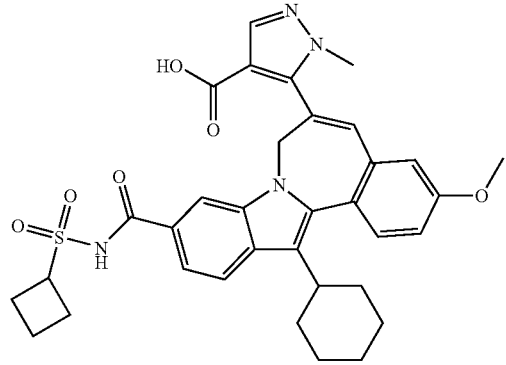 | B | |
| 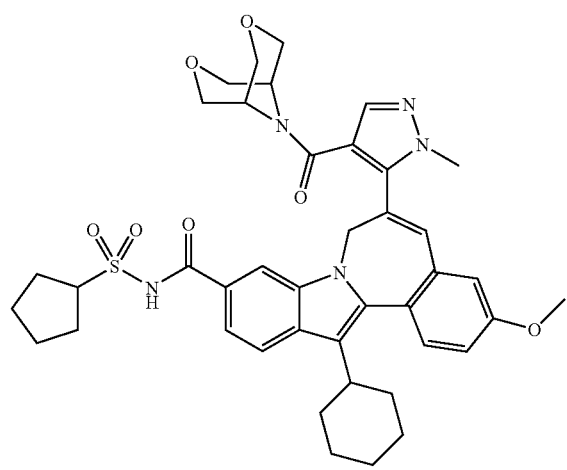 | B | B |
| 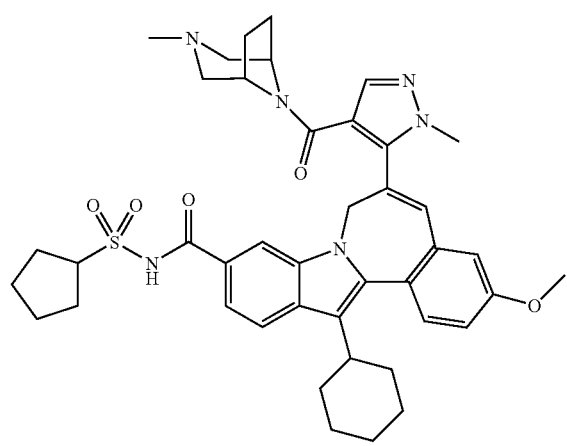 | B | B |

TABLE 1-continued
| Structure | IC$_{50}$ (μM) | EC$_{50}$ (μM) |
|---|---|---|
| 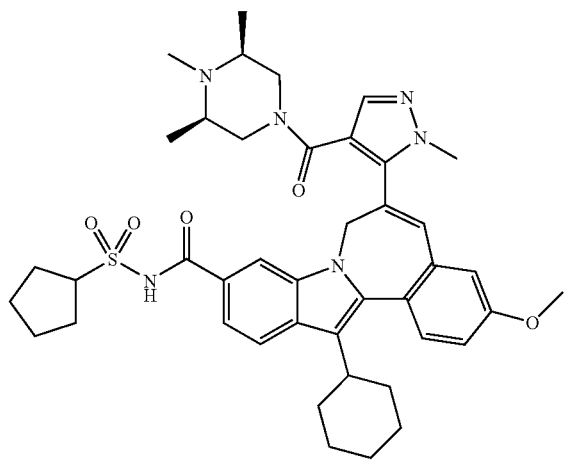 | B | |
| 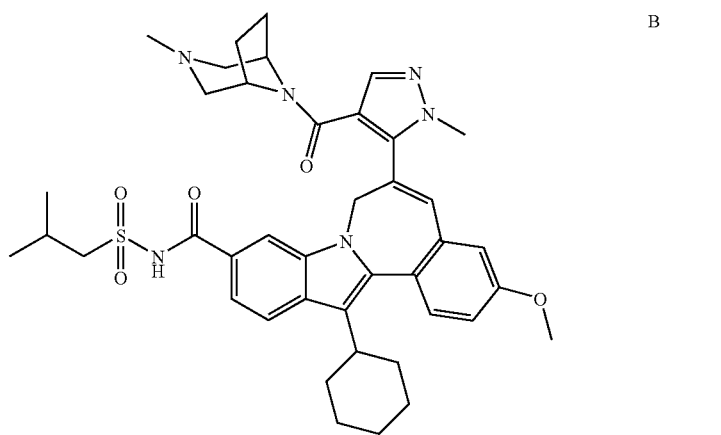 | B | B |
| 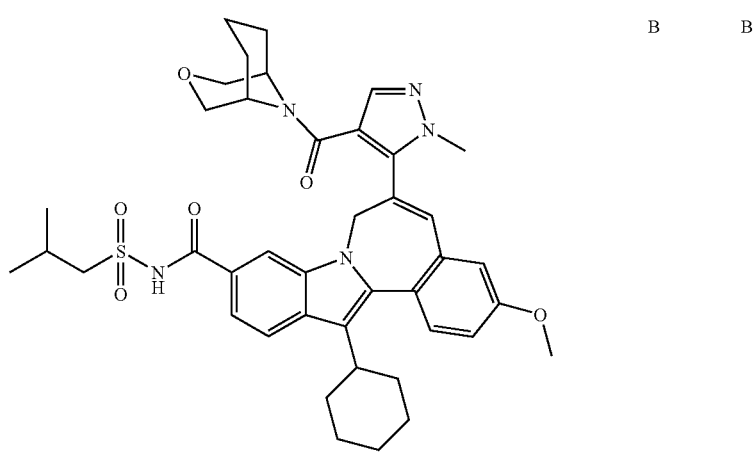 | B | B |

TABLE 1-continued
| Structure | IC$_{50}$ (μM) | EC$_{50}$ (μM) |
|---|---|---|
| 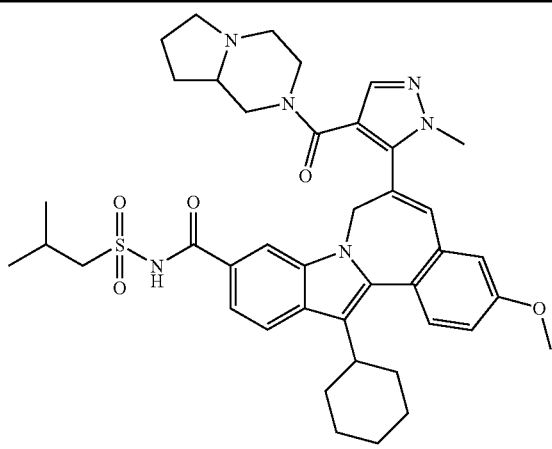 | B | |
| 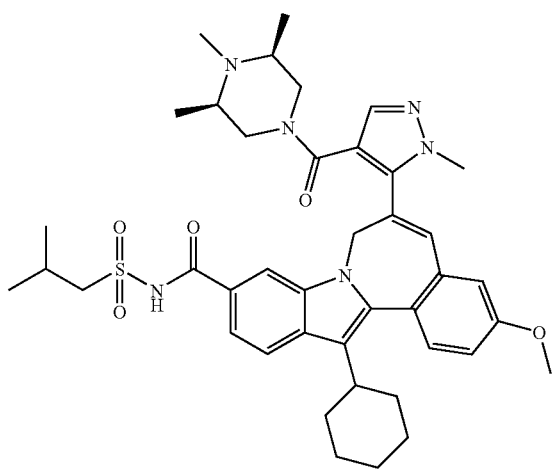 | B | |
| 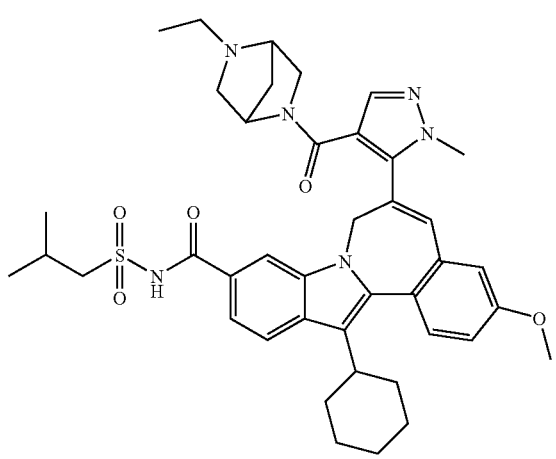 | B | |

TABLE 1-continued
| Structure | IC$_{50}$ (µM) | EC$_{50}$ (µM) |
|---|---|---|
| 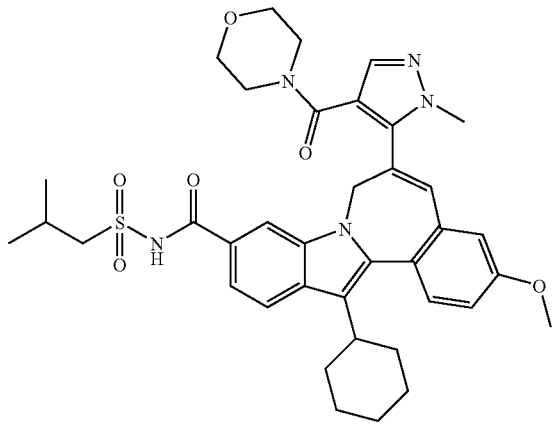 | B | B |
| 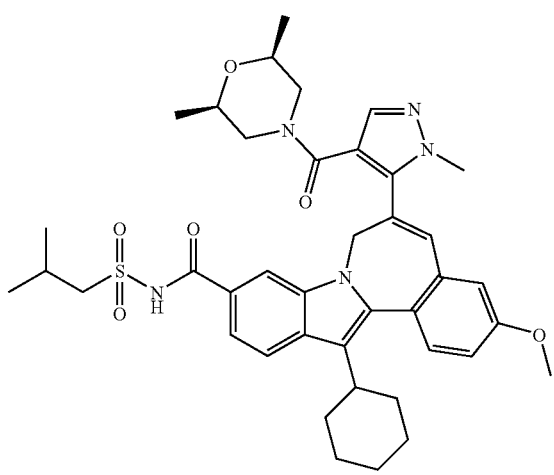 | B | B |
| 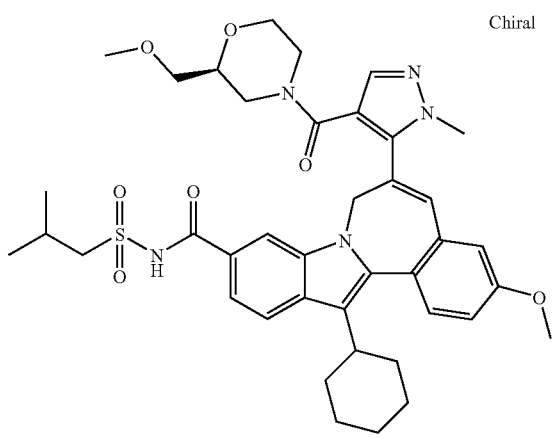 Chiral | B | B |

TABLE 1-continued

| Structure | IC$_{50}$ (μM) | EC$_{50}$ (μM) |
|---|---|---|
| | B | |
| | B | B |
| | B | B |

TABLE 1-continued
| Structure | IC$_{50}$ (μM) | EC$_{50}$ (μM) |
|---|---|---|
| 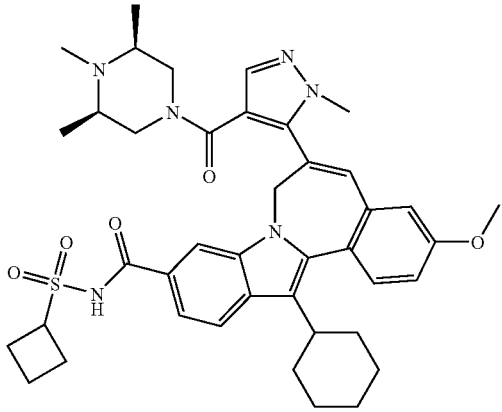 | B | |
| 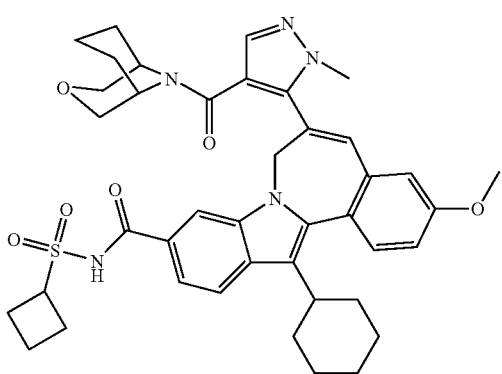 | B | B |
| 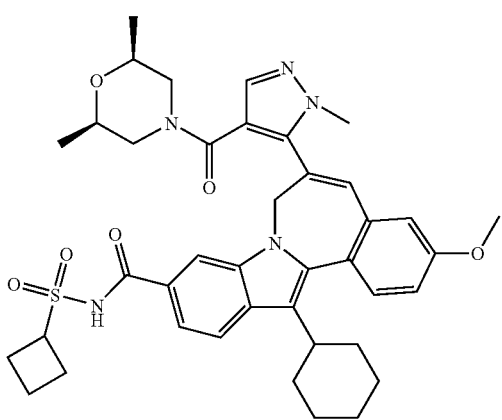 | B | |

TABLE 1-continued
| Structure | IC$_{50}$ (μM) | EC$_{50}$ (μM) |
|---|---|---|
| 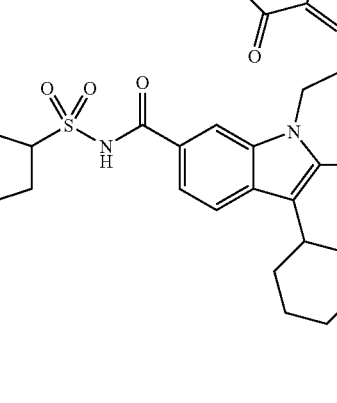 | B | B |
| 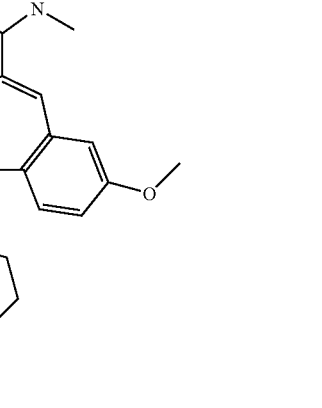 | B | B |
| 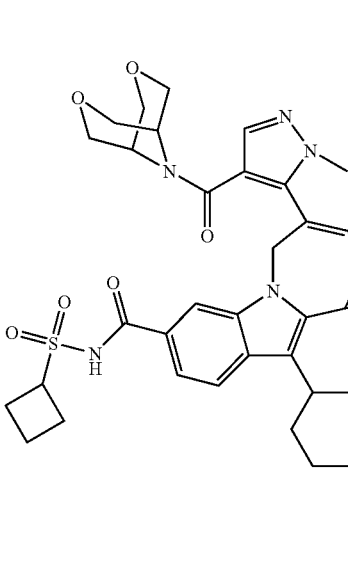 | B | B |

TABLE 1-continued
| Structure | IC$_{50}$ (μM) | EC$_{50}$ (μM) |
|---|---|---|
| Chiral 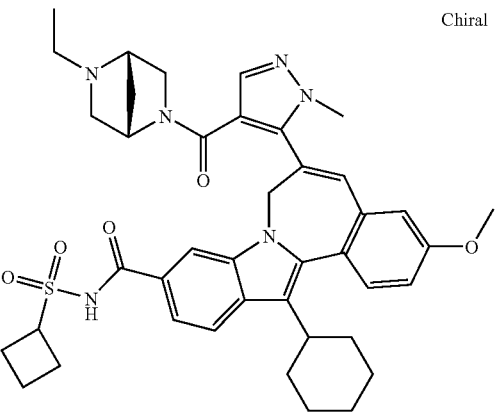 | B | B |
| 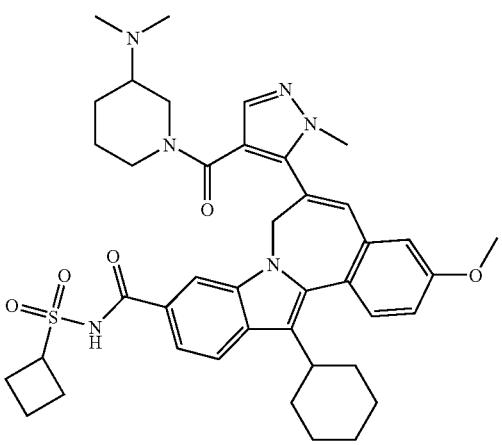 | B | B |
| 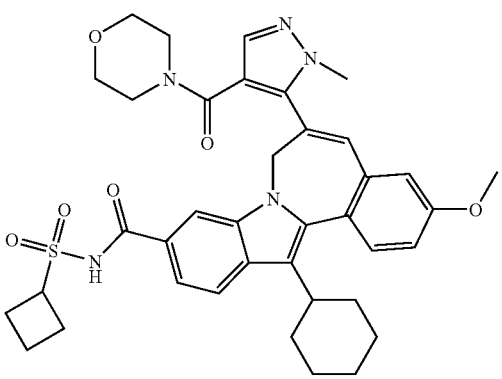 | B | B |

TABLE 1-continued

| Structure | IC$_{50}$ (μM) | EC$_{50}$ (μM) |
|---|---|---|
| | B | B |
| | B | D |
| | B | B |
| | B | B |

TABLE 1-continued

| Structure | IC$_{50}$ (μM) | EC$_{50}$ (μM) |
|---|---|---|
| | B | B |
| | | |
| | B | B |

TABLE 1-continued

| Structure | IC$_{50}$ (μM) | EC$_{50}$ (μM) |
|---|---|---|
| | B | B |
| Chiral | B | B |
| | B | B |

TABLE 1-continued
| Structure | IC$_{50}$ (μM) | EC$_{50}$ (μM) |
|---|---|---|
| 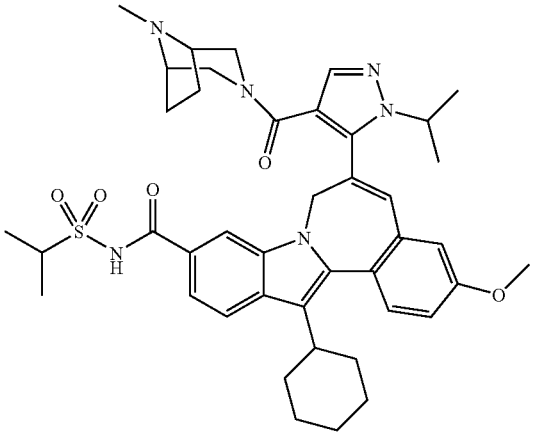 | B | B |
| 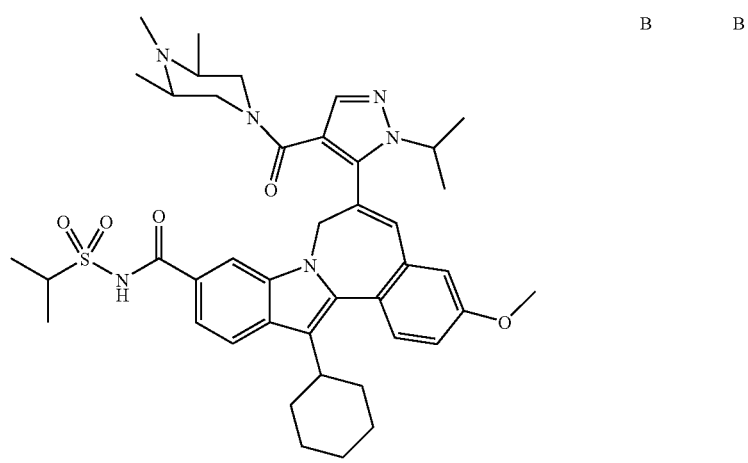 | B | B |
| 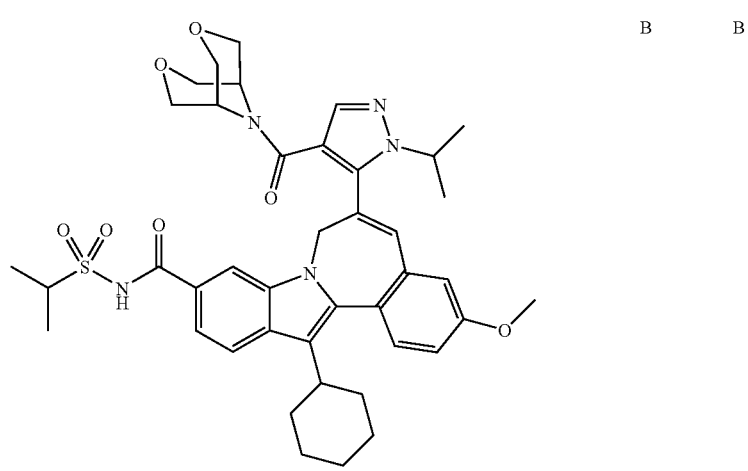 | B | B |

TABLE 1-continued

| Structure | IC$_{50}$ (μM) | EC$_{50}$ (μM) |
|---|---|---|
| | B | B |
| | B | B |
| | B | B |
| | B | B |

TABLE 1-continued

| Structure | IC$_{50}$ (μM) | EC$_{50}$ (μM) |
|---|---|---|
| | B | B |
| | B | B |
| (Chiral) | B | B |
| | B | B |

TABLE 1-continued

| Structure | IC$_{50}$ (μM) | EC$_{50}$ (μM) |
|---|---|---|
| Chiral | B | B |
|  | B | B |
| Chiral | B | B |
| Chiral | B | B |

TABLE 1-continued
| Structure | IC$_{50}$ (μM) | EC$_{50}$ (μM) |
|---|---|---|
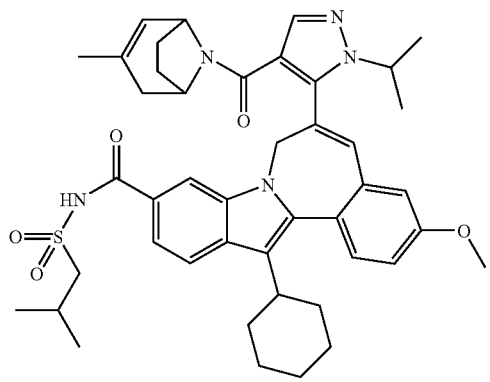
B    B
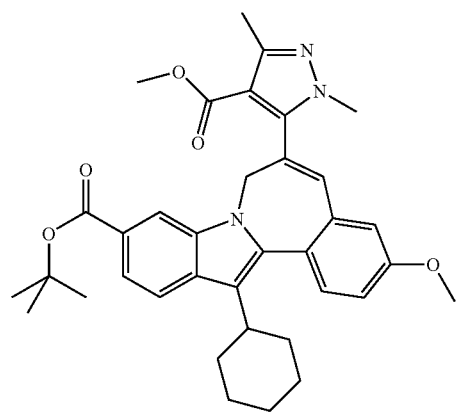
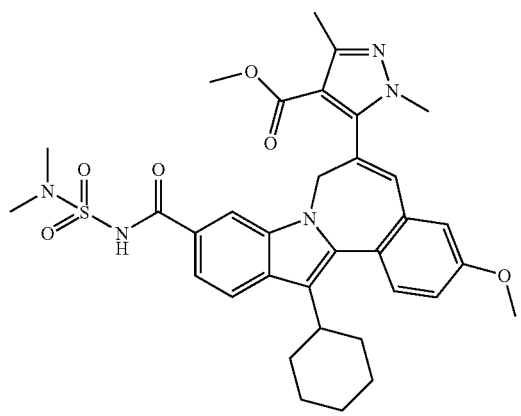
B TABLE 1-continued
| Structure | IC$_{50}$ (μM) | EC$_{50}$ (μM) |
|---|---|---|
| 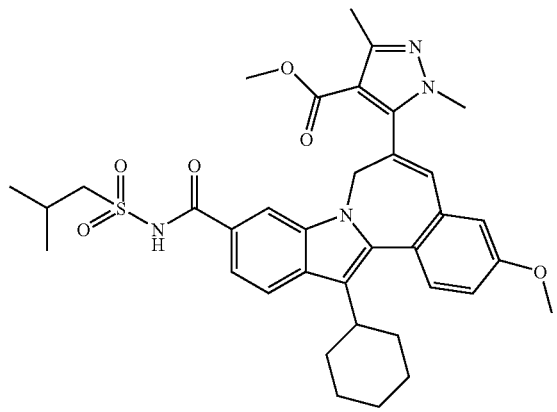 | B | |
| 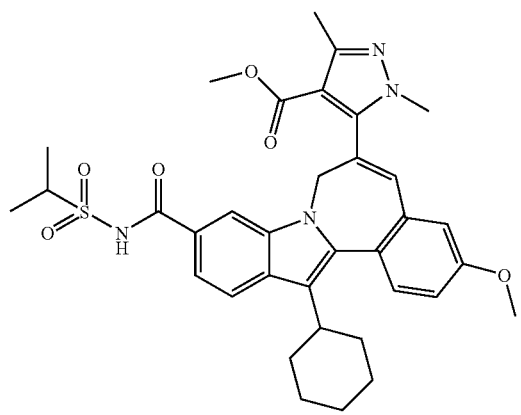 | | |
| 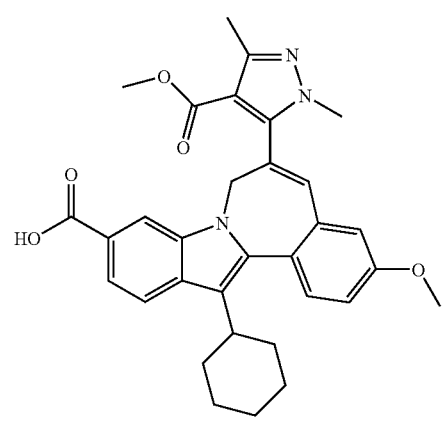 | B | B |

TABLE 1-continued

| Structure | IC$_{50}$ (μM) | EC$_{50}$ (μM) |
|---|---|---|
| | B | D |
| | B | B |
| | B | B |

TABLE 1-continued

| Structure | IC$_{50}$ (μM) | EC$_{50}$ (μM) |
|---|---|---|
| | B | A |
| | B | B |
| | B | B |

TABLE 1-continued
| Structure | IC$_{50}$ (µM) | EC$_{50}$ (µM) |
|---|---|---|
| 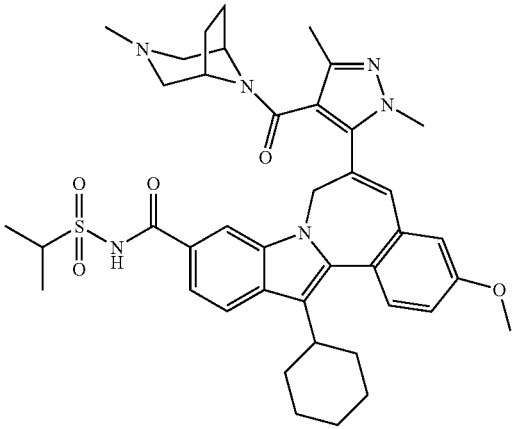 | B | B |
| 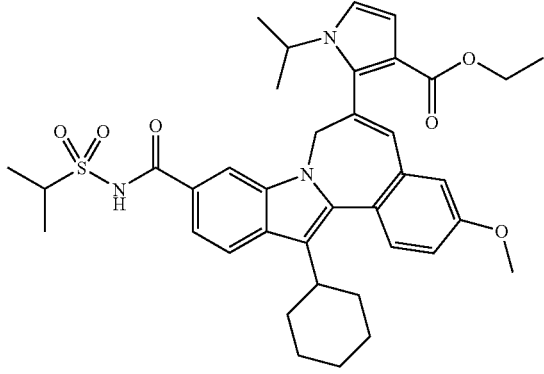 | | |
| 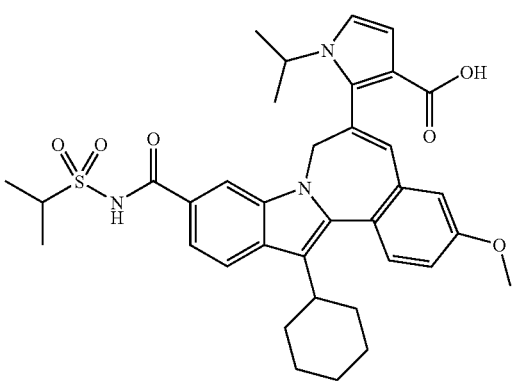 | B | A |

TABLE 1-continued
| Structure | IC$_{50}$ (μM) | EC$_{50}$ (μM) |
|---|---|---|
| 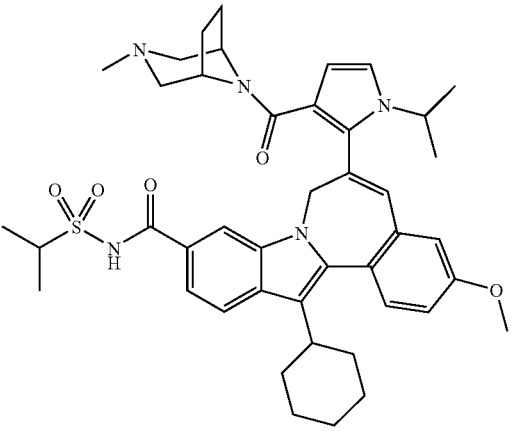 | B | B |
| 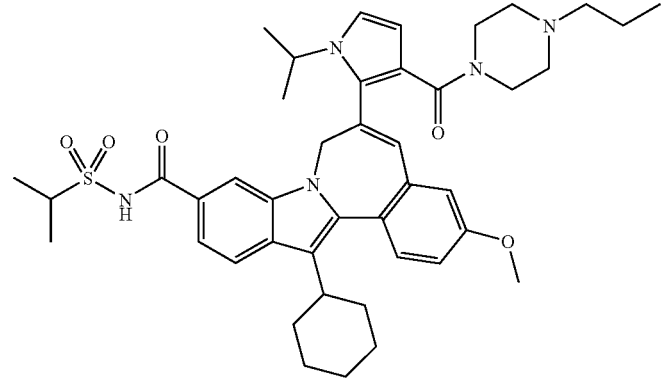 | B | B |
| 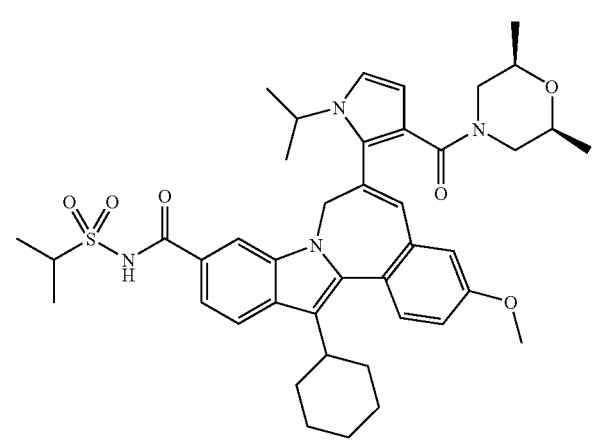 | B | B |

TABLE 1-continued

| Structure | IC$_{50}$ (μM) | EC$_{50}$ (μM) |
|---|---|---|
| | B | B |
| | B | A |
| | B | B |
| | B | B |

TABLE 1-continued

| Structure | IC$_{50}$ (μM) | EC$_{50}$ (μM) |
|---|---|---|
| | B | B |
| Chiral | B | B |
| | B | B |

TABLE 1-continued

| Structure | IC$_{50}$ (μM) | EC$_{50}$ (μM) |
|---|---|---|
|  | B | B |
|  | B | B |
| Chiral | B | B |

TABLE 1-continued

| Structure | IC$_{50}$ (μM) | EC$_{50}$ (μM) |
|---|---|---|
| | B | B |
| | B | B |
| | B | B |

TABLE 1-continued
| Structure | IC$_{50}$ (μM) | EC$_{50}$ (μM) |
|---|---|---|
| 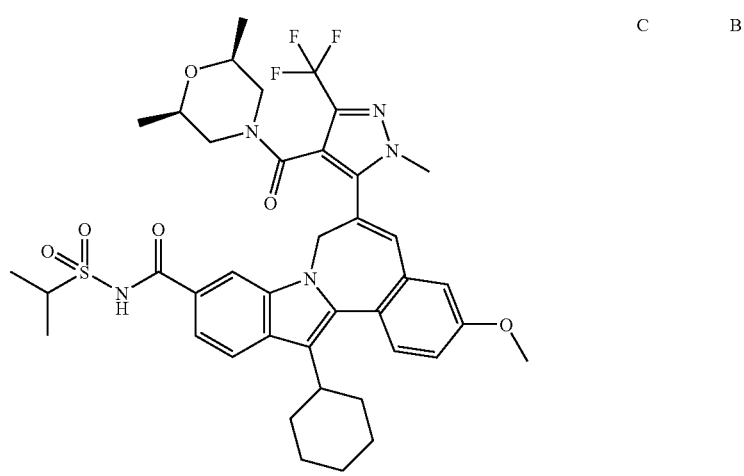 | C | B |
| 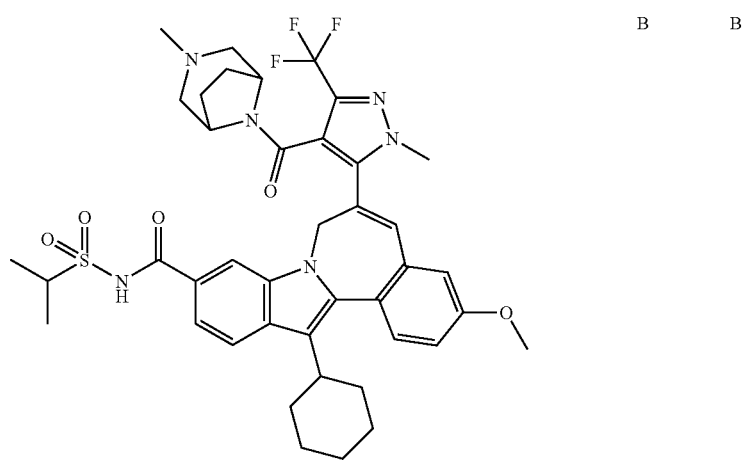 | C | B |
| 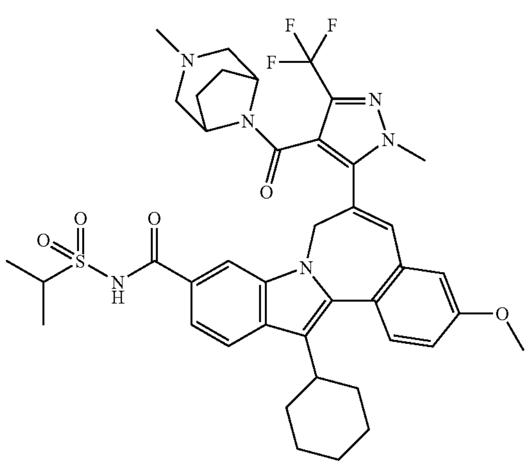 | B | B |

TABLE 1-continued

| Structure | IC$_{50}$ (μM) | EC$_{50}$ (μM) |
|---|---|---|
| | B | B |
| | | |
| | B | B |

TABLE 1-continued
| Structure | IC$_{50}$ (μM) | EC$_{50}$ (μM) |
|---|---|---|
| 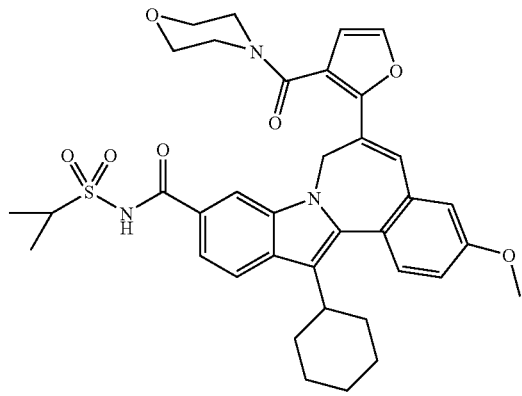 | B | B |
| 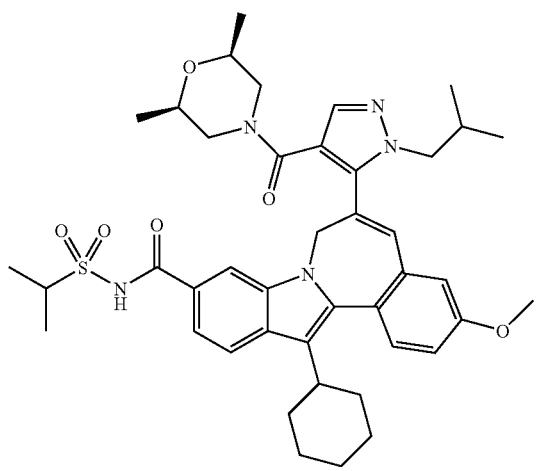 | B | B |
| 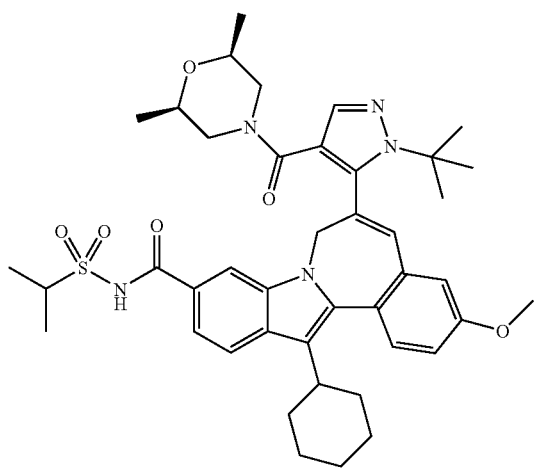 | B | B |

TABLE 1-continued

| Structure | IC$_{50}$ (μM) | EC$_{50}$ (μM) |
|---|---|---|
| | B | B |
| 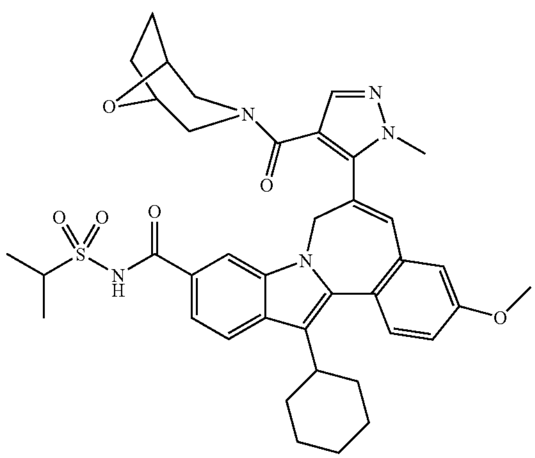 | C | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued
| Structure | IC$_{50}$ (μM) | EC$_{50}$ (μM) |
|---|---|---|
| 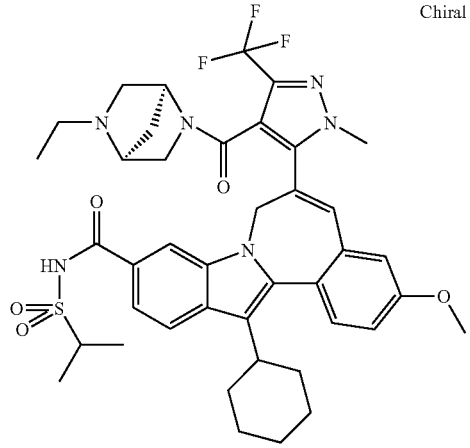 Chiral | B | B |
| 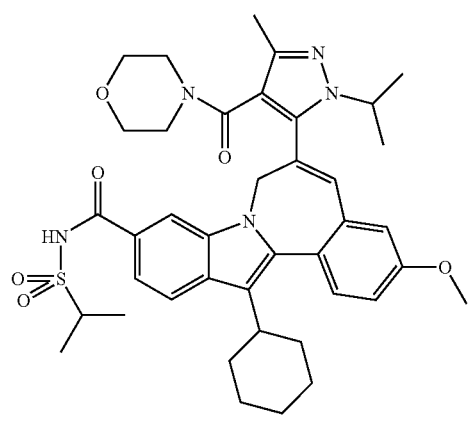 | B | B |
| 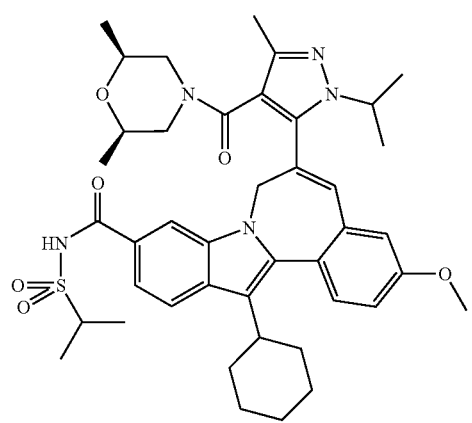 | B | B |

TABLE 1-continued

| Structure | IC$_{50}$ (μM) | EC$_{50}$ (μM) |
|---|---|---|
| | B | B |
| | B | B |
| 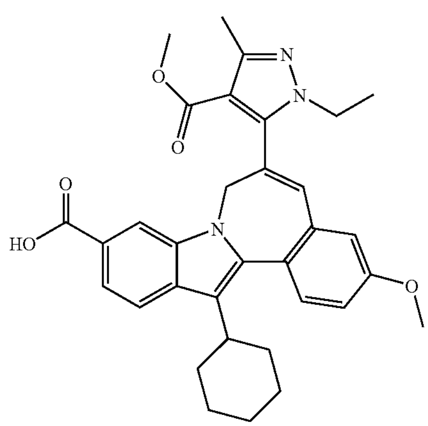 | A | A |

TABLE 1-continued
| Structure | IC$_{50}$ (μM) | EC$_{50}$ (μM) |
|---|---|---|
| | B | B |
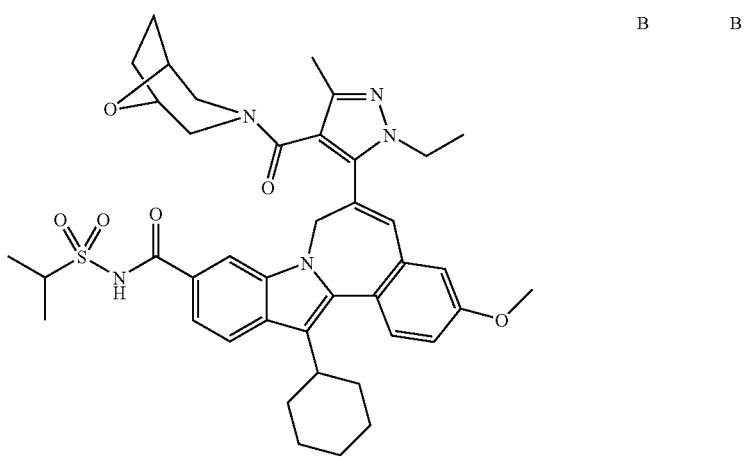
| | B | B |
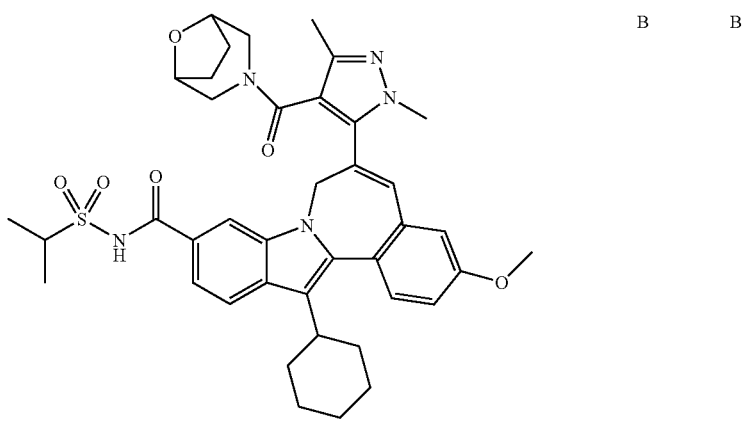
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued
| Structure | IC$_{50}$ (µM) | EC$_{50}$ (µM) |
|---|---|---|
| 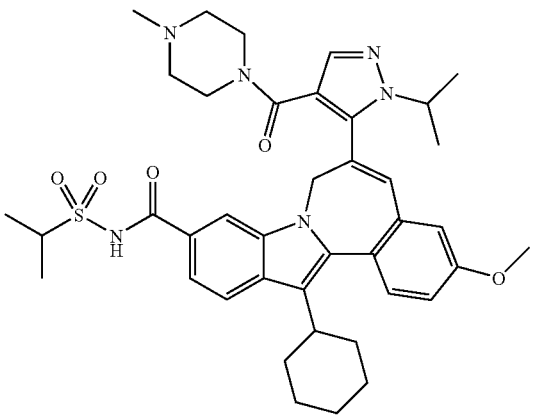 | B | B |
| 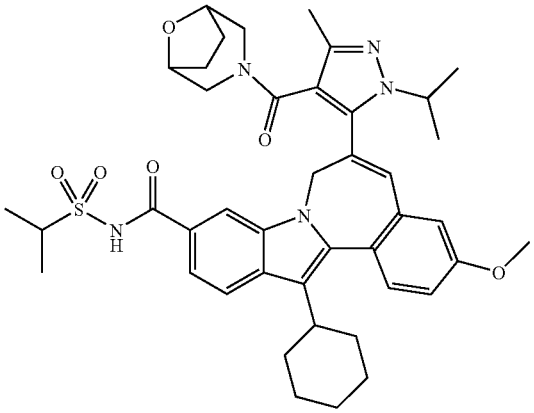 | B | B |
| 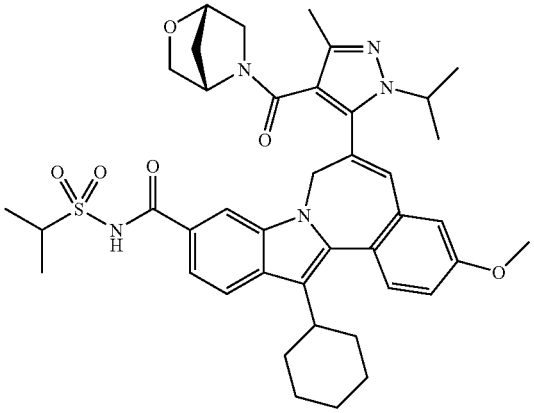 | B | B |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | A |

TABLE 1-continued

| Structure | IC$_{50}$ (μM) | EC$_{50}$ (μM) |
|---|---|---|
| | B | A |
| | B | B |
| | B | A |

TABLE 1-continued

| Structure | IC$_{50}$ (μM) | EC$_{50}$ (μM) |
|---|---|---|
| | A | A |
| | A | A |
| | | |

TABLE 1-continued
| Structure | IC$_{50}$ (μM) | EC$_{50}$ (μM) |
|---|---|---|
| 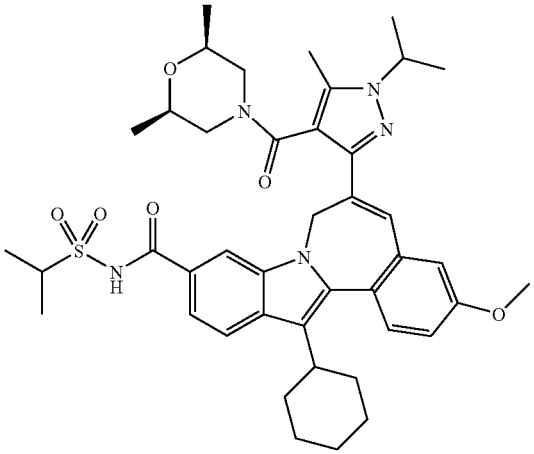 | B | B |
| 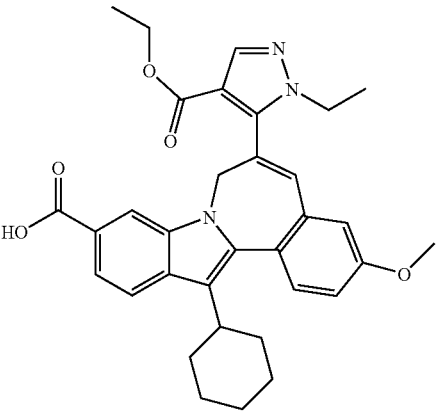 | B | A |
| 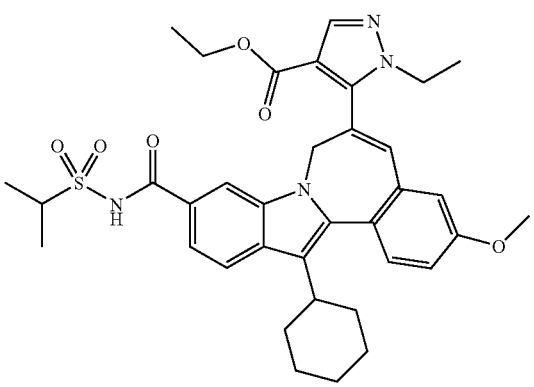 | B | A |

TABLE 1-continued
| Structure | IC$_{50}$ (µM) | EC$_{50}$ (µM) |
|---|---|---|
| 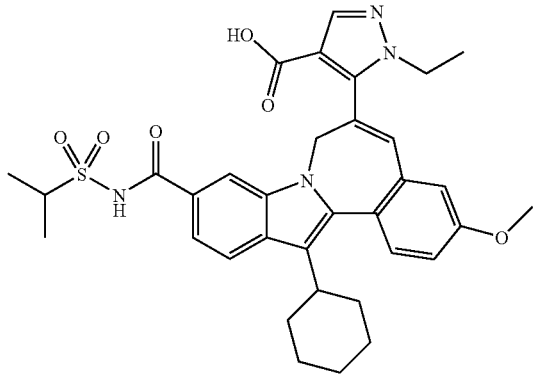 | | |
| 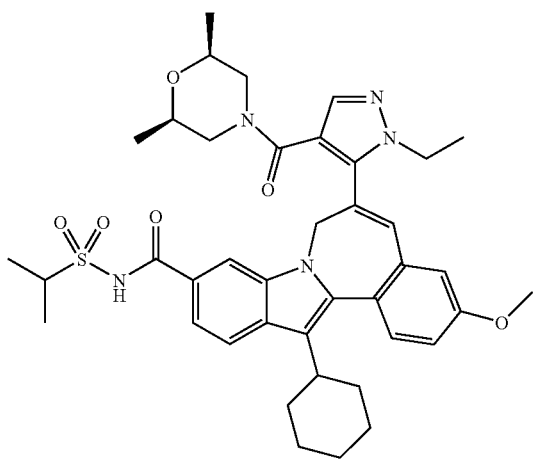 | B | B |
| 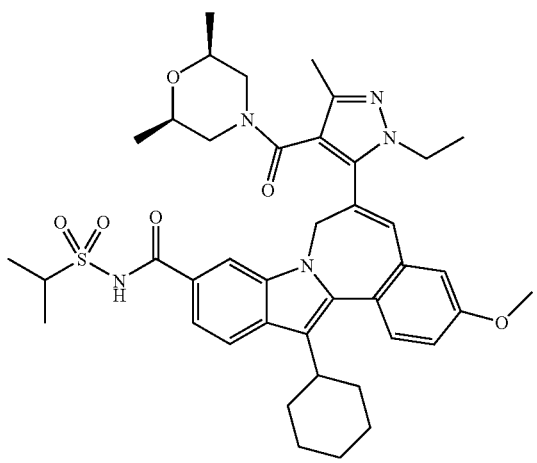 | B | B |

TABLE 1-continued
| Structure | IC$_{50}$ (μM) | EC$_{50}$ (μM) |
|---|---|---|
| 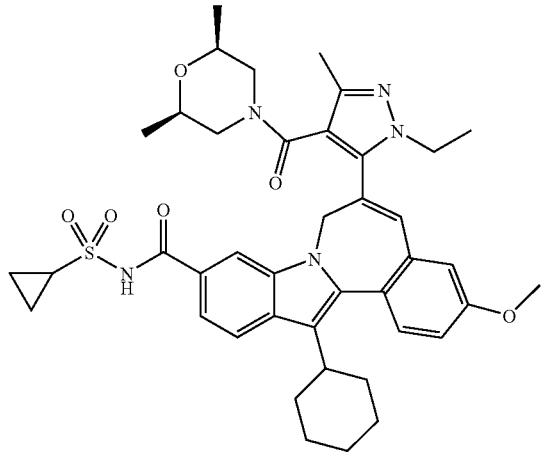 | B | B |
| 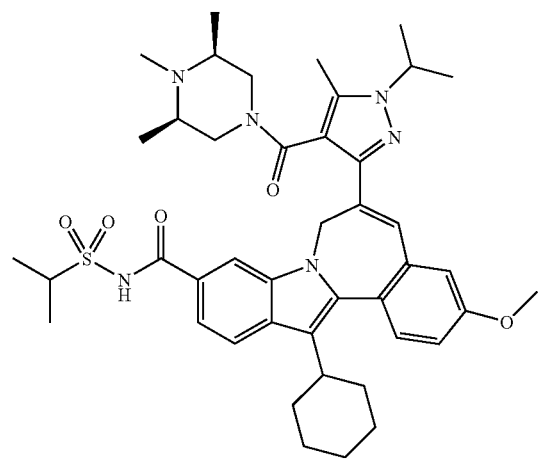 | B | B |
| 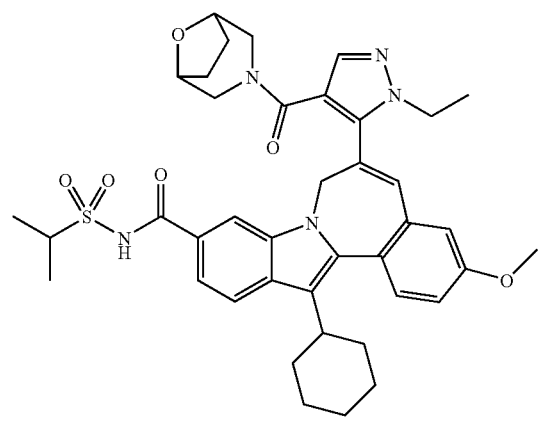 | B | B |

TABLE 1-continued

| Structure | IC$_{50}$ (µM) | EC$_{50}$ (µM) |
|---|---|---|
| 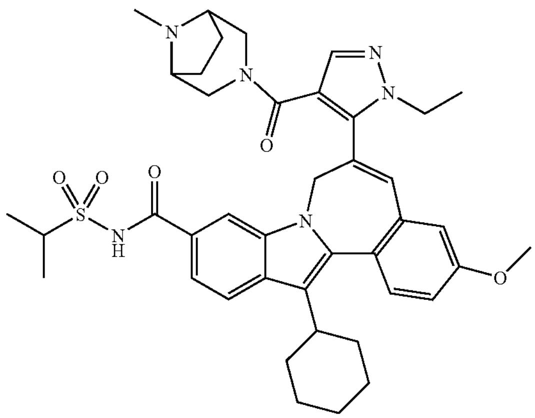 | B | B |
| | | |
| | | |

TABLE 1-continued

| Structure | IC$_{50}$ (µM) | EC$_{50}$ (µM) |
|---|---|---|
| | B | B |
| | B | B |
| | B | B |

TABLE 1-continued

| Structure | IC₅₀ (μM) | EC₅₀ (μM) |
|---|---|---|
| | B | B |
| | B | B |
| | B | B |

TABLE 1-continued

| Structure | IC$_{50}$ (μM) | EC$_{50}$ (μM) |
|---|---|---|
| | B | B |
| | B | B |
| | B | B |

TABLE 1-continued

| Structure | IC$_{50}$ (µM) | EC$_{50}$ (µM) |
|---|---|---|
| | B | B |
| | B | B |
| | B | B |

TABLE 1-continued
| Structure | IC$_{50}$ (μM) | EC$_{50}$ (μM) |
|---|---|---|
| 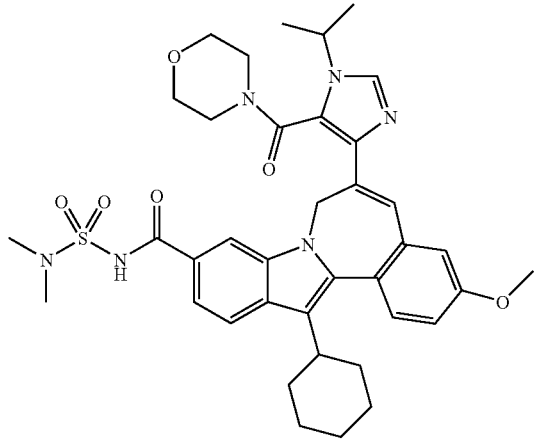 | B | B |
| 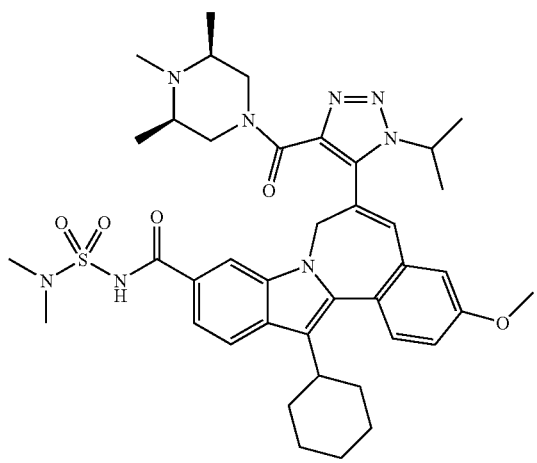 | B | B |
| 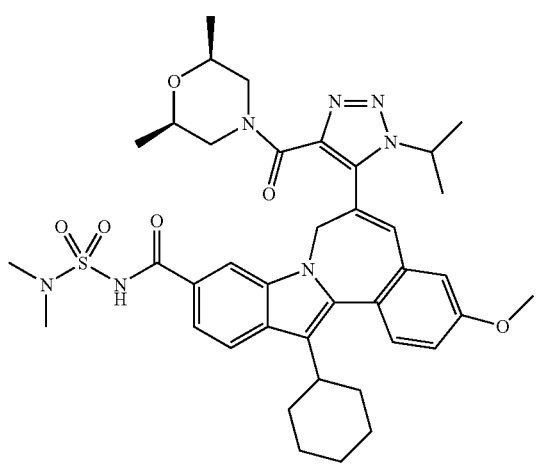 | B | B |

TABLE 1-continued

| Structure | IC$_{50}$ (μM) | EC$_{50}$ (μM) |
|---|---|---|
| [structure] | B | B |
| [structure] | B | B |
| [structure] | B | B |

A >0.5 μM;
B 0.001 μM-0.5 μM;
C <0.02 μM but an exact value was not determined;
D >0.04 μM; but an exact value was not determined.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

We claim:

1. A compound selected from the group consisting of
7H-indolo[2,1-a][2]benzazepine-10-carboxamide, 13-cyclohexyl-[1-ethyl-3-methyl-4-[(3-methyl-3,8-diazabicyclo[3.2.1]oct-8-yl)carbonyl]-1H-pyrazol-5-yl]-3-methoxy-N-[(1-methylethyl)sulfonyl]-;
7H-indolo[2,1-a][2]benzazepine-10-carboxamide, 13-cyclohexyl-6-[1-ethyl-3-methyl-4-[[(3R,5S)-3,4,5-trimethyl-1-piperazinyl]carbonyl]-1H-pyrazol-5-yl]-3-methoxy-N-[(1-methylethyl)sulfonyl]-;
7H-indolo[2-a][2]benzazepine-10-carboxamide, 13-cyclohexyl-[1-ethyl-3-methyl-4-[(1S,4S)-2-oxa-5-azabicyclo[2.2.1]hept-5-ylcarbonyl]-1H-pyrazol-5-yl]-3-methoxy-N-[(1-methylethyl)sulfonyl]-;
7H-indolo[2,1-a][2]benzazepine-10-carboxamide, 13-cyclohexyl-6-[1,3-dimethyl-4-(8-oxa-3-azabicyclo[3.2.1]oct-3-ylcarbonyl)-1H-pyrazol-5-yl]-3-methoxy-N-[(1-methylethyl)sulfonyl]-;
7H-indolo[2,1-a][2]benzazepine-10-carboxamide, 13-cyclohexyl-3-methoxy-6-[4-[[(2S)-2-(methoxymethyl)-4-morpholinyl]carbonyl]-1,3-dimethyl-1H-pyrazol-5-yl]-N-[(1-methylethyl)sulfonyl]-;
7H-indolo[2,1-a][2]benzazepine-10-carboxamide, 13-cyclohexyl-6-[1,3-dimethyl-4-[(4-methyl-1-piperazinyl)carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[1,3-dimethyl-4-[[(3R,5S)-3,4,5-trimethyl-1-piperazinyl]carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[4-[[(2R,6S)-2,6-dimethyl-4-morpholinyl]carbonyl]-1-(1-methylethyl)-1H-1,2,3-triazol-5-yl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[1-(1-methylethyl)-4-[[(3R,5S)-3,4,5-trimethyl-1-piperazinyl]carbonyl]-1H-1,2,3-triazol-5-yl]-;

7H-indolo[2,1-a][2]benzazepine-10-carboxylic acid, 13-cyclohexyl-6-[4-(ethoxycarbonyl)-1-ethyl-3-methyl-1H-pyrazol-5-yl]-3-methoxy-;

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-, ethyl ester;

7H-indolo[2,1-a][2]benzazepine-10-carboxamide, 13-cyclohexyl-6-[4-[[(2R,6S)-2,6-dimethyl-4-morpholinyl]carbonyl]-5-methyl-1-(1-methylethyl)-1H-pyrazol-3-yl]-3-methoxy-N-[(1-methylethyl)sulfonyl]-;

1H-pyrazole-4-carboxylic acid, 5-[10-(aminocarbonyl)-13-cyclohexyl-3-methoxy-7H-indolo[2,1-a][2]benzazepin-6-yl]-1-ethyl-3-methyl-, ethyl ester;

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-, 1,1-dimethylethyl ester;

7H-indolo[2,1-a][2]benzazepine-10-carboxylic acid, 13-cyclohexyl-6-[4-(ethoxycarbonyl)-1-ethyl-1H-1-pyrazol-3-yl]-3-methoxy-, 1,1-dimethylethyl ester;

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-3-methyl-;

7H-indolo[2,1-a][2]benzazepine-10-carboxamide, 13-cyclohexyl-6-[4-[[(2R,6S)-2,6-dimethyl-4-morpholinyl]carbonyl]-1-(1-methylethyl)-1H-imidazol-5-yl]-3-methoxy-N-[(1-methylethyl)sulfonyl]-;

7H-indolo[2,1-a][2]benzazepine-10-carboxamide, 13-cyclohexyl-3-methoxy-6-[1-(1-methylethyl)-4-(4-morpholinylcarbonyl)-1H-imidazol-5-yl]-N-[(1-methylethyl)sulfonyl]-;

7H-indolo[2,1-a][2]benzazepine-10-carboxamide, 13-cyclohexyl-3-methoxy-6-[4-[(3-methyl-3,8-diazabicyclo[3.2.1]oct-8-yl)carbonyl]-1-(1-methylethyl)-1H-imidazol-5-yl]-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[1-(1-methylethyl)-4-[[(3R,5S)-3,4,5-trimethyl-1-piperazinyl]carbonyl]-1H-imidazol-5-yl]-;

7H-indolo[2,1-a][2]benzazepine-10-carboxamide, 13-cyclohexyl-3-methoxy-N-[(1-methylethyl)sulfonyl]-6-[5-methyl-4-[(3-methyl-3,8-diazabicyclo[3.2.1]oct-8-yl)carbonyl]-1-(1-methylethyl)-1H-pyrazol-3-yl]-;

7H-indolo[2,1-a][2]benzazepine-10-carboxylic acid, 13-cyclohexyl-6-[4-(ethoxycarbonyl)-1-ethyl-1H-pyrazol-5-yl]-3-methoxy-;

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-, ethyl ester;

7H-indolo[2,1-a][2]benzazepine-10-carboxamide, 13-cyclohexyl-N-[(di methylamino)sulfonyl]-6-[5-[[(2R,6S)-2,6-dimethyl-4-morpholinyl]carbonyl]-1-(1-methylethyl)-1H-imidazol-4-yl]-3-methoxy-;

7H-indolo[2,1-a][2]benzazepine-10-carboxamide, 13-cyclohexyl-N-[(dimethylamino)sulfonyl]-3-methoxy-6-[1-(1-methylethyl)-5-(4-morpholinylcarbonyl)-1H-imidazol-4-yl]-;

1H-pyrazole-4-carboxylic acid, 5-[13-cyclohexyl-3-methoxy-10-[[[(1-methylethyl)sulfonyl]amino]carbonyl]-7H-indolo[2,1-a][2]benzazepin-6-yl]-1-ethyl-;

7H-indolo[2,1-a][2]benzazepine-10-carboxamide, 13-cyclohexyl-N-[(dimethylamino)sulfonyl]-3-methoxy-6-[1-(1-methylethyl)-4-[[(3R,5S)-3,4,5-trimethyl-1-piperazinyl]carbonyl]-1H-1,2,3-triazol-5-yl]-;

7H-indolo[2,1-a][2]benzazepine-10-carboxamide, 13-cyclohexyl-N-[(dimethylamino)sulfonyl]-6-[4-[[(2R,6S)-2,6-dimethyl-4-morpholinyl]carbonyl]-1-(1-methylethyl)-1H-1,2,3-triazol-5-yl]-3-methoxy-;

7H-indolo[2,1-a][2]benzazepine-10-carboxamide, 13-cyclohexyl-N-[(dimethylamino)sulfonyl]-3-methoxy-6-[4-[(3-methyl-3,8-diazabicyclo[3.2.1]oct-8-yl)carbonyl]-1-(1-methylethyl)-1H-1,2,3-triazol-5-yl]-;

7H-indolo[2,1-a][2]benzazepine-10-carboxamide, 13-cyclohexyl-6-[4-[[(2R,6S)-2,6-dimethyl-4-morpholinyl]carbonyl]-1-ethyl-1H-pyrazol-5-yl]-3-methoxy-N-[(1-methylethyl)sulfonyl]-;

7H-indolo[2,1-a][2]benzazepine-10-carboxamide, 13-cyclohexyl-N-[(dimethyl amino)sulfonyl]6-[4-[[(2R,6S)-2,6-dimethyl-4-morpholinyl]carbonyl]-1-ethyl-3-methyl-1H-pyrazol-5-yl]-3-methoxy-;

7H-indolo[2,1-a][2]benzazepine-10-carboxamide, 13-cyclohexyl-N-[(dimethylamino)sulfonyl]-3-methoxy-6-[1-(1-methylethyl)-4-(4-morpholinylcarbonyl)-1H-1,2,3-triazol-5-yl]-;

7H-indolo[2,1-a][2]benzazepine-10-carboxamide, 13-cyclohexyl-6-[4-[(6,6-difluorohexahydro-4-methyl-1H-1,4-diazepin-1-ylcarbonyl]-1-(1-methylethyl)-1H-1,2,3-triazol-5-yl]-N-[(dimethylamino)sulfonyl]-3-methoxy-;

7H-indolo[2,1-a][2]benzazepine-10-carboxamide, 13-cyclohexyl-6-[1-ethyl-4-[[(2R)-2-(methoxymethyl)-4-morpholinyl]carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-(3-oxa-9-azabicyclo[3.3.1]non-9-ylcarbonyl)-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-(2-oxa-5-azabicyclo[2.2.1]hept-5-ylcarbonyl)-1H-1-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-[[(3R,5S)-3,4,5-trimethyl-1-piperazinyl]carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-[(3-methyl-3,8-diazabicyclo[3.2.1]oct-8-yl)carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-[(5-ethyl-2,5-diazabicyclo[2.2.1]hept-2-yl)carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-(4-morpholinylcarbonyl)-1H-pyrazol-5-yl]-;

7H-indolo[2,1-a][2]benzazepine-10-carboxamide, 13-cyclohexyl-6-[4-[[(2R,6S)-2,6-dimethyl-4-morpholinyl]

carbonyl]-1-methyl-3-(1-methylethyl)-1H-pyrazol-5-yl]-3-methoxy-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-[(4-methyl-1-piperazinyl)carbonyl]-1H-pyrazol-5-yl]-;

7H-indolo[2,1-a][2]benzazepine-10-carboxamide, 13-cyclohexyl-3-methoxy-N-[(1-methylethyl)sulfonyl]-6-[1-methyl-3-(1-methylethyl)-4-[[(3R,5S)-3,4,5-trimethyl-1-piperazinyl]carbonyl]-1H-pyrazol-5-yl]-;

7H-indolo[2,1-a][2]benzazepine-10-carboxamide, 13-cyclohexyl-3-methoxy-N-[(1-methylethyl)sulfonyl]-6-[4-(8-oxa-3-azabicyclo[3.2.1]oct-3-ylcarbonyl)-1-(2,2,2-trifluoroethyl)-1H-pyrazol-5-yl]-;

7H-indolo[2,1-a][2]benzazepine-10-carboxamide, 13-cyclohexyl-6-[4-(3,7-dioxa-9-azabicyclo[3.3.1]non-9-ylcarbonyl)-1-(2,2,2-trifluoroethyl)-1H-pyrazol-5-yl]-3-methoxy-N-[(1-methylethyl)sulfonyl]-;

7H-indo to [2,1-a][2]benzazepine-10-carboxamide, 13-cyclohexyl-3-methoxy-N-[(1-methylethyl)sulfonyl]-6-[4-(2-oxa-5-azabicyclo[2.2.1]hept-5-ylcarbonyl)-1-(2,2,2-trifluoroethyl)-1H-pyrazol-5-yl]-;

7H-indolo[2,1-a][2]benzazepine-10-carboxamide, 13-cyclohexyl-3-methoxy-N-[(1-methylethyl)sulfonyl]-6-[4-[(4-methyl-1-piperazinyl)carbonyl]-1-(2,2,2-trifluoro ethyl)-1H-pyrazol-5-yl]-;

7H-indolo[2,1-a][2]benzazepine-10-carboxamide, 13-cyclohexyl-3-methoxy-6-[1-(1-methylethyl)-4-oxa-3-azabicyclo[3.2.1]oct-3-ylcarbonyl)-1H-pyrazol-5-yl]-N-[(1-methylethyl)sulfonyl]-;

7H-indolo[2,1-a][2]benzazepine-10-carboxamide, 13-cyclohexyl-3-methoxy-6-[1-(1-methylethyl)-4-(3-oxa-9-azabicyclo[3.3.1]non-9-ylcarbonyl)-1H-pyrazol-5-yl]-N-[(1-methylethyl)sulfonyl]-;

7H-indolo[2,1-a][2]benzazepine-10-carboxamide, 13-cyclohexyl-3-methoxy-6-[1-(1-methylethyl)-4-(2-oxa-5-azabicyclo[2.2.1]hept-5-ylcarbonyl)-1H-pyrazol-5-yl]-N-[(1-methylethyl)sulfonyl]-;

7H-indolo[2,1-a][2]benzazepine-10-carboxamide, 13-cyclohexyl-3-methoxy-6-[1-(1-methylethyl)-4-[(4-methyl-1-piperazinyl)carbonyl]-1H-pyrazol-5-yl]-N-[(1-methylethyl)sulfonyl]-;

7H-indolo[2,1-a][2]benzazepine-10-carboxamide, 13-cyclohexyl-3-methoxy-N-[(1-methylethyl)sulfonyl]-6-[3-methyl-1-(1-methylethyl)-4-(8-oxa-3-azabicyclo[3.2.1]oct-3-ylcarbonyl)-1H-pyrazol-5-yl]-;

7H-indolo[2,1-a][2]benzazepine-10-carboxamide, 13-cyclohexyl-3-methoxy-N-[(1-methylethyl)sulfonyl]-6-[3-methyl-1-(1-methylethyl)-4-(2-oxa-5-azabicyclo[2.2.1]hept-5-ylcarbonyl)-1H-pyrazol-5-yl]-;

7H-indolo[2,1-a][2]benzazepine-10-carboxamide, 13-cyclohexyl-3-methoxy-N-[(1-methylethyl)sulfonyl]-6-[3-methyl-4-[(3-methyl-3,8-diazabicyclo[3.2.1]oct-8-yl)carbonyl]-1-(1-methylethyl)-1H-pyrazol-5-yl]-;

7H-indolo[2,1-a][2]benzazepine-10-carboxamide, 13-cyclohexyl-6-[4-[(5-ethyl-2,5-diazabicyclo[2.2.1]hept-2-yl)carbonyl]-3-methyl-1-(1-methylethyl)-1H-pyrazol-5-yl]-3-methoxy-N-[(1-methylethyl)sulfonyl]-;

7H-indolo[2,1-a][2]benzazepine-10-carboxamide, 13-cyclohexyl-N-(cyclopropylsulfonyl)-6-[4-[[(2R,6S)-2,6-dimethyl-4-morpholinyl]carbonyl]-1-ethyl-3-methyl-1H-pyrazol-5-yl]-3-methoxy-;

7H-indolo[2,1-a][2]benzazepine-10-carboxamide, 13-cyclohexyl-3-methoxy-N-[(1-methylethyl)sulfonyl]-6-[5-methyl-1-(1-methylethyl)-4-[[(3R,5S)-3,4,5-trimethyl-1-piperazinyl]carbonyl]-1H-pyrazol-3-yl]-;

7H-indolo[2,1-a][2]benzazepine-10-carboxamide, 13-cyclohexyl-6-[1-ethyl-4-(8-oxa-3-azabicyclo[3.2.1]oct-3-ylcarbonyl)-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-4-[(8-methyl-3,8-diazabicyclo[3.2.1]oct-3-yl)carbonyl]-1H-pyrazol-5-yl]-3-methoxy-N-[(1-methylethyl)sulfonyl]-1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1-ethyl-3-methyl-, ethyl ester;

7H-indolo[2,1-a][2]benzazepine-10-carboxamide, 13-cyclohexyl-6-[1-ethyl-3-methyl-5-(4-morpholinylcarbonyl)-1H-pyrazol-4-yl]-3-methoxy-N-[(1-methylethyl)sulfonyl]-;

7H-indolo[2,1-a][2]benzazepine-10-carboxamide, 13-cyclohexyl-6-[5-[[(2R,6S)-2,6-dimethyl-4-morpholinyl]carbonyl]-1-ethyl-3-methyl-1H-pyrazol-4-yl]-3-methoxy-N-[(1-methylethyl)sulfonyl]-;

7H-indolo[2,1-a][2]benzazepine-10-carboxamide, 13-cyclohexyl-6-[1-ethyl-3-methyl-5-[(4-methyl-1-piperazinyl)carbonyl]-1H-pyrazol-4-yl]-3-methoxy-N-[(1-methylethyl)sulfonyl]-;

7H-indolo[2,1-a][2]benzazepine-10-carboxamide, 13-cyclohexyl-6-[1-ethyl-3-methyl-5-[[(3R,5S)-3,4,5-trimethyl-1-piperazinyl]carbonyl]-1H-pyrazol-4-yl]-3-methoxy-N-[(1-methylethyl)sulfonyl]-1H-pyrazole-4-carboxylic acid, 5-[13-cyclohexyl-10-[[[(dimethylamino)sulfonyl]amino]carbonyl]-3-methoxy-7H-indolo[2,1-a][2]benzazepin-6-yl]-1-ethyl-3-methyl-;

7H-indolo[2,1-a][2]benzazepine-10-carboxamide, 13-cyclohexyl-6-[1-ethyl-4-[(5-ethyl-2,5-diazabicyclo[2.2.1]hept-2-yl)carbonyl]-3-methyl-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-3-methyl-4-[(8-methyl-3,8-diazabicyclo[3.2.1]oct-3-yl)carbonyl]-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-3-methyl-4-(4-morpholinylcarbonyl)-1H-pyrazol-5-yl]-3-methoxy-N-[(1-methylethyl)sulfonyl]-;

7H-indolo[2,1-a][2]benzazepine-10-carboxamide, 13-cyclohexyl-6-[1-ethyl-3-methyl-4-(3-oxa-9-azabicyclo[3.3.1]non-9-ylcarbonyl)-1H-pyrazol-5-yl]-3-methoxy-N-[(1-methylethyl)sulfonyl]-; and 7H-indolo[2,1-a][2]benzazepine-10-carboxamide, 13-cyclohexyl-6-[1-ethyl-4-[[(2S)-2-(methoxymethyl)-4-morpholinyl]carbonyl]-3-methyl-1H-pyrazol-5-yl]-3-methoxy-N-[(1-methylethyl)sulfonyl]-;

or a pharmaceutically acceptable salt thereof.

2. A composition comprising a compound of claim 1, or a pharmaceutically acceptable salt thereof, and a pharmaceutically acceptable carrier.

3. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,143,243 B2
APPLICATION NO. : 12/369222
DATED : March 27, 2012
INVENTOR(S) : Scott W. Martin et al.

Page 1 of 1

It is certified that error appears in the above-identified patent and that said Letters Patent is hereby corrected as shown below:

In the Claims:

Claim 1:

Column 466, lines 45 and 46, change "13-cyclohexyl-[1" to -- 13-cyclohexyl-6-[1 --.

Column 466, line 52, change "[2-a]" to -- [2,1-a] --.

Column 466, lines 52 and 53, change "13-cyclohexyl-[1" to -- 13-cyclohexyl-6-[1 --.

Column 467, lines 31 and 32, change "1H-1-pyrazol" to -- 1H-pyrazol --.

Column 467, line 65, change "[(di methylamino)sulfonyl]" to -- [(dimethylamino)sulfonyl] --.

Column 468, line 26, change "[(dimethyl amino)sulfonyl]6" to -- [(dimethylamino)sulfonyl]-6 --.

Column 468, line 35, change "ylcarbonyl]" to -- yl)carbonyl] --.

Column 468, line 48, change "1H-1-pyrazol" to -- 1H-pyrazol --.

Column 469, line 19, change "7H-indo to [2,1-a][2]benzazepine" to -- 7H-indolo[2,1-a][2]benzazepine --.

Column 469, lines 25 and 26, change "trifluoro ethyl)" to -- trifluoroethyl) --.

Column 469, line 28, change "4-oxa" to -- 4-(8-oxa --.

Signed and Sealed this
Eighteenth Day of March, 2014

Michelle K. Lee
*Deputy Director of the United States Patent and Trademark Office*